US008318952B2

(12) United States Patent
Takeuchi et al.

(10) Patent No.: US 8,318,952 B2
(45) Date of Patent: Nov. 27, 2012

(54) SUBSTITUTED INDOLE DERIVATIVES FOR THE TREATMENT OF RESPIRATORY DISEASES

(75) Inventors: Jun Takeuchi, Mishima-gun (JP); Satoshi Itadani, Mishima-gun (JP); Yoshisuke Nakayama, Mishima-gun (JP); Tadashi Tatsumi, Mishima-gun (JP); Shinya Takahashi, Sakai-gun (JP); Manabu Fujita, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 137 days.

(21) Appl. No.: 12/791,365

(22) Filed: Jun. 1, 2010

(65) Prior Publication Data

US 2010/0234368 A1    Sep. 16, 2010

Related U.S. Application Data

(62) Division of application No. 10/569,482, filed as application No. PCT/JP2004/012563 on Aug. 31, 2004, now Pat. No. 7,763,610.

(30) Foreign Application Priority Data

Sep. 1, 2003 (JP) ................................ 2003-309232
Oct. 29, 2003 (JP) ................................ 2003-369547

(51) Int. Cl.
C07D 209/04    (2006.01)
(52) U.S. Cl. ..................................................... 548/469
(58) Field of Classification Search .................... 548/469
See application file for complete search history.

(56) References Cited

FOREIGN PATENT DOCUMENTS
EP    0 405 116    1/1991

OTHER PUBLICATIONS

Victor G. Matassa et al., "Synthesis and in Vitro LTD$_4$ Antagonist Activity of Bicyclic and Monocyclic Cyclopentylurethane and Cyclopentylacetamide N-Arylsulfonyl Amides", J. Med. Chem., vol. 33, No. 9, pp. 2621-2629 (1990).
International Search Report mailed Nov. 9, 2004 in International (PCT) Application No. PCT/JP2004/012563.
International Preliminary Report on Patentability mailed Jun. 29, 2006 in International (PCT) Application No. PCT/JP2004/012563.
F. Touzeau et al., "Synthesis and Biological Evaluation of New 2-(4,5-Dihydro-1H-imidazol-2-yl)-3,4-dihydro-2H-1,4-benzoxazine Derivatives", Journal of Medicinal Chemistry, vol. 46, No. 10, pp. 1962-1979, 2003.
S. Mayer et al., "Regioselective Formylation of Ethyl 3,4-Dihydro-2H-1,4-Benzoxazine-2-Carboxylate or 2-Acetate Derivatives", Heterocycles, vol. 55, No. 10, pp. 1873-1888, 2001.
Anthony R. West, Solid State Chemistry and its Applications, Wiley, New York, 1988, pp. 358 and 365.
European Office Action dated Feb. 1, 2010, issued in corresponding European Application No. 04 772 519, in the English language.

*Primary Examiner* — Brian McDowell
(74) *Attorney, Agent, or Firm* — Wenderoth, Lind & Ponack, L.L.P.

(57) ABSTRACT

The present invention relates to a compound of formula (I)

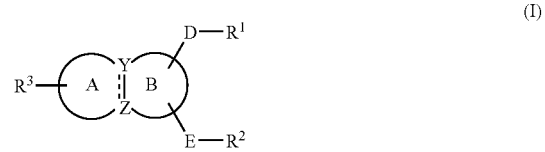

(I)

(wherein all symbols have the same meanings as described hereinbefore). The compound antagonizes cysLT$_2$ and therefore, it is useful as an agent for the prevention and/or treatment of respiratory diseases such as bronchial asthma, bronchial asthma, chronic obstructive pulmonary disease, pneumonectasia, chronic bronchitis, pneumonia (e.g. interstitial pneumonitis etc.), severe acute respiratory syndrome (SARS), acute respiratory distress syndrome (ARDS), allergic rhinitis, sinusitis (e.g. acute sinusitis, chronic sinusitis, etc.), and the like, or as an expectorant or antitussives.

2 Claims, No Drawings

SUBSTITUTED INDOLE DERIVATIVES FOR THE TREATMENT OF RESPIRATORY DISEASES

This application is a divisional application of U.S. application Ser. No. 10/569,482, filed Apr. 5, 2006, now U.S. Pat. No. 7,763,610, now allowed, which is the national phase filing of International Patent Application No. PCT/JP2004/012563, filed Aug. 31, 2004.

TECHNICAL FIELD

The present invention relates to
(1) a compound of formula (I)

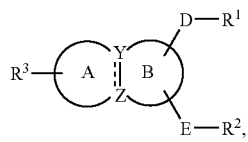

wherein all symbols have the same meanings as defined below, and
(2) a cysLT$_2$ receptor antagonist comprising the compound of formula (I).

BACKGROUND ART

Bronchial asthma is a pathological symptom, in which airway is contracted by airway contraction and inflammation, causing paroxysmal cough, stridor, and breathing difficulty. The drugs for it include steroidal agents for inhalation, which have a strong antiinflammatory effect, β stimulants and theophyllines which are bronchodilating agents, antiallergic agents which inhibit the effect of mediators, etc.

It is known that various chemical mediators are involved in bronchial asthma, among which cysteinyl leukotrienes (cys-LTs) are known to have approximately 1000 times stronger contractile effect on airway as compared to histamine. Moreover, cysLTs promote induction of airway inflammation, typically inflammation cell invasion, airway hypersensitivity and mucus secretion in airway, and they are deeply involved in basic pathology of bronchial asthma.

CysLTs are a physiological active substance in a live body, which is a metabolic product from arachidonic acid by 5-lipoxygenase. CysLTs have at least two types of receptors, and cysLT$_1$ receptor and cysLT$_2$ receptor have been cloned so far (Nature, 399, 789-793, 1999, J. Biol., Chem., 275, 30531-30536, 2000). CysLT$_1$ receptor is mainly expressed in airway smooth muscle and it is deeply concerned with the development of bronchial asthma (Am. J. Respir. Crit. Care Med., 163, 226-233, 2001). Those leukotriene (LT) receptor antagonists which are now placed on the market, e.g. pranlukast hydrate, montelukast sodium and zafirlukast, and are selective cysLT$_1$ receptor antagonist (Nature, 399, 789-793, 1999), are useful agents for the treatment of bronchial asthma, which improves various kinds of symptoms and respiratory functions. However, it is known the LT receptor antagonists placed on the market are more effective for mild or moderate symptoms than for severe symptoms. It is also known that there exist some non-responders with mild or moderate symptoms on whom the pharmaceutical agent does not have effect.

On the other hand, it is reported that the ligands for the newly cloned cysLT$_2$ receptor are LTC$_4$, LTD$_4$ and LTE$_4$, and cysLT$_2$ receptor is expressed in the bronchial smooth muscle like CysLT$_1$ receptor (J. Biol. Chem., 275, 30531-30536, 2000, Am. J. Respir. Crit. Care Med., 164, 2098-2101, 2001). However, the functions and roles of cysLT$_2$ receptor in the pathological conditions have not been elucidated yet.

Therefore, provided that cysLT$_2$ receptor, as well as cysLT$_1$ receptor, is concerned with contraction of bronchial smooth muscle, airway inflammation, reactive airway disease and mucus secretion in airway, by antagonizing cysLT$_2$ receptor, it is conceivably possible to produce an agent for respiratory diseases which is more useful than existing LT receptor antagonists. For example, it is expected that such agent shows an efficacy on more severe bronchial asthma patients and non-responders of existing LT receptor antagonist. Moreover, it is also reported that cysLT$_2$ receptor is expressed in heart, brain and peripheral blood leukocyte, etc. in addition to bronchial smooth muscle (J. Biol. Chem., 275, 30531-30536, 2000). Therefore, cysLT$_2$ receptor antagonists are expected to be agents for the treatment of cardiovascular, central nervous system and various inflammatory diseases.

In Molecular Pharmacology (United States), 2000, 58, p. 1601-1608, it is disclosed that a compound of formula (A)

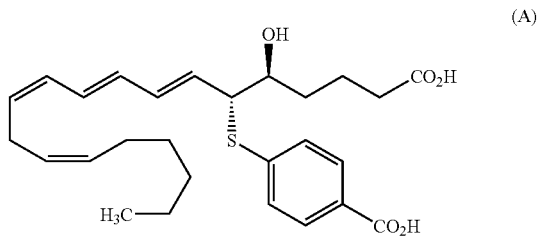

antagonizes both cysLT$_1$ and cysLT$_2$.

And in the gazette of JP9-169712, it is disclosed that a benzoic acid derivative of formula (B)

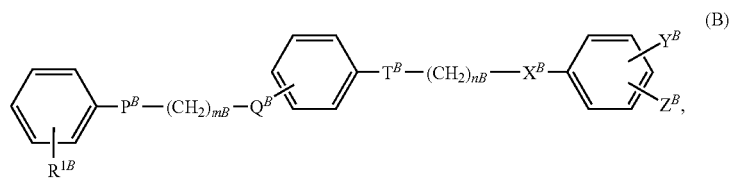

wherein, $R^{1B}$ is hydrogen, alkyl having up to 6 carbons, or substituted phenyl; $P^B$ and $Q^B$ is each oxygen, sulfur or a bond; $X^B$ is oxygen, sulfur or —CONH—; $T^B$ is ethylene, oxygen, sulfur or a bond; $Y^B$ is —COOH, —NHSO$_2$R$^{3B}$ or CONHSO$_2$R$^{3B}$; $Z^B$ is —COOH, COR$^{4B}$, —CO(CH$_2$)$_{pB}$CO$_2$H, —O(CH$_2$)$_{pB}$CO$_2$H, —S(CH$_2$)$_{pB}$CO$_2$H, NO$_2$, —CONHW$^B$CO$_2$H or NHW$^B$CO$_2$H; mB is an integer from 0 to 6; and nB is an integer from 0 to 4 shows leukotriene antagonistic action, that is effective for the treatment of respiratory diseases, and that it antagonizes both cysLT$_1$ receptor and cysLT$_2$ receptors.

Also, in the program of the 98th American Thoracic Society (2002, D38, F4) it is described that DUO-LT, which is a compound whose clinical target is ischemic diseases and inflammatory diseases, antagonizes both cysLT$_1$ and cysLT$_2$ receptors.

In the specification of WO 2004/052839, it is disclosed that a compound of formula (C)

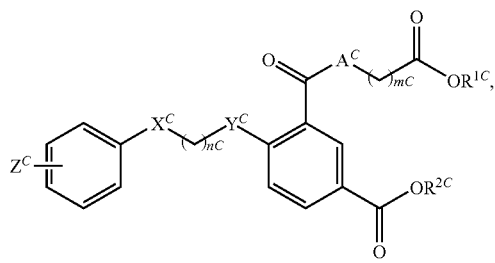

(C)

wherein all symbols have the same meaning as described in the specification, has an antagonizing effect against CysLT$_2$ receptors and the compound is useful for the treatment and/or prevention of cardiovascular diseases such as angina pectoris, cardiac infarction, etc.

DISCLOSURE OF THE INVENTION

Problems to be Solved by the Invention

As described hereinbefore, those LT receptor antagonists which are placed on the market are known to act on mild and moderate symptoms of bronchial asthma and it is also known that there exist some non-responders among patients with mild and moderate symptoms, to whom the agent are not effective. Therefore, those agents for respiratory diseases showing higher efficacy than the existing agents have been hoped for.

DETAILED DESCRIPTION OF THE PRESENT INVENTION

The present inventors have energetically investigated to solve the above-mentioned problems, and have found out that the compound of formula (I) which antagonizes cysLT$_2$ receptor is useful as an agent for respiratory diseases to complete the present invention.

That is, the present invention relates to
[1] a compound of formula (I)

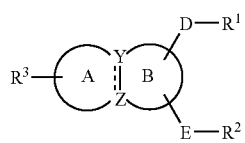

(I)

[wherein R$^1$ and R$^2$ are each independently, an acidic group which may be protected, D and E are each independently, a bond or a spacer consisting of 1-8 atom(s) in the main chain, R$^3$ is a substituent, ring A is a cyclic group which may have more substituent(s), ring B is a cyclic group which may have more substituent(s), Y and Z are each independently, a carbon atom or a nitrogen atom, and ---------- is a single bond or a double bond (provided that Y and/or Z is/are nitrogen atom(s), the bond is a single bond)], an N-oxide thereof, a salt thereof, a solvate thereof or a prodrug thereof, [2] the compound according to the above [1], wherein

is 3,4-dihydro-2H-1,4-benzoxazine, 3,4-dihydro-2H-1,4-benzothiazine, 1,2,3,4-tetrahydroquinoxaline, 1,2,3,4-tetrahydroquinoline, 1,2-dihydroquinoline, 4H-1,4-benzoxazine, 4H-1,4-benzothiazine, quinoline, isoquinoline, quinoxaline, 1,2,3,4-tetrahydroisoquinoline, cinnoline, phthalazine, 4(1H)-quinolinone, 3,4-dihydro-2(1H)-quinolinone, 2(1H)-quinolinone, 1H-indole or indoline ring,
[3] the compound according to the above [1], wherein R$^3$ is

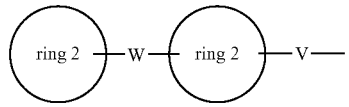

(wherein ring 1 is a cyclic group which may have substituent(s), V is a bond or a spacer having 1-8 atom(s) in the main chain, ring 2 is a cyclic group which may have substituent(s), and W is a bond or a spacer having 1-8 atom(s) in the main chain),
[4] the compound according to the above [1], wherein the acidic group represented by R$^1$ and R$^2$ are each independently, —COOR$^A$ (wherein R$^A$ is hydrogen or C1-8 alkyl), —CONR$^B$SO$_2$Rc (wherein R$^B$ is hydrogen or C1-8 alkyl, Rc is C1-8 hydrocarbon), —SO$_2$NR$^B$CORc (wherein all symbols have the same meaning as described hereinbefore),

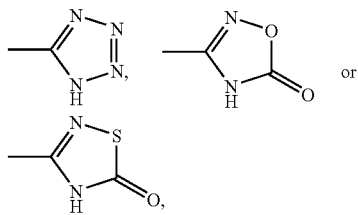

[5] the compound according to the above [1], which is a compound of formula (I-X)

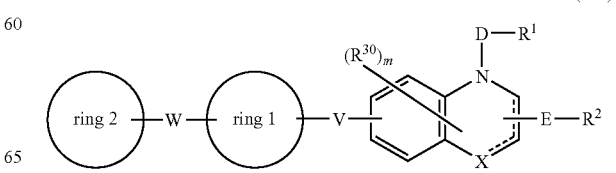

(I-X)

(wherein R³⁰ is hydrogen or a substituent, m is 0 or an integer of 1 to 4, L is a nitrogen atom, an oxygen atom, a sulfur atom which may be oxidized, a carbon atom or a bond, and the other symbols have the same meanings as in claims 1 and 3, and the adjacent two ---------- bonds do not represent a double bond at the same time),

[6] the compound according to the above [3] or [5], wherein V is a divalent group comprising the combination of 1-4 member(s) selected from —CH₂— optionally having 1-2 substituent(s), —CH═CH— optionally having 1-2 substituent(s), —C≡C—, —NH— optionally having a substituent, —CO—, —O—, —S—, —SO— and SO₂—,

[6] the compound according to the above [3] or [5], wherein V is a divalent group comprising the combination of 1-4 member(s) selected from —CH₂— optionally having 1-2 substituent(s), —CH═CH— optionally having 1-2 substituent(s), —C≡C—, —NH— optionally having a substituent, —CO—, —O—, —S—, —SO— and SO₂—,

[7] the compound according to the above [3] or [5], wherein -D-R¹ is —CO—(CH₂)₂—R¹, —CO—(CH₂)₃—R¹, —CO—(CH₂)₄—R¹ or C1-4 alkylene-R¹,

[8] the compound according to the above [3] or [5], wherein E is a bond or C1-4 alkylene,

[9] the compound according to the above [3] or [5] wherein V is

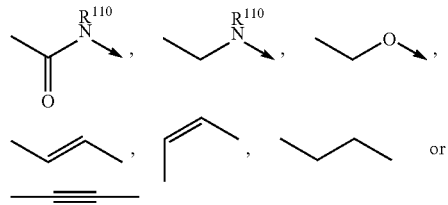

[10] the compound according to the above [1], which is selected from
(1) 4-(3-carboxypropyl)-8-((4-(4-phenylbutoxy)benzoyl)amino)-3,4-dihydro-2H-1,4-benzoxazine-2-carboxylic acid,
(2) 4-(3-carboxypropyl)-8-({(2E)-3-[4-(4-phenylbutyl)phenyl]-2-propenoyl}amino)-3,4-dihydro-2H-1,4-benzoxazine-2-carboxylic acid,
(3) 4-[8-{[4-(4-phenylbutoxy)benzoyl]amino}-2-(1H-tetrazol-5-yl)-2,3-dihydro-4H-1,4-benzoxazin-4-yl]butanoic acid,
(4) 4-(3-carboxypropyl)-8-{[4-(4-phenylbutoxy)benzyl]amino}-3,4-dihydro-2H-1,4-benzoxazine-2-carboxylic acid,
(5) 4-(3-carboxypropyl)-8-{(E)-2-[4-(4-phenylbutoxy)phenyl]vinyl}-3,4-dihydro-2H-1,4-benzoxazine-2-carboxylic acid,
(6) 4-(3-carboxypropyl)-8-{2-[4-(4-phenylbutoxy)phenyl]ethyl}-3,4-dihydro-2H-1,4-benzoxazine-2-carboxylic acid,
(7) (2S)-4-(3-carboxypropyl)-8-{[4-(4-phenylbutoxy)benzoyl]amino}-3,4-dihydro-2H-1,4-benzoxazine-2-carboxylic acid,
(8) (2R)-4-(3-carboxypropyl)-8-{[4-(4-phenylbutoxy)benzoyl]amino}-3,4-dihydro-2H-1,4-benzoxazine-2-carboxylic acid,
(9) 4-(3-carboxypropyl)-8({4-[2-(2,3-dihydro-1H-inden-2-yl)ethoxy]benzoyl}amino)-3,4-dihydro-2H-1,4-benzoxazine-2-carboxylic acid,
(10) 4-(3-carboxypropyl)-8-({4-[(5-phenylpentyl)oxy]benzoyl}amino)-3,4-dihydro-2H-1,4-benzoxazine-2-carboxylic acid,
(11) 4-(3-carboxypropyl)-8-({4-[(7-phenylheptyl)oxy]benzoyl}amino)-3,4-dihydro-2H-1,4-benzoxazine-2-carboxylic acid,
(12) 4-(3-carboxypropyl)-8-({4-[(4-methylpentyl)oxy]benzoyl}amino)-3,4-dihydro-2H-1,4-benzoxazine-2-carboxylic acid,
(13) 4-(3-carboxypropyl)-8-{[4-(4-phenoxybutoxy)benzoyl]amino}-3,4-dihydro-2H-1,4-benzoxazine-2-carboxylic acid,
(14) 4-(3-carboxypropyl)-8-({4-[3-(2,3-dihydro-1H-inden-2-yl)propoxy]benzoyl}amino)-3,4-dihydro-2H-1,4-benzoxazine-2-carboxylic acid,
(15) 4-(3-carboxypropyl)-8-({4-[4-(4-fluorophenyl)butoxy]benzoyl}amino)-3,4-dihydro-2H-1,4-benzoxazine-2-carboxylic acid,
(16) 4-(3-carboxypropyl)-8-({4-[4-(2-methylphenoxy)butoxy]benzoyl}amino)-3,4-dihydro-2H-1,4-benzoxazine-2-carboxylic acid,
(17) 4-(3-carboxypropyl)-8-({4-[4-(2-fluorophenoxy)butoxy]benzoyl}amino)-3,4-dihydro-2H-1,4-benzoxazine-2-carboxylic acid,
(18) 4-(3-carboxypropyl)-8-({4-[4-(2-chlorophenoxy)butoxy]benzoyl}amino)-3,4-dihydro-2H-1,4-benzoxazine-2-carboxylic acid,
(19) 4-(3-carboxypropyl)-8-[(4-{4-[2-(trifluoromethyl)phenoxy]butoxy}benzoyl)amino]-3,4-dihydro-2H-1,4-benzoxazine-2-carboxylic acid,
(20) 4-(3-carboxypropyl)-8-({4-[3-(2-methylphenoxy)propoxy]benzoyl}amino)-3,4-dihydro-2H-1,4-benzoxazine-2-carboxylic acid,
(21) 4-(2-({[(4-methylphenyl)sulfonyl]amino}carbonyl)-8-{[4-(4-phenylbutoxy)benzoyl]amino}-2,3-dihydro-4H-1,4-benzoxazin-4-yl)butanoic acid,
(22) 4-(2-{[(methylsulfonyl)amino]carbonyl}-8-{[4-(4-phenylbutoxy)benzoyl]amino}-2,3-dihydro-4H-1,4-benzoxazin-4-yl)butanoic acid,
(23) 4-(2-{[(benzylsulfonyl)amino]carbonyl}-8-{[4-(4-phenylbutoxy)benzoyl]amino}-2,3-dihydro-4H-1,4-benzoxazin-4-yl)butanoic acid,
(24) 4-(3-carboxypropyl)-8-{(E)-2-[4-(4-phenoxybutoxy)phenyl]vinyl}-3,4-dihydro-2H-1,4-benzoxazine-2-carboxylic acid,
(25) 4-(3-carboxypropyl)-8-{(E)-2-[4-(2,3-dihydro-1H-inden-2-ylmethoxy)phenyl]vinyl}-3,4-dihydro-2H-1,4-benzoxazine-2-carboxylic acid,
(26) 4-(3-carboxypropyl)-8-((E)-2-{4-[3-(2,3-dihydro-1H-inden-2-yl)propoxy]phenyl}vinyl)-3,4-dihydro-2H-1,4-benzoxazine-2-carboxylic acid,
(27) 4-(3-carboxypropyl)-8-((E)-2-{4-[(5-phenoxypentyl)oxy]phenyl}vinyl)-3,4-dihydro-2H-1,4-benzoxazine-2-carboxylic acid,
(28) 4-(3-carboxypropyl)-8-((E)-2-{4-[4-(4-methoxyphenoxy)butoxy]phenyl}vinyl)-3,4-dihydro-2H-1,4-benzoxazine-2-carboxylic acid,
(29) 4-(3-carboxypropyl)-8-((E)-2-{4-[3-(4-fluorophenoxy)propoxy]phenyl}vinyl)-3,4-dihydro-2H-1,4-benzoxazine-2-carboxylic acid,
(30) 4-(3-carboxypropyl)-8-{(E)-2-[4-(3-phenoxypropoxy)phenyl]vinyl}-3,4-dihydro-2H-1,4-benzoxazine-2-carboxylic acid,
(31) 4-(3-carboxypropyl)-8-((E)-2-{4-[3-(2-chlorophenoxy)propoxy]phenyl}vinyl)-3,4-dihydro-2H-1,4-benzoxazine-2-carboxylic acid,

(32) 4-(3-carboxypropyl)-8-{2-[4-(4-phenoxybutoxy)phenyl]ethyl}-3,4-dihydro-2H-1,4-benzoxazine-2-carboxylic acid,

(33) 4-[8-{2-[4-(4-phenylbutoxy)phenyl]ethyl}-2-(1H-tetrazol-5-yl)-2,3-dihydro-4H-1,4-benzoxazin-4-yl]butanoic acid,

(34) 4-[8-{(E)-2-[4-(4-phenylbutoxy)phenyl]vinyl}-2-(1H-tetrazol-5-yl)-2,3-dihydro-4H-1,4-benzoxazin-4-yl]butanoic acid,

(35) 4-(2-(5-oxo-4,5-dihydro-1,2,4-thiadiazol-3-yl)-8-{[4-(4-phenylbutoxy)benzoyl]amino}-2,3-dihydro-4H-1,4-benzoxazin-4-yl)butanoic acid,

(36) 4-(2-(5-oxo-4,5-dihydro-1,2,4-oxadiazol-3-yl)-8-{(E)-2-[4-(4-phenylbutoxy)phenyl]vinyl}-2,3-dihydro-4H-1,4-benzoxazin-4-yl)butanoic acid,

(37) 4-oxo-4-(8-((4-(4-phenylbutoxy)benzoyl)amino)-2-(1H-tetrazol-5-yl)-2,3-dihydro-4H-1,4-benzoxazin-4-yl)butanoic acid, and

(38) 4-(3-carboxypropyl)-8-((4-(4-phenylbutoxy)benzyl)oxy)-3,4-dihydro-2H-1,4-benzoxazine-2-carboxylic acid,

[11] a pharmaceutical composition comprising the compound of formula (I) described in the above [1] or an N-oxide thereof, a salt thereof, a solvate thereof or a prodrug thereof,

[12] the pharmaceutical composition according to the above [11], which is an agent for the prevention and/or treatment of a disease mediated by $cysLT_2$,

[13] the pharmaceutical composition according to the above [12], wherein the disease mediated by $cysLT_2$ is a respiratory disease,

[14] the pharmaceutical composition according to the above [13], wherein the respiratory disease is asthma or chronic obstructive pulmonary disease,

[15] a medicine comprising the compound of formula (I) described in the above [1], an N-oxide thereof, a salt thereof, a solvate thereof or a prodrug thereof and one or more member(s) selected from a $cysLT_1$ receptor antagonist, a steroidal agent, an antihistamine agent, a phosphodiesterase 4 inhibitor, an elastase inhibitor, an anticholinergic agent and a sympathomimetic agent,

[16] a method for the prevention and/or treatment of the diseases mediated by $cysLT_2$ characterized by administering to a mammal an effective amount of the compound of formula (I) described in the above [1], an N-oxide thereof, a salt thereof, a solvate thereof or a prodrug thereof,

[17] a method for the prevention and/or treatment of the diseases mediated by $cysLT_2$ characterized by administering to a mammal an effective amount of the compound of formula (I) described in the above [1], an N-oxide thereof, a salt thereof, a solvate thereof or a prodrug thereof, in combination with a $cysLT_1$ receptor antagonist, a steroidal agent, an antihistamine agent, a phosphodiesterase 4 inhibitor, an elastase inhibitor, an anticholinergic agent and/or a sympathomimetic drug and

[18] use of the compound of formula (I) described in the above [1], for the manufacture of an agent for the prevention and/or treatment of the disease mediated by $cysLT_2$.

In the present specification, the cyclic group in the cyclic group optionally having substituent(s) represented by ring A is, C3-15 carbocyclic ring, or 3-15 membered mono-, bi- or tricyclic partially or completely saturated aromatic heterocyclic ring comprising 1-5 hereto atom(s) selected from oxygen, nitrogen and/or sulfur.

In the present invention, C3-15 carbocyclic ring includes, C3-15 mono-, bi- or tri-cyclic aromatic carbocyclic ring, partly or completely saturated one thereof, spiro bicyclic carbocyclic ring and bridged carbocyclic ring, e.g. cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane or noradamantane ring, etc.

In the present invention, the 3-15 membered mono-, bi- or tri-cyclic partially or completely saturated aromatic heterocyclic ring comprising 1-5 hereto atom(s) selected from oxygen, nitrogen and/or sulfur includes, e.g. pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazane, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, pyrazolopyridine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepin, tetrahydrooxepin, perhydrooxepin, thiirane, thietane dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydro quino line, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane, azaspiro[4.4]nonane, oxazaspiro[4.4]nonane, dioxaspiro[4.4]nonane, azaspiro[4.5]decane, thiaspiro[4.5] decane, dithiaspiro[4.5]decane, dioxaspiro[4.5]decane, oxazaspiro[4.5]decane, azaspiro[5.5]undecane, oxaspiro[5.5] undecane, dioxaspiro[5.5]undecane, azabicyclo[2.2.1] heptane, oxabicyclo[2.2.1]heptane, azabicyclo[3.1.1] heptane, azabicyclo[3.2.1]octane, oxabicyclo[3.2.1]octane, azabicyclo[2.2.2]octane, diazabicyclo[2.2.2]octane, tetrahydro-β-carboline, hexahydroazepinoindole, oxazaspiro[2.5] octane, hexahydroazepinoindazole, hexahydropyrazolopyridoazepine, tetrahydropyrazoloisoquinoline or tetrahydropyrazolonaphthyridine ring, etc.

In the present invention, the "substituent" in the "cyclic group which may have substituent(s)" represented by ring A includes, for example, (1) alkyl which may have substituent(s), (2) alkenyl which may have substituent(s), (3) alkynyl which may have substituent(s), (4) carbocyclic ring which may have substituent(s), (5) heterocyclic ring which may have substituent(s), (6) hydroxy which may be protected, (7) mercapto which may be protected, (8) amino which may be protected, (9) carbamoyl which may have substituent(s), (10) sulfamoyl which may have substituent(s), (11) carboxy, (12) alkoxycarbonyl (e.g. C1-6 alkoxycarbonyl such as methoxycarbonyl, ethoxycarbonyl, tert-butoxycarbonyl, etc.), (13) sulfo, (14) sulfino, (15) phosphono, (16) nitro, (17) cyano, (18) amidino, (19) imino, (20) dihydroborono, (21) halogen (e.g. fluorine, chlorine, bromine, iodine, etc.), (22) alkylsulfinyl (e.g. C1-4 alkylsulfinyl such as methylsulfinyl, ethylsulfinyl, etc.), (23) aromatic ring-sulfinyl (e.g. C6-10 aromatic ring-sulfinyl such as phenylsulfinyl etc.), (24) alkylsulfonyl (e.g. C1-4 alkylsulfonyl such as methylsulfonyl, ethylsulfonyl, etc.), (25) aromatic ring-sulfonyl (e.g. C6-10 aromatic ring-sulfonyl such as phenylsulfonyl etc.), (26) acyl, (27) oxo, (28) thioxo, (29) (C1-6 alkoxyimino)methyl (e.g. (methoxyimino)methyl, etc.), (30) formyl, etc., and 1-5 of these substituents may be positioned where acceptable.

The alkyl in the "(1) alkyl which may have substituent(s)" as a substituent includes straight or branched C1-20 alkyl such as methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, etc.

Hereby the substituent of the alkyl includes, for example, hydroxy, amino, carboxy, nitro, azido, mono- or di-C1-6 alkylamino (e.g. methylamino, ethylamino, propylamino, dimethylamino, diethylamino, etc.), N-aromatic ring-amino (e.g. N-phenylamino etc.), N-aromatic ring-N-alkylamino (e.g. N-phenyl-N-methylamino, N-phenyl-N-ethylamino, N-phenyl-N-propylamino, N-phenyl-N-butylamino, N-phenyl-N-pentylamino, N-phenyl-N-hexylamino, etc.), acylamino, N-acyl-N-alkylamino, C1-6 alkoxy (e.g. methoxy, ethoxy, propoxy, isopropoxy, hexyloxy, etc.), C3-7 cycloalkyl-C1-6 alkoxy (e.g. cyclohexylmethyloxy, cyclopentylethyloxy, etc.), C3-7 cycloalkyloxy (e.g. cyclohexyloxy etc.), C7-15 aralkyloxy (e.g. benzyloxy, phenethyloxy, phenylpropyloxy, naphthylmethyloxy, naphthylethyloxy, etc.), phenoxy, C1-6 alkoxycarbonyl (e.g. methoxycarbonyl, ethoxycarbonyl, tert-butoxycarbonyl, etc.), C1-6 alkylcarbonyloxy (e.g. acetoxy, ethylcarbonyloxy, etc.), C1-4 alkylthio (e.g. methylthio, ethylthio, propylthio, butylthio, etc.), halogen (fluorine, chlorine, bromine, iodine), alkylsulfonyl (e.g. C1-4 alkylsulfonyl such as methylsulfonyl, ethylsulfonyl, etc.), aromatic ring-sulfonyl (e.g. C6-10 aromatic ring-sulfonyl such as phenylsulfonyl etc.), acyl, formyl, carbocyclic ring which may have substituent(s), heterocyclic ring which may have substituent(s), etc. and 1-4 of these substituents may be positioned where acceptable.

Hereby, the acyl in the acyl, acylamino and N-acyl-N-alkylamino has the same meaning as the "(26) acyl" as a substituent hereafter described. And the "alkyl" in the N-acyl-N-alkylamino includes e.g. straight or branched C1-20 alkyl such as methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, etc.

And the carbocyclic ring which may have substituent(s), and the heterocyclic ring which may have substituent(s) has the same meaning as the "(4) carbocyclic ring which may have substituent(s)", and the "(5) heterocyclic ring which may have substituent(s)" respectively.

The alkynyl in the "(3) alkynyl which may have substituent(s)" as a substituent includes e.g. straight or branched C2-20 alkynyl such as ethynyl, propynyl, butynyl, pentynyl, hexynyl, etc. Here the substituent of the alkynyl has the same meaning as the substituent in the above "alkyl which may have substituent(s)".

The carbocyclic ring in the "(4) carbocyclic ring which may have substituent(s)" as a substituent has the same meaning as the C3-15 carbocyclic ring in the cyclic group in the "cyclic ring which may have substituent(s)."

The carbocyclic ring in the "(4) carbocyclic ring which may have substituent(s)" as a substituent has the same meaning as the C3-15 carbocyclic ring in the cyclic group in the "cyclic group which may have substituent(s)" represented by the above ring A. Here the substituent of the carbocyclic ring includes, e.g. C1-8 alkyl (e.g. methyl, ethyl, n-propyl, isopropyl, n-butyl, isobutyl, sec-butyl, tert-butyl, pentyl, hexyl, heptyl, octyl, etc.), C2-8 alkenyl (e.g. ethenyl, propenyl, butenyl, pentenyl, hexenyl, heptenyl, octenyl, etc.), C2-8 alkynyl (e.g. ethynyl, propynyl, butynyl, pentynyl, hexynyl, heptynyl, octynyl, etc.), hydroxy, C1-6 alkoxy (e.g. methoxy, ethoxy, propoxy, butoxy, pentyloxy, hexyloxy, etc.), C1-6 alkoxycarbonyl (e.g. methoxycarbonyl, ethoxycarbonyl, tert-butoxycarbonyl, etc.), C1-6 alkylcarbonyloxy (e.g. acetoxy, ethylcarbonyloxy, etc.), mercapto, C1-6 alkylthio (e.g. methylthio, ethylthio, propylthio, butylthio, pentylthio, hexylthio, etc.), amino, mono- or di-C1-4 alkylamino (e.g. methylamino, ethylamino, propylamino, dimethylamino, diethylamino, etc.), halogen (fluorine, chlorine, bromine, iodine), trihalomethyl (e.g. trifluoromethyl etc.), trihalomethoxy (e.g. trifluoromethoxy etc.), trihalomethylthio (e.g. trifluoromethylthio etc.), dihalomethoxy (e.g. difluoromethoxy etc.), dihalomethylthio (e.g. difluoromethylthio etc.), cyano, nitro, carboxy, a cyclic group which may have substituent(s), in which the cyclic group has the same meaning as the cyclic group in the "cyclic group which may have substituent(s)" represented by the above ring A, and the substituent includes, for example, C1-8 alkyl (e.g. methyl, ethyl, n-propyl, isopropyl, n-butyl, isobutyl, sec-butyl, tert-butyl, pentyl, hexyl, heptyl, octyl, etc.), C2-8 alkenyl (e.g. ethenyl, propenyl, butenyl, pentenyl, hexenyl, heptenyl, octenyl, etc.), C2-8 alkynyl (e.g. ethynyl, propynyl, butynyl, pentynyl, hexynyl, heptynyl, octynyl, etc.), hydroxy, C1-6 alkoxy (e.g. methoxy, ethoxy, propoxy, butoxy, pentyloxy, hexyloxy, etc.), C1-6 alkoxycarbonyl (e.g. methoxycarbonyl, ethoxycarbonyl, tert-butoxycarbonyl, etc.), C1-6 alkylcarbonyloxy (e.g. acetoxy, ethylcarbonyloxy, etc.), mercapto, C1-6 alkylthio (e.g. methylthio, ethylthio, propylthio, butylthio, pentylthio, hexylthio, etc.), amino, mono- or di-C1-4 alkylamino (e.g. methylamino, ethylamino, propylamino, dimethylamino, diethylamino, etc.), halogen (fluorine, chlorine, bromine, iodine), trihalomethyl (e.g. trifluoromethyl etc.), trihalomethoxy (e.g. trifluoromethoxy, etc.), trihalomethylthio (e.g. trifluoromethylthio etc.), dihalomethoxy (e.g. difluoromethoxy etc.), dihalomethylthio (e.g. difluoromethylthio etc.), cyano, nitro, carboxy, etc., and 1-4 of these substituents may be positioned where acceptable. etc., and 1-4 of these substituents may be positioned where acceptable.

The heterocyclic ring in the "(5) heterocyclic ring which may have substituent(s)" as a substituent has the same meaning as the 3-15 membered mono-, bi- or tri-cyclic aromatic heterocyclic ring comprising 1-5 hetero atom(s) selected from oxygen, nitrogen and/or sulfur which may be partially or completely saturated in the "cyclic group which may have substituent(s)" represented by ring A.

Here, the substituent of the heterocyclic ring has the same meaning as the substituent in the above "(4) carbocyclic ring which may have substituent(s)."

The protective groups in "(6) optionally protected hydroxy", "(7) optionally protected mercapto" and "(8) optionally protected amino" as a substituent include, for example, alkyl which may have substituent(s) (it has the same meaning as the above "(1) alkyl which may have substituent(s)"), carbocyclic ring which may have substituent(s) (it has the same meaning as the above "(4) carbocyclic ring which may have substituent(s)"), heterocyclic ring which may have substituent(s) (it has the same meaning as the above "(5) a heterocyclic ring which may have substituent(s)"), alkylsulfonyl (e.g. C1-4 alkylsulfonyl such as methylsulfonyl, ethylsulfonyl, etc.), aromatic ring-sulfonyl (e.g. C6-10 aromatic ring-sulfonyl such as phenylsulfonyl, etc.), acyl (it has the same meaning as the (26) acyl as described hereafter), etc.

The "(9) carbamoyl which may have substituent(s)" as a substituent includes, for example, unsubstituted carbamoyl, N-mono-C1-4 alkylcarbamoyl (e.g. N-methylcarbamoyl, N-ethylcarbamoyl, N-propylcarbamoyl, N-isopropylcarbamoyl, N-butylcarbamoyl, etc.), N,N-di-C1-4 alkylcarbamoyl (e.g. N,N-dimethylcarbamoyl, N,N-diethylcarbamoyl, N,N-dipropylcarbamoyl, N,N-dibutylcarbamoyl, etc.), 1-piperidylcarbonyl, etc.

The "(10) sulfamoyl which may have substituent(s)" as a substituent includes, for example, unsubstituted sulfamoyl, N-mono-C1-4 alkylsulfamoyl (e.g. N-methylsulfamoyl, N-ethylsulfamoyl, N-propylsulfamoyl, N-isopropylsulfamoyl, N-butylsulfamoyl, etc.), N,N-di-C1-4 alkylsulfamoyl (e.g. N,N-dimethylsulfamoyl, N,N-diethylsulfamoyl, N,N-dipropylsulfamoyl, N,N-dibutylsulfamoyl, etc.), etc.

The "(26) acyl" as a substituent includes, for example, alkylcarbonyl which may have substituent(s) (wherein the alkyl which may have substituent(s) has the same meaning as the above "(1) alkyl which may have substituent(s)"), alkenylcarbonyl which may have substituent(s) (wherein the alkenyl which may have substituent(s) has the same meaning as the above "(2) alkenyl which may have substituent(s)"), alkynylcarbonyl which may have substituent(s) (wherein the alkenyl which may have substituent(s) has the same meaning as the above "(3) alkynyl which may have substituent(s)"), carbocyclic ring-carbonyl (wherein the carbocyclic ring-carbonyl which may have substituent(s) has the same meaning as the above "(4) carbocyclic ring-carbonyl which may have substituent(s)"), heterocyclic ring-carbonyl (wherein the heterocyclic ring-carbonyl which may have substituent(s) has the same meaning as the above "(5) heterocyclic ring-carbonyl which may have substituent(s)"), etc.

In the present specification, the "cyclic group which may have substituent(s)" represented by ring B has the same meaning as the "cyclic group which may have substituent(s)" represented by the above ring A.

In the specification, the "acidic group which may be protected" represented by $R^1$ and $R^2$ means an acidic group which may be protected by protective group(s). The "acidic group" in the acidic group which may be protected by protective group(s) includes various kinds of Brönsted acid, e.g. carboxy (—COOH), hydroxamic acid (—CONHOH), acylcyanamide (—CONHCN), sulfo (—SO$_3$H), sulfonamide (—SO$_2$NH$_2$ or NR$^{100}$SO$_3$H, wherein $R^{100}$ is hydrogen or hydrocarbon which may have substituent(s) (it has the same meaning as the "hydrocarbon group which may have substituent(s)" in the protective group in the acidic group which may be protected by protective group(s) described hereafter)), acylsulfonamide (—CONHSO$_2$R$^{100}$ or SO$_2$NHCOR$^{100}$, wherein $R^{100}$ has the same meaning as hereinbefore), phosphono (—P(=O)(OH)$_2$), phosphinico (=P(=O)OH), amino(hydroxy)phosphoryl (—P(=O)(OH)(NH$_2$)), phenol (—C$_6$H$_4$OH) or heterocyclic ring residue which comprises a deprotonable hydrogen atom. The "Brönsted acid" represents a substance which gives a hydrogen ion to another substance. The "Heterocyclic ring residue which comprises a deprotonable hydrogen atom" includes, for example,

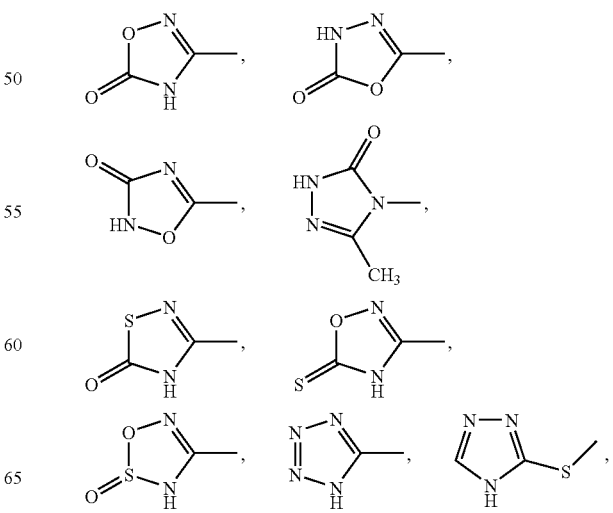

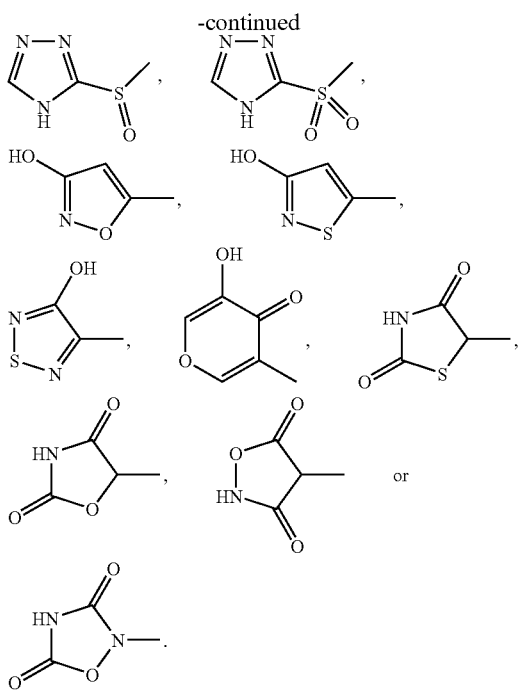

The "protective group" in the acidic group which may be protected by protective group(s) includes, for example, a hydrocarbon which may have substituent(s), C1-6 alkoxy, optionally protected amino, 1-piperidinyl or 4-morpholinyl, etc.

The "hydrocarbon" group in the "hydrocarbon which may have substituent(s)" includes, for example, C1-15 alkyl such as methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, etc.; C3-8 cycloalkyl such as cyclopropyl, cyclobutyl, cyclopentyl, cyclohexyl, etc.; C2-10 alkenyl such as vinyl, allyl, 2-methylallyl, 2-butenyl, 3-butenyl, 3-octenyl, etc.; C2-10 alkynyl such as ethynyl, 2-propynyl, 3-hexynyl, etc.; C3-10 cycloalkenyl such as cyclopropenyl, cyclopentenyl, cyclohexenyl, etc.; C6-14 aryl such as phenyl, naphthyl, etc.; C7-16 aralkyl such as benzyl, phenylethyl, etc.; (C3-8 cycloalkyl)-(C1-4 alkyl) such as cyclohexylmethyl, cyclohexylethyl, cyclohexylpropyl, 1-methyl-1-cyclohexylmethyl, etc.

As the substituent in the "hydrocarbon group which may have substituent(s)" includes, for example, (1) nitro, (2) hydroxy, (3) oxo, (4) thioxo, (5) cyano, (6) carbamoyl, (7) aminocarbonyl substituted by C1-8 hydrocarbon etc. such as N-butylaminocarbonyl, N-cyclohexylmethylaminocarbonyl, N-butyl-N-cyclohexylmethylaminocarbonyl, N-cyclohexylaminocarbonyl, phenylaminocarbonyl, (8) carboxy, (9) C1-4 alkoxycarbonyl such as methoxycarbonyl, ethoxycarbonyl, etc., (10) sulfo, (11) halogen such as fluorine, chlorine, bromine, iodine, etc., (12) C1-4 lower alkoxy such as methoxy, ethoxy, propoxy, isopropoxy, butoxy, isobutoxy, sec-butoxy, tert-butoxy, etc., (13) phenoxy, (14) halogenophenoxy such as o-, m- or p-chlorophenoxy, o-, m- or p-bromophenoxy, (15) C1-4 lower alkylthio such as methylthio, ethylthio, n-propylthio, isopropylthio, n-butylthio, tert-butylthio, etc., (16) phenylthio, (17) C1-4 lower alkylsulfinyl such as methylsulfinyl, ethylsulfinyl, etc., (18) C1-4 lower alkylsulfonyl such as methylsulfonyl, ethylsulfonyl, etc., (19) amino, (20) C1-6 lower acylamino such as acetylamino, propionylamino, etc., (21) primary or secondary amino substituted with hydrocarbon group such as methylamino, ethylamino, n-propylamino, isopropylamino, n-butylamino, dimethylamino, diethylamino, cyclohexylamino, 1-carbamoyl-2-cyclohexylethylamino, N-butyl-N-cyclohexylmethylamino, phenylamino (wherein this "hydrocarbon group" has the same meaning as the above "hydrocarbon group" and it may be substituted with oxo, amino, carbamoyl, etc.),

(22) C1-4 lower acyl such as formyl, acetyl, etc., (23) benzoyl, (24) a 5-6 membered heterocyclic ring comprising 1-4 hetero atom(s) selected from oxygen, sulfur, nitrogen, etc. besides carbon atom which may have 1-4 of substituent(s) selected from 1-4 of substituent(s) selected from (a) halogen such as bromine, chlorine, fluorine, etc., (b) hydrocarbon group such as methyl, ethyl, propyl, isopropyl, benzyl, cyclohexyl, cyclohexylmethyl, cyclohexylethyl which may be substituted with oxo, hydroxy, etc., wherein the "hydrocarbon group" as the same meaning as the above "hydrocarbon group", (c) halogenophenoxy such as o-, m- or p-chlorophenoxy, o-, m- or p-bromophenoxy, etc., and (d) oxo, etc., for example, 2- or 3-thienyl, 2- or 3-furyl, 3-, 4- or 5-pyrazolyl, 4-tetrahydropyranyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H- or 2H-tetrazolyl, 2-, 3- or 4-pyridyl, 2-, 4- or 5-pyrimidyl, 3- or 4-pyridazinyl, quinolyl, isoquinolyl, indolyl, etc., (25) C1-10 haloalkyl such as difluoromethyl, trifluoromethyl, trifluoroethyl, trichloroethyl, etc., (26) hydroxyimino, or (27) alkyloxyimino such as methyloxyimino, ethyloxyimino, etc.

The "hydrocarbon group which may have substituent(s)" may have 1-5 of substituent(s) selected from the above (1) to (27) and, when the "hydrocarbon group" is cycloalkyl, cycloalkenyl, aryl or aralkyl, it may have 1 to 4 lower alkyl(s) having 1-4 carbon atoms such as methyl, ethyl, propyl, isopropyl, butyl, etc. as substituent(s), and also when it has more than one substituents, the substituents may be the same or different.

The protective group of amino in the "amino which may be protected" as a "protective group" in the acidic group which may be protected by a protective group includes, for example, the "hydrocarbon which may have substituent(s)" as defined hereinbefore.

The "C1-6 alkoxy" as the protective group in the acidic group which may be protected by protective group(s) includes, for example, methoxy, ethoxy, propoxy, butoxy, pentyloxy, hexyloxy, etc.

The "acidic group which may be protected" represented by $R^1$ and $R^2$ includes, for example, ester group such as methoxycarbonyl, ethoxycarbonyl, etc., amide group such as carbamoyl, etc.

"Optionally protected acidic group" represented by $R^1$ and $R^2$ includes, e.g. ester groups such as methoxycarbonyl, ethoxycarbonyl etc., amide groups such as carbamoyl etc.

In the present specification, the "spacer consisting of 1-8 of atom in the main chain" represented by D and E means an interval of 1-8 of atom in succession. Here the "atom in the main chain" is counted so as to minimize the atom in the main chain. Here the "spacer consisting of 1-8 atom(s) in the main chain" includes, for example, a divalent radical consisting of 1-8 member(s) selected from —$CH_2$— which may have 1-2 substituent(s), —CH=CH— which may have 1-2 substituent(s), —C=C1-5 —NH— which may have a substituent, —CO—, —O—, —S—, —SO—, —$SO_2$—. Here the substituent of the methylene and the nitrogen atom has the same meaning as the "substituent" in the cyclic ring which may have a substituent represented by the above ring A, concretely, e.g. —$CR^{101}R^{102}$—, —$(CR^{101}R^{102})_2$—, —$(CR^{101}R^{102})_3$—, —$(CR^{101}R^{102})_4$—, —$CO(CR^{101}R^{102})_2$—, —CO(CR$^{101}$R$^{102}$)$_{3-}$, —CO(CR$^{101}$R$^{102}$)$_{4-}$, —NR$^{103}$-, —CO—, —O—, —S—, —NR$^{103}$CO—, —CONR$^{103}$-, —NR$^{103}$COCR$^{101}$R$^{102}$—, —CONR$^{103}$CR$^{101}$R$^{102}$—, —C(R$^{101}$)═C(R$^{102}$)—, —C≡C— (wherein R$^{101}$ to R$^{103}$ are, hydrogen atom or a substituent having the same meaning as the "substituent" in the cyclic group which may have substituent represented by the above ring A), etc.

In the present specification, the "substituent" represented by R$^3$ includes, for example, (1) alkyl which may have substituent(s), (2) alkenyl which may have substituent(s), (3) alkynyl which may have substituent(s), (4) carbocyclic ring which may have substituent(s), (5) heterocyclic ring which may have substituent(s), (6) hydroxy which may be protected, (7) mercapto which may be protected, (8) amino which may be protected, (9) carbamoyl which may have substituent(s), (10) sulfamoyl which may have substituent(s), (11) carboxy, (12) alkoxycarbonyl (e.g. C1-6 alkoxycarbonyl such as methoxycarbonyl, ethoxycarbonyl, tert-butoxycarbonyl, etc.), (13) sulfo, (14) sulfino, (15) phosphono, (16) nitro, (17) cyano, (18) amidino, (19) imino, (20) dihydroborono, (21) halogen (e.g. fluorine chlorine, bromine, iodine, etc.), (22) alkylsulfinyl (e.g. C1-4 alkylsulfinyl such as methylsulfinyl, ethylsulfinyl, etc.), (23) aromatic ring-sulfinyl (e.g. C6-10 aromatic ring-sulfinyl such as phenylsulfonyl), (24) alkylsulfonyl (e.g. C1-4 alkylsulfonyl such as methylsulfonyl, ethylsulfonyl, etc.), (25) aromatic ring-sulfonyl (e.g. C6-10 aromatic ring-sulfonyl such as phenylsulfonyl etc.), (26) acyl, (27) oxo, (28) thioxo, (29) (C1-6 alkoxyimino)methyl (e.g. (methoxyimino)methyl etc.), (30) formyl, (31)

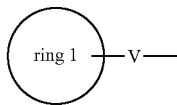

(wherein, ring 1 is a cyclic group which may have substituent(s), and V is a bond or a spacer consisting of 1-8 of atom in the main chain.), etc.

As the "substituent" represented by R$^3$, (1) alkyl which may have substituent(s), (2) alkenyl which may have substituent(s), (3) alkynyl which may have substituent(s), (4) carbocyclic ring which may have substituent(s), (5) heterocyclic ring which may have substituent(s), (6) hydroxy which may be protected, (7) mercapto which may be protected, (8) amino which may be protected, (9) carbamoyl which may have substituent(s), (10) sulfamoyl which may have substituent(s), and (26) acyl have the same meaning as those in the "substituent" in the cyclic group which may have substituent(s) represented by the above ring A.

In the present specification, the "cyclic group" in the cyclic group which may have substituent(s) represented by ring 1 has the same meaning as the "cyclic group" in the cyclic group which may have substituent(s) represented by ring A.

In the present specification, the "substituent" in the cyclic group which may have substituent(s) represented by ring 1 includes, for example, (1) alkyl which may have substituent(s), (2) alkenyl which may have substituent(s), (3) alkynyl which may have substituent(s), (4) carbocyclic ring which may have substituent(s), (5) heterocyclic ring which may have substituent(s), (6) hydroxy which may be protected, (7) mercapto which may be protected, (8) amino which may be protected, (9) carbamoyl which may have substituent(s), (10) sulfamoyl which may have substituent(s), (11) carboxy, (12) alkoxycarbonyl (e.g. C1-6 alkoxycarbonyl such as methoxycarbonyl, ethoxycarbonyl, tert-butoxycarbonyl, etc.), (13) sulfo, (14) sulfino, (15) phosphono, (16) nitro, (17) cyano, (18) amidino, (19) imino, (20) dihydroborono, (21) halogen atom (e.g. fluorine, chlorine, bromine, iodine, etc.), (22) alkylsulfinyl (e.g. C1-4 alkylsulfinyl such as methylsulfinyl, ethylsulfinyl, etc.), (23) aromatic ring-sulfinyl (e.g. C6-10 aromatic ring-sulfinyl such as phenylsulfinyl), (24) alkylsulfonyl (e.g. C1-4 alkylsulfonyl such as methylsulfonyl, ethylsulfonyl, etc.), (25) aromatic ring-sulfonyl (e.g. C6-10 aromatic ring-sulfonyl such as phenylsulfonyl), (26) acyl, (27) oxo, (28) thioxo, (29) (C1-6 alkoxyimino)methyl (e.g. (methoxyimino)methyl etc.), (30) formyl, (31)

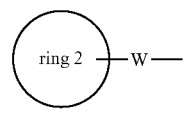

(wherein ring 2 is a cyclic group which may have substituent(s), W is a bond or a spacer consisting of 1-8 of atom in the main chain.), etc., and 1-5 of these substituents may be positioned where acceptable.

In the present specification, as the "substituent" in the cyclic group which may have substituent(s) represented by ring 1, (1) alkyl which may have substituent(s), (2) alkenyl which may have substituent(s), (3) alkynyl which may have substituent(s), (4) carbocyclic ring which may have substituent(s), (5) heterocyclic ring which may have substituent(s), (6) hydroxy which may be protected, (7) mercapto which may be protected, (8) amino which may be protected, (9) carbamoyl which may have substituent(s), (10) sulfamoyl which may have substituent(s), and (26) acyl have the same meaning as those of the "substituent" in the cyclic group which may have substituent(s) represented by the above ring A.

In the present specification, the "cyclic group" in the cyclic group which may have substituent(s) substituent(s) represented by ring 2, has the same meaning as the "cyclic group" in the above cyclic group optionally having substituent(s).

In the present specification, the "cyclic group" in the cyclic group which may have substituent(s) represented by ring 2 has the same meaning as the "cyclic group" in the above cyclic group which may have substituent(s) represented by ring A.

In the present specification, the "substituent" in the cyclic group which may have substituent(s) represented by ring 2 has the same meaning as the "substituent" in the above cyclic group which may have substituent(s) represented by ring A.

In the present specification, the "spacer consisting of 1-8 atom(s) in the main chain" represented by V has the same meaning as the "spacer consisting of 1-8 atom(s) in the main chain" represented by the above D and E.

In the present specification, the "spacer consisting of 1-8 atom(s) in the main chain" represented by W has the same meaning as the "spacer consisting of 1-8 atom(s) in the main chain" represented by the above D and E.

In the present specification, "optionally oxidized sulfur atom" represented by L means —S—, —S(O)—, and —SO$_2$.

The ring A is preferably a C3-15 mono-cyclic aromatic carbocyclic ring or partially or completely saturated one thereof, or a 3-15 membered mono-cyclic aromatic heterocyclic ring comprising 1-5 heteroatom(s) selected from oxygen, nitrogen and/or sulfur which may be partially or completely saturated, and more preferably a C3-8 mono-cyclic aromatic carbocyclic ring, or partially or completely saturated one thereof, and further preferably, cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, or benzene ring.

The ring B is preferably a C3-15 mono-cyclic aromatic carbocyclic ring, partially or completely saturated one thereof, or a 3-15 membered mono-cyclic aromatic heteroring comprising 1-5 hetero atom(s) selected from oxygen, nitrogen and/or sulfur which may be partially or completely saturated, more preferably, a 3-8 membered mono-cyclic aromatic heteroring comprising 1-3 hetero atom(s) selected from oxygen, nitrogen and/or sulfur which may be partially or completely saturated, furthermore preferably, pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepin, tetrahydrooxepin, perhydrooxepin, thiiran, thietane, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane or dithiane ring.

Y is preferably a carbon atom.

Z is preferably carbon atom.

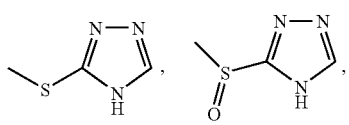
is preferably a double bond.

$R^1$ is preferably, —COOR$^A$ (wherein R$^A$ is hydrogen or C1-8 alkyl), —CONR$^B$SO$_2$R$^C$ (wherein R$^B$ is hydrogen or C1-8 alkyl, and R$^C$ is C1-8 hydrocarbon), —SO$_2$NR$^B$COR$^C$ (wherein all symbols have the same meaning as described hereinbefore), —SO$_2$NHCOR$^C$ (wherein R$^C$ has the same meaning as hereinbefore),

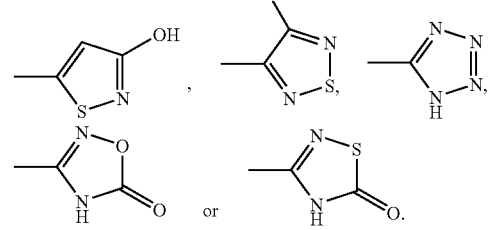

$R^2$ is preferably, —COOR$^A$, —CONR$^B$SO$_2$R$^C$, —SO$_2$NR$^B$COR$^C$ (wherein, R$^A$, R$^B$ and R$^C$ have the same meaning as hereinbefore),

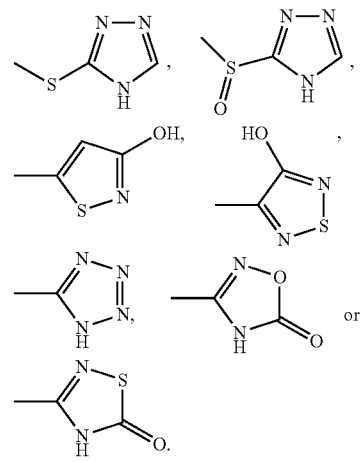

and more preferably —COOH, —CONHSO$_2$R$^C$, —SO$_2$NHCOR$^C$ (wherein all symbols have the same meaning as described hereinbefore),

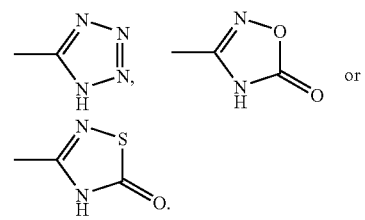

C1-8 alkyl represented by R$^A$ and R$^B$ includes, for example, methyl, ethyl, propyl, isopropyl, butyl, isobutyl, sec-butyl, tert-butyl, pentyl, hexyl, heptyl, octyl, etc.

C1-8 hydrocarbon represented by R$^C$ includes, for example, C1-8 alkyl such as methyl, ethyl, propyl, isopropyl, butyl, isobutyl, sec-butyl, tert-butyl, pentyl, hexyl, heptyl, octyl, etc., C3-8 cycloalkyl such as cyclopropyl, cyclobutyl, cyclopentyl, cyclohexyl, etc., C2-8 alkenyl such as vinyl, allyl, 2-methylallyl, 2-butenyl, 3-butenyl, 3-octenyl, etc., C2-8 alkynyl such as ethynyl, 2-propynyl, 3-hexynyl, etc., C3-8 cycloalkenyl such as cyclobutenyl, cyclopentenyl, cyclohexenyl, etc., C6-8 aryl such as phenyl etc., C7-8 aralkyl such as benzyl, phenylethyl, etc., (C3-8 cycloalkyl)-(C1-4 alkyl) such as cyclohexylmethyl, cyclohexylethyl, cyclopentylmethyl, 1-methyl-1-cyclopentylmethyl, etc.

D is preferably a bond or a spacer consisting of 1-6 of atom in the main chain, more preferably, a divalent radical consisting of a combination of 1-6 member(s) selected from a bond, —CH$_2$— which may have 1-2 substituent(s), —NH— which may have a substituent, —CO—, —O—, —S—, —SO— and —SO$_2$—, furthermore preferably, a bond, —CO—(CH$_2$)$_2$—, —CO—(CH$_2$)$_3$—, —CO—(CH$_2$)$_4$—, C1-6 alkylene (e.g. methylene, ethylene, propylene, butylene, pentylene, hexylene, etc.), particularly preferably —CO—(CH$_2$)$_2$—, —CO—(CH$_2$)$_3$—, —CO—(CH$_2$)$_4$—, C1-4 alkylene.

E is preferably a bond or a spacer consisting of 1-5 of atom in the main chain, more preferably, a divalent radical consisting of 1-5 members selected from a bond, —CH$_2$— which may have 1-2 substituent(s), —NH— which may have a substituent, —CO—, —O—, —S—, —SO— and —SO$_2$—, furthermore preferably, a bond, —CO—(CH$_2$)$_2$—, —CO—(CH$_2$)$_3$—, —CO—(CH$_2$)$_4$—, C1-4 alkylene (e.g. methylene, ethylene, propylene, butylene, etc.), particularly preferably a bond or C1-4 alkylene.

R$^3$ is preferably,

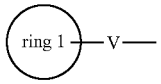

(wherein all symbols have the same meaning as described hereinbefore), more preferably,

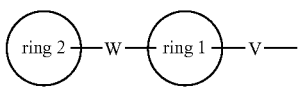

(wherein all symbols have the same meaning as described hereinbefore).

The substituent of ring 1 is preferably,

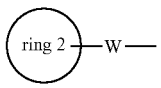

(wherein all symbols have the same meaning as described hereinbefore), hydroxy, halogen, nitro, amino, C5-10 carbocyclic ring, 5-10 membered heterocyclic ring, or C1-20 straight or branched alkyl, alkenyl or alkynyl in which optional 1-3 carbon atom(s) may be replaced by oxygen, sulfur, nitrogen, benzene ring, thiophene ring, C4-7 carbocyclic ring, carbonyl or carbonyloxy, and it may be further substituted with 1-3 halogen, hydroxy, carboxy, azido or nitro, and more preferably,

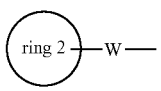

(wherein all symbols have the same meaning as described hereinbefore), or C1-10 straight or branched alkyl, alkenyl or alkynyl in which optional 1-2 of the carbon atom(s) may be replaced by oxygen, sulfur, benzene ring, thiophene ring or C4-7 carbocyclic ring, and it may be further substituted by 1-2 hydroxy, and more preferably,

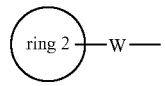

(wherein all symbols have the same meaning as described hereinbefore), or C1-10 straight or branched alkyl, alkenyl or alkynyl in which optional 1-2 of the carbon atom(s) may be replaced by oxygen, benzene ring, C5-7 carbocyclic ring, and most preferably,

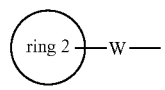

(wherein all symbols have the same meaning as described hereinbefore), n-butyl, n-pentyl, n-hexyl, n-heptyl, n-octyl, n-nonyl, n-butyloxy, n-pentyloxy, n-hexyloxy, n-heptyloxy, n-octyloxy, n-nonyloxy, (2E)-2-pentenyloxy, (2E)-2-hexenyloxy, (2E)-2-heptenyloxy, (2E)-2-octenyloxy, (2E)-2-nonenyloxy, 7-octenyloxy, 2-octynyloxy, (2E)-2,7-octadienyloxy, 2-phenylethoxy, 3-phenylpropoxy, 4-phenylbutoxy or 5-phenylpentyloxy.

The substituent of ring 2 is preferably, 1-3 group(s) arbitrary selected from nitro, amino, hydroxy, C1-8 alkyl, halogen, C1-8 alkoxy, C1-8 alkylthio, C1-4 alkyl substituted with 1-3 halogen atom(s), C1-4 alkoxy substituted with 1-3 halogen atom(s), C5-10 carbocyclic ring and 5-10 membered heterocyclic ring, and more preferably, 1-2 group(s) arbitrary selected from hydroxy, methyl, ethyl, propyl, n-butyl, n-pentyl, n-hexyl, fluorine, chlorine, bromine, methoxy, ethoxy, propoxy, butoxy, trifluoromethyl, methylthio, phenyl and pyridyl.

The ring 1 is preferably, C5-10 carbocyclic ring, or 5-membered mono- or bi-cyclic aromatic carbocyclic ring comprising 1-5 hetero atom(s) selected from oxygen, nitrogen and/or sulfur which may be partially or completely saturated, more preferably, a C5-10 mono-, or bi-cyclic aromatic carbocyclic ring, partially or completely saturated one thereof, a spiro bi-cyclic carbocyclic ring and a bridged bi-cyclic carbocyclic ring, more preferably, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane and noradamantane ring, particularly preferably benzene, naphthalene and pyridine ring.

The ring 2 is preferably a C5-10 carbocyclic ring or a 5-10 membered mono- or bi-cyclic aromatic heterocyclic ring comprising 1-3 heteroatom(s) selected from oxygen, nitrogen and/or sulfur, which may be partially or completely saturated, more preferably, a C5-10 mono- or bi-cyclic aromatic carbocyclic ring, partially or completely saturated one thereof, a spiro bi-cyclic carbocyclic ring and a bridged carbocyclic ring, further more preferably, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane or noradamantane ring, and specially preferably benzene, naphthalene, indan or pyridine ring.

V is preferably, a bond or a spacer consisting of 1-5 of atom in the main chain, more preferably, a bond, a divalent radical consisting of 1-6 member(s) selected from —$CH_2$— optionally having 1-2 substituent(s), —CH=CH— optionally having 1-2 substituent(s), —C≡C—, —NH— optionally having a substituent, —CO—, —O—, —S—, —SO— and $SO_2$—, moreover preferably, —$CONR^{103}$—, —$NR^{103}CO$—, —$CR^{101}R^{102}NR^{103}$—, —$NR^{103}CR^{101}R^{102}$—, —$NR^{103}COCR^{101}R^{102}$—, —$CONR^{103}CR^{101}R^{102}$—, —O—$CR^{101}R^{102}$—, —$CR^{101}R^{102}$—$NR^{103}$—, —$(CR^{101}R^{102})_2$—, —$CR^{101}$=$CR^{102}$—, —C≡C— (wherein, $R^{101}$ to $R^{103}$ are hydrogen or have the same meanings as the "substituent" in the cyclic group which may have substituent(s) represented by the above ring A), and specially preferably

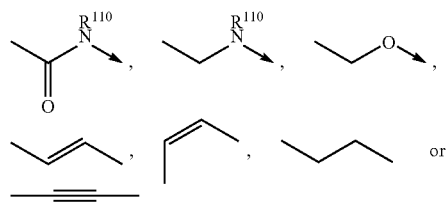

(wherein $R^{110}$ is hydrogen or C1-8 alkyl, and the arrow means that it attaches to the ring A).

W is preferably, a bond or a spacer consisting of 1-6 atom(s) in the main chain, more preferably, a divalent radical consisting of 1-6 member(s) selected from a bond, —$CH_2$— optionally having 1-2 substituent(s), —NH— optionally having a substituent, —CO—, —O—, —S—, —SO—, —$SO_2$-, further preferably, —O—$CH_2$—, —O—$(CH_2)_2$—, —O—$(CH_2)_3$—, —O—$(CH_2)_4$—, —O—$(CH_2)_5$—, —$CH_2$—O—, —$(CH_2)_2$—O—, —$(CH_2)_3$—O—, —$(CH_2)_4$—O—, —$(CH_2)_5$—O—, —O—$(CH_2)_3$—O—, —O—$(CH_2)_4$—O—, —O—$(CH_2)_5$—O—, C1-6 alkylene.

is preferably, 3,4-dihydro-2H-1,4-benzoxazine, chroman, 2,3-dihydro-1,4-benzoxathiin, 2,3-dihydro-1,4-benzodioxin, 3,4-dihydro-2H-1,4-benzothiazine, thiochroman, 2,3-dihydro-1,4-benzodithiine, 1,2,3,4-tetrahydroquinoxaline, 1,2,3,4-tetrahydroquinoline, 1,2,3,4-tetrahydronaphthalene, 2H-chromene, 2H-thiochromene, 1,2-dihydroquinoline, 1,2-dihydronaphthalene, 4H-1,4-benzoxazine, 4H-chromene, 1,4-benzoxathiln, 1,4-benzodioxin, 4H-1,4-benzothiazine, 4H-thiochromene, 1,4-benzodithiln, 1,5-naphthyridine, 1,8-naphthyridine, 2,7-naphthyridine, 1,4-dihydronaphthalene, naphthalene, quinoline, isoquinoline, quinoxaline, 1,2,3,4-tetrahydroisoquinoline, 3,4-dihydro-1H-isochromene, 3,4-dihydro-1H-isothlochromene, cinnoline, phthalazine, 4H-chromen-4-one, 4(1H)-quinolinone, 4H-thlochromen-4-one, 3,4-dihydro-2(1H)-quinolinone, 2(1H)-quinolinone, 2H-chromen-2-one, indan, indoline, 2,3-dihydro-1-benzofuran, 1H-indole, 1-benzofuran, 1-benzothiophene, 1H-indazole, 1,2-benzisoxazole, 1,2-benzisothiazole, 1H-benzimidazole, 1,3-benzoxazole or 1,3-benzothiazole ring and more preferably, 3,4-dihydro-2H-1,4-benzoxazine, chroman, 2,3-dihydro-1,4-benzoxathiin, 2,3-dihydro-1,4-benzodioxin, 3,4-dihydro-2H-1,4-benzothiazine, thiochroman, 2,3-dihydro-1,4-benzodithiin, 1,2,3,4-tetrahydroquinoxaline, 1,2,3,4-tetrahydroquinoline, 1,2,3,4-tetrahydronaphthalene, 2H-chromene, 2H-thiochromene, 1,2-dihydroquinoline, 1,2-dihydronaphthalene, 4H-1,4-benzoxazine, 4H-chromene, 1,4-benzoxathiin, 1,4-benzodioxin, 4H-1,4-benzothiazine, 4H-thiochromene, 1,4-benzodithiin, 1,4-dihydronaphthalene, naphthalene, quinoline, isoquinoline, quinoxaline, 1,2,3,4-tetrahydroisoquinoline, 3,4-dihydro-1H-isochromene, 3,4-dihydro-1H-isothlochromene, cinnoline, phthalazine, 4H-chromen-4-one, 4(1H)-quinolinone, 4H-thiochromen-4-one, 3,4-dihydro-2(1H)-quinolinone, 2(1H)-quinolinone, 2H-chromen-2-one ring or 1H-indole ring, more preferably, 3,4-dihydro-2H-1,4-benzoxazine, 3,4-dihydro-2H-1,4-benzothiazine, 1,2,3,4-tetrahydroquinoxaline, 1,2,3,4-tetrahydroquinoline, 1,2-dihydroquinoline, 4H-1,4-benzoxazine, 4H-1,4-benzothiazine, quinoline, isoquinoline, quinoxaline, 1,2,3,4-tetrahydroisoquinoline, cinnoline, 4(1H)-quinolinone, 3,4-dihydro-2(1H)-quinolinone, 2(1H)-quinolinone, indoline or 1H-indole ring, specially preferably, 3,4-dihydro-2H-1,4-benzoxazine, 1,2,3,4-tetrahydroquinoline, 1,2-dihydroquinoline, 1H-indole ring.

Among the compounds of formula (I), preferable compounds are, the compound of formula (I-a)

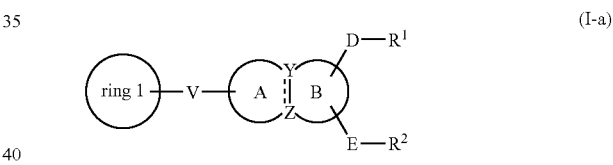

(wherein all symbols have the same meaning as described hereinbefore), more preferably, the compound of formula (I-b)

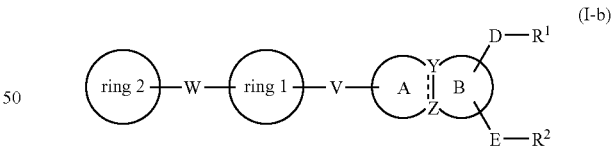

(wherein all symbols have the same meaning as described hereinbefore) and further preferably the compound of formula (I-X)

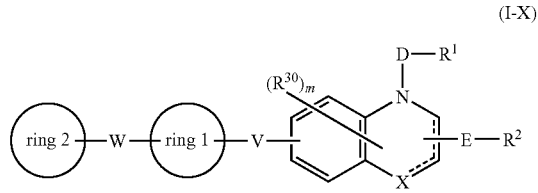

(wherein all symbols have the same meaning as described hereinbefore). In the formula (I-X), $R^{30}$ is hydrogen or a substituent having the same meaning as the "substituent" in the "cyclic group optionally having substituent(s)" shown by the ring A. $R^{30}$ is preferably hydrogen, hydroxy, C1-4 alkyl optionally substituted with 1-3 halogen, C1-4 alkoxy, amino, nitro or halogen.

In the present invention, preferable compounds of formula (I) include, for example, (1) 4-(3-carboxypropyl)-8-((4-(4-phenylbutoxy)benzoyl)amino)-3,4-dihydro-2H-1,4-benzoxazin-2-carboxylic acid, (2) 4-(3-carboxypropyl)-8-({(2E)-3-[4-(4-phenylbutyl)phenyl]-2-propenoyl}amino)-3,4-dihydro-2H-1,4-benzoxazin-2-carboxylic acid, (3) 4-[8-{[4-(4-phenylbutoxy)benzoyl]amino}-2-(1H-tetrazol-5-yl)-2,3-dihydro-4H-1,4-benzoxazin-4-yl]butanoic acid, (4) 4-(3-carboxypropyl)-8-{[4-(4-phenylbutoxy)benzyl]amino}-3,4-dihydro-2H-1,4-benzoxazine-2-carboxylic acid, (5) 4-(3-carboxypropyl)-8-{(E)-2-[4-(4-phenylbutoxy)phenyl]vinyl}-3,4-dihydro-2H-1,4-benzoxazine-2-carboxylic acid, (6) 4-(3-carboxypropyl)-8-{2-[4-(4-phenylbutoxy)phenyl]ethyl}-3,4-dihydro-2H-1,4-benzoxazine-2-carboxylic acid, (7) (2S)-4-(3-carboxypropyl)-8-{[4-(4-phenylbutoxy)benzoyl]amino}-3,4-dihydro-2H-1,4-benzoxazine-2-carboxylic acid, (8) (2R)-4-(3-carboxypropyl)-8-{[4-(4-phenylbutoxy)benzoyl]amino}-3,4-dihydro-2H-1,4-benzoxazine-2-carboxylic acid, (9) 4-(3-carboxypropyl)-8-({4-[2-(2,3-dihydro-1H-inden-2-yl)ethoxy]benzoyl}amino)-3,4-dihydro-2H-1,4-benzoxazine-2-carboxylic acid,

(10) 4-(3-carboxypropyl)-8-({4-[(5-phenylpentyl)oxy]benzoyl}amino)-3,4-dihydro-2H-1,4-benzoxazine-2-carboxylic acid,

(11) 4-(3-carboxypropyl)-8-({4-[(7-phenylheptyl)oxy]benzoyl}amino)-3,4-dihydro-2H-1,4-benzoxazine-2-carboxylic acid,

(12) 4-(3-carboxypropyl)-8-({4-[(4-methylpentyl)oxy]benzoyl}amino)-3,4-dihydro-2H-1,4-benzoxazine-2-carboxylic acid,

(13) 4-(3-carboxypropyl)-8-{[4-(4-phenoxybutoxy)benzoyl]amino}-3,4-dihydro-2H-1,4-benzoxazine-2-carboxylic acid,

(14) 4-(3-carboxypropyl)-8-({4-[3-(2,3-dihydro-1H-inden-2-yl)propoxy]benzoyl}amino)-3,4-dihydro-2H-1,4-benzoxazine-2-carboxylic acid,

(15) 4-(3-carboxypropyl)-8-({4-[4-(4-fluorophenyl)butoxy]benzoyl}amino)-3,4-dihydro-2H-1,4-benzoxazine-2-carboxylic acid,

(16) 4-(3-carboxypropyl)-8-({4-[4-(2-methylphenoxy)butoxy]benzoyl}amino)-3,4-dihydro-2H-1,4-benzoxazine-2-carboxylic acid,

(17) 4-(3-carboxypropyl)-8-({4-[4-(2-fluorophenoxy)butoxy]benzoyl}amino)-3,4-dihydro-2H-1,4-benzoxazine-2-carboxylic acid,

(18) 4-(3-carboxypropyl)-8-({4-[4-(2-chlorophenoxy)butoxy]benzoyl}amino)-3,4-dihydro-2H-1,4-benzoxazine-2-carboxylic acid,

(19) 4-(3-carboxypropyl)-8-[(4-{4-[2-(trifluoromethyl)phenoxy]butoxy}benzoyl)amino]-3,4-dihydro-2H-1,4-benzoxazine-2-carboxylic acid,

(20) 4-(3-carboxypropyl)-8-({4-[3-(2-methylphenoxy)propoxy]benzoyl}amino)-3,4-dihydro-2H-1,4-benzoxazine-2-carboxylic acid,

(21) 4-(2-({[(4-methylphenyl)sulfonyl]amino}carbonyl)-8-{[4-(4-phenylbutoxy)benzoyl]amino}-2,3-dihydro-4H-1,4-benzoxazin-4-yl)butanoic acid,

(22) 4-(2-{[(methylsulfonyl)amino]carbonyl}-8-{[4-(4-phenylbutoxy)benzoyl]amino}-2,3-dihydro-4H-1,4-benzoxazin-4-yl)butanoic acid,

(23) 4-(2-{[(benzylsulfonyl)amino]carbonyl}-8-{[4-(4-phenylbutoxy)benzoyl]amino}-2,3-dihydro-4H-1,4-benzoxazin-4-yl)butanoic acid,

(24) 4-(3-carboxypropyl)-8-{(E)-2-[4-(4-phenoxybutoxy)phenyl]vinyl}-3,4-dihydro-2H-1,4-benzoxazine-2-carboxylic acid,

(25) 4-(3-carboxypropyl)-8-{(E)-2-[4-(2,3-dihydro-1H-inden-2-ylmethoxy)phenyl]vinyl}-3,4-dihydro-2H-1,4-benzoxazine-2-carboxylic acid,

(26) 4-(3-carboxypropyl)-8-((E)-2-{4-[3-(2,3-dihydro-1H-inden-2-yl)propoxy]phenyl}vinyl)-3,4-dihydro-2H-1,4-benzoxazine-2-carboxylic acid,

(27) 4-(3-carboxypropyl)-8-((E)-2-{4-[(5-phenoxypentyl)oxy]phenyl}vinyl)-3,4-dihydro-2H-1,4-benzoxazine-2-carboxylic acid,

(28) 4-(3-carboxypropyl)-8-((E)-2-{4-[4-(4-methoxyphenoxy)butoxy]phenyl}vinyl)-3,4-dihydro-2H-1,4-benzoxazine-2-carboxylic acid,

(29) 4-(3-carboxypropyl)-8-((E)-2-{4-[3-(4-fluorophenoxy)propoxy]phenyl}vinyl)-3,4-dihydro-2H-1,4-benzoxazine-2-carboxylic acid,

(30) 4-(3-carboxypropyl)-8-{(E)-2-[4-(3-phenoxypropoxy)phenyl]vinyl}-3,4-dihydro-2H-1,4-benzoxazine-2-carboxylic acid,

(31) 4-(3-carboxypropyl)-8-((E)-2-{4-[3-(2-chlorophenoxy)propoxy]phenyl}vinyl)-3,4-dihydro-2H-1,4-benzoxazine-2-carboxylic acid,

(32) 4-(3-carboxypropyl)-8-{2-[4-(4-phenoxybutoxy)phenyl]ethyl}-3,4-dihydro-2H-1,4-benzoxazine-2-carboxylic acid,

(33) 4-[8-{2-[4-(4-phenylbutoxy)phenyl]ethyl}-2-(1H-tetrazol-5-yl)-2,3-dihydro-4H-1,4-benzoxazin-4-yl]butanoic acid,

(34) 4-[8-{(E)-2-[4-(4-phenylbutoxy)phenyl]vinyl}-2-(1H-tetrazol-5-yl)-2,3-dihydro-4H-1,4-benzoxazin-4-yl]butanoic acid,

(35) 4-(2-(5-oxo-4,5-dihydro-1,2,4-thiadiazol-3-yl)-8-{[4-(4-phenylbutoxy)benzoyl]amino}-2,3-dihydro-4H-1,4-benzoxazin-4-yl)butanoic acid,

(36) 4-(2-(5-oxo-4,5-dihydro-1,2,4-oxadiazol-3-yl)-8-{(E)-2-[4-(4-phenylbutoxy)phenyl]vinyl}-2,3-dihydro-4H-1,4-benzoxazin-4-yl)butanoic acid,

(37) 4-oxo-4-(8-((4-(4-phenylbutoxy)benzoyl)amino)-2-(1H-tetrazol-5-yl)-2,3-dihydro-4H-1,4-benzoxazin-4-yl)butanoic acid, and

(38) 4-(3-carboxypropyl)-8-((4-(4-phenylbutoxy)benzyl)oxy)-3,4-dihydro-2H-1,4-benzoxazine-2-carboxylic acid.

Additionally, preferable compounds in the present invention are the compounds described in tables 1 to 57 and the compounds shown in the Examples, and salts thereof, solvates thereof, or prodrugs thereof.

In the tables, $R^4$ is alkyl optionally having substituent(s), alkenyl optionally having substituent(s), alkynyl optionally having substituent(s), or

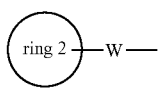
wherein all symbols have the same meaning as described hereinbefore.
TABLE 1
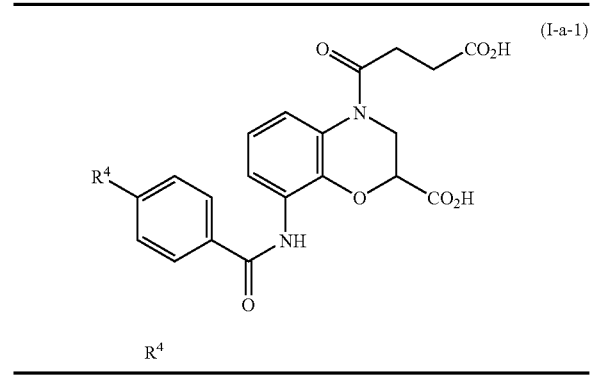
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
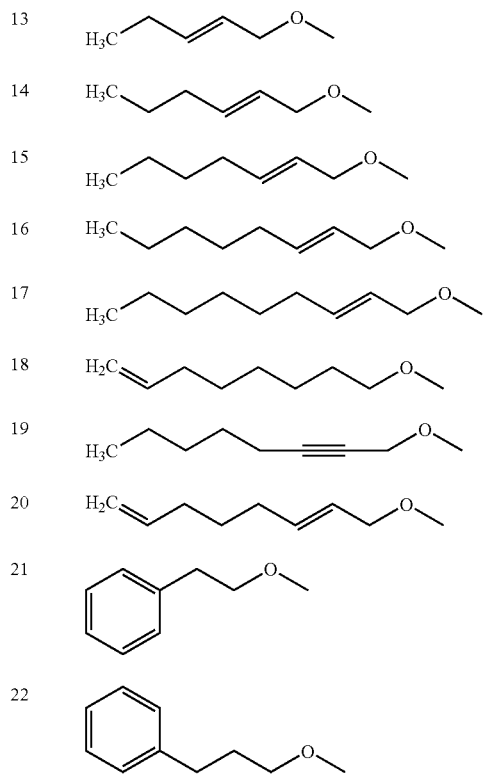
TABLE 1-continued
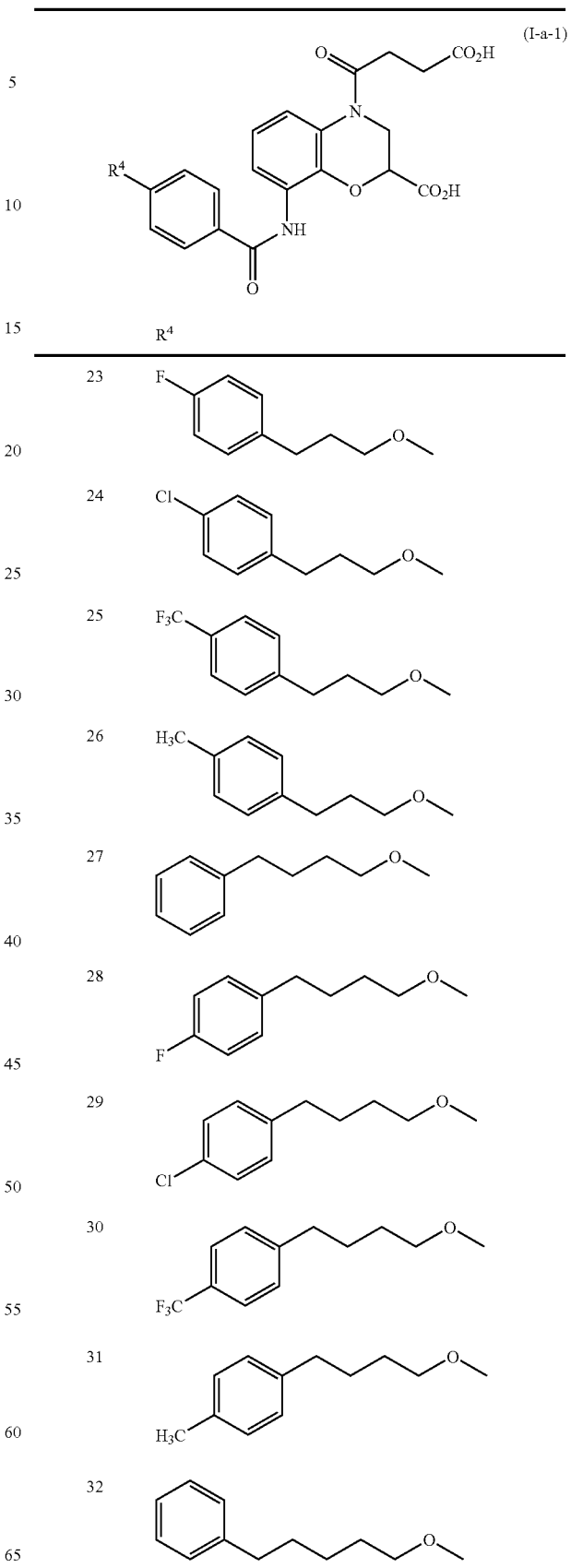

TABLE 1-continued
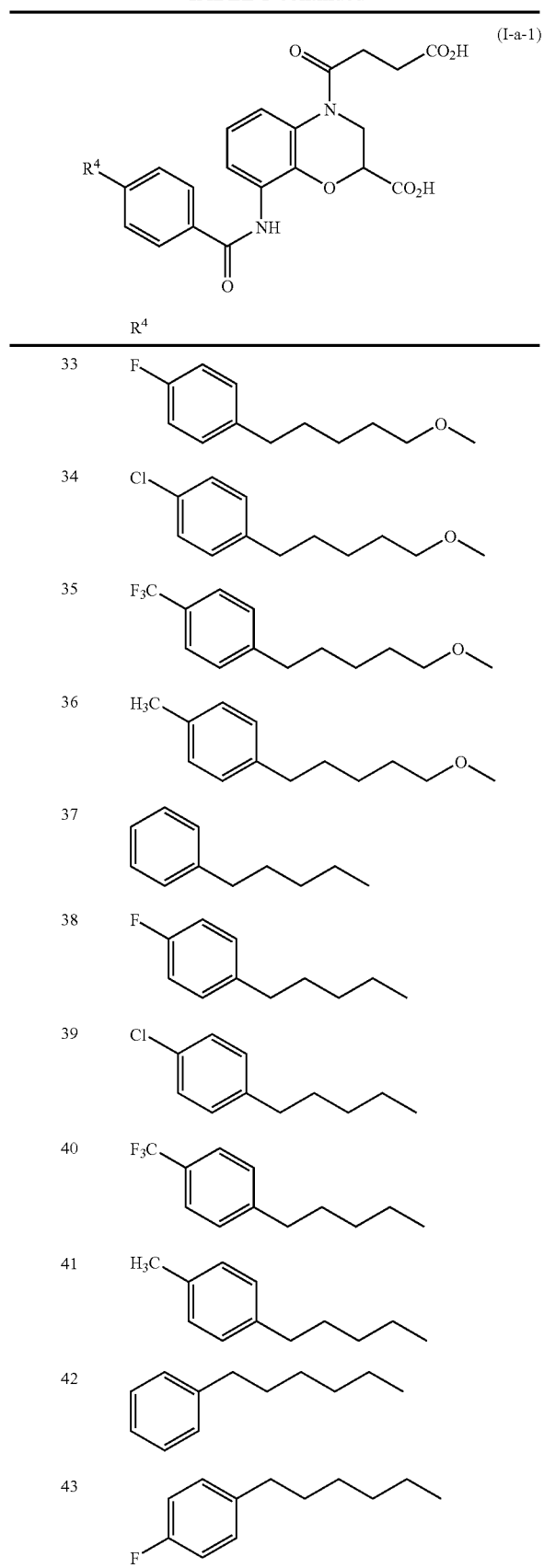
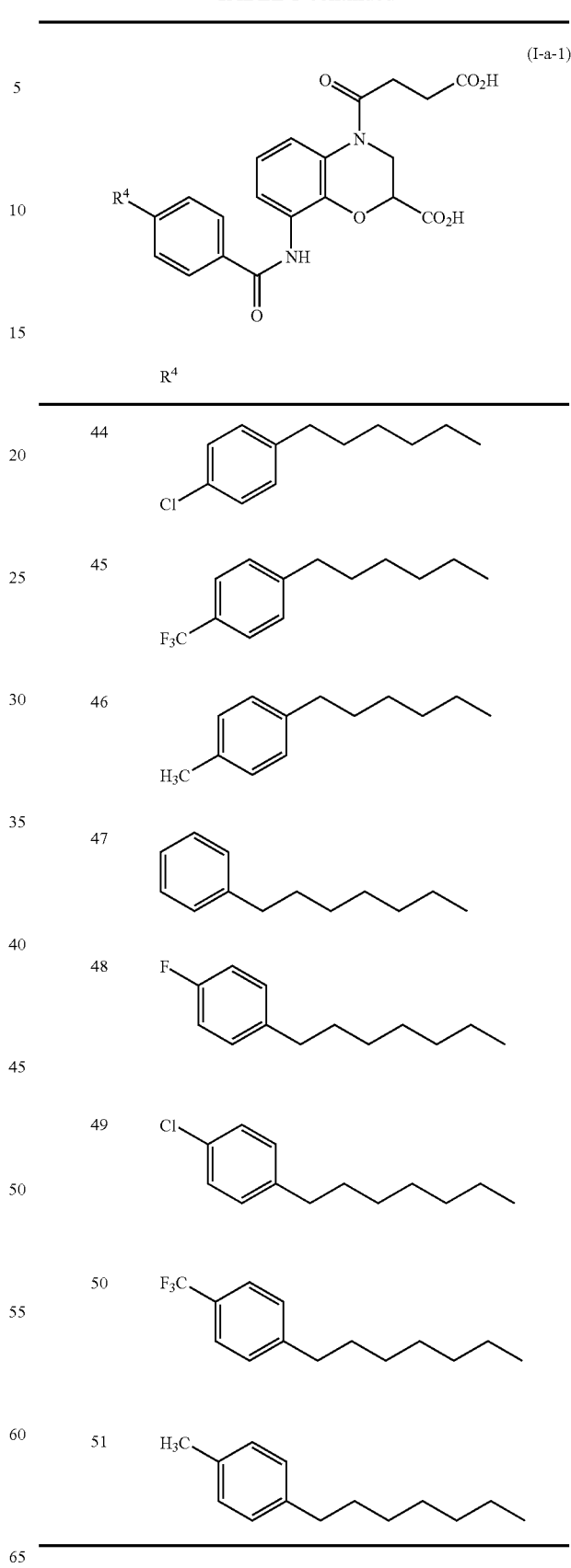

TABLE 2

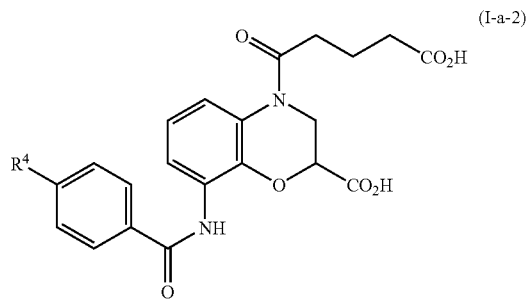

(I-a-2)

| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | H₃C–CH=CH–CH₂–O–CH₃ |
| 14 | H₃C–CH₂–CH=CH–CH₂–O–CH₃ |
| 15 | H₃C–(CH₂)₂–CH=CH–CH₂–O–CH₃ |
| 16 | H₃C–(CH₂)₃–CH=CH–CH₂–O–CH₃ |
| 17 | H₃C–(CH₂)₄–CH=CH–CH₂–O–CH₃ |
| 18 | H₂C=CH–(CH₂)₄–O–CH₃ |
| 19 | H₃C–(CH₂)₃–C≡C–CH₂–O–CH₃ |
| 20 | H₂C=CH–(CH₂)₂–CH=CH–CH₂–O–CH₃ |
| 21 | Ph–CH₂–CH₂–O–CH₃ |
| 22 | Ph–(CH₂)₃–O–CH₃ |
| 23 | 4-F-C₆H₄–(CH₂)₃–O–CH₃ |
| 24 | 4-Cl-C₆H₄–(CH₂)₃–O–CH₃ |

TABLE 2-continued

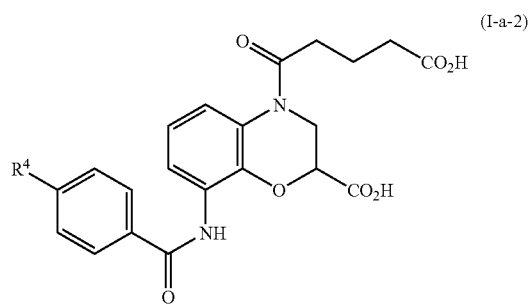

(I-a-2)

| | R⁴ |
|---|---|
| 25 | 4-F₃C-C₆H₄–(CH₂)₃–O–CH₃ |
| 26 | 4-H₃C-C₆H₄–(CH₂)₃–O–CH₃ |
| 27 | Ph–(CH₂)₄–O–CH₃ |
| 28 | 4-F-C₆H₄–(CH₂)₄–O–CH₃ |
| 29 | 4-Cl-C₆H₄–(CH₂)₄–O–CH₃ |
| 30 | 4-F₃C-C₆H₄–(CH₂)₄–O–CH₃ |
| 31 | 4-H₃C-C₆H₄–(CH₂)₄–O–CH₃ |
| 32 | Ph–(CH₂)₅–O–CH₃ |
| 33 | 4-F-C₆H₄–(CH₂)₅–O–CH₃ |
| 34 | 4-Cl-C₆H₄–(CH₂)₅–O–CH₃ |

TABLE 2-continued
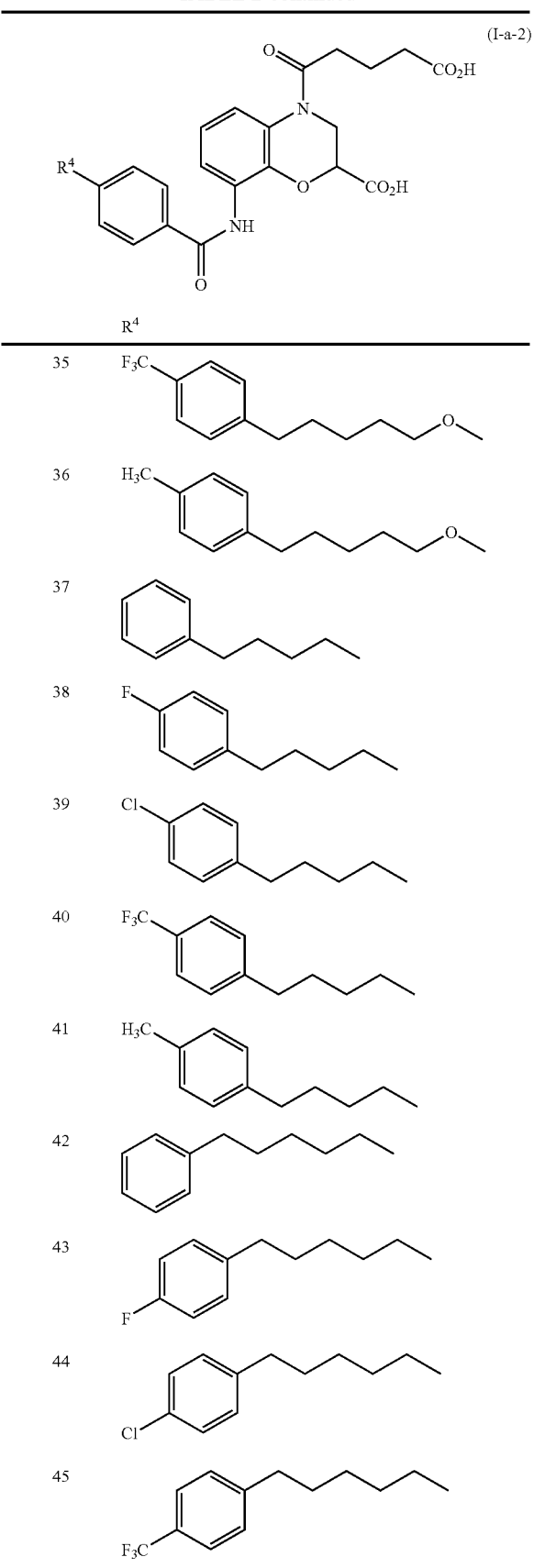
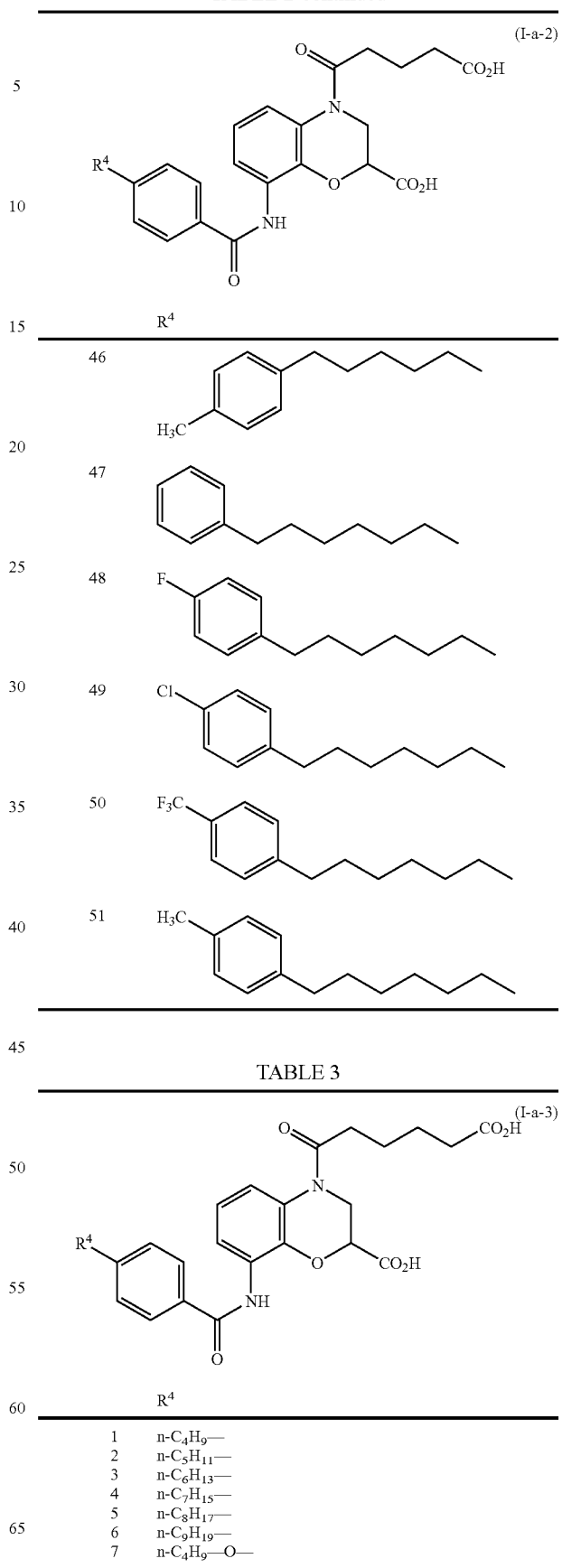
TABLE 3
(I-a-3)
| | $R^4$ |
|---|---|
| 1 | n-$C_4H_9$— |
| 2 | n-$C_5H_{11}$— |
| 3 | n-$C_6H_{13}$— |
| 4 | n-$C_7H_{15}$— |
| 5 | n-$C_8H_{17}$— |
| 6 | n-$C_9H_{19}$— |
| 7 | n-$C_4H_9$—O— |

TABLE 3-continued

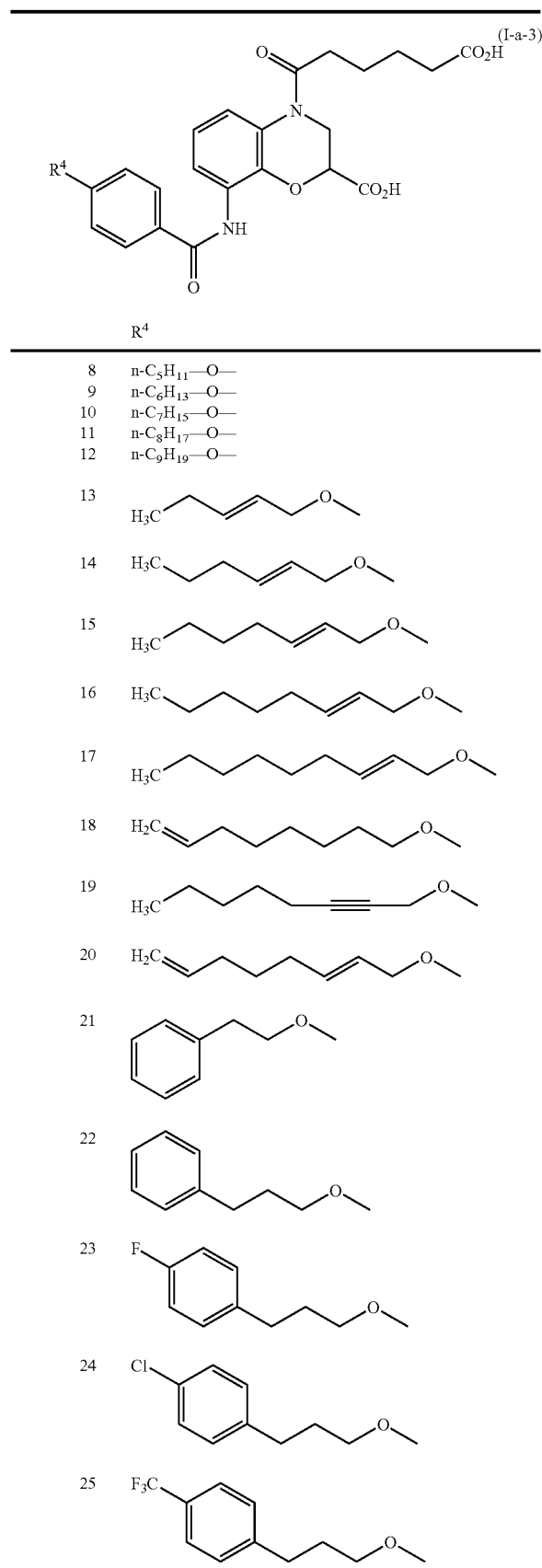
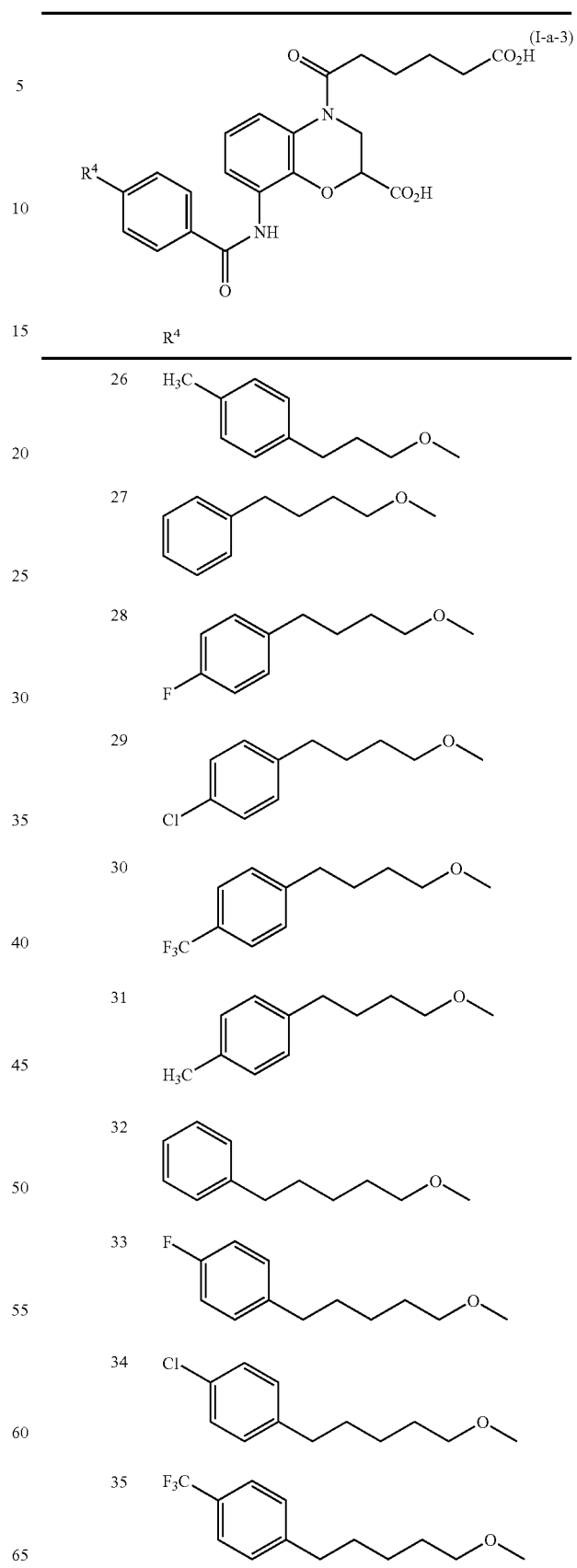

| | R⁴ |
|---|---|
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | H₃C-CH=CH-CH₂-O-CH₃ |
| 14 | H₃C-(CH₂)-CH=CH-CH₂-O-CH₃ |
| 15 | H₃C-(CH₂)₂-CH=CH-CH₂-O-CH₃ |
| 16 | H₃C-(CH₂)₃-CH=CH-CH₂-O-CH₃ |
| 17 | H₃C-(CH₂)₄-CH=CH-CH₂-O-CH₃ |
| 18 | H₂C=CH-(CH₂)₅-O-CH₃ |
| 19 | H₃C-(CH₂)₃-C≡C-CH₂-O-CH₃ |
| 20 | H₂C=CH-(CH₂)₃-CH=CH-CH₂-O-CH₃ |
| 21 | Ph-CH₂-CH₂-O-CH₃ |
| 22 | Ph-(CH₂)₃-O-CH₃ |
| 23 | 4-F-C₆H₄-(CH₂)₃-O-CH₃ |
| 24 | 4-Cl-C₆H₄-(CH₂)₃-O-CH₃ |
| 25 | 4-F₃C-C₆H₄-(CH₂)₃-O-CH₃ |
| 26 | 4-H₃C-C₆H₄-(CH₂)₃-O-CH₃ |
| 27 | Ph-(CH₂)₄-O-CH₃ |
| 28 | 4-F-C₆H₄-(CH₂)₄-O-CH₃ |
| 29 | 4-Cl-C₆H₄-(CH₂)₄-O-CH₃ |
| 30 | 4-F₃C-C₆H₄-(CH₂)₄-O-CH₃ |
| 31 | 4-H₃C-C₆H₄-(CH₂)₄-O-CH₃ |
| 32 | Ph-(CH₂)₅-O-CH₃ |
| 33 | 4-F-C₆H₄-(CH₂)₅-O-CH₃ |
| 34 | 4-Cl-C₆H₄-(CH₂)₅-O-CH₃ |
| 35 | 4-F₃C-C₆H₄-(CH₂)₅-O-CH₃ |

TABLE 3-continued
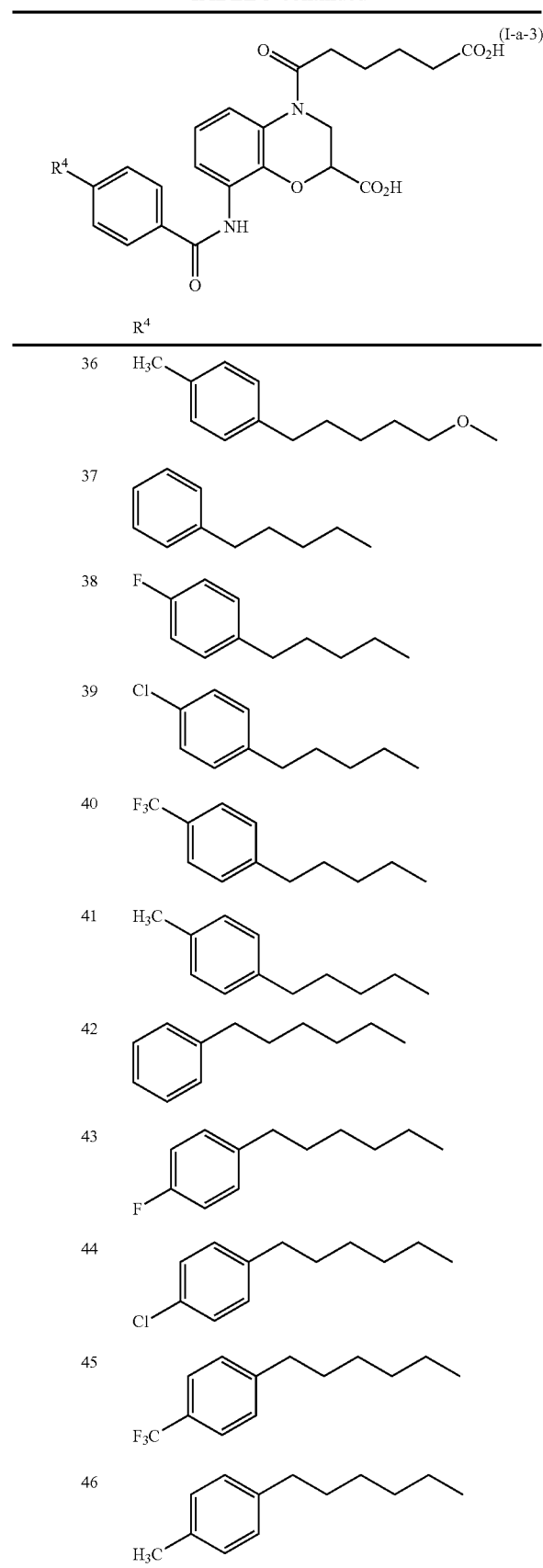
TABLE 3-continued
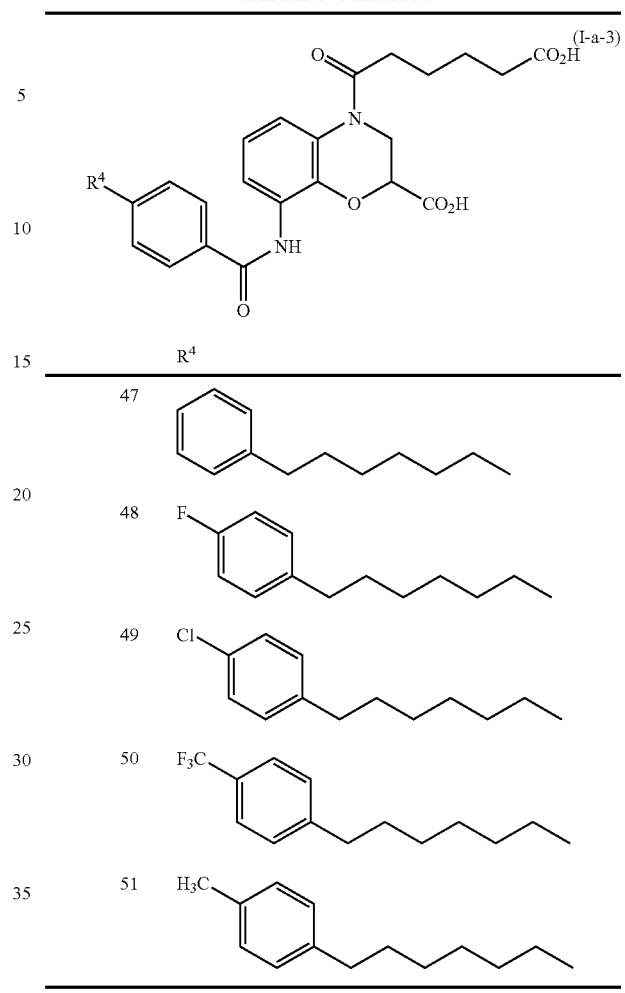
TABLE 4
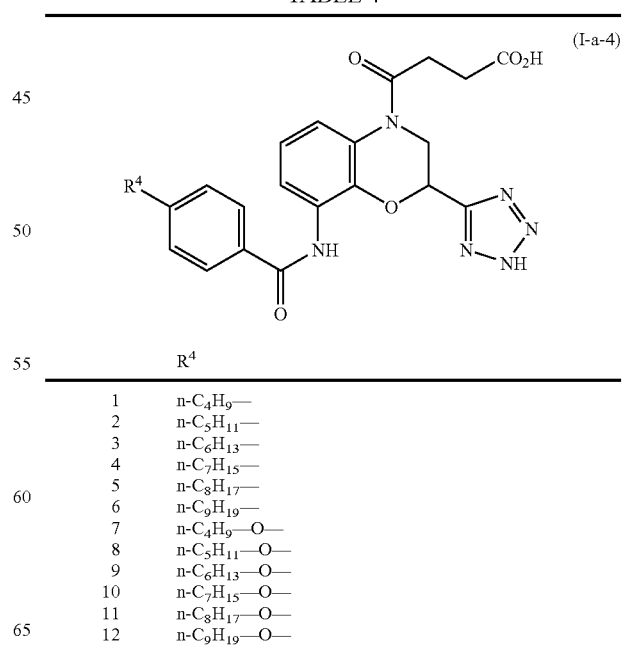
| | $R^4$ |
|---|---|
| 1 | n-$C_4H_9$— |
| 2 | n-$C_5H_{11}$— |
| 3 | n-$C_6H_{13}$— |
| 4 | n-$C_7H_{15}$— |
| 5 | n-$C_8H_{17}$— |
| 6 | n-$C_9H_{19}$— |
| 7 | n-$C_4H_9$—O— |
| 8 | n-$C_5H_{11}$—O— |
| 9 | n-$C_6H_{13}$—O— |
| 10 | n-$C_7H_{15}$—O— |
| 11 | n-$C_8H_{17}$—O— |
| 12 | n-$C_9H_{19}$—O— |

TABLE 4-continued (I-a-4)

| | R⁴ |
|---|---|
| 13 | H₃C–CH=CH–CH₂–O–CH₃ |
| 14 | H₃C–CH₂–CH=CH–CH₂–O–CH₃ |
| 15 | H₃C–(CH₂)₂–CH=CH–CH₂–O–CH₃ |
| 16 | H₃C–(CH₂)₃–CH=CH–CH₂–O–CH₃ |
| 17 | H₃C–(CH₂)₄–CH=CH–CH₂–O–CH₃ |
| 18 | H₂C=CH–(CH₂)₄–O–CH₃ |
| 19 | H₃C–(CH₂)₃–C≡C–CH₂–O–CH₃ |
| 20 | H₂C=CH–(CH₂)₃–CH=CH–CH₂–O–CH₃ |
| 21 | Ph–CH₂–CH₂–O–CH₃ |
| 22 | Ph–(CH₂)₃–O–CH₃ |
| 23 | 4-F–C₆H₄–(CH₂)₃–O–CH₃ |
| 24 | 4-Cl–C₆H₄–(CH₂)₃–O–CH₃ |
| 25 | 4-F₃C–C₆H₄–(CH₂)₃–O–CH₃ |
| 26 | 4-H₃C–C₆H₄–(CH₂)₃–O–CH₃ |

TABLE 4-continued (I-a-4)

| | R⁴ |
|---|---|
| 27 | Ph–(CH₂)₄–O–CH₃ |
| 28 | 4-F–C₆H₄–(CH₂)₄–O–CH₃ |
| 29 | 4-Cl–C₆H₄–(CH₂)₄–O–CH₃ |
| 30 | 4-F₃C–C₆H₄–(CH₂)₄–O–CH₃ |
| 31 | 4-H₃C–C₆H₄–(CH₂)₄–O–CH₃ |
| 32 | Ph–(CH₂)₅–O–CH₃ |
| 33 | 4-F–C₆H₄–(CH₂)₅–O–CH₃ |
| 34 | 4-Cl–C₆H₄–(CH₂)₅–O–CH₃ |
| 35 | 4-F₃C–C₆H₄–(CH₂)₅–O–CH₃ |
| 36 | 4-H₃C–C₆H₄–(CH₂)₅–O–CH₃ |
| 37 | Ph–(CH₂)₄–CH₃ |

TABLE 4-continued
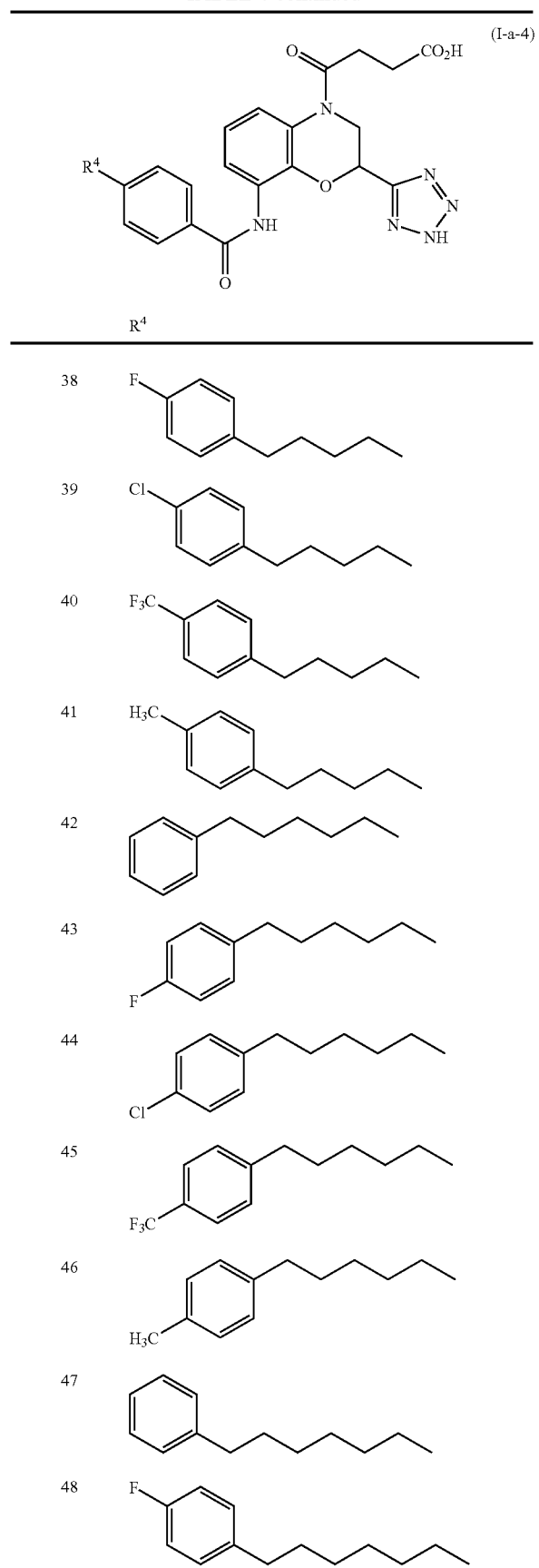
| | R⁴ |
|---|---|
| 38 | 4-F-C₆H₄-(CH₂)₄- |
| 39 | 4-Cl-C₆H₄-(CH₂)₄- |
| 40 | 4-F₃C-C₆H₄-(CH₂)₄- |
| 41 | 4-H₃C-C₆H₄-(CH₂)₄- |
| 42 | C₆H₅-(CH₂)₅- |
| 43 | 4-F-C₆H₄-(CH₂)₅- |
| 44 | 4-Cl-C₆H₄-(CH₂)₅- |
| 45 | 4-F₃C-C₆H₄-(CH₂)₅- |
| 46 | 4-H₃C-C₆H₄-(CH₂)₅- |
| 47 | C₆H₅-(CH₂)₆- |
| 48 | 4-F-C₆H₄-(CH₂)₆- |
TABLE 4-continued
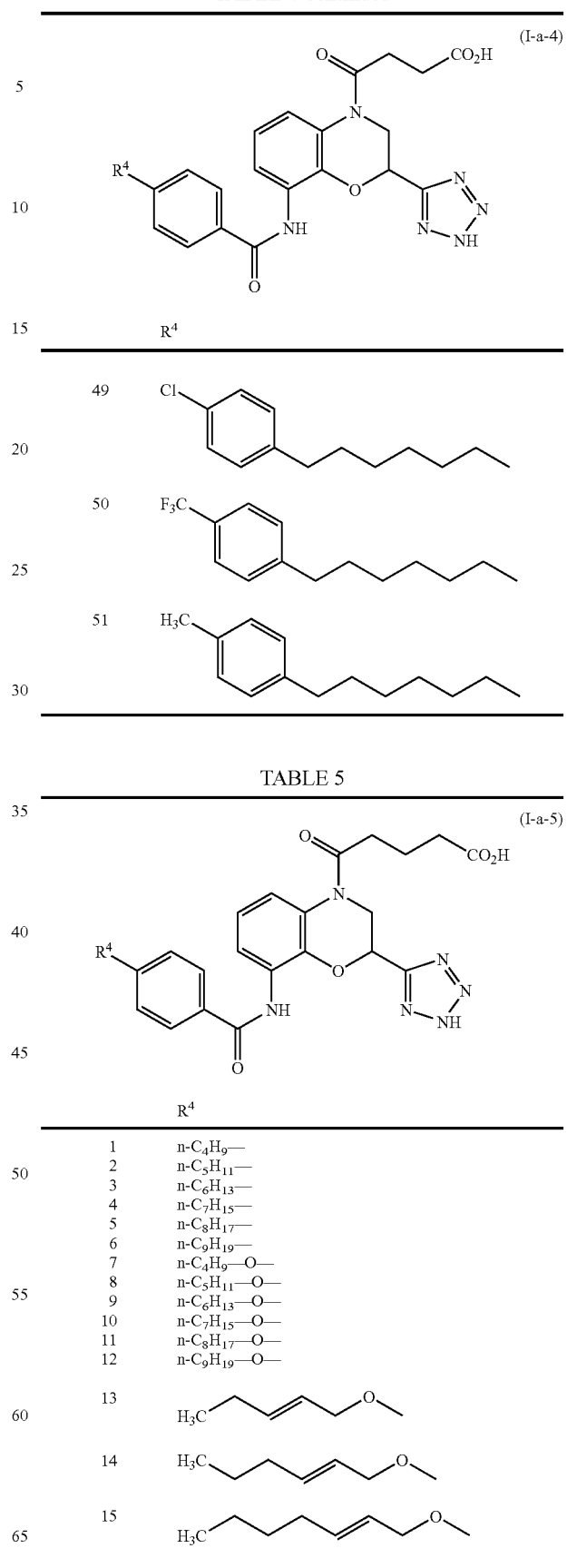
| | R⁴ |
|---|---|
| 49 | 4-Cl-C₆H₄-(CH₂)₆- |
| 50 | 4-F₃C-C₆H₄-(CH₂)₆- |
| 51 | 4-H₃C-C₆H₄-(CH₂)₆- |
TABLE 5
(I-a-5)
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | H₃C-CH=CH-CH₂-O- |
| 14 | H₃C-(CH₂)-CH=CH-CH₂-O- |
| 15 | H₃C-(CH₂)₂-CH=CH-CH₂-O- |

TABLE 5-continued
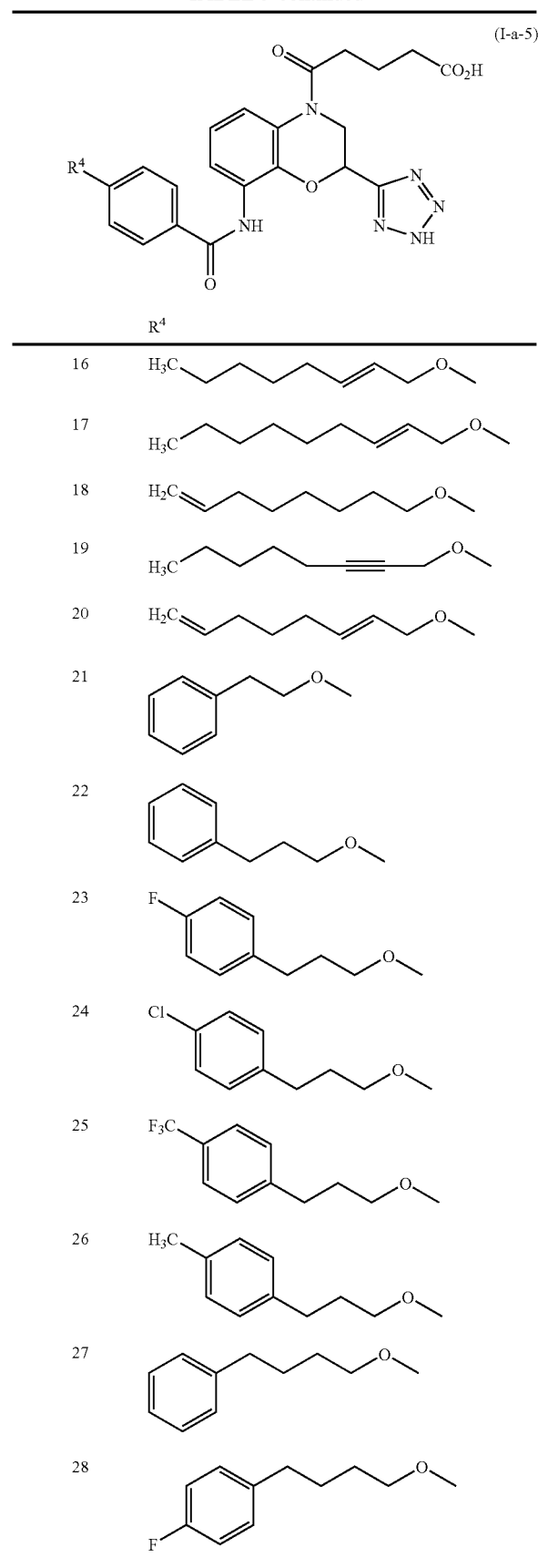
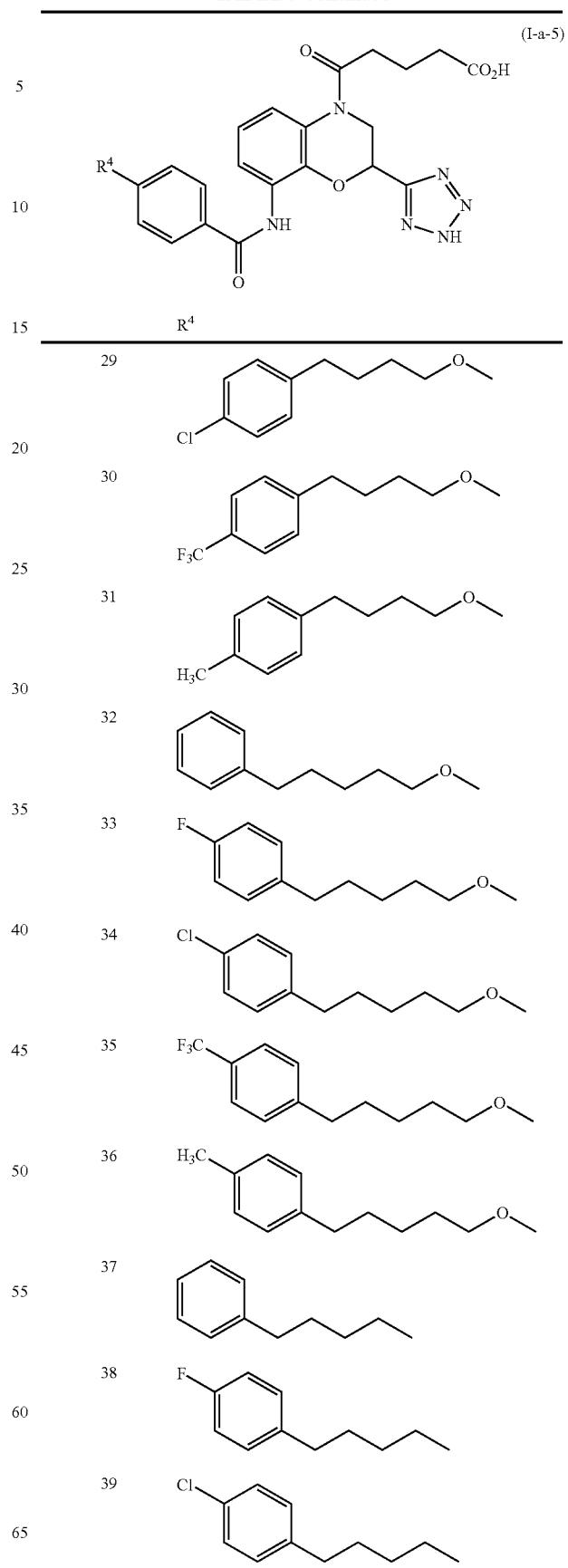

TABLE 5-continued
TABLE 5-continued
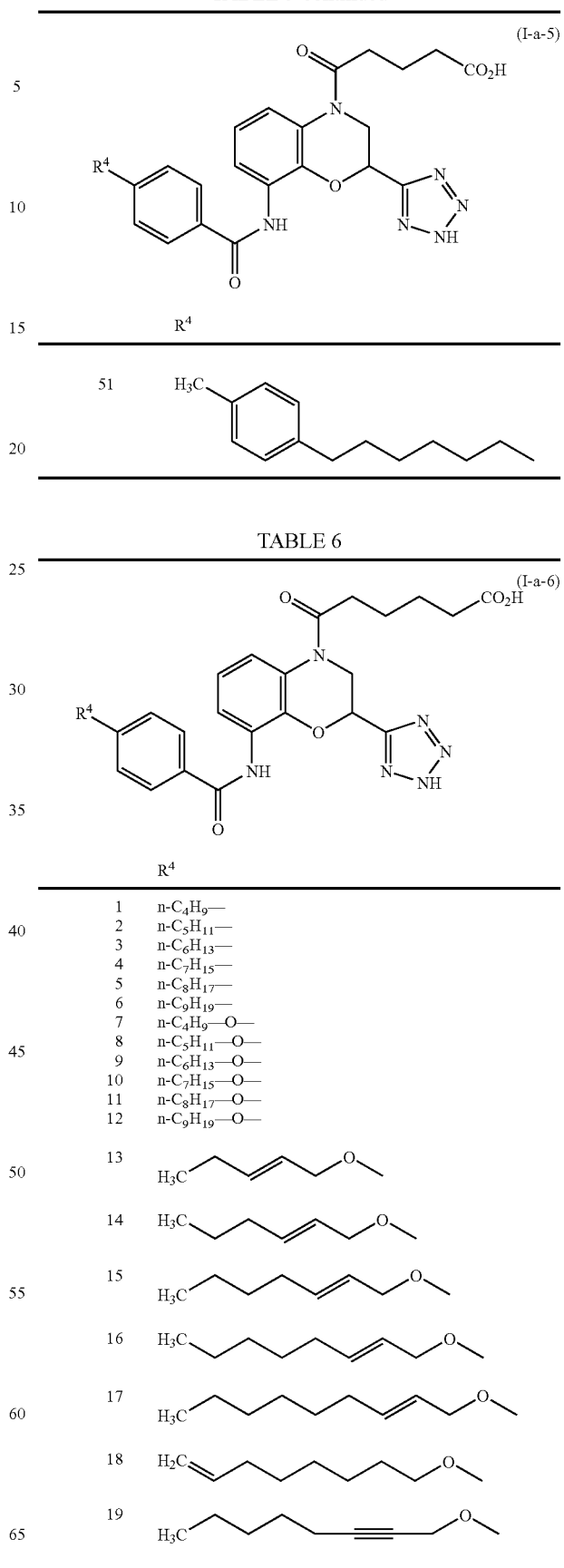

TABLE 6-continued
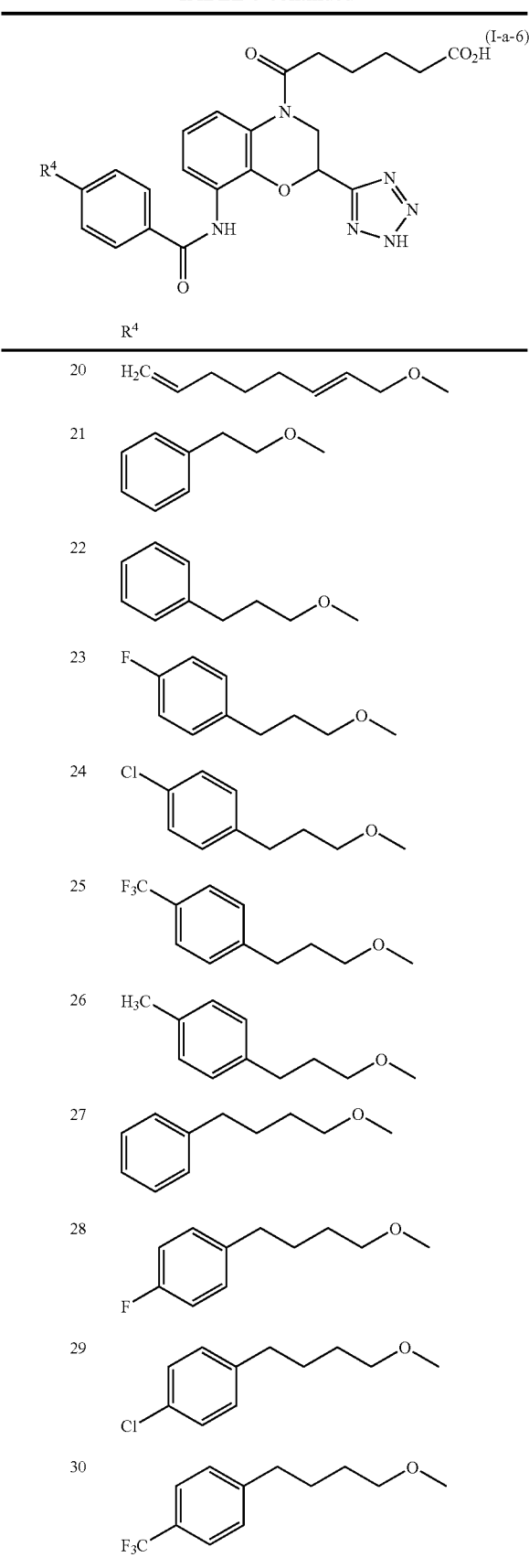
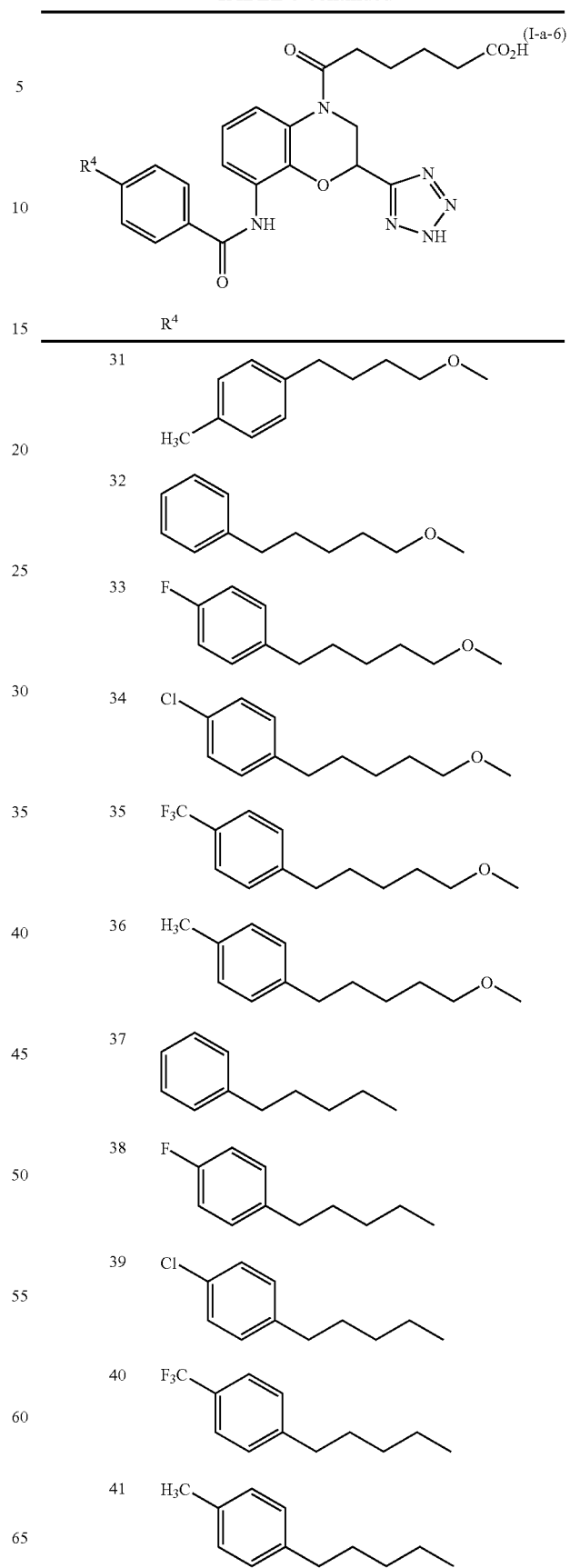

TABLE 6-continued (I-a-6)

[Structure: benzoxazine core with 8-position having NHC(O)-C6H4-R4 substituent, 2-position having tetrazole (2H-tetrazol-5-yl), and N4 bearing -C(O)(CH2)4CO2H]

| | R⁴ |
|---|---|
| 42 | C6H5-C6H13 (n-hexylphenyl) |
| 43 | 4-F-C6H4-C6H13 |
| 44 | 4-Cl-C6H4-C6H13 |
| 45 | 4-CF3-C6H4-C6H13 |
| 46 | 4-CH3-C6H4-C6H13 |
| 47 | C6H5-C7H15 (n-heptylphenyl) |
| 48 | 4-F-C6H4-C7H15 |
| 49 | 4-Cl-C6H4-C7H15 |
| 50 | 4-CF3-C6H4-C7H15 |
| 51 | 4-CH3-C6H4-C7H15 |

TABLE 7

(I-a-7)

[Structure: benzoxazine core with 8-OCH2-C6H4-R4 substituent, 2-position having CO2H, and N4 bearing -C(O)CH2CH2CO2H]

| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | H3C-CH=CH-CH2-O-CH3 (pent-2-enyl methyl ether) |
| 14 | H3C-(CH2)2-CH=CH-CH2-O-CH3 |
| 15 | H3C-(CH2)3-CH=CH-CH2-O-CH3 |
| 16 | H3C-(CH2)4-CH=CH-CH2-O-CH3 |
| 17 | H3C-(CH2)5-CH=CH-CH2-O-CH3 |
| 18 | H2C=CH-(CH2)5-O-CH3 |
| 19 | H3C-(CH2)3-C≡C-CH2-O-CH3 |
| 20 | H2C=CH-(CH2)2-CH=CH-CH2-O-CH3 |
| 21 | C6H5-CH2-CH2-O-CH3 |
| 22 | C6H5-(CH2)3-O-CH3 |
| 23 | 4-F-C6H4-(CH2)3-O-CH3 |
| 24 | 4-Cl-C6H4-(CH2)3-O-CH3 |
| 25 | 4-CF3-C6H4-(CH2)3-O-CH3 |

TABLE 7-continued
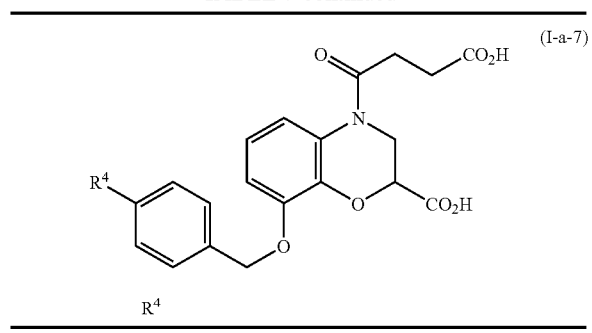
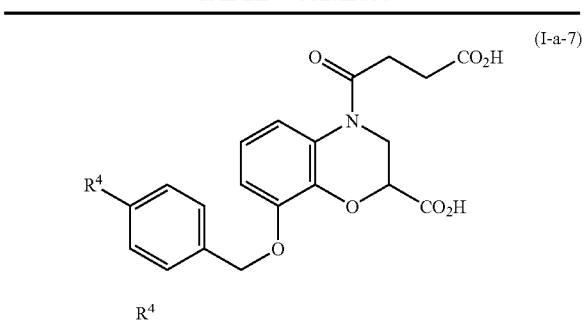

TABLE 7-continued
(I-a-7)
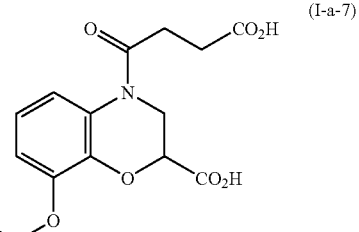
| | $R^4$ |
|---|---|
| 48 | 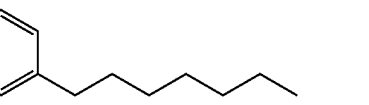 |
| 49 | 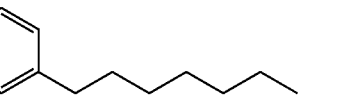 |
| 50 | 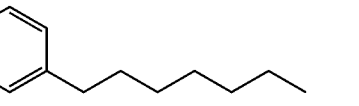 |
| 51 | 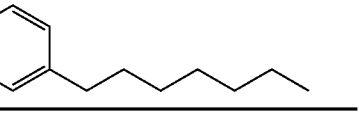 |
TABLE 8
(I-a-8)
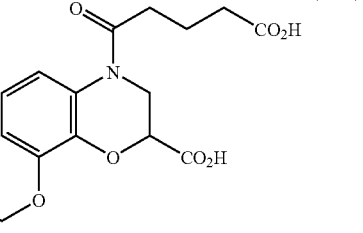
| | $R^4$ |
|---|---|
| 1 | n-$C_4H_9$— |
| 2 | n-$C_5H_{11}$— |
| 3 | n-$C_6H_{13}$— |
| 4 | n-$C_7H_{15}$— |
| 5 | n-$C_8H_{17}$— |
| 6 | n-$C_9H_{19}$— |
| 7 | n-$C_4H_9$—O— |
| 8 | n-$C_5H_{11}$—O— |
| 9 | n-$C_6H_{13}$—O— |
| 10 | n-$C_7H_{15}$—O— |
| 11 | n-$C_8H_{17}$—O— |
| 12 | n-$C_9H_{19}$—O— |
| 13 | 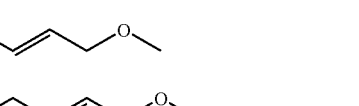 |
| 14 | 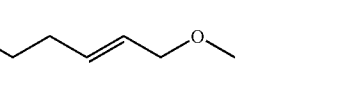 |
| 15 |  |
TABLE 8-continued
(I-a-8)
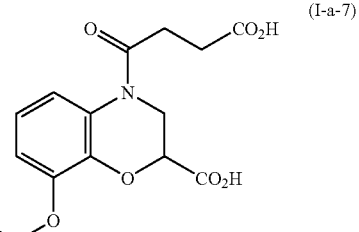
| | $R^4$ |
|---|---|
| 16 | 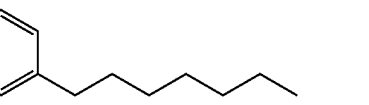 |
| 17 | 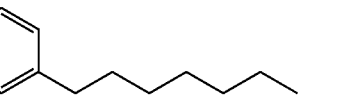 |
| 18 | 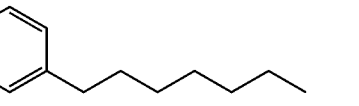 |
| 19 | 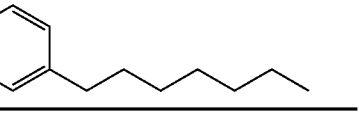 |
| 20 | 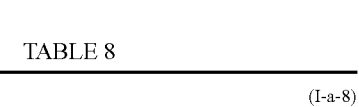 |
| 21 | 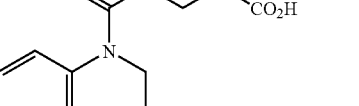 |
| 22 | 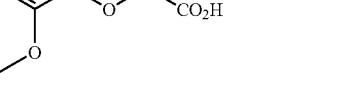 |
| 23 |  |
| 24 |  |
| 25 | 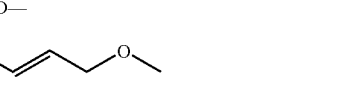 |
| 26 | 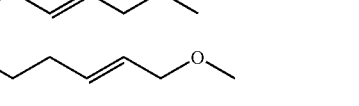 |
| 27 |  |
| 28 |  |

TABLE 8-continued
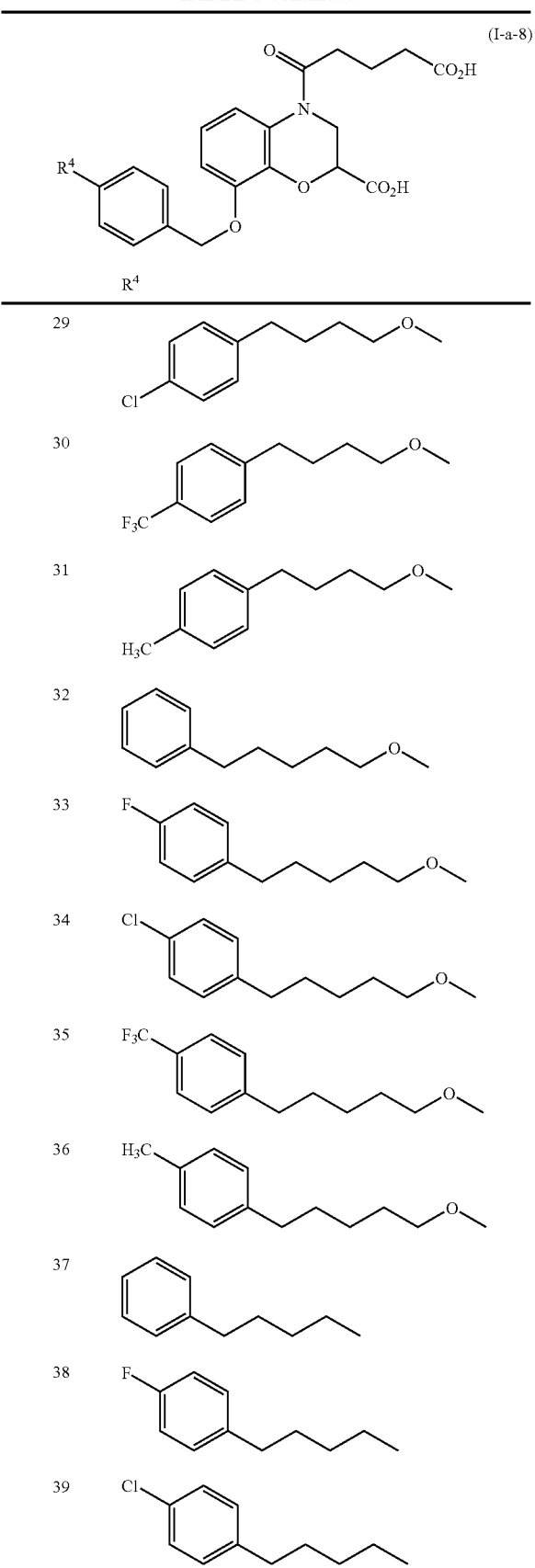
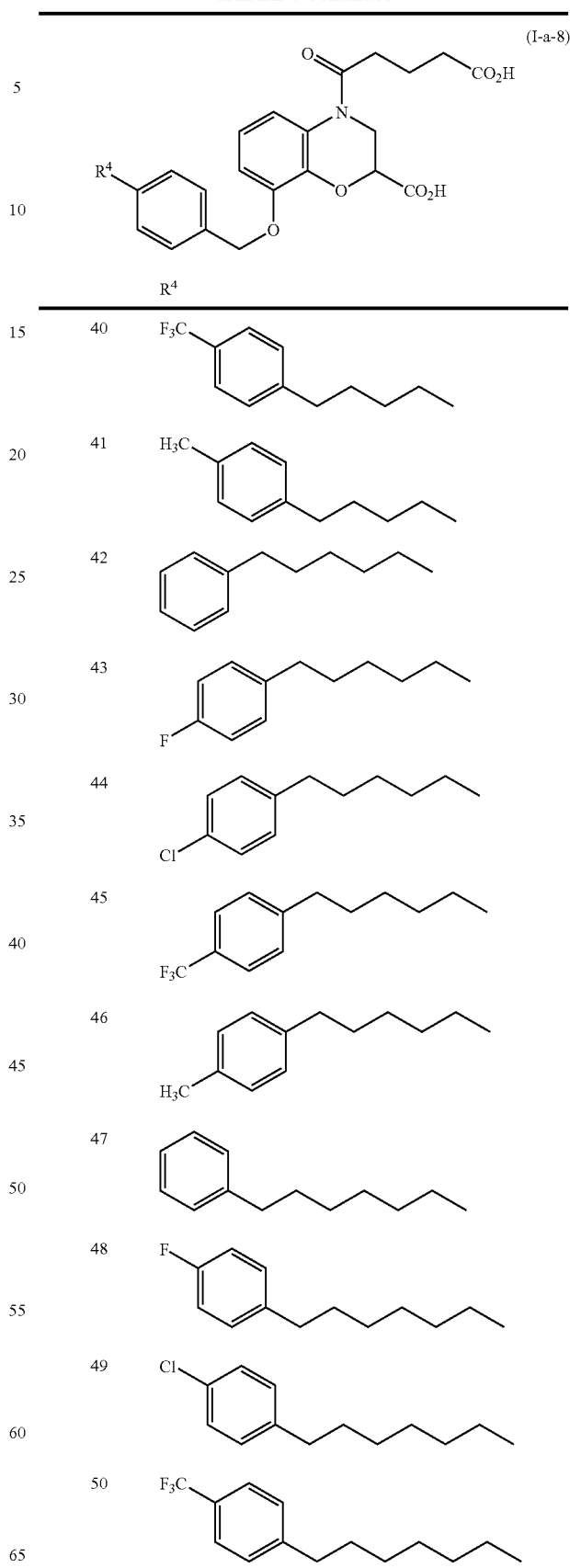

TABLE 8-continued (I-a-8)

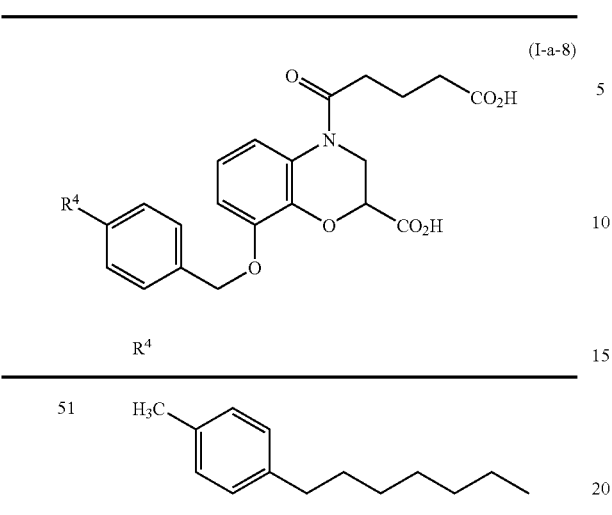

| | R[4] |
|---|---|
| 51 | H₃C-C₆H₄-(CH₂)₆CH₃ |

TABLE 9

(I-a-9)

| | R[4] |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | CH₃CH=CHCH₂OCH₃ |
| 14 | CH₃CH₂CH=CHCH₂OCH₃ |
| 15 | CH₃(CH₂)₂CH=CHCH₂OCH₃ |
| 16 | CH₃(CH₂)₃CH=CHCH₂OCH₃ |
| 17 | CH₃(CH₂)₄CH=CHCH₂OCH₃ |
| 18 | CH₂=CH(CH₂)₄CH₂OCH₃ |
| 19 | CH₃(CH₂)₃C≡CCH₂OCH₃ |
| 20 | CH₂=CH(CH₂)₃CH=CHCH₂OCH₃ |

TABLE 9-continued (I-a-9)

| | R[4] |
|---|---|
| 21 | PhCH₂CH₂OCH₃ |
| 22 | PhCH₂CH₂CH₂OCH₃ |
| 23 | 4-F-C₆H₄-CH₂CH₂CH₂OCH₃ |
| 24 | 4-Cl-C₆H₄-CH₂CH₂CH₂OCH₃ |
| 25 | 4-CF₃-C₆H₄-CH₂CH₂CH₂OCH₃ |
| 26 | 4-CH₃-C₆H₄-CH₂CH₂CH₂OCH₃ |
| 27 | Ph(CH₂)₃CH₂OCH₃ |
| 28 | 4-F-C₆H₄-(CH₂)₃CH₂OCH₃ |
| 29 | 4-Cl-C₆H₄-(CH₂)₃CH₂OCH₃ |
| 30 | 4-CF₃-C₆H₄-(CH₂)₃CH₂OCH₃ |
| 31 | 4-CH₃-C₆H₄-(CH₂)₃CH₂OCH₃ |

TABLE 9-continued
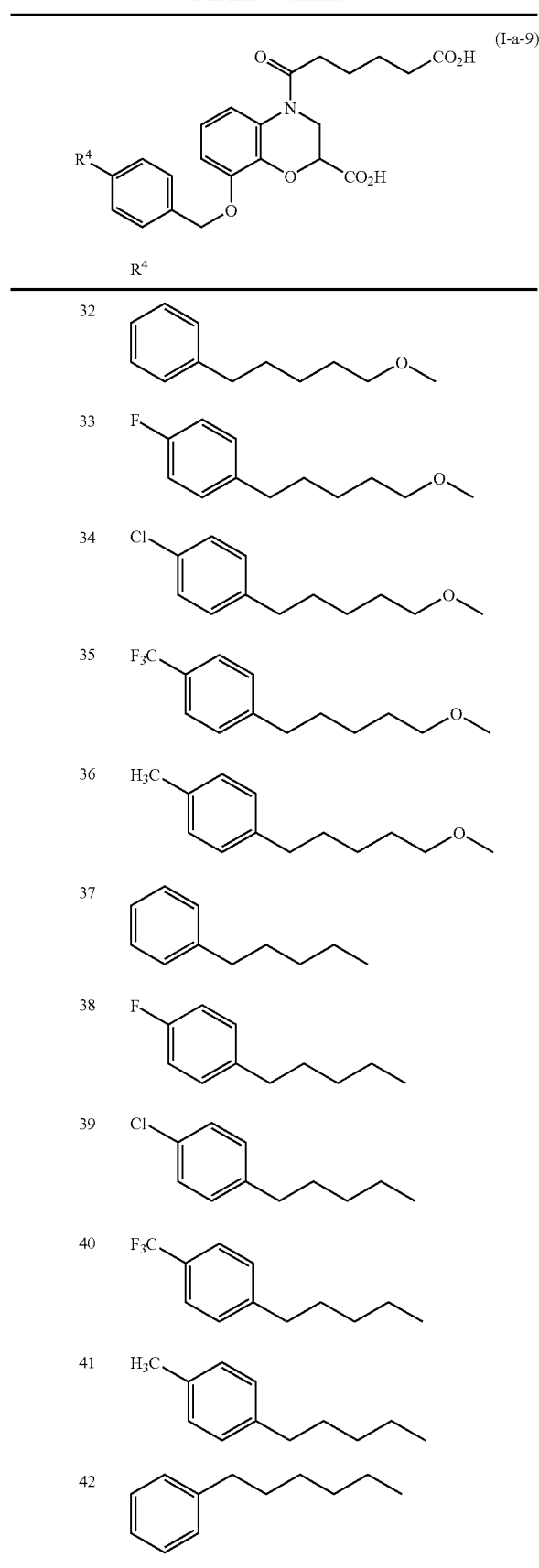
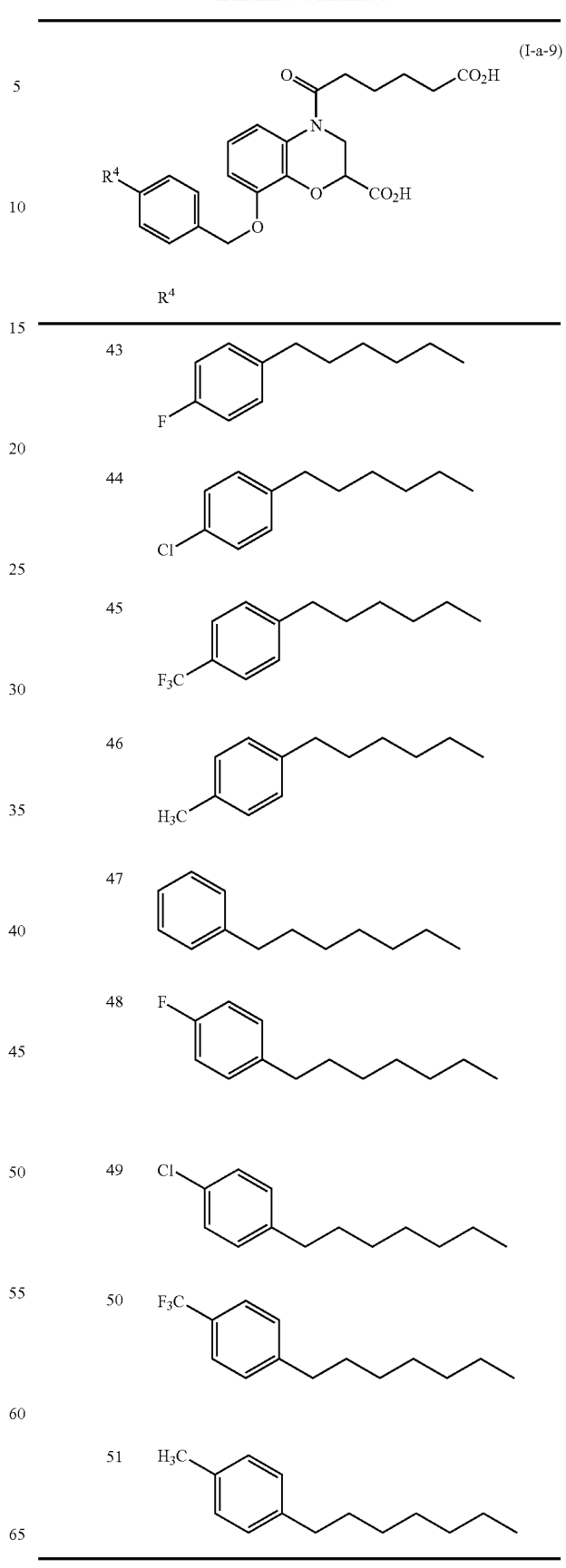

TABLE 10

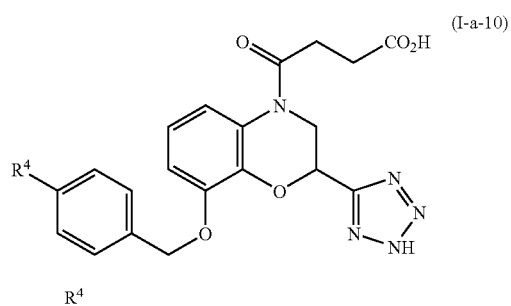

(I-a-10)

| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | H₃C—CH=CH—CH₂—O—CH₃ |
| 14 | H₃C—CH₂—CH=CH—CH₂—O—CH₃ |
| 15 | H₃C—(CH₂)₂—CH=CH—CH₂—O—CH₃ |
| 16 | H₃C—(CH₂)₃—CH=CH—CH₂—O—CH₃ |
| 17 | H₃C—(CH₂)₄—CH=CH—CH₂—O—CH₃ |
| 18 | H₂C=CH—(CH₂)₄—O—CH₃ |
| 19 | H₃C—(CH₂)₂—C≡C—CH₂—O—CH₃ |
| 20 | H₂C=CH—(CH₂)₂—CH=CH—CH₂—O—CH₃ |
| 21 | PhCH₂CH₂—O—CH₃ |
| 22 | Ph(CH₂)₃—O—CH₃ |
| 23 | 4-F-C₆H₄—(CH₂)₃—O—CH₃ |
| 24 | 4-Cl-C₆H₄—(CH₂)₃—O—CH₃ |

TABLE 10-continued

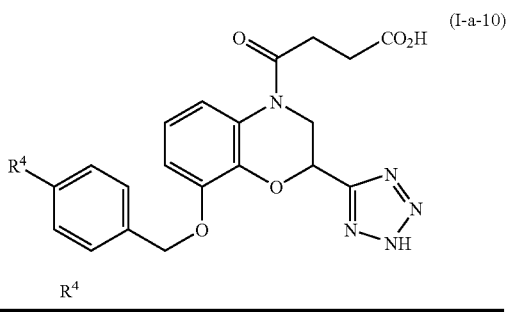

(I-a-10)

| | R⁴ |
|---|---|
| 25 | 4-F₃C-C₆H₄—(CH₂)₃—O—CH₃ |
| 26 | 4-H₃C-C₆H₄—(CH₂)₃—O—CH₃ |
| 27 | Ph—(CH₂)₄—O—CH₃ |
| 28 | 4-F-C₆H₄—(CH₂)₄—O—CH₃ |
| 29 | 4-Cl-C₆H₄—(CH₂)₄—O—CH₃ |
| 30 | 4-F₃C-C₆H₄—(CH₂)₄—O—CH₃ |
| 31 | 4-H₃C-C₆H₄—(CH₂)₄—O—CH₃ |
| 32 | Ph—(CH₂)₅—O—CH₃ |
| 33 | 4-F-C₆H₄—(CH₂)₅—O—CH₃ |
| 34 | 4-Cl-C₆H₄—(CH₂)₅—O—CH₃ |
| 35 | 4-F₃C-C₆H₄—(CH₂)₅—O—CH₃ |

TABLE 10-continued
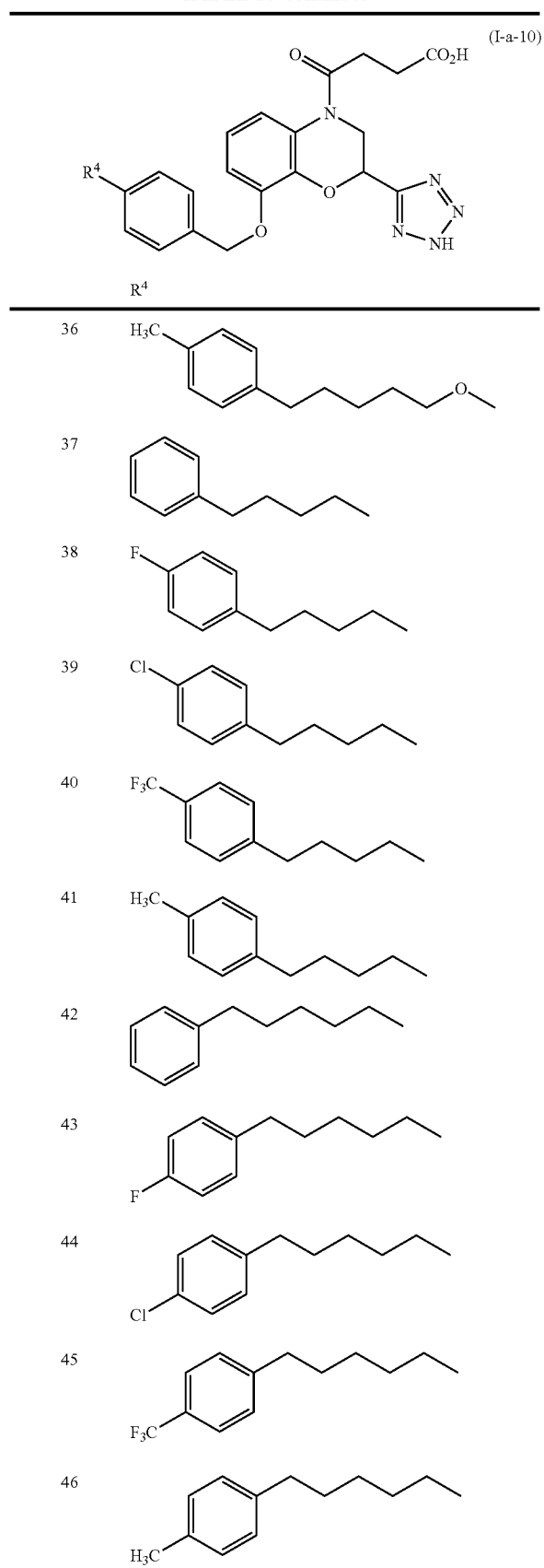
TABLE 10-continued
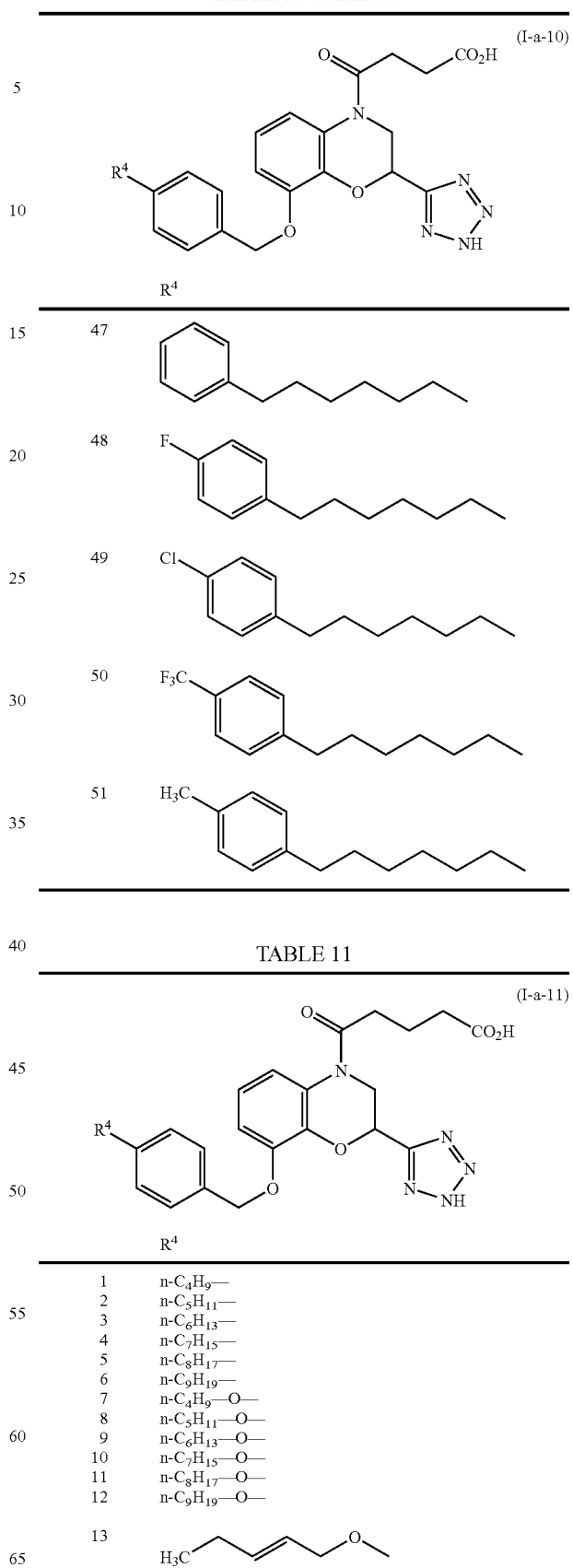
TABLE 11

TABLE 11-continued (I-a-11)

| | R⁴ |
|---|---|
| 14 | H₃C~~~~~O/ (CH₃-CH₂-CH=CH-CH₂-O-CH₃) |
| 15 | H₃C~~~~~~O/ |
| 16 | H₃C~~~~~~~O/ |
| 17 | H₃C~~~~~~~~O/ |
| 18 | H₂C=~~~~~~O/ |
| 19 | H₃C~~~~≡~O/ |
| 20 | H₂C=~~~~~~O/ |
| 21 | Ph-CH₂-CH₂-O-CH₃ |
| 22 | Ph-(CH₂)₃-O-CH₃ |
| 23 | 4-F-C₆H₄-(CH₂)₃-O-CH₃ |
| 24 | 4-Cl-C₆H₄-(CH₂)₃-O-CH₃ |
| 25 | 4-F₃C-C₆H₄-(CH₂)₃-O-CH₃ |
| 26 | 4-H₃C-C₆H₄-(CH₂)₃-O-CH₃ |
| 27 | Ph-(CH₂)₄-O-CH₃ |
| 28 | 4-F-C₆H₄-(CH₂)₄-O-CH₃ |
| 29 | 4-Cl-C₆H₄-(CH₂)₄-O-CH₃ |
| 30 | 4-F₃C-C₆H₄-(CH₂)₄-O-CH₃ |
| 31 | 4-H₃C-C₆H₄-(CH₂)₄-O-CH₃ |
| 32 | Ph-(CH₂)₅-O-CH₃ |
| 33 | 4-F-C₆H₄-(CH₂)₅-O-CH₃ |
| 34 | 4-Cl-C₆H₄-(CH₂)₅-O-CH₃ |
| 35 | 4-F₃C-C₆H₄-(CH₂)₅-O-CH₃ |
| 36 | 4-H₃C-C₆H₄-(CH₂)₅-O-CH₃ |
| 37 | Ph-(CH₂)₄-CH₃ |
| 38 | 4-F-C₆H₄-(CH₂)₄-CH₃ |

TABLE 11-continued
(I-a-11)
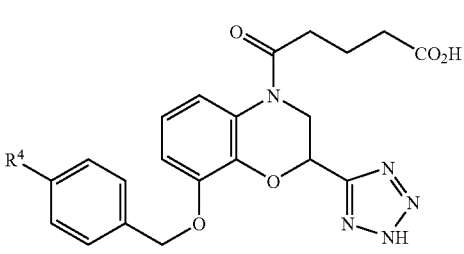
| | R⁴ |
|---|---|
| 39 | 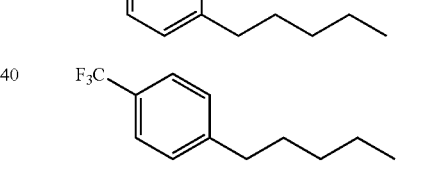 |
| 40 | 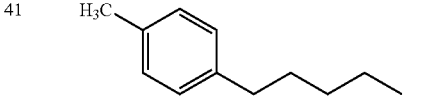 |
| 41 | 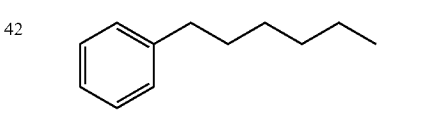 |
| 42 | 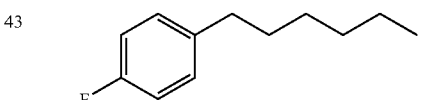 |
| 43 | 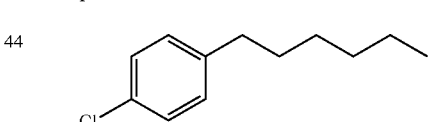 |
| 44 | 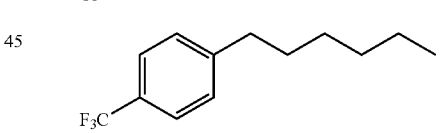 |
| 45 | 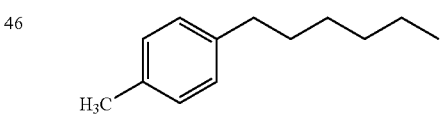 |
| 46 | 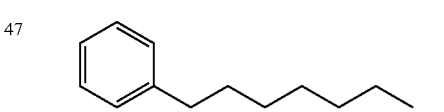 |
| 47 | 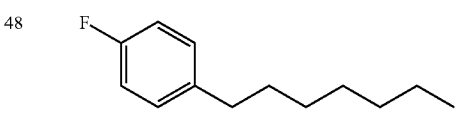 |
| 48 | 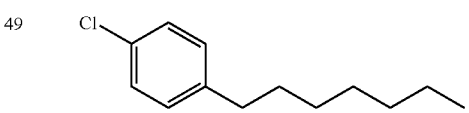 |
| 49 | 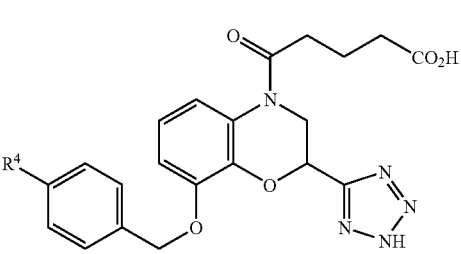 |
TABLE 11-continued
(I-a-11)
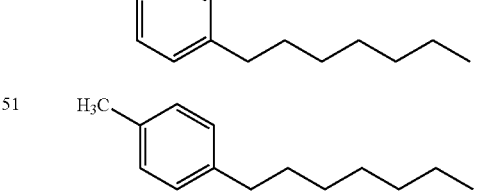
| | R⁴ |
|---|---|
| 50 | 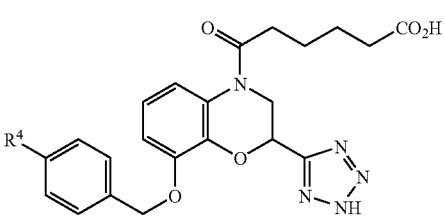 |
| 51 | 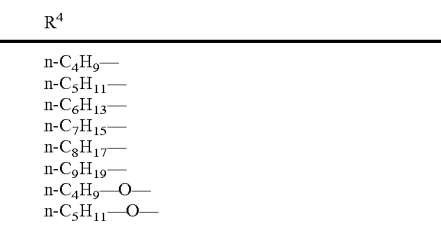 |
TABLE 12
(I-a-12)
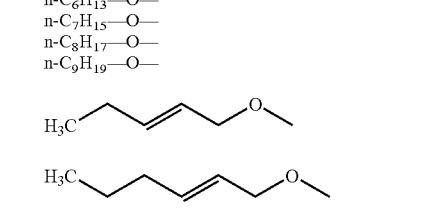
| | R⁴ |
|---|---|
| 1 | n-$C_4H_9$— |
| 2 | n-$C_5H_{11}$— |
| 3 | n-$C_6H_{13}$— |
| 4 | n-$C_7H_{15}$— |
| 5 | n-$C_8H_{17}$— |
| 6 | n-$C_9H_{19}$— |
| 7 | n-$C_4H_9$—O— |
| 8 | n-$C_5H_{11}$—O— |
| 9 | n-$C_6H_{13}$—O— |
| 10 | n-$C_7H_{15}$—O— |
| 11 | n-$C_8H_{17}$—O— |
| 12 | n-$C_9H_{19}$—O— |
| 13 | 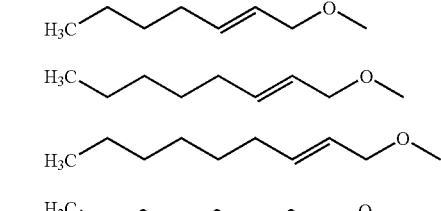 |
| 14 | 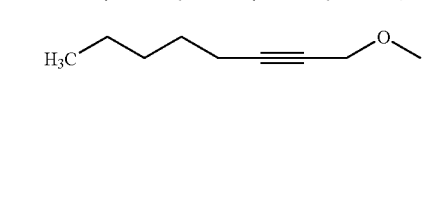 |
| 15 | 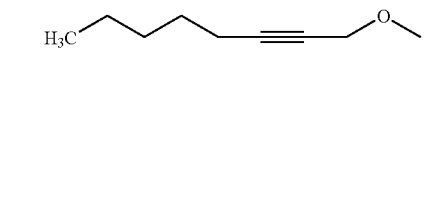 |
| 16 | 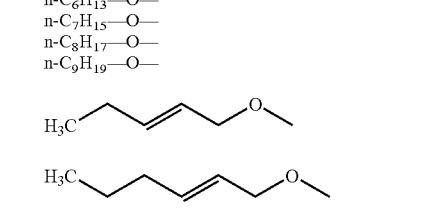 |
| 17 | 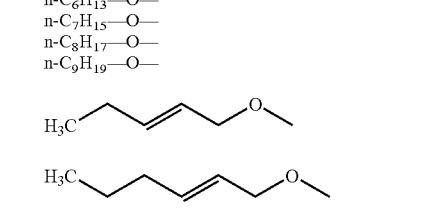 |
| 18 | 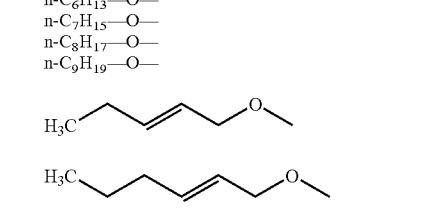 |
| 19 | 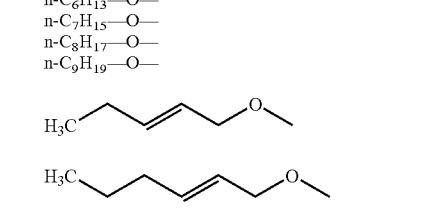 |

TABLE 12-continued (I-a-12)

[Structure: benzoxazine core with N-acyl group (pentanoic acid), 8-(R4-benzyloxy) substituent, and 2-(2H-tetrazol-5-yl) group]

R⁴

| # | R⁴ |
|---|---|
| 20 | H₂C=CH-CH₂-CH₂-CH=CH-CH₂-O-CH₃ |
| 21 | C₆H₅-CH₂-CH₂-O-CH₃ |
| 22 | C₆H₅-(CH₂)₃-O-CH₃ |
| 23 | 4-F-C₆H₄-(CH₂)₃-O-CH₃ |
| 24 | 4-Cl-C₆H₄-(CH₂)₃-O-CH₃ |
| 25 | 4-F₃C-C₆H₄-(CH₂)₃-O-CH₃ |
| 26 | 4-H₃C-C₆H₄-(CH₂)₃-O-CH₃ |
| 27 | C₆H₅-(CH₂)₄-O-CH₃ |
| 28 | 4-F-C₆H₄-(CH₂)₄-O-CH₃ |
| 29 | 4-Cl-C₆H₄-(CH₂)₄-O-CH₃ |
| 30 | 4-F₃C-C₆H₄-(CH₂)₄-O-CH₃ |
| 31 | 4-H₃C-C₆H₄-(CH₂)₄-O-CH₃ |

TABLE 12-continued (I-a-12)

[Structure: benzoxazine core with N-acyl group (pentanoic acid), 8-(R4-benzyloxy) substituent, and 2-(2H-tetrazol-5-yl) group]

R⁴

| # | R⁴ |
|---|---|
| 32 | C₆H₅-(CH₂)₅-O-CH₃ |
| 33 | 4-F-C₆H₄-(CH₂)₅-O-CH₃ |
| 34 | 4-Cl-C₆H₄-(CH₂)₅-O-CH₃ |
| 35 | 4-F₃C-C₆H₄-(CH₂)₅-O-CH₃ |
| 36 | 4-H₃C-C₆H₄-(CH₂)₅-O-CH₃ |
| 37 | C₆H₅-(CH₂)₄-CH₃ |
| 38 | 4-F-C₆H₄-(CH₂)₄-CH₃ |
| 39 | 4-Cl-C₆H₄-(CH₂)₄-CH₃ |
| 40 | 4-F₃C-C₆H₄-(CH₂)₄-CH₃ |
| 41 | 4-H₃C-C₆H₄-(CH₂)₄-CH₃ |
| 42 | C₆H₅-(CH₂)₅-CH₃ |

TABLE 12-continued
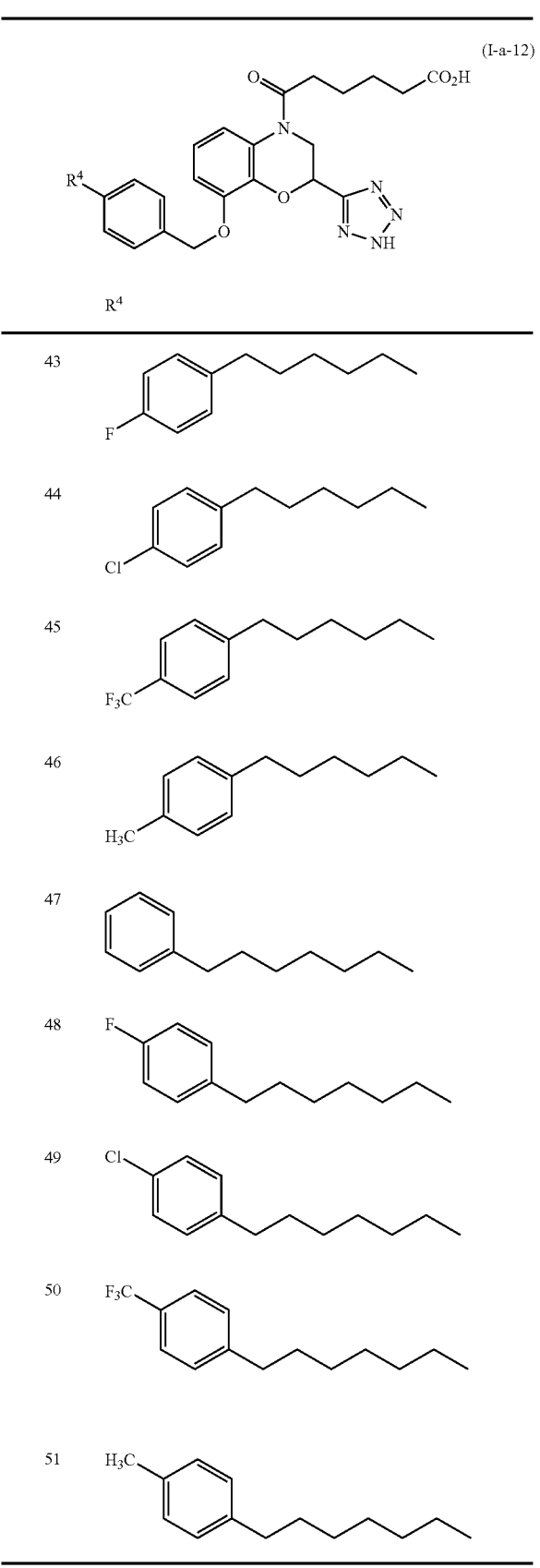
TABLE 13
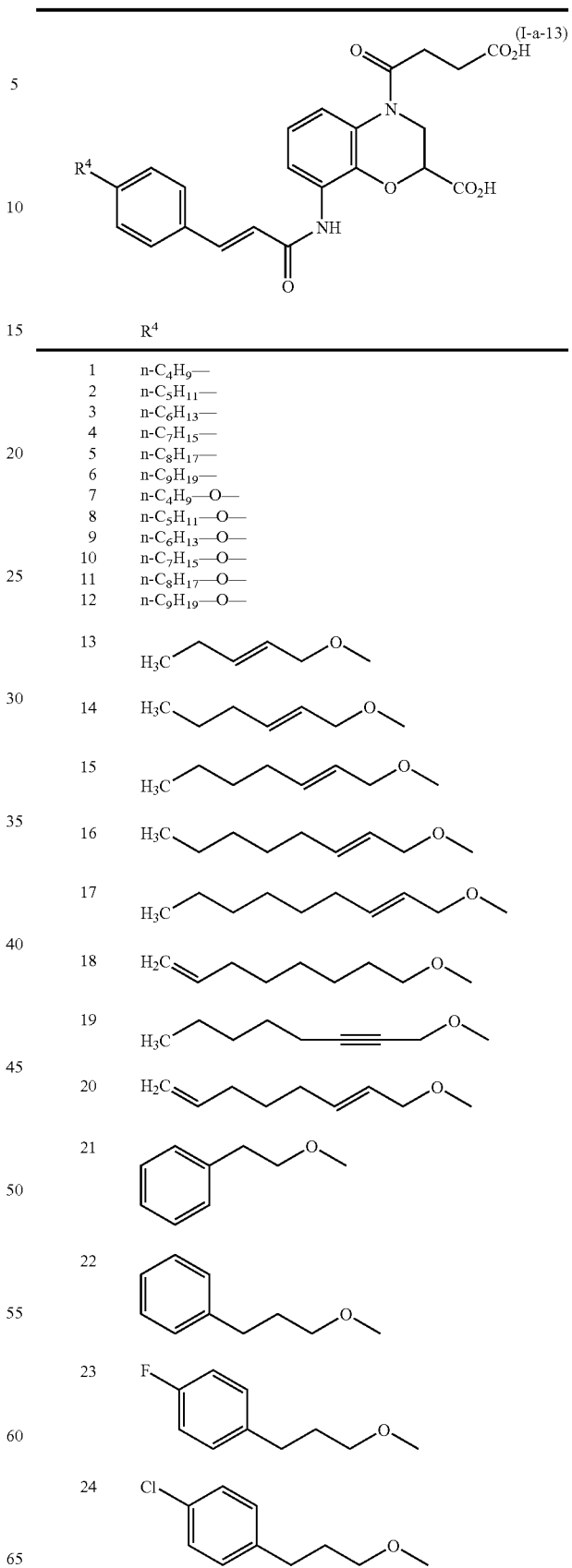
| | $R^4$ |
|---|---|
| 1 | n-C$_4$H$_9$— |
| 2 | n-C$_5$H$_{11}$— |
| 3 | n-C$_6$H$_{13}$— |
| 4 | n-C$_7$H$_{15}$— |
| 5 | n-C$_8$H$_{17}$— |
| 6 | n-C$_9$H$_{19}$— |
| 7 | n-C$_4$H$_9$—O— |
| 8 | n-C$_5$H$_{11}$—O— |
| 9 | n-C$_6$H$_{13}$—O— |
| 10 | n-C$_7$H$_{15}$—O— |
| 11 | n-C$_8$H$_{17}$—O— |
| 12 | n-C$_9$H$_{19}$—O— |

TABLE 13-continued
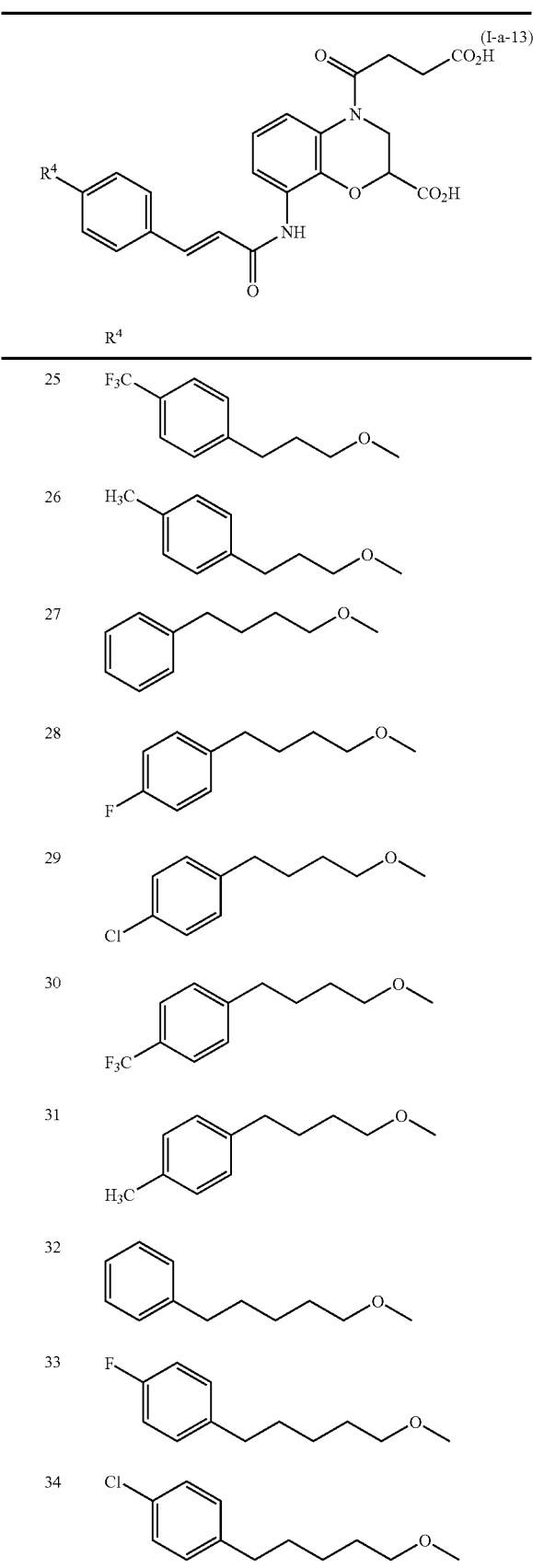
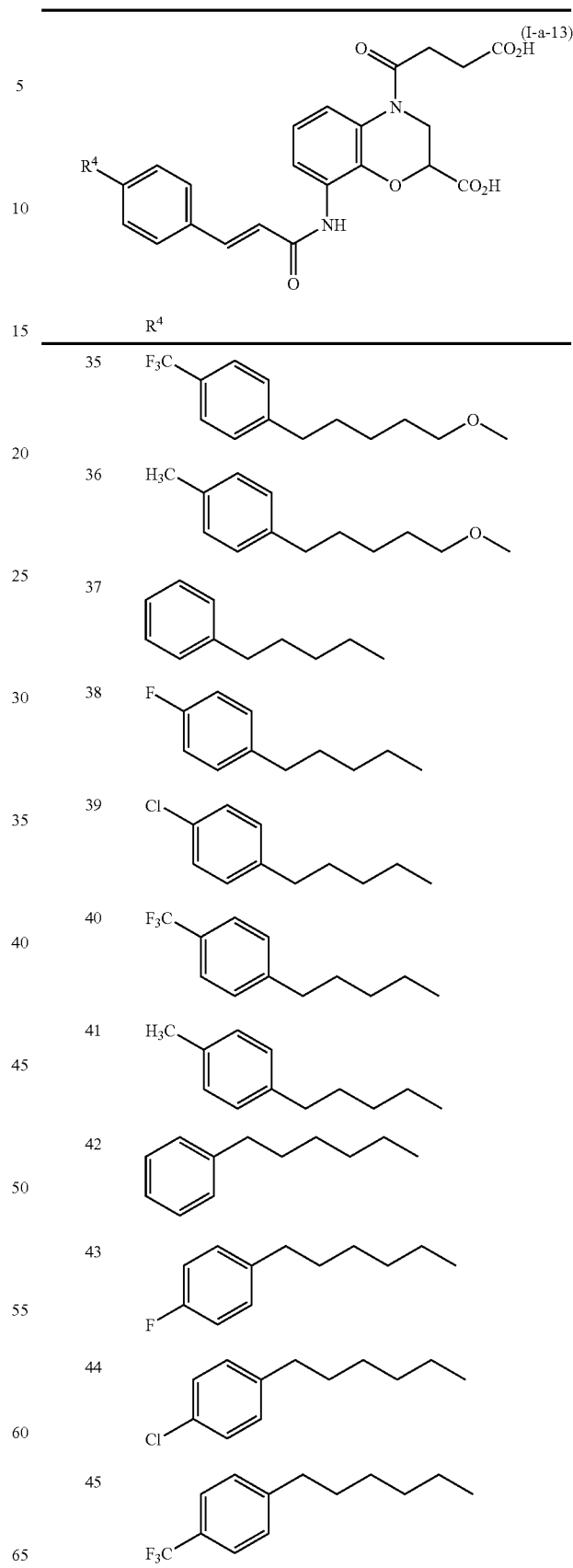

TABLE 13-continued (I-a-13)

| 46 | 4-(n-hexyl)-3-methylphenyl (H₃C-, C₆H₁₃-) |
| 47 | 4-(n-heptyl)phenyl |
| 48 | 4-(n-hexyl)-3-fluorophenyl (F-, C₆H₁₃-) |
| 49 | 4-(n-hexyl)-3-chlorophenyl (Cl-, C₆H₁₃-) |
| 50 | 4-(n-hexyl)-3-trifluoromethylphenyl (F₃C-, C₆H₁₃-) |
| 51 | 4-(n-heptyl)-3-methylphenyl (H₃C-, C₇H₁₅-) |

TABLE 14

(I-a-14)

| R⁴ | |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |

TABLE 14-continued (I-a-14)

| R⁴ | |
|---|---|
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | H₃C—CH=CH—CH₂—O— |
| 14 | H₃C—(CH₂)₂—CH=CH—CH₂—O— |
| 15 | H₃C—(CH₂)₃—CH=CH—CH₂—O— |
| 16 | H₃C—(CH₂)₄—CH=CH—CH₂—O— |
| 17 | H₃C—(CH₂)₅—CH=CH—CH₂—O— |
| 18 | H₂C=CH—(CH₂)₅—O— |
| 19 | H₃C—(CH₂)₃—C≡C—CH₂—O— |
| 20 | H₂C=CH—(CH₂)₃—CH=CH—CH₂—O— |
| 21 | PhCH₂CH₂—O— |
| 22 | Ph(CH₂)₃—O— |
| 23 | 4-F-C₆H₄-(CH₂)₃—O— |
| 24 | 4-Cl-C₆H₄-(CH₂)₃—O— |
| 25 | 4-F₃C-C₆H₄-(CH₂)₃—O— |

TABLE 14-continued
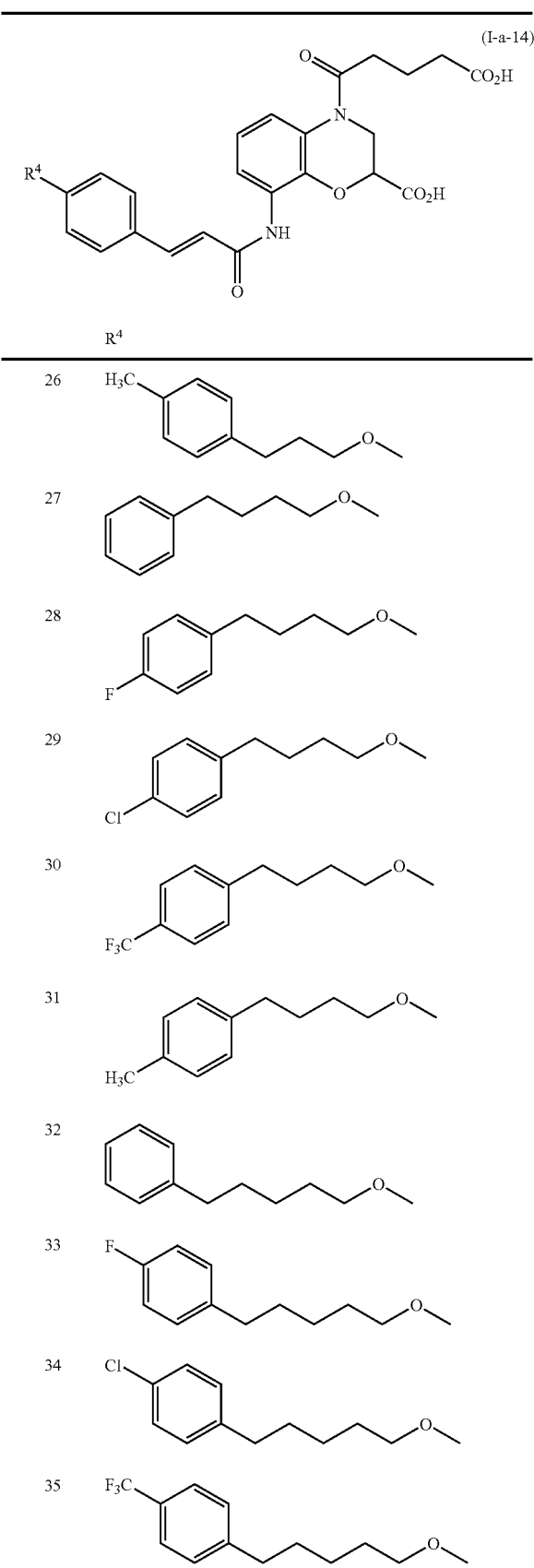
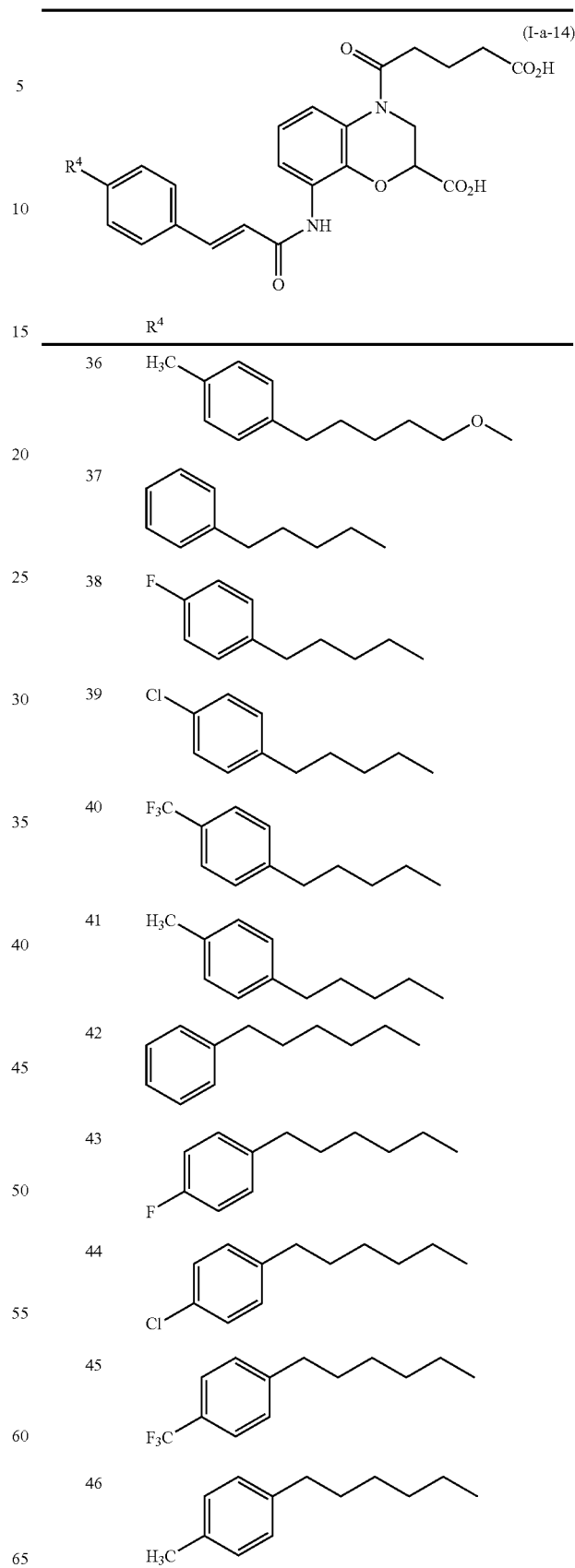

TABLE 14-continued
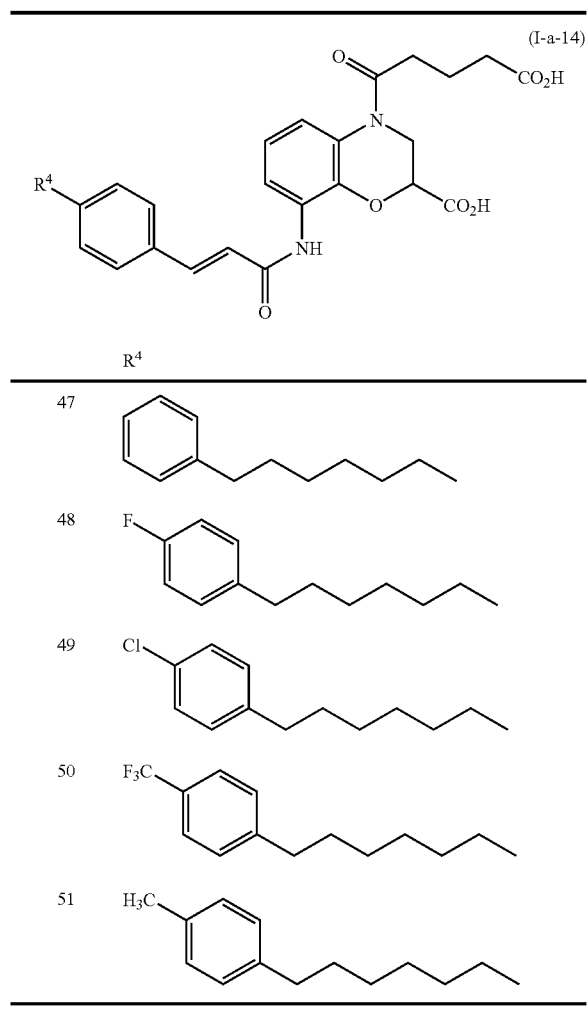
| | R⁴ |
|---|---|
| 47 | (phenyl-heptyl) |
| 48 | (4-F-phenyl-heptyl) |
| 49 | (4-Cl-phenyl-heptyl) |
| 50 | (4-CF₃-phenyl-heptyl) |
| 51 | (4-CH₃-phenyl-heptyl) |
TABLE 15
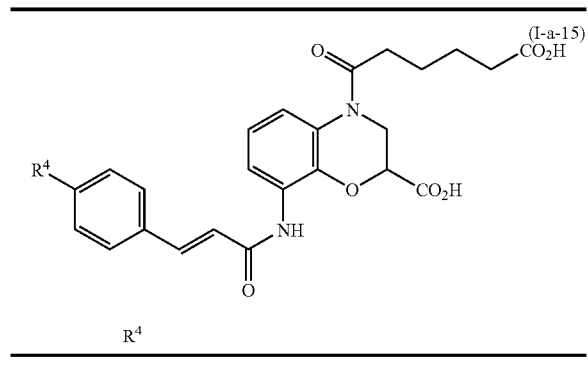
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
TABLE 15-continued
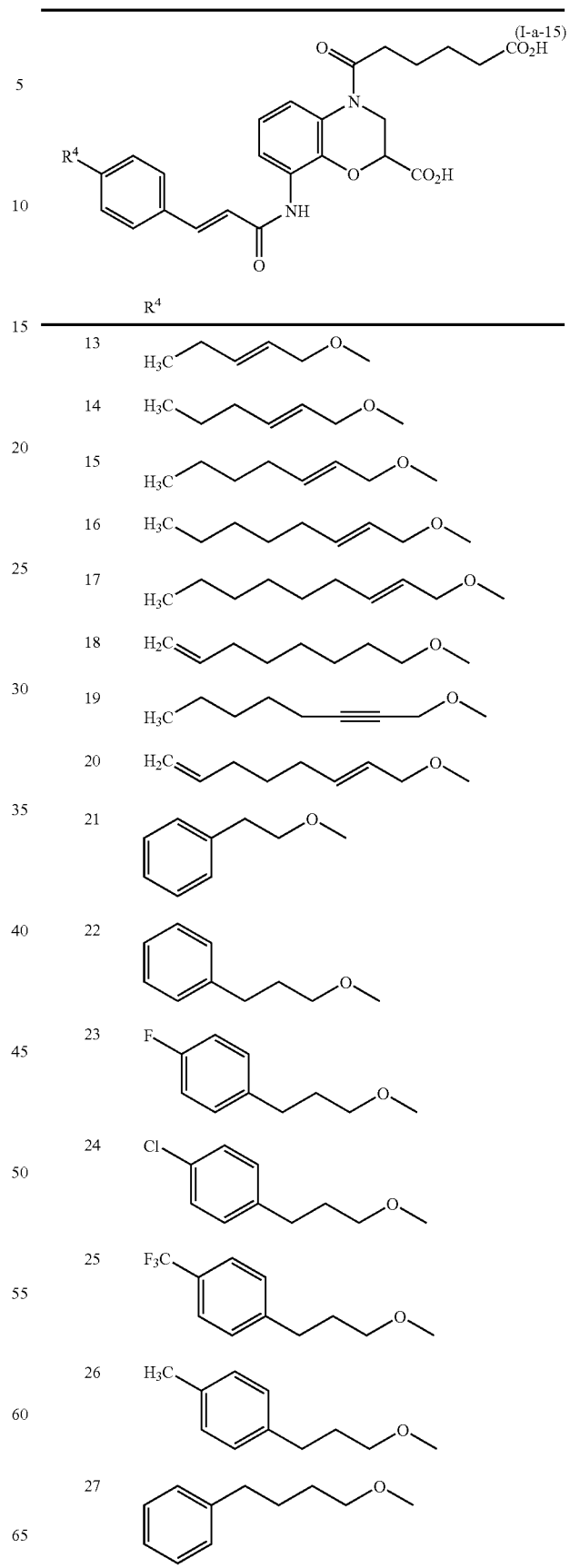

TABLE 15-continued
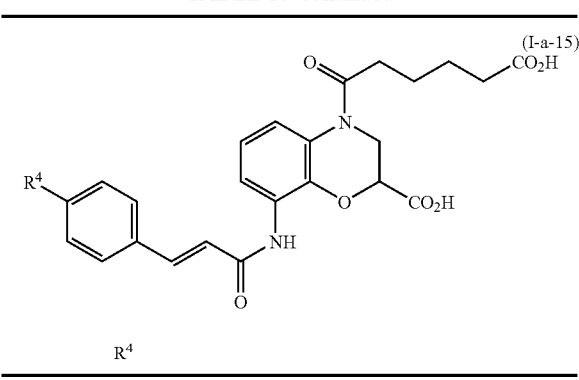
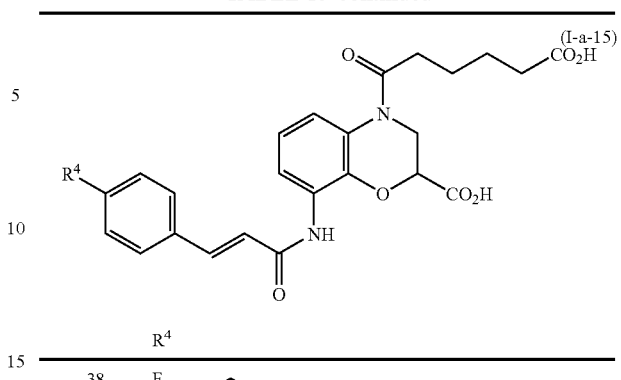

TABLE 15-continued

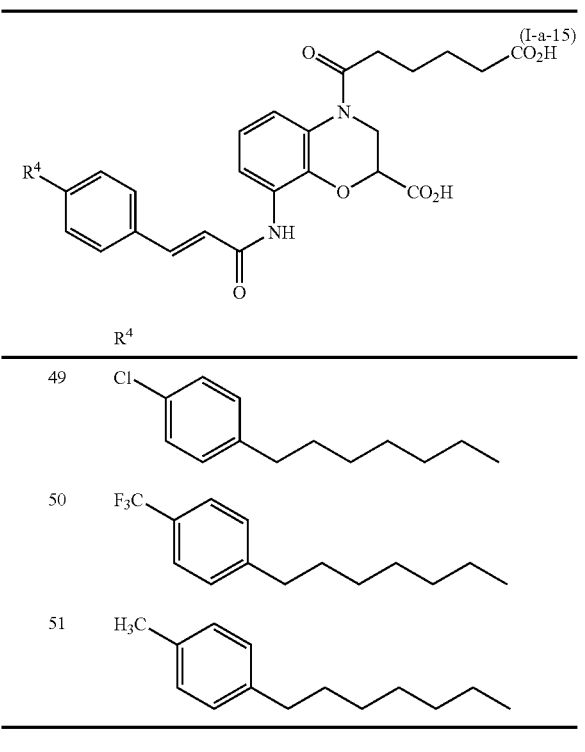
(I-a-15)

| | R⁴ |
|---|---|
| 49 | 4-Cl-C₆H₄-(CH₂)₆- |
| 50 | 4-F₃C-C₆H₄-(CH₂)₆- |
| 51 | 4-H₃C-C₆H₄-(CH₂)₆- |

TABLE 16

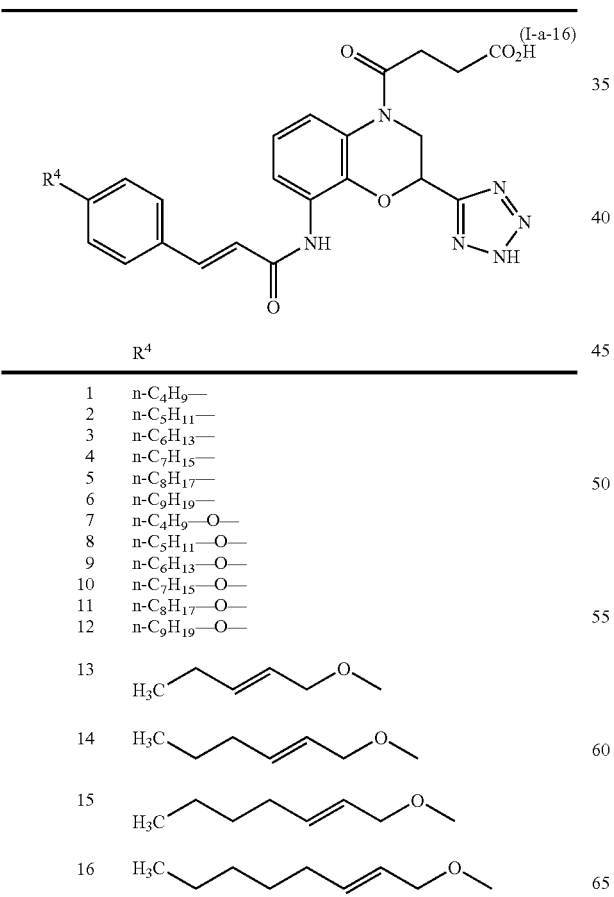
(I-a-16)

| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | H₃C-CH=CH-CH₂-O-CH₃ (pentenyl methyl ether) |
| 14 | H₃C-(CH₂)₂-CH=CH-CH₂-O-CH₃ |
| 15 | H₃C-(CH₂)₃-CH=CH-CH₂-O-CH₃ |
| 16 | H₃C-(CH₂)₄-CH=CH-CH₂-O-CH₃ |

TABLE 16-continued

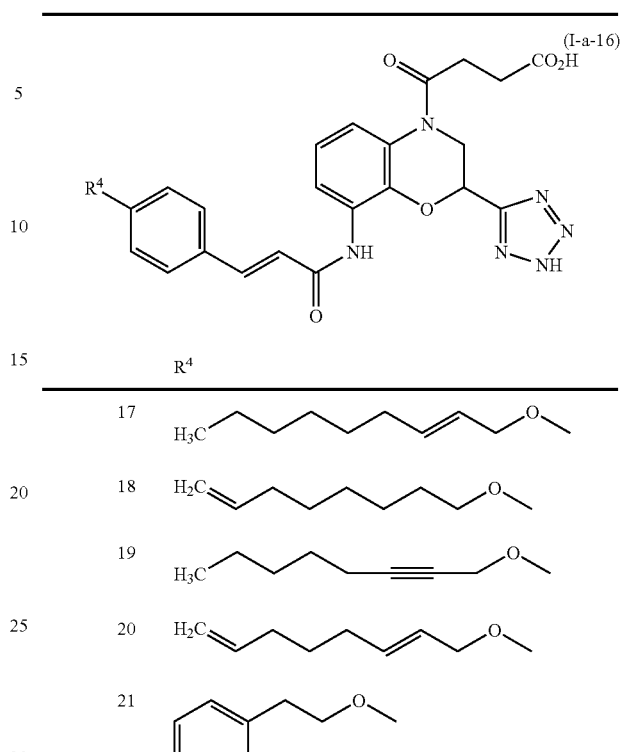
(I-a-16)

| | R⁴ |
|---|---|
| 17 | H₃C-(CH₂)₅-CH=CH-CH₂-O-CH₃ |
| 18 | H₂C=CH-(CH₂)₅-CH₂-O-CH₃ |
| 19 | H₃C-(CH₂)₃-C≡C-CH₂-O-CH₃ |
| 20 | H₂C=CH-(CH₂)₃-CH=CH-CH₂-O-CH₃ |
| 21 | C₆H₅-(CH₂)₂-O-CH₃ |
| 22 | C₆H₅-(CH₂)₃-O-CH₃ |
| 23 | 4-F-C₆H₄-(CH₂)₃-O-CH₃ |
| 24 | 4-Cl-C₆H₄-(CH₂)₃-O-CH₃ |
| 25 | 4-F₃C-C₆H₄-(CH₂)₃-O-CH₃ |
| 26 | 4-H₃C-C₆H₄-(CH₂)₃-O-CH₃ |
| 27 | C₆H₅-(CH₂)₄-O-CH₃ |
| 28 | 4-F-C₆H₄-(CH₂)₄-O-CH₃ |

TABLE 16-continued
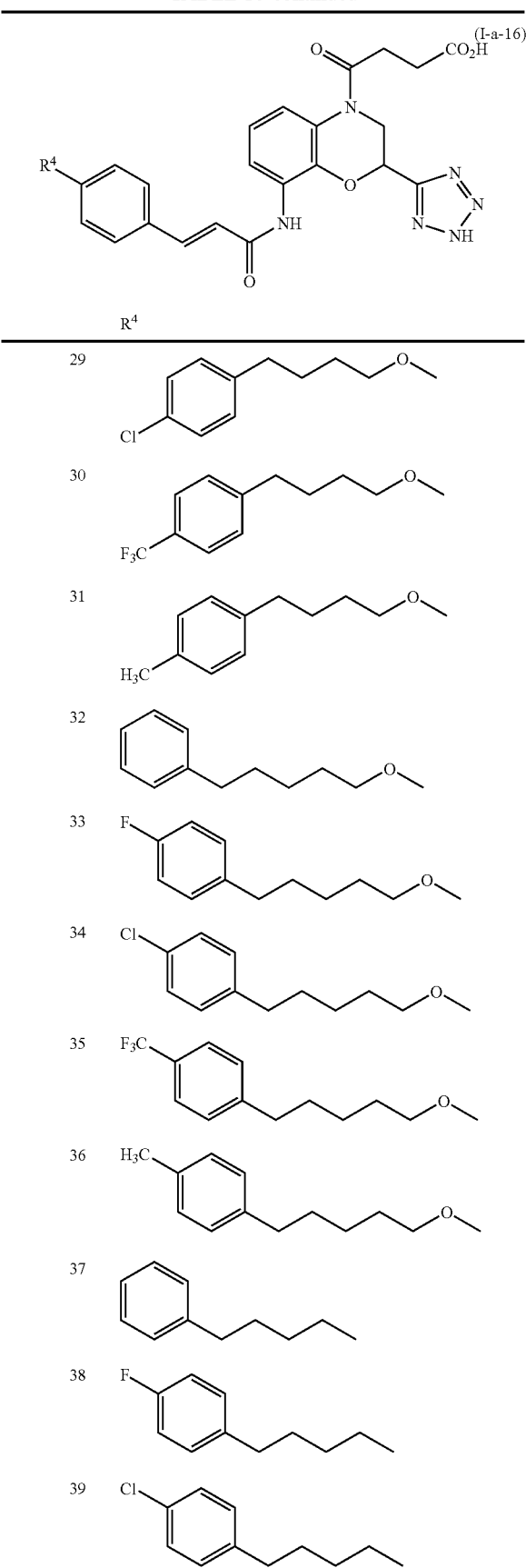
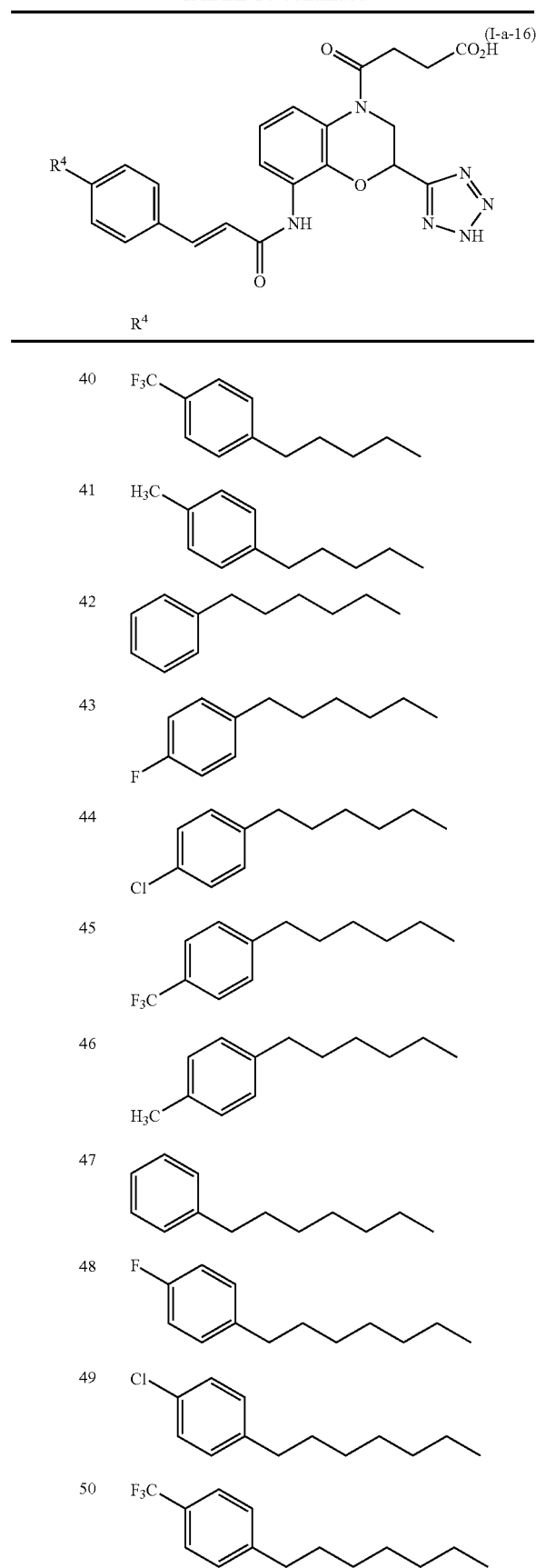

TABLE 16-continued

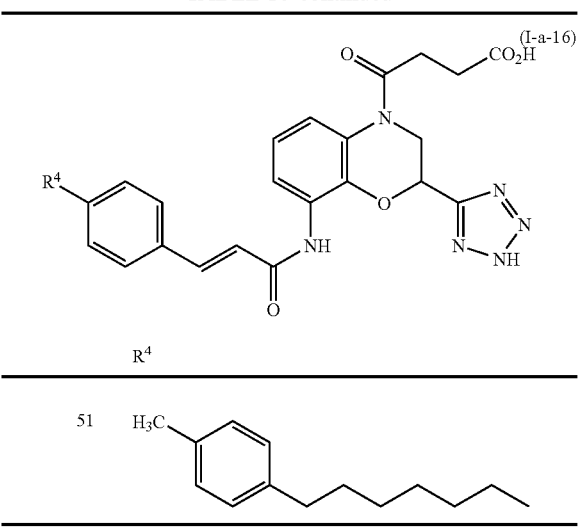
(I-a-16)

| | R⁴ |
|---|---|
| 51 | 4-heptyl-phenyl (H₃C on ring, heptyl chain) |

TABLE 17

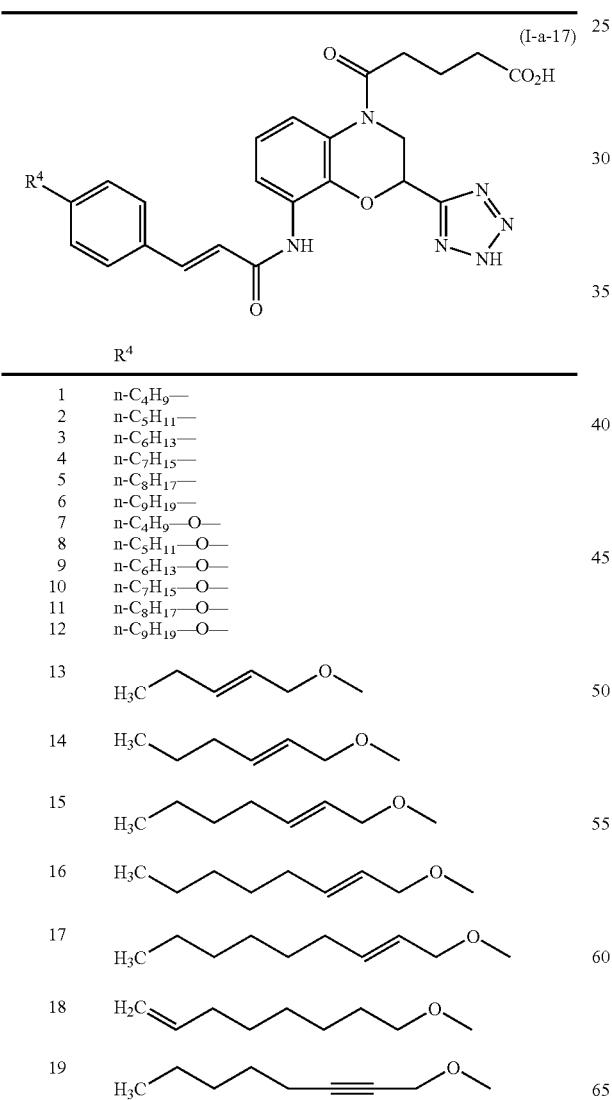
(I-a-17)

| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | H₃C—CH=CH—CH₂—O—CH₃ |
| 14 | H₃C—(CH₂)₂—CH=CH—CH₂—O—CH₃ |
| 15 | H₃C—(CH₂)₃—CH=CH—CH₂—O—CH₃ |
| 16 | H₃C—(CH₂)₄—CH=CH—CH₂—O—CH₃ |
| 17 | H₃C—(CH₂)₅—CH=CH—CH₂—O—CH₃ |
| 18 | H₂C=CH—(CH₂)₄—O—CH₃ |
| 19 | H₃C—(CH₂)₃—C≡C—CH₂—O—CH₃ |

TABLE 17-continued

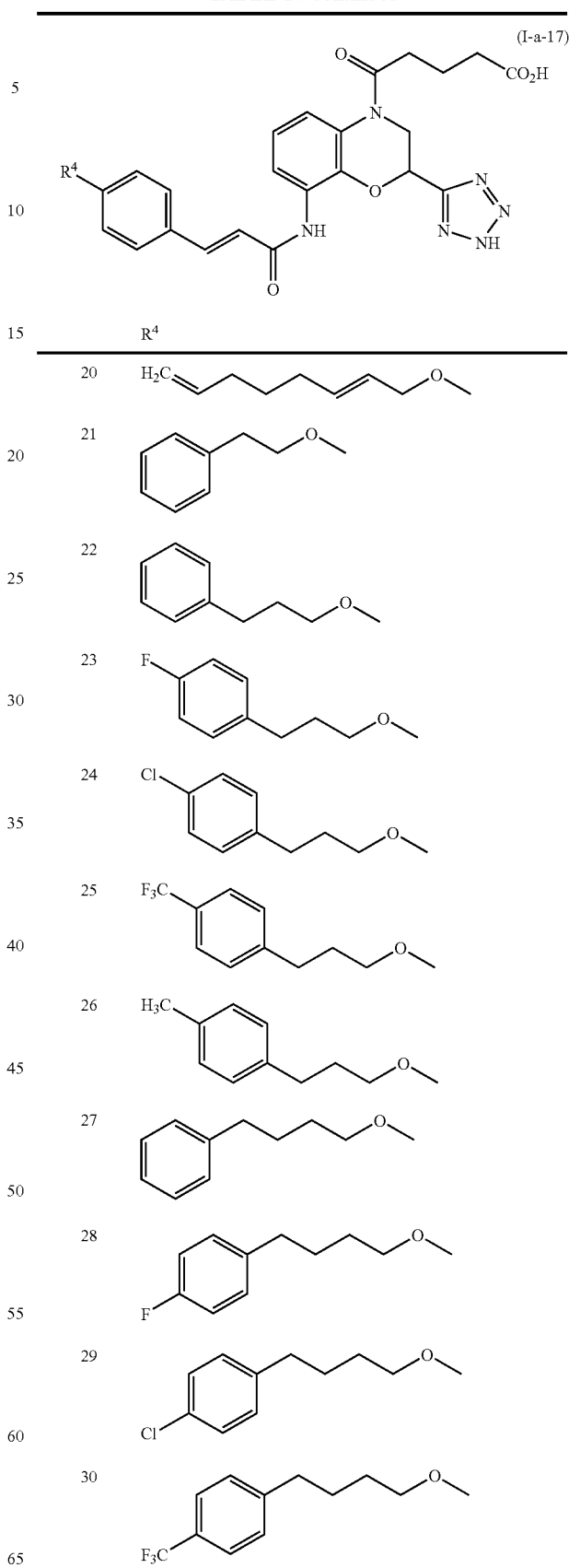
(I-a-17)

| | R⁴ |
|---|---|
| 20 | H₂C=CH—(CH₂)₂—CH=CH—CH₂—O—CH₃ |
| 21 | phenyl—(CH₂)₂—O—CH₃ |
| 22 | phenyl—(CH₂)₃—O—CH₃ |
| 23 | 4-F-phenyl—(CH₂)₃—O—CH₃ |
| 24 | 4-Cl-phenyl—(CH₂)₃—O—CH₃ |
| 25 | 4-F₃C-phenyl—(CH₂)₃—O—CH₃ |
| 26 | 4-H₃C-phenyl—(CH₂)₃—O—CH₃ |
| 27 | phenyl—(CH₂)₄—O—CH₃ |
| 28 | 4-F-phenyl—(CH₂)₄—O—CH₃ |
| 29 | 4-Cl-phenyl—(CH₂)₄—O—CH₃ |
| 30 | 4-F₃C-phenyl—(CH₂)₄—O—CH₃ |

TABLE 17-continued
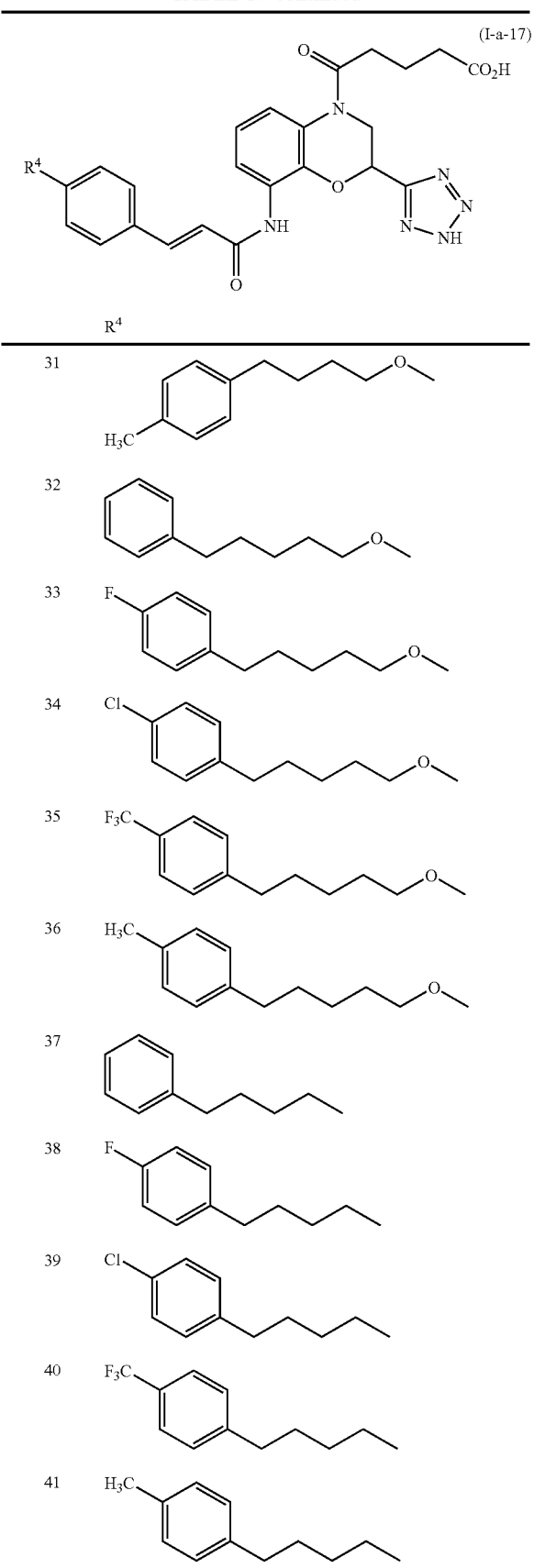
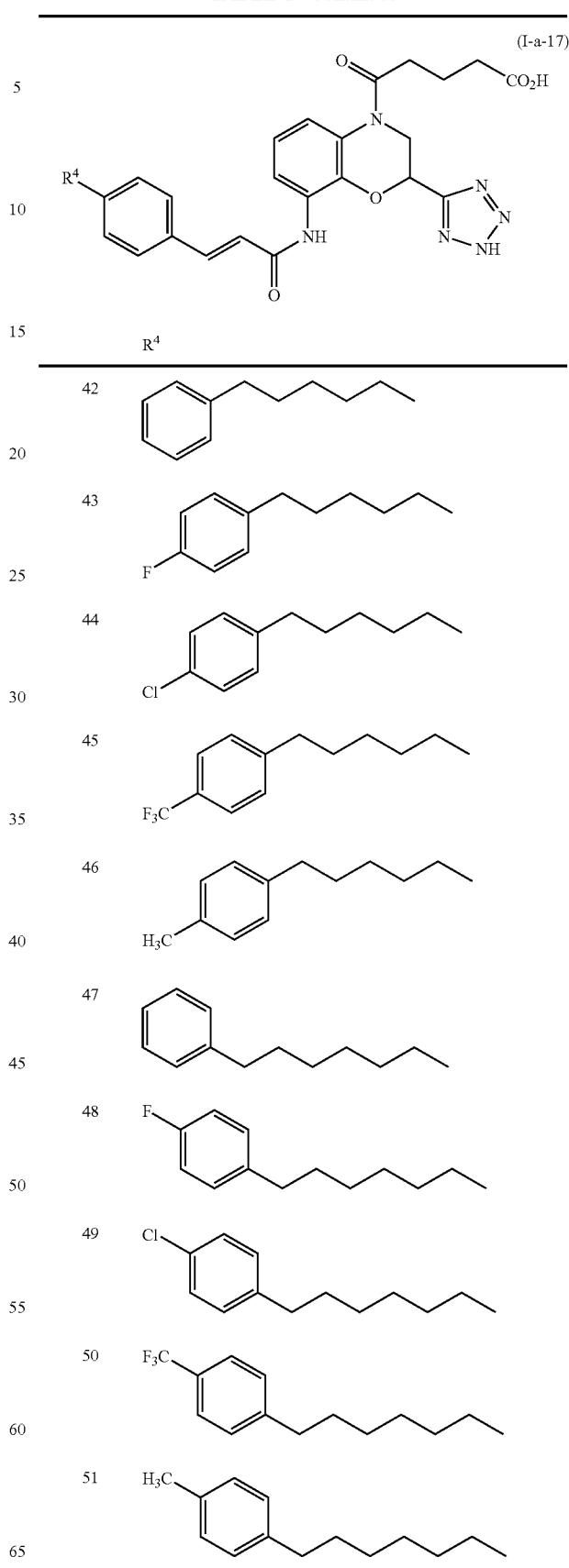

TABLE 18

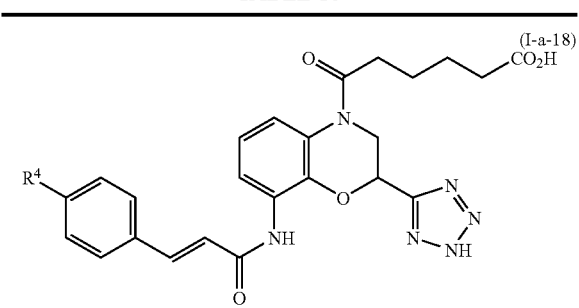

(I-a-18)

| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | H₃C—CH=CH—CH₂—O—CH₃ |
| 14 | H₃C—CH₂—CH=CH—CH₂—O—CH₃ |
| 15 | H₃C—(CH₂)₂—CH=CH—CH₂—O—CH₃ |
| 16 | H₃C—(CH₂)₃—CH=CH—CH₂—O—CH₃ |
| 17 | H₃C—(CH₂)₄—CH=CH—CH₂—O—CH₃ |
| 18 | H₂C=CH—(CH₂)₄—O—CH₃ |
| 19 | H₃C—(CH₂)₃—C≡C—CH₂—O—CH₃ |
| 20 | H₂C=CH—(CH₂)₂—CH=CH—CH₂—O—CH₃ |
| 21 | PhCH₂CH₂—O—CH₃ |
| 22 | Ph(CH₂)₃—O—CH₃ |
| 23 | 4-F-C₆H₄-(CH₂)₃—O—CH₃ |
| 24 | 4-Cl-C₆H₄-(CH₂)₃—O—CH₃ |

TABLE 18-continued

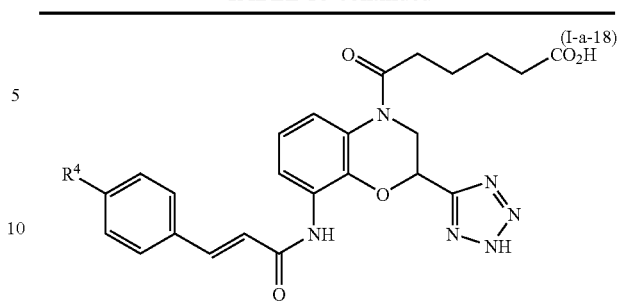

(I-a-18)

| | R⁴ |
|---|---|
| 25 | 4-F₃C-C₆H₄-(CH₂)₃—O—CH₃ |
| 26 | 4-H₃C-C₆H₄-(CH₂)₃—O—CH₃ |
| 27 | Ph-(CH₂)₄—O—CH₃ |
| 28 | 4-F-C₆H₄-(CH₂)₄—O—CH₃ |
| 29 | 4-Cl-C₆H₄-(CH₂)₄—O—CH₃ |
| 30 | 4-F₃C-C₆H₄-(CH₂)₄—O—CH₃ |
| 31 | 4-H₃C-C₆H₄-(CH₂)₄—O—CH₃ |
| 32 | Ph-(CH₂)₅—O—CH₃ |
| 33 | 4-F-C₆H₄-(CH₂)₅—O—CH₃ |
| 34 | 4-Cl-C₆H₄-(CH₂)₅—O—CH₃ |
| 35 | 4-F₃C-C₆H₄-(CH₂)₅—O—CH₃ |

TABLE 18-continued
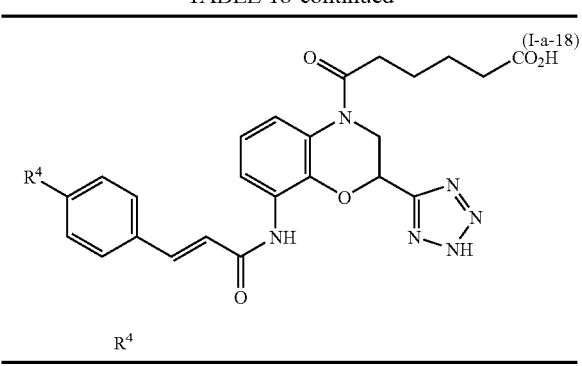
(I-a-18)
| | $R^4$ |
|---|---|
| 36 | 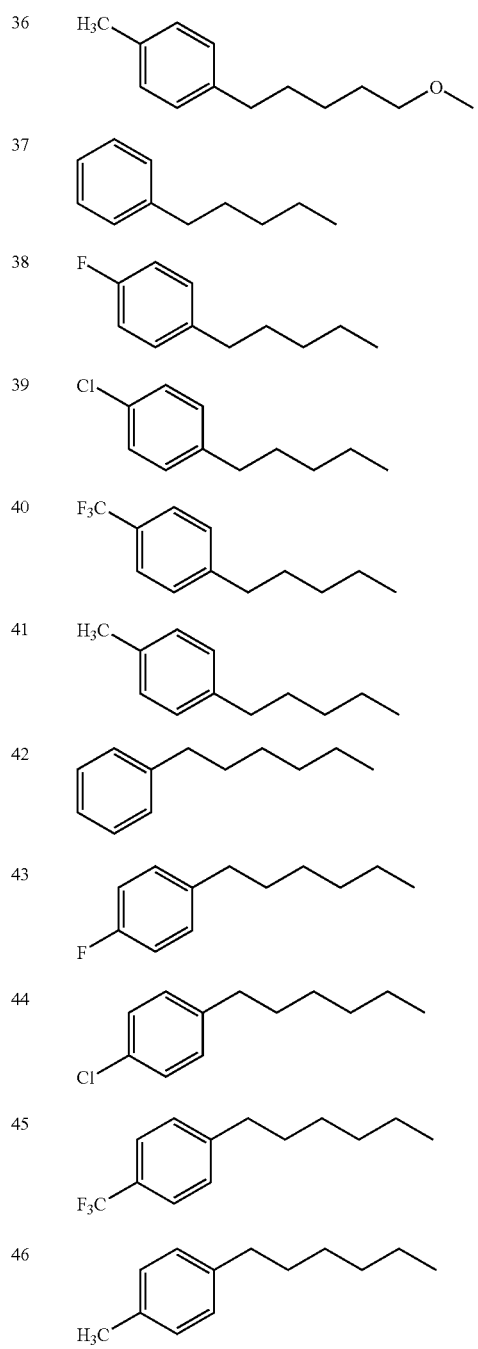 |
TABLE 18-continued
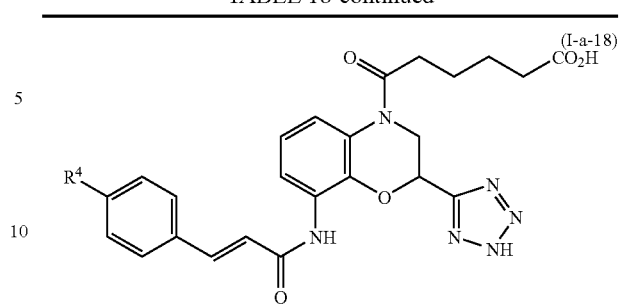
(I-a-18)
| | $R^4$ |
|---|---|
| 47 | |
| 48 | |
| 49 | |
| 50 | |
| 51 | |
TABLE 19
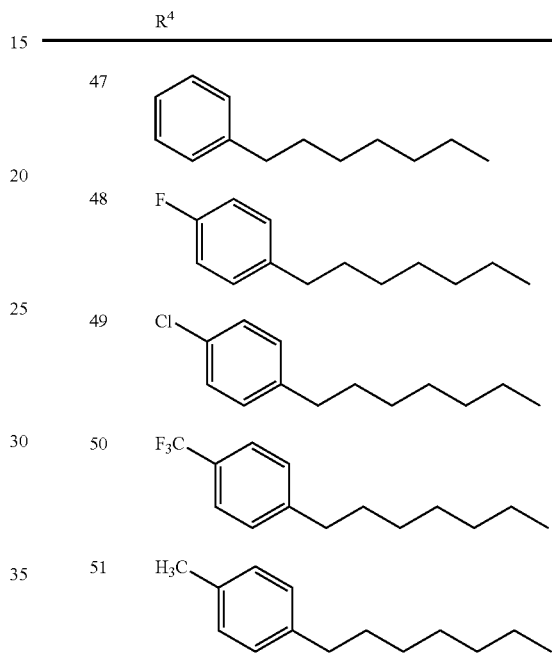
(I-a-19)
| | $R^4$ |
|---|---|
| 1 | n-C$_4$H$_9$— |
| 2 | n-C$_5$H$_{11}$— |
| 3 | n-C$_6$H$_{13}$— |
| 4 | n-C$_7$H$_{15}$— |
| 5 | n-C$_8$H$_{17}$— |
| 6 | n-C$_9$H$_{19}$— |
| 7 | n-C$_4$H$_9$—O— |
| 8 | n-C$_5$H$_{11}$—O— |
| 9 | n-C$_6$H$_{13}$—O— |
| 10 | n-C$_7$H$_{15}$—O— |
| 11 | n-C$_8$H$_{17}$—O— |
| 12 | n-C$_9$H$_{19}$—O— |

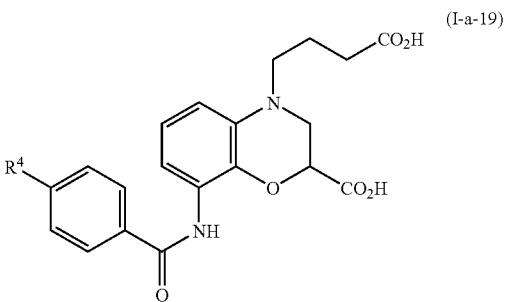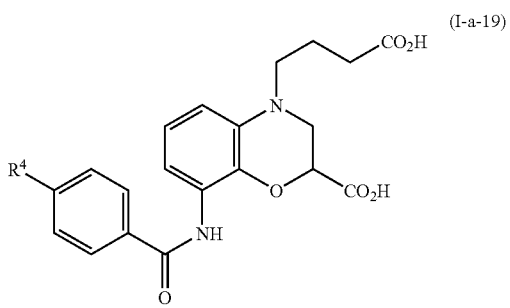

TABLE 19-continued (I-a-19)

| 37 | phenyl-pentyl |
| 38 | 4-F-phenyl-pentyl |
| 39 | 4-Cl-phenyl-pentyl |
| 40 | 4-F$_3$C-phenyl-pentyl |
| 41 | 4-H$_3$C-phenyl-pentyl |
| 42 | phenyl-hexyl |
| 43 | 4-F-phenyl-hexyl |
| 44 | 4-Cl-phenyl-hexyl |
| 45 | 4-F$_3$C-phenyl-hexyl |
| 46 | 4-H$_3$C-phenyl-hexyl |
| 47 | phenyl-heptyl |

TABLE 19-continued (I-a-19)

| 48 | 4-F-phenyl-heptyl |
| 49 | 4-Cl-phenyl-heptyl |
| 50 | 4-F$_3$C-phenyl-heptyl |
| 51 | 4-H$_3$C-phenyl-heptyl |

TABLE 20

(I-a-20)

R$^4$

| 1 | n-C$_4$H$_9$— |
| 2 | n-C$_5$H$_{11}$— |
| 3 | n-C$_6$H$_{13}$— |
| 4 | n-C$_7$H$_{15}$— |
| 5 | n-C$_8$H$_{17}$— |
| 6 | n-C$_9$H$_{19}$— |
| 7 | n-C$_4$H$_9$—O— |
| 8 | n-C$_5$H$_{11}$—O— |
| 9 | n-C$_6$H$_{13}$—O— |
| 10 | n-C$_7$H$_{15}$—O— |
| 11 | n-C$_8$H$_{17}$—O— |
| 12 | n-C$_9$H$_{19}$—O— |
| 13 | H$_3$C—CH=CH—CH$_2$—O— |
| 14 | H$_3$C—CH$_2$—CH=CH—CH$_2$—O— |

TABLE 20-continued
(I-a-20)
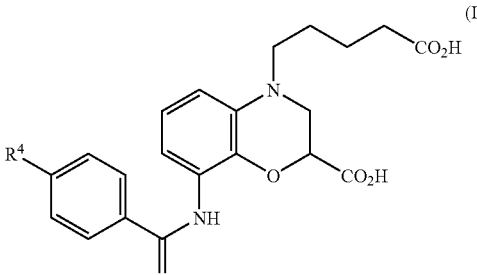
| | R⁴ |
|---|---|
| 15 | 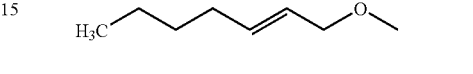 |
| 16 | 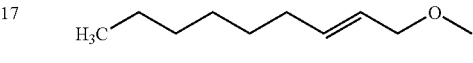 |
| 17 | 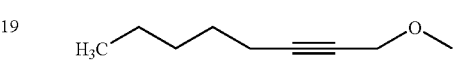 |
| 18 | 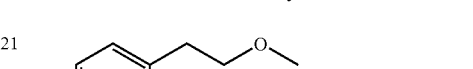 |
| 19 |  |
| 20 |  |
| 21 |  |
| 22 |  |
| 23 |  |
| 24 | 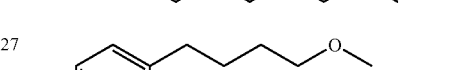 |
| 25 |  |
| 26 |  |
| 27 | 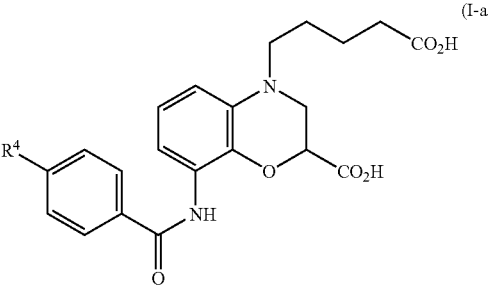 |
TABLE 20-continued
(I-a-20)
| | R⁴ |
|---|---|
| 28 |  |
| 29 |  |
| 30 |  |
| 31 | 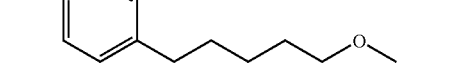 |
| 32 | 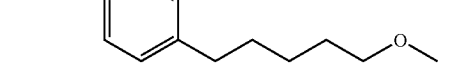 |
| 33 | 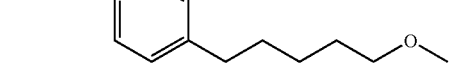 |
| 34 | 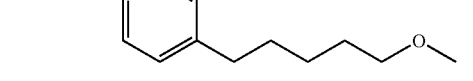 |
| 35 | 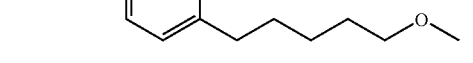 |
| 36 | 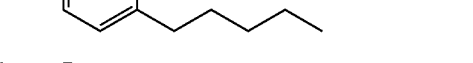 |
| 37 | 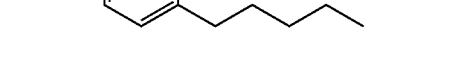 |
| 38 |  |

TABLE 20-continued
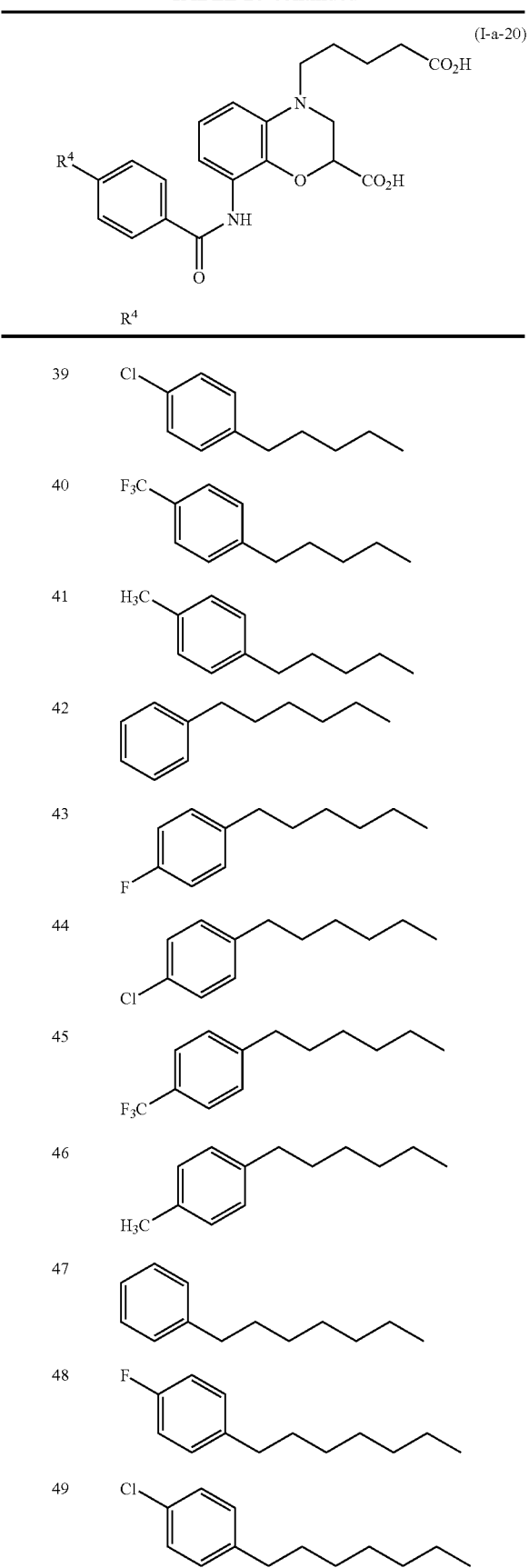
TABLE 20-continued
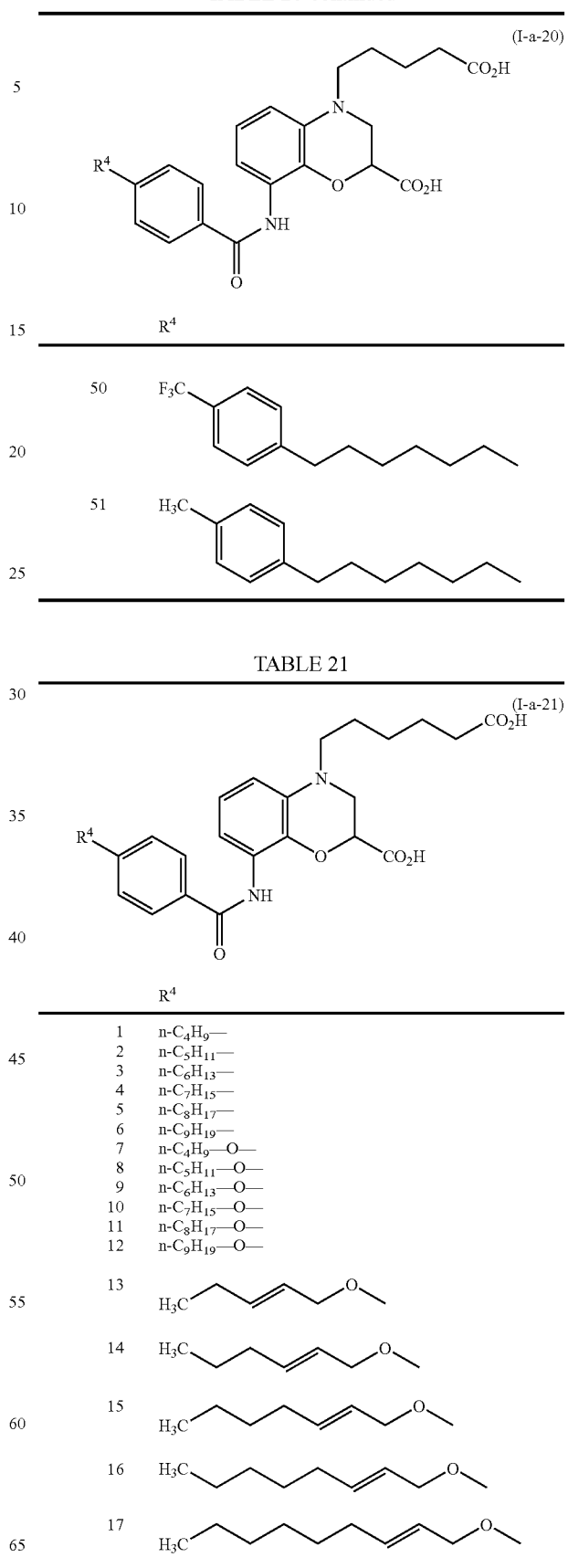

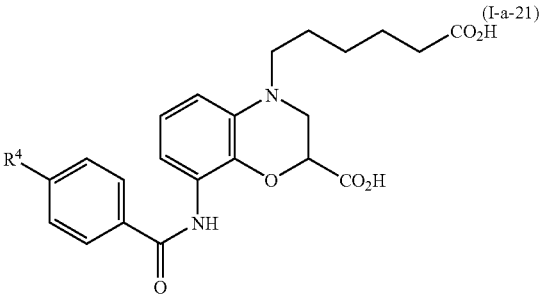

TABLE 21-continued
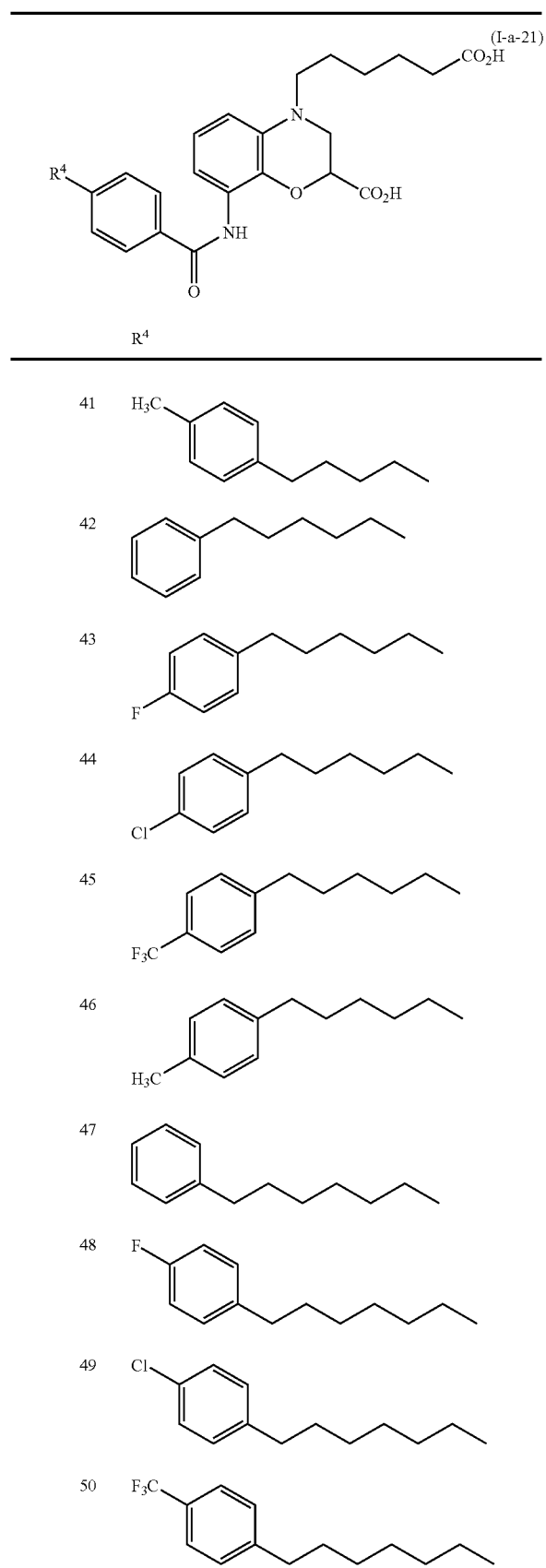
TABLE 22
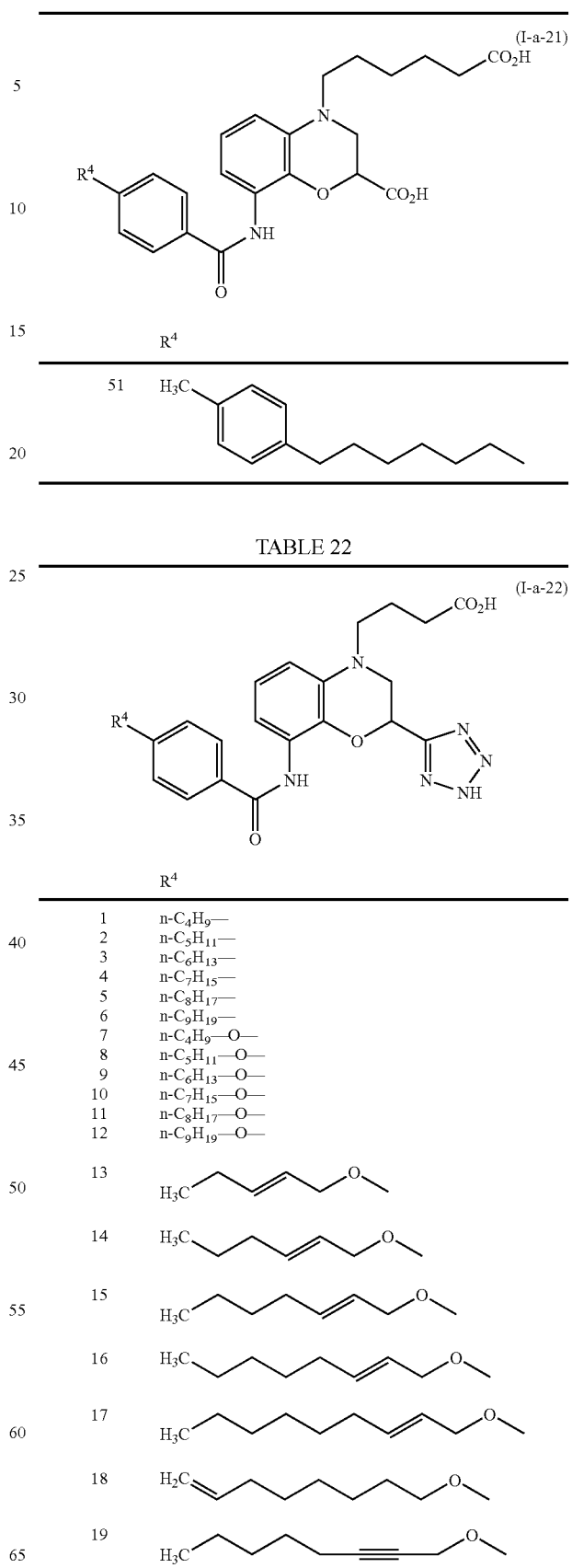

TABLE 22-continued (I-a-22)

| | R⁴ |
|---|---|
| 20 | H₂C=CH-CH₂-CH₂-CH=CH-CH₂-OCH₃ |
| 21 | Ph-CH₂-CH₂-OCH₃ |
| 22 | Ph-(CH₂)₃-OCH₃ |
| 23 | 4-F-C₆H₄-(CH₂)₃-OCH₃ |
| 24 | 4-Cl-C₆H₄-(CH₂)₃-OCH₃ |
| 25 | 4-F₃C-C₆H₄-(CH₂)₃-OCH₃ |
| 26 | 4-H₃C-C₆H₄-(CH₂)₃-OCH₃ |
| 27 | Ph-(CH₂)₄-OCH₃ |
| 28 | 4-F-C₆H₄-(CH₂)₄-OCH₃ |
| 29 | 4-Cl-C₆H₄-(CH₂)₄-OCH₃ |
| 30 | 4-F₃C-C₆H₄-(CH₂)₄-OCH₃ |
| 31 | 4-H₃C-C₆H₄-(CH₂)₄-OCH₃ |
| 32 | Ph-(CH₂)₅-OCH₃ |
| 33 | 4-F-C₆H₄-(CH₂)₅-OCH₃ |
| 34 | 4-Cl-C₆H₄-(CH₂)₅-OCH₃ |
| 35 | 4-F₃C-C₆H₄-(CH₂)₅-OCH₃ |
| 36 | 4-H₃C-C₆H₄-(CH₂)₅-OCH₃ |
| 37 | Ph-(CH₂)₄-CH₃ |
| 38 | 4-F-C₆H₄-(CH₂)₄-CH₃ |
| 39 | 4-Cl-C₆H₄-(CH₂)₄-CH₃ |
| 40 | 4-F₃C-C₆H₄-(CH₂)₄-CH₃ |
| 41 | 4-H₃C-C₆H₄-(CH₂)₄-CH₃ |

TABLE 22-continued
(I-a-22)
| | R⁴ |
|---|---|
| 42 |  |
| 43 |  |
| 44 |  |
| 45 |  |
| 46 |  |
| 47 |  |
| 48 |  |
| 49 |  |
| 50 |  |
| 51 | 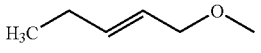 |
TABLE 23
(I-a-23)
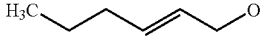
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | 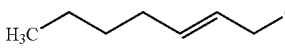 |
| 14 | 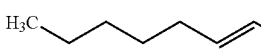 |
| 15 | 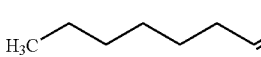 |
| 16 |  |
| 17 | 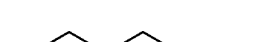 |
| 18 |  |
| 19 | 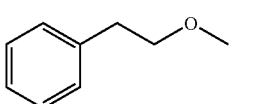 |
| 20 |  |
| 21 | 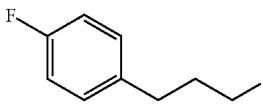 |
| 22 | 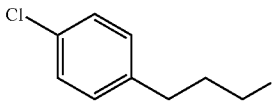 |
| 23 |  |
| 24 |  |

TABLE 23-continued (I-a-23)

| | R⁴ |
|---|---|
| 25 | 4-(trifluoromethyl)phenyl-(CH₂)₃-OCH₃ |
| 26 | 4-methylphenyl-(CH₂)₃-OCH₃ |
| 27 | phenyl-(CH₂)₄-OCH₃ |
| 28 | 4-fluorophenyl-(CH₂)₄-OCH₃ |
| 29 | 4-chlorophenyl-(CH₂)₄-OCH₃ |
| 30 | 4-(trifluoromethyl)phenyl-(CH₂)₄-OCH₃ |
| 31 | 4-methylphenyl-(CH₂)₄-OCH₃ |
| 32 | phenyl-(CH₂)₅-OCH₃ |
| 33 | 4-fluorophenyl-(CH₂)₅-OCH₃ |
| 34 | 4-chlorophenyl-(CH₂)₅-OCH₃ |
| 35 | 4-(trifluoromethyl)phenyl-(CH₂)₅-OCH₃ |
| 36 | 4-methylphenyl-(CH₂)₅-OCH₃ |
| 37 | phenyl-(CH₂)₄-CH₃ |
| 38 | 4-fluorophenyl-(CH₂)₄-CH₃ |
| 39 | 4-chlorophenyl-(CH₂)₄-CH₃ |
| 40 | 4-(trifluoromethyl)phenyl-(CH₂)₄-CH₃ |
| 41 | 4-methylphenyl-(CH₂)₄-CH₃ |
| 42 | phenyl-(CH₂)₅-CH₃ |
| 43 | 4-fluorophenyl-(CH₂)₅-CH₃ |
| 44 | 4-chlorophenyl-(CH₂)₅-CH₃ |
| 45 | 4-(trifluoromethyl)phenyl-(CH₂)₅-CH₃ |

TABLE 23-continued

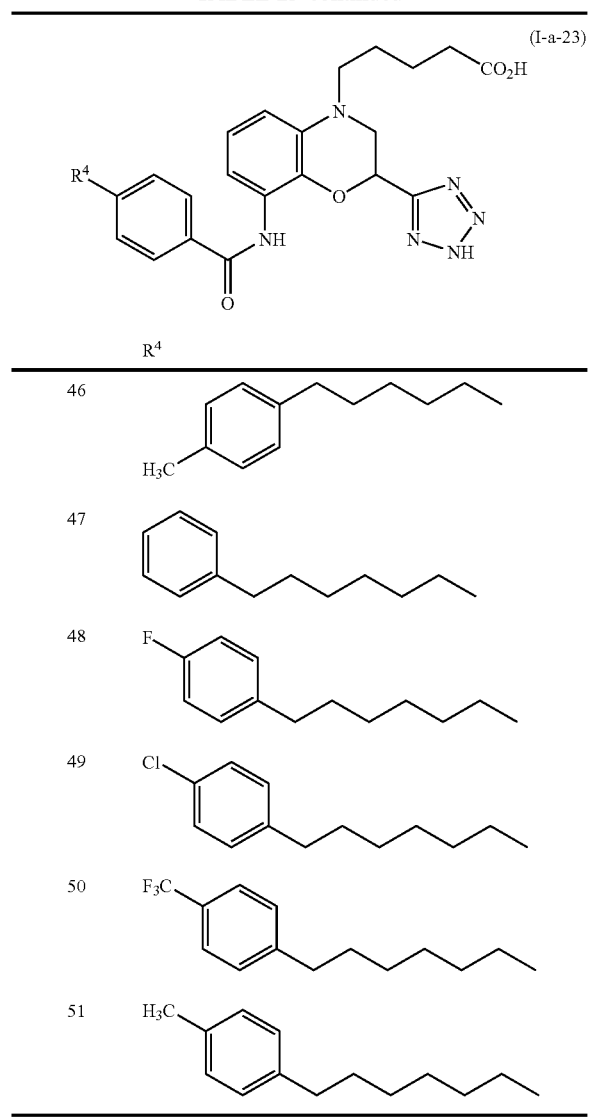

| | $R^4$ |
|---|---|
| 46 | 4-methylphenyl-hexyl (H3C-C6H4-C6H12-) |
| 47 | phenyl-heptyl |
| 48 | 4-F-phenyl-heptyl |
| 49 | 4-Cl-phenyl-heptyl |
| 50 | 4-F3C-phenyl-heptyl |
| 51 | 4-methylphenyl-heptyl |

TABLE 24

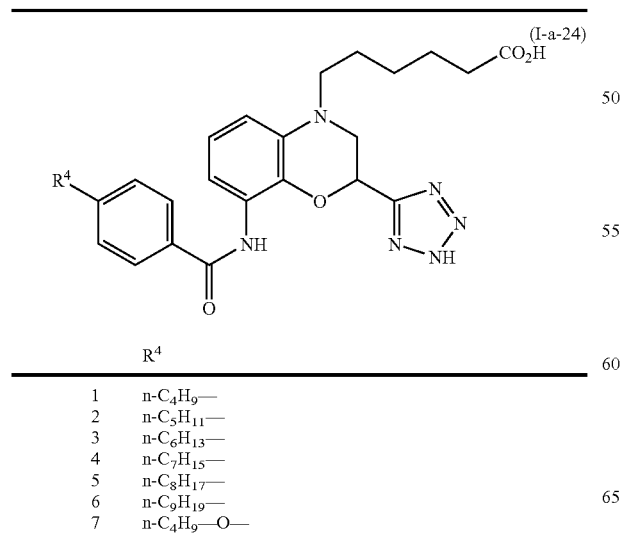

| | $R^4$ |
|---|---|
| 1 | n-$C_4H_9$— |
| 2 | n-$C_5H_{11}$— |
| 3 | n-$C_6H_{13}$— |
| 4 | n-$C_7H_{15}$— |
| 5 | n-$C_8H_{17}$— |
| 6 | n-$C_9H_{19}$— |
| 7 | n-$C_4H_9$—O— |

TABLE 24-continued

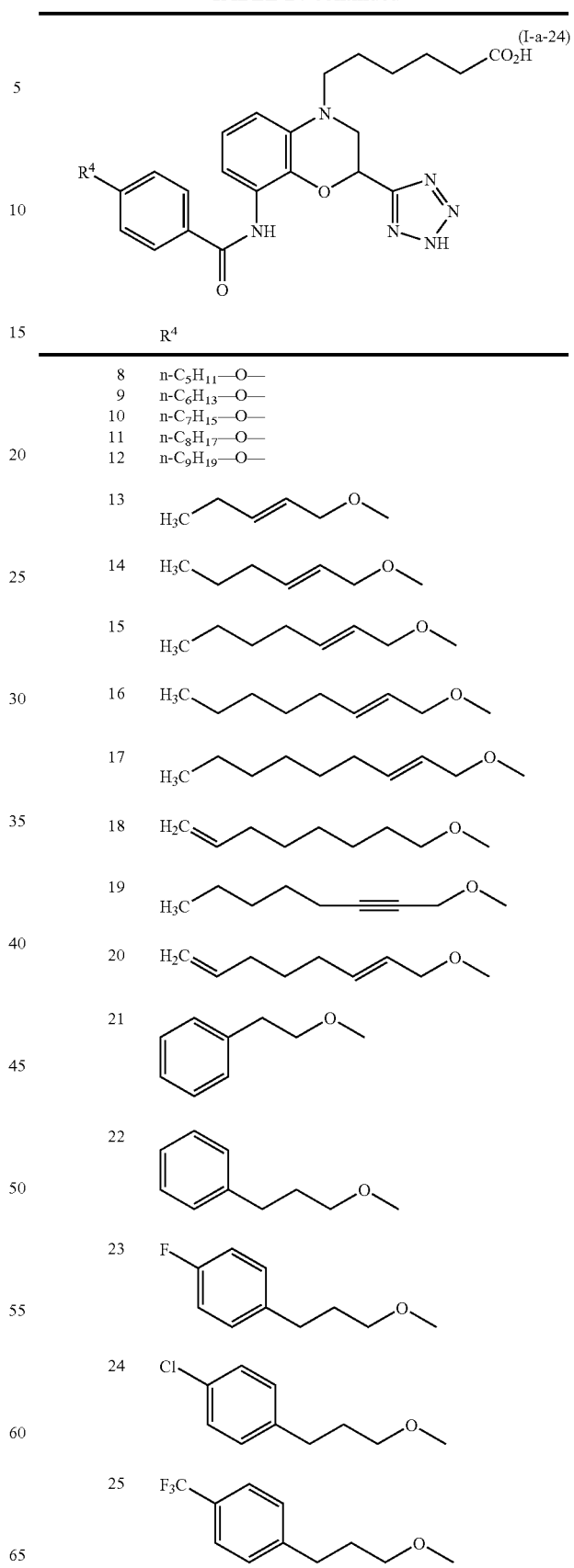

| | $R^4$ |
|---|---|
| 8 | n-$C_5H_{11}$—O— |
| 9 | n-$C_6H_{13}$—O— |
| 10 | n-$C_7H_{15}$—O— |
| 11 | n-$C_8H_{17}$—O— |
| 12 | n-$C_9H_{19}$—O— |
| 13 | $H_3C$-CH=CH-CH$_2$-O-CH$_3$ |
| 14 | $H_3C$-(CH$_2$)-CH=CH-CH$_2$-O-CH$_3$ |
| 15 | $H_3C$-(CH$_2$)$_2$-CH=CH-CH$_2$-O-CH$_3$ |
| 16 | $H_3C$-(CH$_2$)$_3$-CH=CH-CH$_2$-O-CH$_3$ |
| 17 | $H_3C$-(CH$_2$)$_4$-CH=CH-CH$_2$-O-CH$_3$ |
| 18 | $H_2C$=CH-(CH$_2$)$_4$-O-CH$_3$ |
| 19 | $H_3C$-(CH$_2$)$_3$-C≡C-CH$_2$-O-CH$_3$ |
| 20 | $H_2C$=CH-(CH$_2$)$_2$-CH=CH-CH$_2$-O-CH$_3$ |
| 21 | phenyl-CH$_2$CH$_2$-O-CH$_3$ |
| 22 | phenyl-(CH$_2$)$_3$-O-CH$_3$ |
| 23 | 4-F-phenyl-(CH$_2$)$_3$-O-CH$_3$ |
| 24 | 4-Cl-phenyl-(CH$_2$)$_3$-O-CH$_3$ |
| 25 | 4-F$_3$C-phenyl-(CH$_2$)$_3$-O-CH$_3$ |

TABLE 24-continued
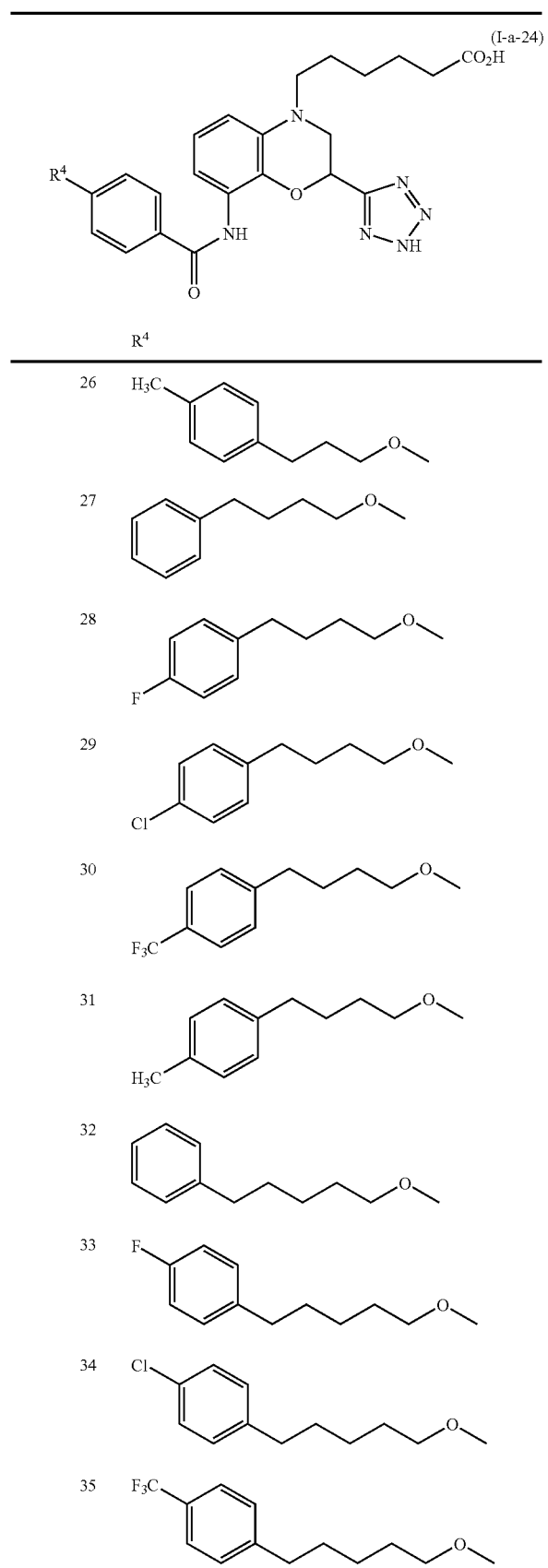
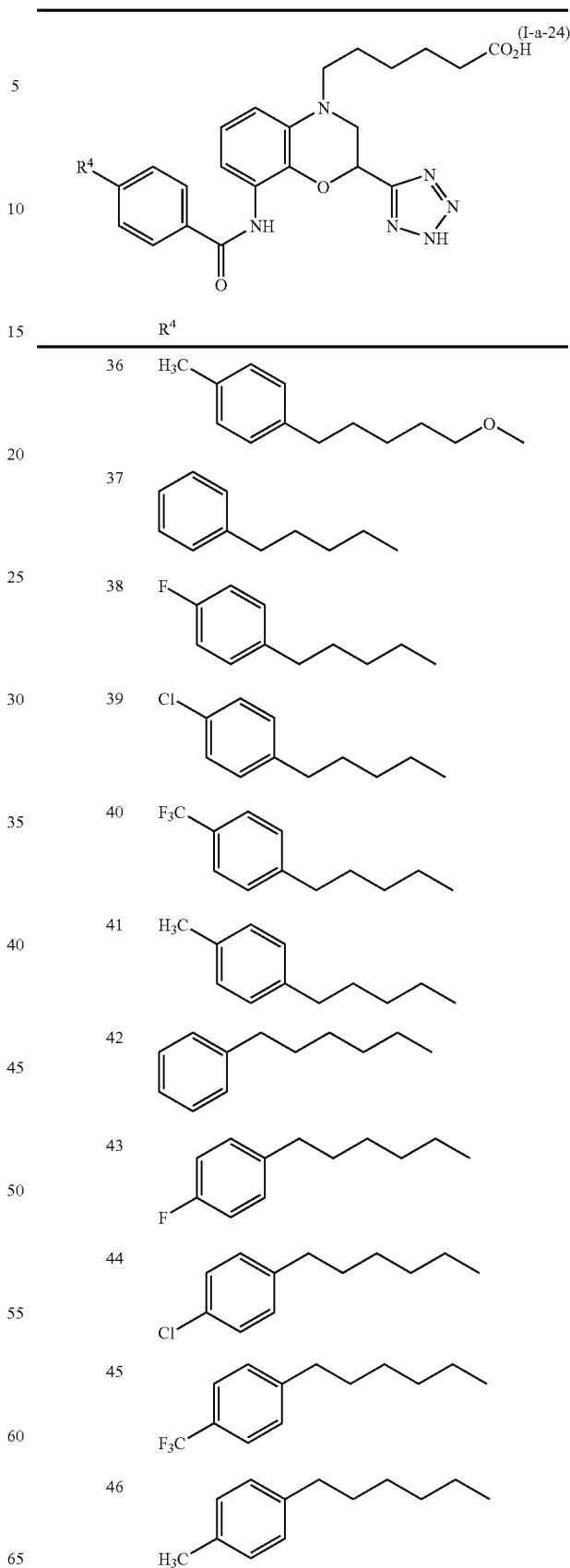

TABLE 24-continued
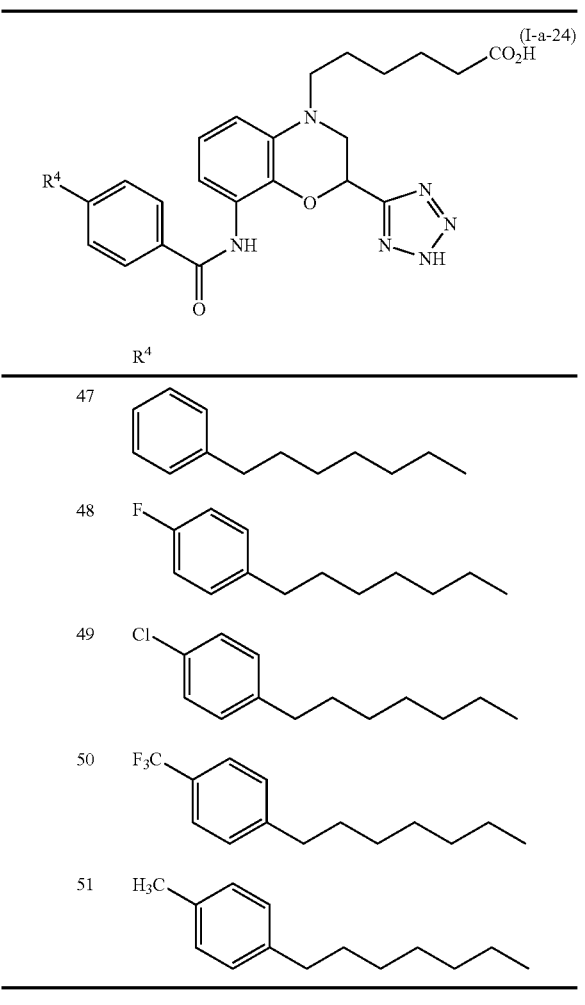
| | R⁴ |
|---|---|
| 47 | phenyl-C₆H₁₃ |
| 48 | 4-F-C₆H₄-C₆H₁₃ |
| 49 | 4-Cl-C₆H₄-C₆H₁₃ |
| 50 | 4-CF₃-C₆H₄-C₆H₁₃ |
| 51 | 4-CH₃-C₆H₄-C₆H₁₃ |
TABLE 25
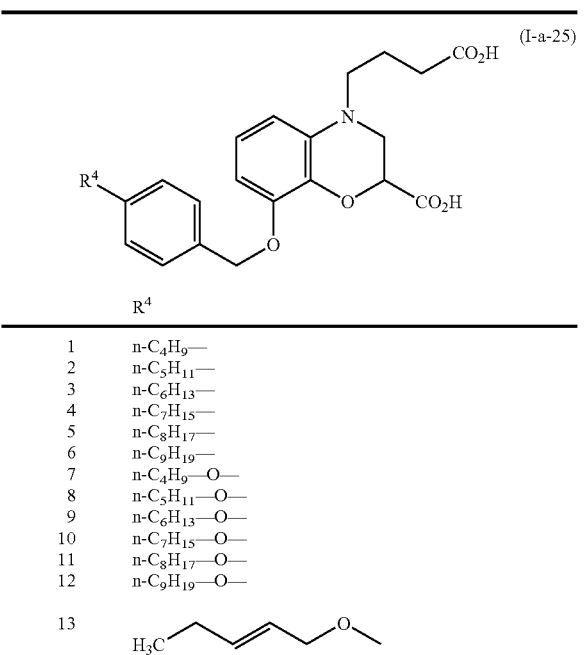
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | H₃C-CH=CH-CH₂-O-CH₃ |
TABLE 25-continued
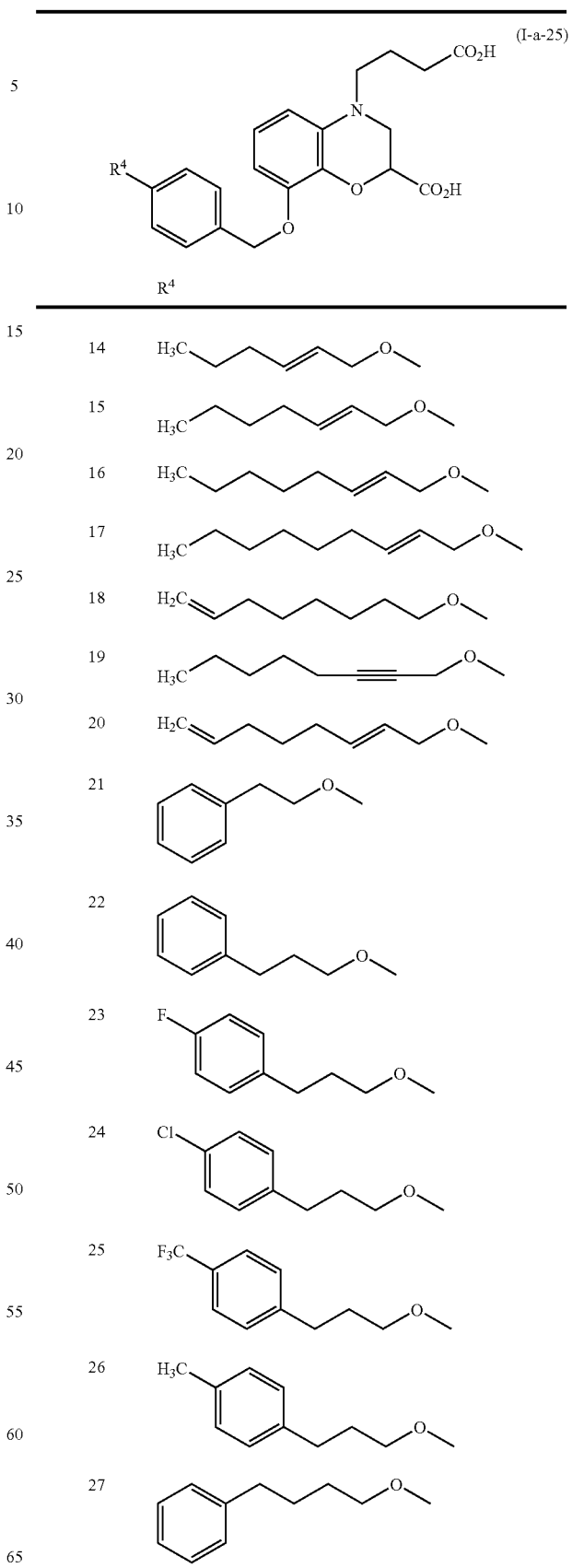

TABLE 25-continued (I-a-25)

[Structure: benzoxazine core with N-CH₂CH₂CH₂-CO₂H substituent, 2-CO₂H, and 8-O-CH₂-C₆H₄-R⁴]

| # | R⁴ |
|---|---|
| 28 | 4-F-C₆H₄-(CH₂)₃-OCH₃ |
| 29 | 4-Cl-C₆H₄-(CH₂)₃-OCH₃ |
| 30 | 4-CF₃-C₆H₄-(CH₂)₃-OCH₃ |
| 31 | 4-CH₃-C₆H₄-(CH₂)₃-OCH₃ |
| 32 | C₆H₅-(CH₂)₄-OCH₃ |
| 33 | 4-F-C₆H₄-(CH₂)₄-OCH₃ |
| 34 | 4-Cl-C₆H₄-(CH₂)₄-OCH₃ |
| 35 | 4-CF₃-C₆H₄-(CH₂)₄-OCH₃ |
| 36 | 4-CH₃-C₆H₄-(CH₂)₄-OCH₃ |
| 37 | C₆H₅-(CH₂)₄-CH₃ |
| 38 | 4-F-C₆H₄-(CH₂)₄-CH₃ |
| 39 | 4-Cl-C₆H₄-(CH₂)₄-CH₃ |
| 40 | 4-CF₃-C₆H₄-(CH₂)₄-CH₃ |
| 41 | 4-CH₃-C₆H₄-(CH₂)₄-CH₃ |
| 42 | C₆H₅-(CH₂)₅-CH₃ |
| 43 | 4-F-C₆H₄-(CH₂)₅-CH₃ |
| 44 | 4-Cl-C₆H₄-(CH₂)₅-CH₃ |
| 45 | 4-CF₃-C₆H₄-(CH₂)₅-CH₃ |
| 46 | 4-CH₃-C₆H₄-(CH₂)₅-CH₃ |
| 47 | C₆H₅-(CH₂)₆-CH₃ |
| 48 | 4-F-C₆H₄-(CH₂)₆-CH₃ |
| 49 | 4-Cl-C₆H₄-(CH₂)₆-CH₃ |

TABLE 25-continued
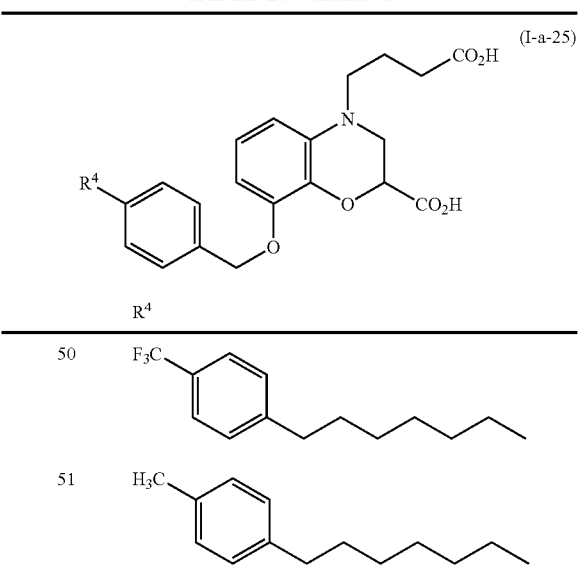
| | R⁴ |
|---|---|
| 50 | F₃C— |
| 51 | H₃C— |
TABLE 26
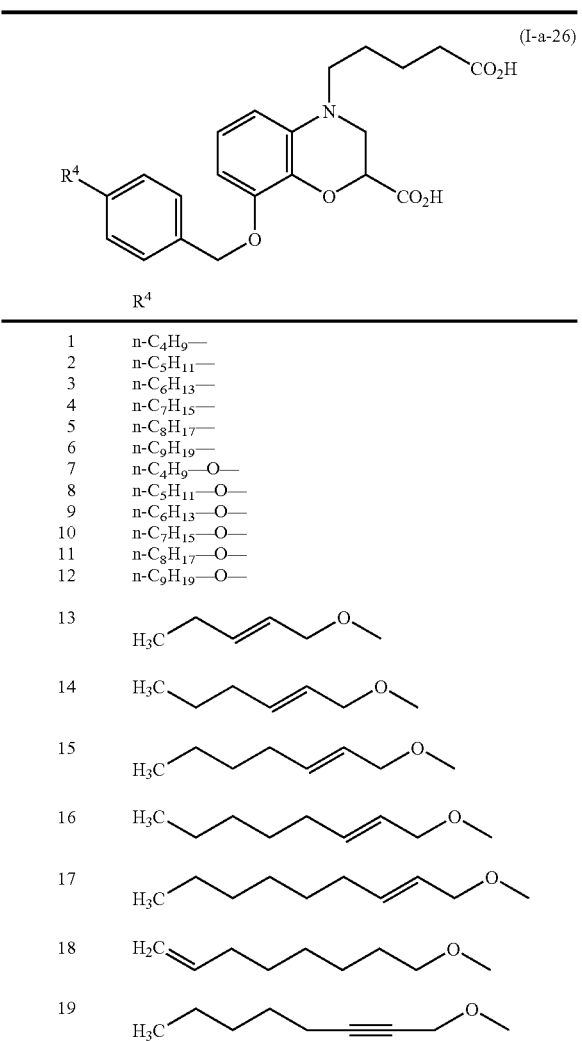
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | |
| 14 | |
| 15 | |
| 16 | |
| 17 | |
| 18 | |
| 19 | |
TABLE 26-continued
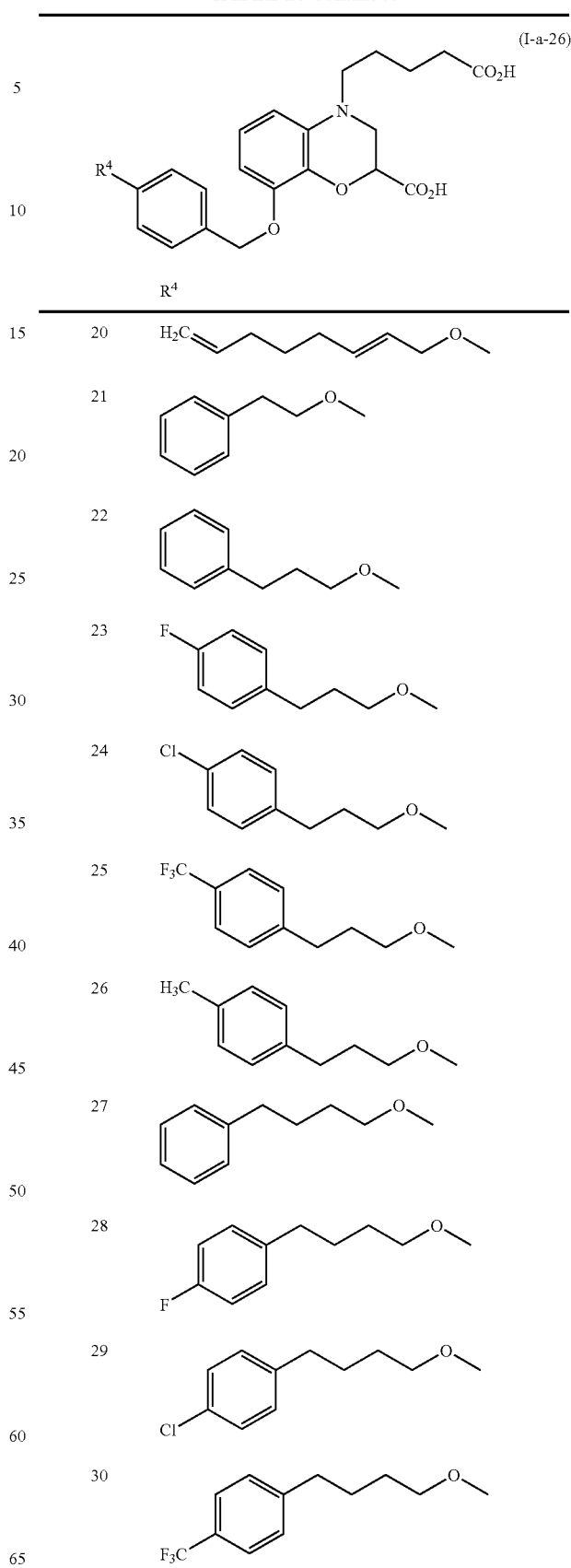

TABLE 26-continued
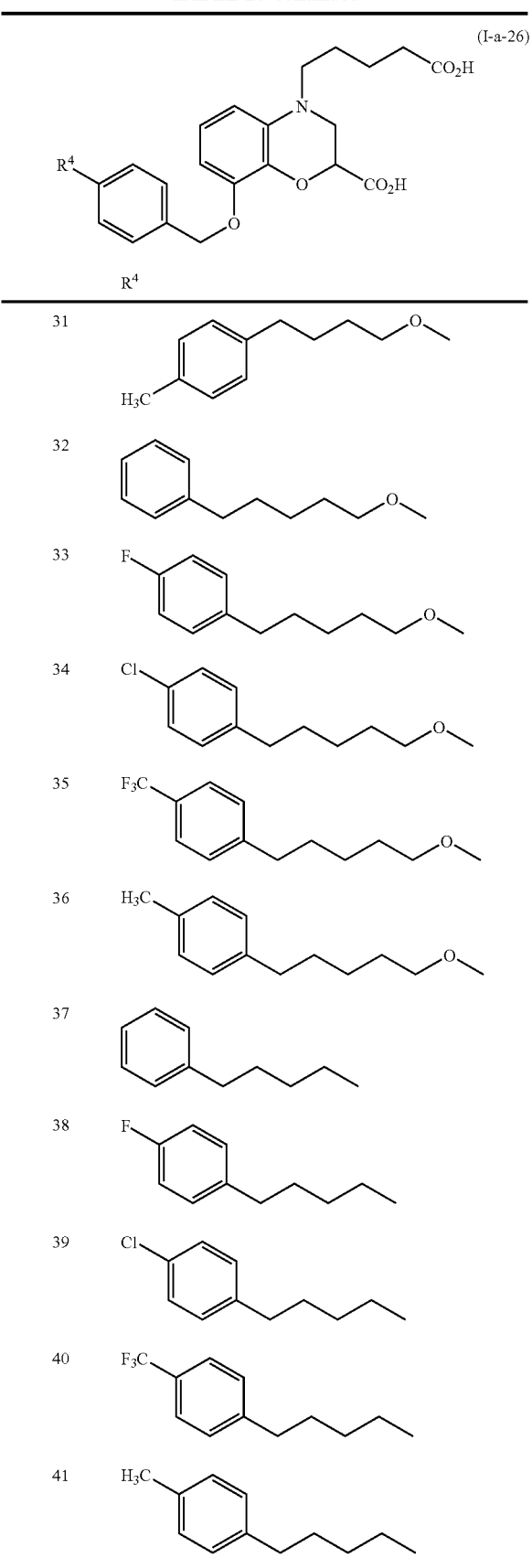
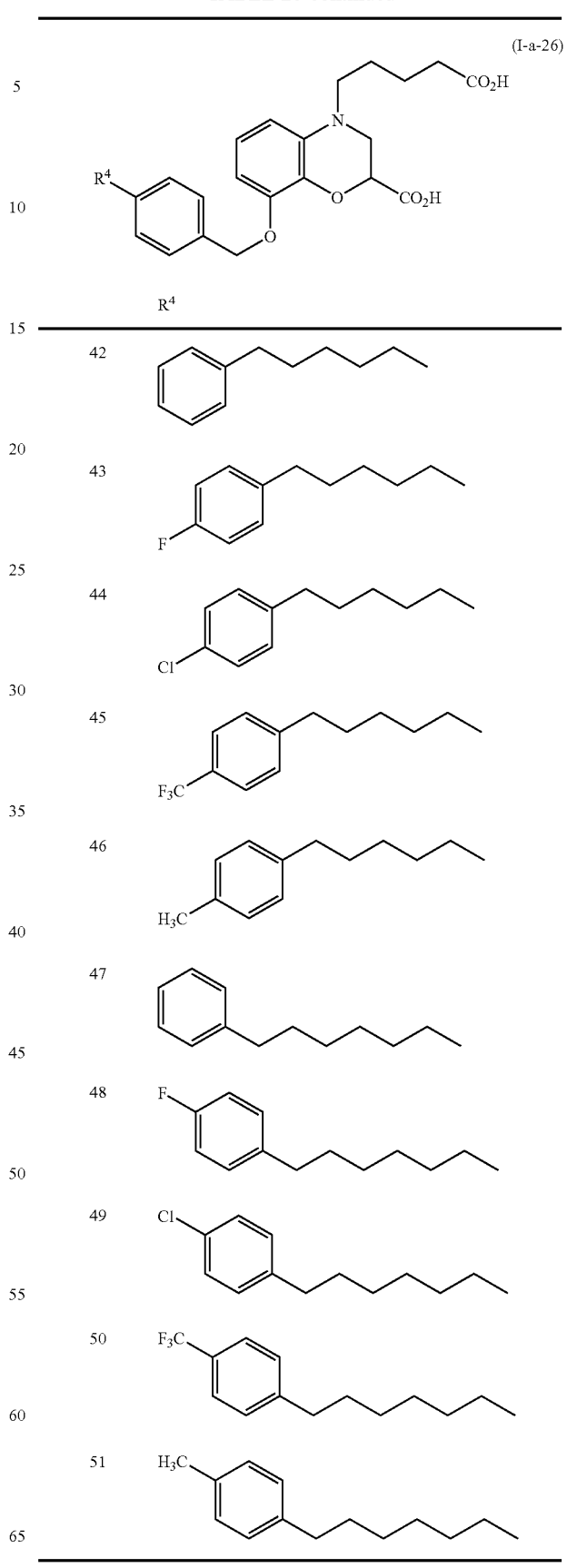

TABLE 27
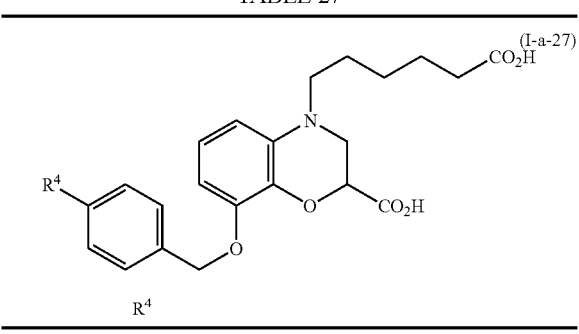
(I-a-27)
R⁴
| | R⁴ |
|---|---|
| 1 | n-C$_4$H$_9$— |
| 2 | n-C$_5$H$_{11}$— |
| 3 | n-C$_6$H$_{13}$— |
| 4 | n-C$_7$H$_{15}$— |
| 5 | n-C$_8$H$_{17}$— |
| 6 | n-C$_9$H$_{19}$— |
| 7 | n-C$_4$H$_9$—O— |
| 8 | n-C$_5$H$_{11}$—O— |
| 9 | n-C$_6$H$_{13}$—O— |
| 10 | n-C$_7$H$_{15}$—O— |
| 11 | n-C$_8$H$_{17}$—O— |
| 12 | n-C$_9$H$_{19}$—O— |
13–36: (structures as depicted)
TABLE 27-continued
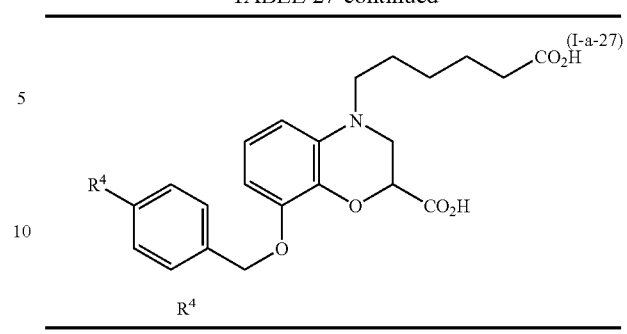
(I-a-27)

TABLE 27-continued
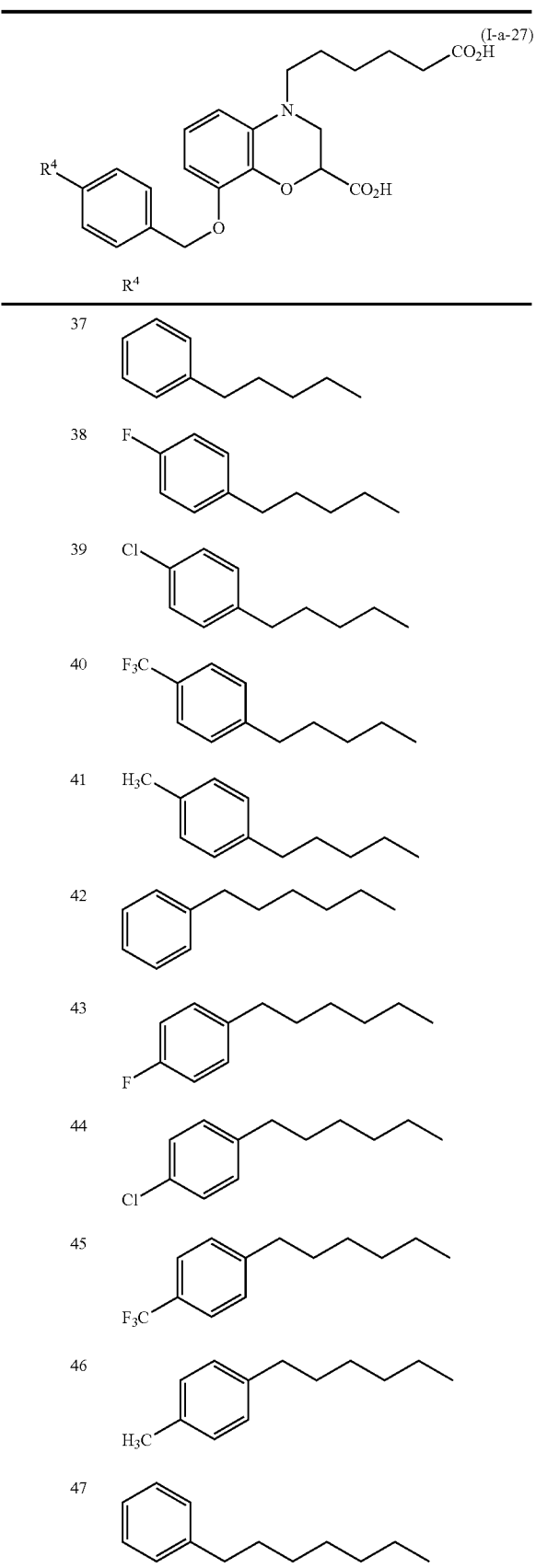
TABLE 27-continued
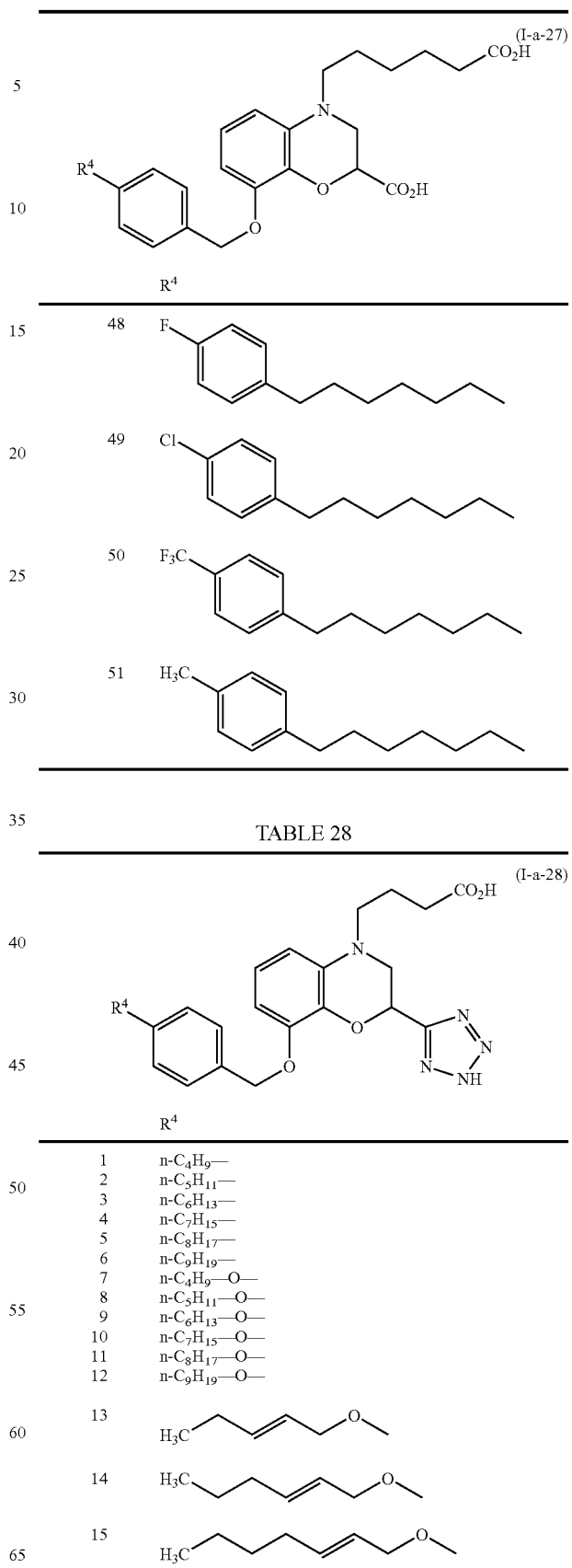
TABLE 28
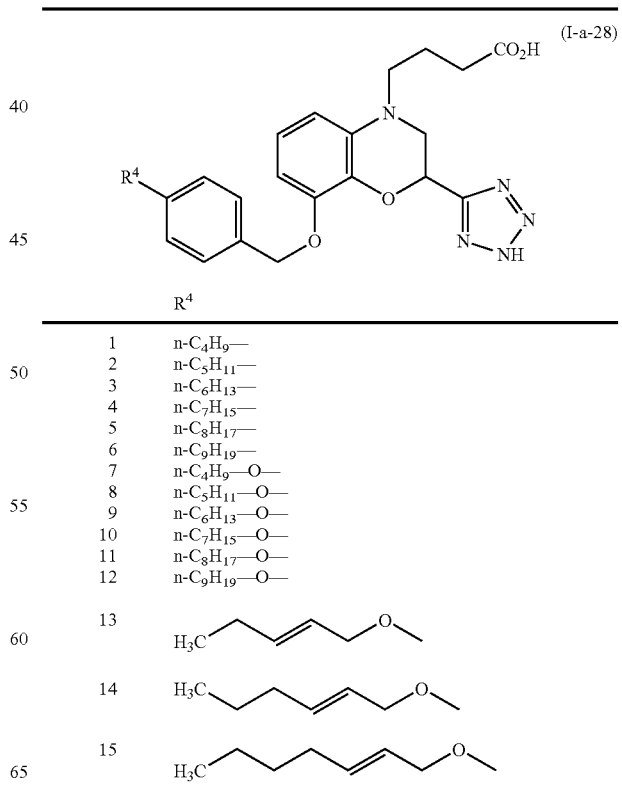
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |

TABLE 28-continued (I-a-28)

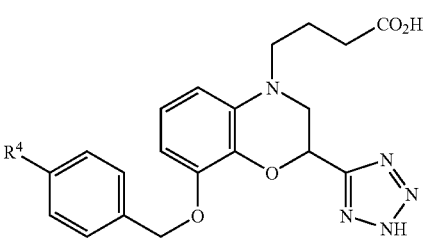

| | R⁴ |
|---|---|
| 16 | H₃C–CH₂–CH₂–CH=CH–CH₂–O–CH₃ |
| 17 | H₃C–CH₂–CH₂–CH₂–CH=CH–CH₂–O–CH₃ |
| 18 | H₂C=CH–CH₂–CH₂–CH₂–CH₂–O–CH₃ |
| 19 | H₃C–CH₂–CH₂–C≡C–CH₂–O–CH₃ |
| 20 | H₂C=CH–CH₂–CH₂–CH=CH–CH₂–O–CH₃ |
| 21 | phenyl–CH₂–CH₂–O–CH₃ |
| 22 | phenyl–CH₂–CH₂–CH₂–O–CH₃ |
| 23 | 4-F-phenyl–CH₂–CH₂–CH₂–O–CH₃ |
| 24 | 4-Cl-phenyl–CH₂–CH₂–CH₂–O–CH₃ |
| 25 | 4-F₃C-phenyl–CH₂–CH₂–CH₂–O–CH₃ |
| 26 | 4-H₃C-phenyl–CH₂–CH₂–CH₂–O–CH₃ |
| 27 | phenyl–CH₂–CH₂–CH₂–CH₂–O–CH₃ |
| 28 | 4-F-phenyl–CH₂–CH₂–CH₂–CH₂–O–CH₃ |

TABLE 28-continued (I-a-28)

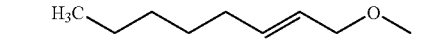

| | R⁴ |
|---|---|
| 29 | 4-Cl-phenyl–CH₂–CH₂–CH₂–CH₂–O–CH₃ |
| 30 | 4-F₃C-phenyl–CH₂–CH₂–CH₂–CH₂–O–CH₃ |
| 31 | 4-H₃C-phenyl–CH₂–CH₂–CH₂–CH₂–O–CH₃ |
| 32 | phenyl–CH₂–CH₂–CH₂–CH₂–CH₂–O–CH₃ |
| 33 | 4-F-phenyl–CH₂–CH₂–CH₂–CH₂–CH₂–O–CH₃ |
| 34 | 4-Cl-phenyl–CH₂–CH₂–CH₂–CH₂–CH₂–O–CH₃ |
| 35 | 4-F₃C-phenyl–CH₂–CH₂–CH₂–CH₂–CH₂–O–CH₃ |
| 36 | 4-H₃C-phenyl–CH₂–CH₂–CH₂–CH₂–CH₂–O–CH₃ |
| 37 | phenyl–CH₂–CH₂–CH₂–CH₂–CH₃ |
| 38 | 4-F-phenyl–CH₂–CH₂–CH₂–CH₂–CH₃ |
| 39 | 4-Cl-phenyl–CH₂–CH₂–CH₂–CH₂–CH₃ |

TABLE 28-continued
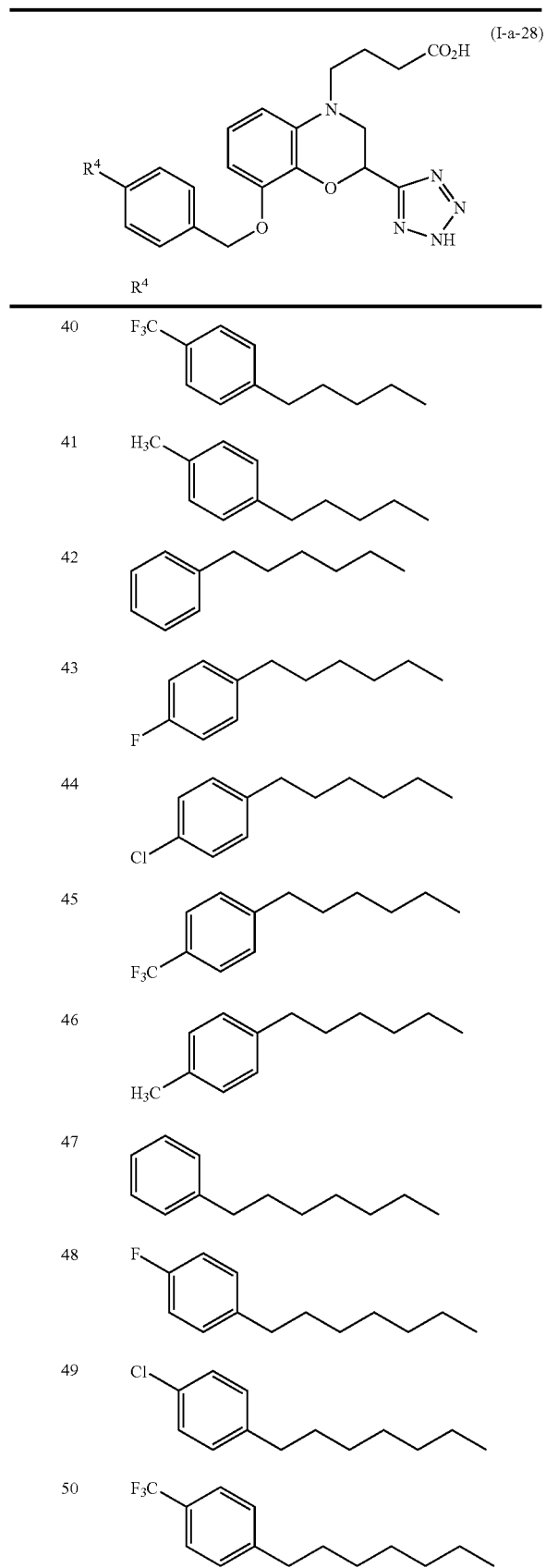
TABLE 28-continued
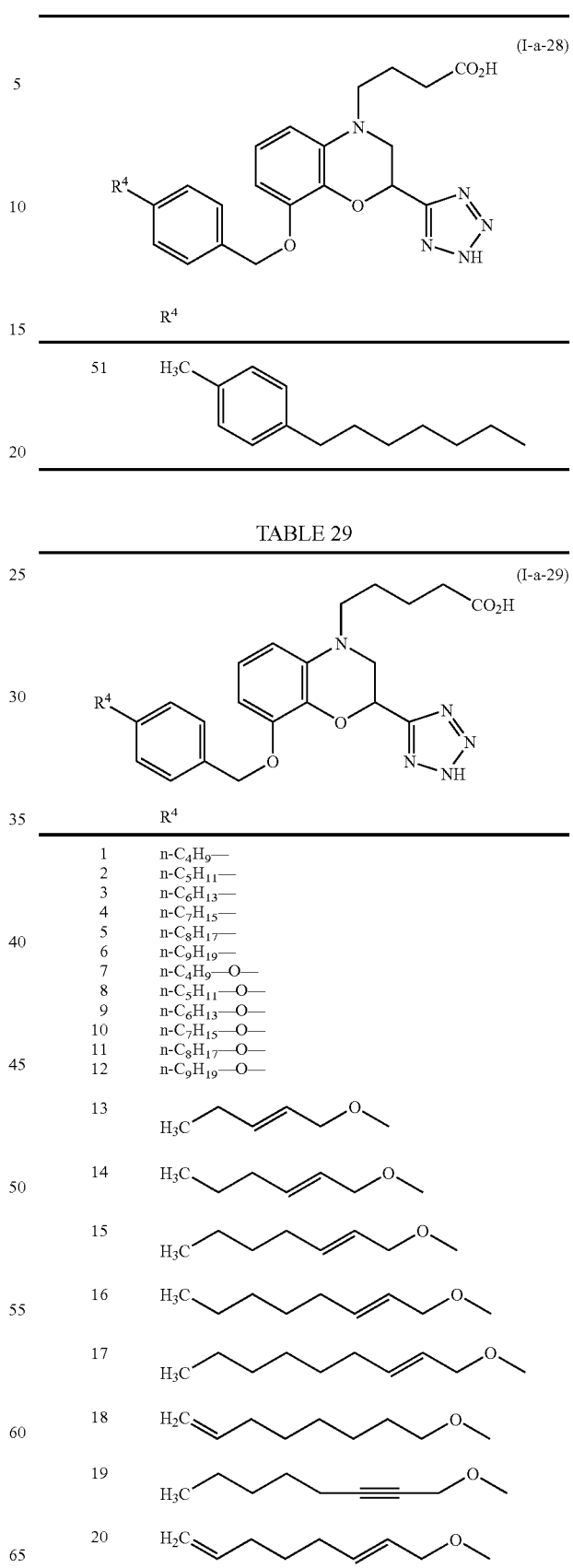

TABLE 29-continued (I-a-29)

| | R⁴ |
|---|---|
| 21 | phenyl-(CH₂)₂-OCH₃ |
| 22 | phenyl-(CH₂)₃-OCH₃ |
| 23 | 4-F-phenyl-(CH₂)₃-OCH₃ |
| 24 | 4-Cl-phenyl-(CH₂)₃-OCH₃ |
| 25 | 4-F₃C-phenyl-(CH₂)₃-OCH₃ |
| 26 | 4-H₃C-phenyl-(CH₂)₃-OCH₃ |
| 27 | phenyl-(CH₂)₄-OCH₃ |
| 28 | 4-F-phenyl-(CH₂)₄-OCH₃ |
| 29 | 4-Cl-phenyl-(CH₂)₄-OCH₃ |
| 30 | 4-F₃C-phenyl-(CH₂)₄-OCH₃ |
| 31 | 4-H₃C-phenyl-(CH₂)₄-OCH₃ |
| 32 | phenyl-(CH₂)₅-OCH₃ |
| 33 | 4-F-phenyl-(CH₂)₅-OCH₃ |
| 34 | 4-Cl-phenyl-(CH₂)₅-OCH₃ |
| 35 | 4-F₃C-phenyl-(CH₂)₅-OCH₃ |
| 36 | 4-H₃C-phenyl-(CH₂)₅-OCH₃ |
| 37 | phenyl-(CH₂)₄-CH₃ |
| 38 | 4-F-phenyl-(CH₂)₄-CH₃ |
| 39 | 4-Cl-phenyl-(CH₂)₄-CH₃ |
| 40 | 4-F₃C-phenyl-(CH₂)₄-CH₃ |
| 41 | 4-H₃C-phenyl-(CH₂)₄-CH₃ |
| 42 | phenyl-(CH₂)₅-CH₃ |

TABLE 29-continued
(I-a-29)
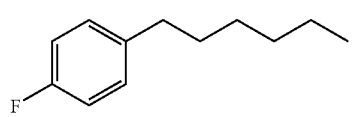
| | R⁴ |
|---|---|
| 43 | 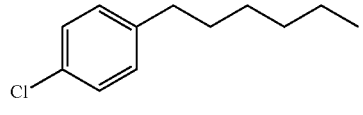 |
| 44 | 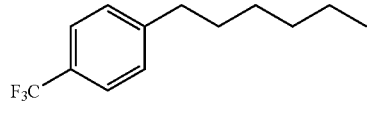 |
| 45 | 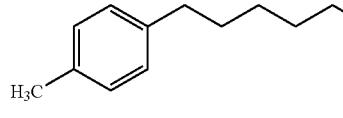 |
| 46 | 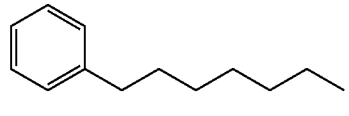 |
| 47 | 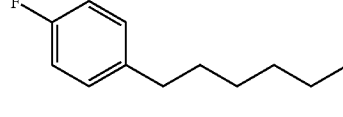 |
| 48 | 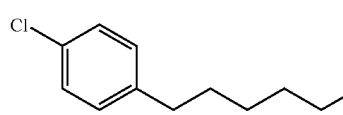 |
| 49 | 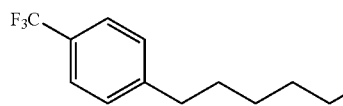 |
| 50 | 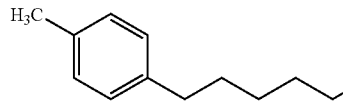 |
| 51 | 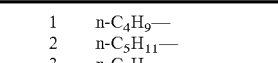 |
TABLE 30
(I-a-30)
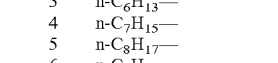
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | 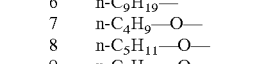 |
| 14 | 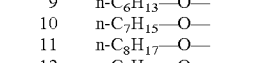 |
| 15 | 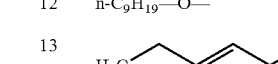 |
| 16 | 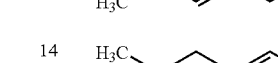 |
| 17 | 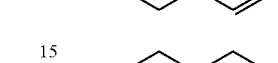 |
| 18 | 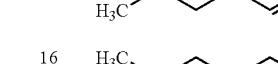 |
| 19 | 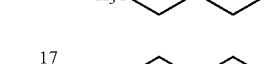 |
| 20 | 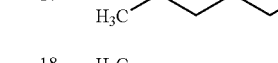 |
| 21 | 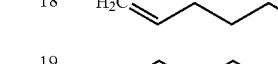 |
| 22 | 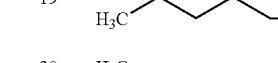 |
| 23 | 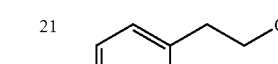 |
| 24 | 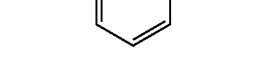 |
| 25 | 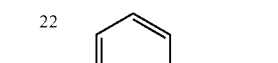 |

TABLE 30-continued
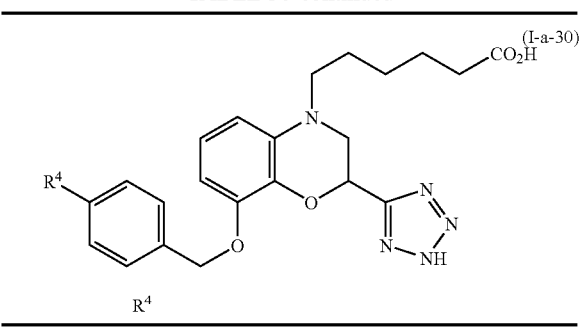
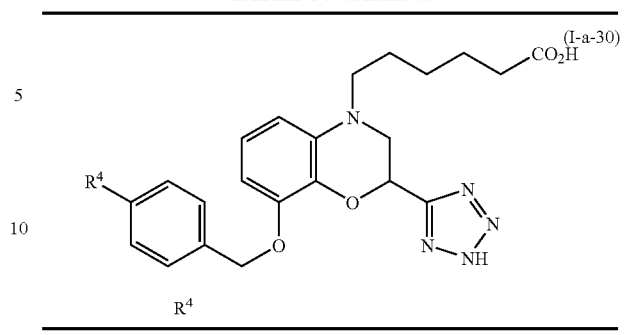

TABLE 30-continued

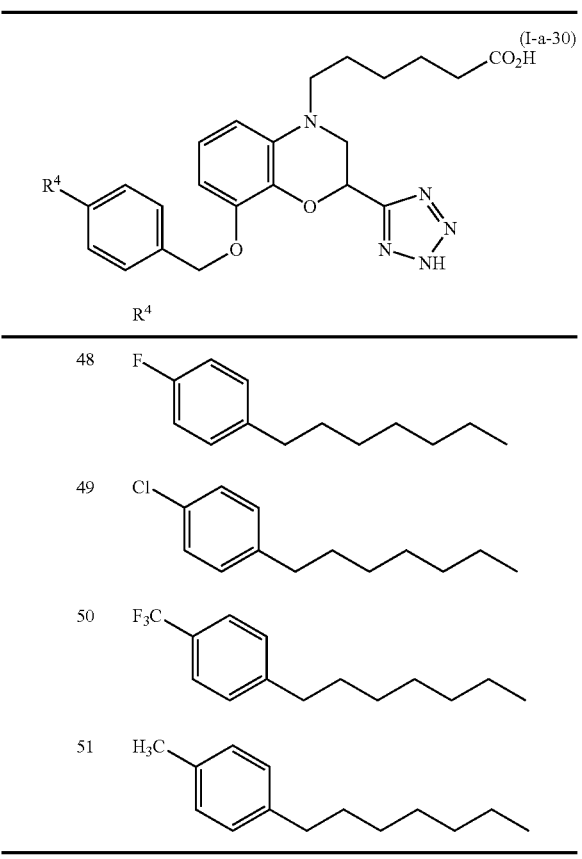

(I-a-30)

| | R⁴ |
|---|---|
| 48 | 4-F-C₆H₄- (hexyl) |
| 49 | 4-Cl-C₆H₄- (hexyl) |
| 50 | 4-F₃C-C₆H₄- (hexyl) |
| 51 | 4-H₃C-C₆H₄- (hexyl) |

TABLE 31

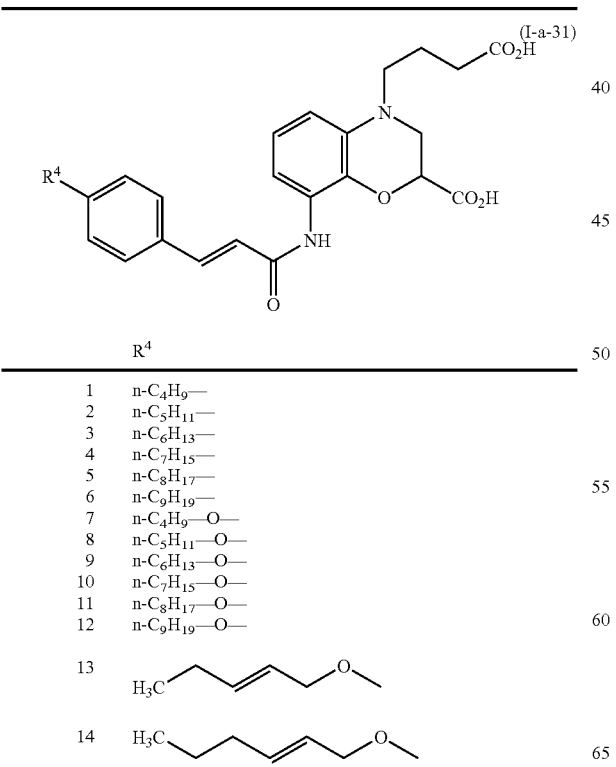

(I-a-31)

| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | H₃C-CH=CH-CH₂-O- |
| 14 | H₃C-(CH₂)₂-CH=CH-CH₂-O- |

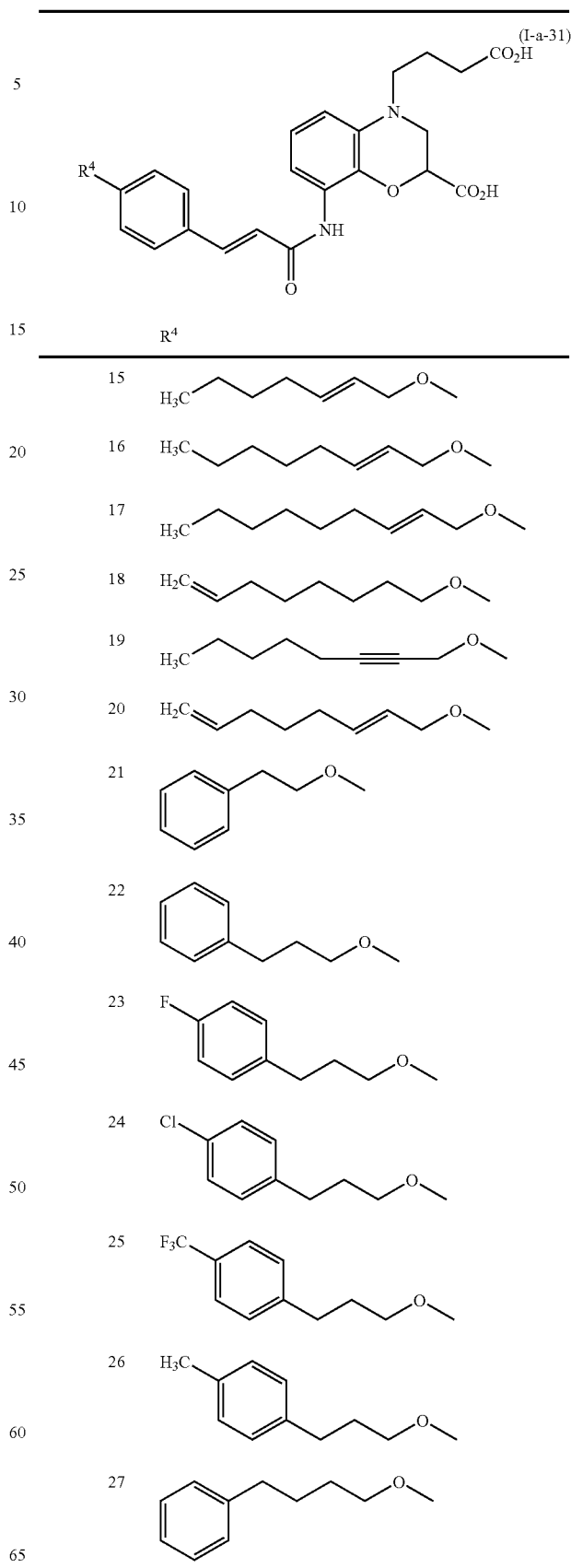

TABLE 31-continued (I-a-31)

| | R⁴ |
|---|---|
| 15 | H₃C-CH=CH-CH₂-O- variant |
| 16 | H₃C-(CH₂)₃-CH=CH-CH₂-O- |
| 17 | H₃C-(CH₂)₄-CH=CH-CH₂-O- |
| 18 | H₂C=CH-(CH₂)₄-O- |
| 19 | H₃C-(CH₂)₃-C≡C-CH₂-O- |
| 20 | H₂C=CH-(CH₂)₂-CH=CH-CH₂-O- |
| 21 | Ph-CH₂-CH₂-O- |
| 22 | Ph-(CH₂)₃-O- |
| 23 | 4-F-C₆H₄-(CH₂)₃-O- |
| 24 | 4-Cl-C₆H₄-(CH₂)₃-O- |
| 25 | 4-F₃C-C₆H₄-(CH₂)₃-O- |
| 26 | 4-H₃C-C₆H₄-(CH₂)₃-O- |
| 27 | Ph-(CH₂)₄-O- |

TABLE 31-continued
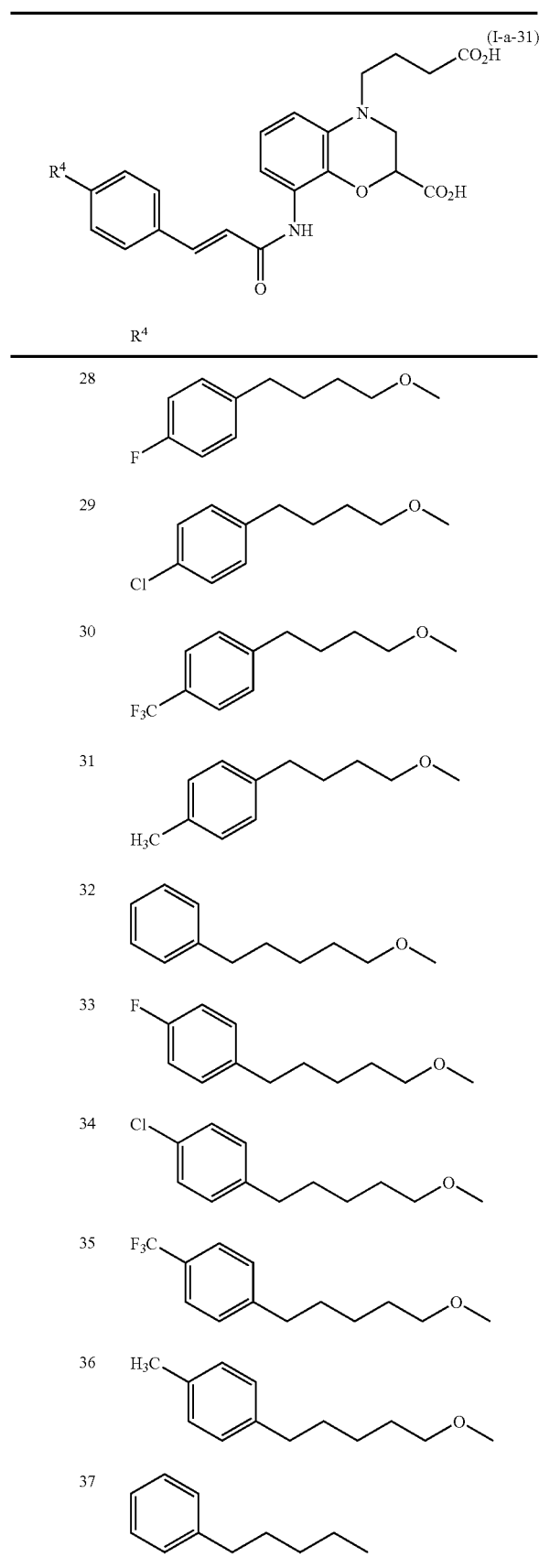
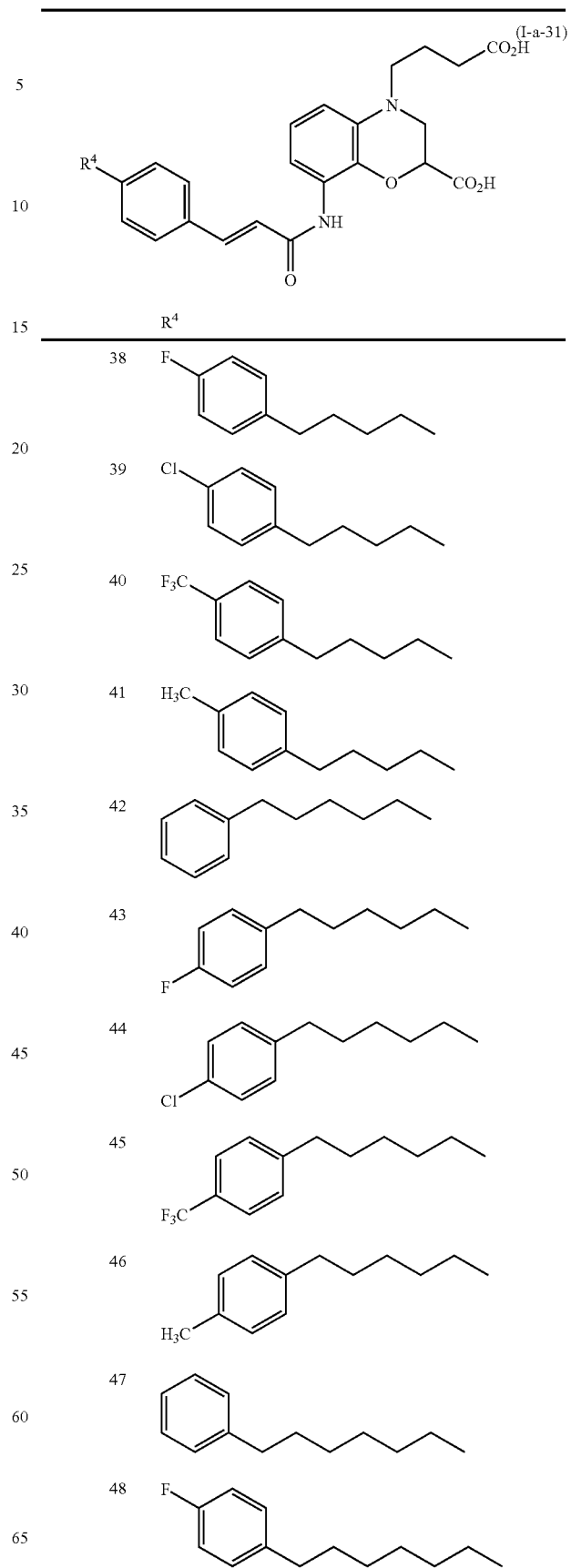

TABLE 31-continued

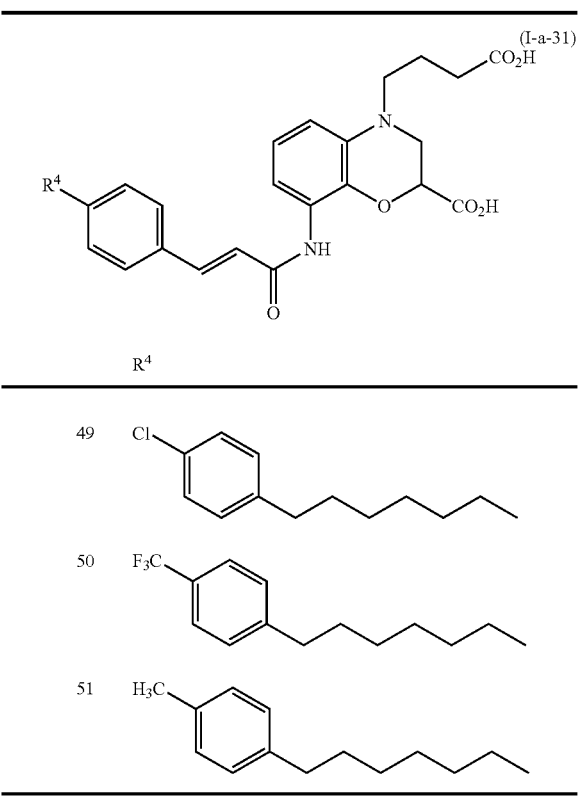

(I-a-31)

R⁴

| 49 | Cl—C₆H₄—(CH₂)₆CH₃ (4-chloro, heptyl) |
| 50 | F₃C—C₆H₄—(CH₂)₆CH₃ |
| 51 | H₃C—C₆H₄—(CH₂)₆CH₃ |

TABLE 32

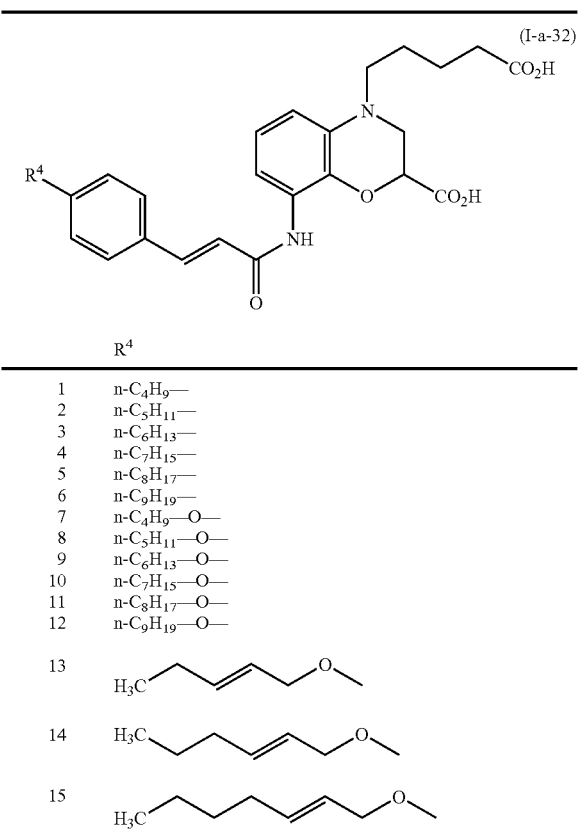

(I-a-32)

R⁴

| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |

13 H₃C—CH=CH—CH₂—O—CH₃

14 H₃C—(CH₂)₂—CH=CH—CH₂—O—CH₃

15 H₃C—(CH₂)₃—CH=CH—CH₂—O—CH₃

TABLE 32-continued

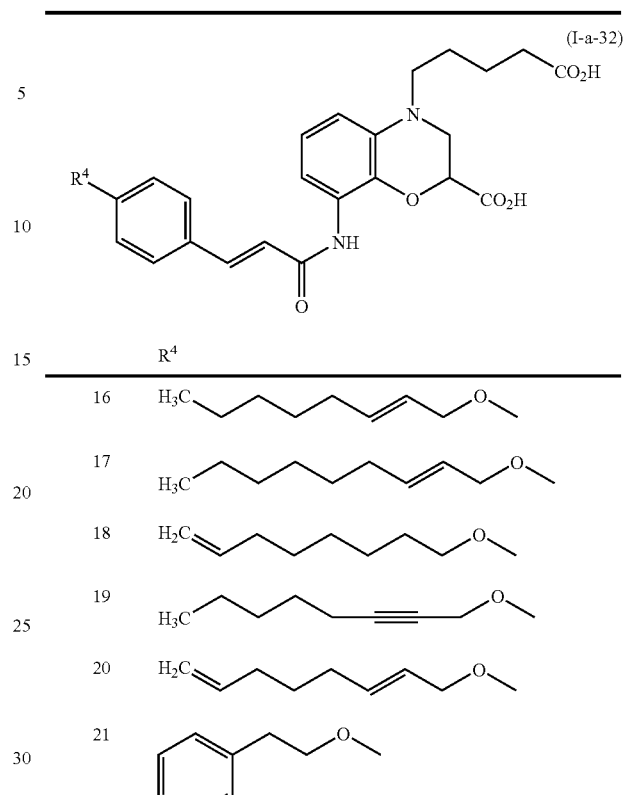

(I-a-32)

R⁴

16 H₃C—(CH₂)₄—CH=CH—CH₂—O—CH₃

17 H₃C—(CH₂)₅—CH=CH—CH₂—O—CH₃

18 H₂C=CH—(CH₂)₅—O—CH₃

19 H₃C—(CH₂)₃—C≡C—CH₂—O—CH₃

20 H₂C=CH—(CH₂)₂—CH=CH—CH₂—O—CH₃

21 Ph—(CH₂)₂—O—CH₃

22 Ph—(CH₂)₃—O—CH₃

23 F—C₆H₄—(CH₂)₃—O—CH₃

24 Cl—C₆H₄—(CH₂)₃—O—CH₃

25 F₃C—C₆H₄—(CH₂)₃—O—CH₃

26 H₃C—C₆H₄—(CH₂)₃—O—CH₃

27 Ph—(CH₂)₄—O—CH₃

28 F—C₆H₄—(CH₂)₄—O—CH₃

TABLE 32-continued
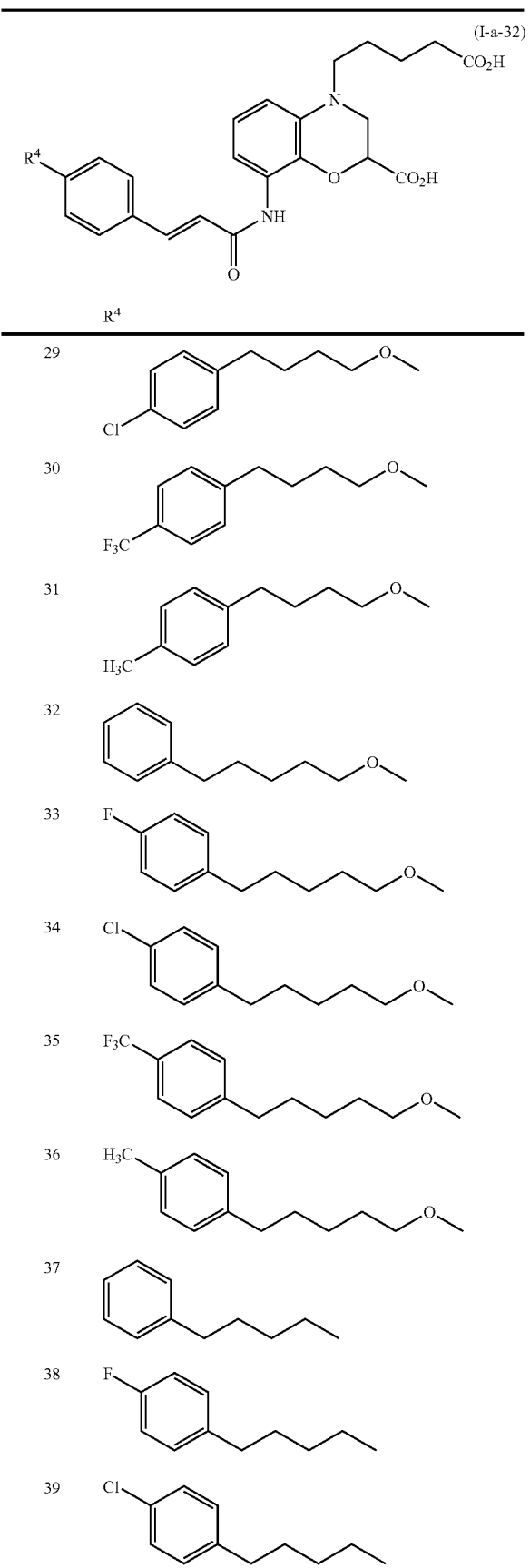
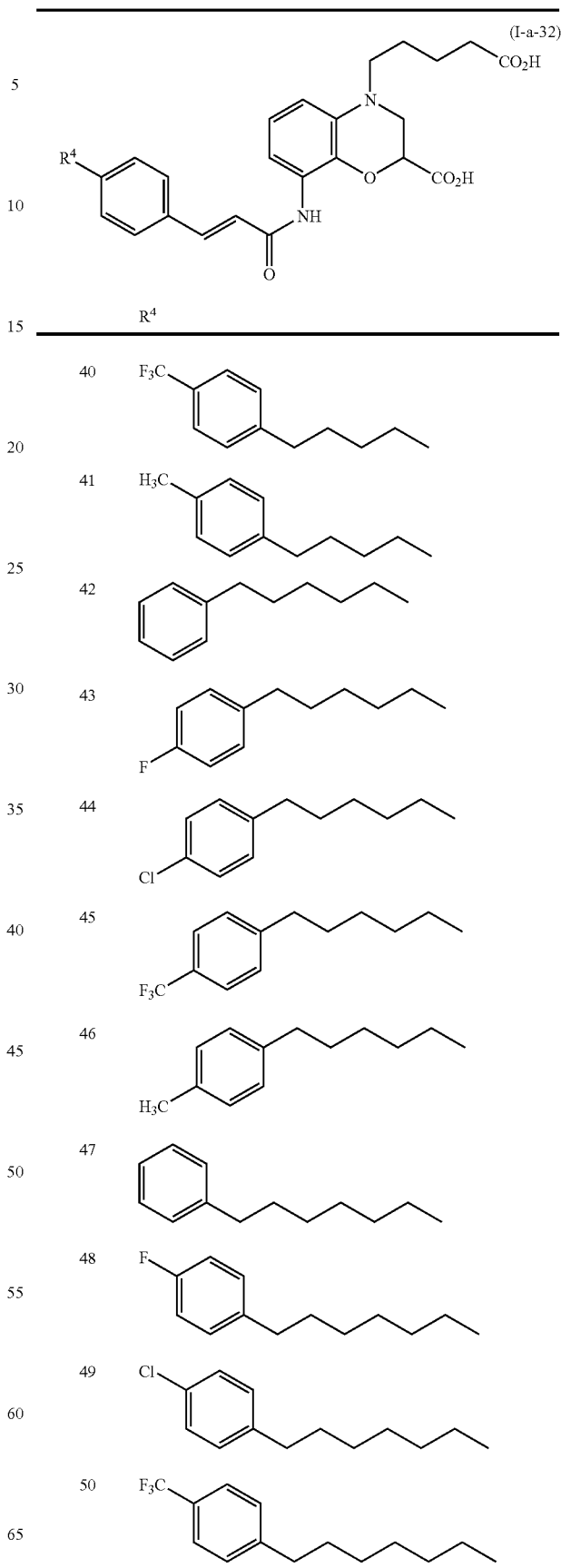

TABLE 32-continued
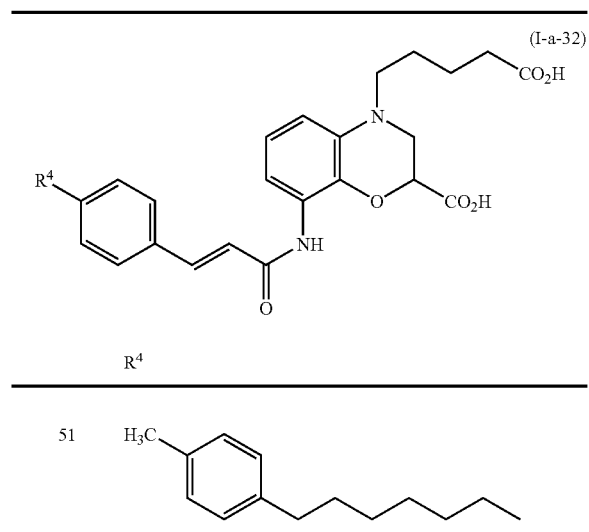
(I-a-32)
| R⁴ | |
|---|---|
| 51 | H₃C—C₆H₄—(CH₂)₆CH₃ |
TABLE 33
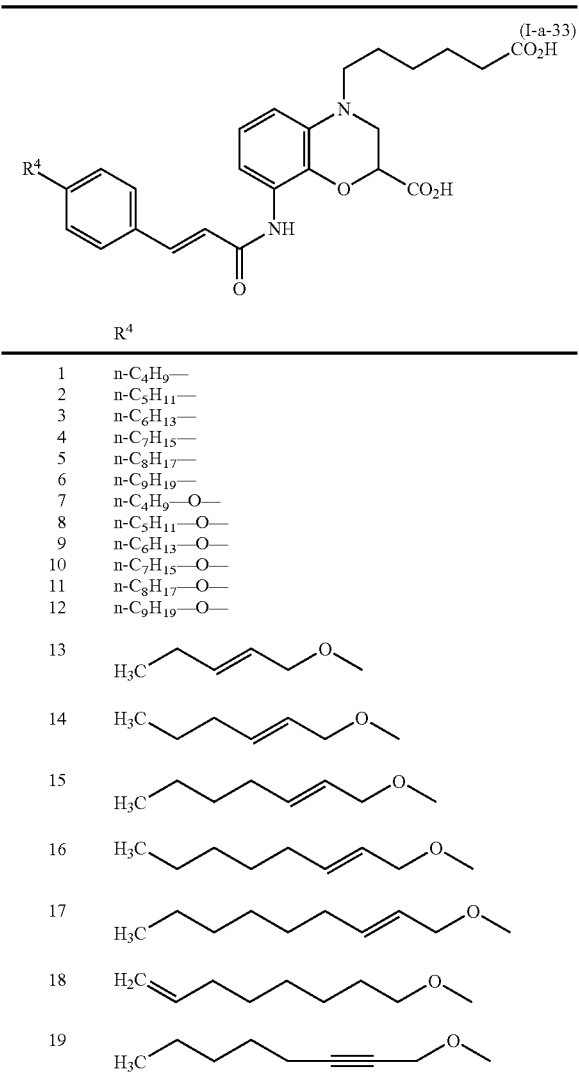
(I-a-33)
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
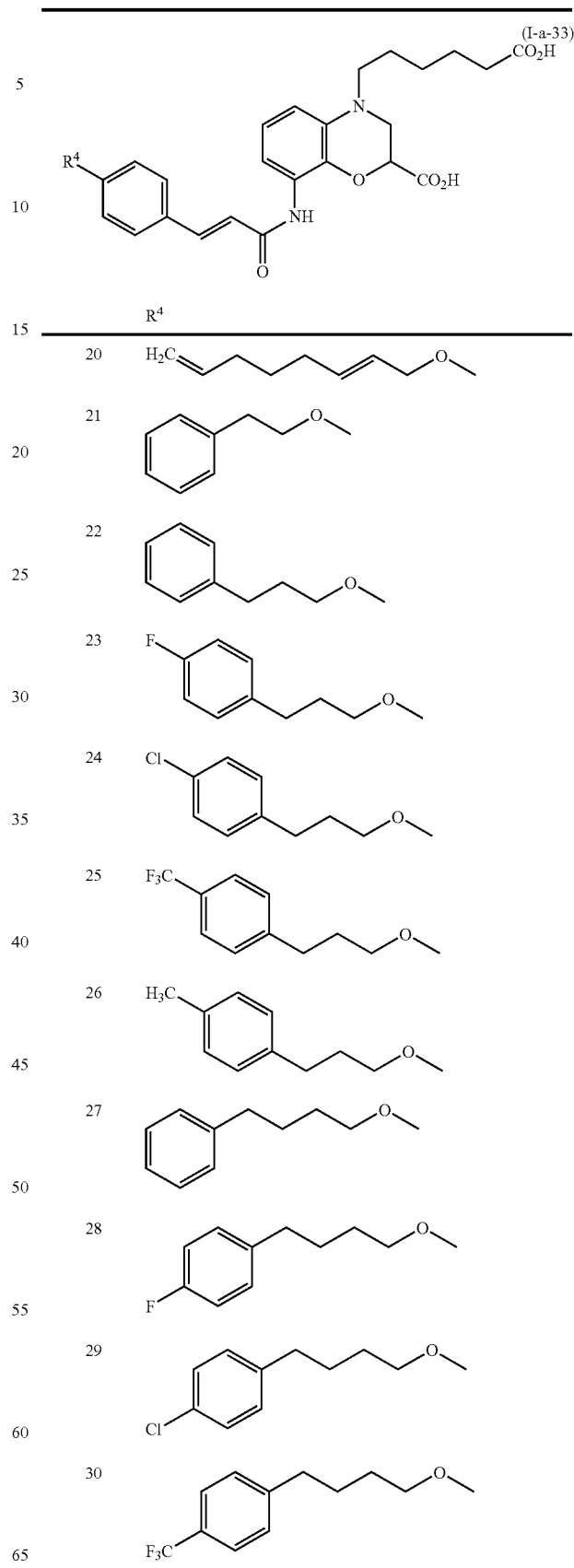
TABLE 33-continued TABLE 33-continued
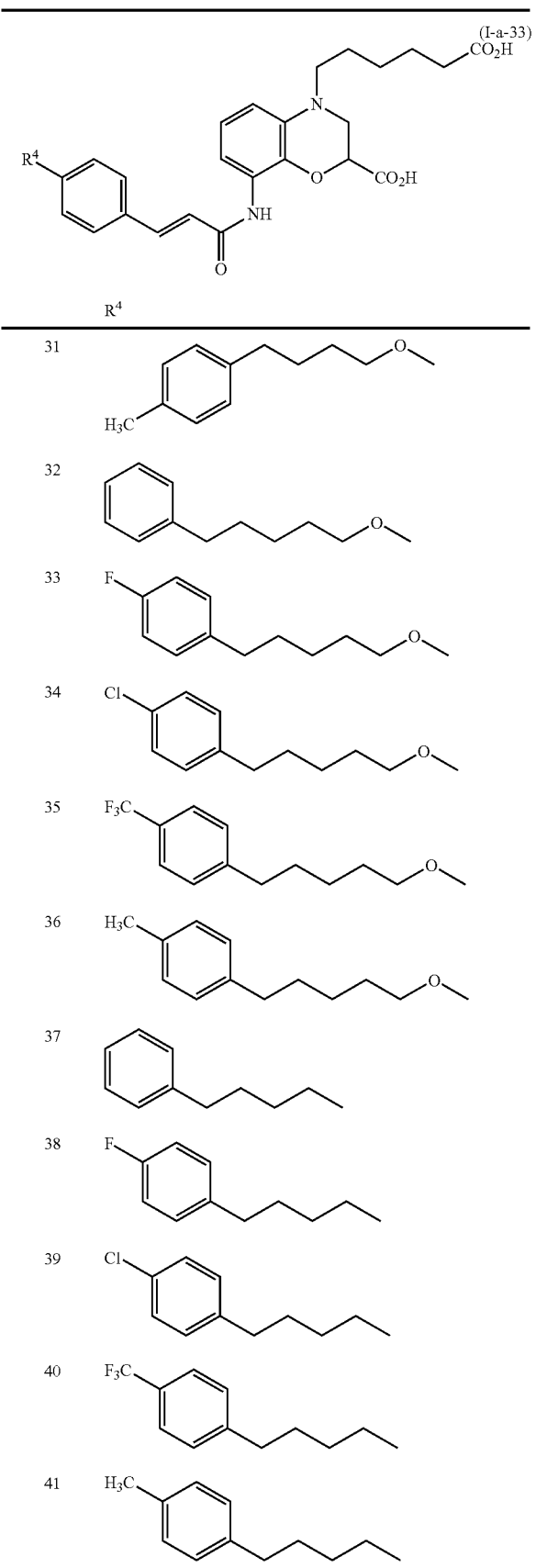
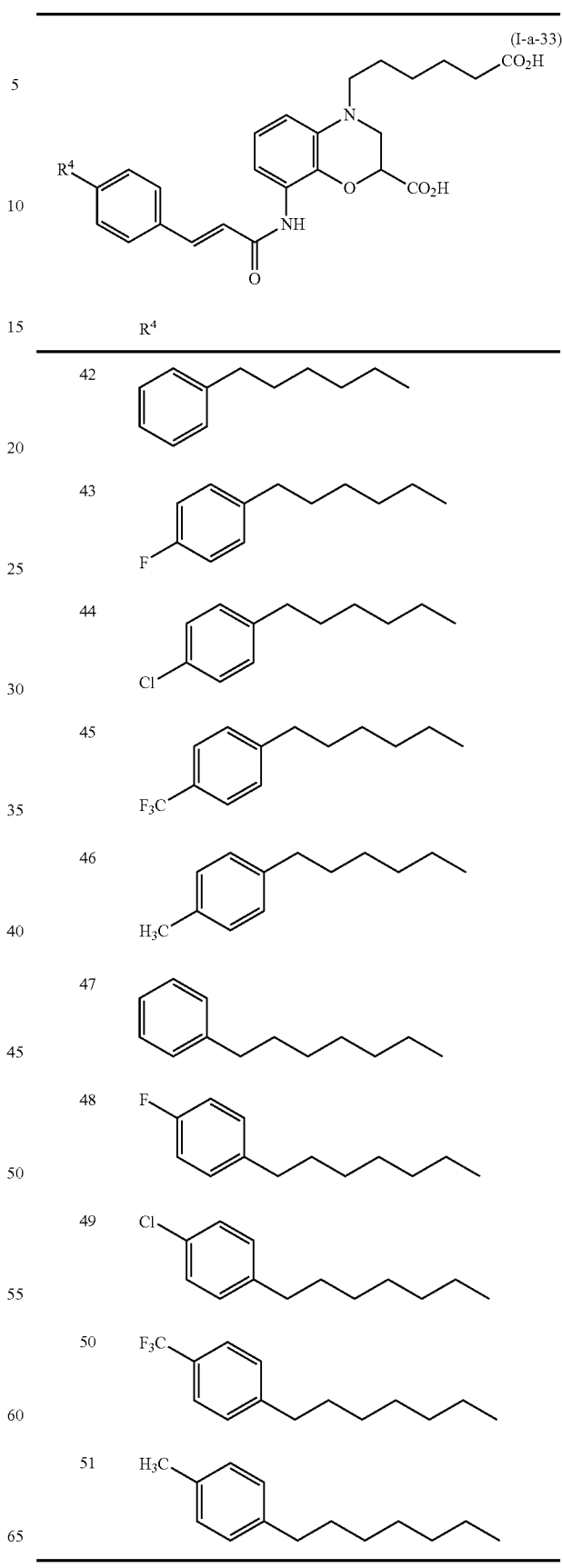

TABLE 34
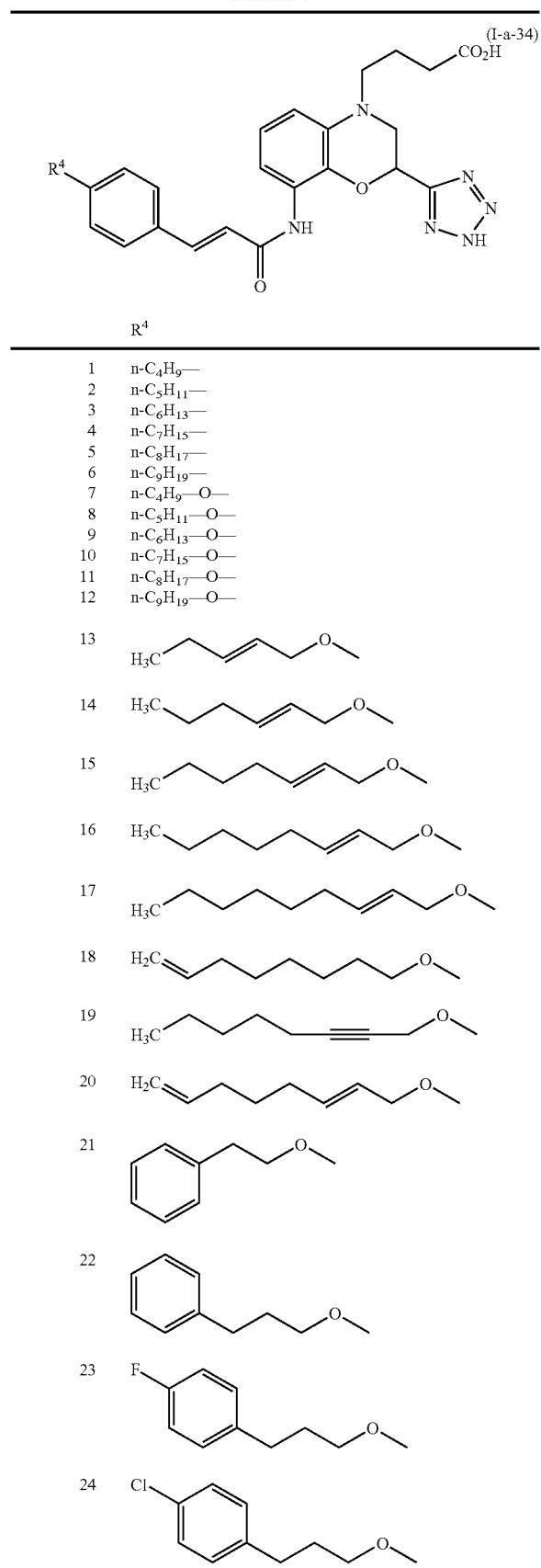
(I-a-34)
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
TABLE 34-continued
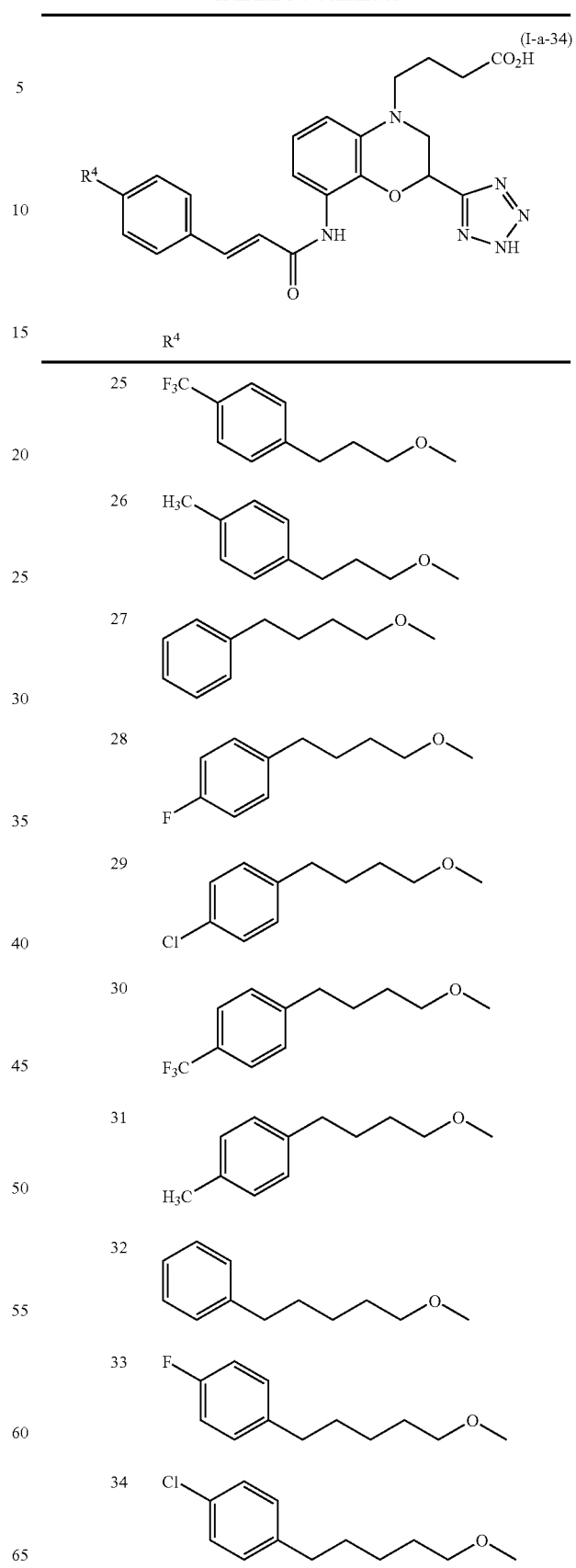
(I-a-34)

TABLE 34-continued
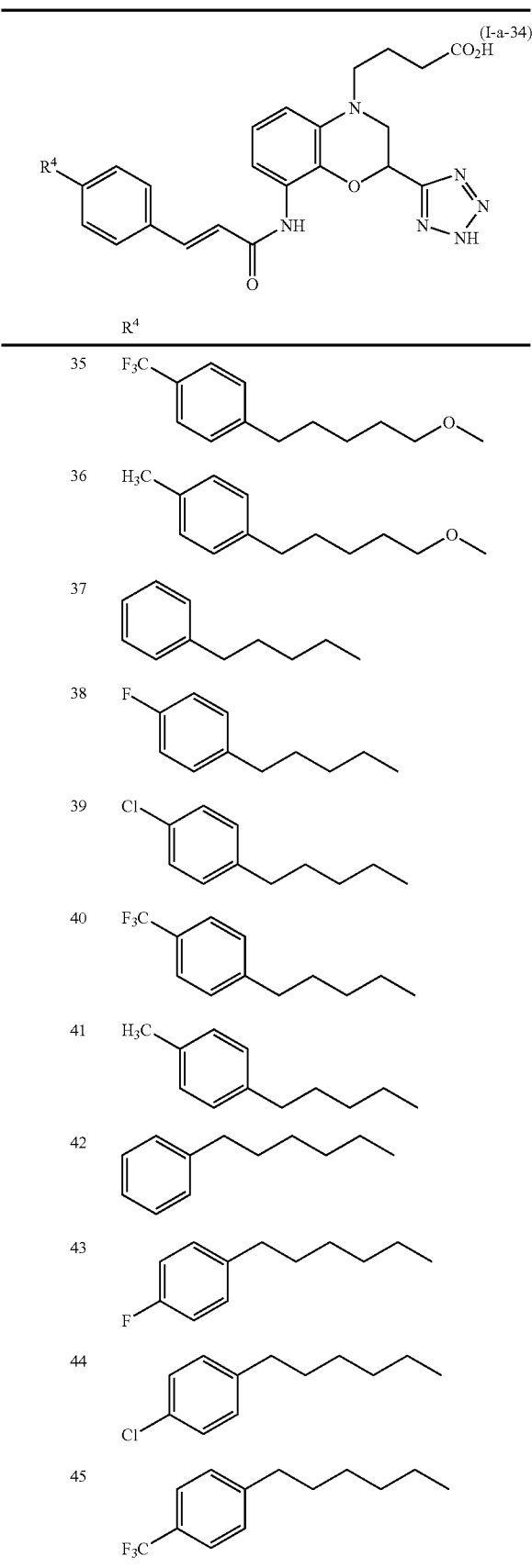
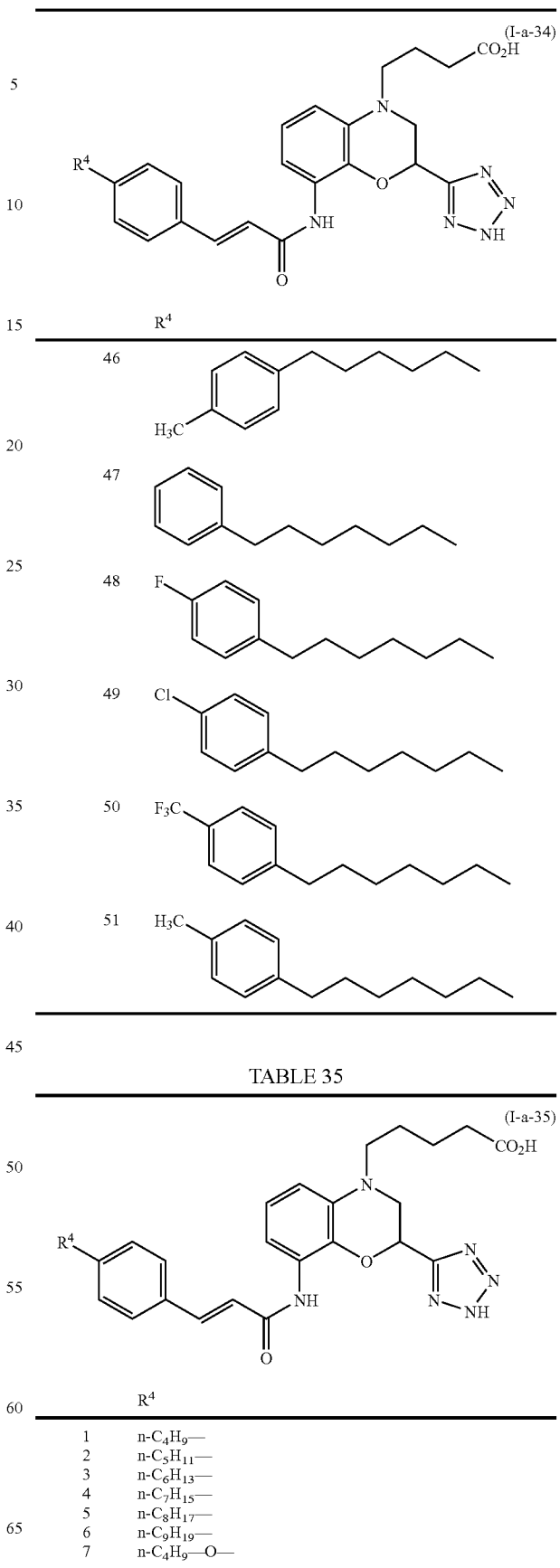
TABLE 35

TABLE 35-continued
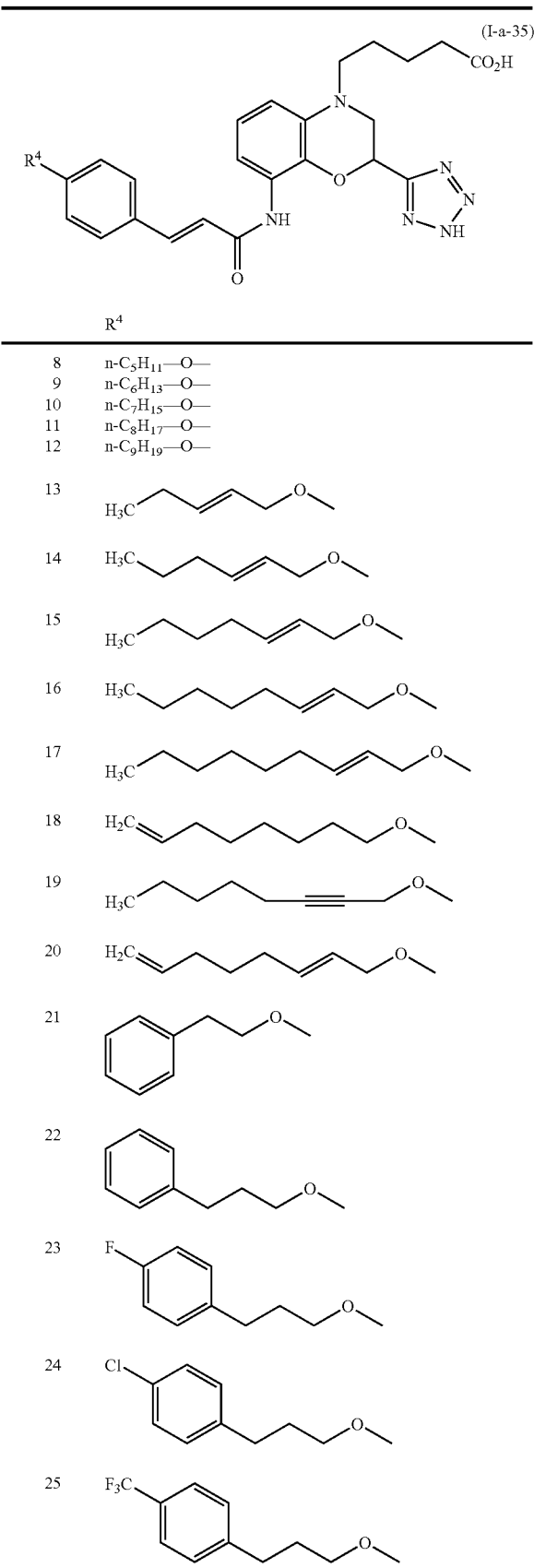
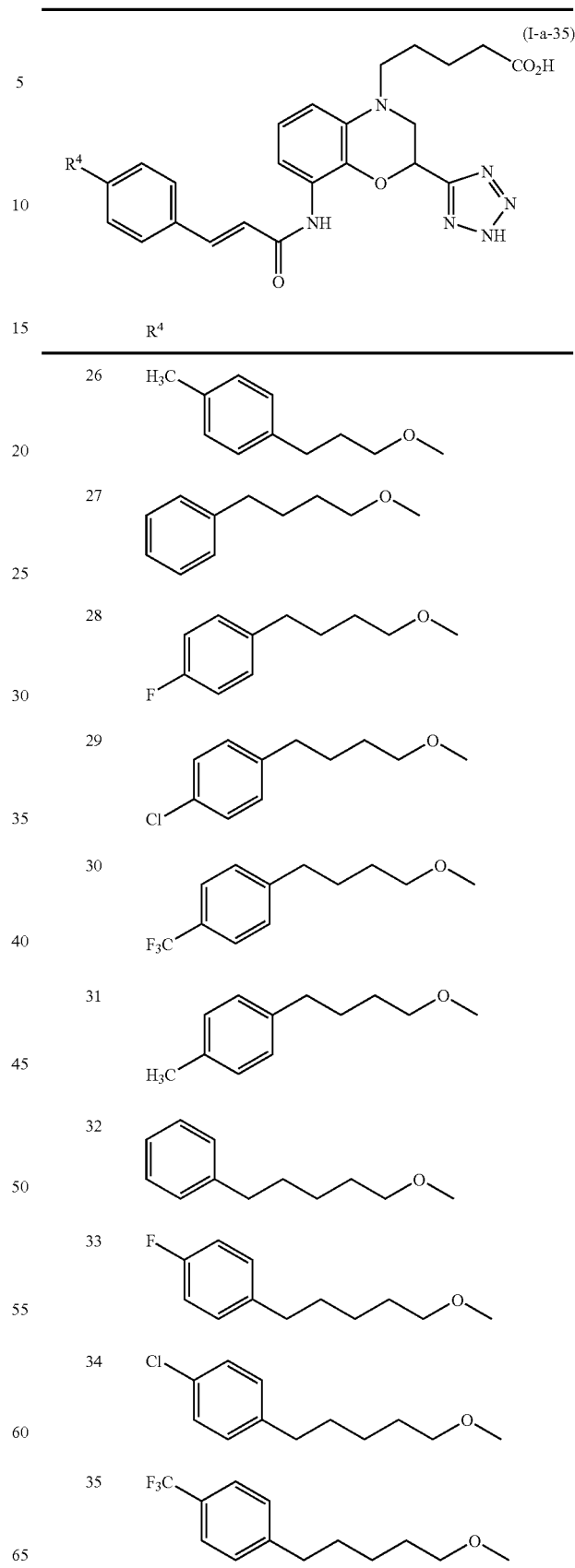

TABLE 35-continued
(I-a-35)
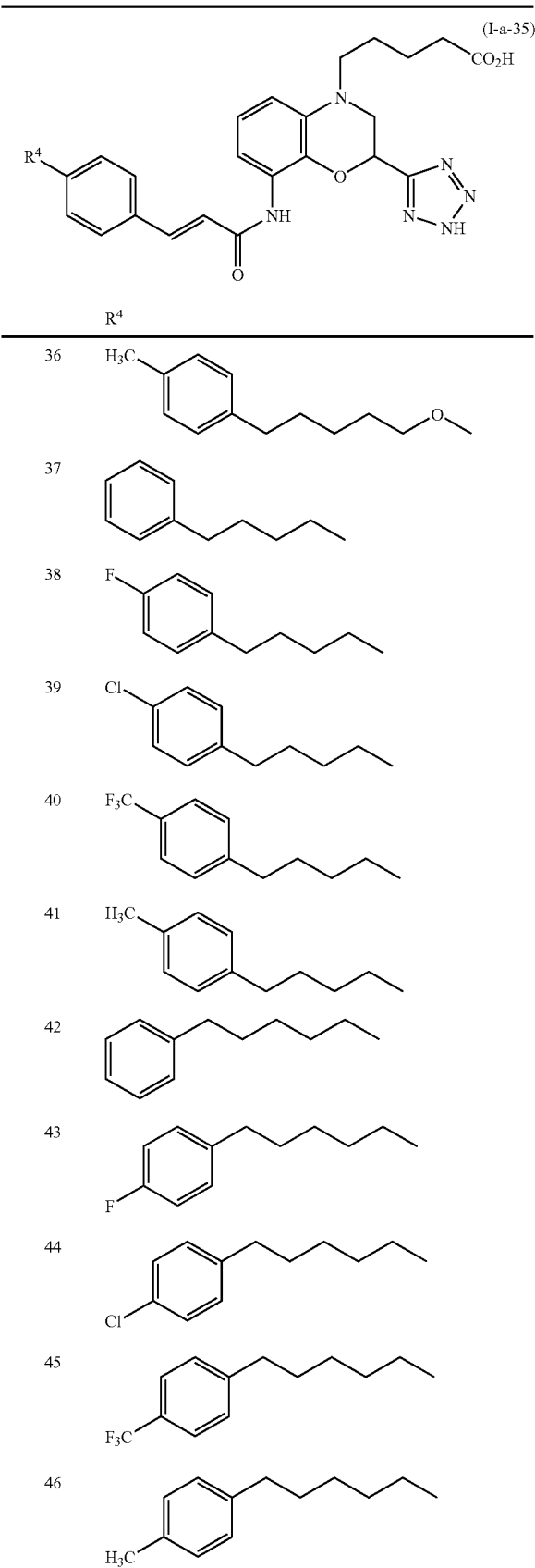
| | R⁴ |
|---|---|
| 36 | H₃C—C₆H₄—(CH₂)₄—O—CH₃ |
| 37 | C₆H₅—(CH₂)₄— |
| 38 | F—C₆H₄—(CH₂)₄— |
| 39 | Cl—C₆H₄—(CH₂)₄— |
| 40 | F₃C—C₆H₄—(CH₂)₄— |
| 41 | H₃C—C₆H₄—(CH₂)₄— |
| 42 | C₆H₅—(CH₂)₅— |
| 43 | F—C₆H₄—(CH₂)₅— |
| 44 | Cl—C₆H₄—(CH₂)₅— |
| 45 | F₃C—C₆H₄—(CH₂)₅— |
| 46 | H₃C—C₆H₄—(CH₂)₅— |
TABLE 35-continued
(I-a-35)
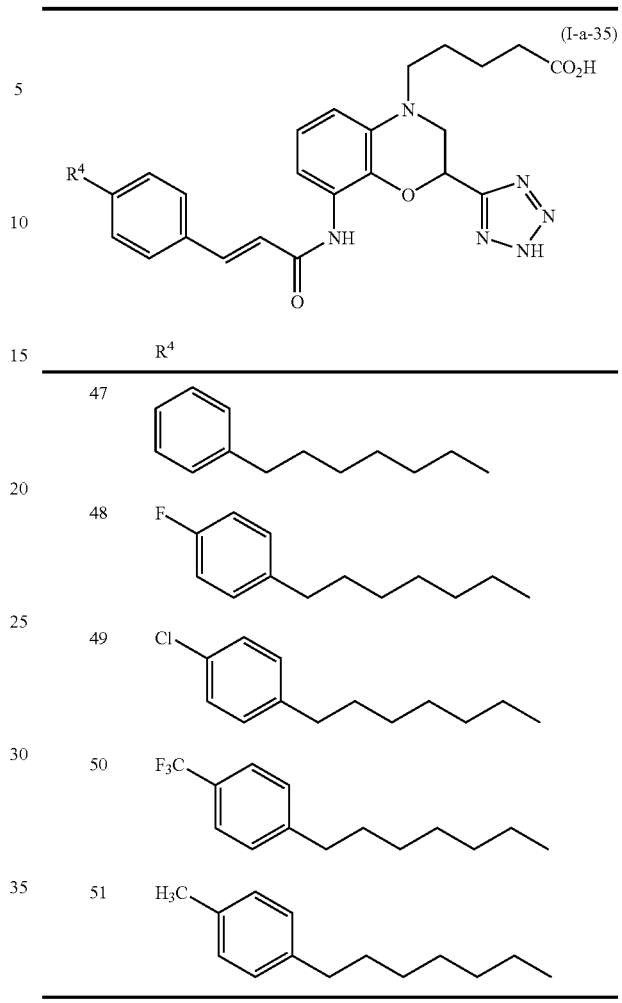
| | R⁴ |
|---|---|
| 47 | C₆H₅—(CH₂)₆— |
| 48 | F—C₆H₄—(CH₂)₆— |
| 49 | Cl—C₆H₄—(CH₂)₆— |
| 50 | F₃C—C₆H₄—(CH₂)₆— |
| 51 | H₃C—C₆H₄—(CH₂)₆— |
TABLE 36
(I-a-36)
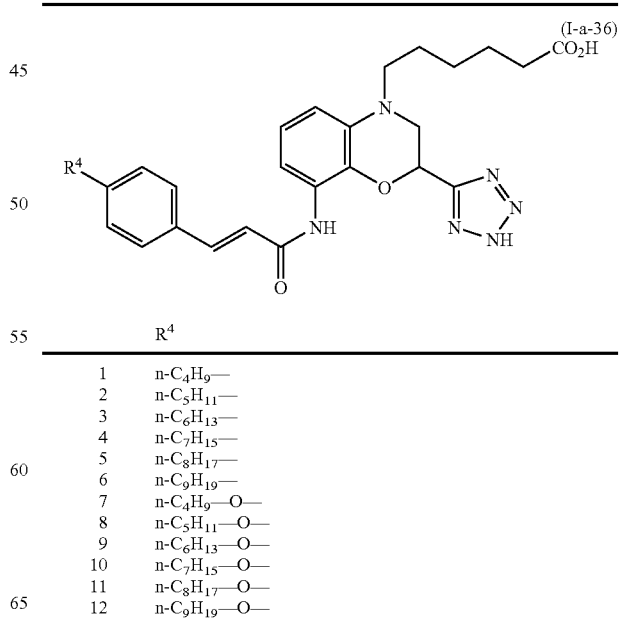
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |

TABLE 36-continued

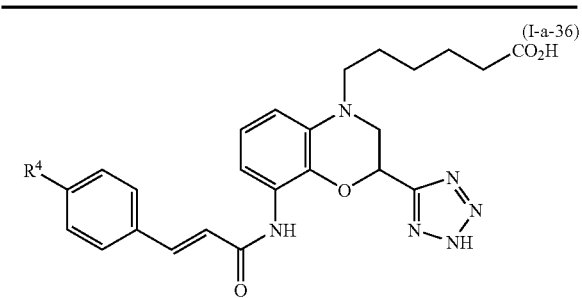

| | R⁴ |
|---|---|
| 13 | H₃C–CH=CH–CH₂–O–CH₃ |
| 14 | H₃C–CH₂–CH=CH–CH₂–O–CH₃ |
| 15 | H₃C–(CH₂)₂–CH=CH–CH₂–O–CH₃ |
| 16 | H₃C–(CH₂)₃–CH=CH–CH₂–O–CH₃ |
| 17 | H₃C–(CH₂)₄–CH=CH–CH₂–O–CH₃ |
| 18 | H₂C=CH–(CH₂)₄–O–CH₃ |
| 19 | H₃C–CH₂–C≡C–CH₂–O–CH₃ |
| 20 | H₂C=CH–(CH₂)₂–CH=CH–CH₂–O–CH₃ |
| 21 | Ph–CH₂–O–CH₃ |
| 22 | Ph–(CH₂)₂–O–CH₃ |
| 23 | 4-F-C₆H₄–(CH₂)₂–O–CH₃ |
| 24 | 4-Cl-C₆H₄–(CH₂)₂–O–CH₃ |
| 25 | 4-F₃C-C₆H₄–(CH₂)₂–O–CH₃ |
| 26 | 4-H₃C-C₆H₄–(CH₂)₂–O–CH₃ |
| 27 | Ph–(CH₂)₃–O–CH₃ |

TABLE 36-continued

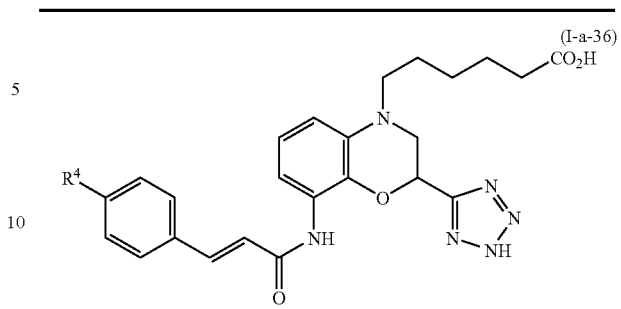

| | R⁴ |
|---|---|
| 28 | 4-F-C₆H₄–(CH₂)₃–O–CH₃ |
| 29 | 4-Cl-C₆H₄–(CH₂)₃–O–CH₃ |
| 30 | 4-F₃C-C₆H₄–(CH₂)₃–O–CH₃ |
| 31 | 4-H₃C-C₆H₄–(CH₂)₃–O–CH₃ |
| 32 | Ph–(CH₂)₄–O–CH₃ |
| 33 | 4-F-C₆H₄–(CH₂)₄–O–CH₃ |
| 34 | 4-Cl-C₆H₄–(CH₂)₄–O–CH₃ |
| 35 | 4-F₃C-C₆H₄–(CH₂)₄–O–CH₃ |
| 36 | 4-H₃C-C₆H₄–(CH₂)₄–O–CH₃ |
| 37 | Ph–(CH₂)₄–CH₃ |

TABLE 36-continued
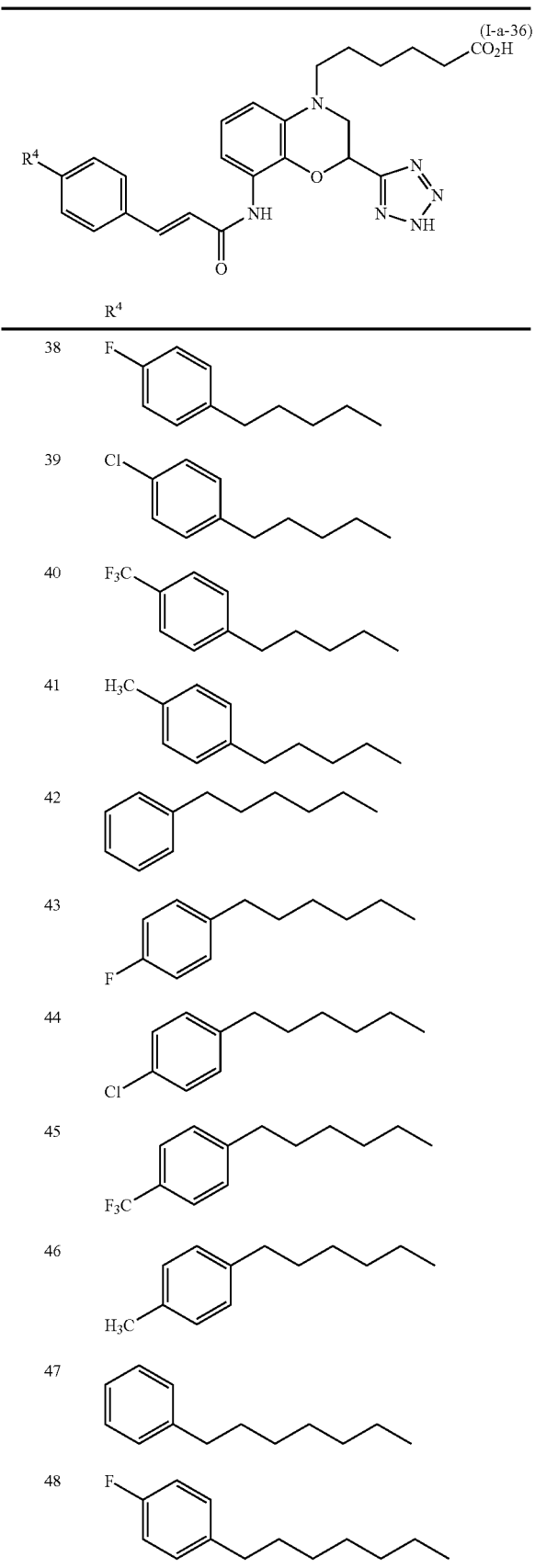
| | R[4] |
|---|---|
| 38 | 4-F-C6H4-(CH2)4- |
| 39 | 4-Cl-C6H4-(CH2)4- |
| 40 | 4-F3C-C6H4-(CH2)4- |
| 41 | 4-H3C-C6H4-(CH2)4- |
| 42 | C6H5-(CH2)5- |
| 43 | 4-F-C6H4-(CH2)5- |
| 44 | 4-Cl-C6H4-(CH2)5- |
| 45 | 4-F3C-C6H4-(CH2)5- |
| 46 | 4-H3C-C6H4-(CH2)5- |
| 47 | C6H5-(CH2)6- |
| 48 | 4-F-C6H4-(CH2)6- |
TABLE 36-continued
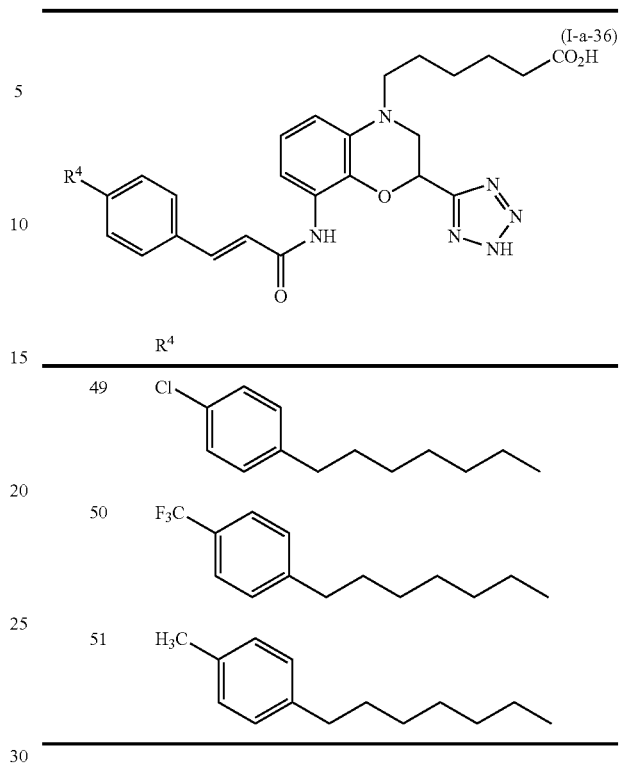
| | R[4] |
|---|---|
| 49 | 4-Cl-C6H4-(CH2)6- |
| 50 | 4-F3C-C6H4-(CH2)6- |
| 51 | 4-H3C-C6H4-(CH2)6- |
TABLE 37
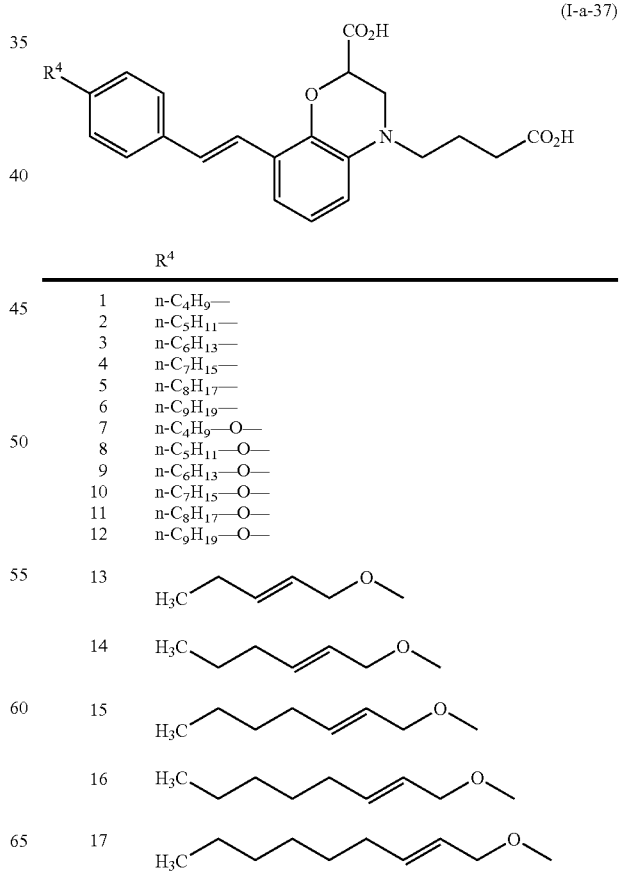
| | R[4] |
|---|---|
| 1 | n-C4H9— |
| 2 | n-C5H11— |
| 3 | n-C6H13— |
| 4 | n-C7H15— |
| 5 | n-C8H17— |
| 6 | n-C9H19— |
| 7 | n-C4H9—O— |
| 8 | n-C5H11—O— |
| 9 | n-C6H13—O— |
| 10 | n-C7H15—O— |
| 11 | n-C8H17—O— |
| 12 | n-C9H19—O— |
| 13 | H3C-CH=CH-CH2-O-CH3 |
| 14 | H3C-(CH2)-CH=CH-CH2-O-CH3 |
| 15 | H3C-(CH2)2-CH=CH-CH2-O-CH3 |
| 16 | H3C-(CH2)3-CH=CH-CH2-O-CH3 |
| 17 | H3C-(CH2)4-CH=CH-CH2-O-CH3 |

TABLE 37-continued

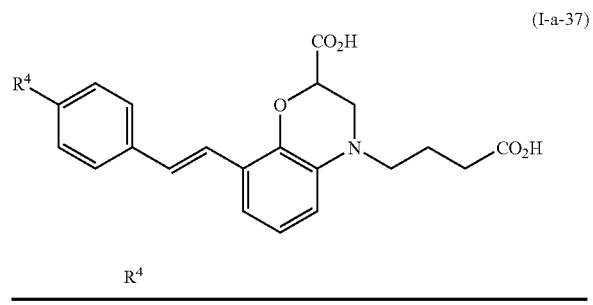

(I-a-37)

| | $R^4$ |
|---|---|
| 18 | $H_2C$=CH-(CH$_2$)$_5$-O-CH$_3$ |
| 19 | $H_3C$-(CH$_2$)$_3$-C≡C-CH$_2$-O-CH$_3$ |
| 20 | $H_2C$=CH-(CH$_2$)$_3$-CH=CH-CH$_2$-O-CH$_3$ |
| 21 | Ph-CH$_2$CH$_2$-O-CH$_3$ |
| 22 | Ph-(CH$_2$)$_3$-O-CH$_3$ |
| 23 | 4-F-C$_6$H$_4$-(CH$_2$)$_3$-O-CH$_3$ |
| 24 | 4-Cl-C$_6$H$_4$-(CH$_2$)$_3$-O-CH$_3$ |
| 25 | 4-F$_3$C-C$_6$H$_4$-(CH$_2$)$_3$-O-CH$_3$ |
| 26 | 4-H$_3$C-C$_6$H$_4$-(CH$_2$)$_3$-O-CH$_3$ |
| 27 | Ph-(CH$_2$)$_4$-O-CH$_3$ |
| 28 | 4-F-C$_6$H$_4$-(CH$_2$)$_4$-O-CH$_3$ |
| 29 | 4-Cl-C$_6$H$_4$-(CH$_2$)$_4$-O-CH$_3$ |

TABLE 37-continued

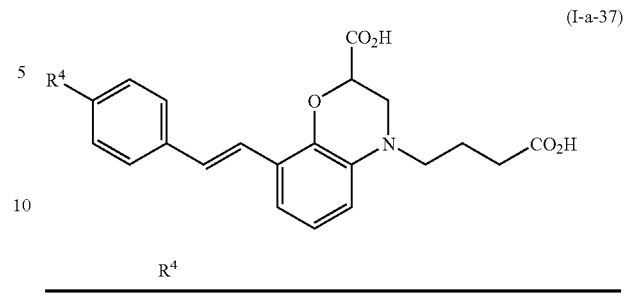

(I-a-37)

| | $R^4$ |
|---|---|
| 30 | 4-F$_3$C-C$_6$H$_4$-(CH$_2$)$_4$-O-CH$_3$ |
| 31 | 4-H$_3$C-C$_6$H$_4$-(CH$_2$)$_4$-O-CH$_3$ |
| 32 | Ph-(CH$_2$)$_5$-O-CH$_3$ |
| 33 | 4-F-C$_6$H$_4$-(CH$_2$)$_5$-O-CH$_3$ |
| 34 | 4-Cl-C$_6$H$_4$-(CH$_2$)$_5$-O-CH$_3$ |
| 35 | 4-F$_3$C-C$_6$H$_4$-(CH$_2$)$_5$-O-CH$_3$ |
| 36 | 4-H$_3$C-C$_6$H$_4$-(CH$_2$)$_5$-O-CH$_3$ |
| 37 | Ph-(CH$_2$)$_4$-CH$_3$ |
| 38 | 4-F-C$_6$H$_4$-(CH$_2$)$_4$-CH$_3$ |
| 39 | 4-Cl-C$_6$H$_4$-(CH$_2$)$_4$-CH$_3$ |
| 40 | 4-F$_3$C-C$_6$H$_4$-(CH$_2$)$_4$-CH$_3$ |

TABLE 37-continued
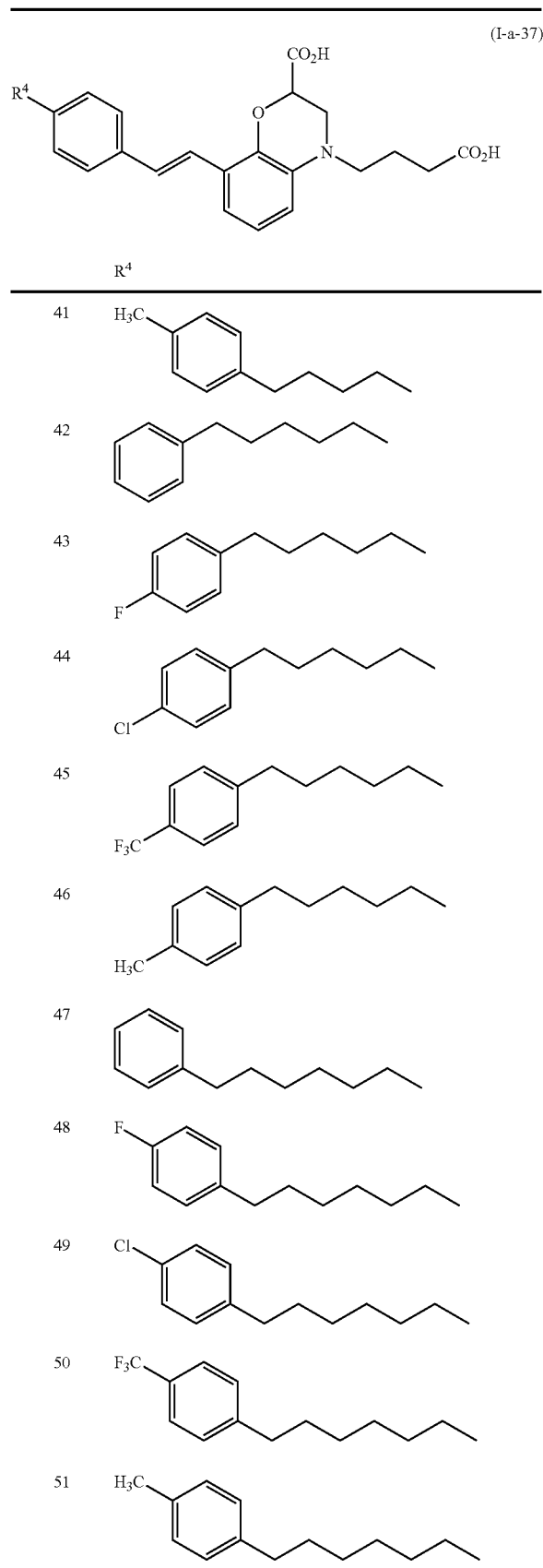
TABLE 37-continued
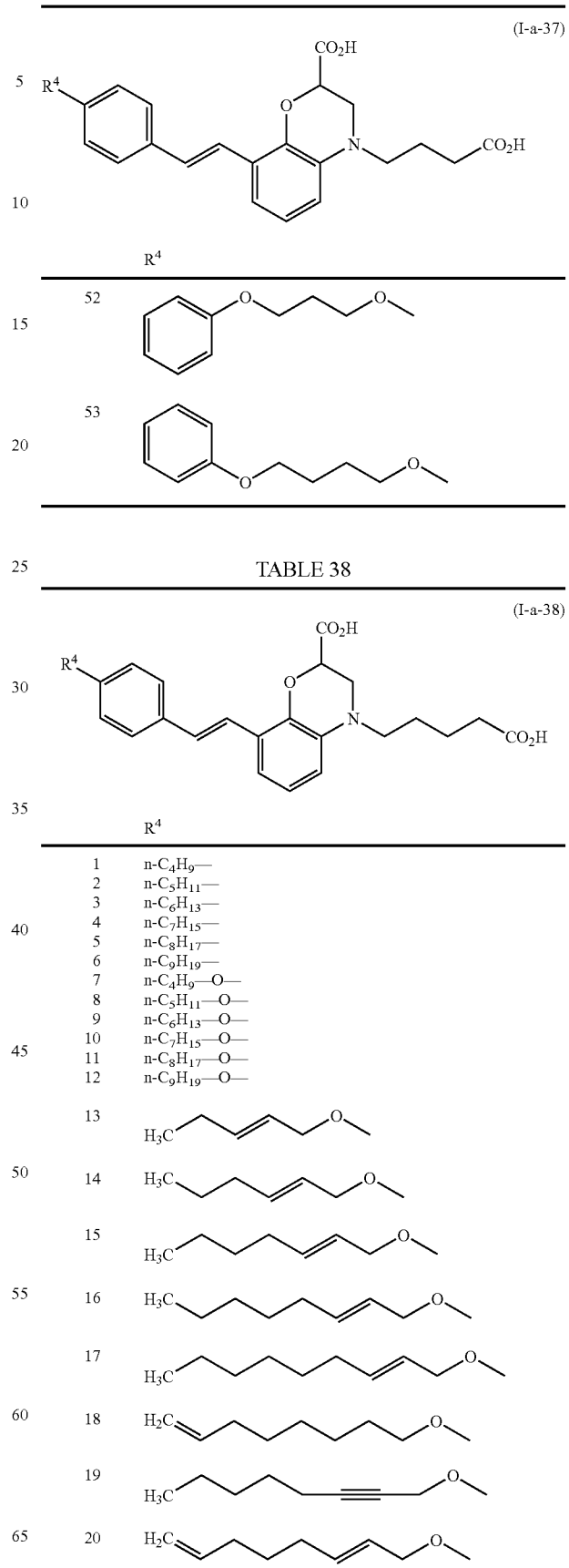

TABLE 38-continued

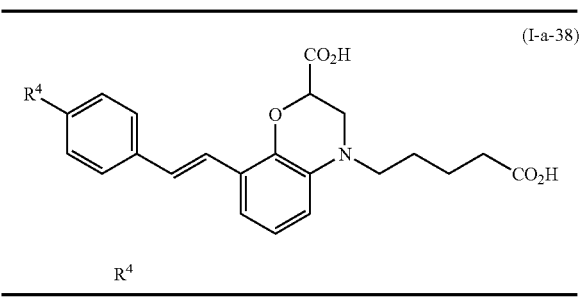

(I-a-38)

R⁴

| | R⁴ |
|---|---|
| 21 | phenyl-CH₂CH₂-OCH₃ |
| 22 | phenyl-(CH₂)₃-OCH₃ |
| 23 | 4-F-phenyl-(CH₂)₃-OCH₃ |
| 24 | 4-Cl-phenyl-(CH₂)₃-OCH₃ |
| 25 | 4-F₃C-phenyl-(CH₂)₃-OCH₃ |
| 26 | 4-H₃C-phenyl-(CH₂)₃-OCH₃ |
| 27 | phenyl-(CH₂)₄-OCH₃ |
| 28 | 4-F-phenyl-(CH₂)₄-OCH₃ |
| 29 | 4-Cl-phenyl-(CH₂)₄-OCH₃ |
| 30 | 4-F₃C-phenyl-(CH₂)₄-OCH₃ |
| 31 | 4-H₃C-phenyl-(CH₂)₄-OCH₃ |

TABLE 38-continued

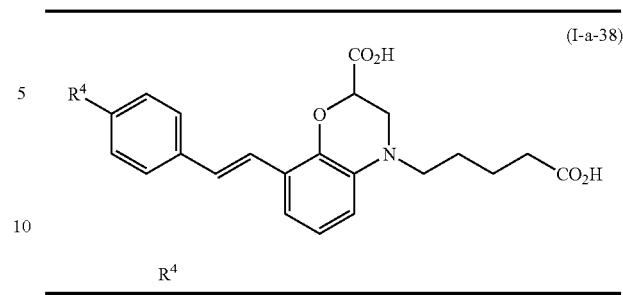

(I-a-38)

R⁴

| | R⁴ |
|---|---|
| 32 | phenyl-(CH₂)₅-OCH₃ |
| 33 | 4-F-phenyl-(CH₂)₅-OCH₃ |
| 34 | 4-Cl-phenyl-(CH₂)₅-OCH₃ |
| 35 | 4-F₃C-phenyl-(CH₂)₅-OCH₃ |
| 36 | 4-H₃C-phenyl-(CH₂)₅-OCH₃ |
| 37 | phenyl-(CH₂)₄-CH₃ |
| 38 | 4-F-phenyl-(CH₂)₄-CH₃ |
| 39 | 4-Cl-phenyl-(CH₂)₄-CH₃ |
| 40 | 4-F₃C-phenyl-(CH₂)₄-CH₃ |
| 41 | 4-H₃C-phenyl-(CH₂)₄-CH₃ |
| 42 | phenyl-(CH₂)₅-CH₃ |
| 43 | 4-F-phenyl-(CH₂)₅-CH₃ |

TABLE 38-continued
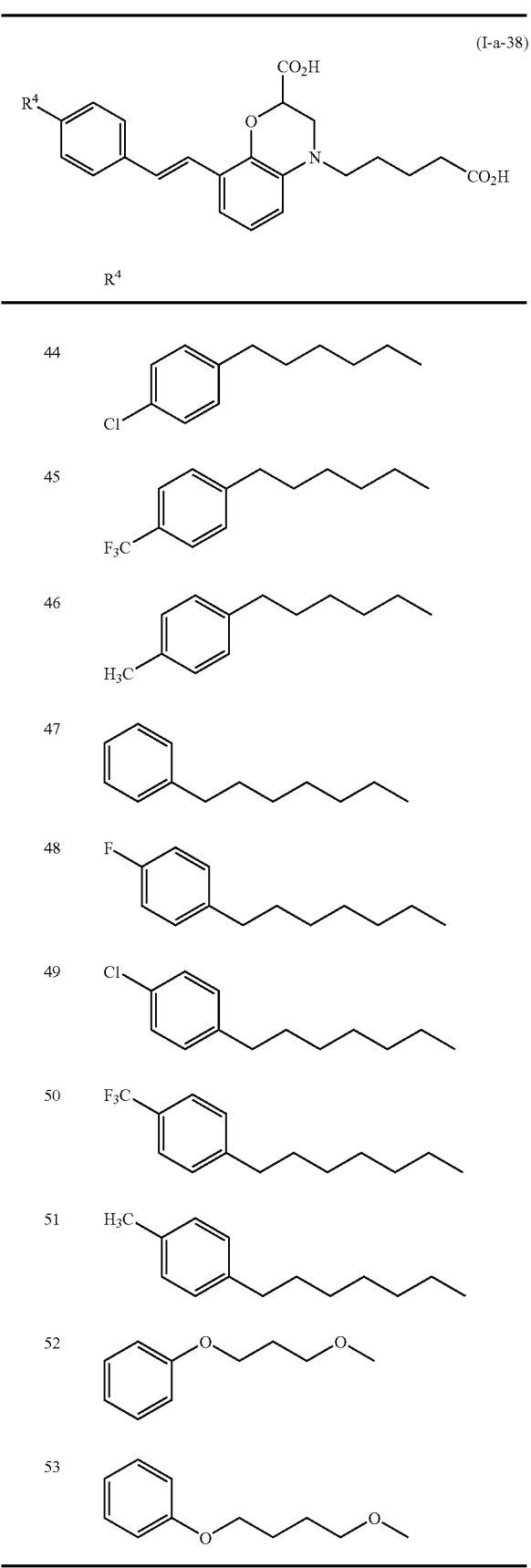
TABLE 39
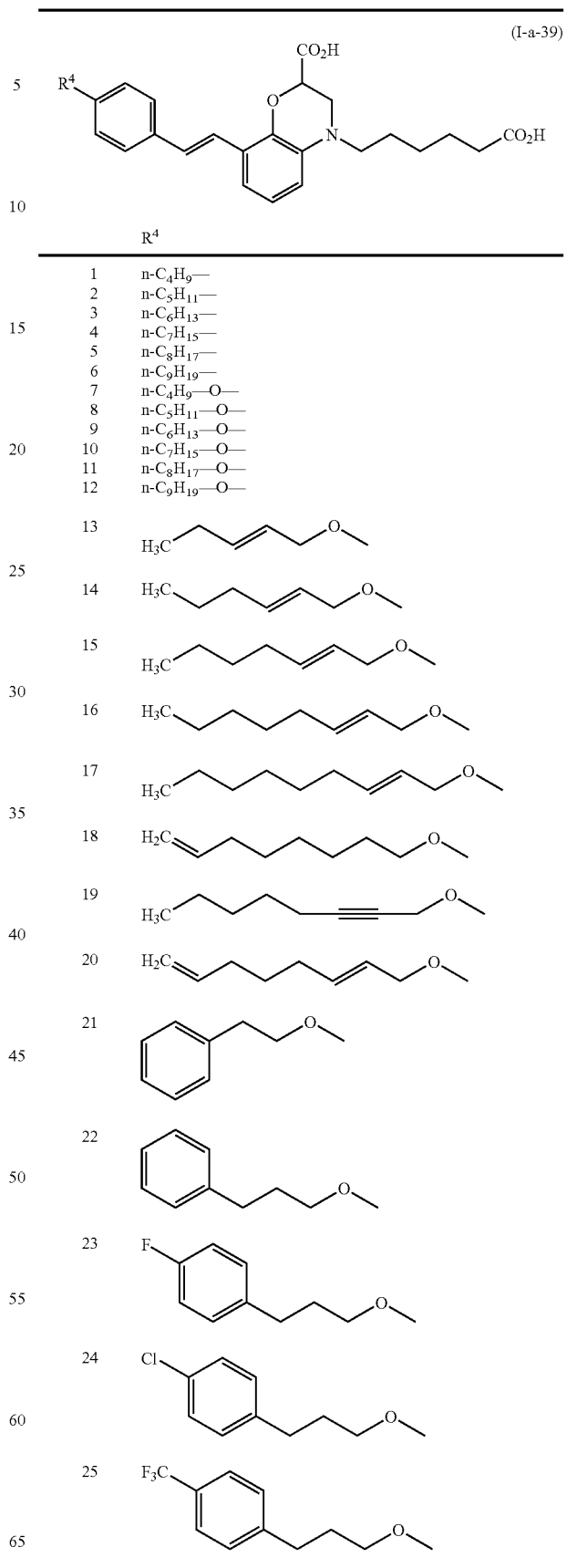

TABLE 39-continued
(I-a-39)
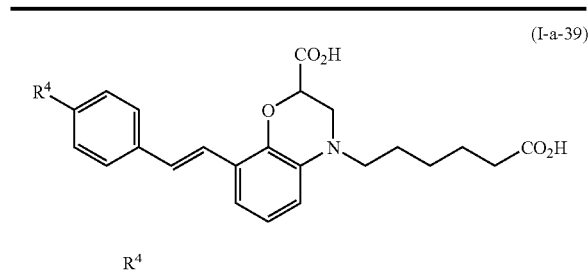
| | $R^4$ |
|---|---|
| 26 | 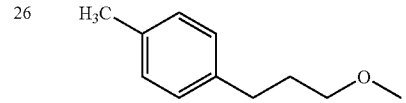 |
| 27 | 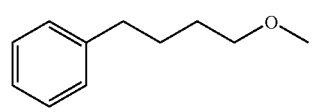 |
| 28 | 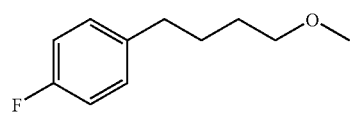 |
| 29 | 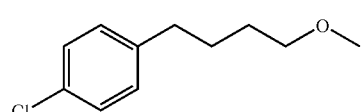 |
| 30 | 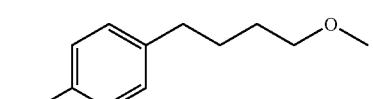 |
| 31 | 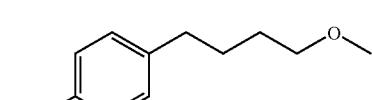 |
| 32 | 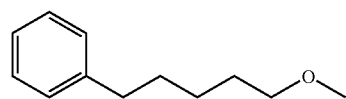 |
| 33 | 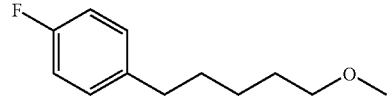 |
| 34 | 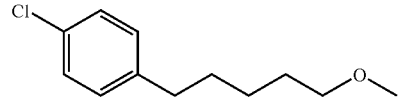 |
| 35 | 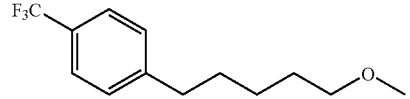 |
| 36 | 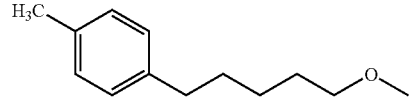 |
TABLE 39-continued
(I-a-39)
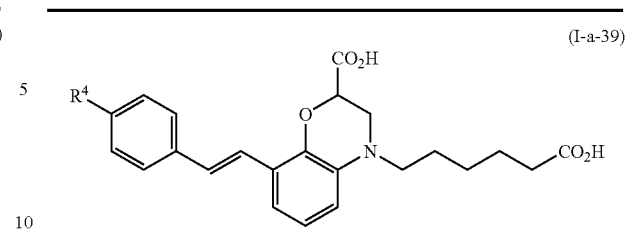
| | $R^4$ |
|---|---|
| 37 | 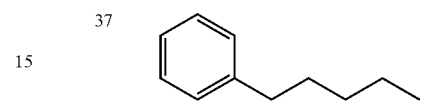 |
| 38 | 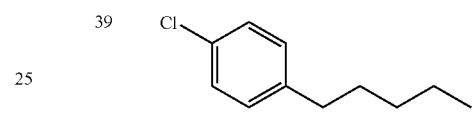 |
| 39 | 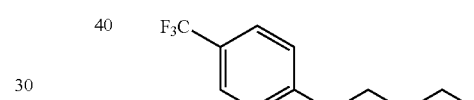 |
| 40 | 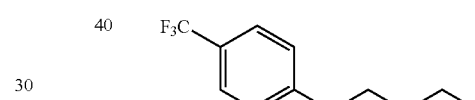 |
| 41 | 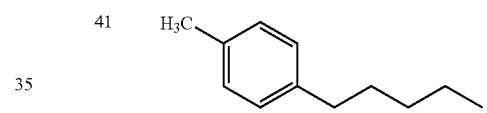 |
| 42 | 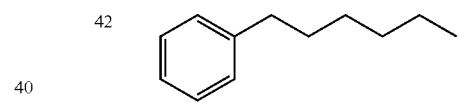 |
| 43 | 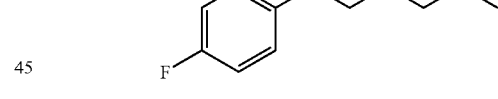 |
| 44 | 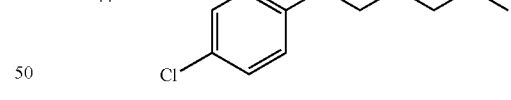 |
| 45 | 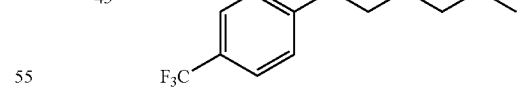 |
| 46 | 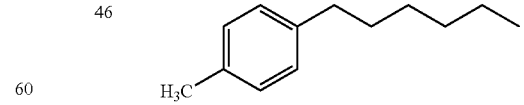 |
| 47 | 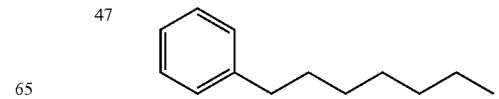 |

TABLE 39-continued

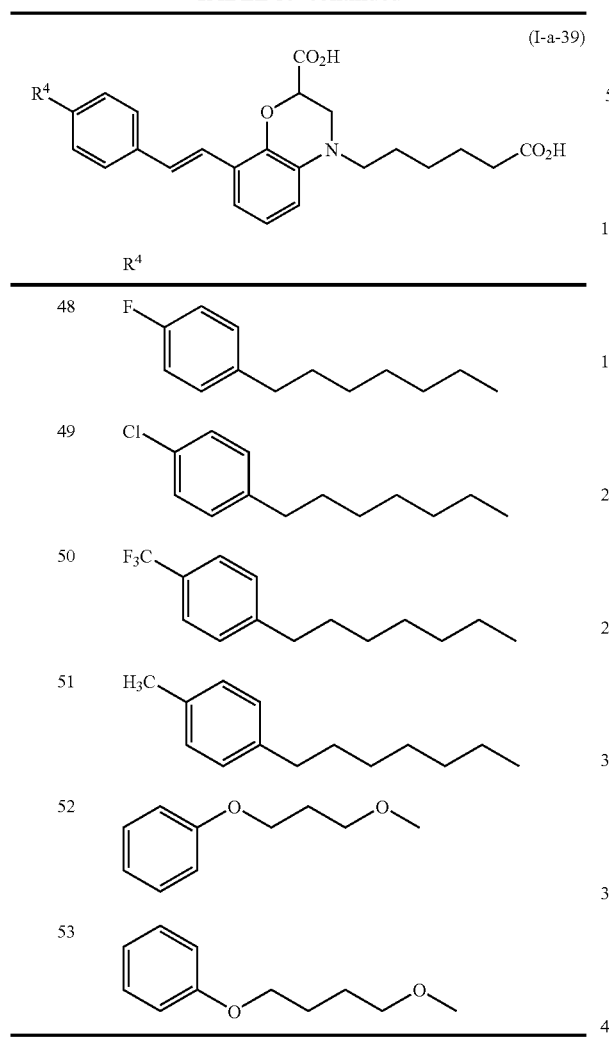

| | $R^4$ |
|---|---|
| 48 | 4-F-C6H4-C7H15 (4-fluorophenyl heptyl) |
| 49 | 4-Cl-C6H4-C7H15 |
| 50 | 4-F3C-C6H4-C7H15 |
| 51 | 4-H3C-C6H4-C7H15 |
| 52 | PhO-CH2CH2-O-CH3 (phenoxy propyl methyl ether) |
| 53 | PhO-(CH2)3-O-CH3 |

TABLE 40

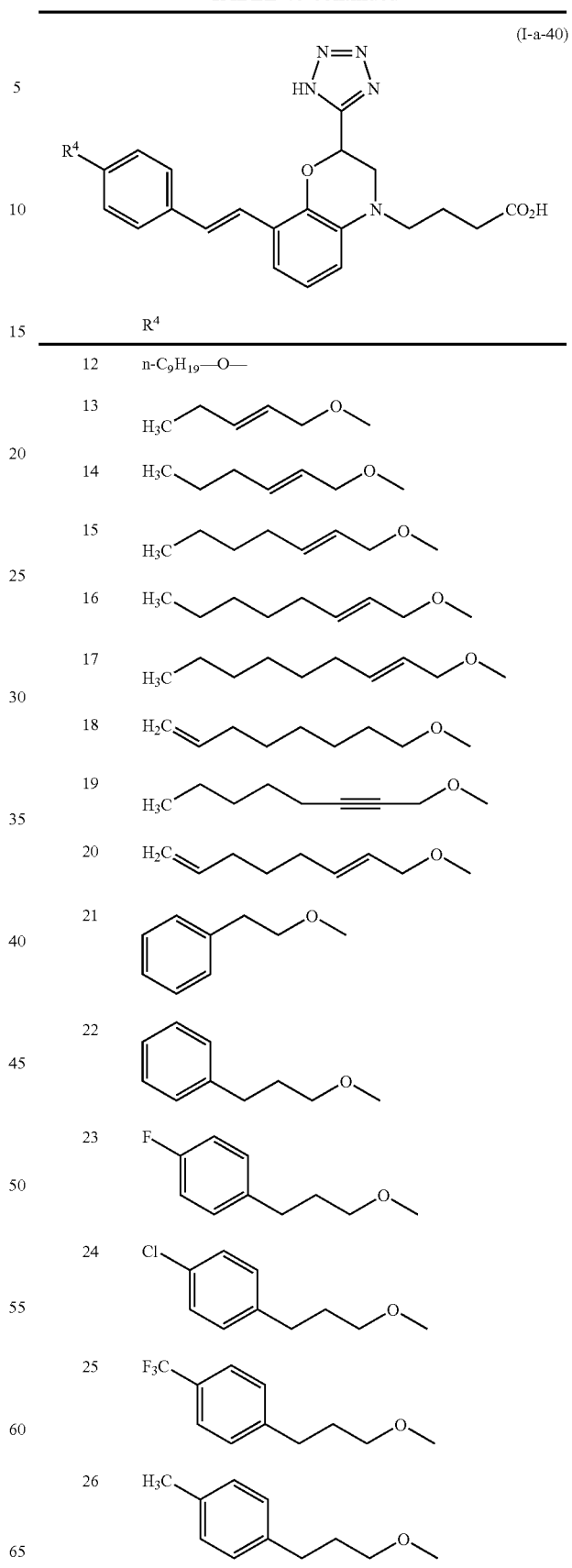

| | $R^4$ |
|---|---|
| 1 | n-C$_4$H$_9$— |
| 2 | n-C$_5$H$_{11}$— |
| 3 | n-C$_6$H$_{13}$— |
| 4 | n-C$_7$H$_{15}$— |
| 5 | n-C$_8$H$_{17}$— |
| 6 | n-C$_9$H$_{19}$— |
| 7 | n-C$_4$H$_9$—O— |
| 8 | n-C$_5$H$_{11}$—O— |
| 9 | n-C$_6$H$_{13}$—O— |
| 10 | n-C$_7$H$_{15}$—O— |
| 11 | n-C$_8$H$_{17}$—O— |

TABLE 40-continued

| | $R^4$ |
|---|---|
| 12 | n-C$_9$H$_{19}$—O— |
| 13 | H$_3$C–CH=CH–CH$_2$–O–CH$_3$ |
| 14 | H$_3$C–(CH$_2$)–CH=CH–CH$_2$–O–CH$_3$ |
| 15 | H$_3$C–(CH$_2$)$_2$–CH=CH–CH$_2$–O–CH$_3$ |
| 16 | H$_3$C–(CH$_2$)$_3$–CH=CH–CH$_2$–O–CH$_3$ |
| 17 | H$_3$C–(CH$_2$)$_4$–CH=CH–CH$_2$–O–CH$_3$ |
| 18 | H$_2$C=CH–(CH$_2$)$_4$–O–CH$_3$ |
| 19 | H$_3$C–(CH$_2$)$_3$–C≡C–CH$_2$–O–CH$_3$ |
| 20 | H$_2$C=CH–(CH$_2$)$_3$–CH=CH–CH$_2$–O–CH$_3$ |
| 21 | Ph–CH$_2$CH$_2$–O–CH$_3$ |
| 22 | Ph–(CH$_2$)$_3$–O–CH$_3$ |
| 23 | 4-F-C$_6$H$_4$–(CH$_2$)$_3$–O–CH$_3$ |
| 24 | 4-Cl-C$_6$H$_4$–(CH$_2$)$_3$–O–CH$_3$ |
| 25 | 4-F$_3$C-C$_6$H$_4$–(CH$_2$)$_3$–O–CH$_3$ |
| 26 | 4-H$_3$C-C$_6$H$_4$–(CH$_2$)$_3$–O–CH$_3$ |

TABLE 40-continued

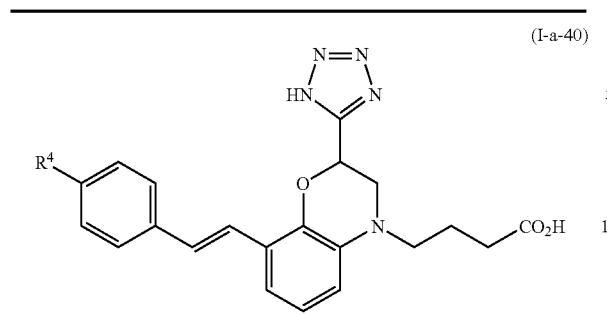

(I-a-40)

| | $R^4$ |
|---|---|
| 27 | phenyl-(CH$_2$)$_3$-OCH$_3$ |
| 28 | 4-F-phenyl-(CH$_2$)$_3$-OCH$_3$ |
| 29 | 4-Cl-phenyl-(CH$_2$)$_3$-OCH$_3$ |
| 30 | 4-F$_3$C-phenyl-(CH$_2$)$_3$-OCH$_3$ |
| 31 | 4-H$_3$C-phenyl-(CH$_2$)$_3$-OCH$_3$ |
| 32 | phenyl-(CH$_2$)$_4$-OCH$_3$ |
| 33 | 4-F-phenyl-(CH$_2$)$_4$-OCH$_3$ |
| 34 | 4-Cl-phenyl-(CH$_2$)$_4$-OCH$_3$ |
| 35 | 4-F$_3$C-phenyl-(CH$_2$)$_4$-OCH$_3$ |
| 36 | 4-H$_3$C-phenyl-(CH$_2$)$_4$-OCH$_3$ |
| 37 | phenyl-(CH$_2$)$_4$-CH$_3$ |

TABLE 40-continued

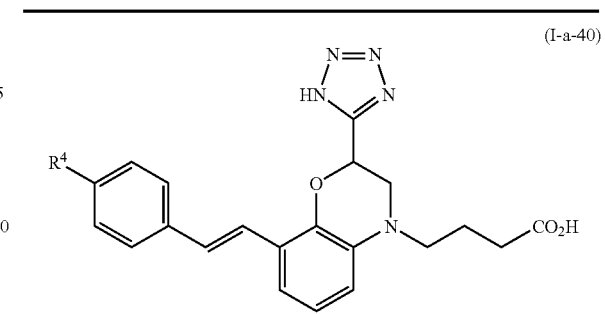

(I-a-40)

| | $R^4$ |
|---|---|
| 38 | 4-F-phenyl-(CH$_2$)$_4$-CH$_3$ |
| 39 | 4-Cl-phenyl-(CH$_2$)$_4$-CH$_3$ |
| 40 | 4-F$_3$C-phenyl-(CH$_2$)$_4$-CH$_3$ |
| 41 | 4-H$_3$C-phenyl-(CH$_2$)$_4$-CH$_3$ |
| 42 | phenyl-(CH$_2$)$_5$-CH$_3$ |
| 43 | 4-F-phenyl-(CH$_2$)$_5$-CH$_3$ |
| 44 | 4-Cl-phenyl-(CH$_2$)$_5$-CH$_3$ |
| 45 | 4-F$_3$C-phenyl-(CH$_2$)$_5$-CH$_3$ |
| 46 | 4-H$_3$C-phenyl-(CH$_2$)$_5$-CH$_3$ |
| 47 | phenyl-(CH$_2$)$_6$-CH$_3$ |
| 48 | 4-F-phenyl-(CH$_2$)$_6$-CH$_3$ |

TABLE 40-continued (I-a-40)

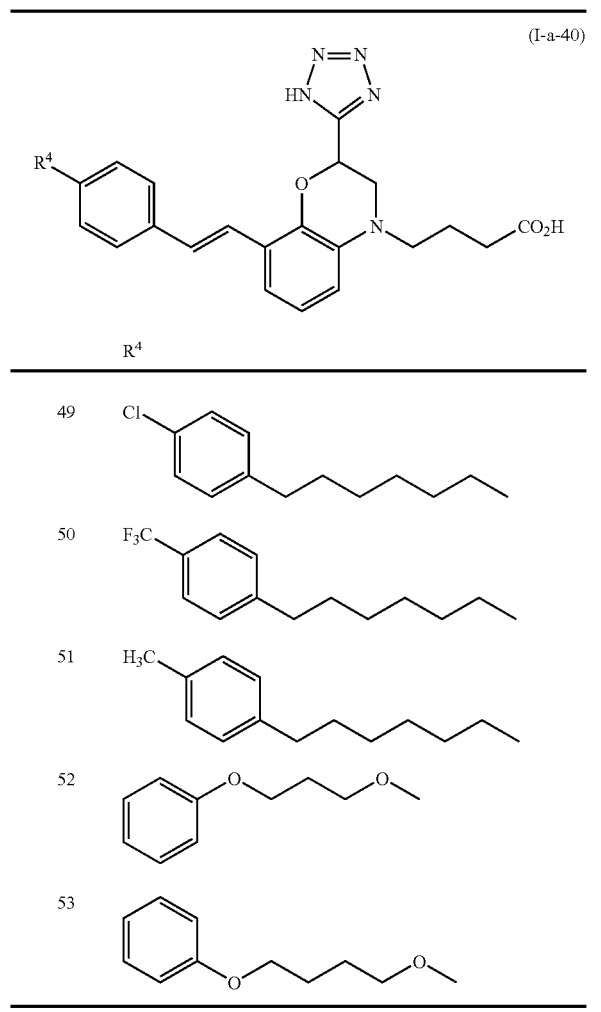

| | R⁴ |
|---|---|
| 49 | Cl–C₆H₄–CH₂CH₂CH₂CH₂CH₂CH₂CH₂– |
| 50 | F₃C–C₆H₄–CH₂CH₂CH₂CH₂CH₂CH₂CH₂– |
| 51 | H₃C–C₆H₄–CH₂CH₂CH₂CH₂CH₂CH₂CH₂– |
| 52 | C₆H₅–O–CH₂CH₂CH₂–O–CH₃ |
| 53 | C₆H₅–O–CH₂CH₂CH₂CH₂–O–CH₃ |

TABLE 41

(I-a-41)

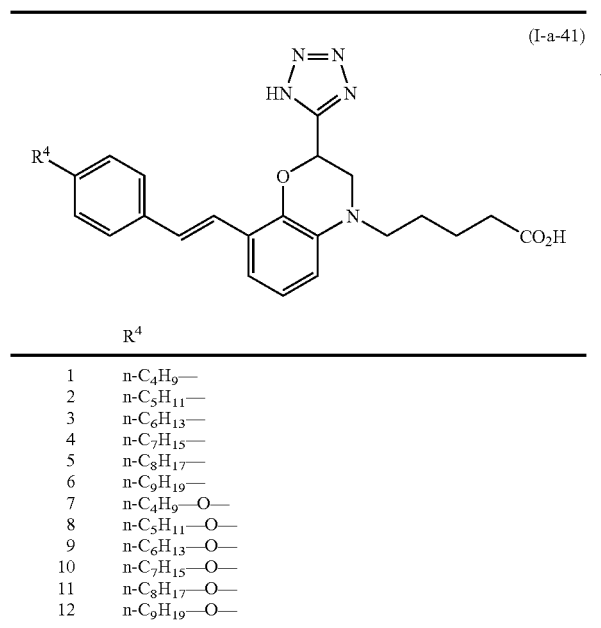

| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |

TABLE 41-continued (I-a-41)

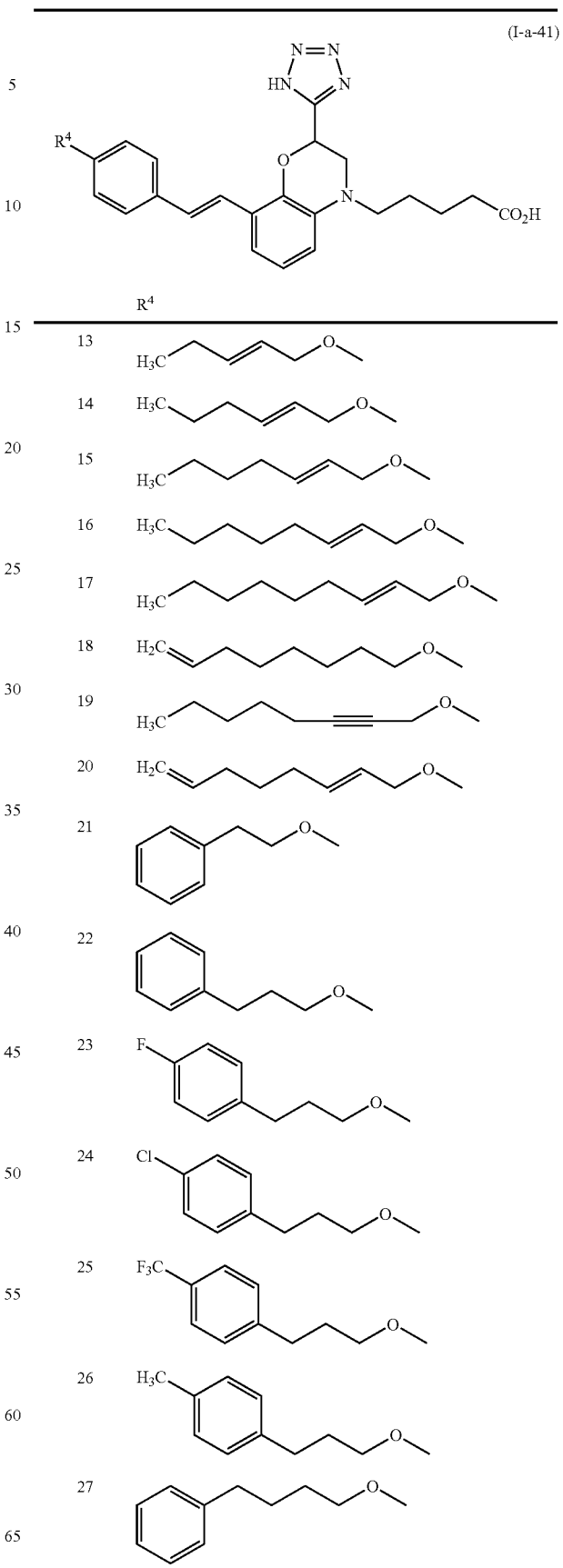

| | R⁴ |
|---|---|
| 13 | H₃C–CH₂–CH=CH–CH₂–O–CH₃ |
| 14 | H₃C–CH₂–CH₂–CH=CH–CH₂–O–CH₃ |
| 15 | H₃C–(CH₂)₃–CH=CH–CH₂–O–CH₃ |
| 16 | H₃C–(CH₂)₄–CH=CH–CH₂–O–CH₃ |
| 17 | H₃C–(CH₂)₅–CH=CH–CH₂–O–CH₃ |
| 18 | H₂C=CH–(CH₂)₅–O–CH₃ |
| 19 | H₃C–(CH₂)₃–C≡C–CH₂–O–CH₃ |
| 20 | H₂C=CH–(CH₂)₃–CH=CH–CH₂–O–CH₃ |
| 21 | C₆H₅–CH₂–CH₂–O–CH₃ |
| 22 | C₆H₅–CH₂–CH₂–CH₂–O–CH₃ |
| 23 | F–C₆H₄–CH₂–CH₂–CH₂–O–CH₃ |
| 24 | Cl–C₆H₄–CH₂–CH₂–CH₂–O–CH₃ |
| 25 | F₃C–C₆H₄–CH₂–CH₂–CH₂–O–CH₃ |
| 26 | H₃C–C₆H₄–CH₂–CH₂–CH₂–O–CH₃ |
| 27 | C₆H₅–CH₂–CH₂–CH₂–CH₂–O–CH₃ |

TABLE 41-continued (I-a-41)

[Structure: benzoxazine with R⁴-phenyl-vinyl substituent, tetrazole group, and N-(CH₂)₄-CO₂H chain]

| | R⁴ |
|---|---|
| 28 | 4-F-C₆H₄-(CH₂)₃-OCH₃ |
| 29 | 4-Cl-C₆H₄-(CH₂)₃-OCH₃ |
| 30 | 4-F₃C-C₆H₄-(CH₂)₃-OCH₃ |
| 31 | 4-H₃C-C₆H₄-(CH₂)₃-OCH₃ |
| 32 | C₆H₅-(CH₂)₄-OCH₃ |
| 33 | 4-F-C₆H₄-(CH₂)₄-OCH₃ |
| 34 | 4-Cl-C₆H₄-(CH₂)₄-OCH₃ |
| 35 | 4-F₃C-C₆H₄-(CH₂)₄-OCH₃ |
| 36 | 4-H₃C-C₆H₄-(CH₂)₄-OCH₃ |
| 37 | C₆H₅-(CH₂)₄-CH₃ |
| 38 | 4-F-C₆H₄-(CH₂)₄-CH₃ |
| 39 | 4-Cl-C₆H₄-(CH₂)₄-CH₃ |
| 40 | 4-F₃C-C₆H₄-(CH₂)₄-CH₃ |
| 41 | 4-H₃C-C₆H₄-(CH₂)₄-CH₃ |
| 42 | C₆H₅-(CH₂)₅-CH₃ |
| 43 | 4-F-C₆H₄-(CH₂)₅-CH₃ |
| 44 | 4-Cl-C₆H₄-(CH₂)₅-CH₃ |
| 45 | 4-F₃C-C₆H₄-(CH₂)₅-CH₃ |
| 46 | 4-H₃C-C₆H₄-(CH₂)₅-CH₃ |
| 47 | C₆H₅-(CH₂)₆-CH₃ |
| 48 | 4-F-C₆H₄-(CH₂)₆-CH₃ |

TABLE 41-continued

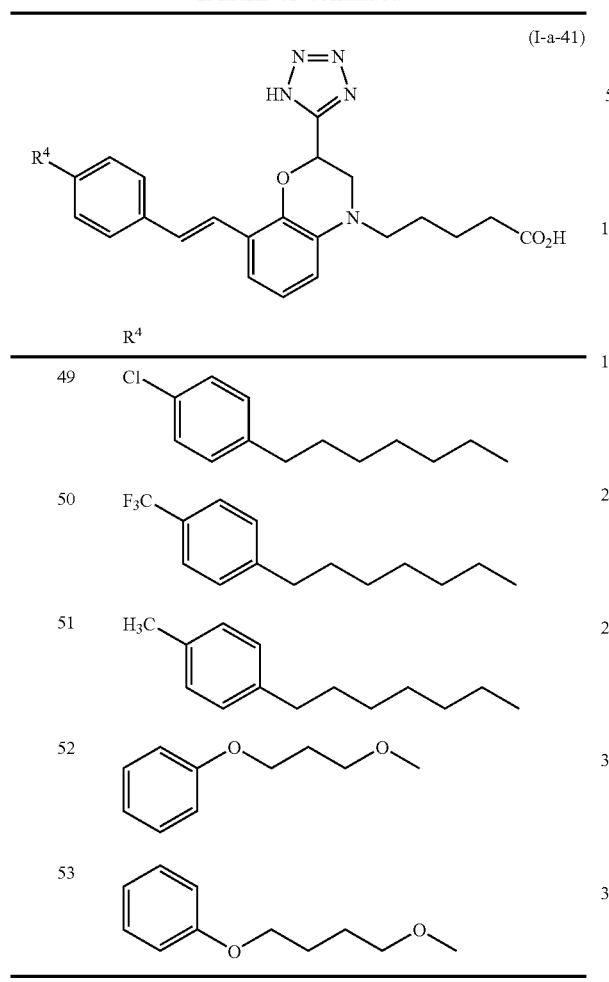

| | R⁴ |
|---|---|
| 49 | 4-Cl-C₆H₄-(CH₂)₆- |
| 50 | 4-F₃C-C₆H₄-(CH₂)₆- |
| 51 | 4-H₃C-C₆H₄-(CH₂)₆- |
| 52 | C₆H₅-O-(CH₂)₂-O-CH₃ |
| 53 | C₆H₅-O-(CH₂)₃-O-CH₃ |

TABLE 42

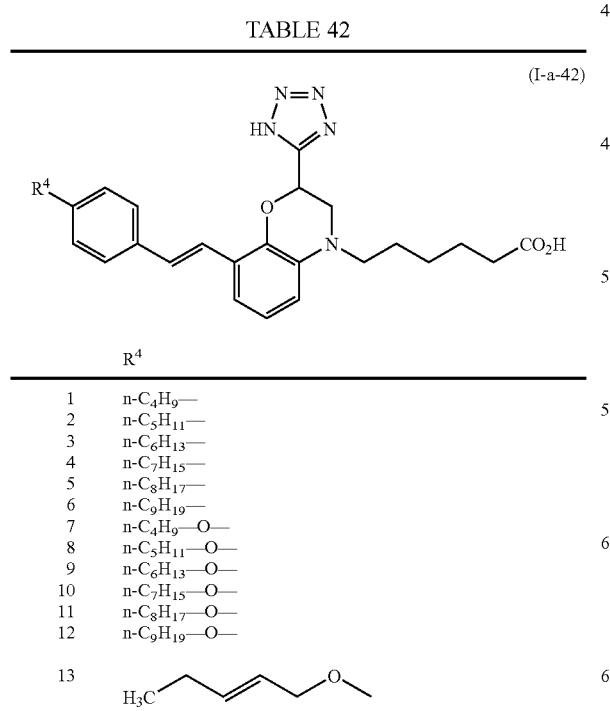

| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | H₃C-CH=CH-CH₂-O-CH₃ |

TABLE 42-continued

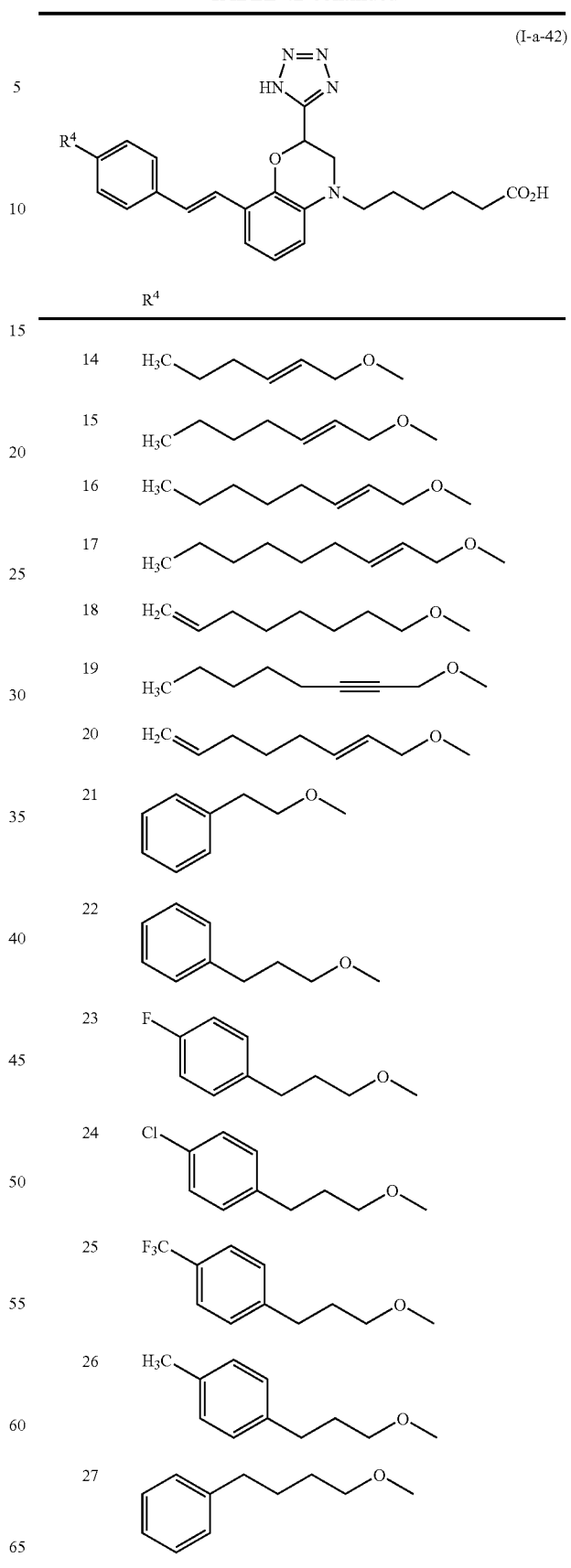

| | R⁴ |
|---|---|
| 14 | H₃C-CH₂-CH=CH-CH₂-O-CH₃ |
| 15 | H₃C-(CH₂)₂-CH=CH-CH₂-O-CH₃ |
| 16 | H₃C-(CH₂)₃-CH=CH-CH₂-O-CH₃ |
| 17 | H₃C-(CH₂)₄-CH=CH-CH₂-O-CH₃ |
| 18 | H₂C=CH-(CH₂)₄-O-CH₃ |
| 19 | H₃C-(CH₂)₃-C≡C-CH₂-O-CH₃ |
| 20 | H₂C=CH-(CH₂)₂-CH=CH-CH₂-O-CH₃ |
| 21 | C₆H₅-(CH₂)₂-O-CH₃ |
| 22 | C₆H₅-(CH₂)₃-O-CH₃ |
| 23 | 4-F-C₆H₄-(CH₂)₂-O-CH₃ |
| 24 | 4-Cl-C₆H₄-(CH₂)₂-O-CH₃ |
| 25 | 4-F₃C-C₆H₄-(CH₂)₂-O-CH₃ |
| 26 | 4-H₃C-C₆H₄-(CH₂)₂-O-CH₃ |
| 27 | C₆H₅-(CH₂)₄-O-CH₃ |

TABLE 42-continued
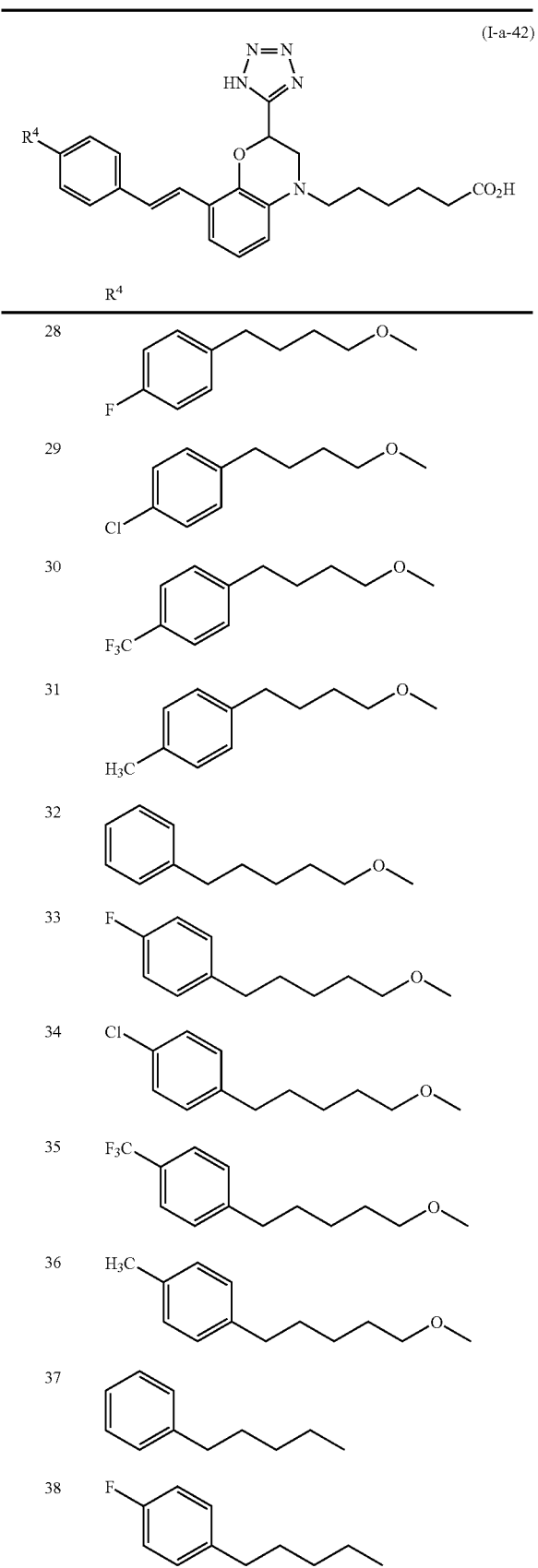
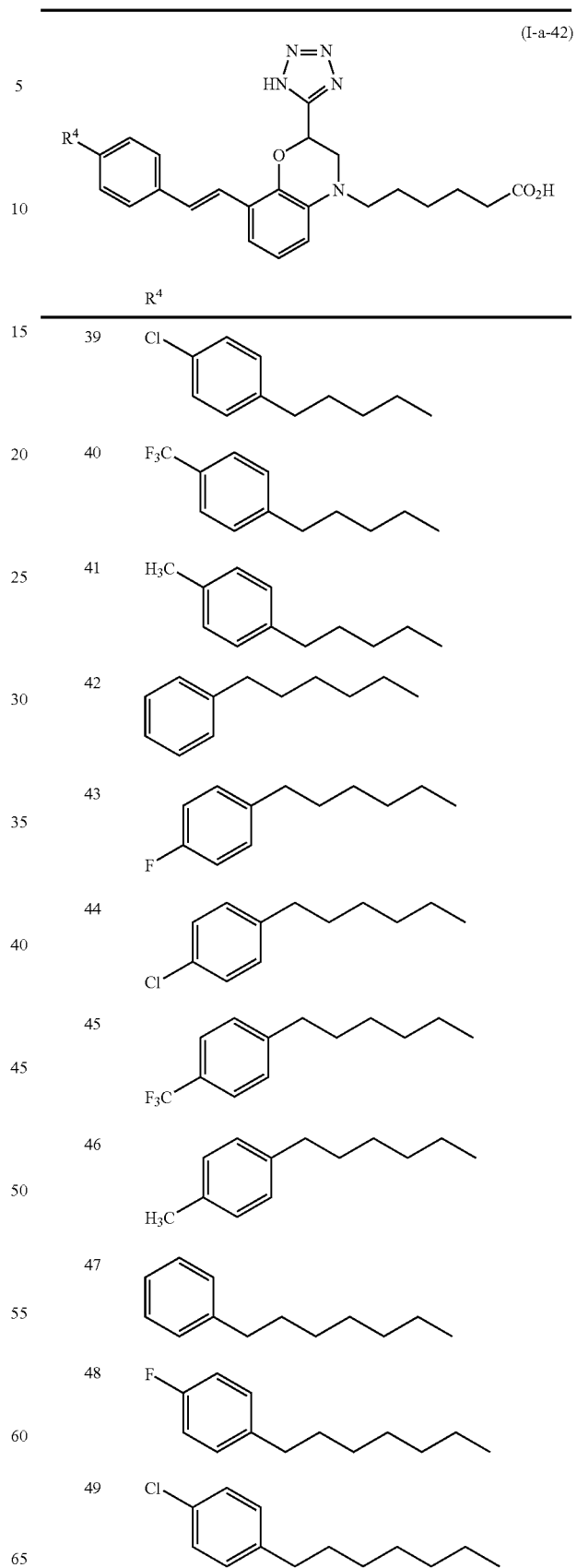

TABLE 42-continued

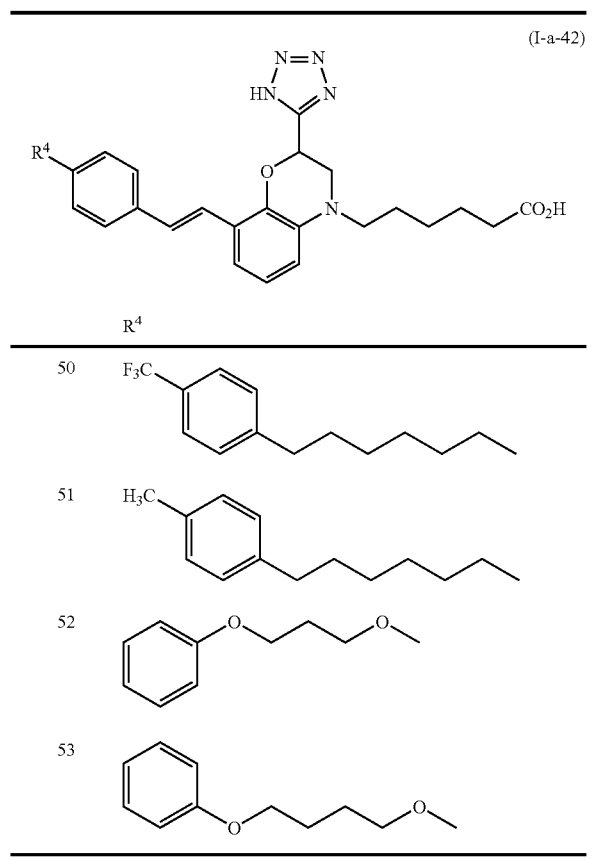
(I-a-42)

| | R⁴ |
|---|---|
| 50 | 4-(CF₃)C₆H₄–(CH₂)₆– |
| 51 | 4-(CH₃)C₆H₄–(CH₂)₆– |
| 52 | PhO–(CH₂)₃–OCH₃ |
| 53 | PhO–(CH₂)₄–OCH₃ |

TABLE 43

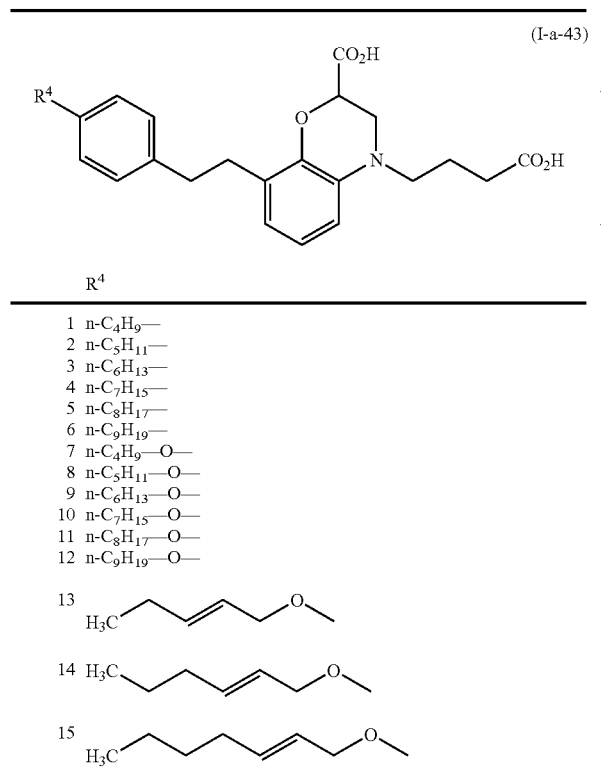
(I-a-43)

| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | CH₃–CH=CH–CH₂–OCH₃ |
| 14 | CH₃–CH₂–CH=CH–CH₂–OCH₃ |
| 15 | CH₃–(CH₂)₂–CH=CH–CH₂–OCH₃ |

TABLE 43-continued

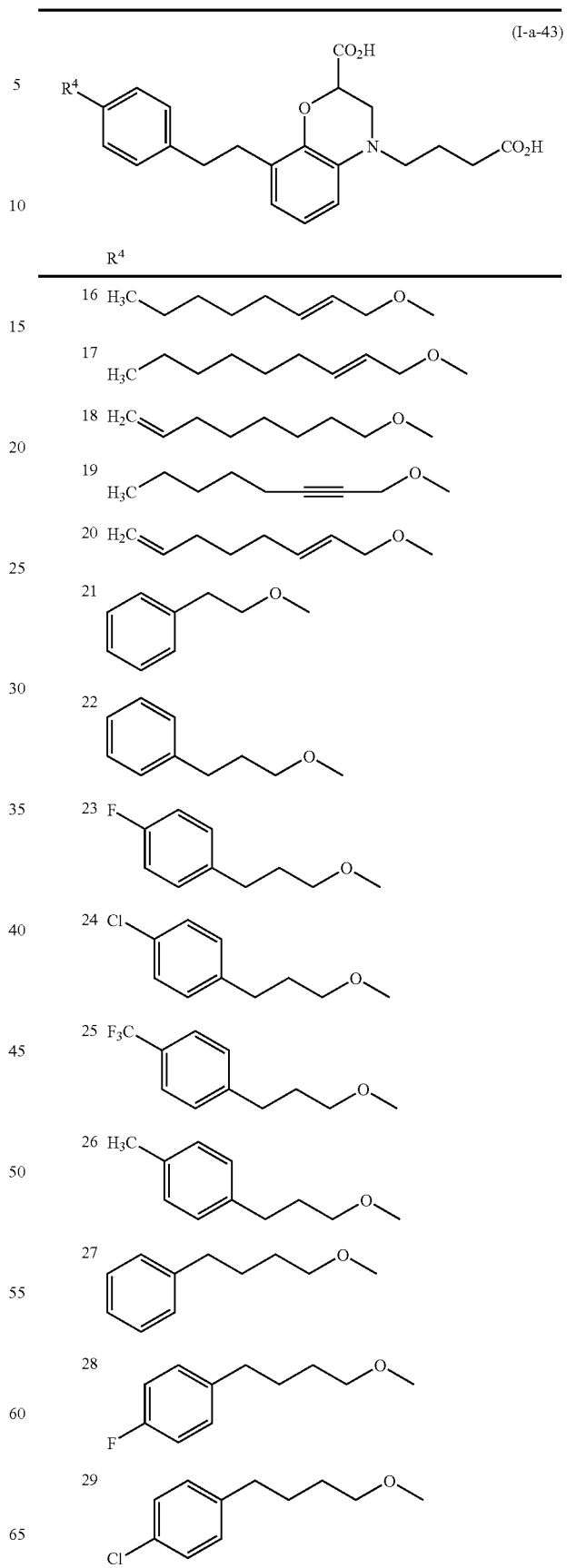
(I-a-43)

| | R⁴ |
|---|---|
| 16 | CH₃–(CH₂)₃–CH=CH–CH₂–OCH₃ |
| 17 | CH₃–(CH₂)₄–CH=CH–CH₂–OCH₃ |
| 18 | CH₂=CH–(CH₂)₅–OCH₃ |
| 19 | CH₃–(CH₂)₂–C≡C–CH₂–OCH₃ |
| 20 | CH₂=CH–(CH₂)₂–CH=CH–CH₂–OCH₃ |
| 21 | Ph–(CH₂)₂–OCH₃ |
| 22 | Ph–(CH₂)₃–OCH₃ |
| 23 | 4-F-C₆H₄–(CH₂)₃–OCH₃ |
| 24 | 4-Cl-C₆H₄–(CH₂)₃–OCH₃ |
| 25 | 4-(CF₃)C₆H₄–(CH₂)₃–OCH₃ |
| 26 | 4-(CH₃)C₆H₄–(CH₂)₃–OCH₃ |
| 27 | Ph–(CH₂)₄–OCH₃ |
| 28 | 4-F-C₆H₄–(CH₂)₄–OCH₃ |
| 29 | 4-Cl-C₆H₄–(CH₂)₄–OCH₃ |

TABLE 43-continued
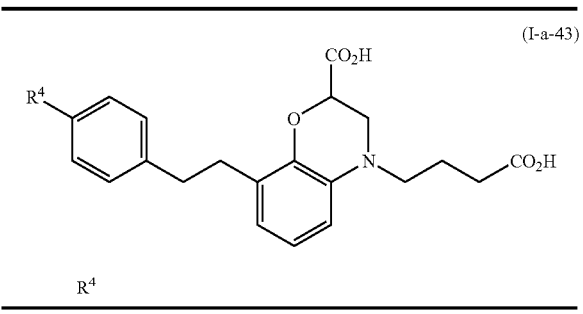
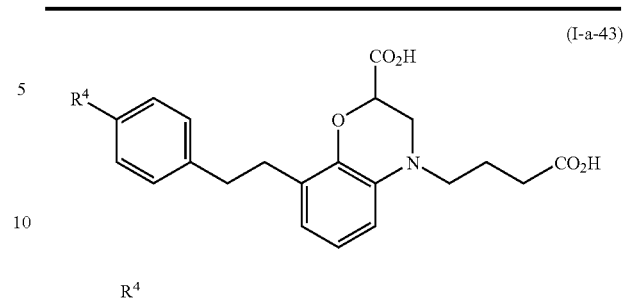

TABLE 43-continued
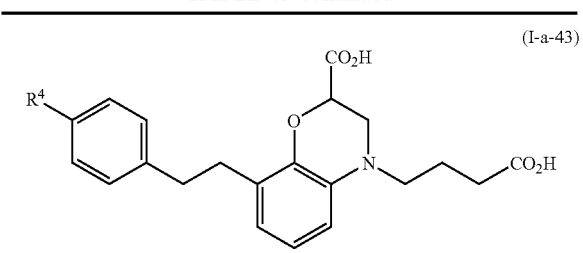
(I-a-43)
R⁴
52 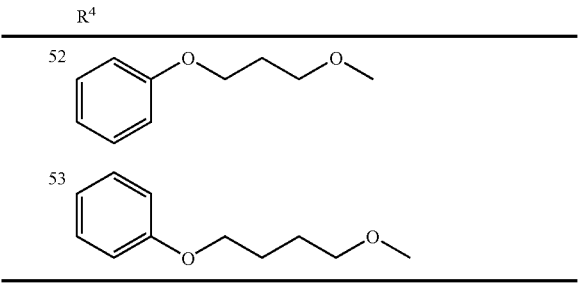
53 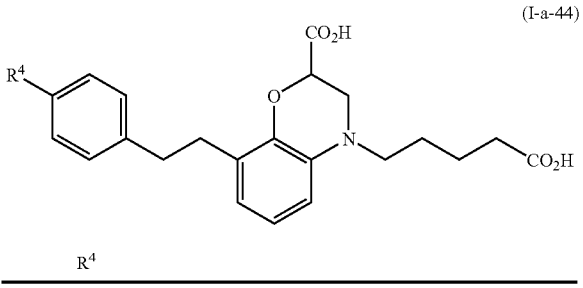
TABLE 44
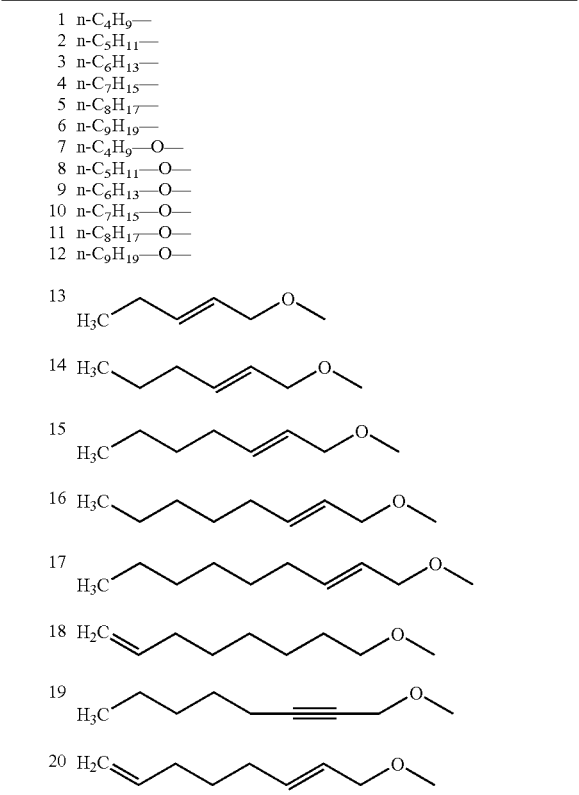
(I-a-44)
R⁴
1  n-C₄H₉—
2  n-C₅H₁₁—
3  n-C₆H₁₃—
4  n-C₇H₁₅—
5  n-C₈H₁₇—
6  n-C₉H₁₉—
7  n-C₄H₉—O—
8  n-C₅H₁₁—O—
9  n-C₆H₁₃—O—
10 n-C₇H₁₅—O—
11 n-C₈H₁₇—O—
12 n-C₉H₁₉—O—
TABLE 44-continued
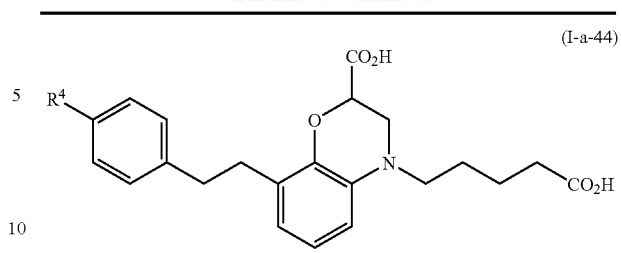
(I-a-44)
R⁴
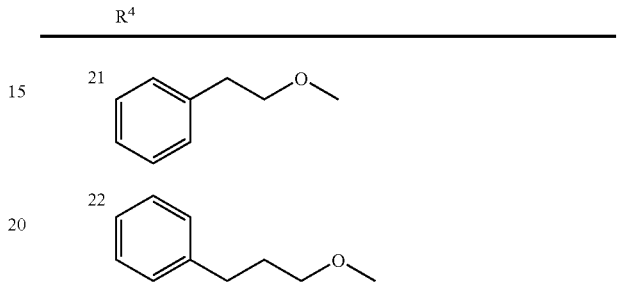
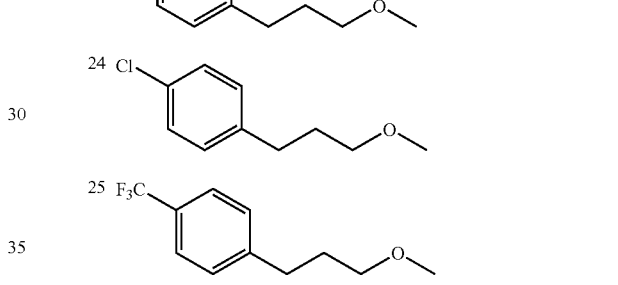
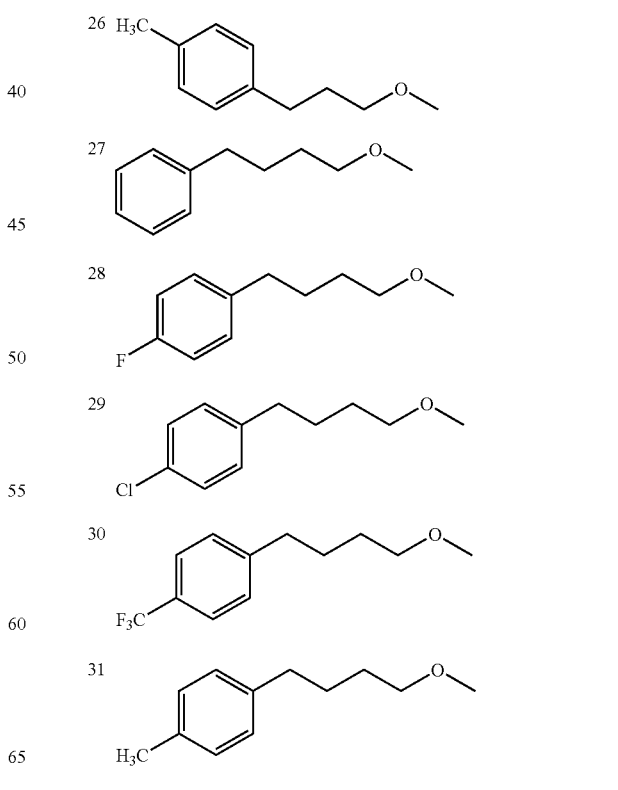

TABLE 44-continued
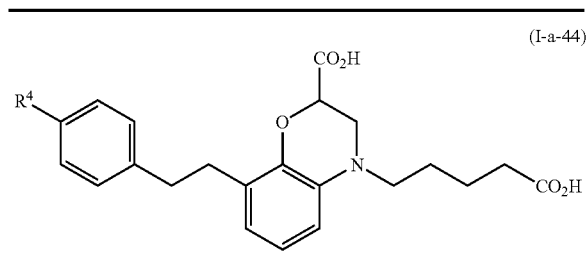
(I-a-44)
| | R[4] |
|---|---|
| 32 | 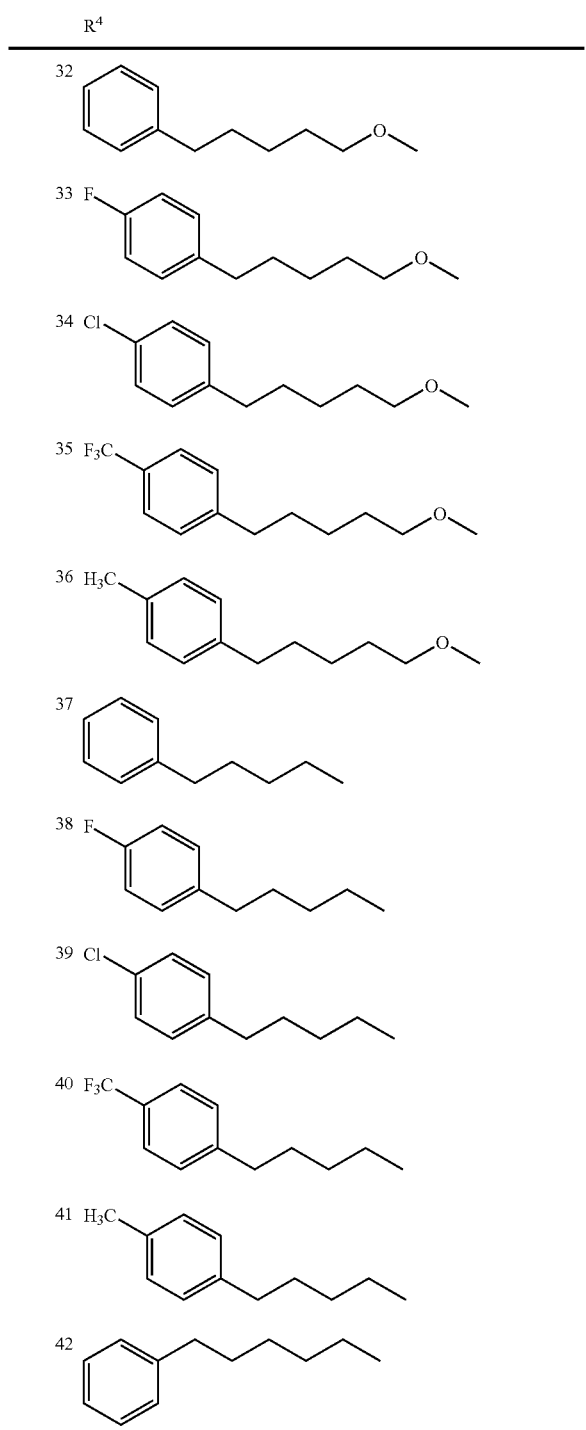 |
| 33 | |
| 34 | |
| 35 | |
| 36 | |
| 37 | |
| 38 | |
| 39 | |
| 40 | |
| 41 | |
| 42 | |
TABLE 44-continued
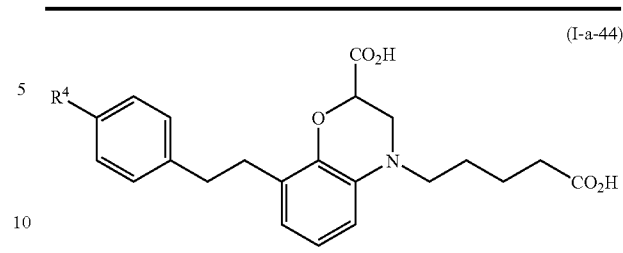
(I-a-44)
| | R[4] |
|---|---|
| 43 | 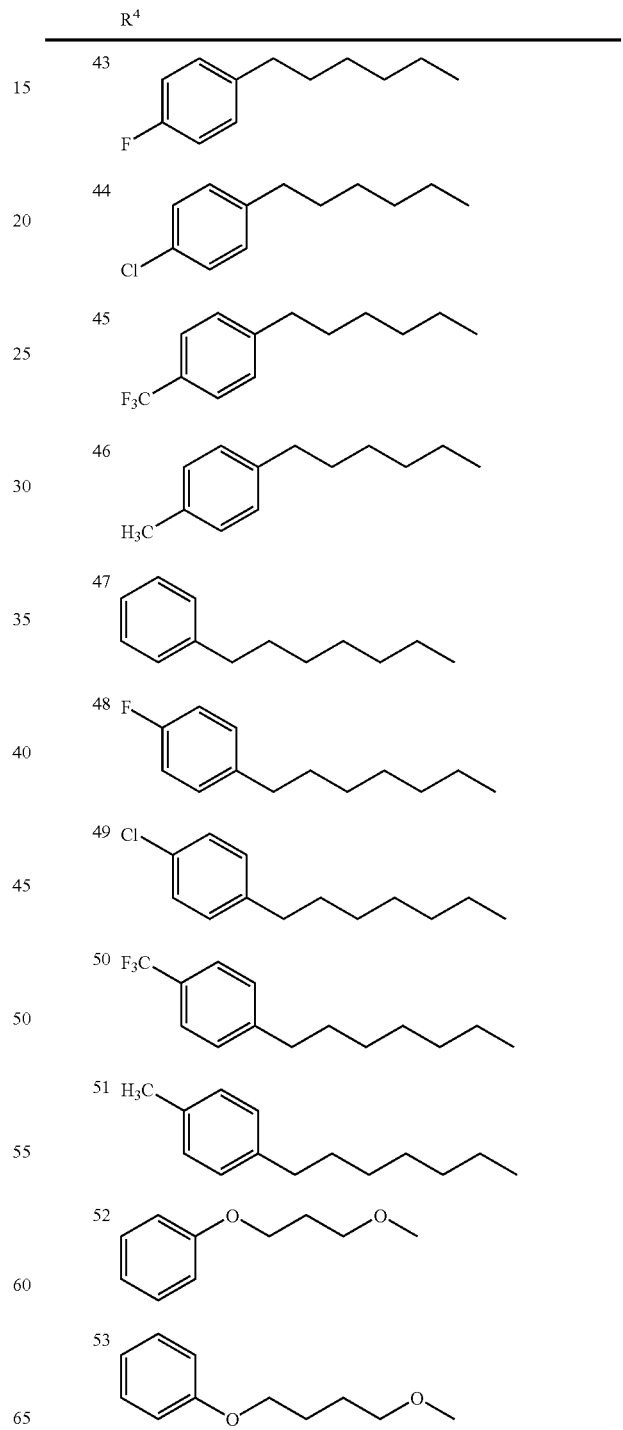 |
| 44 | |
| 45 | |
| 46 | |
| 47 | |
| 48 | |
| 49 | |
| 50 | |
| 51 | |
| 52 | |
| 53 | |

TABLE 45
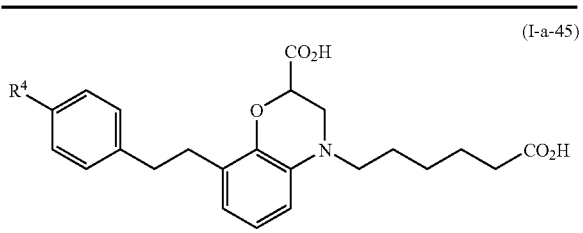
(I-a-45)
R⁴
1  n-C₄H₉—
2  n-C₅H₁₁—
3  n-C₆H₁₃—
4  n-C₇H₁₅—
5  n-C₈H₁₇—
6  n-C₉H₁₉—
7  n-C₄H₉—O—
8  n-C₅H₁₁—O—
9  n-C₆H₁₃—O—
10 n-C₇H₁₅—O—
11 n-C₈H₁₇—O—
12 n-C₉H₁₉—O—
TABLE 45-continued
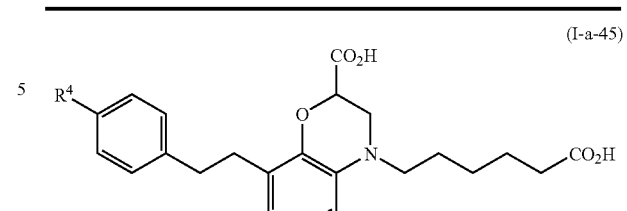
(I-a-45)

TABLE 45-continued
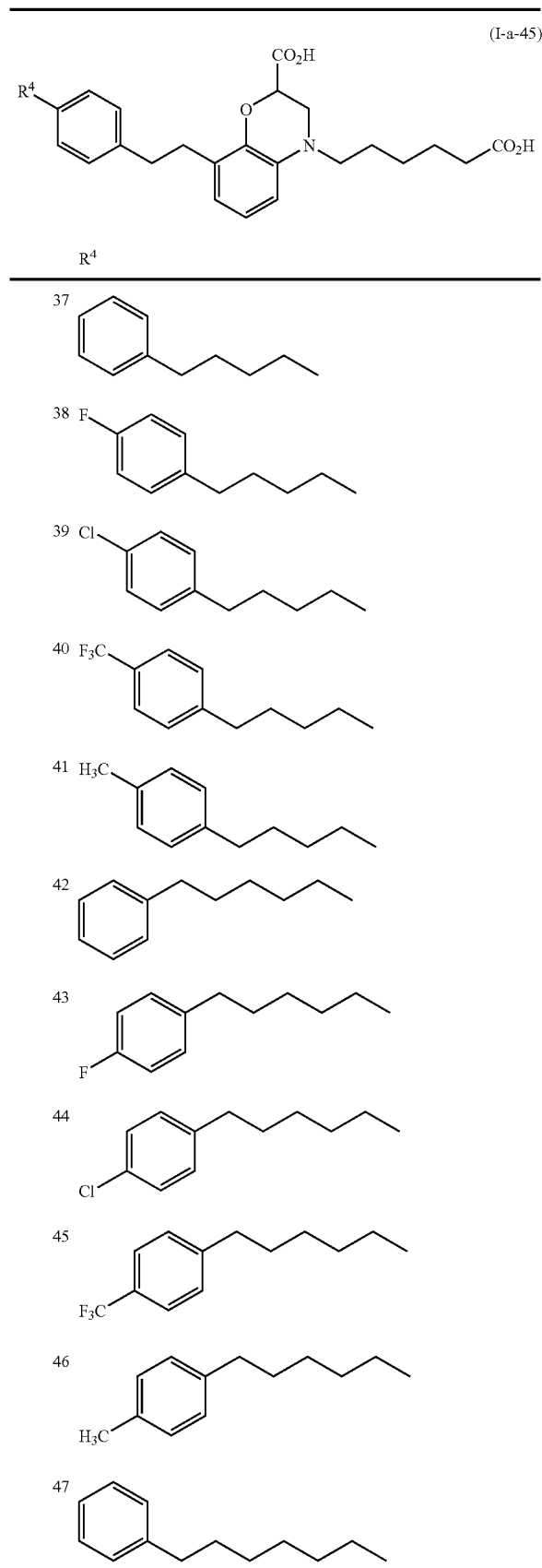
TABLE 45-continued
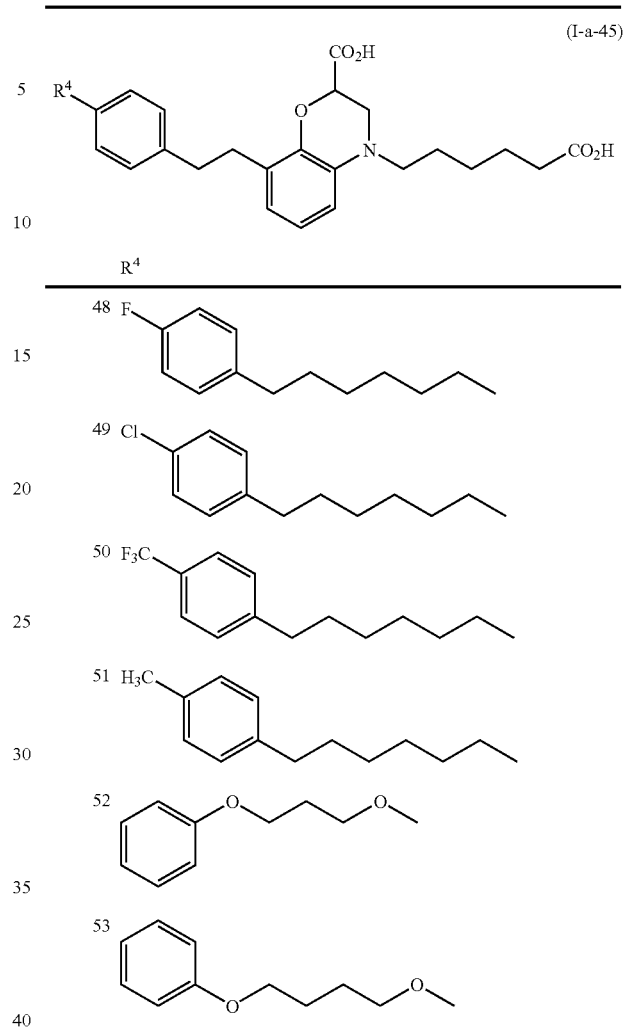
TABLE 46
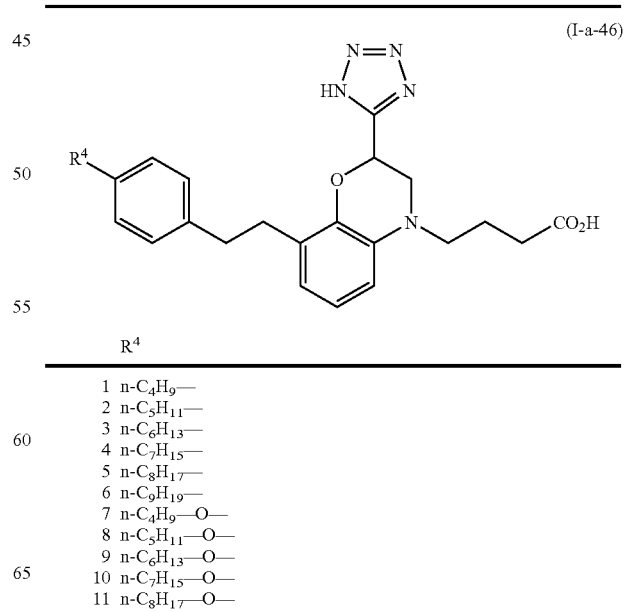
| | $R^4$ |
|---|---|
| 1 | n-$C_4H_9$— |
| 2 | n-$C_5H_{11}$— |
| 3 | n-$C_6H_{13}$— |
| 4 | n-$C_7H_{15}$— |
| 5 | n-$C_8H_{17}$— |
| 6 | n-$C_9H_{19}$— |
| 7 | n-$C_4H_9$—O— |
| 8 | n-$C_5H_{11}$—O— |
| 9 | n-$C_6H_{13}$—O— |
| 10 | n-$C_7H_{15}$—O— |
| 11 | n-$C_8H_{17}$—O— |

TABLE 46-continued
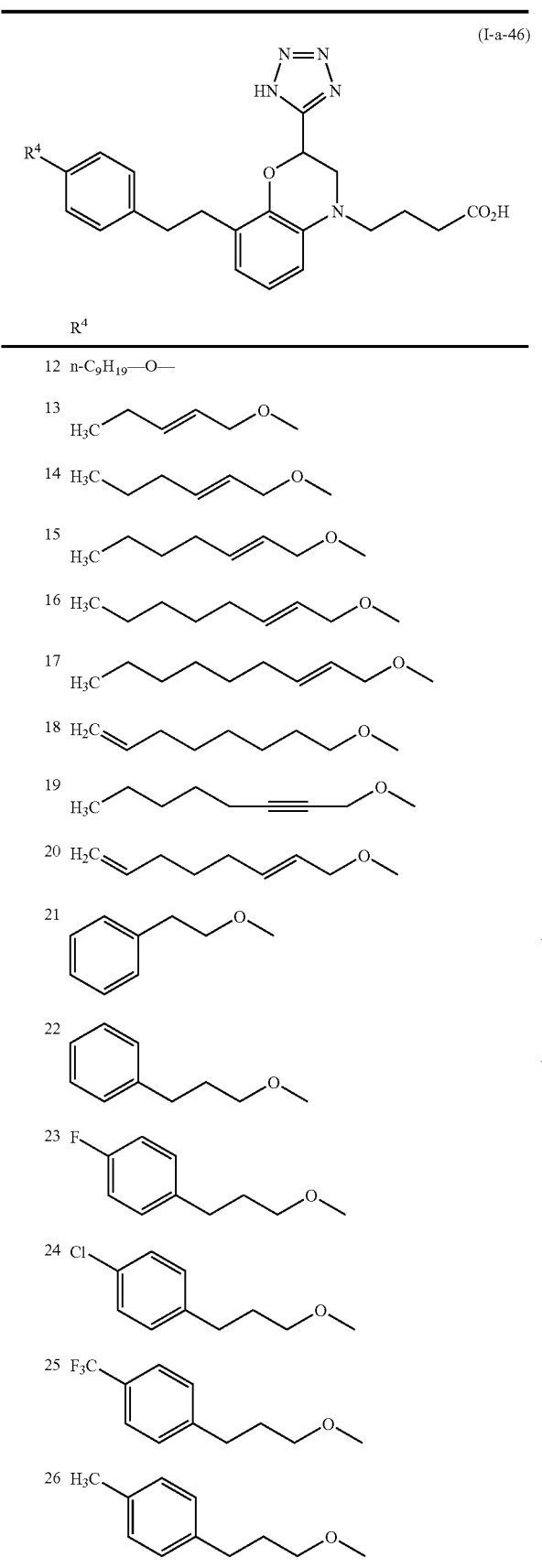
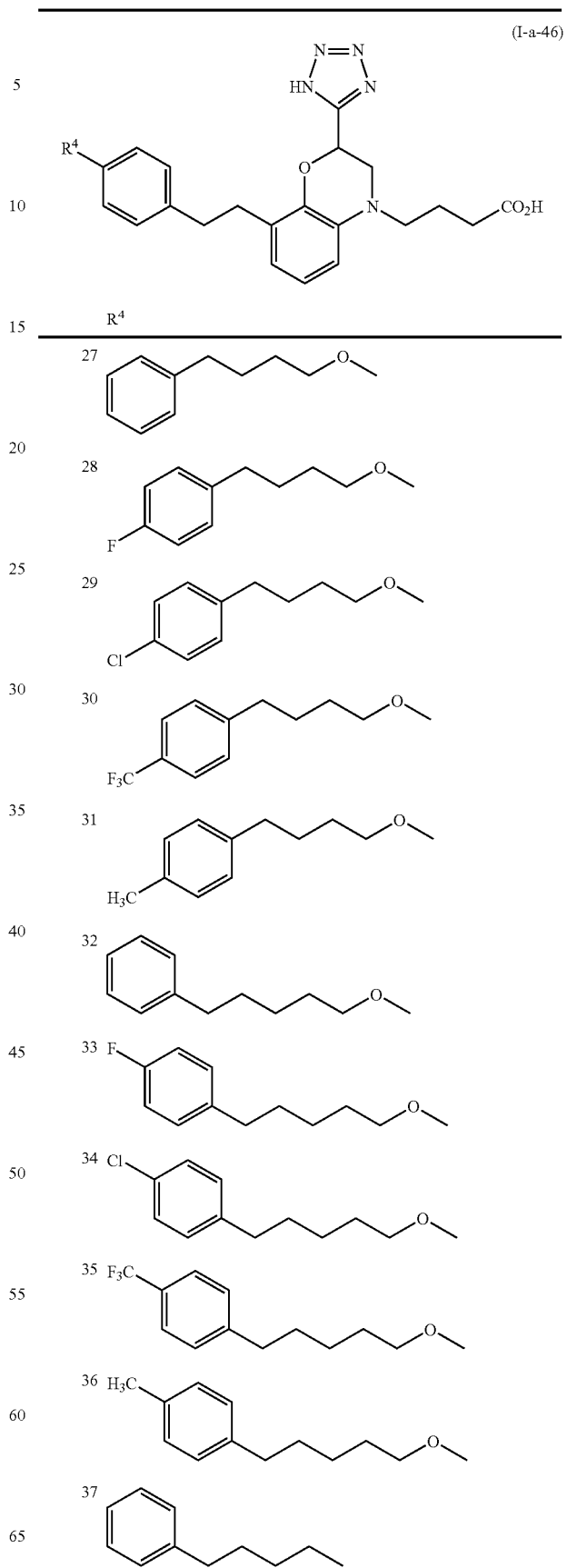

TABLE 46-continued
(I-a-46)
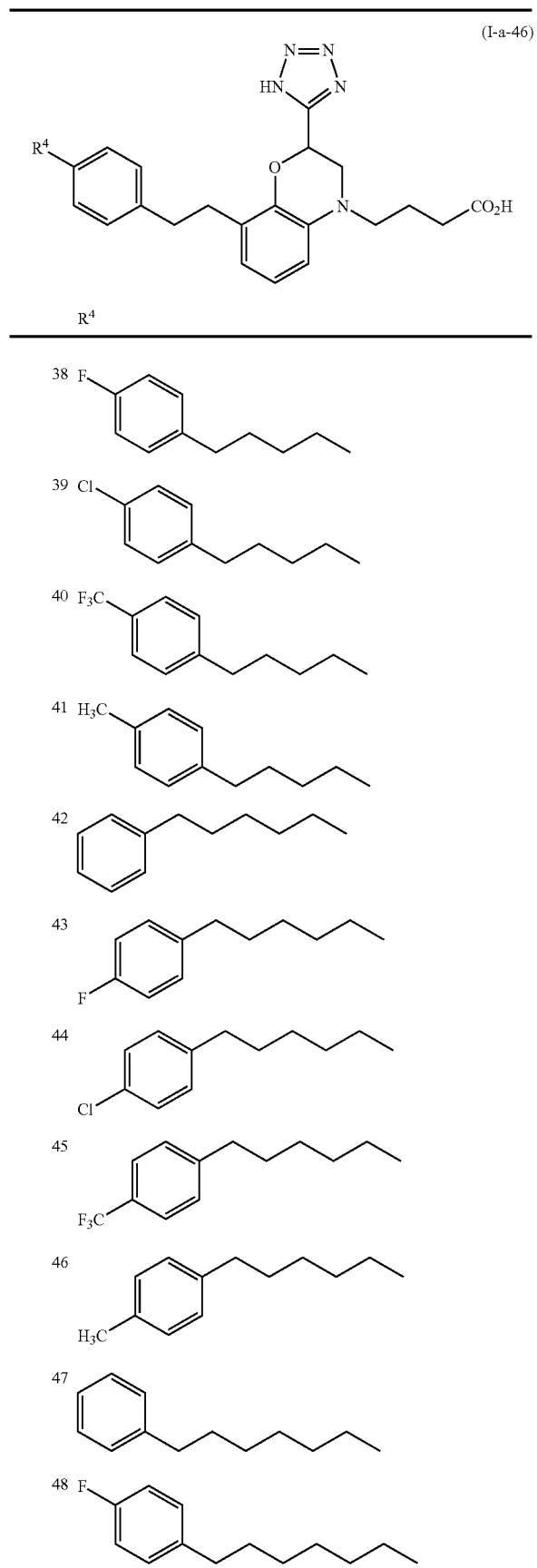
TABLE 47
(I-a-47)
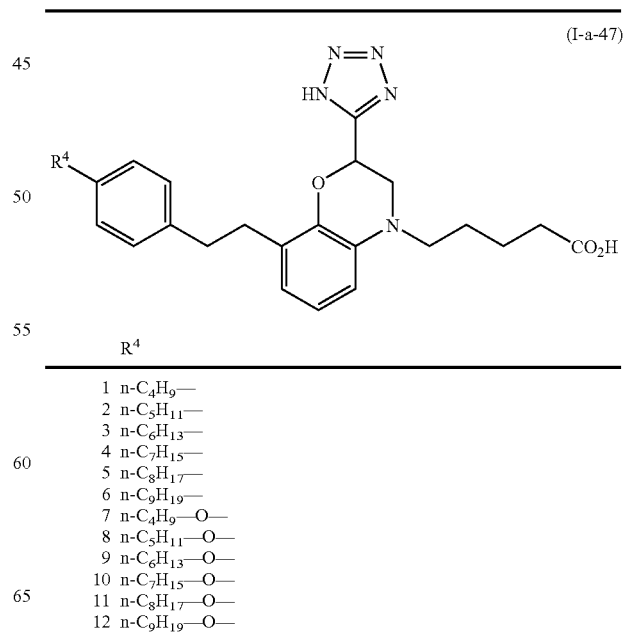
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |

TABLE 47-continued (I-a-47)

[Structure: benzoxazine core with tetrazole substituent at position 2, R⁴-CH₂CH₂- group on aromatic ring, and N-(CH₂)₄CO₂H chain]

| # | R⁴ |
|---|---|
| 13 | H₃C-CH=CH-CH₂-O-CH₃ |
| 14 | H₃C-CH₂-CH=CH-CH₂-O-CH₃ |
| 15 | H₃C-(CH₂)₂-CH=CH-CH₂-O-CH₃ |
| 16 | H₃C-(CH₂)₃-CH=CH-CH₂-O-CH₃ |
| 17 | H₃C-(CH₂)₄-CH=CH-CH₂-O-CH₃ |
| 18 | H₂C=CH-(CH₂)₅-O-CH₃ |
| 19 | H₃C-(CH₂)₃-C≡C-CH₂-O-CH₃ |
| 20 | H₂C=CH-(CH₂)₃-CH=CH-CH₂-O-CH₃ |
| 21 | Ph-CH₂-CH₂-O-CH₃ |
| 22 | Ph-(CH₂)₃-O-CH₃ |
| 23 | 4-F-C₆H₄-(CH₂)₃-O-CH₃ |
| 24 | 4-Cl-C₆H₄-(CH₂)₃-O-CH₃ |
| 25 | 4-F₃C-C₆H₄-(CH₂)₃-O-CH₃ |
| 26 | 4-H₃C-C₆H₄-(CH₂)₃-O-CH₃ |
| 27 | Ph-(CH₂)₄-O-CH₃ |
| 28 | 4-F-C₆H₄-(CH₂)₄-O-CH₃ |
| 29 | 4-Cl-C₆H₄-(CH₂)₄-O-CH₃ |
| 30 | 4-F₃C-C₆H₄-(CH₂)₄-O-CH₃ |
| 31 | 4-H₃C-C₆H₄-(CH₂)₄-O-CH₃ |
| 32 | Ph-(CH₂)₅-O-CH₃ |
| 33 | 4-F-C₆H₄-(CH₂)₅-O-CH₃ |
| 34 | 4-Cl-C₆H₄-(CH₂)₅-O-CH₃ |
| 35 | 4-F₃C-C₆H₄-(CH₂)₅-O-CH₃ |
| 36 | 4-H₃C-C₆H₄-(CH₂)₅-O-CH₃ |
| 37 | Ph-(CH₂)₄-CH₃ |

TABLE 47-continued
(I-a-47)
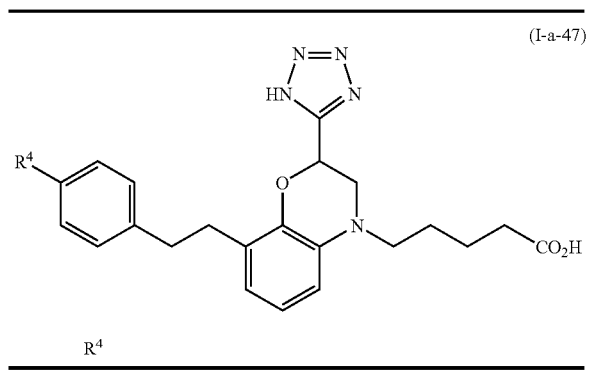
| | R⁴ |
|---|---|
| 38 | 4-F-C₆H₄-(CH₂)₄- |
| 39 | 4-Cl-C₆H₄-(CH₂)₄- |
| 40 | 4-F₃C-C₆H₄-(CH₂)₄- |
| 41 | 4-H₃C-C₆H₄-(CH₂)₄- |
| 42 | C₆H₅-(CH₂)₅- |
| 43 | 4-F-C₆H₄-(CH₂)₅- |
| 44 | 4-Cl-C₆H₄-(CH₂)₅- |
| 45 | 4-F₃C-C₆H₄-(CH₂)₅- |
| 46 | 4-H₃C-C₆H₄-(CH₂)₅- |
| 47 | C₆H₅-(CH₂)₆- |
| 48 | 4-F-C₆H₄-(CH₂)₆- |
TABLE 47-continued
(I-a-47)
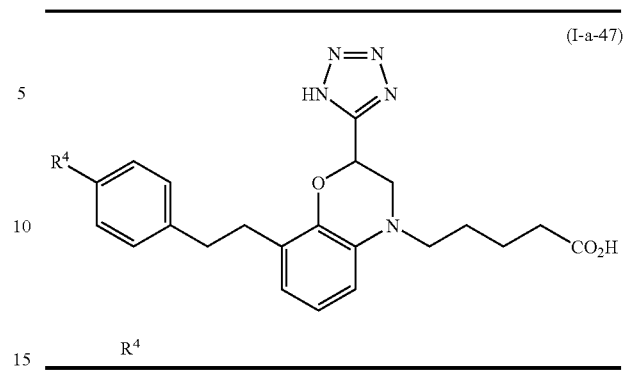
| | R⁴ |
|---|---|
| 49 | 4-Cl-C₆H₄-(CH₂)₅- |
| 50 | 4-F₃C-C₆H₄-(CH₂)₅- |
| 51 | 4-H₃C-C₆H₄-(CH₂)₅- |
| 52 | C₆H₅-O-(CH₂)₃-O-CH₃ |
| 53 | C₆H₅-O-(CH₂)₄-O-CH₃ |
TABLE 48
(I-a-48)
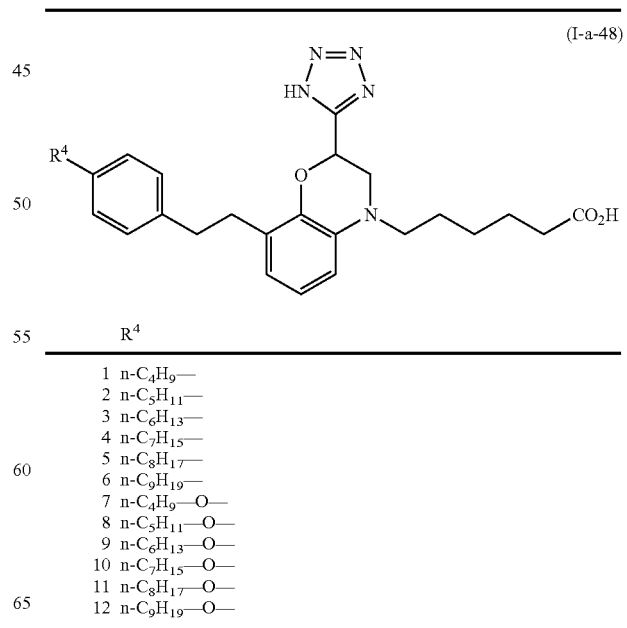
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |

TABLE 48-continued
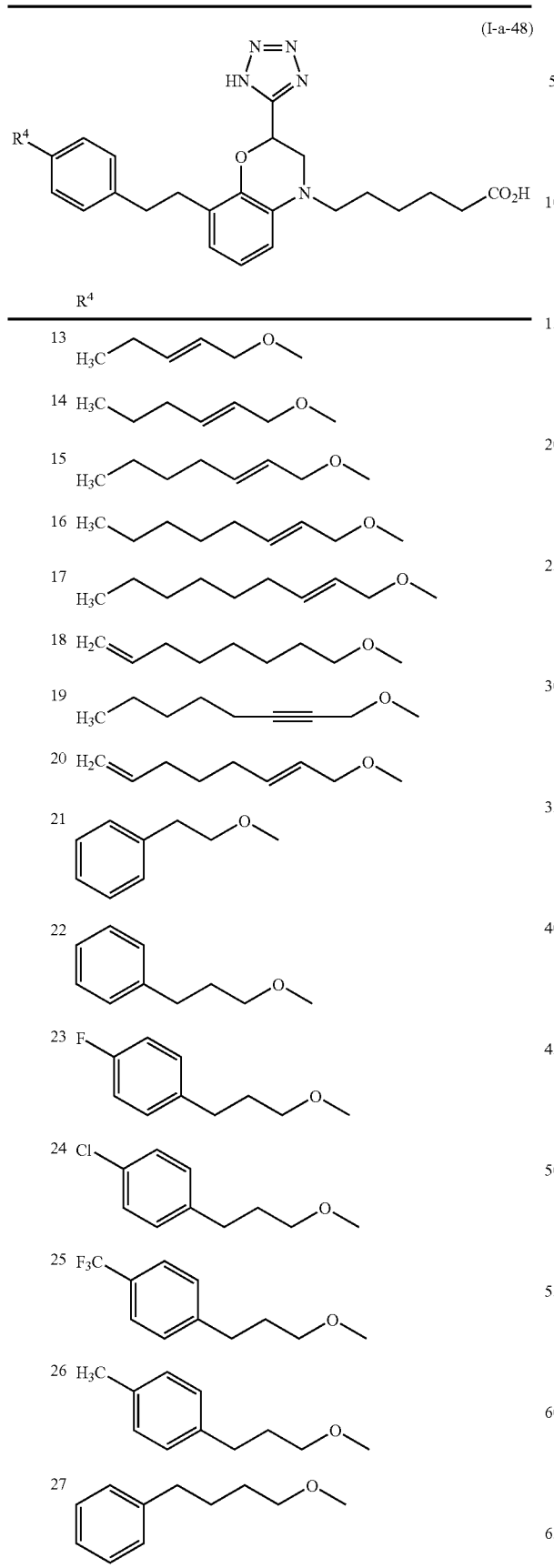
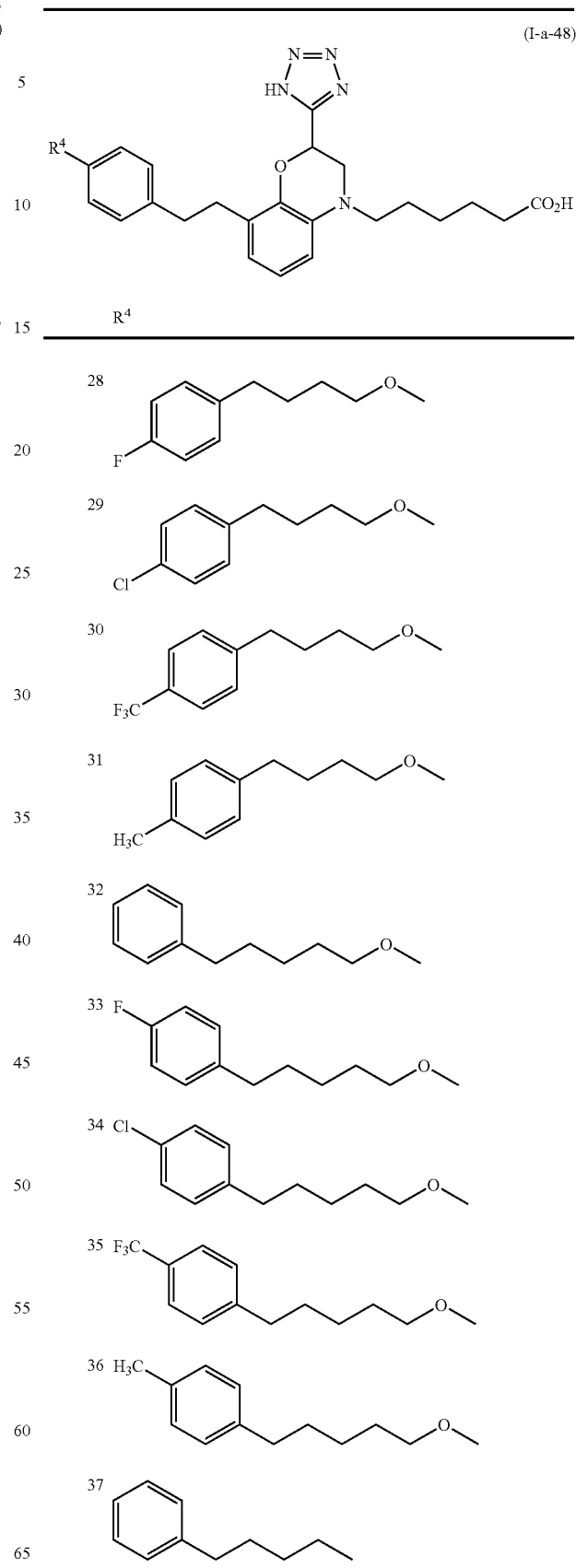

TABLE 48-continued
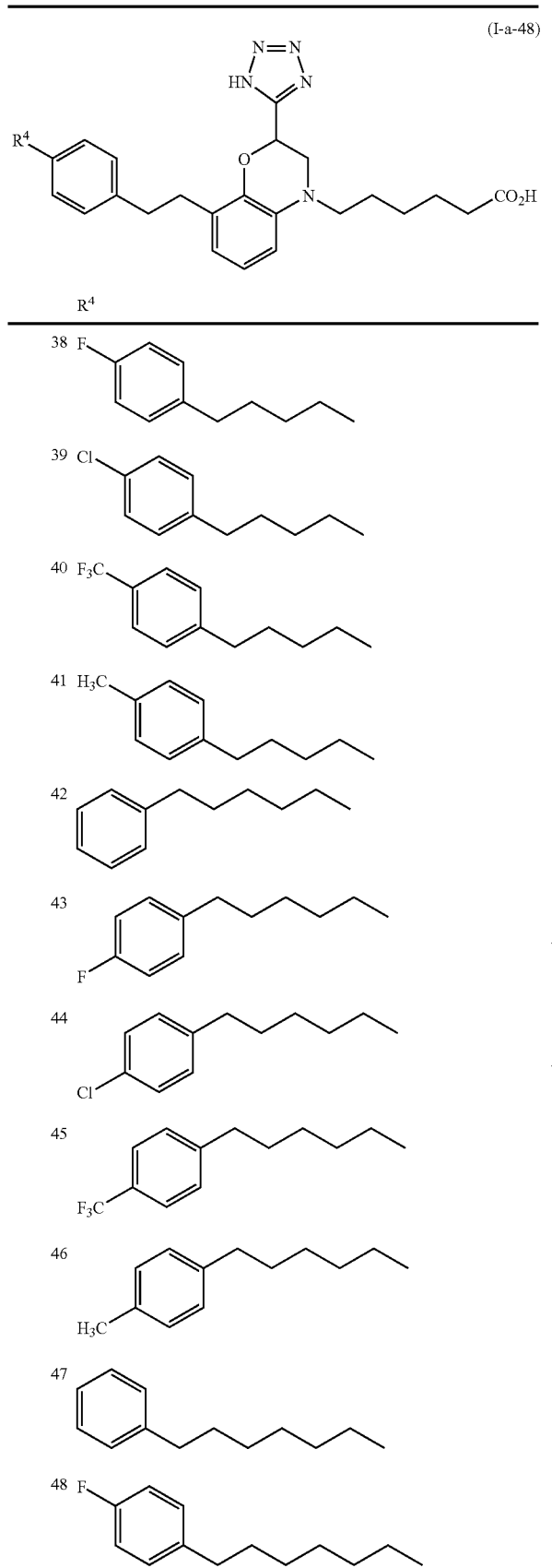
TABLE 48-continued
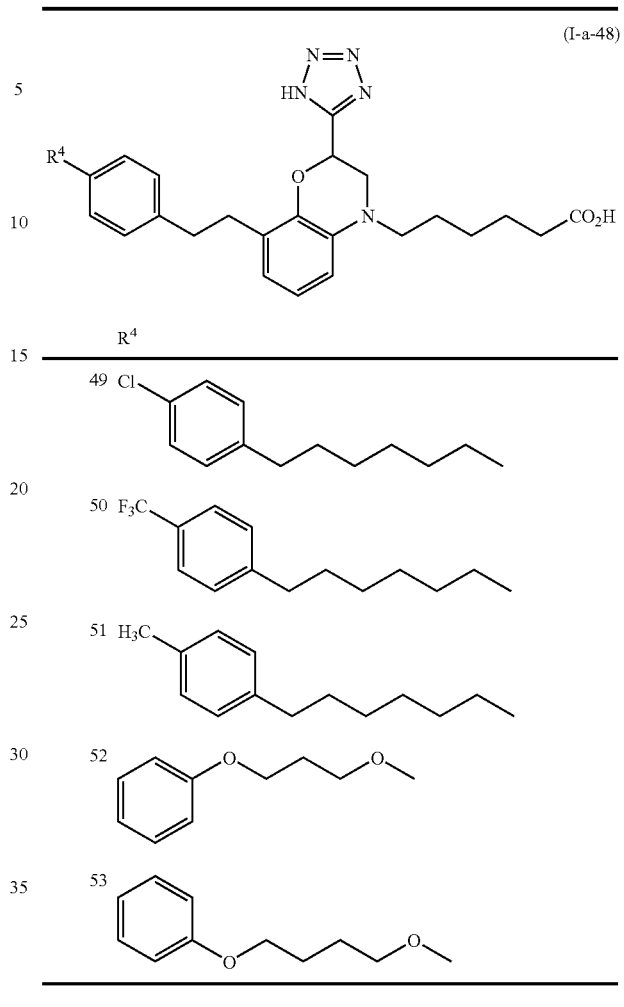
TABLE 49
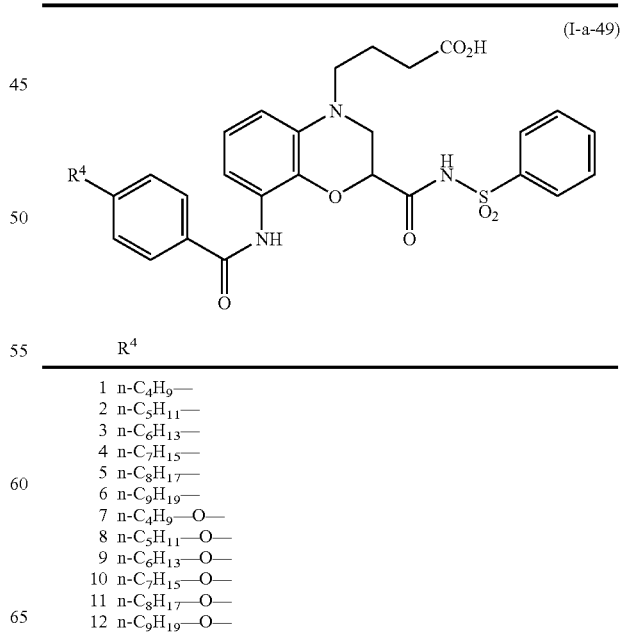
| | $R^4$ |
|---|---|
| 1 | n-$C_4H_9$— |
| 2 | n-$C_5H_{11}$— |
| 3 | n-$C_6H_{13}$— |
| 4 | n-$C_7H_{15}$— |
| 5 | n-$C_8H_{17}$— |
| 6 | n-$C_9H_{19}$— |
| 7 | n-$C_4H_9$—O— |
| 8 | n-$C_5H_{11}$—O— |
| 9 | n-$C_6H_{13}$—O— |
| 10 | n-$C_7H_{15}$—O— |
| 11 | n-$C_8H_{17}$—O— |
| 12 | n-$C_9H_{19}$—O— |

TABLE 49-continued
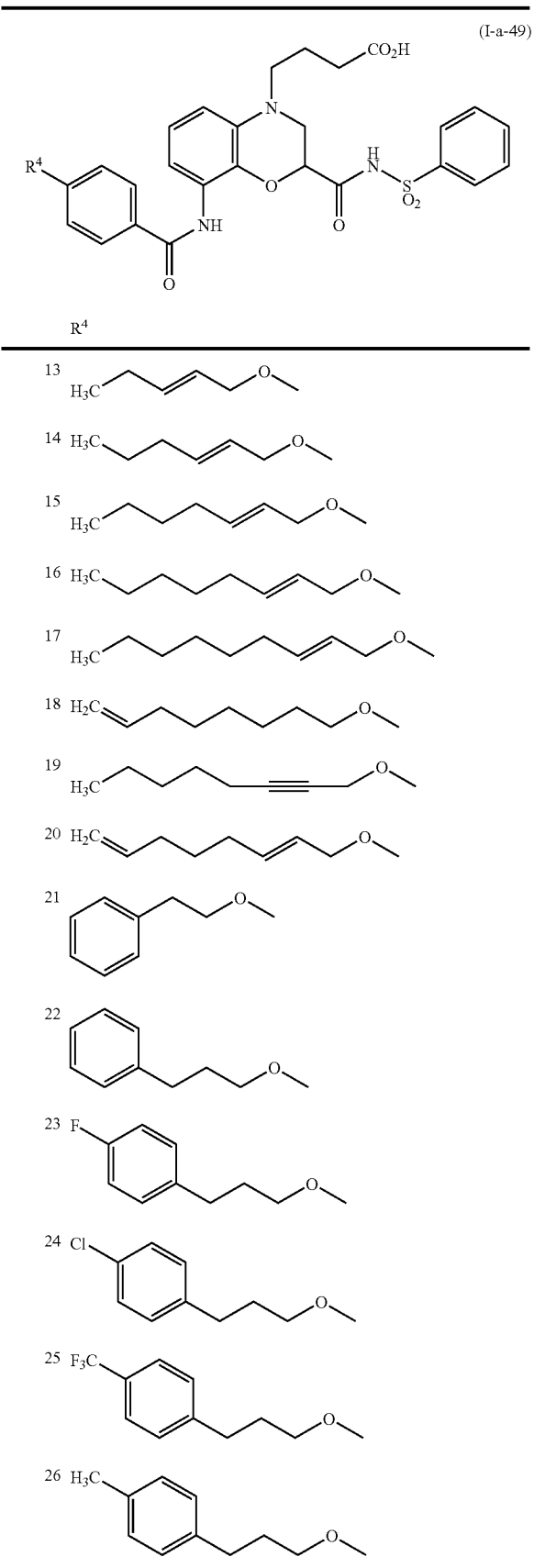
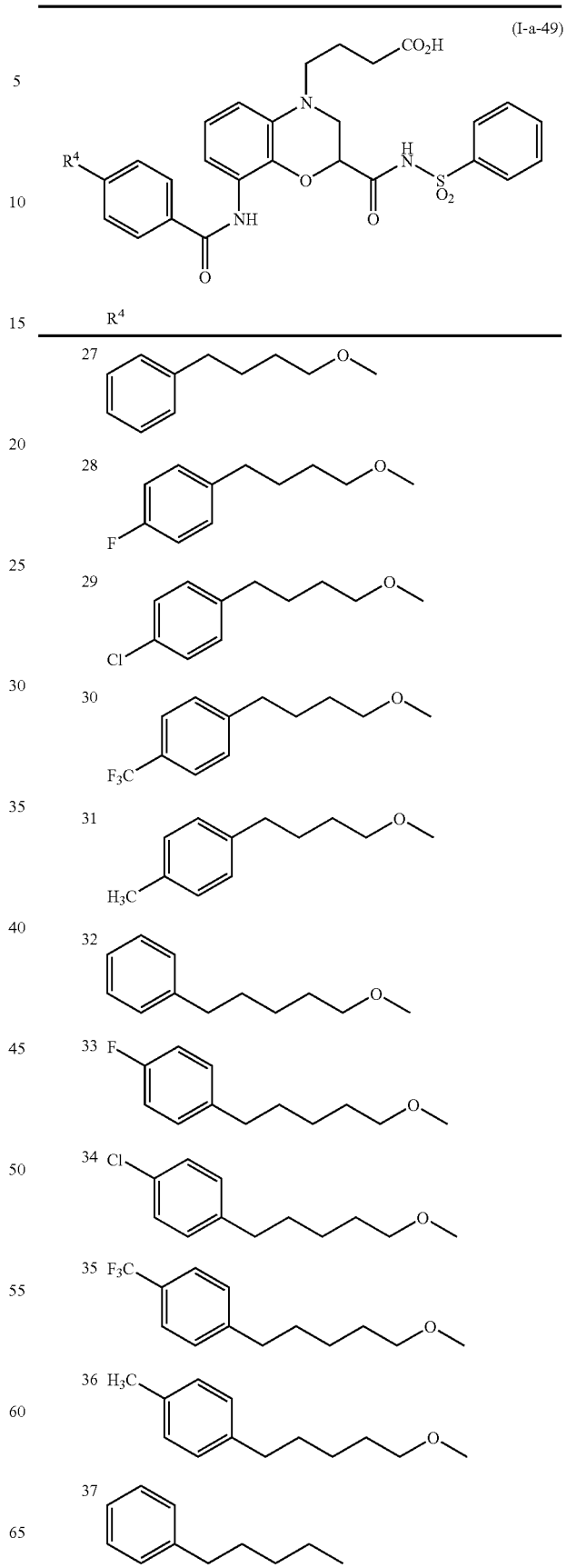

TABLE 49-continued
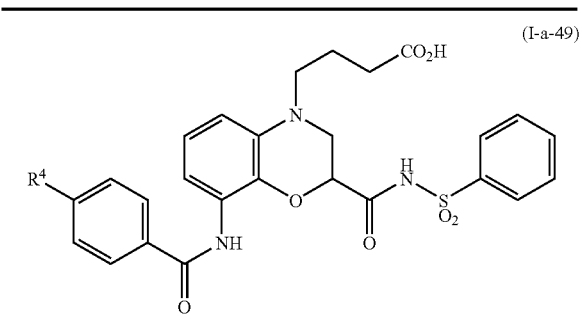
(I-a-49)
| | R⁴ |
|---|---|
| 38 | 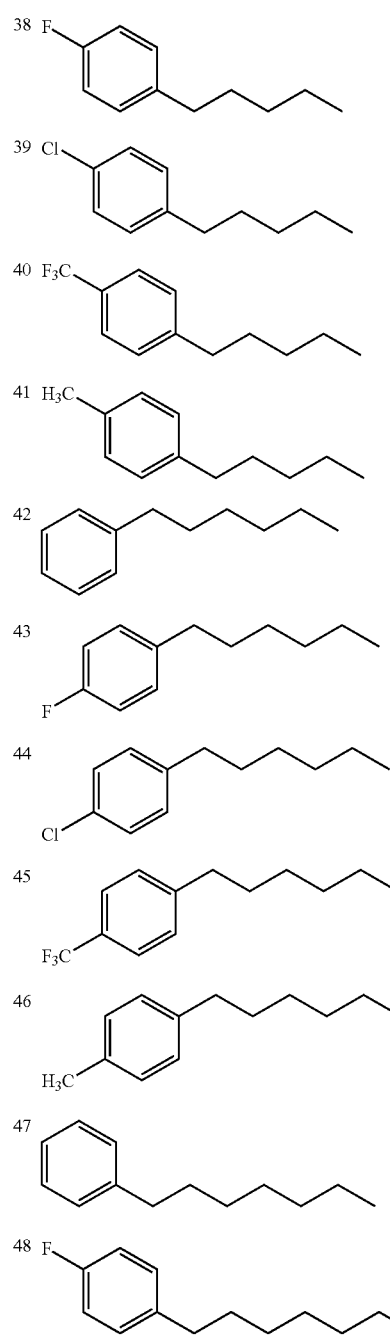 |
| 39 | |
| 40 | |
| 41 | |
| 42 | |
| 43 | |
| 44 | |
| 45 | |
| 46 | |
| 47 | |
| 48 | |
TABLE 49-continued
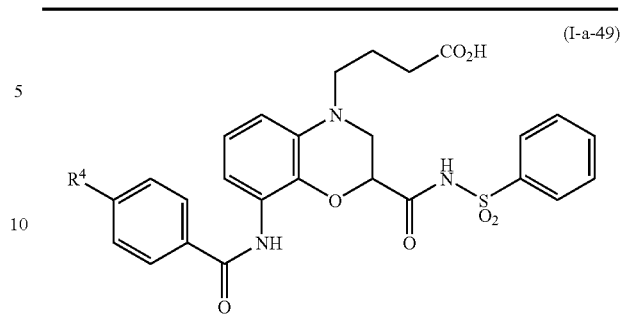
(I-a-49)
| | R⁴ |
|---|---|
| 49 | 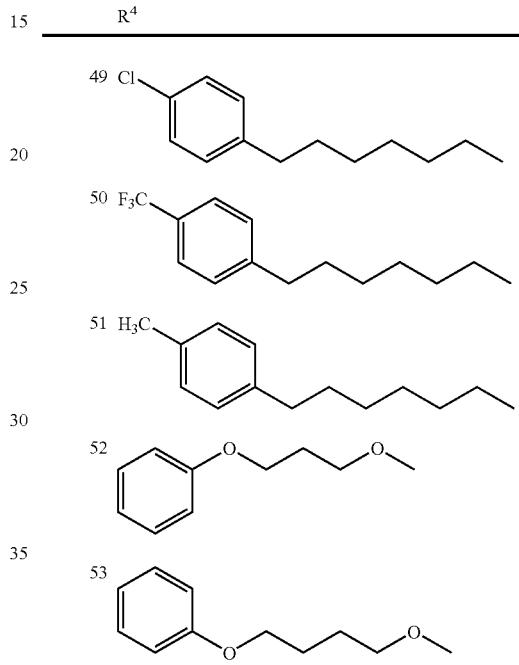 |
| 50 | |
| 51 | |
| 52 | |
| 53 | |
TABLE 50
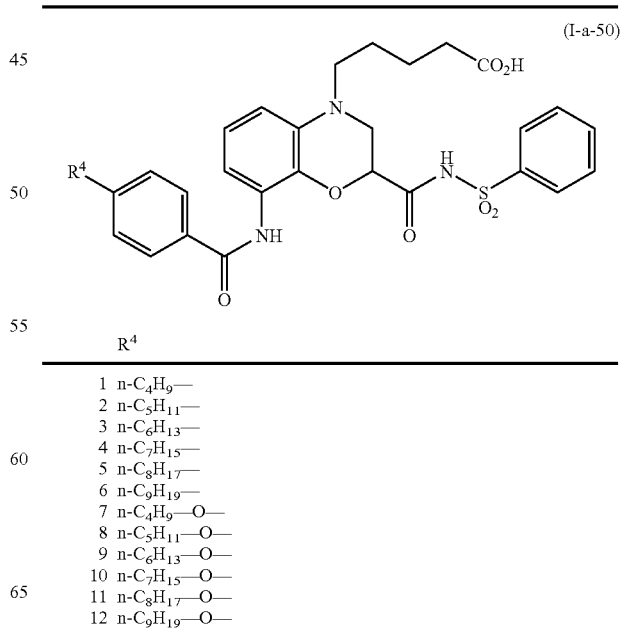
(I-a-50)
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |

TABLE 50-continued

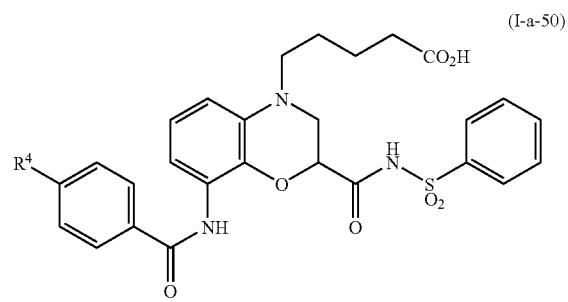

(I-a-50)

R[4]

| 13 | H₃C–CH=CH–CH₂–O–CH₃ |
| 14 | H₃C–CH₂–CH=CH–CH₂–O–CH₃ |
| 15 | H₃C–(CH₂)₂–CH=CH–CH₂–O–CH₃ |
| 16 | H₃C–(CH₂)₃–CH=CH–CH₂–O–CH₃ |
| 17 | H₃C–(CH₂)₄–CH=CH–CH₂–O–CH₃ |
| 18 | H₂C=CH–(CH₂)₄–O–CH₃ |
| 19 | H₃C–(CH₂)₃–C≡C–CH₂–O–CH₃ |
| 20 | H₂C=CH–(CH₂)₂–CH=CH–CH₂–O–CH₃ |
| 21 | Ph–(CH₂)₂–O–CH₃ |
| 22 | Ph–(CH₂)₃–O–CH₃ |
| 23 | 4-F-C₆H₄–(CH₂)₃–O–CH₃ |
| 24 | 4-Cl-C₆H₄–(CH₂)₃–O–CH₃ |
| 25 | 4-F₃C-C₆H₄–(CH₂)₃–O–CH₃ |
| 26 | 4-H₃C-C₆H₄–(CH₂)₃–O–CH₃ |

TABLE 50-continued

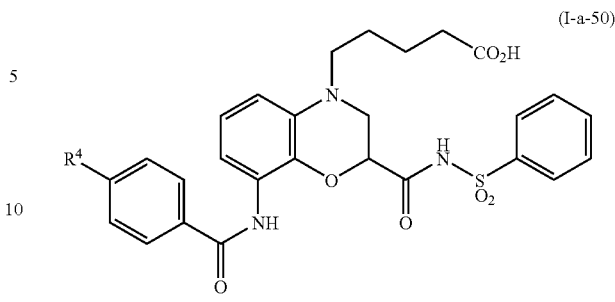

(I-a-50)

R[4]

| 27 | Ph–(CH₂)₄–O–CH₃ |
| 28 | 4-F-C₆H₄–(CH₂)₄–O–CH₃ |
| 29 | 4-Cl-C₆H₄–(CH₂)₄–O–CH₃ |
| 30 | 4-F₃C-C₆H₄–(CH₂)₄–O–CH₃ |
| 31 | 4-H₃C-C₆H₄–(CH₂)₄–O–CH₃ |
| 32 | Ph–(CH₂)₅–O–CH₃ |
| 33 | 4-F-C₆H₄–(CH₂)₅–O–CH₃ |
| 34 | 4-Cl-C₆H₄–(CH₂)₅–O–CH₃ |
| 35 | 4-F₃C-C₆H₄–(CH₂)₅–O–CH₃ |
| 36 | 4-H₃C-C₆H₄–(CH₂)₅–O–CH₃ |
| 37 | Ph–(CH₂)₄–CH₃ |

TABLE 50-continued
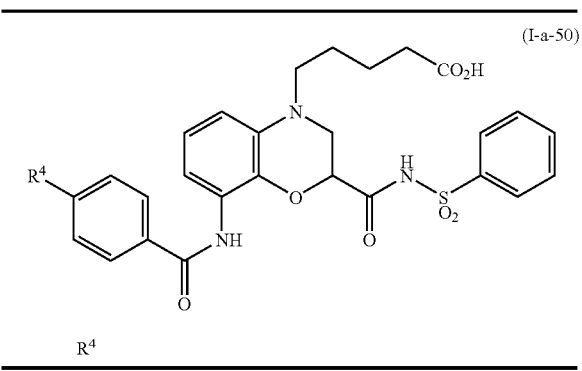
(I-a-50)
| | R⁴ |
|---|---|
| 38 | 4-F-C₆H₄-(CH₂)₄- |
| 39 | 4-Cl-C₆H₄-(CH₂)₄- |
| 40 | 4-F₃C-C₆H₄-(CH₂)₄- |
| 41 | 4-H₃C-C₆H₄-(CH₂)₄- |
| 42 | C₆H₅-(CH₂)₅- |
| 43 | 4-F-C₆H₄-(CH₂)₅- |
| 44 | 4-Cl-C₆H₄-(CH₂)₅- |
| 45 | 4-F₃C-C₆H₄-(CH₂)₅- |
| 46 | 4-H₃C-C₆H₄-(CH₂)₅- |
| 47 | C₆H₅-(CH₂)₆- |
| 48 | 4-F-C₆H₄-(CH₂)₆- |
TABLE 50-continued
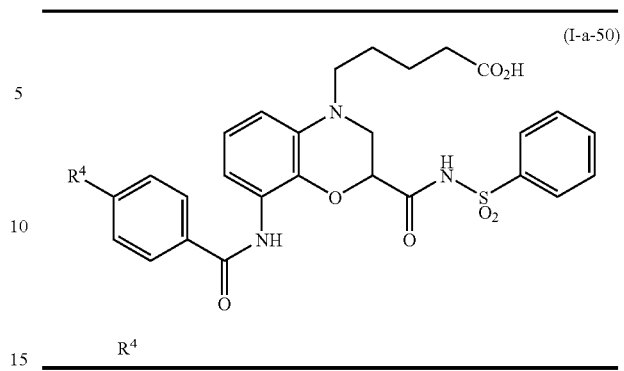
(I-a-50)
| | R⁴ |
|---|---|
| 49 | 4-Cl-C₆H₄-(CH₂)₆- |
| 50 | 4-F₃C-C₆H₄-(CH₂)₆- |
| 51 | 4-H₃C-C₆H₄-(CH₂)₆- |
| 52 | C₆H₅-O-(CH₂)₃-O-CH₃ |
| 53 | C₆H₅-O-(CH₂)₄-O-CH₃ |
TABLE 51
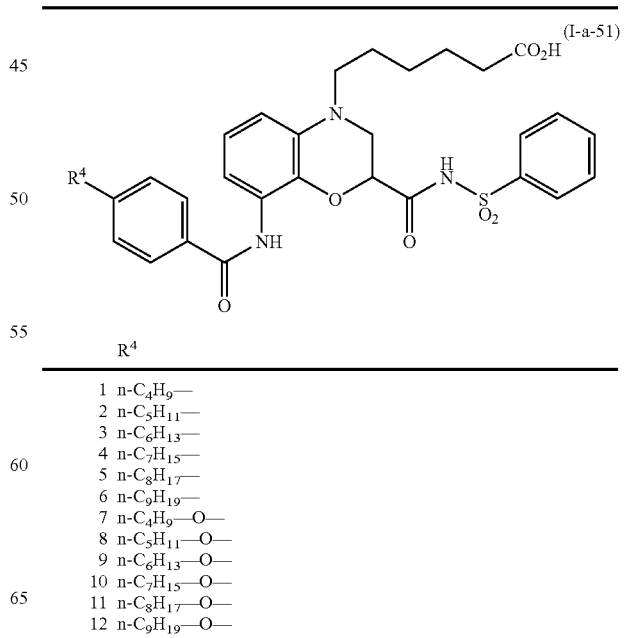
(I-a-51)
| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |

TABLE 51-continued
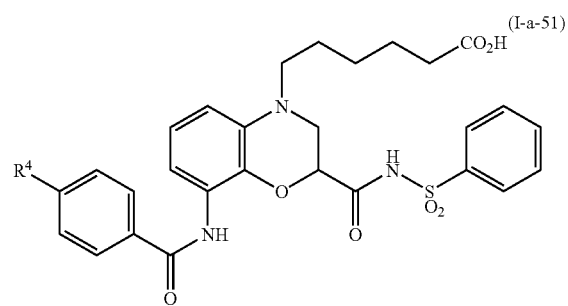
(I-a-51)
| R⁴ |
|---|
| 13 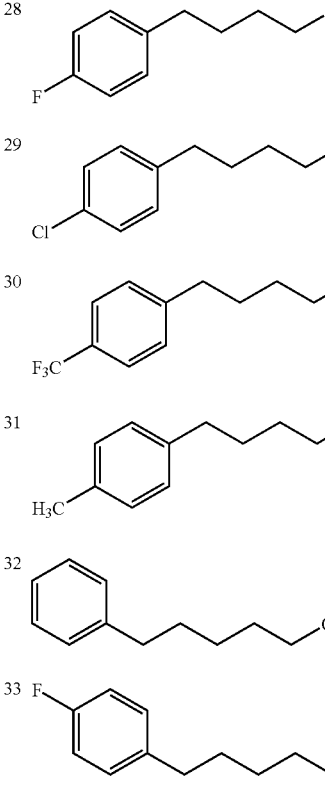 |
| 14 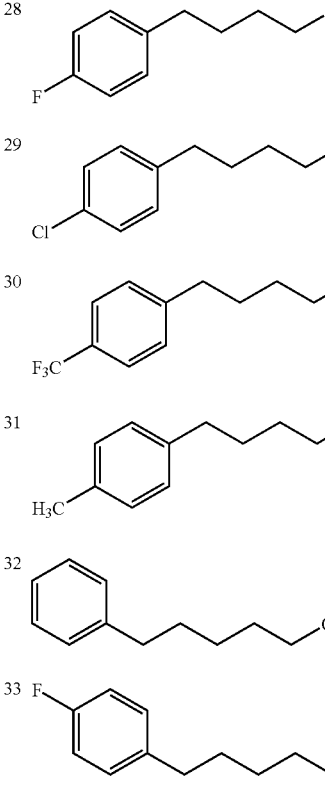 |
| 15 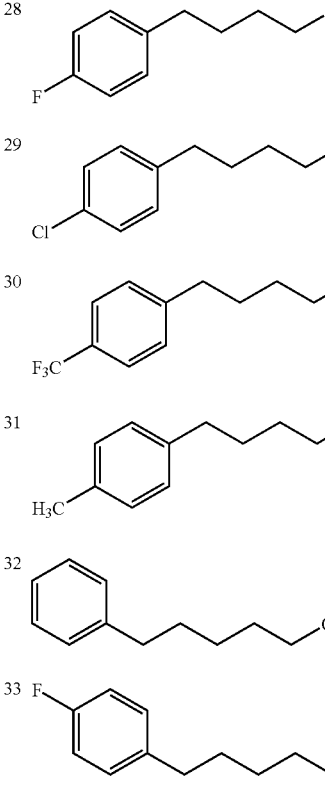 |
| 16 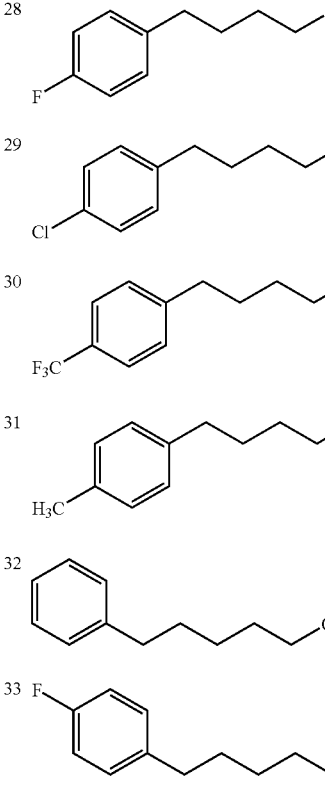 |
| 17 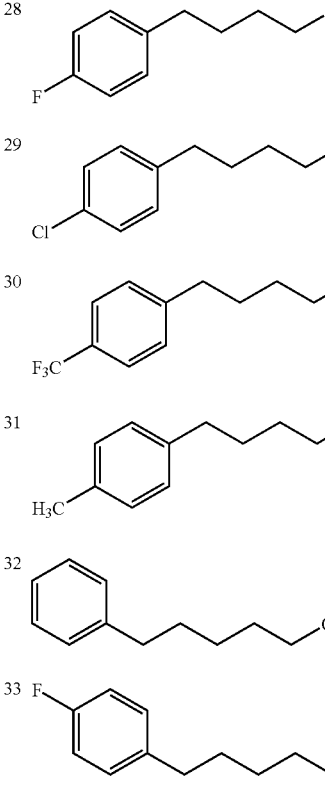 |
| 18 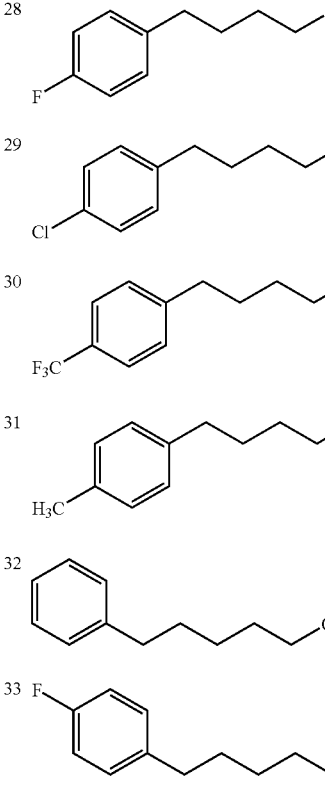 |
| 19 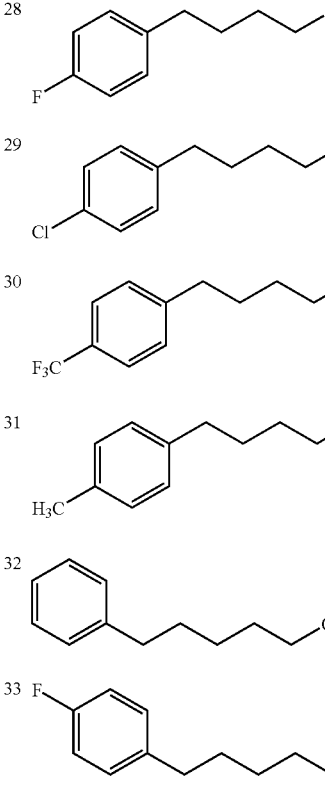 |
| 20 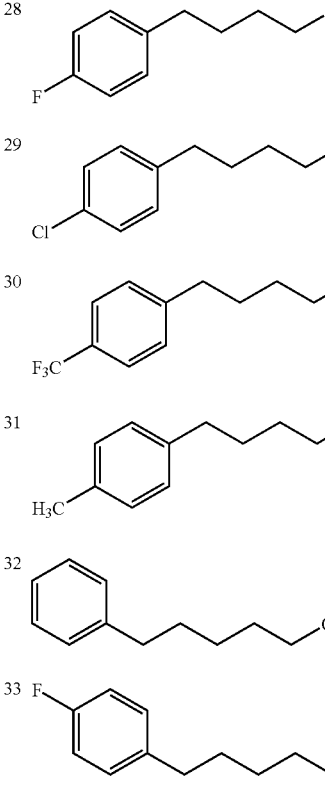 |
| 21 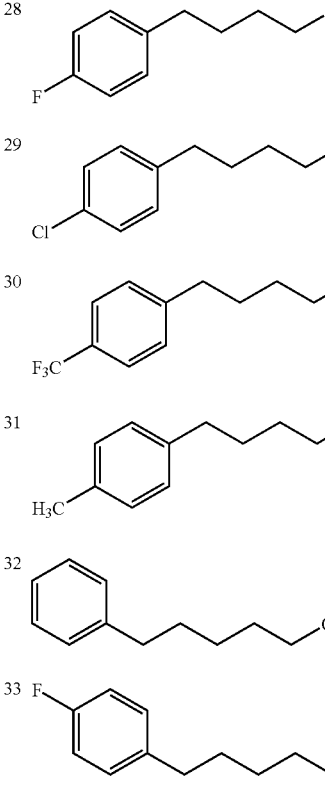 |
| 22 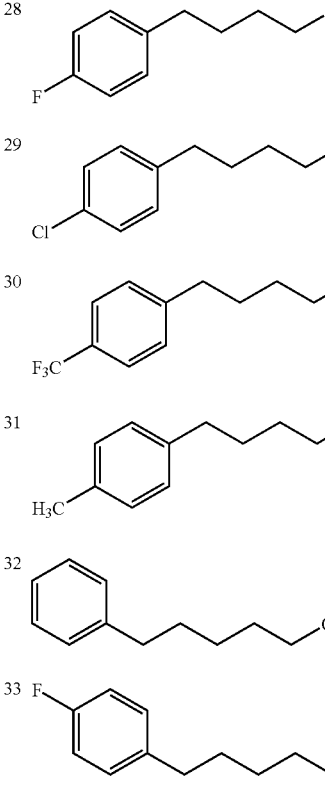 |
| 23 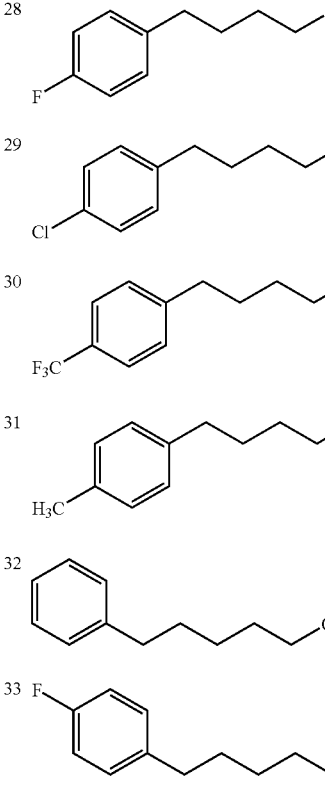 |
| 24 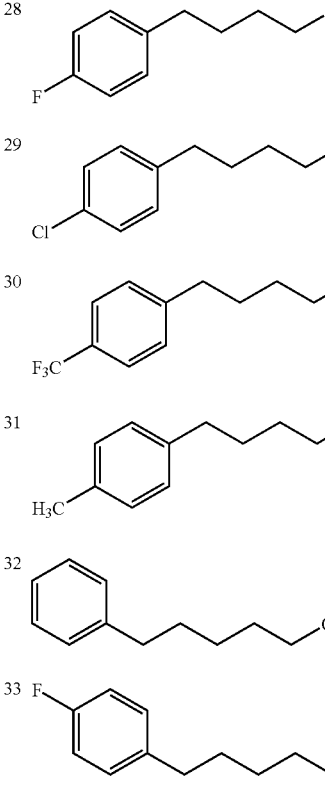 |
| 25 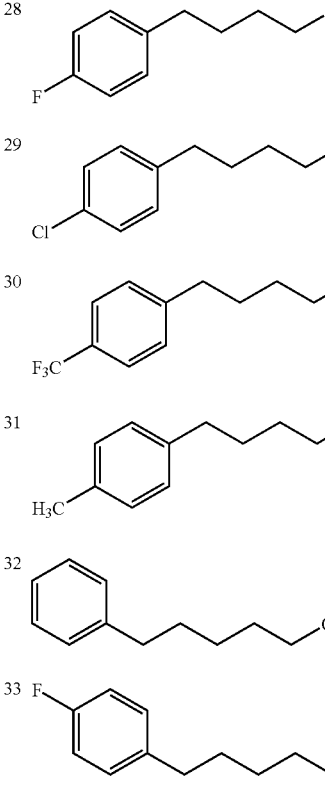 |
| 26 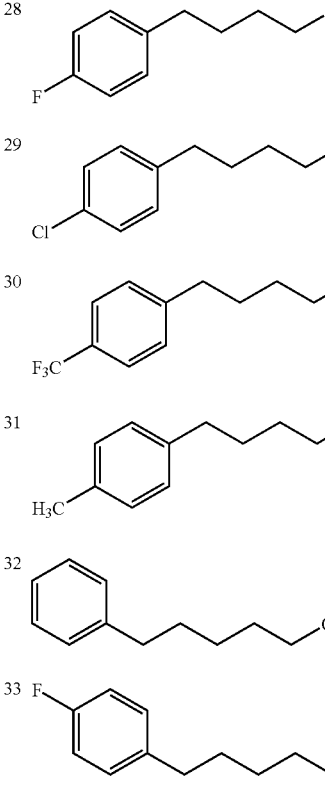 |
TABLE 51-continued
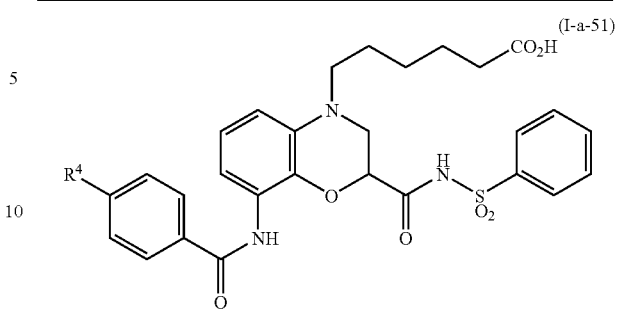
(I-a-51)
| R⁴ |
|---|
| 27 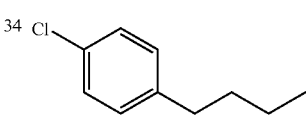 |
| 28 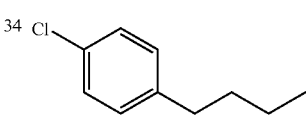 |
| 29 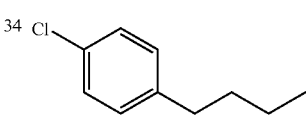 |
| 30 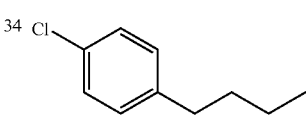 |
| 31 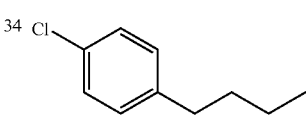 |
| 32 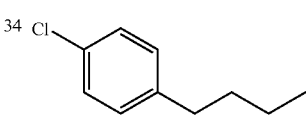 |
| 33 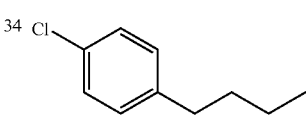 |
| 34 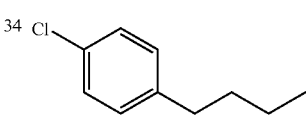 |
| 35 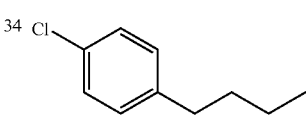 |
| 36 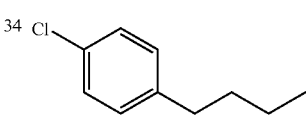 |

TABLE 51-continued

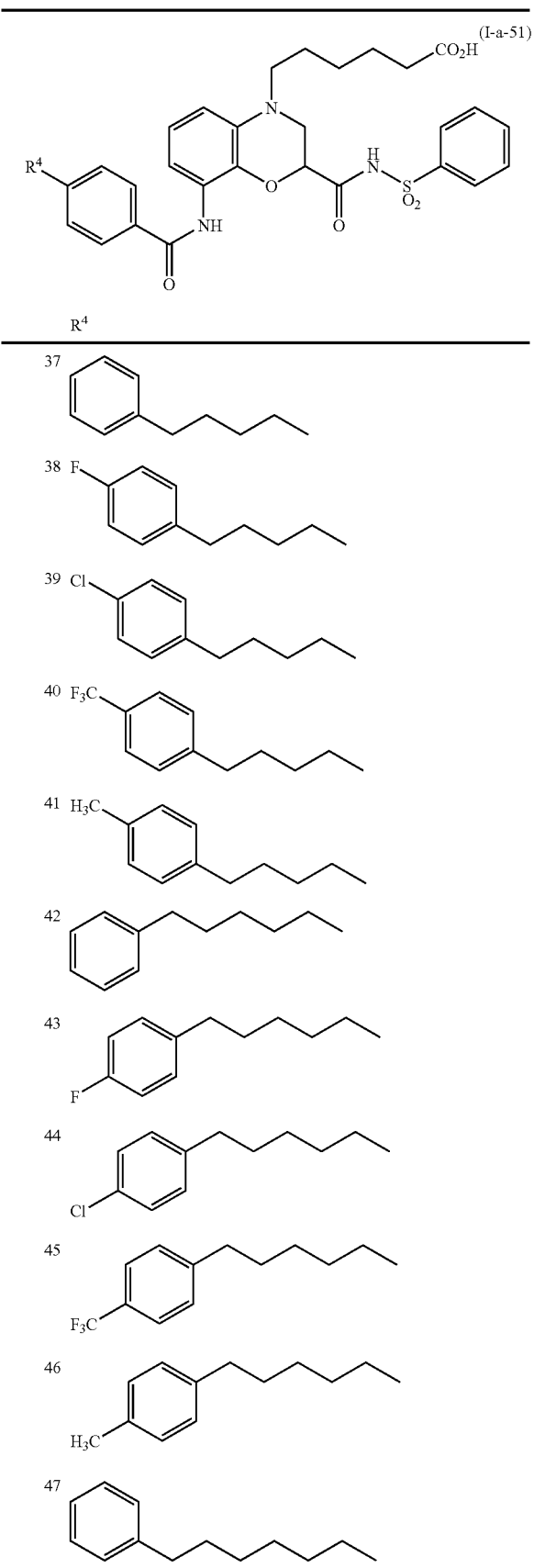

| | R⁴ |
|---|---|
| 37 | phenyl-pentyl |
| 38 | 4-F-phenyl-pentyl |
| 39 | 4-Cl-phenyl-pentyl |
| 40 | 4-F₃C-phenyl-pentyl |
| 41 | 4-H₃C-phenyl-pentyl |
| 42 | phenyl-hexyl |
| 43 | 4-F-phenyl-hexyl |
| 44 | 4-Cl-phenyl-hexyl |
| 45 | 4-F₃C-phenyl-hexyl |
| 46 | 4-H₃C-phenyl-hexyl |
| 47 | phenyl-heptyl |

TABLE 51-continued

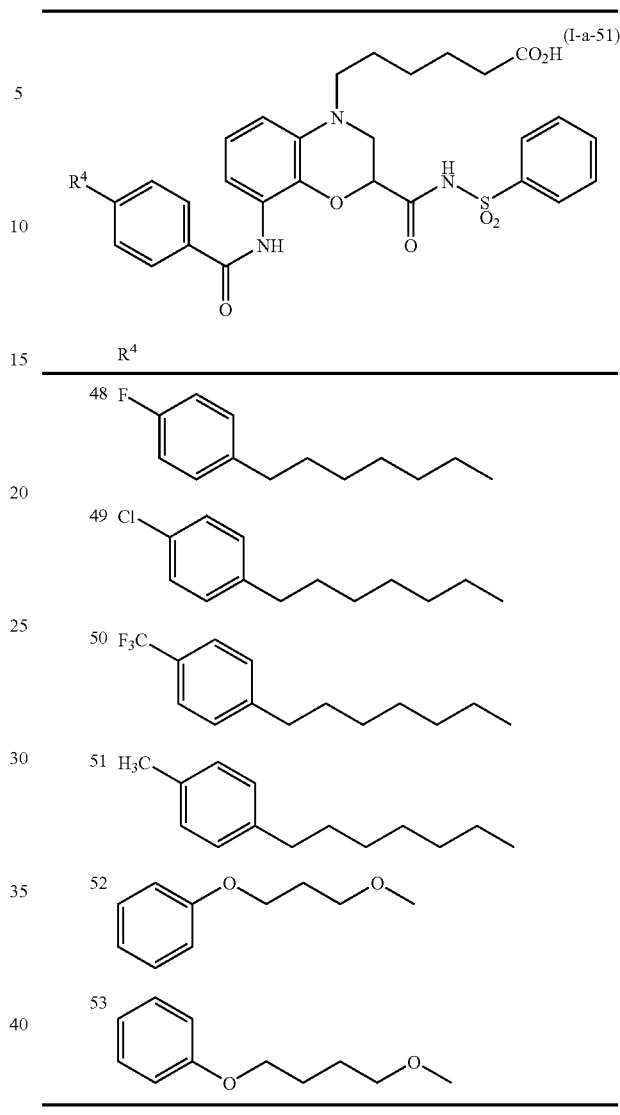

| | R⁴ |
|---|---|
| 48 | 4-F-phenyl-hexyl |
| 49 | 4-Cl-phenyl-hexyl |
| 50 | 4-F₃C-phenyl-hexyl |
| 51 | 4-H₃C-phenyl-hexyl |
| 52 | phenyl-O-CH₂CH₂-O-CH₃ |
| 53 | phenyl-O-(CH₂)₃-O-CH₃ |

TABLE 52

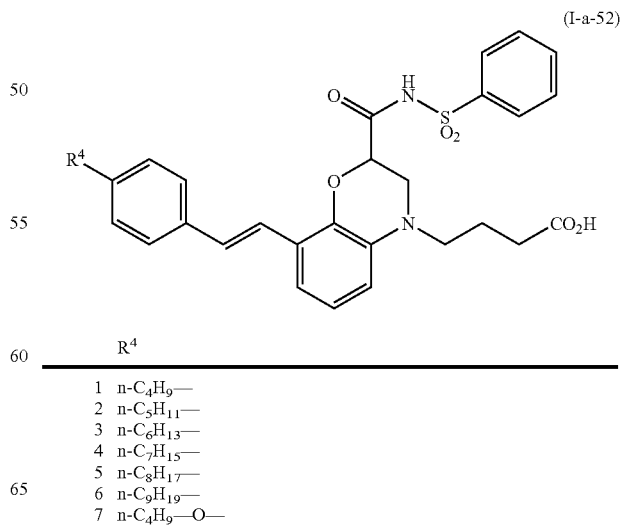

| | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |

TABLE 52-continued (I-a-52)

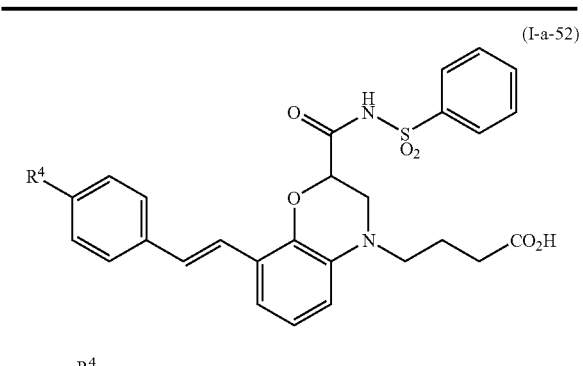

| | R⁴ |
|---|---|
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | H₃C~~~O~ |
| 14 | H₃C~~~~O~ |
| 15 | H₃C~~~~~O~ |
| 16 | H₃C~~~~~~O~ |
| 17 | H₃C~~~~~~~O~ |
| 18 | H₂C=~~~~~~O~ |
| 19 | H₃C~~~≡~~O~ |
| 20 | H₂C=~~~~=~O~ |
| 21 | Ph-CH₂CH₂-O-CH₃ |
| 22 | Ph-(CH₂)₃-O-CH₃ |
| 23 | 4-F-C₆H₄-(CH₂)₃-O-CH₃ |
| 24 | 4-Cl-C₆H₄-(CH₂)₃-O-CH₃ |
| 25 | 4-F₃C-C₆H₄-(CH₂)₃-O-CH₃ |

TABLE 52-continued (I-a-52)

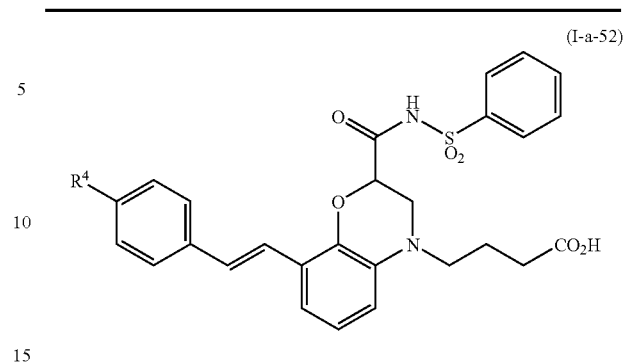

| | R⁴ |
|---|---|
| 26 | 4-H₃C-C₆H₄-(CH₂)₃-O-CH₃ |
| 27 | Ph-(CH₂)₄-O-CH₃ |
| 28 | 4-F-C₆H₄-(CH₂)₄-O-CH₃ |
| 29 | 4-Cl-C₆H₄-(CH₂)₄-O-CH₃ |
| 30 | 4-F₃C-C₆H₄-(CH₂)₄-O-CH₃ |
| 31 | 4-H₃C-C₆H₄-(CH₂)₄-O-CH₃ |
| 32 | Ph-(CH₂)₅-O-CH₃ |
| 33 | 4-F-C₆H₄-(CH₂)₅-O-CH₃ |
| 34 | 4-Cl-C₆H₄-(CH₂)₅-O-CH₃ |
| 35 | 4-F₃C-C₆H₄-(CH₂)₅-O-CH₃ |

TABLE 52-continued
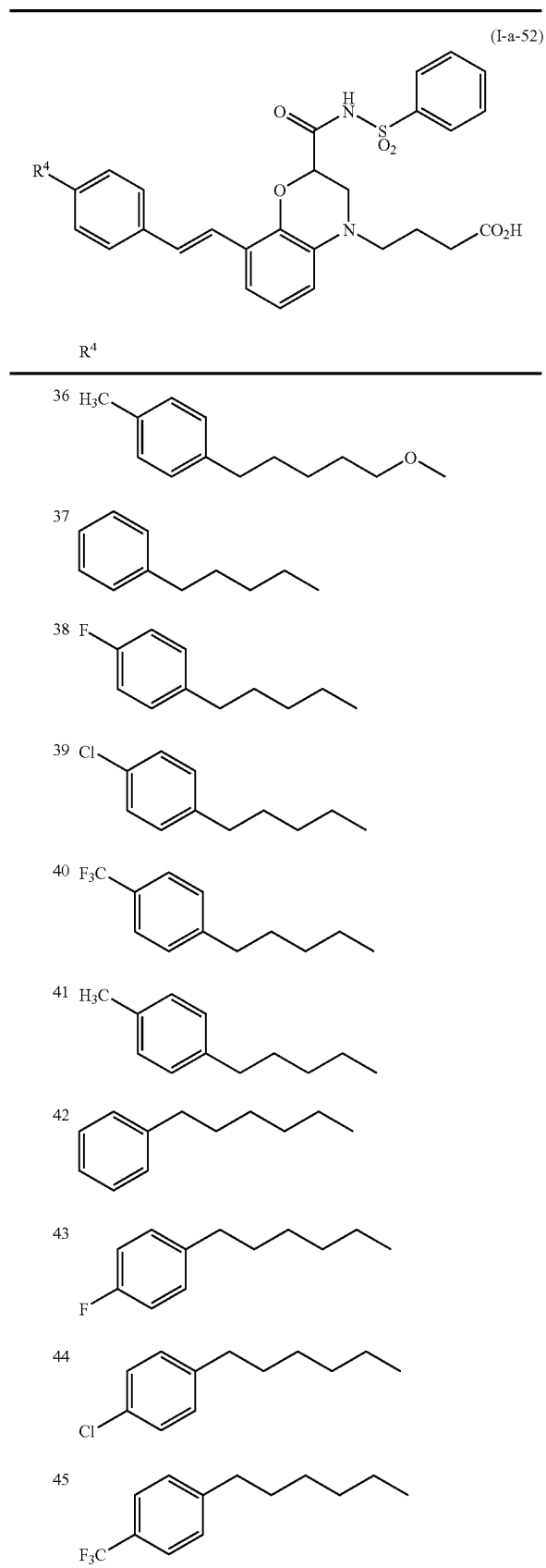
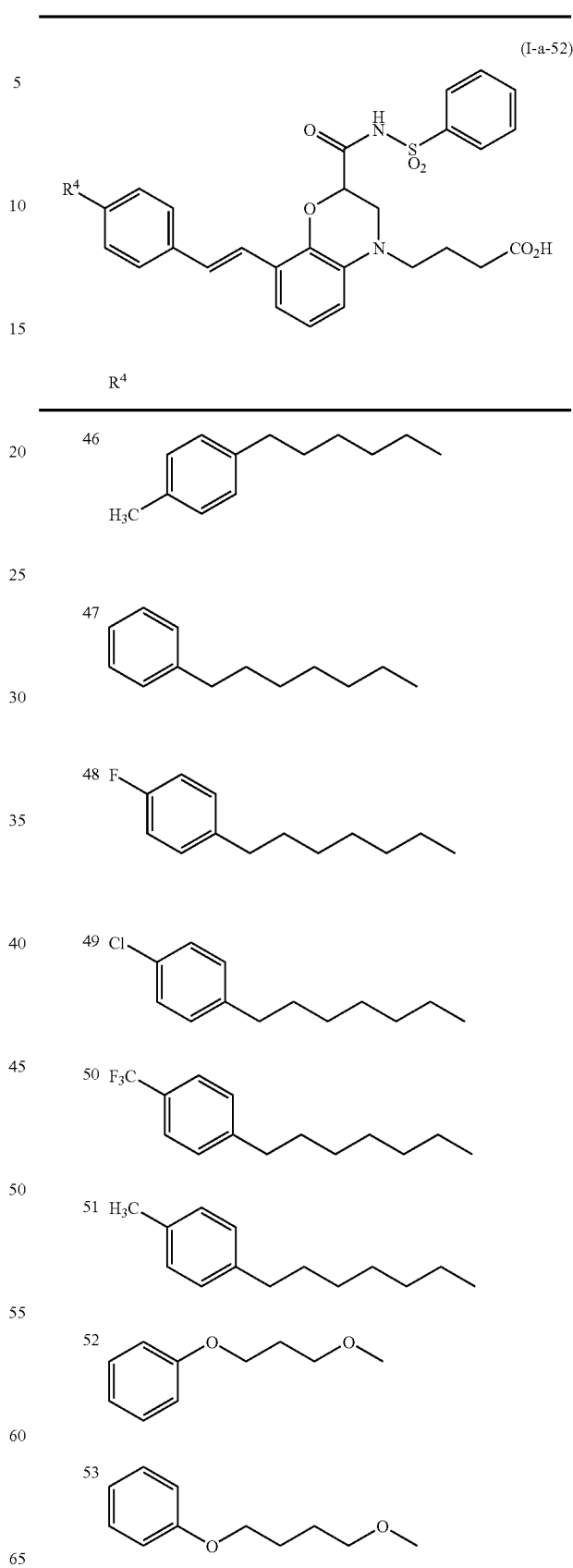

TABLE 53
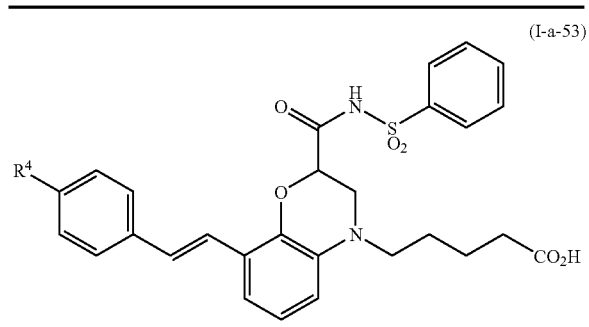
(I-a-53)
| # | R⁴ |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |
| 13 | 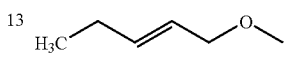 |
| 14 | 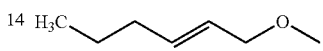 |
| 15 | 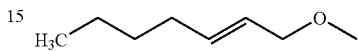 |
| 16 | 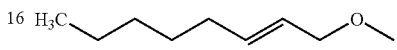 |
| 17 | 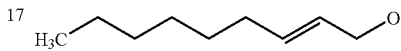 |
| 18 | 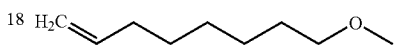 |
| 19 | 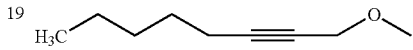 |
| 20 | 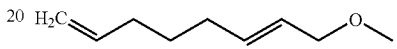 |
| 21 | 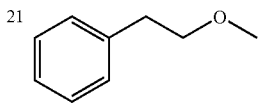 |
| 22 | 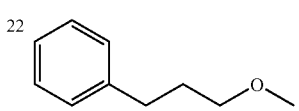 |
| 23 | 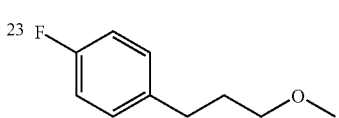 |
| 24 | 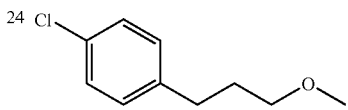 |
TABLE 53-continued
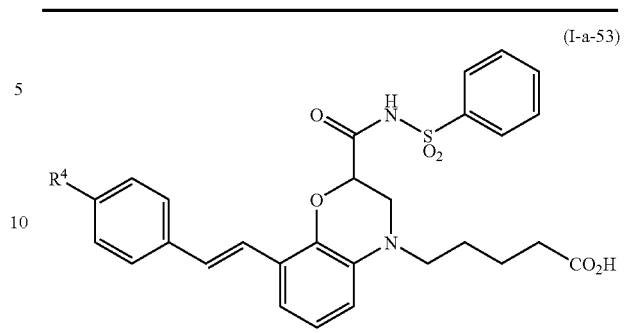
(I-a-53)
| # | R⁴ |
|---|---|
| 25 | (4-F₃C-C₆H₄)-(CH₂)₃-OCH₃ |
| 26 | (4-H₃C-C₆H₄)-(CH₂)₃-OCH₃ |
| 27 | C₆H₅-(CH₂)₄-OCH₃ |
| 28 | (4-F-C₆H₄)-(CH₂)₄-OCH₃ |
| 29 | (4-Cl-C₆H₄)-(CH₂)₄-OCH₃ |
| 30 | (4-F₃C-C₆H₄)-(CH₂)₄-OCH₃ |
| 31 | (4-H₃C-C₆H₄)-(CH₂)₄-OCH₃ |
| 32 | C₆H₅-(CH₂)₅-OCH₃ |
| 33 | (4-F-C₆H₄)-(CH₂)₅-OCH₃ |
| 34 | (4-Cl-C₆H₄)-(CH₂)₅-OCH₃ |

TABLE 53-continued
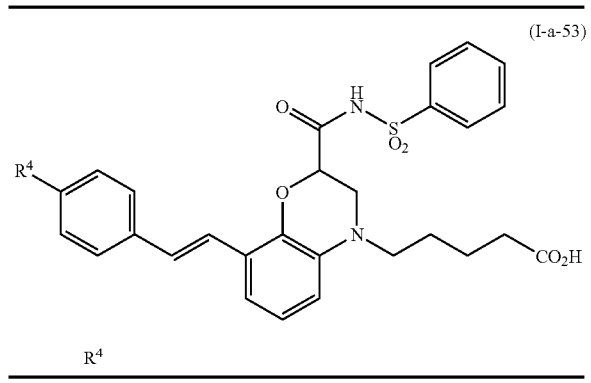
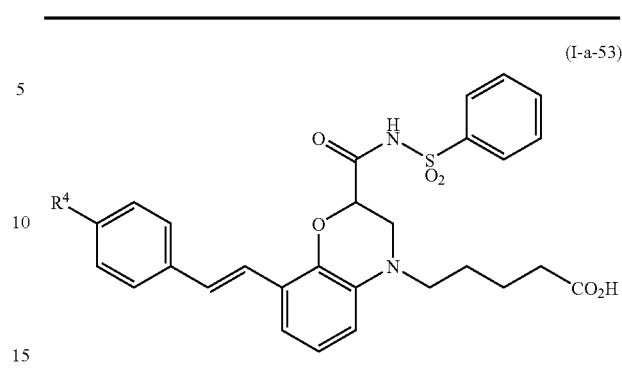

TABLE 54

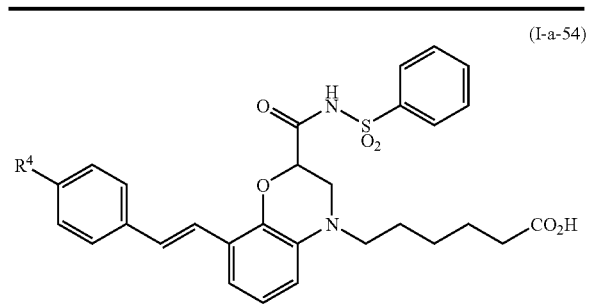

(I-a-54)

R⁴

| | |
|---|---|
| 1 | n-C₄H₉— |
| 2 | n-C₅H₁₁— |
| 3 | n-C₆H₁₃— |
| 4 | n-C₇H₁₅— |
| 5 | n-C₈H₁₇— |
| 6 | n-C₉H₁₉— |
| 7 | n-C₄H₉—O— |
| 8 | n-C₅H₁₁—O— |
| 9 | n-C₆H₁₃—O— |
| 10 | n-C₇H₁₅—O— |
| 11 | n-C₈H₁₇—O— |
| 12 | n-C₉H₁₉—O— |

13 H₃C–CH=CH–CH₂–O–CH₃

14 H₃C–CH₂–CH=CH–CH₂–O–CH₃

15 H₃C–(CH₂)₂–CH=CH–CH₂–O–CH₃

16 H₃C–(CH₂)₃–CH=CH–CH₂–O–CH₃

17 H₃C–(CH₂)₄–CH=CH–CH₂–O–CH₃

18 H₂C=CH–(CH₂)₄–O–CH₃

19 H₃C–(CH₂)₃–C≡C–CH₂–O–CH₃

20 H₂C=CH–(CH₂)₃–CH=CH–CH₂–O–CH₃

21 Ph–CH₂–CH₂–O–CH₃

22 Ph–(CH₂)₃–O–CH₃

23 4-F-C₆H₄–(CH₂)₃–O–CH₃

24 4-Cl-C₆H₄–(CH₂)₃–O–CH₃

TABLE 54-continued

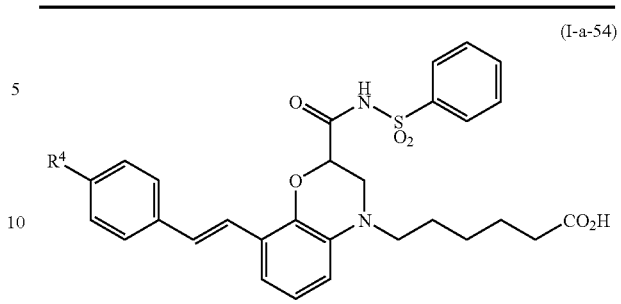

(I-a-54)

R⁴

25 4-F₃C-C₆H₄–(CH₂)₃–O–CH₃

26 4-H₃C-C₆H₄–(CH₂)₃–O–CH₃

27 Ph–(CH₂)₄–O–CH₃

28 4-F-C₆H₄–(CH₂)₄–O–CH₃

29 4-Cl-C₆H₄–(CH₂)₄–O–CH₃

30 4-F₃C-C₆H₄–(CH₂)₄–O–CH₃

31 4-H₃C-C₆H₄–(CH₂)₄–O–CH₃

32 Ph–(CH₂)₅–O–CH₃

33 4-F-C₆H₄–(CH₂)₅–O–CH₃

34 4-Cl-C₆H₄–(CH₂)₅–O–CH₃

35 4-F₃C-C₆H₄–(CH₂)₅–O–CH₃

TABLE 54-continued
(I-a-54)
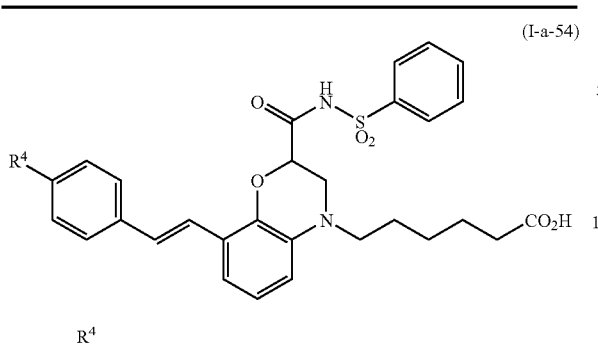
| | $R^4$ |
|---|---|
| 36 | 4-H₃C-C₆H₄-(CH₂)₄-OCH₃ |
| 37 | C₆H₅-(CH₂)₅- |
| 38 | 4-F-C₆H₄-(CH₂)₅- |
| 39 | 4-Cl-C₆H₄-(CH₂)₅- |
| 40 | 4-F₃C-C₆H₄-(CH₂)₅- |
| 41 | 4-H₃C-C₆H₄-(CH₂)₅- |
| 42 | C₆H₅-(CH₂)₆- |
| 43 | 4-F-C₆H₄-(CH₂)₆- |
| 44 | 4-Cl-C₆H₄-(CH₂)₆- |
| 45 | 4-F₃C-C₆H₄-(CH₂)₆- |
| 46 | 4-H₃C-C₆H₄-(CH₂)₆- |
TABLE 54-continued
(I-a-54)
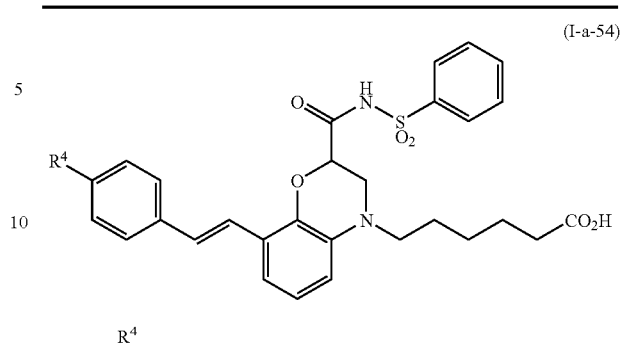
| | $R^4$ |
|---|---|
| 47 | C₆H₅-(CH₂)₆- |
| 48 | 4-F-C₆H₄-(CH₂)₆- |
| 49 | 4-Cl-C₆H₄-(CH₂)₆- |
| 50 | 4-F₃C-C₆H₄-(CH₂)₆- |
| 51 | 4-H₃C-C₆H₄-(CH₂)₆- |
| 52 | C₆H₅-O-(CH₂)₃-OCH₃ |
| 53 | C₆H₅-O-(CH₂)₄-OCH₃ |
TABLE 55
(I-a-55)
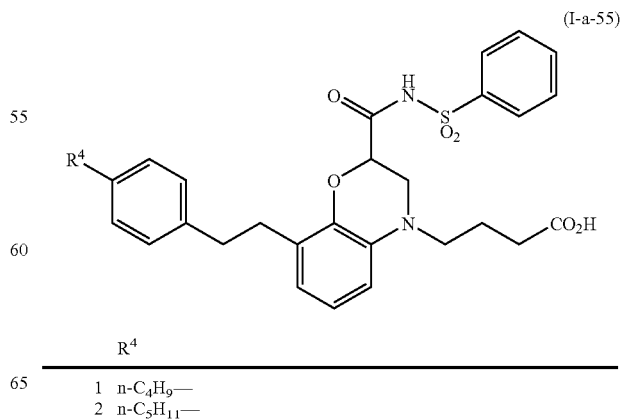
| | $R^4$ |
|---|---|
| 1 | n-C₄H₉— |
| 2 | n-C₅H₁₁— |

TABLE 55-continued

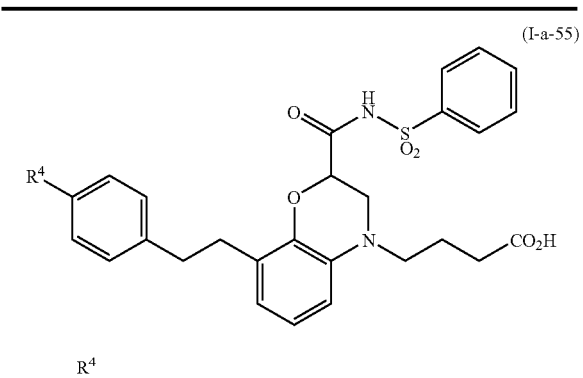

(I-a-55)

R⁴

3  n-C₆H₁₃—
4  n-C₇H₁₅—
5  n-C₈H₁₇—
6  n-C₉H₁₉—
7  n-C₄H₉—O—
8  n-C₅H₁₁—O—
9  n-C₆H₁₃—O—
10 n-C₇H₁₅—O—
11 n-C₈H₁₇—O—
12 n-C₉H₁₉—O—

13 H₃C–CH=CH–CH₂–O–CH₃

14 H₃C–CH₂–CH=CH–CH₂–O–CH₃

15 H₃C–(CH₂)₂–CH=CH–CH₂–O–CH₃

16 H₃C–(CH₂)₃–CH=CH–CH₂–O–CH₃

17 H₃C–(CH₂)₄–CH=CH–CH₂–O–CH₃

18 H₂C=CH–(CH₂)₄–O–CH₃

19 H₃C–(CH₂)₃–C≡C–CH₂–O–CH₃

20 H₂C=CH–(CH₂)₃–CH=CH–CH₂–O–CH₃

21 Ph–CH₂–CH₂–O–CH₃

22 Ph–(CH₂)₃–O–CH₃

23 4-F-C₆H₄–(CH₂)₃–O–CH₃

24 4-Cl-C₆H₄–(CH₂)₃–O–CH₃

TABLE 55-continued

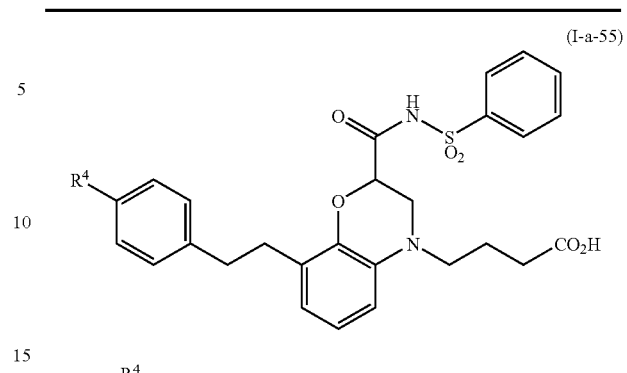

(I-a-55)

R⁴

25 4-F₃C-C₆H₄–(CH₂)₃–O–CH₃

26 4-H₃C-C₆H₄–(CH₂)₃–O–CH₃

27 Ph–(CH₂)₄–O–CH₃

28 4-F-C₆H₄–(CH₂)₄–O–CH₃

29 4-Cl-C₆H₄–(CH₂)₄–O–CH₃

30 4-F₃C-C₆H₄–(CH₂)₄–O–CH₃

31 4-H₃C-C₆H₄–(CH₂)₄–O–CH₃

32 Ph–(CH₂)₅–O–CH₃

33 4-F-C₆H₄–(CH₂)₅–O–CH₃

34 4-Cl-C₆H₄–(CH₂)₅–O–CH₃

TABLE 55-continued
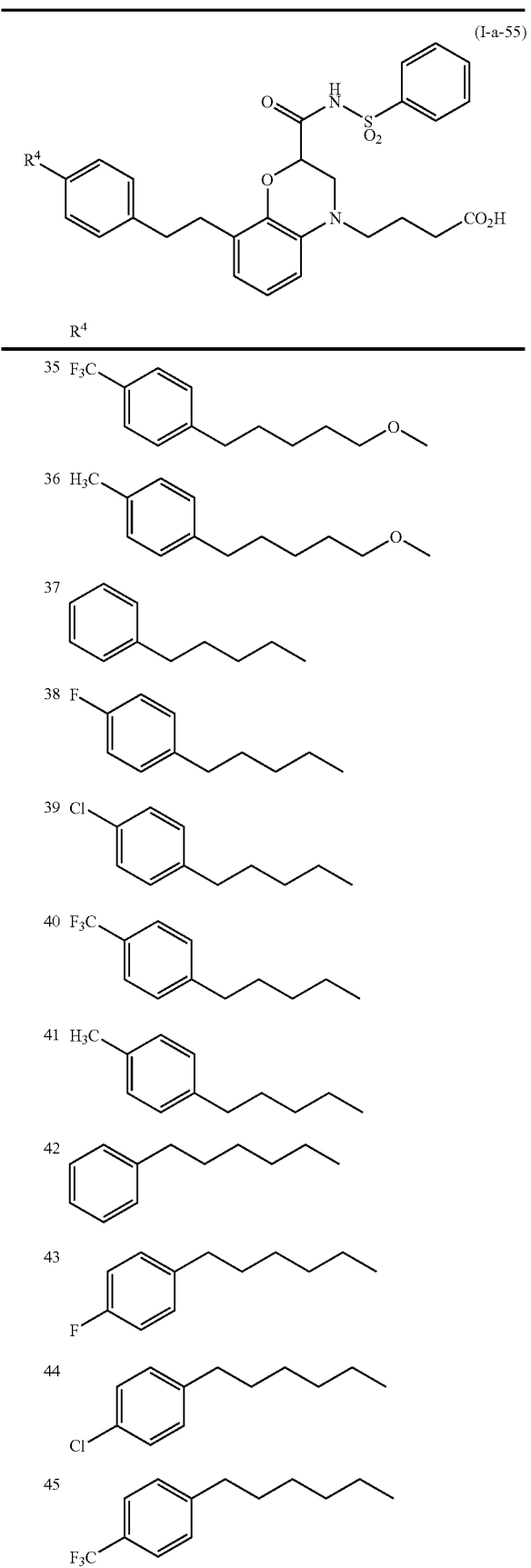
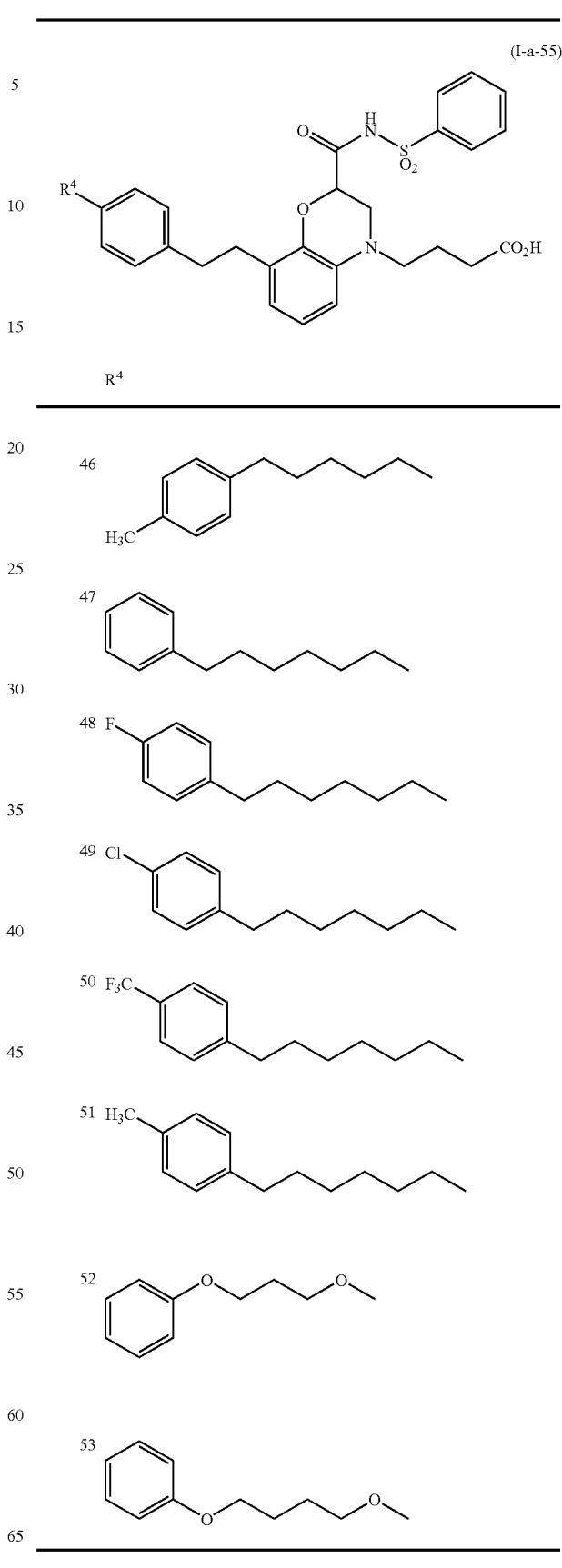

TABLE 56
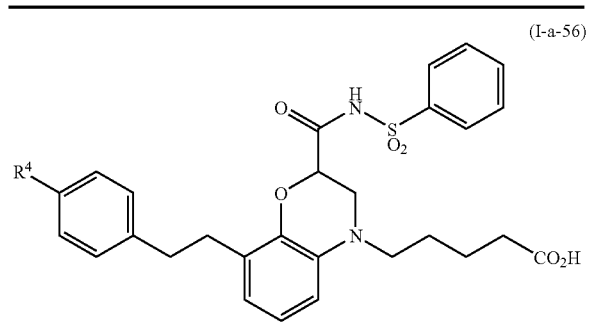
(I-a-56)
R⁴
1 n-C₄H₉—
2 n-C₅H₁₁—
3 n-C₆H₁₃—
4 n-C₇H₁₅—
5 n-C₈H₁₇—
6 n-C₉H₁₉—
7 n-C₄H₉—O—
8 n-C₅H₁₁—O—
9 n-C₆H₁₃—O—
10 n-C₇H₁₅—O—
11 n-C₈H₁₇—O—
12 n-C₉H₁₉—O—
13 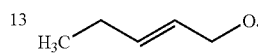
14 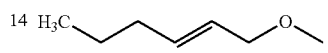
15 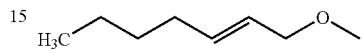
16 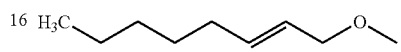
17 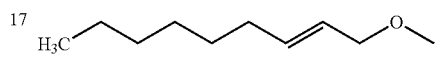
18 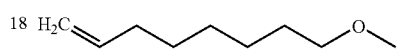
19 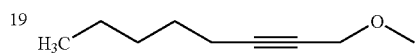
20 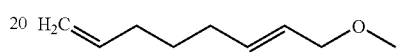
21 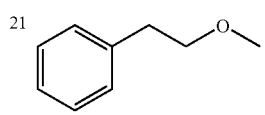
22 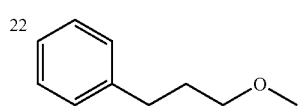
23 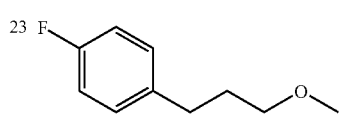
24 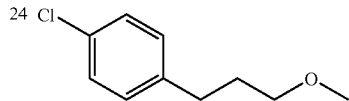
TABLE 56-continued
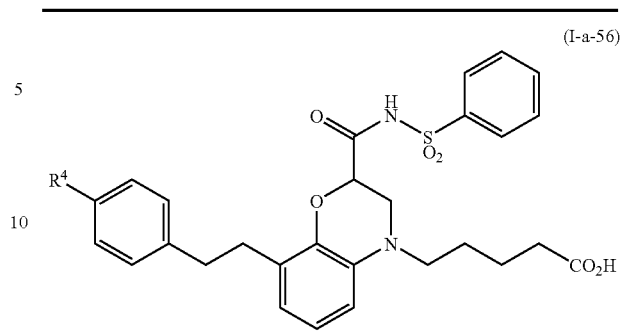
(I-a-56)
R⁴
25 F₃C—⟨phenyl⟩—(CH₂)₃—O—CH₃
26 H₃C—⟨phenyl⟩—(CH₂)₃—O—CH₃
27 ⟨phenyl⟩—(CH₂)₄—O—CH₃
28 F—⟨phenyl⟩—(CH₂)₄—O—CH₃
29 Cl—⟨phenyl⟩—(CH₂)₄—O—CH₃
30 F₃C—⟨phenyl⟩—(CH₂)₄—O—CH₃
31 H₃C—⟨phenyl⟩—(CH₂)₄—O—CH₃
32 ⟨phenyl⟩—(CH₂)₅—O—CH₃
33 F—⟨phenyl⟩—(CH₂)₅—O—CH₃
34 Cl—⟨phenyl⟩—(CH₂)₅—O—CH₃

TABLE 56-continued
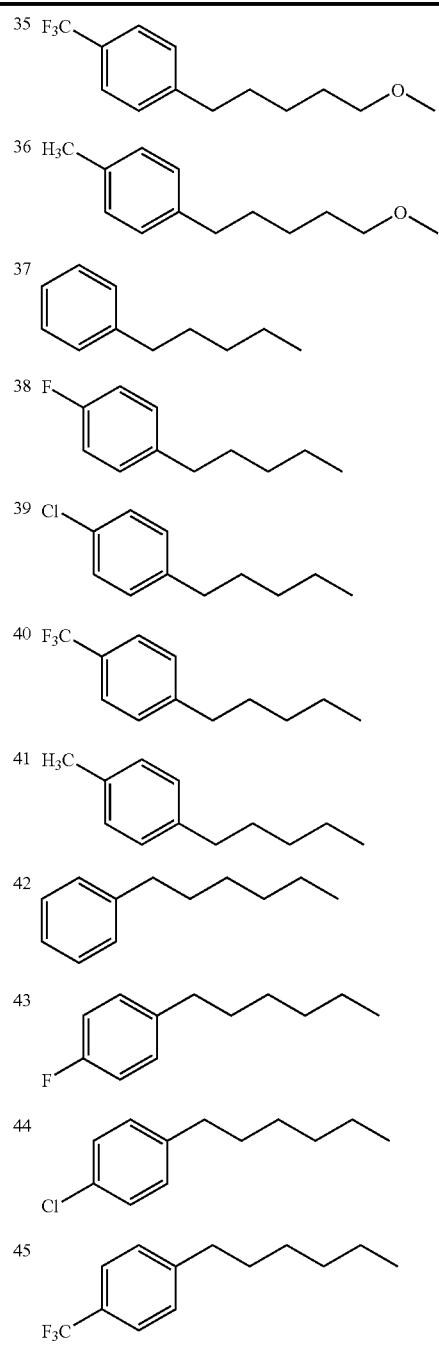
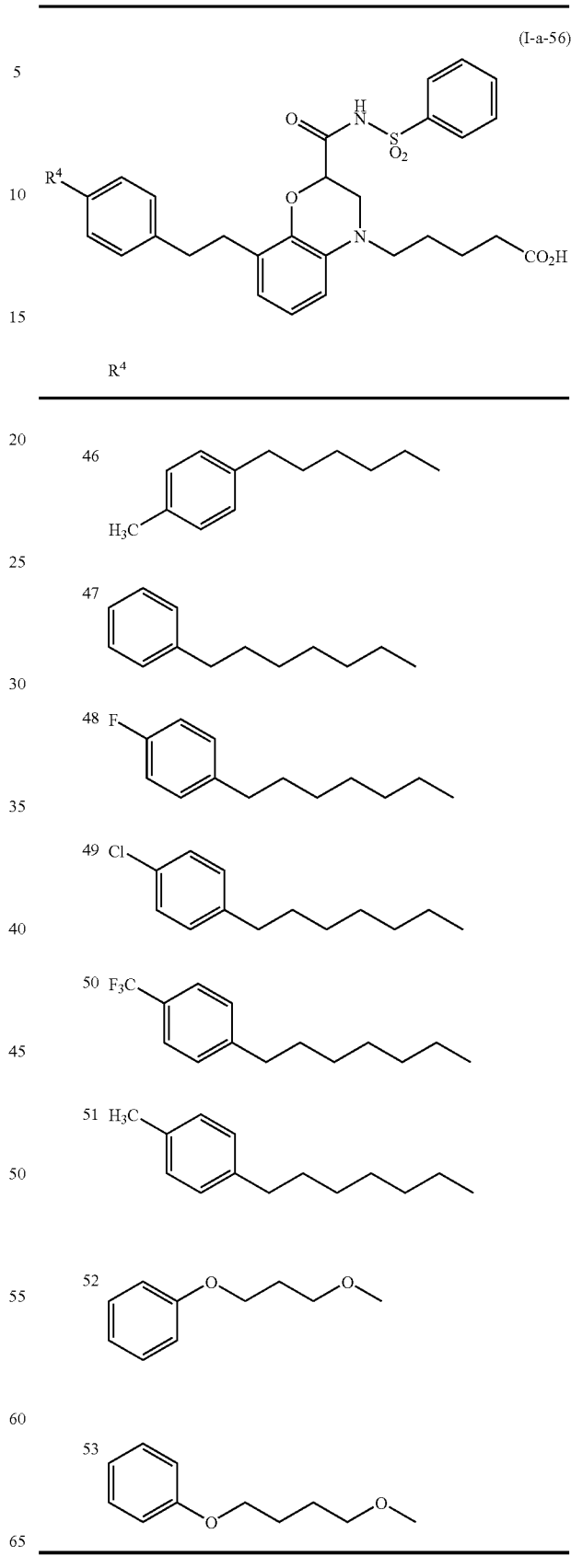

TABLE 57
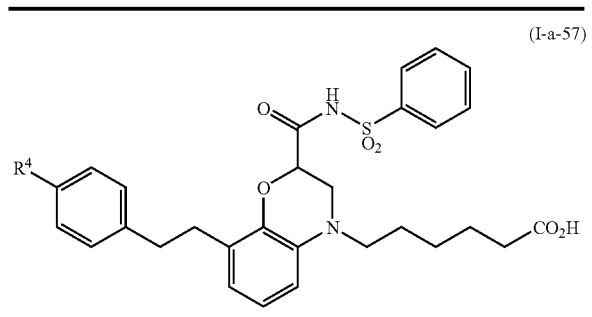
(I-a-57)
R⁴
1 n-C₄H₉—
2 n-C₅H₁₁—
3 n-C₆H₁₃—
4 n-C₇H₁₅—
5 n-C₈H₁₇—
6 n-C₉H₁₉—
7 n-C₄H₉—O—
8 n-C₅H₁₁—O—
9 n-C₆H₁₃—O—
10 n-C₇H₁₅—O—
11 n-C₈H₁₇—O—
12 n-C₉H₁₉—O—
13 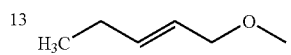
14 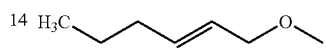
15 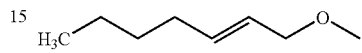
16 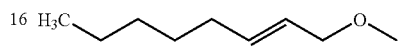
17 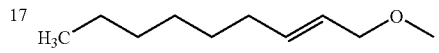
18 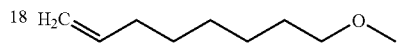
19 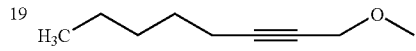
20 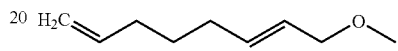
21 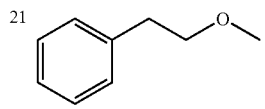
22 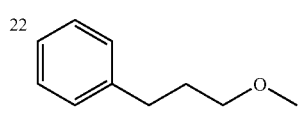
23 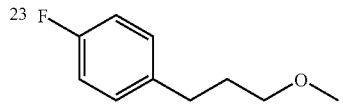
24 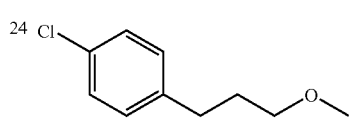
TABLE 57-continued
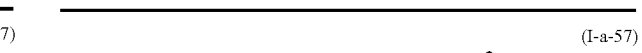
(I-a-57)
R⁴
25 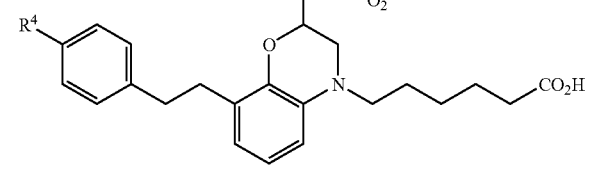
26 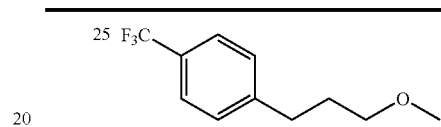
27 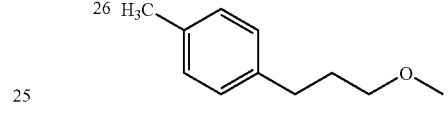
28 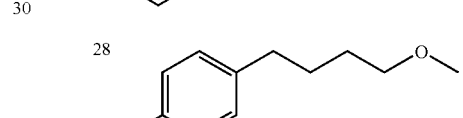
29 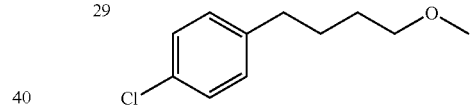
30 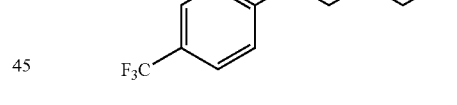
31 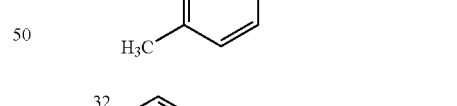
32 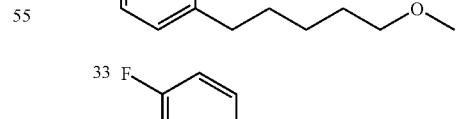
33 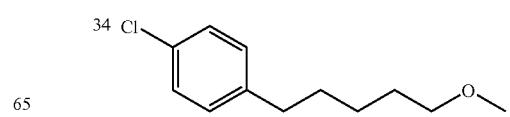
34 

TABLE 57-continued

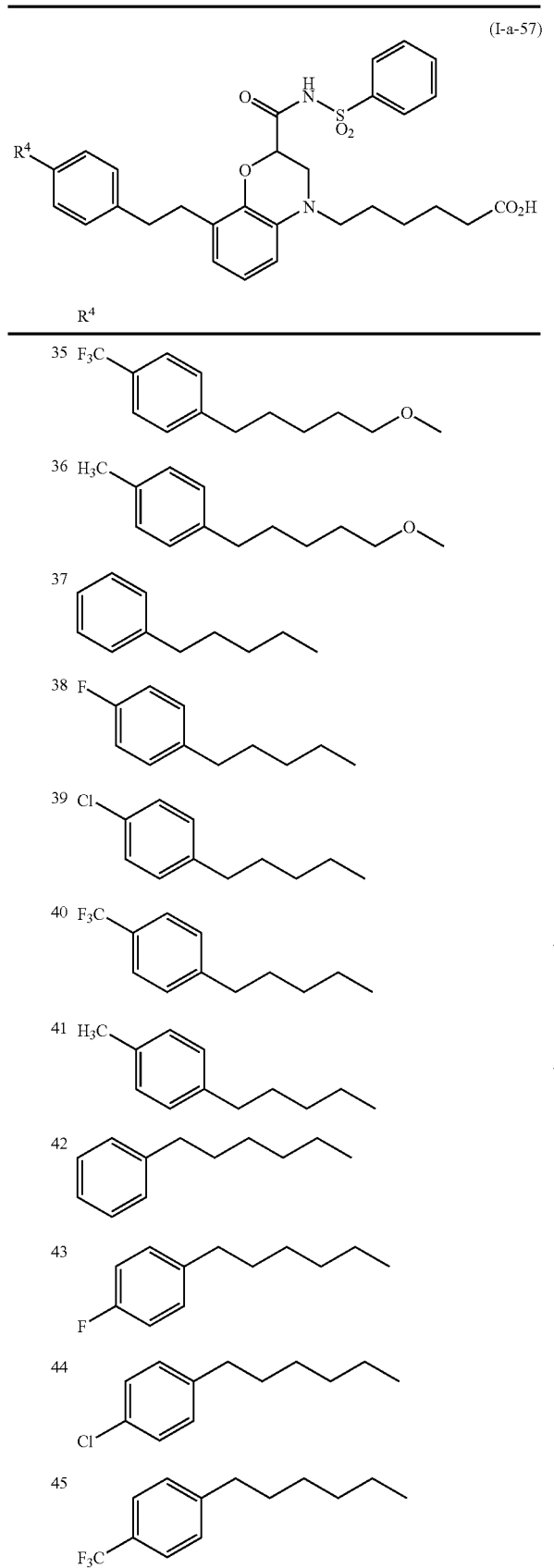

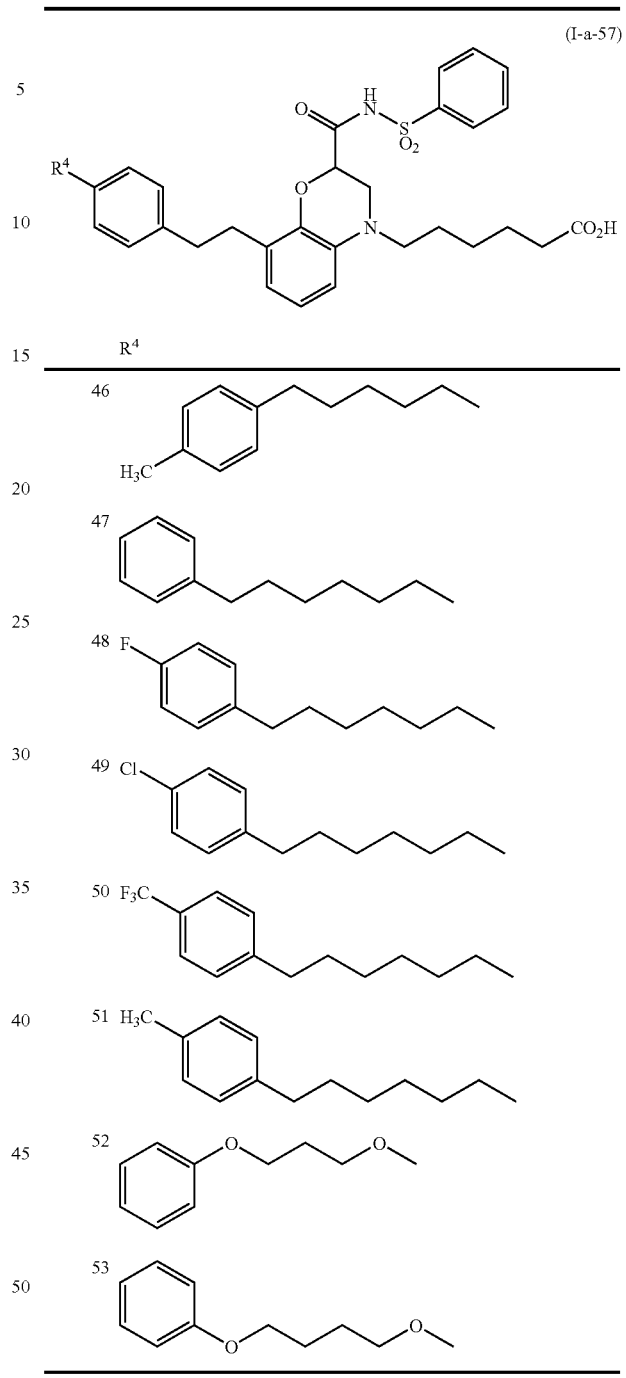

[The Method for the Preparation of the Compound of the Present Invention]

The compound of formula (I) of the present invention may be prepared by known methods, for example, a method combining the following methods and/or the methods described in Examples which are appropriately modified methods described in Comprehensive Organic Transformations: A Guide to Functional Group Preparations, 2nd Edition (Richard C. Larock, John Wiley & Sons Inc, 1999), etc. In each following method for the preparation, salts of the starting materials may be used. The above salts of the compound (I) may be used.

a) Among the compound of formula (I), the compound wherein

is a ring represented by

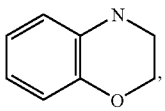

$R^1$ is carboxy and $R^2$ is carboxy or 5-tetrazolyl, i.e. the compound of formula (I-1)

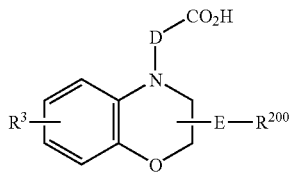

(wherein $R^{200}$ is carboxy or 5-tetrazolyl, and the other symbols have the same meanings as hereinbefore) may be prepared according to the following method.

The compound of formula (I-1) may be prepared by subjecting the compound of formula (II)

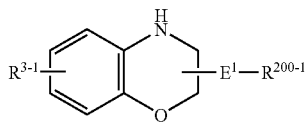

(wherein $R^{200-1}$ is carboxy or 5-tetrazolyl protected by a protective group, $R^{3-1}$ and $E^1$ have the same meaning as $R^3$ and E, in which the carboxy, hydroxy, amino or mercapto included in the groups represented by $R^{3-1}$ and $E^1$ are protected if necessary) to a reaction with the compound of formula (III)

$$X\text{-}D^1\text{-}CO_2R^{100-1} \qquad (III)$$

(wherein X is a leaving group such as, for example, halogen, mesyloxy, tosyloxy, oxo, etc., and $R^{100-1}$ is a protective group of carboxy, $D^1$ has the same meaning as D, and carboxy, hydroxy, amino or mercapto included in the groups represented by $R^{3-1}$ and $E^1$ are protected if necessary.), optionally followed by subjecting to a deprotection reaction of the protective groups.

The reaction of the compound wherein X-$D^1$ is an active acyl group among the compounds of formula (III), i.e. the compound of formula (III-1)

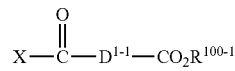

(wherein $D^{1-1}$ represents a spacer consisting of 1-7 of atom in the main chain, in which the carboxy, hydroxy, amino or mercapto in the groups represented by $R^{3-1}$ and $E^1$ are protected if necessary, and the other symbols have the same meanings as hereinbefore) and the compound of formula (II), may be carried out by, for example, (1) a method using acid halide,
(2) a method using mixed anhydride,
(3) a method using a condensing agent, etc.

To explain these methods specifically;

(1) the method using acid halide is carried out, for example, by subjecting a carboxylic acid to a reaction with an acid-halogenating agent (e.g. oxalyl chloride, thionyl chloride, etc.) in an organic solvent (e.g. chloroform, dichloromethane, diethyl ether, tetrahydrofuran, etc.) or without a solvent, at a temperature of about −20° C. to a refluxing temperature, and then subjecting the thus obtained acid halide to a reaction with an amine in the presence of a base (e.g. pyridine, triethylamine, dimethylaniline, dimethylaminopyridine, diisopropylethylamine, etc.) in an organic solvent (e.g. chloroform, dichloromethane, diethyl ether, tetrahydrofuran, acetonitorile, acetic ether, etc.) at a temperature of about 0 to 40° C. Also, the reaction may be carried out by subjecting the thus obtained acidic halide to a reaction with an amine in an organic solvent (e.g. dioxane, tetrahydrofuran, dichloromethane, etc.) using an alkali aqueous solution (e.g. an aqueous solution of sodium bicarbonate, sodium hydroxide, etc.) in the presence or absence of a phase-transfer catalyst (e.g. tetraammonium salts such as tetrabutylammoniumchloride, triethylbenzylammoniumchloride, tri-n-octylmethylammoniumchloride, trimethyldecylammoniumchloride, tetramethylammoniumbromide, etc.) at a temperature between about 0 to 40° C.;

(2) the method using mixed anhydride is carried out, for example, by subjecting a carboxylic acid to a reaction with an acid halide (e.g. pivaloyl chloride, tosyl chloride, mesyl-chloride, etc.) or an acid derivative (e.g. chloroethyl formate, chloroisobutyl formate, etc.) in an organic solvent (e.g. chloroform, dichloromethane, diethyl ether, tetrahydrofuran, etc.) or without a solvent in the presence of a base (pyridine, triethylamine, dimethylaniline, dimethylaminopyridine, diisopropylethylamine, etc.) at a temperature of 0 to 40° C., and then subjecting the thus obtained mixed anhydride to a reaction with an amine in an organic solvent (e.g. chloroform, methylene chloride, diethyl ether, tetrahydrofuran, etc.) at a temperature of about 0 to 40° C.;

(3) the method using a condensing agent is carried out, for example, by subjecting a carboxylic acid to a reaction with an amine in an organic solvent (e.g. chloroform, methylene chloride, dimethylformamide, diethyl ether, tetrahydrofuran, etc.) or without a solvent, in the presence or absence of a base (e.g. pyridine, triethylamine, dimethylaniline, dimethylaminopyridine, etc.), using a condensing agent (e.g. 1,3-dicyclohexylcarbodiimide (DCC), 1-ethyl-3-[3-(dimethyl amino)propyl]carbodiimide (EDC), 1,1′-carbonyldiimidazole (CDI), 2-chloro-1-methylpyridinium iodide, 1-propylphosphonic acid cyclic anhydride (PPA), etc.) in the presence or absence of 1-hydroxybenzotriazole (1-HOBt) at a temperature of about 0 to 40° C.

The reactions (1), (2) and (3) are desirably carried out under atmosphere of inert gas (argon, nitrogen, etc.) and anhydrous conditions.

The reaction of the compound of formula (III), wherein X-D$^1$ possesses formyl group, i.e. the compound of formula (III-2)

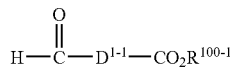
(III-2)

(wherein all symbols have the same meaning as described hereinbefore) and the compound of formula (II) is carried out, for example, in an organic solvent (e.g. tetrahydrofuran, diethyl ether, dichloroethane, dichloromethane, dimethylformamide, acetic acid, methanol, ethanol or a mixture thereof, etc.), in the presence of a reducing agent (sodium triacetoxyborohydride, sodium cyanoborohydride, sodium borohydride, zinc borohydride, diisobutylaluminum hydride, etc.) at a temperature of about 0 to 40° C., or in a solvent (e.g. ethers such as tetrahydrofuran, dioxane, dimethoxyethane, diethyl ether, etc.; alcohols such as methanol, ethanol, etc.; benzenes such as benzene, toluene, etc.; ketones such as acetone, methylethyl ketone, etc.; nitriles such as acetonitrile etc.; amides such as dimethylformamide etc.; water, ethyl acetate, acetic acid, or a mixture of two or more thereof, etc.), in the presence of a catalyst (e.g. palladium carbon, palladium black, palladium hydroxide, platinum oxide, Raney nickel, etc.), under hydrogen atmosphere of normal or compressed pressure, at a temperature of about 0 to 200° C.

The deprotection reaction of the protective groups of carboxy, hydroxy, amino, mercapto or tetrazolyl is well-known and includes, for example, (1) alkali hydrolysis, (2) a deprotection under acidic conditions, (3) a deprotection reaction by hydration, (4) a deprotection of silyl group, (5) a deprotection reaction using a metal, (6) a deprotection reaction using a metal complex, etc.

To explain these methods concretely,
(1) the deprotection reaction by alkali hydrolysis is carried out, for example, in an organic solvent (methanol, tetrahydrofuran, 1,4-dioxane, etc.) using a hydroxide of alkali metals (sodium hydroxide, potassium hydroxide, lithium hydroxide, etc.), hydroxide of alkaline earth metals (barium hydroxide, calcium hydroxide, etc.), carbonate (sodium carbonate, potassium carbonate, etc.) or a solution thereof or a mixture thereof at a temperature of 0 to 40° C.;
(2) the deprotection reaction under acidic conditions is carried out, for example, in an organic solvent (dichloromethane, chloroform, dioxane, ethyl acetate, anisole, etc.), in an organic acid (acetic acid, trifluoroacetic acid, methanesulfonic acid, p-toluenesulfonic acid, etc.) or an inorganic acid (hydrochloric acid, sulfuric acid, etc.) or a mixture thereof (hydrobromic acid/acetic acid, etc.) in the presence or absence of 2,2,2-trifluoroethanol at a temperature of 0 to 100° C.;
(3) the deprotection reaction by hydration is, for example, carried out in a solvent (e.g. ethers such as tetrahydrofuran, 1,4-dioxane, dimethoxyethane, diethyl ether, etc.; alcohols such as methanol, ethanol, etc.; benzenes such as benzene, toluene, etc.; ketones such as acetone, methyl ethyl ketone, etc.; nitriles such as acetonitrile etc.; amides such as dimethylformamide etc.; water, ethyl acetate, acetic acid or a mixture of two or more thereof, etc.) in the presence of a catalyst (palladium-carbon, palladium black, palladium hydroxide, platinum oxide, Raney nickel, etc.) under the atmosphere of hydrogen of normal or suppressed pressure, or in the presence of ammonium formate at a temperature of 0 to 200° C.;
(4) the deprotection of a silyl group is, for example, carried out in a water-miscible organic solvent (tetrahydrofuran, acetonitrile, etc.) using tetrabutylammonium fluoride at a temperature of 0 to 40° C.;
(5) the deprotection reaction using a metal is carried out, for example, in an acidic solvent (acetic acid, a buffer of pH 4.2 to 7.2 or a mixture of the solution thereof and an organic solvent such as tetrahydrofuran etc.) in the presence of zinc powder at a temperature of 0 to 40° C. optionally under sonication;
(6) the deprotection reaction using a metal complex is carried out, for example, in an organic solvent (dichloromethane, dimethylformamide, tetrahydrofuran, ethyl acetate, acetonitrile, dioxane, ethanol, etc.), water or a mixture thereof, in the presence of a trap reagent (tributyltin hydride, triethylsilane, dimedone, morpholine, diethylamine, pyrrolidine, etc.), an organic acid (acetic acid, formic acid, 2-ethylhexane, etc.) and/or a salt of an organic acid (sodium 2-ethylhexanoate, potassium 2-ethylhexanoate, etc.) in the presence or absence of a phosphine reagent (triphenylphosphine etc.) using a metal complex (palladium tetrakistriphenylphosphine (0), palladium bis(triphenylphosphine) dichloride (II), palladium acetate (II), rhodium tris(triphenylphosphine) chloride (I), etc. at a temperature of 0 to 40° C.

In addition to the above, deprotection reaction may be carried out by the method, for example, described in T. W. Greene, Protective Groups in Organic Synthesis, Wiley, New York, 1999.

Protective groups for carboxy include, for example, methyl, ethyl, allyl, tert-butyl, trichloroethyl, benzyl (Bn), phenacyl, p-methoxybenzyl, trityl, 2-chlorotrityl or a solid carrier containing these structure, etc.

Protective groups for hydroxy include, for example, methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), tert-butyldimethylsilyl (TBDMS), tert-butyldiphenylsilyl (TBDPS), acetyl (Ac), pivaolyl, benzoyl, benzyl (Bn), p-methoxybenzyl, allyloxycarbonyl (Alloc) or 2,2,2-trichloroethoxycarbonyl (Troc), etc.

Protective groups for amino include, for example, benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl or benzyloxymethyl (BOM), 2-(trimethylsilyl)ethoxymethyl (SEM), etc.

Protective groups for mercapto include, for example, methoxybenzyl, methoxymethyl (MOM), 2-tetrahydropyranyl (THP), diphenylmethyl, acetyl (Ac), etc.

The protective groups for tetrazolyl include, for example, tert-butyl, methyloxycarbonyl, benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), α,α-dimethylbenzyl, trityl, p-methoxybenzyl, benzyloxymethyl (BOM), 2-(trimethylsilyl)ethoxymethyl (SEM), trimethylsilyl (TMS), triethylsilyl (TES) or 2-cyanoethyl, etc.

Protective groups for carboxy, hydroxy, amino, mercapto or tetrazolyl are not limited to the above ones, but those groups which are easily and selectively eliminated are also acceptable. For example, those groups described in T. W. Greene, Protective Groups in Organic Synthesis, Wiley, New York, 1999 are used.

As is easily understood by those skilled in the art, the target compound of the present invention may be prepared easily by selecting these deprotection reactions.

b) Among the compound of formula (I), wherein

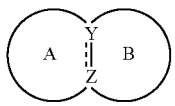

is a ring represented by

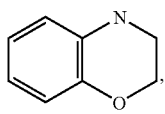

$R^1$ is carboxy, and $R^2$ is —CONHSO$_2$R$^{100}$, i.e. the compound of formula (I-2)

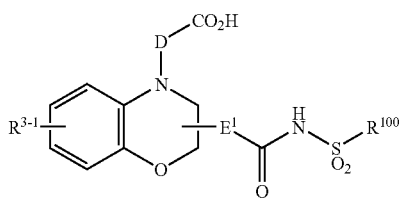

(I-2)

(wherein $R^{100}$ has the same meanings as hereinbefore) may be prepared by subjecting the compound formula (I-1), in which $R^{200}$ is carboxy, i.e. the compound of formula (I-1-a)

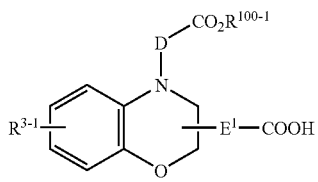

(I-1-a)

(wherein all symbols have the same meaning as described hereinbefore) and the compound represented by H$_2$NSO$_2$R$^{200}$ to an amidation reaction, followed by subjecting to a deprotection reaction of the protective group of carboxylic acid.

Amidation reactions and deprotection reactions of protective groups of carboxylic acid are known, and they may be carried out, for example, by the same methods as described hereinbefore.

c) Among the compounds of formula (I), the compound wherein

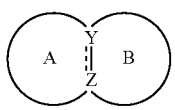

is a ring represented by

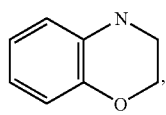

$R^1$ is —CONHSO$_2$R$^{100}$ and $R^2$ is carboxy, i.e. the compound of formula (I-3)

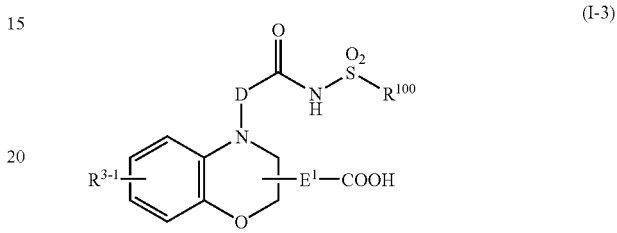

(I-3)

(wherein all symbols have the same meaning as described hereinbefore) may be prepared by subjecting a compound of formula (I-1) wherein $R^1$ is carboxy and $R^2$ is CO$_2$R$^{100\text{-}1}$, i.e. the compound of formula (I-1-b)

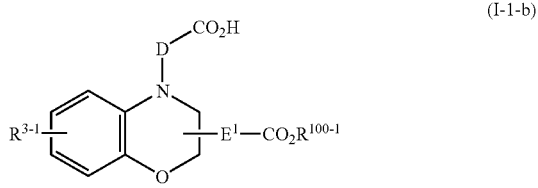

(I-1-b)

(wherein all symbols have the same meaning as described hereinbefore) and the compound of formula H$_2$NSO$_2$R$^{200}$ to an amidation reaction, followed by subjecting to a deprotection reaction of the protective group of carboxylic acid.

The amidation reactions and the deprotection reactions of the protective groups are known, and they may be carried out, for example, by the methods as described hereinbefore.

d) Among the compounds of formula (I), the compound wherein

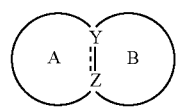

is a ring represented by

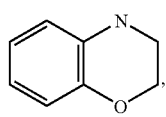

$R^1$ is carboxy, $R^2$ is

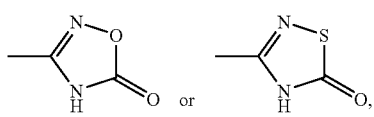

i.e. the compound of formula (I-4)

(I-4)

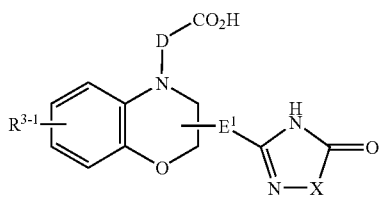

(wherein Q is oxygen or sulfur) may be prepared by subjecting the compound of formula (I-5)

(I-5)

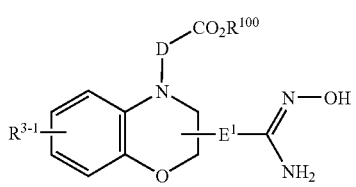

(wherein all symbols have the same meaning as described hereinbefore) to a reaction with carbonyldiimidazole (CDI) or thiocarbonyldiimidazole (TCDI), then subjecting to a cyclizing reaction, followed by a deprotection reaction of carbonyl.

The reaction of the compound of formula (I-5) and CDI or TCDI is known and can be carried out, for example, in the presence of CDI or TCDI in an inert organic solvent (ethyl acetate, tetrahydrofuran, methylene chloride, chloroform, benzene, toluene, etc.) at a temperature of −78° C. to refluxing temperature.

The cyclization reaction is known and may be carried out, for example, by subjecting the resulting compound given by a reaction of the compound (I-5) with CDI or TCDI, further to a reaction in the presence or absence of an acidic catalyst (e.g. Lewis acid such as trifluoroboran-diethyl ether complex, titan chloride, iron chloride, aluminum chloride, etc.; inorganic acid such as hydrochloric acid, sulfuric acid, nitric acid, etc.; organic acid such as acetic acid, propionic acid, lactic acid, oxalic acid, benzoic acid, etc.; silica gel; etc.) or a base (e.g. pyridine, triethylamine, dimethylaniline, dimethylaminopyridine, diisopropylethylamine, diisopropylethylamine, 1,8-diazabicyclo[5.4.0]undec-7-ene (DBU), 1,5-diazabicyclo[4.3.9]non-5-ene (DBN), etc.), in an inert organic solvent (chloroform, dichloromethane, diethyl ether, tetrahydrofuran, dioxane, N,N-dimethylformamide, etc.) at a temperature of −78° C. to refluxing temperature.

The deprotection reaction of the protective groups of carboxy is known and may be carried out by the same method as described hereinbefore.

The compound of formula (II) may be prepared by the method described in the reaction scheme 1. The compound of formula (I-4) may be prepared by the method described in the reaction scheme 2. In these reaction schemes, all symbols have the same meaning as described hereinbefore.

Reaction Scheme 1

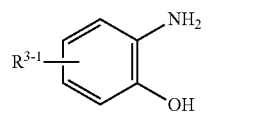

(IV)

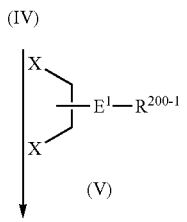

(V)

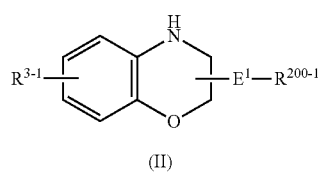

(II)

Reaction Scheme 2

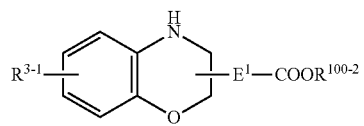

(I-9)

↓ aqueous ammonia

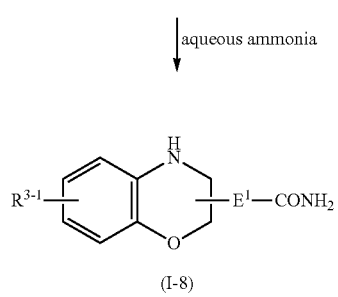

(I-8)

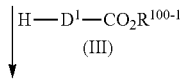

↓

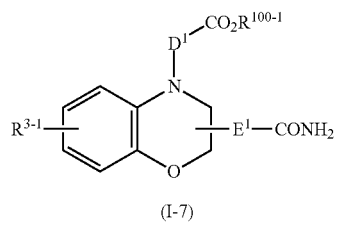

(I-7)

↓

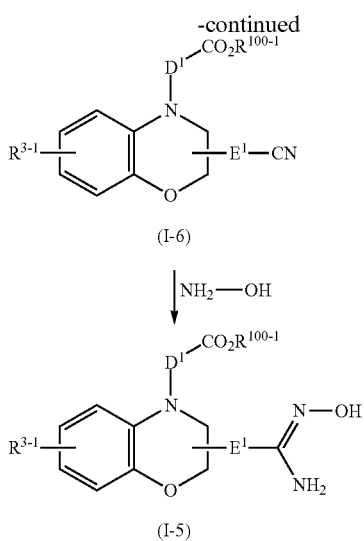

The compounds of formula (III), (III-1), (III-2), (IV) and (V), which are used as starting materials or reagents, are known per se, or may be easily prepared by known methods, e.g. described in "Comprehensive Organic Transformations: A Guide to Functional Group Preparations 2nd Edition (Richard C. Larock, John Wiley & Sons Inc, 1999)".

Among the compounds of formula (I) of the present invention, the compounds other than those described above may be prepared by combining the methods described in the examples of the present specification and/or known methods, e.g. described in "Comprehensive Organic Transformations: A Guide to Functional Group Preparations 2nd Edition (Richard C. Larock, John Wiley & Sons Inc, 1999)".

In each reaction of the present specification, the reactions accompanied by heating, as is obvious to those skilled in the art, may be carried out in a water bath, an oil bath, a sand bath or they may be carried out using a microwave.

In each reaction of the present specification, if required, reagents which are supported with high molecular polymers (e.g. polystyrene, polyacrylamide, polypropylene, polyethyleneglycol, etc.) may also be used.

In each reaction of the present specification, reaction products may be purified by conventional techniques, e.g. distillation under atmospheric or reduced pressure, high performance liquid chromatography, thin layer chromatography or ion exchange chromatography using silica gel or magnesium silicate, washing, recrystallization, etc. Purification may be carried out after each reaction, or after a series of reactions.

In the present invention, as is easily understood by those skilled in the art, the symbol ⋯⋯ indicates that the substituent attached thereto is behind the sheet (i.e. α-position), the symbol ━ indicates that the substituent attached thereto is in front of the sheet (i.e. β-position), and the symbol ∼ indicates that the substituent attached thereto is in α-position, β-position, or a mixture thereof, and the symbol ━ indicates that the substituent attached thereto is a mixture of the compounds in α-position or β-position.

Unless otherwise specified, all isomers are included in the present invention. For example, alkyl, alkenyl, alkynyl, alkoxy, alkylthio, alkylene, alkenylene or alkynylene group includes straight or branched ones. In addition, isomers on double bonds, rings, fused rings (E-, Z-, cis-, trans-isomer), isomers generated from asymmetric carbon atom(s) (R-, S-, α-, β-isomer, enantiomer, diastereomer), optically active isomers having optical activity (D-, L-, d-, l-isomer), tautomers, polar compounds generated by chromatographic separation (more polar compounds, less polar compounds), equilibrium compounds, rotational isomers, mixtures thereof at optional ratios and racemic mixtures are also included in the present invention.

The salts of the compounds of formula (I) include all pharmaceutically acceptable ones. Non-toxic, and water-soluble pharmaceutically acceptable salts are preferable. Preferable salts include, for example, salts of alkali metals (potassium, sodium, lithium, etc.), salts of alkaline earth metals (calcium, magnesium, etc.), ammonium salts (tetramethylammonium salt, tetrabutylammonium salt, etc.), organic amine salts (triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid addition salts (inorganic acid salts such as hydrochloride, hydrobromide, hydroiodide, sulfate, phosphate, nitrate, etc.; organic acid salts such as acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, etc.; etc.).

The N-oxides of the compound of formula (I) represent the compound of formula (I), whose nitrogen atom is oxidized. Also, the N-oxides of the compound of the present invention may be converted to the alkali (earth) metal salts, ammonium salts, organic amine salts or acid addition salts.

Appropriate solvates of the compound of formula (I) include, for example, the solvates of water or alcohol solvents (ethanol etc.). Solvates are preferably non-toxic and water-soluble ones. In the present invention, the solvates include solvates of salts of alkali (earth) metals, ammonium salts, organic amine salts, acid addition salts or N-oxides.

The compound of the present invention may be converted into the solvates as described hereinbefore according to the known methods.

The prodrugs of the compound of formula (I) mean the compounds which are converted into the compound (I) by an enzyme, gastric acid, etc. in the body.

The prodrugs of the compound of formula (I) are, when the compound of formula (I) possesses an amino group, the amino group is acylated, alkylated, phosphorylated (e.g. the amino group of the compound of formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, t-butylated, etc.); when the compound of formula (I) possesses a hydroxy group, the hydroxy group is acylated, alkylated, phosphorylated, borated (e.g. the hydroxy group of the compound of formula (I) is acetylated, palmitoylated, propanoylated, pivaloylated, succinylated, fumarylated, alanylated, dimethylaminomethylcarbonylated, etc.); when the compound of formula (I) possesses a carboxy group, the carboxy group is esterified, or amidated (e.g. the carboxy group of the compound of formula (I) is converted into ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexylcarbonylethyl ester, methyl amide, etc.), etc. These compounds may be prepared by known methods. The prodrug of the compound (I) may be a hydrate or a non-hydrate. Also, the prodrugs of the compound of formula (I) may be converted into the compounds of formula (I) under such physiological conditions as described in "Molecular Design" pages 163-198, in the "Development of pharmaceuticals" Vol. 7, 1990. The compound of formula (I) may be labeled with isotope (e.g. $^3$H, $^{14}$C, $^{35}$S, $^{125}$I, etc.).

The toxicity of the compound of formula (I) is very low for pharmaceutical use.

The compound of formula (I), an N-oxide thereof, a salt thereof, a solvate thereof or a prodrug thereof antagonizes cysLT$_2$ receptor, and therefore, it is useful as an inhibitor of airway contraction, inhibitor of infiltration of inflammatory cells (e.g. eosinophils, neutrophils, lymphocytes, basophils, etc.), an inhibitor of mucus secretion or an inhibitor of increased airway hyperreactivity. Also, the compound of formula (I), an N-oxide thereof, a salt thereof, a solvate thereof or a prodrug thereof is useful for the prevention and/or treatment of those diseases in which cysLT$_2$ receptor is involved, for example, respiratory diseases (e.g. bronchial asthma, chronic obstructive pulmonary diseases, lung emphysema, chronic bronchitis, pneumonia including interstitial pneumonitis, etc.), severe acute respiratory syndrome (SARS), acute respiratory distress syndrome (ARDS), allergic rhinitis, sinusitis including acute sinusitis, chronic sinusitis, etc., and the like), and as an expectorant or an antitussive agent. Furthermore, the compound of formula (I) of the present invention, an N-oxide thereof, a salt thereof, a solvate thereof or a prodrug thereof is useful as an agent for the improvement of respiratory functions.

The respiratory function is defined as, e.g. the function of taking air in and out (i.e. function of pulmonary capacity), the function of taking oxygen from lungs into blood and taking carbon dioxide from blood out of the body (i.e. function of oxygen exchange), and the function of respiratory resistance.

In the present invention, respiratory organs mean, body parts concerned with respiration e.g. airway, oral cavity, nasal cavity, nasal sinuses, trachea, bronchus, bronchiole, lungs, etc.

CysLT$_2$ receptor is also concerned with cardiovascular diseases, e.g. angina pectoris, cardiac infarction, acute coronary syndromes, heart failure, arrhythmia, cardiomyopathy (dilative cardiomyopathy, hypertrophic cardiomyopathy, etc.), pericarditis, valvulitis, myocarditis, cardiac tamponade, low cardiac output syndrome, mitral stenosis, etc. The compound of formula (I), an N-oxide thereof, a salt thereof, a solvate thereof or a prodrug thereof is useful for the treatment and/or prevention of these diseases.

In the present invention, non-responders are defined as those patients to whom existing LT receptor antagonists give insufficient effect or no effect. Since the agent for the treatment of the present invention is more useful for respiratory diseases than an existing LT receptor antagonist, it is preferable to administer it to non-responders and those patients with severe disorders in respiratory functions (e.g. severe bronchial asthma patients).

In the present invention, the measuring method of IC$_{50}$ values or Ki values of antagonizing effect against cysLT$_2$ receptor is not limited in particular, and it may be carried out by known methods. For example, it may be carried out according to the methods described in J. Biol. Chem., 275, 30531-30536, (2000), Mol. Pharmacol., 58, 1601-1608, (2000), or Biochem. Biophys. Res. Commun., 274, 316-322, (2000), etc.

In the present invention, the compound of formula (I) may have an antagonizing effect against cysLT$_1$ receptor, in addition to an antagonizing effect against cysLT$_2$ receptor. The cysLT$_2$ receptor antagonists may be in the form of a prodrug of the compound of formula (I).

The compound of formula (I), an N-oxide thereof, a salt thereof, a solvate thereof or a prodrug thereof may be administered in combination with other agents for the purpose of (1) supplementing and/or reinforcement of preventive and/or treating effect, (2) improvement in kinetics and absorption and reduction of dose, and/or (3) reduction of side effect, of the agent for the treatment of the present invention.

Concomitant agents of the agent for the treatment of the present invention with other agents may be administered in a mode of an agent in which both components are compounded in a single preparation or in a mode of separate preparations. When administration is conducted using separate preparations, a simultaneous administration and administrations with time difference are included. In the case of administrations with time difference, the agent for the treatment of the present invention may be firstly administered and then the other drug may be administered, and vice versa. Each of the methods for the administration may be the same or different.

The other agents as described above may be low molecular compounds, high molecular protein, polypeptides, polynucleotides (DNA, RNA, genes), anti-sense, decoy, antibody, vaccines, etc. The dose of the other agents may be determined taking the clinically used dose as a reference appropriately. The ratio of the agent for the treatment of the present invention and the other agents may be determined according to the age, weight, route of administration, time of administration, the target disease, symptom or combination, etc. For example, approximately 0.01 to 100 of the other agents in weight ratio may be used versus the agent for the treatment of the present invention. One or more of the other agent(s) may be selected from the same group or different groups described hereafter, and may be administered alone or in combination thereof in optional ratios. The other agents which supplement and/or reinforce the preventing and/or treating effect of the agent for the treatment of the present invention include not only those have been found out so far, but also those are to be found out from now on, based on the above mechanism.

The diseases on which the concomitant agents show the preventing and/or treating effect are not limited in particular, and those diseases in which the preventing and/or treating effect of the agent of the present invention are supplemented and/or reinforced are included.

For example, the other agents for supplement and/or reinforcement of the preventing and/or treating effect of the agent of the present invention against respiratory diseases include, for example, cysLT$_1$ receptor antagonists, antihistamine agents, phosphodiesterase 4 inhibitors, elastase inhibitors, anticholinergic agents, antiallergic agents (e.g. chemical mediator release inhibitors, histamine antagonists, thromboxane synthase inhibitors, thromboxane antagonists, Th$_2$ cytokine inhibitors), steroidal agents, bronchodilating agents (e.g. xanthine derivatives, sympathomimetic agents, parasympatholytic agents), vaccine therapy agents, gold formulations, Chinese medicines, basic non-steroidal antiinflammatory agents, 5-lipoxygenase inhibitors, 5-lipoxygenase activated protein antagonists, leukotriene synthesis inhibitors, prostaglandin agents, cannabinoid-2 receptor agonists, antitussive agents, expectorant agents or extract from inflammatory rabbit skin inoculated by vaccinia virus, etc.

CysLT$_1$ receptor antagonists include, for example, pranlukast hydrate, montelukast sodium, zafirlukast, MK-571, LY-203647, WY-46016, WY-48422, WY-49353, WY-49451, RG-12553, MDL-43291, CGP-44044A, RG-14524, LY-287192, LY-290324, L-695499, RPR-105735B, WAY-125007, OT-4003, LM-1376, LY-290154, SR-2566, L-740515, LM-1453, CP-195494, LM-1484, CR-3465, ablukast, pobilukast, sulukast, L-648051, RG-12525, RG-7152, SK&F-106203, SR-2640, WY-50295, iralukast sodium, verlukast, MCC-847, BAY-x-7195, ritolukast, cinalukast, CGP-44826, FK-011, YM-158, MEN-91507, KCA-757, RS-601, RS-635, S-36496, ZD-3523, DS-4574, pirodomast, AS-35, YM-57158, MCI826, NZ-107, 4414-CERM, YM-16638, Wy-48252, Wy-44329, Wy-48090, VUF-4679, tomelukast, SM-11044, SC-39070, OT-3473, N-2401, LY-243364, L-649923, doqualast, DP-1934, YM-17551, Wy-47120, VUF-K-8707, SK&F-88046, SK&F-101132, SK&F-102922, LY-137617, LY-163443, LY-302905, L-647438, L-708738, KY-234, FPL-55712, CP-288886, S-36527, CGP-35949, CS-615, MDL-19301D, SCH-40120, ZD-3705, etc.

$CysLT_1$ receptor antagonists are preferably, pranlukast hydrate, montelukast sodium, zafirlukast or MK-571, more preferably, pranlukast hydrate, montelukast sodium or zafirlukast.

Antihistamine agents include, for example, diphenhydramine hydrochloride, diphenylpyraline hydrochloride, diphenylpyraline chlorotheophyllinate, clemastine fumarate, dimenhydrinate, dl-chlorpheniramine maleate, d-chlorpheniramine maleate, triprolidine hydrochloride, promethazine hydrochloride, alimemazine tartrate, isothipendyl hydrochloride, homochlorcyclizine hydrochloride, hydroxyzine, cyproheptadine hydrochloride, levocabastine hydrochloride, astemizole, bepotastine, desloratadine, TAK-427, ZCR-2060, NIP-530, mometasone furoate, mizolastine, BP-294, andolast, auranofin, acrivastine, hydroxyzine pamoate, terfenadine, mequitazine, etc.

Phosphodiesterase 4 inhibitors include, for example, rolipram, cilomilast (brand name: Ariflo), Bay19-8004, NIK-616, roflumilast (BY-217), cipamfylline (BRL-61063), atizoram (CP-80633), SCH-351591, YM-976, V-11294A, PD-168787, D-4396 or IC-485, etc.

Elastase inhibitors include, for example, sivelestat sodium hydrate (ONO-5046), ONO-6818, MR-889, PBI-1101, EPI-HNE-4, R-665, ZD-0892, ZD-8321, GW-311616, AE-3763, DMP-777, L-659286, L-658758, L-680833, L-683845, etc.

Anticholinergic agents include, for example, ipratropium bromide, oxitropium bromide, flutropium bromide, cimetropium, temiverine, tiotropium bromide, revatropate (UK-112166), etc.

Among the antiallergic agents, chemical mediator release inhibitors include, for example, sodium cromoglicate, tranilast, anlexanox, repirinast, ibudilast, potassium pemilolast, tazanolast, nedocromil, cromoglicate, israpafant, etc.

Among the antiallergic agents, histamine antagonists include, for example, ketotifen fumarate, azelastine hydrochloride, oxatomide, mequitazine, terfenadine, emedastine difumarate, epinastine hydrochloride, ebastin, cetirizine hydrochloride, olopatadine hydrochloride, loratadine, fexofenadine, etc.

Among the antiallergic agents, thromboxane synthase inhibitors include, for example, ozagrel hydrochloride or imitrodast sodium, etc.

Among the antiallergic agents, thromboxane antagonists are, for example, seratrodast, ramatoroban, domitroban calcium hydrate, KT-2-962, etc.

Among the antiallergic agents, TH2 cytokine inhibitors include, for example, suplatast tosylate, etc.

Steroidal agents as external medicines include, for example, clobetasol propionate, diflorasone acetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclomethasone dipropionate, triamcinolone acetonide, flumethasone pivalate, alclometasone dipropionate, clobetasone butyrate, prednisolone, beclomethasone dipropionate, fludroxycortide, etc. Internal medicines and injections include, for example, cortisone acetate, hydrocortisone, sodium hydrocortisone phosphate, sodium hydrocortisone succinate, fludrocortisone acetate, prednisolone, prednisolone acetate, sodium prednisolone succinate, butyl prednisolone acetate, prednisolone sodium phosphate, halopredone acetate, methyl prednisolone, methyl prednisolone acetate, sodium methyl prednisolone succinate, triamcinolone, triamcinolone acetate, triamcinolone acetonide, dexamethasone, dexamethasone acetate, sodium dexamethasone phosphate, dexamethasone palmitate, paramethasone acetate, betamethasone, etc. Inhalant medicines include, for example, beclometasone dipropionate, fluticasone propionate, budesonide, flunisolide, triamcinolone, ST-126P, ciclesonide, dexamethasone paromitionate, mometasone furoate, prasterone sulfonate, deflazacort, methylprednisolone, sleptanate, methylprednisolone sodium succinate, etc.

Among the bronchodilating agents, the xanthine derivatives include, for example, aminophylline, theophylline, doxophylline, cipamphilline, diprophilline, proxyphylline, choline theophylline, etc.

Among the bronchodilating agents, sympathomimetic agents include, for example, epinephrine, ephedrine hydrochloride, dl-methylephedrine hydrochloride, methoxyphenamine hydrochloride, isoproterenol sulfate, isoproterenol hydrochloride, orciprenaline sulfate, clorprenaline hydrochloride, trimetoquinol hydrochloride, salbutamol sulfate, terbutaline sulfate, hexoprenaline sulfate, tulobuterol hydrochloride, procaterol hydrochloride, formoterol fumarate, clenbuterol hydrochloride, mabuterol hydrochloride, salmeterol xinafoate, R,R-formoterol, tulobuterol, pirbuterol hydrochloride, ritodrine hydrochloride, bambuterol, dopexamine hydrochloride, meluadrine tartrate, AR-C68397, levosalbutamol, KUR-1246, KUL-7211, AR-C89855, S-1319, etc.

Among the bronchodilating agents, parasympatholytic agents include, for example, ipratropium bromide, flutropium bromide, oxitropium bromide, cimetropium bromide, temiverine, tiotropium bromide, revatropate (UK-112166), etc.

Vaccine therapy agents include, for example, paspat, astremesin, broncasma berna, CS-560, etc.

Gold formulations include, for example, gold sodium thiomalate etc.

Basic non-steroidal antiinflammatory agents include, for example, tiaramide hydrochloride, tinoridine hydrochloride, epirizole, emorfazone, etc.

5-lipoxygenase inhibitors include, for example, diruton, docebenone, piripost, SCH-40120, WY-50295, E-6700, ML-3000, TMK-688, ZD-2138, darbufelone mesylate, R-68151, E-6080, DuP-654, SC-45662, CV-6504, NE-11740, CMI-977, NC-2000, E-3040, PD-136095, CMI-392, TZI-41078, Orf-20485, IDB-18024, BF-389, A-78773, TA-270, FLM-5011, CGS-23885, A-79175 or ETH-615, etc.

5-lipoxygenase activating protein antagonists include, for example, MK-591 or MK-886, etc.

Leukotriene synthase inhibitors include, for example, auranofin, proglumetacin maleate, L-674636, A-81834, UPA-780, A-93178, MK-886, REV-5901A, SCH-40120, MK-591, Bay-x-1005, Bay-y-1015, DTI-0026, amlexanox or E-6700, etc.

Prostaglandins (abbreviated as PG hereafter) include, for example, PG receptor agonist, PG receptor antagonist, etc.

PG receptors include, for example, PGE receptor ($EP_1$, $EP_2$, $EP_3$, $EP_4$), PGD receptor (DP, $CRTH_2$), PGF receptor (FP) or PGI receptor (IP), TX receptor (TP), etc.

Antitussive agents include, for example, codeine phosphate, dihydrocodeine phosphate, dextromethorphan hydrobromide, pentoxyverine citrate, dimemorfan phosphate, oxeladin citrate, chloperastine, benproperine phosphate, clofedanol hydrochloride, fominoben hydrochloride, noscapine, tipepidine hibenzate, eprazinone hydrochloride, plantago, etc.

Expectorants include, for example, fennel ammonium spirit, sodium bicarbonate, potassium iodide, bromhexine hydrochloride, cherry bark extract, carbocysteine, fudostein, ambroxol hydrochloride, ambroxol hydrochloride extended release drug, methylcysteine hydrochloride, acetylcysteine, L-ethylcycteine hydrochloride, cysteine, tyloxapol, etc.

The other agents to be used in combination with the compound of the present invention are preferably, $cysLT_1$ receptor antagonists, steroidal agents or sympathomimetics.

The formulation to be used in the present invention may contain the $cysLT_2$ receptor antagonists and the other agent(s) supplementing and/or reinforcing the treating effect of the compound which are compounded in a single preparation or in separate preparations. These are formulated by known methods.

The formulation is administered normally systemically or topically, orally or parenterally, for the purpose of the present invention.

The dosages are determined depending on age, body weight, symptom, therapeutic effect, administration route, duration of the treatment and the like. Generally, for an adult, approximately 1 mg to 1000 mg per dose is orally administered once to several times per day, or approximately 1 mg to 100 mg is parenterally administered once to several times per day, or continuously administered from vein for 1 to 24 hours per day.

As described hereinbefore, since the dosage changes depending on various conditions as described above, there are cases in which doses lower than or greater than the above ranges may be used.

The compound is administered in the form of solid compositions for oral administration or liquid compositions for oral administration, or injectable compositions, external medicine, suppositories, eye lotions, inhalants and the like for parenteral administration, for the purpose of the present invention.

The solid formulations for oral administration include, for example, tablets, pills, capsules, powdered drugs, granulated drugs, etc.

Capsules include hard capsules and soft capsules.

In such solid formulations, said one or more active agent(s) are formulated according to usual methods as it is, or mixed with one or more of an excipient (lactose, mannitol, glucose, microcrystalline cellulose, starch, etc.), a binding agent (hydroxypropyl cellulose, polyvinylpyrrolidone, magnesium aluminometasilicate, etc.), a disintegrating agent (calcium glycolate cellulose, carmellose, starch, crystalline cellulose, etc.), a lubricant (magnesium stearate etc.), a stabilizing agent or a solubilizing agent (glutamic acid, aspartic acid, etc.), etc. If necessary, the formulations may be coated with a coating agent such as sugar, gelatin, hydroxypropyl cellulose, hydroxypropylmethyl cellulose phthalate, or may be coated with two or more layers thereof. Alternatively, the solid agent may be capsulized by an absorbable material such as gelatin.

The liquid formulations for oral administration include pharmaceutically acceptable aqueous solution, suspension, emulsion, syrup, elixir, etc. In such liquid formulations, one or more of the active agent(s) are dissolved, suspended or emulsified in a commonly used diluent (e.g., purified water, ethanol, or a mixture thereof). Furthermore, such liquid formulations may comprise a wetting agent (glycerine, D-sorbitol, propylene glycol, etc.), a suspending agent (gum arabic, hydroxypropyl cellulose, methyl cellulose, popidon, etc.), an emulsifier (Polysorbate80 etc.), a sweetening agent (fructose, glucose, simple syrup, white sugar, etc.), a flavoring agent, an aromatic agent, a preservative (benzoic acid, sodium benzoate, etc.), a buffer (sodium citrate, citric acid, sodium acetate, sodium hydrogenphosphate, etc.), etc.

Injectable formulations for parenteral administration include, for example, a solution, a suspension, an emulsion or solid formulation for injection which is dissolved or suspended in use. The injectable formulation is prepared by dissolving, suspending or emulsifying one or more of active substance in a solubilizing agent. The solubilizing agents include, for example, distilled water for injection, saline, vegetable oil, propylene glycol, polyethyleneglycol or alcohols such as ethanol, and a combination thereof. The injectable formulation may further contain a stabilizing agent (disodium edetate, thioglycolic acid, etc.), a solubilizing agent (glutamic acid, aspartic acid, polysorbate 80, propyleneglycol, etc.), a suspending agent (gum aracbic, hydroxypropyl cellulose, methyl cellulose, popidon, etc.), emulsifying agent (Polysorbate 80 etc.), a soothing agent (benzylalcohol, etc.), a tonicity agent (sodium chloride, glycerine, concentrated glycerine, mannitol, etc.), a buffer (sodium citrate, citric acid, sodium acetate, sodium hydrogenphosphate, etc.) or a preservative (chlorobutanol etc.), etc. These are sterilized in the final step or are prepared by aseptic manipulation. Sterile solid formulation, such as freeze-dried formulation, may be prepared, to sterilize or to solve in sterile distilled water for injection or other sterile solvents before use.

The eye drops for parenteral administration may be in the form of liquid eye drops, suspended eye drops, emulsified eye drops or eyedrops which is used by dissolving in a solvent in use or eye ointment.

These eye drops are prepared by known methods. For example, in the case of liquid eye drops, they may be prepared by appropriately selecting and comprising one or more agent(s) such as an isotonic agent (sodium chloride, glycerin, concentrated glycerin, mannitol, etc.), a buffer (sodium citrate, citric acid, sodium acetate, sodium hydrogenphosphate, boric acid, borax, etc.), a surface active agent (Polysolvate 80 (trade name), polyoxyl stearate 40, polyoxyethylene-hardened castor oil, etc.), a stabilizer (sodium bisulrite, sodium citrate, sodium edentate, etc.), and a preservative (benzalconium chloride, Paraben, etc.), and the like depending on the needs. The eye drops are sterilized at the final step or prepared by an aseptic process.

The inhalable formulation for parenteral administration may be in the form of aerosol, inhalable powder or inhalable liquid formulation. The inhalable liquid formulation may be dissolved or suspended in water or other appropriate medium in use.

These inhalable formulations may be prepared according to known methods.

For example, inhalable liquid formulations may further contain antiseptics (benzalkonium chloride, paraben, etc.), a coloring agent, a buffer (sodium citrate, citric acid, sodium acetate, sodium hydrogenphosphate, boric acid, borax, etc.), a tonicity agent (sodium chloride, glycerine, concentrated glycerine, mannitol, etc.), a thickening agent (carboxyvinyl polymer, etc.), an absorption promoter, and the like.

Inhalable powders may be prepared by appropriately selecting and comprising one or more agent(s) such as a lubricant (stearic acid, a salt thereof, etc.), a binding agent (starch, dextrin, etc.), an excipient (lactose, cellulose, etc.), a coloring agent, an antiseptic agent (benzalchonium chloride, parabens, etc.), an absorption promoter, and the like.

Inhalable liquid formulations may normally be administered by sprayer (e.g. atomizer, nebulizer, etc.) and inhalable powders may be administered by using inhalers for powder formulations. The other compositions for parenteral administration include a liquid preparation for external application, an ointment, a liniment, a spray formulation, a suppository, a pessary for intravaginal administration, and the like.

The spray formulation may include, besides generally used diluents, a stabilizing agent (sodium hydrogensulfite, sodium citrate, sodium edetate, etc.), a buffert (e.g. sodium citrate, citric acid, sodium acetate, sodium hydrogenphosphate, boric acid, borax, etc.), a tonicity agent (e.g. sodium chloride, glycerine, concentrated glycerine, mannitol, etc.), and the like. For the preparation of the spray formulation, for example, the methods described in the U.S. Pat. No. 2,868,691 and ibid. U.S. Pat. No. 3,095,355 may be used.

Effect of the Invention

The compound of formula (I), an N-oxide thereof, a salt thereof, a solvate thereof or a prodrug thereof antagonizes $cysLT_2$ receptor, and therefore, it is useful as an inhibitor of airway contraction, inhibitor of infiltration of inflammatory cells (e.g. eosinophils, neutrophils, lymphocytes, basophils, etc.), an inhibitor of mucus secretion or an inhibitor of increased airway hyperreactivity. Also, the compound of formula (I), an N-oxide thereof, a salt thereof, a solvate thereof or a prodrug thereof is useful for the prevention and/or treatment of those diseases in which $cysLT_2$ receptor is involved, for example, respiratory diseases (e.g. bronchial asthma, chronic obstructive pulmonary diseases, lung emphysema, chronic bronchitis, pneumonia including interstitial pneumonitis, etc.), severe acute respiratory syndrome (SARS), acute respiratory distress syndrome (ARDS), allergic rhinitis, sinusitis including acute sinusitis, chronic sinusitis, etc., and the like), and as an expectorant or an antitussive agent. Furthermore, the compound of formula (I) of the present invention, an N-oxide thereof, a salt thereof, a solvate thereof or a prodrug thereof is useful as an agent for the improvement of respiratory functions.

The diseases also $cysLT_2$ receptor is concerned with include, for example, cardiovascular diseases such as angina pectoris, cardiac infarction, acute coronary syndromes, heart failure, arrhythmia, cardiomyopathy (e.g. dilative cardiomyopathy, hypertrophic cardiomyopathy, etc.), pericarditis, valvulitis, myocarditis, cardiac tamponade, low cardiac output syndrome, mitral stenosis, etc. The compound of formula (I), an N-oxide thereof, a salt thereof, a solvate thereof, or a prodrug thereof is useful for the treatment and/or prevention of these diseases.

BEST MODE FOR CARRYING OUT THE INVENTION

The present invention is illustrated by the following Examples and biological Examples, but it is not limited thereto.

The solvents in the parentheses described in chromatography separation and TLC show the eluting or developing solvents, and the ratios of the solvents used are by volume in chromatographic separations or TLC. NMR means $^1$H-NMR and the solvents in the parentheses in NMR show the solvents used in measurement. TFA represents trifluoroacetic acid.

The nomenclature in the present invention was carried out according to ACD/Name (Brand Name; Advanced Chemistry Development Inc.), which generates nomenclature of IUPAC rules.

Example 1

2-(benzyloxy)-3-nitrobenzoic acid

To a solution of 2-hydroxy-3-nitrobenzoic acid (36.6 g) in N,N-dimethylformamide (500 mL) were added benzyl bromide (50.0 mL) and potassium carbonate (66.3 g), and the mixture was stirred overnight at 60° C. The reaction mixture was poured into water and the resulting mixture was extracted with a mixture of ethyl acetate and n-hexane (1:1). The organic layer was washed with water and saturated brine, dried over anhydrous sodium sulfate and concentrated. The residue was dissolved in a mixture of tetrahydrofuran (100 mL) and methanol (200 mL), and the resulting mixture was stirred for 30 minutes at 50° C. The reaction mixture was concentrated and the residue was acidified with 2N hydrochloric acid and extracted with ethyl acetate. The organic layer was washed with water and saturated brine, dried over anhydrous sodium sulfate and concentrated. The residue was recrystallized from isopropanol (50 mL)/n-hexane (200 mL) to give the title compound (31.99 g) having the following physical data.

TLC: Rf 0.43 (methylene chloride:methanol:acetic acid 19:1:0.1).

Example 2 tert-butyl (2-(benzyloxy)-3-nitrophenyl)carbamate

To a solution of the compound prepared in Example 1 (30.0 g) and triethylamine (16.2 mL) in toluene (440 mL) was added diphenylphosphorylazide (24.9 mL) dropwise at room temperature. The reaction mixture was stirred for 2 hours at 80° C. To the reaction mixture was added tert-butanol (52.6 mL) and the mixture was stirred for 3 hours at 80° C. The reaction mixture was cooled down to room temperature, washed successively with water, 0.1N hydrochloric acid, water, saturated aqueous sodium bicarbonate solution and saturated brine, dried over sodium sulfate and concentrated. The residue was purified by column chromatography on silica gel (n-hexane:ethyl acetate=9:1) to give the title compound (32.98 g) having the following physical data.

TLC: Rf 0.40 (n-hexane:ethyl acetate=9:1).

Example 3

(2-(benzyloxy)-3-nitrophenyl)amine hydrochloride

To the compound prepared in Example 2 (20.66 g) was added 4N hydrochloric acid solution in dioxane (120 mL), and the mixture was stirred overnight at room temperature. To the reaction mixture was added n-hexane (120 mL), and the resulting mixture was stirred for 1 hour with ice cooling. The resulting solid was collected by filtration, and it was washed with ethyl acetate to give the title compound (15.2 g) having the following physical data.

TLC: Rf 0.40 (n-hexane:ethyl acetate=2:1).

Example 4

N-(2-(benzyloxy)-3-nitrophenyl)-4-(4-phenylbutoxy)benzamide

To a suspension of 4-(4-phenylbutoxy)benzoic acid (5.40 g) in methylene chloride (20 mL) were added oxalyl chloride (2.09 mL) and N,N-dimethylformamide (1 drop), and the resulting mixture was stirred for 2 hours at room temperature and then concentrated. To a suspension of the compound prepared in Example 3 (5.61 g) in methylene chloride (60 mL) were added pyridine (4.85 mL) and the previously prepared acid chloride in methylene chloride (20 mL), with ice cooling and the resulting mixture was stirred for 3 hours at room temperature. The reaction mixture was concentrated and the residue was diluted with ethyl acetate. The diluted solution was washed sequentially with water, 1N hydrochloric acid, water, saturated aqueous sodium bicarbonate solution and saturated brine, dried over anhydrous sodium sulfate and concentrated. The residue was recrystallized from a mixed solvent of ethyl acetate (100 mL) and n-hexane (100 mL) to give the title compound (8.58 g) having the following physical data.

TLC: Rf 0.54 (n-hexane:ethyl acetate=2:1).

Example 5

N-(3-amino-2-hydroxyphenyl)-4-(4-phenylbutoxy)benzamide

A mixture of the compound prepared in Example 4 (8.58 g), 10% palladium-carbon (429 mg), tetrahydrofuran (60 mL) and methanol (30 mL) was stirred for 5.5 hours under atmosphere of hydrogen. The catalyst was filtered off and the filtrate was concentrated. The residue was recrystallized from a mixed solvent of isopropanol (13 mL) and n-hexane (52 mL) to give the title compound (6.07 g) having the following physical data.

TLC: Rf 0.46 (n-hexane:ethyl acetate=1:1).

Example 6 ethyl 8-((4-(4-phenylbutoxy)benzoyl)amino)-3,4-dihydro-2H-1,4-benzoxazine-2-carboxylate To a solution of the compound prepared in Example 5 (3.76 g) in acetone (40 mL) were added potassium carbonate (4.15 g) and ethyl 2,3-dibromopropionate (1.74 mL), and the mixture was stirred overnight at 50° C. The reaction mixture was concentrated and the residue was diluted with ethyl acetate. The diluted solution was washed with water and saturated brine sequentially, dried over anhydrous sodium sulfate and concentrated. The residue was purified by column chromatography on silica gel (n-hexane:ethyl acetate=(4:1) to (2:1)) to give the title compound (3.51 g) having the following physical data.

TLC: Rf 0.48 (n-hexane:ethyl acetate=1:1).

Example 7 ethyl 4-(4-methoxy-4-oxobutanoyl)-8-((4-(4-phenylbutoxy)benzoyl)amino)-3,4-dihydro-2H-1,4-benzoxazine-2-carboxylate To a solution of the compound prepared in Example 6 (776 mg) in pyridine (5 mL) was added 3-(carbomethoxy)propionyl chloride (302 μL), and the mixture was stirred for 1 hour at room temperature. The reaction mixture was poured into water and the resulting mixture was extracted with ethyl acetate. The organic layer was washed sequentially with 1N hydrochloric acid, water, saturated aqueous sodium bicarbonate solution and saturated brine, dried over anhydrous sodium sulfate and concentrated. The residue was recrystallized from a mixed solvent of ethyl acetate (5 mL) and n-hexane (5 mL) to give the title compound (711 mg) having the following physical data.

TLC: Rf 0.38 (n-hexane:ethyl acetate=1:1).

Example 8

4-(3-carboxypropanoyl)-8-((4-(4-phenylbutoxy)benzoyl)amino)-3,4-dihydro-2H-1,4-benzoxazine-2-carboxylic acid

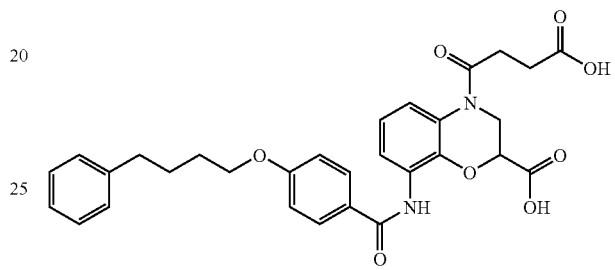

To a mixture of the compound prepared in Example 7 (700 mg), tetrahydrofuran (2 mL) and ethanol (2 mL) was added 2N aqueous solution of sodium hydroxide (2 mL), and the mixture was stirred for 1 hour at room temperature. The reaction mixture was acidified with 2N hydrochloric acid and extracted with ethyl acetate. The organic layer was washed sequentially with water and saturated brine, dried over anhydrous sodium sulfate and concentrated. The residue was recrystallized from ethanol to give the compound of the present invention (486 mg) having the following physical data.

TLC: Rf 0.21 (methylene chloride:methanol:acetic acid=90:10:1);

NMR(CD$_3$CO$_2$D): δ 1.73-1.92 (m, 4H), 2.60-2.97 (m, 5H), 2.98-3.14 (m, 1H), 4.05-4.22 (m, 3H), 4.38 (dd, 1H), 5.19 (t, 1H), 6.97-7.06 (m, 3H), 7.11-7.30 (m, 6H), 7.90-7.98 (m, 2H), 8.13 (br. s., 1H).

Example 8(1)-Example 8(4)

The compounds of the present invention having the following physical data were prepared by using corresponding hydroxynitrobenzoic acids instead of 2-hydroxy-3-nitrobenzoic acid, and using corresponding acid chlorides in stead of 3-(carbomethoxy)propionyl chloride in the process of Example 1→Example 2→Example 3→Example 4→Example 5→Example 6→Example 7→Example 8.

Example 8(1)

4-(4-carboxybutanoyl)-8-((4-(4-phenylbutoxy)benzoyl)amino)-3,4-dihydro-2H-1,4-benzoxazine-2-carboxylic acid TLC: Rf 0.25 (methylene chloride:methanol:acetic acid=90:10:1);

NMR(DMSO-d$_6$): δ 1.74 (m, 6H), 2.24 (m, 2H), 2.64 (m, 4H), 3.69 (m, 1H), 4.07 (m, 2H), 4.47 (m, 1H), 5.15 (m, 1H), 6.92 (t, 1H), 7.03 (d, 2H), 7.21 (m, 6H), 7.67 (m, 1H), 7.91 (d, 2H), 9.30 (s, 1H), 12.06 (br. s., 1H).

Example 8(2)

4-(5-carboxypentanoyl)-8-((4-(4-phenylbutoxy)benzoyl)amino)-3,4-dihydro-2H-1,4-benzoxazine-2-carboxylic acid TLC: Rf 0.32 (methylene chloride:methanol:acetic acid=90:10:1);
NMR(DMSO-$d_6$): δ 1.53 (m, 4H), 1.72 (m, 4H), 2.20 (m, 2H), 2.60 (m, 4H), 3.67 (m, 1H), 4.07 (m, 2H), 4.48 (m, 1H), 5.14 (m, 1H), 6.91 (t, 1H), 7.03 (d, 2H), 7.21 (m, 6H), 7.66 (m, 1H), 7.91 (d, 2H), 9.29 (s, 1H), 12.71 (br. s., 1H).

Example 8(3)

4-(3-carboxypropanoyl)-6-((4-(4-phenylbutoxy)benzoyl)amino)-3,4-dihydro-2H-1,4-benzoxazine-2-carboxylic acid TLC: Rf 0.26 (methylene chloride:methanol:acetic acid=40:10:1);
NMR(CD$_3$CO$_2$D): δ 1.72-1.92 (m, 4H), 2.61-2.84 (m, 4H), 2.85-3.02 (m, 1H), 3.01-3.23 (m, 1H), 3.95 (dd, 1H), 4.07 (t, 2H), 4.42-4.61 (m, 1H), 5.06 (br. s., 1H), 6.94-7.07 (m, 3H), 7.11-7.33 (m, 5H), 7.36-7.77 (m, 1H), 7.77-8.29 (m, 3H).

Example 8(4)

4-(3-carboxypropanoyl)-7-((4-(4-phenylbutoxy)benzoyl)amino)-3,4-dihydro-2H-1,4-benzoxazine-2-carboxylic acid TLC: Rf 0.25 (methylene chloride:methanol:acetic acid=40:10:1);
NMR(CD$_3$CO$_2$D): δ 1.73-1.91 (m, 4H), 2.60-2.96 (m, 5H), 2.96-3.17 (m, 1H), 3.93 (dd, 1H), 4.07 (t, 2H), 4.42-4.64 (m, 1H), 4.97-5.15 (m, 1H), 6.95-7.03 (m, 2H), 7.10-7.63 (m, 8H), 7.89-7.98 (m, 2H).

Example 9

8-((4-(4-phenylbutoxy)benzoyl)amino)-3,4-dihydro-2H-1,4-benzoxazine-2-carboxamide To a solution of the compound prepared in Example 6 (1.80 g) in ethanol (11 mL) was added 28 v/v % aqueous ammonia solution (2.6 mL) with ice cooling, and the resulting mixture was stirred overnight at room temperature. The reaction mixture was neutralized with 2N hydrochloric acid and extracted with ethyl acetate. The organic layer was washed with water and brine sequentially and dried over anhydrous sodium sulfate. The residue was stirred for 30 minutes in isopropanol (20 mL) under heating and filtered to obtain a solid. The resulting solid was dried to give the title compound (1.37 g) having the following physical data.
TLC: Rf 0.47 (methylene chloride:methanol:acetic acid=90:10:1).

Example 10

N-(2-cyano-3,4-dihydro-2H-1,4-benzoxazin-8-yl)-4-(4-phenylbutoxy)benzamide

To a solution of the compound prepared in Example 9 (1.11 g) in pyridine (10 mL) was added trifluoroacetic anhydride (1.06 ml) with ice cooling, and the mixture was stirred for 15 minutes, and Luther stirred for 30 minutes at room temperature. The reaction mixture was poured into 2N hydrochloric acid and extracted with ethyl acetate. The organic layer was washed sequentially with water, saturated aqueous sodium bicarbonate solution and saturated brine, dried over anhydrous sodium sulfate and concentrated. To the residue were added tetrahydrofuran (5 ml) and ethanol (5 mL), and 1N aqueous potassium carbonate solution (2.5 mL) was further added thereto. The mixture was stirred for 15 minutes. After further addition of 1N aqueous potassium carbonate solution (2.5 mL), the mixture was stirred at room temperature for 15 minutes. The reaction mixture was poured into water and extracted with ethyl acetate. The organic layer was washed sequentially with water and saturated brine, dried over anhydrous sodium sulfate, and concentrated. The residue was purified by column chromatography on silica gel (n-hexane:ethyl acetate=1:1) and then recrystallized from a mixed solvent of isopropanol (2 mL) and n-hexane (2 mL) to give the title compound (870 mg) having the following physical data.
TLC: Rf 0.52 (n-hexane:ethyl acetate=2:3).

Example 11 methyl 4-(2-cyano-8-((4-(4-phenylbutoxy)benzoyl)amino)-2,3-dihydro-4H-1,4-benzoxazin-4-yl)-4-oxobutanoate To a solution of the compound prepared in Example 10 (214 mg) in pyridime (2 mL) was added 3-(carbomethoxy)propionyl chloride (92 µL), and the mixture was stirred overnight at room temperature. Thereto was added another 3-(carbomethoxy)propionyl chloride (92 µL) and the resulting mixture was stirred for 4 hours. The reaction mixture was poured into 1N hydrochloric acid and extracted with ethyl acetate. The organic layer was washed sequentially with water, saturated aqueous sodium bicarbonate solution and saturated brine, dried over anhydrous sodium sulfate and concentrated. The residue was recrystallized from a mixed solvent of ethyl acetate and n-hexane (1:1) to give the title compound (200 mg) having the following physical data.
TLC: Rf 0.37 (n-hexane:ethyl acetate=2:3).

Example 12

4-oxo-4-(8-((4-(4-phenylbutoxy)benzoyl)amino)-2-(1H-tetrazol-5-yl)-2,3-dihydro-4H-1,4-benzoxazin-4-yl)butanoic acid

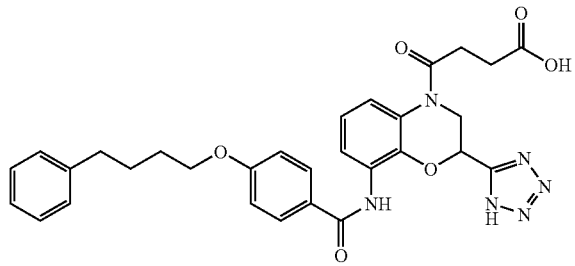

To a solution of the compound prepared in Example 11 (196 mg) in N,N-dimethylformamide (2 mL) were added sodium azide (71 mg) and ammonium chloride (58 mg), and the mixture was stirred for 1 hour at 100° C. The reaction mixture was poured into 1N hydrochloric acid and the resulting mixture was extracted with ethyl acetate. The organic layer was washed sequentially with water and saturated brine, dried over anhydrous sodium sulfate and concentrated. The residue was dissolved in a mixture of tetrahydrofuran (1 mL) and methanol (1 mL), and thereto was added 1N aqueous solution of sodium hydroxide (1 mL) and the resulting mixture was stirred for 2 hours at room temperature. The reaction mixture was acidified with 2N hydrochloric acid and extracted with ethyl acetate. The organic layer was washed sequentially with water and saturated brine, dried over anhydrous sodium sulfate and concentrated. The residue was stirred in ethyl acetate (4 mL) for 30 minutes under heating, and the resulting solid was collected by filtration and it was dried to give the compound of the present invention (177 mg) having the following physical data.

TLC: Rf 0.40 (methylene chloride:methanol:acetic acid=80:20:1);
NMR(CD$_3$CO$_2$D): δ 1.71-1.92 (m, 4H), 2.58-2.81 (m, 4H), 2.82-3.06 (m, 2H), 4.07 (t, 2H), 4.42 (br. s., 2H), 6.13 (t, 1H), 6.96-7.30 (m, 8H), 7.50 (br. s., 1H), 7.84 (br. s., 1H), 7.95 (d, 2H).

Example 12(1)-Example 12(4)

The compounds of the present invention having the following physical data were prepared by using a corresponding hydroxynitrobenzoic acid instead of 2-hydroxy-3-nitrobenzoic acid, and using a corresponding acid chloride instead of 3-(carbomethoxy)propionyl chloride in the process of Example 1→Example 2→Example 3→Example 4→Example 5→Example 6→Example 9→Example 10→Example 11→Example 12.

Example 12(1)

5-oxo-5-(8-((4-(4-phenylbutoxy)benzoyl)amino)-2-(1H-tetrazol-5-yl)-2,3-dihydro-4H-1,4-benzoxazin-4-yl)pentanoic acid TLC: Rf 0.44 (methylene chloride:methanol:acetic acid=80:20:1);
NMR(DMSO-d$_6$): δ 1.72 (m, 6H), 2.22 (m, 2H), 2.63 (m, 4H), 4.06 (m, 2H), 4.22 (m, 2H), 6.09 (t, 1H), 6.97 (t, 1H), 7.03 (d, 2H), 7.22 (m, 5H), 7.45 (m, 1H), 7.68 (m, 1H), 7.90 (d, 2H), 9.40 (s, 1H), 12.02 (br. s., 1H).

Example 12(2)

6-oxo-6-((8-((4-(4-phenylbutoxy)benzoyl)amino)-2-(1H-tetrazol-5-yl)-2,3-dihydro-4H-1,4-benzoxazin-4-yl)hexanoic acid TLC: Rf 0.50 (methylene chloride:methanol:acetic acid=80:20:1);
NMR(DMSO-d$_6$): δ 1.49 (m, 4H), 1.72 (m, 4H), 2.20 (m, 2H), 2.62 (m, 4H), 4.06 (m, 2H), 4.21 (m, 2H), 6.09 (t, 1H), 6.96 (t, 1H), 7.04 (d, 2H), 7.22 (m, 5H), 7.47 (m, 1H), 7.67 (m, 1H), 7.90 (d, 2H), 9.41 (s, 1H), 11.99 (br. s., 1H).

Example 12(3)

4-oxo-4-(6-((4-(4-phenylbutoxy)benzoyl)amino)-2-(1H-tetrazol-5-yl)-2,3-dihydro-4H-1,4-benzoxazin-4-yl)butanoic acid TLC: Rf 0.36 (methylene chloride:methanol:acetic acid=40:10:1);
NMR(CD$_3$CO$_2$D): δ 1.73-1.91 (m, 4H), 2.58-2.84 (m, 4H), 2.91-3.12 (m, 2H), 3.99-4.29 (m, 3H), 4.46-4.70 (m, 1H), 5.88-6.01 (m, 1H), 6.99 (d, 2H), 7.05 (d, 1H), 7.11-7.34 (m, 5H), 7.45-7.84 (m, 1H), 7.86-8.17 (m, 3H).

Example 12(4)

4-oxo-4-(7-((4-(4-phenylbutoxy)benzoyl)amino)-2-(1H-tetrazol-5-yl)-2,3-dihydro-4H-1,4-benzoxazin-4-yl)butanoic acid TLC: Rf 0.39 (methylene chloride:methanol:acetic acid=40:10:1);
NMR(CD$_3$CO$_2$D): δ 1.73-1.91 (m, 4H), 2.58-2.86 (m, 4H), 2.88-3.05 (m, 2H), 3.97-4.38 (m, 3H), 4.41-4.71 (m, 1H), 5.91-6.07 (m, 1H), 6.96-7.03 (m, 2H), 7.10-7.59 (m, 7H), 7.62-7.87 (m, 1H), 7.90-7.97 (m, 2H).

Example 13

2-hydroxyphenyl benzoate

Sodium carbonate (63.6 g) was added to a solution of pyrocatechol (55 g) in water (230 mL), and to the resulting mixture was added dropwise benzoyl chloride (58 mL) over a period of 2 hours with vigorous stirring. The reaction mixture was stirred for 1 hour at room temperature. The reaction mixture was acidified carefully by dropwise addition of 2N hydrochloric acid (350 mL) and then extracted with ethyl acetate. The organic layer was washed sequentially with water and saturated brine, dried over anhydrous sodium sulfate and concentrated. The residue was recrystallized from a mixed solvent of ethyl acetate (100 mL) and n-hexane (400 mL) to give the title compound (64.6 g) having the following physical data.

TLC: Rf 0.50 (n-hexane:ethyl acetate=2:1).

Example 14

2-hydroxy-3-nitrophenyl benzoate

To a suspension of the compound prepared in Example 13 (53.56 g) in acetic acid (500 mL) was added dropwise concentrated nitric acid (61%, 18.7 mL) over a period of approximately 1 hour at 10° C. After 1 hour stirring, the reaction mixture was poured into ice water (1 L) and a precipitated solid was washed with water. The solid was recrystallized from isopropanol to give the title compound (19.6 g) having the following physical data.

TLC: Rf 0.68 (n-hexane:ethyl acetate=2:1).

Example 15

2-(benzyloxy)-3-nitrophenyl benzoate

The compound prepared in Example 14 (24.6 g) in N,N-dimethylformamide (95 mL) were added potassium carbonate (19.7 g) and benzyl bromide (12.4 mL), and the mixture was stirred overnight at room temperature. The reaction mixture was poured into water and the resulting mixture was extracted with ethyl acetate. The organic layer was washed with water and brine sequentially, dried over anhydrous sodium sulfate and concentrated. The residue was recrystallized from a mixture of ethyl acetate (50 mL) and n-hexane (200 mL) to give the title compound (29.4 g) having the following physical data.

TLC: Rf 0.47 (n-hexane:ethyl acetate=4:1).

Example 16

2-(benzyloxy)-3-nitrophenol

To a mixture of the compound prepared in Example 15 (27.9 g), tetrahydrofuran (100 mL) and ethanol (100 mL) was added 2N aqueous solution of sodium hydroxide (100 mL), and the mixture was stirred for 30 minutes at 50° C. The reaction mixture was ice-cooled and thereto was added 1N hydrochloric acid (120 mL), followed by concentration. The residue was purified by column chromatography on silica gel (n-hexane:ethyl acetate=5:1) to give the title compound (19.6 g) having the following physical data.
TLC: Rf 0.40 (n-hexane:ethyl acetate=2:1).

Example 17

2-(benzyloxy)-1-(methoxymethoxy)-3-nitrobenzene

To a solution of the compound prepared in Example 16 (3.92 g) in methylene chloride (48 mL) were added N,N-diisopropylethylamine (4.18 mL) and chloromethyl methyl ether (1.46 mL) at 0° C., and the mixture was stirred for 1 hour at 25° C. The reaction mixture was concentrated, and water was added to the resulting residue and then the mixture was extracted with ethyl acetate. The organic layer was washed sequentially with 0.5N hydrochloric acid, water, saturated aqueous solution of sodium bicarbonate and brine, dried over anhydrous sodium sulfate and concentrated to give the title compound (4.63 g) having the following physical data.
TLC: Rf 0.58 (n-hexane:ethyl acetate=2:1).

Example 18

2-amino-6-(methoxymethoxy)phenol

To a mixture of the compound prepared in Example 17 (12.5 g), ethyl acetate (75 mL) and ethanol (75 mL) was added 10% palladium-carbon (314 mg), and the mixture was stirred for 5 hours under atmosphere of hydrogen. The catalyst was filtered off and the filtrate was concentrated. The residue was recrystallized from a mixture of ethyl acetate and n-hexane to give the title compound (5.45 g) having the following physical data.
TLC: Rf 0.50 (n-hexane:ethyl acetate=1:1).

Example 19 ethyl 8-(methoxymethoxy)-3,4-dihydro-2H-1,4-benzoxazine-2-carboxylate

To a solution of the compound prepared in Example 18 (777 mg) in acetone (20 mL) were added ethyl 2,3-dibromopropionate (1.0 mL) and potassium carbonate (1.90 g) under atmosphere of argon, and the mixture was stirred overnight at 50° C. After further addition of ethyl 2,3-dibromopropionate (1.0 mL) and potassium carbonate (1.90 g) under atmosphere of argon, the mixture was stirred for 2 hours at 50° C. The reaction mixture was poured into water and extracted with ethyl acetate. The organic layer was washed sequentially with water and saturated brine, dried over anhydrous magnesium sulfate and concentrated. The residue was purified by column chromatography on silica gel (methylene chloride:ethyl acetate=40:1) to give the title compound (416 mg) having the following physical data.
TLC: Rf 0.53 (methylene chloride:ethyl acetate=10:1).

Example 20 ethyl 8-(methoxymethoxy)-4-(4-methoxy-4-oxobutanoyl)-3,4-dihydro-2H-1,4-benzoxazine-2-carboxylate To a solution of the compound prepared in Example 19 (416 mg) in pyridine (10 mL) was added 3-(carbomethoxy)propionyl chloride (288 μl), and the mixture was stirred for 1.5 hours at room temperature. The reaction mixture was diluted with water, and extracted with ethyl acetate. The organic layer was washed with 1N hydrochloric acid, water, a saturated aqueous solution of sodium bicarbonate and saturated brine, dried over anhydrous magnesium sulfate and concentrated. The residue was purified by column chromatography on silica gel (n-hexane:ethyl acetate=3:2) to give the title compound (509 mg) having the following physical data.
TLC: Rf 0.38 (n-hexane:ethyl acetate=1:1).

Example 21 ethyl 8-hydroxy-4-(4-methoxy-4-oxobutanoyl)-3,4-dihydro-2H-1,4-benzoxazine-2-carboxylate To the compound prepared in Example 20 (509 mg) was added 4N hydrochloric acid in ethyl acetate (1.6 mL), and the mixture was stirred for 45 minutes at 0° C. The reaction mixture was concentrated and the residue was azeotroped with benzene. The residue was purified by column chromatography on silica gel (n-hexane:ethyl acetate=1:1) to give the title compound (437 mg) having the following physical data.
TLC: Rf 0.32 (n-hexane:ethyl acetate=1:1).

Example 22 ethyl 4-(4-methoxy-4-oxobutanoyl)-8-((4-(4-phenylbutoxy)benzyl)oxy)-3,4-dihydro-2H-1,4-benzoxazine-2-carboxylate To a mixture of the compound prepared in Example 21 (430 mg), 1-(chloromethyl)-4-(4-phenylbutoxy)benzene (420 mg) and N,N-dimethylformamide (5 mL) was added potassium carbonate (263 mg), and the mixture was stirred for 3 hours at room temperature and for 5 hours at 50° C. The reaction mixture was diluted with water and extracted with ethyl acetate. The organic layer was washed with water and saturated brine, dried over anhydrous magnesium sulfate and concentrated. The residue was purified by column chromatography on silica gel (n-hexane:ethyl acetate=2:1) to give the title compound (540 mg) having the following physical data.
TLC: Rf 0.42 (benzene:ethyl acetate=4:1).

Example 23

4-(3-carboxypropanoyl)-8-((4-(4-phenylbutoxy)benzyl)oxy)-3,4-dihydro-2H-1,4-benzoxazine-2-carboxylic acid

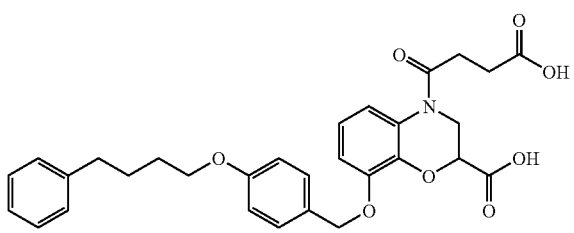

To a mixture of the compound prepared in Example 22 (193 mg), tetrahydrofuran (1 mL) and ethanol (1 mL) was added 2N aqueous sodium hydroxide solution (1 mL), and the mixture was stirred for 2 hours at room temperature and for 1 hour at 50° C. The reaction mixture was concentrated and the residue was diluted with water, acidified with 2N hydrochloric acid and extracted with ethyl acetate. The organic layer was washed with water and saturated brine, dried over anhydrous magnesium sulfate and concentrated. The resulting solid was recrystallized from a mixture of ethyl acetate, tetrahydrofuran and n-hexane to give the compound of the present invention (57 mg) having the following physical data.

TLC: Rf 0.44 (methylene chloride:methanol=5:1);
NMR(DMSO-$d_6$): δ 1.71 (m, 4H), 2.32-2.94 (m, 6H), 3.67 (dd, 1H), 3.98 (m, 2H), 4.37 (dd, 1H), 4.92-5.12 (m, 3H), 6.74-6.96 (m, 4H), 7.12-7.31 (m, 6H), 7.35 (d, 2H).

Example 24 ethyl 4-(4-methoxy-4-oxobutyl)-8-((4-(4-phenylbutoxy)benzyl)oxy)-3,4-dihydro-2H-1,4-benzoxazine-2-carboxylate To a solution of the compound prepared in Example 22 (301 mg) in anhydrous tetrahydrofuran (3 mL) was added borane-dimethylsulfide complex (148 μl) in argon atmosphere with ice cooling, and the mixture was stirred for 45 hours at room temperature. To the reaction mixture was added acetone, and the mixture was stirred for another 30 minutes. The reaction mixture was concentrated and to the resulting residue was added ethyl acetate. The organic layer was washed sequentially with water and saturated brine, dried over anhydrous magnesium sulfate and concentrated. The residue was purified by column chromatography on silica gel (n-hexane:ethyl acetate=3:1) to give the title compound (136 mg) having the following physical data.

TLC: Rf 0.51 (n-hexane:ethyl acetate=1:1).

Example 25

4-(3-carboxypropyl)-8-((4-(4-phenylbutoxy)benzyl)oxy)-3,4-dihydro-2H-1,4-benzoxazine-2-carboxylic acid

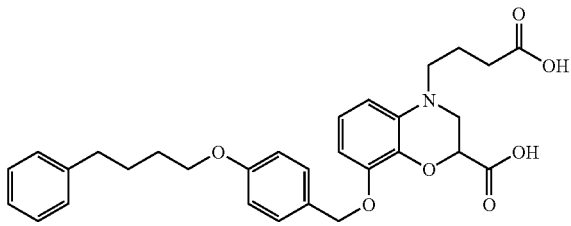

To a mixture of the compound prepared in Example 24 (134 mg), tetrahydrofuran (1 mL) and ethanol (1 mL) was added 2N aqueous sodium hydroxide solution (715 (L), and the mixture was stirred for 2 hours at room temperature. The reaction mixture was concentrated and the residue was diluted with water. The solution was acidified with 2N hydrochloric acid and extracted with ethyl acetate. The organic layer was washed sequentially with water and saturated brine, dried over anhydrous sodium sulfate and concentrated. The residue was recrystallized from a mixture of ethyl acetate, tetrahydrofuran and n-hexane to give the compound of the present invention (84 mg) having the following physical data.

TLC: Rf 0.64 (methylene chloride:methanol=5:1);
NMR(CDCl$_3$): δ 1.73-1.95 (m, 6H), 2.37 (t, 2H), 2.68 (m, 2H), 3.07 (m, 1H), 3.42 (m, 1H), 3.52 (d, 2H), 3.95 (m, 2H), 4.94 (t, 1H), 5.02 (d, 1H), 5.08 (d, 1H), 6.38 (m, 2H), 6.73 (t, 1H), 6.85 (d, 2H), 7.14-7.37 (m, 7H).

Example 25(1)

4-(4-carboxybutyl)-8-((4-(4-phenylbutoxy)benzyl)oxy)-3,4-dihydro-2H-1,4-benzoxazine-2-carboxylic acid The compound of the present invention having the following physical data was prepared by using a corresponding acid chloride in stead of 3-(carbomethoxy)propionyl chloride in the process of Example 20→Example 21→Example 22→Example 24→Example 25.

TLC: Rf 0.43 (methylene chloride:methanol=5:1);
NMR(CDCl$_3$): δ 1.53-1.74 (m, 4H), 1.75-1.85 (m, 4H), 2.30-2.39 (m, 2H), 2.68 (m, 2H), 3.00 (m, 1H), 3.34-3.60 (m, 3H), 3.95 (m, 2H), 4.97 (t, 1H), 5.04 (d, 1H), 5.10 (d, 1H), 6.38 (m, 2H), 6.72 (dd, 1H), 6.85 (d, 2H), 7.14-7.22 (m, 3H), 7.24-7.37 (m, 4H).

Example 26 tert-butyl (3-amino-2-hydroxyphenyl)carbamate

To a solution of the compound prepared in Example 2 (2.93 g) in ethanol (20 mL) was added 10% palladium carbon (50 w/w %, hydroscopic, 400 mg) under atmosphere of argon, and the mixture was stirred for 5.5 hours under atmosphere of hydrogen. The catalyst was filtered off and the filtrate was concentrated to give the title compound having the following physical data.

TLC: Rf 0.32 (n-hexane:ethyl acetate=3:1).

Example 27 ethyl 8-((tert-butoxycarbonyl)amino)-3,4-dihydro-2H-1,4-benzoxazine-2-carboxylate The title compound having the following physical date (1.61 g) was obtained by substituting the compound prepared in Example 26 for the compound prepared in Example 18 in the process of Example 19.

TLC: Rf 0.24 (n-hexane:ethyl acetate=2:1).

Example 28

4-(8-((tert-butoxycarbonyl)amino)-2-(ethoxycarbonyl)-2,3-dihydro-4H-1,4-benzoxazin-4-yl)butanoic acid Under atmosphere of argon, to a solution of the compound prepared in Example 27 (100 mg), 4-oxobutanoic acid (15 w/w % aqueous solution, 422 mg) and acetic acid (45 mg) in ethanol was added 10% palladium-carbon (50 w/w %, hydroscopic, 10 mg), and the mixture was stirred for 30 minutes under atmosphere of hydrogen at room temperature. The catalyst was filtered off and the filtrate was concentrated. The residue was dissolved in a saturated aqueous solution of sodium bicarbonate and the resulting mixture was extracted with ethyl acetate. The organic layer was washed with saturated brine, dried over anhydrous magnesium sulfate and concentrated to give the title compound (110 mg) having the following physical data.

TLC: Rf 0.34 (n-hexane:ethyl acetate=1:2).

Example 29 ethyl 8-((tert-butoxycarbonyl)amino)-4-(4-methoxy-4-oxobutyl)-3,4-dihydro-2H-1,4-benzoxazine-2-carboxylate The compound prepared in Example 28 (110 mg) was dissolved in ethyl acetate (2 mL), and to the solution was added trimethylsilyldiazomethane (2M solution in hexane, 0.40 mL). The mixture was stirred for 1 hour at room temperature and concentrated. The residue was purified by column chromatography on silica gel (n-hexane:ethyl acetate=85:15→80:20) to give the title compound (65 mg) having the following physical data.

TLC: Rf 0.28 (n-hexane:ethyl acetate=3:1).

Example 30 ethyl 4-(4-methoxy-4-oxobutyl)-8-((4-(4-phenylbutoxy)benzoyl)amino)-3,4-dihydro-2H-1,4-benzoxazine-2-carboxylate The title compound (26 mg) having the following physical data was obtained by substituting the compound prepared in Example 29 (61 mg) for the compound prepared in Example 2 in the process of Example 3→Example 4.

TLC: Rf 0.26 (n-hexane:ethyl acetate=2:1).

Example 31

4-(3-carboxypropyl)-8-((4-(4-phenylbutoxy)benzoyl)amino)-3,4-dihydro-2H-1,4-benzoxazine-2-carboxylic acid

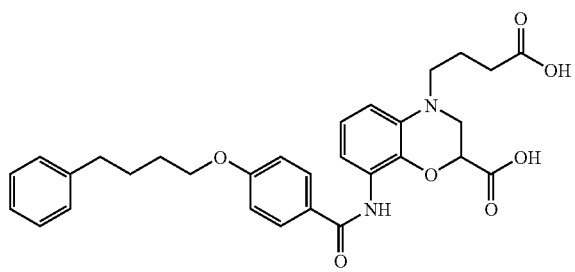

The title compound (15 mg) having the following physical data was obtained by substituting the compound prepared in Example 30 (25 mg) for the compound prepared in Example 7 in the process of Example 8.

TLC: Rf 0.12 (methylene chloride:methanol=9:1);

NMR(DMSO-$d_6$): δ 1.64-1.80 (m, 6H), 2.14-2.34 (m, 2H), 2.63 (t, 2H), 3.08-3.38 (m, 4H), 4.05 (t, 2H), 4.49-4.56 (m, 1H), 6.47 (d, 1H), 6.68 (t, 1H), 7.02 (d, 2H), 7.13-7.31 (m, 6H), 7.85 (d, 2H), 9.07 (s, 1H).

Example 32

4-(2-carboxyethyl)-8-([4-(4-phenylbutoxy)benzyl]oxy)-3,4-dihydro-2H-1,4-benzoxazine-2-carboxylic acid The compound of the present invention having the following physical data was obtained by substituting methyl 3-chloro-3-oxopropanoate for 3-(carbomethoxy)propionyl chloride in the process of Example 20→Example 21→Example 22→Example 24→Example 25.

TLC: Rf 0.43 (methylene chloride:methanol=5:1);

NMR(CDCl$_3$): δ 1.79 (m, 4H), 2.50 (m, 1H), 2.63-2.86 (m, 3H), 3.36 (m, 1H), 3.53 (m, 2H), 3.77 (m, 1H), 3.93 (m, 2H), 4.96 (br, 1H), 5.02 (d, 1H), 5.08 (d, 1H), 6.26 (d, 1H), 6.42 (d, 1H), 6.72 (dd, 1H), 6.84 (d, 2H), 7.14-7.23 (m, 3H), 7.25-7.37 (m, 4H).

Example 33

4-(2-(ethoxycarbonyl)-8-{[4-(4-phenylbutoxy)benzoyl]amino}-2,3-dihydro-4H-1,4-benzoxazin-4-yl)butanoic acid By the same procedure as described in Example 28 using the compound prepared in Example 6 or Example 9 in place of the compound prepared in Example 27, the compound of the present invention having the following physical data was obtained.

TLC: Rf 0.52 (methylene chloride:methanol=9:1);

NMR(CDCl$_3$): δ 1.28 (t, 3H), 1.75-2.00 (m, 6H), 2.43 (t, 2H), 2.70 (t, 2H), 3.22-3.40 (m, 2H), 3.48-3.59 (m, 2H), 4.03 (t, 2H), 4.25 (q, 2H), 4.86-4.89 (m, 1H), 6.49 (dd, 1H), 6.86-6.95 (m, 3H), 7.19-7.32 (m, 5H), 7.87 (d, 2H), 7.90-7.93 (m, 1H), 8.49 (s, 1H).

Example 33(1)

4-(2-(aminocarbonyl)-8-{[4-(4-phenylbutoxy)benzoyl]amino}-2,3-dihydro-4H-1,4-benzoxazin-4-yl)butanoic acid TLC: Rf 0.53 (methylene chloride:methanol:acetic acid=90:10:1);

NMR(DMSO-$d_6$): δ 1.63-1.76 (m, 6H), 2.26 (t, 2H), 2.63 (t, 2H), 3.19-3.49 (m, 4H), 4.04 (t, 2H), 4.70 (t, 1H), 6.64 (dd, 1H), 6.73-6.81 (m, 2H), 7.01 (d, 2H), 7.12-7.30 (m, 5H), 7.41 (brs, 1H), 7.89 (d, 2H), 8.13 (brs, 1H), 9.68 (s, 1H).

Example 34

4-(3-carboxypropyl)-8-({(2E)-3-[4-(4-phenylbutyl)phenyl]-2-propenoyl}amino)-3,4-dihydro-2H-1,4-benzoxazin-2-carboxylic acid The compound of the present invention having the following physical data was obtained by substituting the compound prepared in Example 29 for the compound prepared in Example 2 and substituting (2E)-3-[4-(4-phenylbutyl)phenyl]acrylic acid for 4-(4-phenylbutoxy)benzoic acid, in the process of Example 3→Example 4→Example 25.

TLC: Rf 0.52 (methylene chloride:methanol:acetic acid=85:15:1);

NMR(DMSO-$d_6$): δ 1.51-1.78 (m, 6H), 2.26 (t, 2H), 2.54-2.68 (m, 4H), 3.12-3.53 (m, 4H), 5.02 (t, 1H), 6.52 (d, 1H), 6.72 (t, 1H), 7.09-7.27 (m, 8H), 7.43-7.53 (m, 4H), 9.16 (s, 1H), 12.50 (brs, 1H).

Example 35

4-[8-{[4-(4-phenylbutoxy)benzoyl]amino}-2-(1H-tetrazol-5-yl)-2,3-dihydro-4H-1,4-benzoxazin-4-yl] butanoic acid The title compound having the following physical data was prepared by substituting the compound prepared in Example 10 for the compound prepared in Example 27 according to the process of Example 28→Example 29→Example 12.

TLC: Rf 0.41 (methylene chloride:methanol:acetic acid=90:10:1);

NMR(DMSO-$d_6$): δ 1.65-1.80 (m, 6H), 2.24 (t, 2H), 2.63 (t, 2H), 3.22-3.38 (m, 2H), 3.65-3.76 (m, 2H), 4.06 (t, 2H), 5.84 (t, 1H), 6.61 (dd, 1H), 6.81 (t, 1H), 7.03 (d, 2H), 7.09-7.29 (m, 6H), 7.90 (d, 2H), 9.46 (s, 1H), 12.07 (brs, 1H), 16.51 (brs, 1H).

Example 36

4-(5-carboxypentyl)-8-{[4-(4-phenylbutoxy)benzoyl] amino}-3,4-dihydro-2H-1,4-benzoxazine-2-carboxylic acid The compound having the following physical data was prepared by substituting the compound prepared in Example 6 for the compound prepared in Example 27 in the process of Example 28→Example 25.

TLC: Rf 0.36 (methylene chloride:methanol:acetic acid=90:10:1);

NMR(DMSO-$d_6$): δ 1.23-1.33 (m, 2H), 1.44-1.56 (m, 4H), 1.68-1.78 (m, 4H), 2.19 (t, 2H), 2.63 (t, 2H), 3.12-3.54 (m, 4H), 4.05 (t, 2H), 4.97 (t, 1H), 6.52 (dd, 1H), 6.75 (t, 1H), 7.02 (d, 2H), 7.12-7.30 (m, 6H), 7.86 (d, 2H), 9.16 (s, 1H), 12.47 (brs, 1H).

Example 37

The compound of the present invention having the following physical data was prepared by substituting a corresponding compound for 1-(chloromethyl)-4-(4-phenylbutoxy)benzene in the process of Example 22→Example 24→Example 25.

Example 37

4-(3-carboxypropyl)-8-({4-[(3-phenylpropoxy)methyl]benzyl}oxy)-3,4-dihydro-2H-1,4-benzoxazine-2-carboxylic acid TLC: Rf 0.26 (methylene chloride:methanol=5:1);

NMR(CDCl$_3$): δ 1.81-1.97 (m, 4H), 2.37 (t, 2H), 2.70 (t, 2H), 3.05 (m, 1H), 3.37-3.60 (m, 5H), 4.48 (s, 2H), 4.99 (t, 1H), 5.12 (d, 1H), 5.18 (d, 1H), 6.36 (m, 2H), 6.70 (dd, 1H), 7.13-7.20 (m, 3H), 7.24-7.36 (m, 4H), 7.41 (d, 2H).

Example 37(1)

8-({4-[3-(benzyloxy)propyl]benzyl}oxy)-4-(3-carboxypropyl)-3,4-dihydro-2H-1,4-benzoxazine-2-carboxylic acid TLC: Rf 0.25 (methylene chloride:methanol=5:1);
NMR(CDCl$_3$): δ 1.80-1.97 (m, 4H), 2.37 (t, 2H), 2.69 (t, 2H), 3.06 (m, 1H), 3.37-3.60 (m, 5H), 4.50 (s, 2H), 4.98 (t, 1H), 5.07 (d, 1H), 5.14 (d, 1H), 6.35 (d, 1H), 6.40 (d, 1H), 6.72 (dd, 1H), 7.15 (d, 2H), 7.25-7.36 (m, 3H).

Example 37(2)

4-(3-carboxypropyl)-8-{[4-(4-phenoxybutyl)benzyl] oxy}-3,4-dihydro-2H-1,4-benzoxazine-2-carboxylic acid TLC: Rf 0.29 (methylene chloride:methanol=5:1);
NMR(CDCl$_3$): δ 1.70-1.94 (m, 6H), 2.37 (t, 2H), 2.66 (m, 2H), 3.07 (m, 1H), 3.34-3.61 (m, 3H), 3.96 (m, 2H), 4.98 (m, 1H), 5.07 (d, 1H), 5.14 (d, 1H), 6.37 (m, 2H), 6.71 (dd, 1H), 6.85-6.96 (m, 3H), 7.17 (d, 2H), 7.27 (m, 2H), 7.34 (d, 2H).

Example 38

2-(benzyloxy)-3-nitro-N-[4-(4-phenylbutoxy)phenyl] benzamide

To a solution of the compound prepared in Example 1 (3.40 g) in dimethylformamide (20 mL) were added 1-hydroxybenzotriazole hydrate (2.47 g) and 1-ethyl-3-(3-dimethylaminopropyl)carbodiimide hydrochloride (3.11 g), and the mixture was stirred for 30 minutes at room temperature. To the reaction mixture were added [4-(4-phenylbutoxy)phenyl]amine (3 g) and triethylamine (1.75 mL), and the mixture was stirred overnight. The reaction mixture was poured into ice water and the mixture was extracted with ethyl acetate. The extract was washed sequentially with a saturated aqueous solution of sodium bicarbonate, water and saturated brine, dried over anhydrous sodium sulfate and concentrated. The residue was washed with a mixture of n-hexane and ethyl acetate (1:1) to give the title compound (4.33 g) having the following physical data.

TLC: Rf 0.60 (n-hexane:ethyl acetate=2:1);
NMR(DMSO-$d_6$): δ 1.65-1.76 (m, 4H), 2.63 (t, 2H), 3.95 (t, 2H), 5.06 (s, 2H), 6.90 (d, 2H), 7.12-7.30 (m, 10H), 7.45 (t, 1H), 7.56 (d, 2H), 7.85 (dd, 1H), 8.03 (dd, 1H).

Example 39

4-(3-carboxypropyl)-8-({[4-(4-phenylbutoxy)phenyl] amino}carbonyl)-3,4-dihydro-2H-1,4-benzoxazine-2-carboxylic acid The compound of the present invention having the following physical data was prepared by substituting the compound prepared in Example 38 for the compound prepared in Example 4 in the process of Example 5→Example 6→Example 28→Example 29→Example 25.

TLC: Rf 0.44 (methylene chloride:methanol:acetic acid=90:10:1);

NMR(DMSO-$d_6$): δ 1.69-1.75 (m, 6H), 2.28 (t, 2H), 2.58-2.65 (m, 2H), 3.28 (t, 2H), 3.46-3.59 (m, 2H), 3.88-3.95 (m, 2H), 5.02 (t, 1H), 6.84-6.89 (m, 4H), 6.98-7.04 (m, 1H), 7.12-7.29 (m, 5H), 7.63 (d, 2H), 10.41 (s, 1H).

Example 40 ethyl 4-(4-methoxy-4-oxobutyl)-8-{[4-(4-phenylbutoxy)benzyl]amino}-3,4-dihydro-2H-1,4-benzoxazine-2-carboxylate Ethyl 8-amino-4-(4-methoxy-4-oxobutyl)-3,4-dihydro-2H-1,4-benzoxazine-2-carboxylate (80 mg; prepared by subjecting the compound prepared in Example 3 to the same procedure as described in Example 29) and 4-(4-phenylbutoxy)benzaldehyde (60 mg) were dissolved in 1,2-dichloroethane (4 mL), and to this solution was added sodium triacetoxyborohydride (96 mg) with ice cooling, and the mixture was stirred for 2 hours at room temperature. To the reaction mixture was added water and the resulting mixture was extracted with ethyl acetate. The extract was washed sequentially with a saturated aqueous solution of sodium bicarbonate and saturated brine, dried over anhydrous sodium sulfate and concentrated. The residue was purified by column chromatography on silica gel (n-hexane:ethyl acetate=8:2) to give the title compound (121 mg) having the following physical data.

TLC: Rf 0.59 (n-hexane:ethyl acetate=3:2);
NMR(CDCl$_3$): δ 1.26 (t, 3H), 1.76-1.95 (m, 6H), 2.36 (t, 2H), 2.66-2.71 (m, 2H), 3.16-3.34 (m, 2H), 3.47-3.48 (m, 2H), 3.67 (s, 3H), 3.93-3.96 (m, 2H), 4.18-4.26 (m, 2H), 4.28 (s, 2H), 4.53 (brs, 1H), 4.76-4.78 (m, 1H), 6.10-6.14 (m, 2H), 6.70 (t, 1H), 6.84 (d, 2H), 7.18-7.21 (m, 3H), 7.25-7.30 (m, 4H).

Example 41

4-(3-carboxypropyl)-8-{[4-(4-phenylbutoxy)benzyl]amino}-3,4-dihydro-2H-1,4-benzoxazine-2-carboxylic acid The compound of the present invention having the following physical data was prepared by substituting the compound prepared in Example 40 for the compound prepared in Example 24 in the process of Example 25

TLC: Rf 0.51 (methylene chloride:methanol:acetic acid=90:10:1);
NMR(DMSO-d$_6$): δ 1.61-1.72 (m, 6H), 2.23 (t, 2H), 2.56-2.67 (m, 2H), 3.15 (t, 2H), 3.38 (d, 2H), 3.91-3.98 (m, 2H), 4.18 (s, 2H), 4.83-4.85 (m, 1H), 5.03 (brs, 1H), 5.90 (d, 1H), 6.04 (d, 1H), 6.48 (t, 1H), 6.83 (d, 2H), 7.11-7.28 (m, 7H).

Example 42

2-[(4-methoxybenzyl)oxy]-3-nitrobenzaldehyde

To a solution of 2-hydroxy-3-nitrobenzaldehyde (3 g) in dimethylformamide (20 mL) were sequentially added potassium carbonate (3.72 g), tetra-n-butylammonium fluoride (331 mg) and 1-(chloromethyl)-4-methoxybenzene (3.37 g), and the mixture was stirred for 11 hours at room temperature. The reaction mixture was poured into ice-water and the resulting mixture was extracted with ethyl acetate. The organic layer was washed sequentially with water and saturated brine, dried over anhydrous sodium sulfate and concentrated. The residue was washed with tert-butyl methyl ether to give the title compound (4.17 g) having the following physical data.

TLC: Rf 0.55 (n-hexane:ethyl acetate=2:1);
NMR(CDCl$_3$): δ 3.81 (s, 3H), 5.12 (s, 2H), 6.90 (d, 2H), 7.27-7.38 (m, 3H), 8.05 (dd, 1H), 8.12 (dd, 1H), 10.15 (s, 1H).

Example 43

A mixture of 2-[(4-methoxybenzyl)oxy]-1-nitro-3-{(Z)-2-[4-(4-phenylbutoxy)phenyl]vinyl}benzene and 2-[(4-methoxybenzyl)oxy]-1-nitro-3-{(E)-2-[4-(4-phenylbutoxy)phenyl]vinyl}benzene A suspension of the compound prepared in Example 42 (950 mg) and triphenyl[4-(4-phenylbutoxy)benzyl]phosphonium chloride (6.20 g) in tetrahydrofuran (6 mL) was cooled to −25° C. and thereto was added a solution of potassium tert-butoxide (1.26 g) in tetrahydrofuran (6 mL), and the mixture was stirred for 1 hour at −40 to −30° C. To the reaction mixture was added water and the mixture was extracted with ethyl acetate. The extract was washed sequentially with water and saturated brine, dried over anhydrous sodium sulfate and concentrated. The residue was purified by column chromatography on silica gel (n-hexane:ethyl acetate=92:8) to give the title compound (1.85 g; a mixture of E-isomer and Z-isomer).

TLC (E isomer): Rf 0.55 (n-hexane:ethyl acetate=3:1);
TLC (Z izomer): Rf 0.60 (n-hexane:ethyl acetate=3:1).

Example 44

2-nitro-6-{(E)-2-[4-(4-phenylbutoxy)phenyl]vinyl}phenol

To a solution of the compound prepared in Example 43 (1.68 g) in toluene (35 mL) was added p-toluenesulfonic acid hydrate (112 mg), and the mixture was refluxed for 3 hours. The reaction mixture was cooled to ambient temperature and thereto was added water, and the resulting mixture was extracted with ethyl acetate. The extract was washed sequentially with a saturated aqueous solution of sodium bicarbonate and saturated brine, dried over anhydrous sodium sulfate and concentrated. The residue was washed with diisopropyl ether to give the title compound (700 mg) having the following physical data.

TLC: Rf 0.42 (n-hexane:ethyl acetate=6:1);
NMR(CDCl$_3$): δ 1.80-1.84 (m, 4H), 2.70 (t, 2H), 4.00 (t, 2H), 6.89 (d, 2H), 6.97 (t, 1H), 7.15 (d, 1H), 7.19-7.21 (m, 3H), 7.25-7.32 (m, 2H), 7.34 (d, 1H), 7.48 (d, 2H), 7.86 (dd, 1H), 8.00 (dd, 1H), 11.17 (s, 1H).

Example 45

2-amino-6-{(E)-2-[4-(4-phenylbutoxy)phenyl]vinyl}phenol

To a solution of the compound prepared in Example 44 (860 mg) in ethanol (30 mL) was added tin chloride hydrate (4.99 g), and the mixture was refluxed for 4 hours. The reaction mixture was cooled to ambient temperature and the reaction mixture was alkalified by an aqueous solution of sodium bicarbonate. The precipitated solid was filtered over celite. The filtrate was extracted with ethyl acetate. The extract was washed with saturated brine, dried over anhydrous sodium sulfate and concentrated to give the title compound (618 mg) having the following physical data.

TLC: Rf 0.37 (n-hexane:ethyl acetate=2:1);
NMR (CDCl$_3$): δ 1.72-1.91 (m, 4H), 2.69 (t, 2H), 3.99 (t, 2H), 6.72 (dd, 1H), 6.78 (t, 1H), 6.88 (d, 2H), 6.95-7.04 (m, 2H), 7.13 (d, 1H), 7.19-7.21 (m, 2H), 7.25-7.31 (m, 2H), 7.43 (d, 2H).

Example 46

4-(2-(ethoxycarbonyl)-8-{(E)-2-[4-(4-phenylbutoxy)phenyl]vinyl}-2,3-dihydro-4H-1,4-benzoxazin-4-yl)butanoic acid By the same procedure as described in Example 6→Example 28 using the compound prepared in Example 45 in place of the compound prepared in Example 5.

TLC: Rf 0.50 (methylene chloride:methanol=9:1);
NMR(CDCl$_3$): δ 1.26 (t, 3H), 1.73-1.98 (m, 6H), 2.43 (t, 2H), 2.69 (t, 2H), 3.21-3.41 (m, 2H), 3.53 (d, 2H), 3.98 (t, 2H), 4.19-4.30 (m, 2H), 4.87 (t, 1H), 6.59 (dd, 1H), 6.81-6.89 (m, 3H), 6.98-7.01 (m, 1H), 7.07 (d, 1H), 7.16-7.31 (m, 5H), 7.37 (d, 1H), 7.45 (d, 2H).

Example 47 ethyl 4-(4-ethoxy-4-oxobutyl)-8-{(E)-2-[4-(4-phenylbutoxy)phenyl]vinyl}-3,4-dihydro-2H-1,4-benzoxazine-2-carboxylate To a solution of the compound prepared in Example 46 (330 mg) in dimethylformamide (5 mL) were added potassium carbonate (252 mg) and ethyl iodide (142 mg), and the mixture was stirred for 2 hours at room temperature. To the reaction mixture was added water and the mixture was extracted with ethyl acetate. The extract was washed with water and saturated brine sequentially, dried over anhydrous sodium sulfate and concentrated. The residue was purified by column chromatography on silica gel (n-hexane:ethyl acetate=8:2) to give the title compound (210 mg) having the following physical data.

TLC: Rf 0.49 (n-hexane:ethyl acetate=2:1);
NMR(CDCl$_3$): δ 1.23-1.29 (m, 6H), 1.75-1.98 (m, 6H), 2.36 (t, 2H), 2.69 (t, 2H), 3.21-3.39 (m, 2H), 3.51-3.53 (m, 2H), 3.96-4.00 (m, 2H), 4.08-4.28 (m, 4H), 4.86 (t, 1H), 6.60 (dd, 1H), 6.81-6.87 (m, 3H), 6.98 (dd, 1H), 7.07 (d, 1H), 7.18-7.21 (m, 3H), 7.26-7.31 (m, 2H), 7.36 (d, 1H), 7.45 (d, 2H).

Example 48 ethyl 4-(4-ethoxy-4-oxobutyl)-8-{2-[4-(4-phenylbutoxy)phenyl]ethyl}-3,4-dihydro-2H-1,4-benzoxazine-2-carboxylate To a solution of the compound prepared in Example 47 (100 mg) in ethanol (3 mL) was added 10% palladium carbon (50 w/w %, hydroscopic, 20 mg) under atmosphere of argon and under suppressed atmosphere of hydrogen, and the mixture was stirred for 3 hours at room temperature. The reaction mixture was filtered over celite. The filtrate was concentrated to give the title compound (103 mg) having the following physical data.

TLC: Rf 0.61 (n-hexane:ethyl acetate=2:1);
NMR(CDCl$_3$): δ 1.25 (t, 6H), 1.74-1.95 (m, 6H), 2.35 (t, 2H), 2.68 (t, 2H), 2.77-2.95 (m, 4H), 3.18-3.35 (m, 2H), 3.50 (d, 2H), 3.92-3.97 (m, 2H), 4.14 (q, 2H), 4.22 (q, 2H), 4.80 (t, 1H), 6.51 (dd, 1H), 6.57 (dd, 1H), 6.75 (t, 1H), 6.80 (d, 2H), 7.14 (d, 2H), 7.18-7.21 (m, 3H), 7.25-7.30 (m, 2H).

Example 49-Example 49(1)

The compounds of the present invention having the following physical data were prepared by substituting the compound prepared in Example 47→Example 48 for the compound prepared in Example 2 in the process of Example 25.

Example 49

4-(3-carboxypropyl)-8-{(E)-2-[4-(4-phenylbutoxy)phenyl]vinyl}-3,4-dihydro-2H-1,4-benzoxazine-2-carboxylic acid TLC: Rf 0.45 (methylene chloride:methanol:acetic acid=90:10:1);
NMR (DMSO-d$_6$): δ 1.65-1.78 (m, 6H), 2.26 (t, 2H), 2.58-2.65 (m, 2H), 3.18-3.30 (m, 2H), 3.44 (d, 2H), 3.95-4.02 (m, 2H), 4.97 (t, 1H), 6.62 (d, 1H), 6.74 (t, 1H), 6.88-6.94 (m, 2H), 7.08 (d, 1H), 7.13-7.29 (m, 6H), 7.42 (d, 2H).

Example 49(1)

4-(3-carboxypropyl)-8-{2-[4-(4-phenylbutoxy)phenyl]ethyl}-3,4-dihydro-2H-1,4-benzoxazine-2-carboxylic acid TLC: Rf 0.43 (methylene chloride:methanol:acetic acid=90:10:1);
NMR(DMSO-d$_6$): δ 1.63-1.75 (m, 6H), 2.25 (t, 2H), 2.59-2.88 (m, 6H), 3.19 (t, 2H), 3.35-3.46 (m, 2H), 3.91 (t, 2H), 4.91 (t, 1H), 6.38 (dd, 1H), 6.55-6.64 (m, 2H), 6.78 (d, 2H), 7.08 (d, 2H), 7.12-7.28 (m, 5H).

Example 50

(2S)-4-(3-carboxypropyl)-8-{[4-(4-phenylbutoxy)benzoyl]amino}-3,4-dihydro-2H-1,4-benzoxazine-2-carboxylic acid and (2R)-4-(3-carboxypropyl)-8-{[4-(4-phenylbutoxy)benzoyl]amino}-3,4-dihydro-2H-1,4-benzoxazine-2-carboxylic acid (optical separation)

The compound prepared in Example 31 was optically separated using a column for optical separation; giving a compound whose retention time was 29.8 minutes (21 mg, >97% e.e.) and a compound whose retention time was 34.5 minutes (21 mg >98% e.e.). These two compounds correspond to two diastereomers of the compound prepared in Example 31.

The stereochemistry is undetermined, but one is (2S)-4-(3-carboxypropyl)-8-{[4-(4-phenylbutoxy)benzoyl]amino}-3,4-dihydro-2H-1,4-benzoxazine-2-carboxylic acid, and the other is (2R)-4-(3-carboxypropyl)-8-{[4-(4-phenylbutoxy)benzoyl]amino}-3,4-dihydro-2H-1,4-benzoxazine-2-carboxylic acid.

The conditions for separation and the method for purification are shown below.

Column: CHIRALCEL OD (10 mm I.D.×250 mm)
Eluting solution: 0.1% TFA in n-hexane solution/0.1% TFA in isopropanol solution=70:30
Rate of flow: 2 ml/minute
Column temperature: 40° C.
Amount of injection: 200 μL (a solution of the compound which is prepared in Example 3 (45 mg) in isopropanol (6 mL))
Injection times: 30

The method for the purification of the separated fractions: In order to remove TFA, to the collected fraction was added triethylamine (5 mL), and the mixture was concentrated. To the residue were added ethyl acetate and water, and the resulting mixture was extracted. The extract was washed with water and saturated brine sequentially, dried over anhydrous sodium sulfate and concentrated to give the target optical active isomer.

The optical purity was determined according to the following analysis condition.

Column: CHIRALCEL OD (0.46 mm I.D.×250 mm)
Eluting solution: 0.1% TFA in n-hexane/0.1% TFA in isopropanol=70:30
Rate of flow: 0.5 mL/minute
Column temperature: 40° C.
Injection amount: 1 μL [a solution of the compound (1 mg) in isopropanol (1 mL)]

Example 51

4-(3-carboxypropyl)-8-{[2-methyl-4-(4-phenylbutoxy)benzoyl]amino}-3,4-dihydro-2H-1,4-benzoxazine-2-carboxylic acid By the same procedure as described in Example 47→Example 3→Example 4→Example 25 using the compound prepared in Example 28 in place of the compound prepared in Example 46, and using 2-methyl-4-(4-phenylbutoxy)benzoic acid in place of 4-(4-phenylbutoxy)benzoic acid, the compound having the following physical data was obtained.

TLC: Rf 0.41 (methylene chloride:methanol:acetic acid=90:10:1);
NMR(DMSO-$d_6$): δ 1.62-1.78 (m, 6H), 2.26 (t, 2H), 2.39 (s, 3H), 2.59-2.68 (m, 2H), 3.18-3.48 (m, 4H), 3.96-4.08 (m, 2H), 4.91-4.99 (m, 1H), 6.56 (d, 1H), 6.72-6.83 (m, 3H), 7.12-7.29 (m, 6H), 7.44 (d, 1H), 8.87 (s, 1H).

Example 52

By the same procedure as described in Example 28→Example 25 using a corresponding compound in place of the compound prepared in Example 27, the compound of the present invention having the following physical data was obtained.

Example 52

4-(3-carboxypropyl)-8-{[2,6-dimethyl-4-(4-phenylbutoxy)benzoyl]amino}-3,4-dihydro-2H-1,4-benzoxazine-2-carboxylic acid TLC: Rf 0.29 (methylene chloride:methanol:acetic acid=90:10:1);
NMR(DMSO-d6): δ 1.63-1.85 (m, 6H), 2.15-2.39 (m, 8H), 2.58-2.78 (m, 2H), 3.11-3.35 (m, 2H), 3.39-3.60 (m, 2H), 3.96-4.11 (m, 2H), 4.79-4.88 (m, 1H), 6.50-6.82 (m, 5H), 7.11-7.40 (m, 5H), 8.64 (brs., 1H).

Example 52(1)

4-(3-carboxypropyl)-8-({4-[(E)-2-(7-chloro-2-quinolinyl)vinyl]benzoyl}amino)-3,4-dihydro-2H-1,4-benzoxazine-2-carboxylic acid TLC: Rf 0.27 (methylene chloride:methanol:acetic acid=90:10:1);
NMR(DMSO-$d_6$): δ 1.63-1.78 (m, 2H), 2.24-2.29 (m, 2H), 3.23-3.30 (m, 2H), 3.41-3.52 (m, 2H), 4.96-5.01 (m, 1H), 6.61 (d, 1H), 6.78 (t, 1H), 7.19 (d, 1H), 7.58-7.64 (m, 2H), 7.87-8.03 (m, 8H), 8.43 (d, 1H), 9.39 (s, 1H).

Example 52(2)

4-(3-carboxypropyl)-8-{(Z)-2-[4-(4-phenylbutoxy)phenyl]vinyl}-3,4-dihydro-2H-1,4-benzoxazine-2-carboxylic acid TLC: Rf 0.45 (methylene chloride:methanol:acetic acid=90:10:1);
NMR(DMSO-$d_6$): δ 1.60-1.81 (m, 6H), 2.26 (t, 2H), 2.60 (t, 2H), 3.22 (t, 2H), 3.83-3.97 (m, 2H), 4.90 (t, 1H), 6.36 (dd, 1H), 6.44-6.47 (m, 2H), 6.51-6.60 (m, 2H), 6.74 (d, 2H), 7.12-7.28 (m, 7H), 12.59 (brs, 1H).

Example 52(3)

4-(3-carboxypropyl)-8-({4-[2-(2,3-dihydro-1H-inden-2-yl)ethoxy]benzoyl}amino)-3,4-dihydro-2H-1,4-benzoxazine-2-carboxylic acid TLC: Rf 0.29 (methylene chloride:methanol:acetic acid=95:5:0.5);
NMR(DMSO-$d_6$): δ 1.67-1.77 (m, 2H), 1.91-1.98 (m, 2H), 2.27 (t, 2H), 2.55-2.67 (m, 3H), 2.98-3.07 (m, 2H), 3.22-3.30 (m, 2H), 3.41-3.52 (m, 2H), 4.14 (t, 2H), 5.00 (t, 1H), 6.60 (dd, 1H), 6.77 (t, 1H), 7.04-7.25 (m, 7H), 7.89 (d, 2H), 9.20 (s, 1H).

Example 52(4)

8-{[4-(benzyloxy)benzoyl]amino}-4-(3-carboxypropyl)-3,4-dihydro-2H-1,4-benzoxazine-2-carboxylic acid TLC: Rf 0.39 (methylene chloride:methanol:acetic acid=90:10:0.5);
NMR(DMSO-$d_6$): δ 1.66-1.76 (m, 2H), 2.26 (t, 2H), 3.20-3.30 (m, 2H), 3.40-3.51 (m, 2H), 4.99 (t, 1H), 5.19 (s, 2H), 6.59 (dd, 1H), 6.76 (t, 1H), 7.11-7.18 (m, 3H), 7.32-7.46 (m, 5H), 7.88 (d, 2H), 9.20 (s, 1H), 12.13 (brs, 1H), 13.00 (brs, 1H).

Example 52(5)

4-(3-carboxypropyl)-8-[(4-hydroxybenzoyl)amino]-3,4-dihydro-2H-1,4-benzoxazine-2-carboxylic acid TLC: Rf 0.32 (methylene chloride:methanol:acetic acid=80:20:1);
NMR(DMSO-$d_6$): δ 1.63-1.78 (m, 2H), 2.26 (t, 2H), 3.20-3.30 (m, 2H), 3.39-3.51 (m, 2H), 5.00 (t, 1H), 6.57 (d, 1H), 6.75 (t, 1H), 6.85 (d, 2H), 7.19 (d, 1H), 7.77 (d, 2H), 9.09 (s, 1H).

Example 52(6)

4-(3-carboxypropyl)-8-{[4-(3-phenylpropoxy)benzoyl]amino}-3,4-dihydro-2H-1,4-benzoxazine-2-carboxylic acid TLC: Rf 0.24 (methylene chloride:methanol:acetic acid=90:10:0.5);
NMR(DMSO-$d_6$): δ 1.65-1.77 (m, 2H), 1.97-2.08 (m, 2H), 2.27 (t, 2H), 2.74 (t, 2H), 3.20-3.30 (m, 2H), 3.40-3.50 (m, 2H), 4.03 (t, 2H), 5.00 (t, 1H), 6.59 (d, 1H), 6.76 (t, 1H), 7.04 (d, 2H), 7.15-7.30 (m, 6H), 7.87 (d, 2H), 9.19 (s, 1H).

Example 52(7)

4-(3-carboxypropyl)-8-({4-[(5-phenylpentyl)oxy]benzoyl}amino)-3,4-dihydro-2H-1,4-benzoxazine-2-carboxylic acid TLC: Rf 0.29 (methylene chloride:methanol:acetic acid=90:10:0.5);
NMR(DMSO-$d_6$): δ 1.38-1.47 (m, 2H), 1.57-1.79 (m, 6H), 2.26 (t, 2H), 2.59 (t, 2H), 3.21-3.30 (m, 2H), 3.39-3.50 (m, 2H), 4.02 (t, 2H), 4.91-4.98 (m, 1H), 6.57 (d, 1H), 6.75 (t, 1H), 7.02 (d, 2H), 7.12-7.28 (m, 6H), 7.86 (d, 2H), 9.16 (s, 1H).

Example 52(8)

4-(3-carboxypropyl)-8-({4-[(6-phenylhexyl)oxy]benzoyl}amino)-3,4-dihydro-2H-1,4-benzoxazine-2-carboxylic acid TLC: Rf 0.33 (methylene chloride:methanol:acetic acid=90:10:0.5);
NMR(DMSO-$d_6$): δ 1.26-1.51 (m, 4H), 1.52-1.65 (m, 2H), 1.65-1.83 (m, 4H), 2.27 (t, 2H), 2.57 (t, 2H), 3.12-3.30 (m, 2H), 3.38-3.56 (m, 2H), 4.02 (t, 2H), 4.90-4.98 (m, 1H), 6.58 (d, 1H), 6.76 (t, 1H), 7.02 (d, 2H), 7.09-7.40 (m, 6H), 7.87 (d, 2H).

Example 52(9)

4-(3-carboxypropyl)-8-[(2,3-dihydro-1H-inden-2-ylacetyl)amino]-3,4-dihydro-2H-1,4-benzoxazine-2-carboxylic acid TLC: Rf 0.29 (methylene chloride:methanol:acetic acid=90:10:0.5);
NMR(DMSO-$d_6$): δ 1.55-1.87 (m, 2H), 2.26 (t, 2H), 2.41-2.90 (m, 5H), 2.94-3.12 (m, 2H), 3.13-3.31 (m, 2H), 3.34-3.60 (m, 2H), 4.94 (t, 1H), 6.52 (d, 1H), 6.70 (t, 1H), 7.04-7.14 (m, 2H), 7.15-7.32 (m, 3H), 8.98 (s, 1H), 12.55 (s, 2H).

Example 52(10)

4-(3-carboxypropyl)-8-({4-[(7-phenylheptyl)oxy]benzoyl}amino)-3,4-dihydro-2H-1,4-benzoxazine-2-carboxylic acid TLC: Rf 0.51 (methylene chloride:methanol:acetic acid=90:10:1);
NMR(DMSO-$d_6$): δ 1.20-1.48 (m, 6H), 1.50-1.64 (m, 2H), 1.64-1.84 (m, 4H), 2.27 (t, 2H), 2.56 (t, 2H), 3.14-3.59 (m, 4H), 4.03 (t, 2H), 4.98 (t, 1H), 6.59 (d, 1H), 6.77 (t, 1H), 7.03 (d, 2H), 7.09-7.34 (m, 6H), 7.87 (d, 2H), 9.18 (s, 1H), 12.61 (s, 2H).

Example 52(11)

4-(3-carboxypropyl)-8-{[4-(cycloheptyloxy)benzoyl]amino}-3,4-dihydro-2H-1,4-benzoxazine-2-carboxylic acid TLC: Rf 0.56 (methylene chloride:methanol:acetic acid=90:10:1);
NMR(DMSO-$d_6$): δ 1.34-1.83 (m, 12H), 1.84-2.08 (m, 2H), 2.26 (t, 2H), 2.94-3.73 (m, 4H), 4.46-4.73 (m, 1H), 4.77-5.04 (m, 1H), 6.56 (d, 1H), 6.74 (t, 1H), 6.99 (d, 2H), 7.23 (d, 1H), 7.85 (d, 2H), 9.14 (s, 1H).

Example 52(12)

8-{[2-(benzylbenzyloxy)benzoyl]amino}-4-(3-carboxypropyl)-3,4-dihydro-2H-1,4-benzoxazine-2-carboxylic acid TLC: Rf 0.33 (methylene chloride:methanol:acetic acid=90:10:1);
NMR(DMSO-$d_6$): δ 1.54-1.84 (m, 2H), 2.26 (t, 2H), 3.00-3.60 (m, 4H), 4.50-4.81 (m, 1H), 5.48 (s, 2H), 6.53 (d, 1H), 6.76 (t, 1H), 7.09 (t, 1H), 7.22-7.41 (m, 4H), 7.42-7.60 (m, 3H), 7.80 (d, 1H), 8.06 (dd, 1H), 10.53 (s, 1H).

Example 52(13)

8-{[3-(benzyloxy)benzoyl]amino}-4-(3-carboxypropyl)-3,4-dihydro-2H-1,4-benzoxazine-2-carboxylic acid TLC: Rf 0.33 (methylene chloride:methanol:acetic acid=90:10:1);
NMR(DMSO-$d_6$): δ 1.53-1.88 (m, 2H), 2.27 (t, 2H), 3.08-3.59 (m, 4H), 4.97 (t, 1H), 5.17 (s, 2H), 6.60 (d, 1H), 6.78 (t, 1H), 7.09-7.28 (m, 2H), 7.27-7.66 (m, 8H), 9.29 (s, 1H), 11.85-13.34 (m, 2H).

Example 52(14)

4-(3-carboxypropyl)-8-{[4-(2-phenylethoxy)benzoyl]amino}-3,4-dihydro-2H-1,4-benzoxazine-2-carboxylic acid TLC: Rf 0.49 (methylene chloride:methanol:acetic acid=90:10:1);
NMR(DMSO-$d_6$): δ 1.57-1.83 (m, 2H), 2.27 (t, 2H), 2.93-3.14 (m, 2H), 3.15-3.63 (m, 4H), 4.27 (t, 2H), 4.98 (t, 1H), 6.58 (d, 1H), 6.76 (t, 1H), 7.05 (d, 2H), 7.12-7.62 (m, 6H), 7.87 (d, 2H), 9.19 (s, 1H).

Example 52(15)

4-(3-carboxypropyl)-8-{[2-(3-phenylpropoxy)benzoyl]amino}-3,4-dihydro-2H-1,4-benzoxazine-2-carboxylic acid TLC: Rf 0.26 (methylene chloride:methanol:acetic acid=90:10:1);
NMR(DMSO-$d_6$): δ 1.59-1.79 (m, 2H), 2.05-2.21 (m, 2H), 2.26 (t, 2H), 2.59-2.85 (m, 2H), 3.04-3.58 (m, 4H), 4.03-4.46 (m, 2H), 4.86 (t, 1H), 6.39-6.63 (m, 1H), 6.76 (t, 1H), 7.02-7.37 (m, 7H), 7.42-7.66 (m, 1H), 7.82 (d, 1H), 8.07 (dd, 1H), 10.28 (s, 1H).

Example 52(16)

4-(3-carboxypropyl)-8-{[3-(3-phenylpropoxy)benzoyl]amino}-3,4-dihydro-2H-1,4-benzoxazine-2-carboxylic acid TLC: Rf 0.27 (methylene chloride:methanol:acetic acid=90:10:1);
NMR(DMSO-$d_6$): δ 1.59-1.83 (m, 2H), 1.92-2.13 (m, 2H), 2.27 (t, 2H), 2.64-2.87 (m, 2H), 3.06-3.60 (m, 4H), 4.04 (t, 2H), 4.96 (t, 1H), 6.51-6.68 (m, 1H), 6.78 (t, 1H), 7.07-7.56 (m, 10H), 9.30 (s, 1H).

Example 52(17)

4-(3-carboxypropyl)-8-({2-[(5-phenylpentyl)oxy]benzoyl}amino)-3,4-dihydro-2H-1,4-benzoxamine-2-carboxylic acid TLC: Rf 0.38 (methylene chloride:methanol:acetic acid=90:10:1);
NMR(DMSO-$d_6$): δ 1.28-1.49 (m, 2H), 1.50-1.92 (m, 6H), 2.26 (t, 2H), 2.47-2.59 (m, 2H), 3.08-3.63 (m, 4H), 4.24 (t, 2H), 5.00 (t, 1H), 6.53 (dd, 1H), 6.75 (t, 1H), 7.03-7.29 (m, 7H), 7.47-7.58 (m, 1H), 7.81 (dd, 1H), 8.08 (dd, 1H), 10.32 (s, 1H).

Example 52(18)

4-(3-carboxypropyl)-8-({2-[(6-phenylhexyl)oxy]benzoyl}amino)-3,4-dihydro-2H-1,4-benzoxazine-2-carboxylic acid TLC: Rf 0.34 (methylene chloride:methanol:acetic acid=90:10:1);
NMR(DMSO-$d_6$): δ 1.12-1.63 (m, 6H), 1.60-1.99 (m, 4H), 2.27 (t, 2H), 2.38-2.63 (m, 2H), 2.95-3.66 (m, 4H), 4.01-4.44 (m, 2H), 4.83-5.11 (m, 1H), 6.53 (d, 1H), 6.75 (t, 1H), 7.01-7.32 (m, 7H), 7.41-7.63 (m, 1H), 7.81 (d, 1H), 8.08 (d, 1H), 10.31 (s, 1H).

Example 52(19)

4-(3-carboxypropyl)-8-[(2-hydroxybenzoyl)amino]-3,4-dihydro-2H-1,4-benzoxazine-2-carboxylic acid TLC: Rf 0.40 (methylene chloride:methanol:acetic acid=9:1:0.05);
NMR(DMSO-$d_6$): δ 1.72 (t, 2H), 2.27 (t, 2H), 3.23-3.25 (m, 2H), 3.47-3.49 (m, 2H), 5.03 (dd, 1H), 6.53 (d, 1H), 6.74 (dd, 1H), 6.92-7.01 (m, 2H), 7.38 (ddd, 1H), 7.72 (d, 1H), 7.99 (dd, 1H), 10.65 (s, 1H), 11.71 (s, 1H), 12.15 (s, 1H), 13.28 (s, 1H).

Example 52(20)

4-(3-carboxypropyl)-8-[(3-hydroxybenzoyl)amino]-3,4-dihydro-2H-1,4-benzoxazine-2-carboxylic acid TLC: Rf 0.20 (methylene chloride:methanol:acetic acid=9:1:0.05);
NMR(DMSO-$d_6$): δ 1.69-1.76 (m, 2H), 2.27 (t, 2H), 3.22-3.25 (m, 2H), 3.41-3.52 (m, 2H), 5.01 (dd, 1H), 6.59 (dd, 1H), 6.77 (dd, 1H), 6.94-6.98 (m, 1H), 7.22-7.31 (m, 4H), 9.13 (s, 1H), 9.76 (s, 1H), 12.22 (s, 1H), 12.91 (s, 1H).

Example 52(21)

4-(3-carboxypropyl)-8-{[2-(2-phenylethoxy)benzoyl]amino}-3,4-dihydro-2H-1,4-benzoxazine-2-carboxylic acid TLC: Rf 0.72 (methylene chloride:methanol:acetic acid=9:1:0.05);
NMR(DMSO-$d_6$): δ 1.61-1.80 (m, 2H), 2.27 (t, 2H), 3.16 (t, 2H), 3.23-3.32 (m, 2H), 3.39-3.60 (m, 2H), 4.30-4.54 (m, 2H), 5.05 (t, 1H), 6.55 (dd, 1H), 6.77 (dd, 1H), 7.12 (dd, 1H), 7.16-7.35 (m, 6H), 7.53 (ddd, 1H), 7.79 (dd, 1H), 8.08 (dd, 1H), 10.29 (s, 1H), 12.19 (s, 2H).

Example 52(22)

4-(3-carboxypropyl)-8-{[2-(4-phenylbutoxy)benzoyl]amino}-3,4-dihydro-2H-1,4-benzoxazine-2-carboxylic acid TLC: Rf 0.72 (methylene chloride:methanol:acetic acid=9:1:0.05);
NMR(DMSO-$d_6$): δ 1.63-1.78 (m, 4H), 1.79-1.93 (m, 2H), 2.27 (t, 2H), 2.61 (t, 2H), 3.19-3.26 (m, 2H), 3.35-3.55 (m, 2H), 4.28 (t, 2H), 4.93 (t, 1H), 6.53 (dd, 1H), 6.76 (dd, 1H), 7.05-7.27 (m, 7H), 7.53 (ddd, 1H), 7.80 (dd, 1H), 8.07 (dd, 1H), 10.29 (s, 1H), 12.31 (s, 2H).

Example 52(23)

4-(3-carboxypropyl)-8-{[3-(4-phenylbutoxy)benzoyl]amino}-3,4-dihydro-2H-1,4-benzoxazine-2-carboxylic acid TLC: Rf 0.61 (methylene chloride:methanol:acetic acid=9:1:0.05);
NMR(DMSO-$d_6$): δ 1.69-1.79 (m, 6H), 2.27 (t, 2H), 2.58-2.70 (m, 2H), 3.20-3.28 (m, 2H), 3.42-3.49 (m, 2H), 4.01-4.10 (m, 2H), 4.97 (t, 1H), 6.61 (d, 1H), 6.78 (dd, 1H), 7.05-7.32 (m, 7H), 7.36-7.50 (m, 3H), 9.29 (s, 1H), 12.47 (s, 2H).

Example 52(24)

4-(3-carboxypropyl)-8-{[3-(2-phenylethoxy)benzoyl]amino}-3,4-dihydro-2H-1,4-benzoxazine-2-carboxylic acid TLC: Rf 0.59 (methylene chloride:methanol:acetic acid=9:1:0.05);
NMR(DMSO-$d_6$): δ 1.72 (qd, 2H), 2.27 (t, 2H), 3.06 (t, 2H), 3.15-3.29 (m, 2H), 3.39-3.51 (m, 2H), 4.27 (t, 2H), 4.98 (t, 1H), 6.57-6.65 (m, 1H), 6.78 (dd, 1H), 7.11-7.25 (m, 3H), 7.28-7.36 (m, 4H), 7.38-7.49 (m, 3H), 9.32 (s, 1H), 12.30 (s, 2H).

Example 52(25)

4-(3-carboxypropyl)-8-({3-[(6-phenylhexyl)oxy]benzoyl}amino)-3,4-dihydro-2H-1,4-benzoxazine-2-carboxylic acid TLC: Rf 0.53 (methylene chloride:methanol:acetic acid=9:1:0.05);
NMR(DMSO-$d_6$): δ 1.29-1.51 (m, 4H), 1.59 (dt, 2H), 1.67-1.78 (m, 4H), 2.27 (t, 2H), 2.52-2.60 (m, 2H), 3.22-3.35 (m, 2H), 3.41-3.51 (m, 2H), 4.02 (t, 2H), 4.96 (t, 1H), 6.61 (dd, 1H), 6.78 (dd, 1H), 7.11-7.20 (m, 5H), 7.21-7.29 (m, 2H), 7.38-7.48 (m, 3H), 9.29 (s, 1H), 12.37 (s, 2H).

Example 52(26)

4-(3-carboxypropyl)-8-({3-[(5-phenylpentyl)oxy]benzoyl}amino)-3,4-dihydro-2H-1,4-benzoxazine-2-carboxylic acid TLC: Rf 0.53 (methylene chloride:methanol:acetic acid=9:1:0.05);
NMR(DMSO-$d_6$): δ 1.39-1.52 (m, 2H), 1.56-1.83 (m, 6H), 2.27 (t, 2H), 2.54-2.64 (m, 2H), 3.16-3.27 (m, 2H), 3.40-3.50 (m, 2H), 4.03 (t, 2H), 4.95 (d, 1H), 6.60 (d, 1H), 6.78 (dd, 1H), 7.10-7.30 (m, 7H), 7.36-7.50 (m, 3H), 9.29 (s, 1H).

Example 52(27)

4-(3-carboxypropyl)-8-{[4-(4-pentenyloxy)benzoyl]amino}-3,4-dihydro-2H-1,4-benzoxazine-2-carboxylic acid TLC: Rf 0.51 (methylene chloride:methanol:acetic acid=9:1:0.05);
NMR(DMSO-$d_6$): δ 1.61-1.94 (m, 4H), 2.10-2.34 (m, 4H), 3.13-3.27 (m, 2H), 3.38-3.57 (m, 2H), 4.05 (t, 2H), 4.92-5.10 (m, 3H), 5.73-5.98 (m, 1H), 6.59 (dd, 1H), 6.77 (dd, 1H), 6.99-7.09 (m, 2H), 7.19 (d, 1H), 7.88 (d, 2H), 9.19 (s, 1H), 12.17 (s, 2H).

Example 52(28)

4-(3-carboxypropyl)-8-({4-[(4-methyl-3-pentenyl)oxy]benzoyl}amino)-3,4-dihydro-2H-1,4-benzoxazine-2-carboxylic acid TLC: Rf 0.47 (methylene chloride:methanol:acetic acid=9:1:0.05);
NMR(DMSO-$d_6$): δ 1.53-1.81 (m, 8H), 2.16-2.32 (m, 2H), 2.35-2.47 (m, 2H), 3.18-3.28 (m, 2H), 3.39-3.56 (m, 2H), 4.02 (t, 2H), 4.99 (s, 1H), 5.12-5.26 (m, 1H), 6.59 (d, 1H), 6.77 (dd, 1H), 7.03 (d, 2H), 7.12-7.26 (m, 1H), 7.88 (d, 2H), 9.19 (s, 1H), 12.09 (s, 2H).

Example 52(29)

4-(3-carboxypropyl)-8-{[4-(5-hexenyloxy)benzoyl]amino}-3,4-dihydro-2H-1,4-benzoxazine-2-carboxylic acid TLC: Rf 0.64 (methylene chloride:methanol:acetic acid=9:1:0.05);
NMR(DMSO-$d_6$): δ 1.43-1.58 (m, 2H), 1.66-1.80 (m, 4H), 2.03-2.14 (m, 2H), 2.27 (t, 2H), 3.20-3.27 (m, 2H), 3.39-3.54 (m, 2H), 4.05 (t, 2H), 4.92-5.08 (m, 3H), 5.74-5.91 (m, 1H), 6.59 (d, 1H), 6.77 (dd, 1H), 6.99-7.07 (m, 2H), 7.18 (dd, 1H), 7.83-7.91 (m, 2H), 9.19 (s, 1H), 12.13 (s, 1H), 12.91 (s, 1H).

Example 52(30)

4-(3-carboxypropyl)-8-({4-[(4-methylpentyl)oxy]benzoyl}amino)-3,4-dihydro-2H-1,4-benzoxazine-2-carboxylic acid TLC:Rf 0.66 (methylene chloride:methanol:acetic acid=9:1:0.05);
NMR(DMSO-$d_6$): δ 0.88 (s, 3H), 0.90 (s, 3H), 1.22-1.36 (m, 2H), 1.57 (td, 1H), 1.67-1.80 (m, 4H), 2.27 (t, 2H), 3.19-3.26 (m, 2H), 3.38-3.54 (m, 2H), 4.03 (t, 2H), 5.00 (t, 1H), 6.59 (d, 1H), 6.77 (dd, 1H), 7.03 (d, 2H), 7.18 (d, 1H), 7.87 (d, 2H), 9.19 (s, 1H), 12.12 (s, 1H), 13.00 (s, 1H).

Example 52(31)

4-(3-carboxypropyl)-8-{[4-(4-fluorobutoxy)benzoyl]amino}-3,4-dihydro-2H-1,4-benzoxazine-2-carboxylic acid TLC: Rf 0.52 (methylene chloride:methanol:acetic acid=9:1:0.05);
NMR(DMSO-$d_6$): δ 1.63-1.92 (m, 6H), 2.19-2.34 (m, 2H), 3.16-3.28 (m, 2H), 3.39-3.57 (m, 2H), 4.09 (t, 2H), 4.43 (t, 1H), 4.59 (t, 1H), 5.01 (t, 1H), 6.59 (dd, 1H), 6.77 (dd, 1H), 7.05 (d, 2H), 7.18 (d, 1H), 7.78-7.97 (m, 2H), 9.19 (s, 1H), 12.07 (s, 1H), 13.02 (s, 1H).

Example 52(32)

4-(3-carboxypropyl)-8-{[4-(4,4,4-trifluorobutoxy)benzoyl]amino}-3,4-dihydro-2H-1,4-benzoxazine-2-carboxylic acid TLC: Rf 0.55 (methylene chloride:methanol:acetic acid=9:1:0.05);
NMR(DMSO-$d_6$): δ 1.64-1.79 (m, 2H), 1.88-2.03 (m, 2H), 2.23-2.32 (m, 2H), 2.34-2.46 (m, 2H), 3.17-3.27 (m, 2H), 3.39-3.54 (m, 2H), 4.12 (t, 2H), 5.00 (t, 1H), 6.60 (dd, 1H), 6.77 (dd, 1H), 7.03-7.11 (m, 2H), 7.18 (d, 1H), 7.82-7.97 (m, 2H), 9.20 (s, 1H), 12.09 (s, 1H), 13.02 (s, 1H).

Example 52(33)

4-(3-carboxypropyl)-8-{[4-(2-phenoxyethoxy)benzoyl]amino}-3,4-dihydro-2H-1,4-benzoxazine-2-carboxylic acid TLC: Rf 0.64 (methylene chloride:methanol:acetic acid=9:1:0.05);
NMR(DMSO-$d_6$): δ 1.63-1.81 (m, 2H), 2.28 (t, 2H), 3.16-3.27 (m, 2H), 3.38-3.55 (m, 2H), 4.30-4.36 (m, 2H), 4.38-4.43 (m, 2H), 4.98-5.05 (m, 1H), 6.60 (d, 1H), 6.77 (dd, 1H), 6.91-7.02 (m, 3H), 7.07-7.14 (m, 2H), 7.18 (dd, 1H), 7.25-7.34 (m, 2H), 7.90 (d, 2H), 9.22 (s, 1H), 12.16 (s, 1H), 12.95 (s, 1H).

Example 52(34)

4-(3-carboxypropyl)-8-({4-[(5-methyl-3-isoxazolyl)methoxy]benzoyl}amino)-3,4-dihydro-2H-1,4-benzoxazine-2-carboxylic acid TLC: Rf 0.50 (methylene chloride:methanol:acetic acid=9:1:0.05);
NMR(DMSO-$d_6$): δ 1.64-1.80 (m, 2H), 2.27 (t, 2H), 2.40 (s, 3H), 3.19-3.27 (m, 2H), 3.37-3.55 (m, 2H), 5.00 (t, 1H), 5.24 (s, 2H), 6.34 (s, 1H), 6.60 (dd, 1H), 6.77 (dd, 1H), 7.06-7.21 (m, 3H), 7.84-7.93 (m, 2H), 9.22 (s, 1H), 12.07 (s, 1H), 12.90 (s, 1H).

Example 52(35)

8-({4-[3-(benzyloxy)propoxy]benzoyl}amino)-4-(3-carboxypropyl)-3,4-dihydro-2H-1,4-benzoxazine-2-carboxylic acid TLC: Rf 0.70 (methylene chloride:methanol:acetic acid=9:1:0.05);
NMR(DMSO-$d_6$): δ 1.64-1.80 (m, 2H), 1.94-2.09 (m, 2H), 2.22-2.32 (m, 2H), 3.18-3.27 (m, 2H), 3.38-3.53 (m, 2H), 3.60 (t, 2H), 4.14 (t, 2H), 4.48 (s, 2H), 5.00 (dd, 1H), 6.59 (d, 1H), 6.77 (dd, 1H), 6.97-7.08 (m, 2H), 7.19 (dd, 1H), 7.22-7.37 (m, 4H), 7.81-7.91 (m, 2H), 9.18 (s, 1H), 12.09 (s, 1H), 13.03 (s, 1H).

Example 52(36)

8-{[4-(1,3-benzothiazol-2-ylmethoxy)benzoyl]amino}-4-(3-carboxypropyl)-3,4-dihydro-2H-1,4-benzoxazine-2-carboxylic acid TLC: Rf 0.58 (methylene chloride:methanol:acetic acid=9:1:0.05);
NMR(DMSO-$d_6$): δ 1.65-1.80 (m, 2H), 2.20-2.34 (m, 2H), 3.19-3.27 (m, 2H), 3.39-3.53 (m, 2H), 4.99 (t, 1H), 5.71 (s, 2H), 6.55-6.63 (m, 1H), 6.77 (dd, 1H), 7.16 (d, 1H), 7.19-7.28 (m, 2H), 7.41-7.50 (m, 1H), 7.51-7.59 (m, 1H), 7.87-7.95 (m, 2H), 7.99-8.06 (m, 1H), 8.09-8.16 (m, 1H), 9.24 (s, 1H), 12.13 (s, 1H), 12.93 (s, 1H).

Example 52(37)

4-(3-carboxypropyl)-8-[(4-{4-[(4'-methoxy-1,1'-biphenyl-4-yl)oxy]butoxy}benzoyl)amino]-3,4-dihydro-2H-1,4-benzoxazine-2-carboxylic acid TLC: Rf 0.76 (methylene chloride:methanol:acetic acid=9:1:0.05);
NMR(DMSO-$d_6$): δ 1.73 (t, 2H), 1.85-1.94 (m, 4H), 2.21-2.36 (m, 2H), 3.19-3.26 (m, 2H), 3.40-3.51 (m, 2H), 3.77 (s, 3H), 3.99-4.19 (m, 4H), 4.88-5.04 (m, 1H), 6.59 (dd, 1H), 6.77 (dd, 1H), 6.92-7.02 (m, 4H), 7.03-7.12 (m, 2H), 7.20 (d, 1H), 7.44-7.58 (m, 4H), 7.83-7.98 (m, 2H), 9.18 (s, 1H), 12.01 (s, 1H), 12.94 (s, 1H).

Example 52(38)

4-(3-carboxypropyl)-8-{[4-(3-phenoxypropoxy)benzoyl]amino}-3,4-dihydro-2H-1,4-benzoxazine-2-carboxylic acid TLC: Rf 0.41 (methylene chloride:methanol:acetic acid=9:1:0.05);
NMR(DMSO-$d_6$): δ 1.62-1.82 (m, 2H), 2.08-2.37 (m, 4H), 3.15-3.27 (m, 2H), 3.36-3.52 (m, 2H), 4.13 (t, 2H), 4.22 (t, 2H), 5.00 (t, 1H), 6.59 (d, 1H), 6.77 (dd, 1H), 6.85-6.98 (m, 3H), 7.07 (d, 2H), 7.18 (d, 1H), 7.24-7.38 (m, 2H), 7.89 (d, 2H), 9.19 (s, 1H), 12.16 (s, 1H), 12.92 (s, 1H).

Example 52(39)

4-(3-carboxypropyl)-8-{[4-(4-phenoxybutoxy)benzoyl]amino}-3,4-dihydro-2H-1,4-benzoxazine-2-carboxylic acid TLC: Rf 0.43 (methylene chloride:methanol:acetic acid=9:1:0.05);
NMR(DMSO-$d_6$): δ 1.63-1.79 (m, 2H), 1.83-1.95 (m, 4H), 2.23-2.33 (m, 2H), 3.18-3.28 (m, 2H), 3.38-3.53 (m, 2H), 3.97-4.07 (m, 2H), 4.08-4.17 (m, 2H), 4.99 (t, 1H), 6.59 (dd, 1H), 6.77 (dd, 1H), 6.86-6.98 (m, 3H), 7.05 (d, 2H), 7.16-7.21 (m, 1H), 7.23-7.33 (m, 2H), 7.88 (d, 2H), 9.19 (s, 1H), 12.19 (s, 1H), 13.02 (s, 1H).

Example 52(40)

8-({4-[2-(benzyloxy)ethoxy]benzoyl}amino)-4-(3-carboxypropyl)-3,4-dihydro-2H-1,4-benzoxazine-2-carboxylic acid TLC: Rf 0.40 (methylene chloride:methanol:acetic acid=9:1:0.05);
NMR(DMSO-$d_6$): δ 1.65-1.81 (m, 2H), 2.27 (t, 2H), 3.19-3.27 (m, 2H), 3.39-3.55 (m, 2H), 3.73-3.83 (m, 2H), 4.19-4.27 (m, 2H), 4.56 (s, 2H), 5.01 (t, 1H), 6.59 (dd, 1H), 6.77 (dd, 1H), 7.07 (d, 2H), 7.18 (d, 1H), 7.24-7.39 (m, 5H), 7.88 (d, 2H), 9.20 (s, 1H), 12.09 (s, 1H), 12.81 (s, 1H).

Example 52(41)

4-(3-carboxypropyl)-8-({4-[2-(2-naphthyl)ethoxy]benzoyl}amino)-3,4-dihydro-2H-1,4-benzoxazine-2-carboxylic acid TLC: Rf 0.38 (methylene chloride:methanol:acetic acid 9:1:0.05);
NMR(DMSO-$d_6$): δ 1.59-1.81 (m, 2H), 2.27 (t, 2H), 3.17-3.27 (m, 2H), 3.37-3.55 (m, 2H), 4.38 (t, 2H), 4.92-5.03 (m, 2H), 5.37 (s, 1H), 6.59 (dd, 1H), 6.77 (dd, 1H), 7.01-7.23 (m, 3H), 7.38-7.63 (m, 3H), 7.81-8.03 (m, 6H), 9.14-9.25 (m, 1H), 12.14 (s, 1H), 12.90 (s, 1H).

Example 52(42)

4-(3-carboxypropyl)-8-({4-[2-(1-naphthyl)ethoxy]benzoyl}amino)-3,4-dihydro-2H-1,4-benzoxazine-2-carboxylic acid TLC: Rf 0.38 (methylene chloride:methanol:acetic acid=9:1:0.05);
NMR(DMSO-$d_6$): δ 1.63-1.80 (m, 2H), 2.27 (t, 2H), 3.14-3.30 (m, 2H), 3.38-3.52 (m, 2H), 3.56 (t, 2H), 4.39 (t, 2H), 4.84-5.02 (m, 1H), 6.58 (d, 1H), 6.76 (dd, 1H), 7.05 (d, 2H), 7.18 (d, 1H), 7.42-7.62 (m, 4H), 7.79-7.99 (m, 4H), 8.17 (d, 1H), 9.18 (s, 1H), 12.51 (s, 2H).

Example 52(43)

4-(3-carboxypropyl)-8-{[4-(2,3-dihydro-1H-inden-2-ylmethoxy)benzoyl]amino}-3,4-dihydro-2H-1,4-benzoxazine-2-carboxylic acid TLC: Rf 0.56 (methylene chloride:methanol:acetic acid=9:1:0.05);
NMR(DMSO-$d_6$): δ 1.61-1.80 (m, 2H), 2.27 (t, 2H), 2.74-2.84 (m, 2H), 2.86-2.99 (m, 1H), 3.02-3.17 (m, 2H), 3.17-3.28 (m, 2H), 3.38-3.55 (m, 2H), 4.06 (d, 2H), 4.93-5.03 (m, 1H), 6.59 (dd, 1H), 6.77 (dd, 1H), 6.96-7.30 (m, 7H), 7.82-7.95 (m, 2H), 9.19 (s, 1H), 12.10 (s, 2H).

Example 52(44)

4-(3-carboxypropyl)-8-{[4-(2-naphthylmethoxy)benzoyl]amino}-3,4-dihydro-2H-1,4-benzoxazine-2-carboxylic acid TLC:Rf 0.32 (methylene chloride:methanol:acetic acid=9:1:0.05);
NMR(DMSO-$d_6$): δ 1.54-1.79 (m, 2H), 2.27 (t, 2H), 3.12-3.27 (m, 2H), 3.38-3.58 (m, 2H), 4.93-5.03 (m, 1H), 5.37 (s, 2H), 6.52-6.63 (m, 1H), 6.77 (dd, 1H), 7.13-7.25 (m, 3H), 7.46-7.65 (m, 3H), 7.84-8.05 (m, 6H), 9.20 (s, 1H), 12.23 (s, 2H).

Example 52(45)

4-(3-carboxypropyl)-8-{[4-(1-naphthylmethoxy)benzoyl]amino}-3,4-dihydro-2H-1,4-benzoxazine-2-carboxylic acid TLC: Rf 0.28 (methylene chloride:methanol:acetic acid=9:1:0.05);
NMR(DMSO-$d_6$): δ 1.64-1.80 (m, 2H), 2.17-2.33 (m, 2H), 3.17-3.27 (m, 2H), 3.39-3.53 (m, 2H), 4.90-5.05 (m, 1H), 5.65 (s, 2H), 6.52-6.63 (m, 1H), 6.77 (dd, 1H), 7.12-7.28 (m, 3H), 7.44-7.63 (m, 3H), 7.70 (d, 1H), 7.83-8.02 (m, 4H), 8.06-8.20 (m, 1H), 9.21 (s, 1H), 12.44 (s, 1H), 12.98 (s, 1H).

Example 52(46)

4-(3-carboxypropyl)-8-{[4-(2,3-dihydro-1H-inden-2-yloxy)benzoyl]amino}-3,4-dihydro-2H-1,4-benzoxazine-2-carboxylic acid TLC: Rf 0.39 (methylene chloride:methanol:acetic acid=9:1:0.05);
NMR(DMSO-$d_6$): δ 1.59-1.87 (m, 2H), 2.27 (t, 2H), 3.04 (dd, 2H), 3.18-3.27 (m, 2H), 3.32-3.56 (m, 4H), 5.00 (t, 1H), 5.24-5.44 (m, 1H), 6.54-6.64 (m, 1H), 6.77 (d, 1H), 7.00-7.10 (m, 2H), 7.11-7.31 (m, 5H), 7.79-7.95 (m, 2H), 9.19 (s, 1H), 12.18 (s, 1H), 12.93 (s, 1H).

Example 52(47)

4-(3-carboxypropyl)-8-({4-[3-(2,3-dihydro-1H-inden-2-yl)propoxy]benzoyl}amino)-3,4-dihydro-2H-1,4-benzoxazine-2-carboxylic acid TLC: Rf 0.40 (methylene chloride:methanol:acetic acid=9:1:0.05);
NMR(DMSO-$d_6$): δ 1.53-1.93 (m, 7H), 2.13-2.33 (m, 2H), 2.57 (t, 2H), 3.00 (d, 1H), 3.05 (d, 1H), 3.17-3.27 (m, 2H), 3.38-3.54 (m, 2H), 4.08 (t, 2H), 4.99 (t, 1H), 6.59 (dd, 1H), 6.77 (dd, 1H), 6.96-7.12 (m, 4H), 7.14-7.23 (m, 3H), 7.88 (d, 2H), 9.18 (s, 1H), 12.19 (s, 1H), 12.99 (s, 1H).

Example 52(48)

4-(3-carboxypropyl)-8-{[(1-phenyl-5-propyl-1H-pyrazol-4-yl)carbonyl]amino}-3,4-dihydro-2H-1,4-benzoxazine-2-carboxylic acid TLC: Rf 0.26 (chloroform:methanol:acetic acid=90:10:1);
NMR(DMSO-$d_6$): δ 0.72 (t, 3H), 1.43 (sixtet, 2H), 1.73 (quintet, 2H), 2.27 (t, 2H), 2.92 (t, 2H), 3.23-3.30 (m, 2H), 3.44-3.46 (m, 2H), 4.94 (t, 1H), 6.58 (d, 1H), 6.76 (t, 1H), 7.16 (d, 1H), 7.47-7.60 (m, 5H), 8.19 (s, 1H), 9.01 (s, 1H), 12.48 (bs, 2H).

Example 52(49)

4-(3-carboxypropyl)-8-[(2-quinoxalinylcarbonyl)amino]-3,4-dihydro-2H-1,4-benzoxazine-2-carboxylic acid TLC: Rf 0.24 (chloroform:methanol:acetic acid=90:10:1);
NMR(DMSO-$d_6$): δ 1.75 (quintet, 2H), 2.29 (t, 2H), 3.28-3.31 (m, 2H), 3.54 (d, 2H), 5.16 (t, 1H), 6.62 (d, 1H), 6.85 (t, 1H), 7.79 (d, 1H), 8.01-8.06 (m, 2H), 8.20-8.26 (m, 2H), 9.61 (s, 1H), 10.44 (s, 1H), 12.09 (bs, 1H), 13.26 (bs, 1H).

Example 52(50)

8-[(1-benzothien-2-ylcarbonyl)amino]-4-(3-carboxypropyl)-3,4-dihydro-2H-1,4-benzoxazine-2-carboxylic acid TLC: Rf 0.21 (chloroform:methanol:acetic acid=90:10:1);
NMR(DMSO-$d_6$): δ 1.74 (quintet, 2H), 2.27 (t, 2H), 3.24-3.30 (m, 2H), 3.47-3.50 (m, 2H), 5.02 (t, 1H), 6.64 (d, 1H), 6.79 (t, 1H), 7.09 (d, 1H), 7.43-7.51 (m, 2H), 7.96-8.06 (m, 2H), 9.61 (s, 1H), 12.09 (bs, 1H), 13.03 (bs, 1H).

Example 52(51)

4-(3-carboxypropyl)-8-[(4-pentylbenzoyl)amino]-3,4-dihydro-2H-1,4-benzoxazine-2-carboxylic acid TLC: Rf 0.32 (chloroform:methanol:acetic acid=90:10:1);
NMR(DMSO-$d_6$): δ 0.86 (t, 3H), 1.22-1.34 (m, 4H), 1.60 (quintet, 2H), 1.73 (quintet, 2H), 2.26-2.30 (m, 2H), 2.62 (t, 2H), 3.25-3.30 (m, 2H), 3.46-3.48 (m, 2H), 4.99-5.01 (m, 1H), 6.60 (d, 1H), 6.78 (t, 1H), 7.21 (d, 1H), 7.34 (d, 2H), 7.83 (d, 2H), 9.23 (bs, 1H), 12.05 (bs, 1H), 13.02 (bs, 1H).

Example 52(52)

8-[(1,1'-biphenyl-4-ylcarbonyl)amino]-4-(3-carboxypropyl)-3,4-dihydro-2H-1,4-benzoxazine-2-carboxylic acid TLC: Rf 0.27 (chloroform:methanol:acetic acid=90:10:1);
NMR(DMSO-$d_6$): δ 1.74 (quintet, 2H), 2.28 (t, 2H), 3.23-3.30 (m, 2H), 3.47-3.48 (m, 2H), 4.96-4.98 (m, 1H), 6.61 (d, 1H), 6.79 (t, 1H), 7.23 (d, 1H), 7.39-7.44 (m, 1H), 7.49 (d, 1H), 7.51 (d, 1H), 7.75 (d, 2H), 7.83 (d, 2H), 8.01 (d, 2H), 9.36 (s, 1H), 12.43 (bs, 2H).

Example 52(53)

4-(3-carboxypropyl)-8-({[3-(2-chlorophenyl)-5-methyl-4-isoxazolyl]carbonyl}amino)-3,4-dihydro-2H-1,4-benzoxazine-2-carboxylic acid TLC: Rf 0.29 (chloroform:methanol:acetic acid=90:10:1);
NMR(DMSO-$d_6$): δ 1.66 (quintet, 2H), 2.23 (t, 2H), 2.76 (s, 3H), 3.16-3.21 (m, 2H), 3.28-3.42 (m, 2H), 4.62 (t, 1H), 6.49 (t, 1H), 6.69 (t, 1H), 7.37-7.40 (m, 1H), 7.48-7.62 (m, 4H), 8.25 (s, 1H), 12.28 (bs, 2H).

Example 52(54)

4-(3-carboxypropyl)-8-(heptanoylamino)-3,4-dihydro-2H-1,4-benzoxazine-2-carboxylic acid TLC: Rf 0.17 (chloroform:methanol:acetic acid=90:10:1);
NMR(DMSO-$d_6$): δ 0.85 (t, 3H), 1.23-1.39 (m, 6H), 1.55 (quintet, 2H), 1.70 (quintet, 2H), 2.26 (t, 2H), 2.34 (t, 2H), 3.19-3.40 (m, 2H), 3.43 (dd, 2H), 4.95 (t, 1H), 6.52 (d, 1H), 6.68 (t, 1H), 7.22 (d, 1H), 8.86 (s, 1H), 12.45 (bs, 2H).

Example 52(55)

4-(3-carboxypropyl)-7-{[4-(4-phenylbutoxy)benzoyl]amino}-3,4-dihydro-2H-1,4-benzoxazine-2-carboxylic acid TLC: Rf 0.23 (methylene chloride:methanol:acetic acid=90:10:0.5);
NMR(DMSO-$d_6$): δ 1.49-1.93 (m, 6H), 2.26 (t, 2H), 2.63 (t, 2H), 3.11-3.56 (m, 4H), 4.05 (t, 2H), 4.85 (t, 1H), 6.67 (d, 1H), 6.99 (d, 2H), 7.06-7.42 (m, 7H), 7.87 (d, 2H), 9.75 (s, 1H).

Example 52(56)

4-(3-carboxypropyl)-7-{[3-(4-phenylbutoxy)benzoyl]amino}-3,4-dihydro-2H-1,4-benzoxazine-2-carboxylic acid TLC: Rf 0.33 (methylene chloride:methanol:acetic acid=90:10:0.5);
NMR(DMSO-$d_6$): δ 1.51-1.98 (m, 6H), 2.27 (t, 2H), 2.65 (t, 2H), 2.95-3.60 (m, 4H), 3.92-4.24 (m, 2H), 4.84 (t, 1H), 6.69 (d, 1H), 6.99-7.34 (m, 8H), 7.33-7.70 (m, 3H), 9.87 (s, 1H).

Example 52(57)

4-(3-carboxypropyl)-8-({4-[4-(4-fluorophenyl)butoxy]benzoyl}amino)-3,4-dihydro-2H-1,4-benzoxazine-2-carboxylic acid TLC: Rf 0.30 (methylene chloride:methanol:acetic acid=9:1:0.05);
NMR(DMSO-$d_6$): δ 1.62-1.82 (m, 6H), 2.27 (t, 2H), 2.63 (t, 2H), 3.15-3.27 (m, 2H), 3.38-3.58 (m, 2H), 4.06 (t, 2H), 4.99 (t, 1H), 6.58 (dd, 1H), 6.76 (dd, 1H), 6.92-7.13 (m, 4H), 7.15-7.33 (m, 3H), 7.78-7.99 (m, 2H), 9.17 (s, 1H), 12.13 (s, 2H).

Example 52(58)

4-(3-carboxypropyl)-6-{[4-(4-phenylbutoxy)benzoyl]amino}-3,4-dihydro-2H-1,4-benzoxazine-2-carboxylic acid TLC: Rf 0.31 (methylene chloride:methanol:acetic acid=90:10:0.5);
NMR(DMSO-$d_6$): δ 1.62-1.87 (m, 6H), 2.28 (t, 2H), 2.64 (t, 2H), 3.09-3.56 (m, 4H), 3.96-4.15 (m, 2H), 4.83 (t, 1H), 6.69 (d, 1H), 7.01 (d, 2H), 7.07-7.40 (m, 7H), 7.89 (d, 2H), 9.74 (s, 1H).

Example 52(59)

4-(3-carboxypropyl)-6-{[3-(4-phenylbutoxy)benzoyl]amino}-3,4-dihydro-2H-1,4-benzoxazine-2-carboxylic acid TLC: Rf 0.31 (methylene chloride:methanol:acetic acid=90:10:0.5);
NMR(DMSO-$d_6$): δ 1.64-1.90 (m, 6H), 2.27 (t, 2H), 2.56-2.71 (m, 2H), 3.10-3.57 (m, 4H), 3.92-4.17 (m, 2H), 4.81 (t, 1H), 6.69 (d, 1H), 7.00 (dd, 1H), 7.05-7.53 (m, 10H), 9.85 (s, 1H).

Example 52(60)

8-({4-[4-(benzyloxy)butoxy]benzoyl}amino)-4-(3-carboxypropyl)-3,4-dihydro-2H-1,4-benzoxazine-2-carboxylic acid TLC: Rf 0.37 (methylene chloride:methanol:acetic acid=90:10:0.5);
NMR(DMSO-$d_6$): δ 1.51-1.96 (m, 6H), 2.27 (t, 2H), 3.11-3.58 (m, 6H), 4.06 (t, 2H), 4.46 (s, 2H), 4.99 (t, 1H), 6.59 (d, 1H), 6.77 (t, 1H), 7.03 (d, 2H), 7.13-7.42 (m, 6H), 7.87 (d, 2H), 9.18 (s, 1H).

Example 52(61)

4-(3-carboxypropyl)-8-({4-[4-(4-methylphenyl)butoxy]benzoyl}amino)-3,4-dihydro-2H-1,4-benzoxazine-2-carboxylic acid TLC: Rf 0.37 (methylene chloride:methanol:acetic acid=90:10:0.5);
NMR(DMSO-$d_6$): δ 1.58-1.84 (m, 6H), 2.14-2.34 (m, 5H), 2.59 (t, 2H), 3.14-3.31 (m, 2H), 3.37-3.59 (m, 2H), 4.06 (t, 2H), 4.99 (t, 1H), 6.59 (t, 1H), 6.77 (t, 1H), 6.95-7.13 (m, 6H), 7.19 (d, 1H), 7.87 (d, 2H), 9.17 (s, 1H).

Example 52(62)

4-(3-carboxypropyl)-8-({4-[4-(4-methoxyphenyl)butoxy]benzoyl}amino)-3,4-dihydro-2H-1,4-benzoxazine-2-carboxylic acid TLC: Rf 0.37 (methylene chloride:methanol:acetic acid=90:10:0.5);
NMR(DMSO-$d_6$): δ 1.56-1.87 (m, 6H), 2.17-2.36 (m, 2H), 2.58 (t, 2H), 3.12-3.38 (m, 2H), 3.38-3.56 (m, 2H), 3.71 (s, 3H), 4.06 (t, 2H), 4.83-5.12 (m, 1H), 6.59 (dd, 1H), 6.77 (t, 1H), 6.80-6.89 (m, 2H), 7.03 (d, 2H), 7.07-7.17 (m, 2H), 7.19 (d, 1H), 7.87 (d, 2H), 9.17 (s, 1H).

Example 52(63)

4-(3-carboxypropyl)-8-({4-[4-(2-methylphenoxy)butoxy]benzoyl}amino)-3,4-dihydro-2H-1,4-benzoxazine-2-carboxylic acid TLC: Rf 0.36 (methylene chloride:methanol:acetic acid=90:10:0.5);
NMR(DMSO-$d_6$): δ 1.58-2.03 (m, 6H), 2.12 (s, 3H), 2.27 (t, 2H), 3.11-3.61 (m, 4H), 3.96-4.09 (m, 2H), 4.13 (t, 2H), 4.92 (t, 1H), 6.52-6.63 (m, 1H), 6.69-6.86 (m, 2H), 6.91 (d, 1H), 7.05 (d, 2H), 7.09-7.17 (m, 2H), 7.21 (d, 1H), 7.88 (d, 2H), 9.16 (s, 1H).

Example 52(64)

4-(3-carboxypropyl)-8-({4-[4-(3-methylphenoxy)butoxy]benzoyl}amino)-3,4-dihydro-2H-1,4-benzoxazine-2-carboxylic acid TLC: Rf 0.36 (methylene chloride:methanol:acetic acid=90:10:0.5);
NMR(DMSO-$d_6$): δ 1.58-2.02 (m, 6H), 2.17-2.34 (m, 5H), 3.09-3.56 (m, 4H), 3.95-4.05 (m, 2H), 4.06-4.19 (m, 2H), 4.80-4.97 (m, 1H), 6.57 (dd, 1H), 6.66-6.83 (m, 4H), 7.05 (d, 2H), 7.14 (t, 1H), 7.22 (d, 1H), 7.74-8.00 (m, 2H), 9.16 (s, 1H).

Example 52(65)

4-(3-carboxypropyl)-8-({4-[4-(4-methylphenoxy)butoxy]benzoyl}amino)-3,4-dihydro-2H-1,4-benzoxazine-2-carboxylic acid TLC: Rf 0.36 (methylene chloride:methanol:acetic acid=90:10:0.5);
NMR(DMSO-$d_6$): δ 1.63-1.95 (m, 6H), 2.21 (s, 3H), 2.27 (t, 2H), 3.14-3.54 (m, 4H), 3.92-4.05 (m, 2H), 4.11 (t, 2H), 4.96 (t, 1H), 6.58 (dd, 1H), 6.69-6.87 (m, 3H), 6.97-7.12 (m, 4H), 7.13-7.25 (m, 1H), 7.88 (d, 2H), 9.17 (s, 1H).

Example 52(66)

4-(3-carboxypropyl)-8-({4-[4-(2-fluorophenoxy)butoxy]benzoyl}amino)-3,4-dihydro-2H-1,4-benzoxazine-2-carboxylic acid TLC: Rf 0.29 (methylene chloride:methanol:acetic acid=90:10:0.5);
NMR(DMSO-$d_6$): δ 1.58-1.97 (m, 6H), 2.26 (t, 2H), 3.03-3.57 (m, 4H), 4.03-4.23 (m, 4H), 4.76-4.94 (m, 1H), 6.56 (d, 1H), 6.74 (t, 1H), 6.85-6.97 (m, 1H), 6.98-7.31 (m, 6H), 7.87 (d, 2H), 9.17 (s, 1H).

Example 52(67)

4-(3-carboxypropyl)-8-({4-[4-(2-methoxyphenoxy)butoxy]benzoyl}amino)-3,4-dihydro-2H-1,4-benzoxazine-2-carboxylic acid TLC: Rf 0.29 (methylene chloride:methanol:acetic acid=90:10:0.5);
NMR(DMSO-$d_6$): δ 1.56-2.03 (m, 6H), 2.26 (t, 2H), 3.14-3.54 (m, 4H), 3.73 (s, 3H), 4.00 (t, 2H), 4.12 (t, 2H), 4.75-4.96 (m, 1H), 6.56 (d, 1H), 6.74 (t, 1H), 6.81-6.99 (m, 4H), 7.05 (d, 2H), 7.22 (d, 1H), 7.88 (d, 2H), 9.17 (s, 1H).

Example 52(68)

4-(3-carboxypropyl)-8-({4-[4-(2-chlorophenoxy)butoxy]benzoyl}amino)-3,4-dihydro-2H-1,4-benzoxazine-2-carboxylic acid TLC: Rf 0.29 (methylene chloride:methanol:acetic acid=90:10:0.5);
NMR(DMSO-$d_6$): δ 1.58-2.03 (m, 6H), 2.27 (t, 2H), 3.11-3.56 (m, 4H), 4.05-4.20 (m, 4H), 4.95 (t, 1H), 6.58 (dd, 1H), 6.76 (t, 1H), 6.89-6.98 (m, 1H,) 7.05 (d, 2H), 7.12-7.23 (m, 2H), 7.24-7.33 (m, 1H), 7.41 (dd, 1H), 7.88 (d, 2H), 9.19 (s, 1H).

Example 52(69)

4-(3-carboxypropyl)-8-[(4-{4-[2-(trifluoromethyl)phenoxy]butoxy)benzoyl}amino]-3,4-dihydro-2H-1,4-benzoxazine-2-carboxylic acid TLC: Rf 0.29 (methylene chloride:methanol:acetic acid=90:10:0.5);
NMR(DMSO-$d_6$): δ 1.60-2.00 (m, 6H), 2.27 (t, 2H), 2.93-3.61 (m, 4H), 3.96-4.29 (m, 4H), 4.95 (t, 1H), 6.58 (dd, 1H), 6.76 (t, 1H), 6.99-7.13 (m, 3H), 7.19 (d, 1H), 7.26 (d, 1H), 7.56-7.68 (m, 2H), 7.88 (d, 2H), 9.19 (s, 1H).

Example 52(70)

4-(3-carboxypropyl)-8-({4-[3-(2-fluorophenoxy)propoxy]benzoyl}amino)-3,4-dihydro-2H-1,4-benzoxazine-2-carboxylic acid TLC: Rf 0.35 (methanol:methylene chloride:acetic acid=1:9:0.1);
NMR(DMSO-$d_5$): δ 1.60-1.82 (m, 2H), 2.09-2.36 (m, 4H), 3.13-3.61 (m, 4H), 4.10-4.33 (m, 4H), 5.00 (t, 1H), 6.58 (d, 1H), 6.77 (t, 1H), 6.85-6.99 (m, 1H), 7.01-7.30 (m, 6H), 7.88 (d, 2H), 9.21 (s, 1H).

Example 52(71)

4-(3-carboxypropyl)-8-({4-[3-(3-fluorophenoxy)propoxy]benzoyl}amino)-3,4-dihydro-2H-1,4-benzoxazine-2-carboxylic acid TLC: Rf 0.34 (methanol:methylene chloride:acetic acid=1:9:0.1);
NMR(DMSO-$d_6$): δ 1.61-1.81 (m, 2H), 2.10-2.34 (m, 4H), 3.10-3.56 (m, 4H), 4.05-4.31 (m, 4H), 4.89-5.06 (m, 1H), 6.59 (d, 1H), 6.68-6.88 (m, 4H), 7.07 (d, 2H), 7.13-7.37 (m, 2H), 7.88 (d, 2H), 9.20 (s, 1H).

Example 52(72)

4-(3-carboxypropyl)-8-({4-[3-(3-chlorophenoxy)propoxy]benzoyl}amino)-3,4-dihydro-2H-1,4-benzoxazine-2-carboxylic acid TLC: Rf 0.51 (methylene chloride: methanol:water=8:2:0.2);
NMR(DMSO-$d_6$): δ 1.65-1.79 (m, 2H), 2.13-2.32 (m, 4H), 3.20-3.28 (m, 2H), 3.40-3.50 (m, 2H), 4.12-4.25 (m, 4H), 4.96-4.92 (s, 1H), 6.58 (d, 1H), 6.76 (t, 1H), 6.90-7.11 (m, 5H), 7.20 (d, 1H), 7.29 (t, 1H), 7.89 (d, 2H), 9.19 (s, 1H).

Example 52(73)

4-(3-carboxypropyl)-8-({4-[3-(2-chlorophenoxy)propoxy]benzoyl}amino)-3,4-dihydro-2H-1,4-benzoxazine-2-carboxylic acid TLC: Rf 0.51 (methylene chloride:methanol:water=8:2:0.2);
NMR(DMSO-$d_6$): δ 1.65-1.78 (m, 2H), 2.17-2.32 (m, 4H), 3.20-3.30 (m, 2H), 3.43-3.50 (m, 2H), 4.18-4.29 (m, 4H), 4.98 (t, 1H), 6.59 (d, 1H), 6.76 (t, 1H), 6.91-6.98 (m, 1H), 7.07 (d, 2H), 7.18 (d, 2H), 7.25-7.33 (m, 1H), 7.41 (dd, 1H), 7.89 (d, 2H), 9.21 (s, 1H).

Example 52(74)

4-(3-carboxypropyl)-8-[(4-{3-[3-(trifluoromethyl)phenoxy]propoxy}benzoyl)amino]-3,4-dihydro-2H-1,4-benzoxazine-2-carboxylic acid TLC: Rf 0.51 (methylene chloride:methanol:water=8:2:0.2);
NMR(DMSO-$d_6$): δ 1.65-1.78 (m, 2H), 2.16-2.31 (m, 4H), 3.20-3.29 (m, 2H), 3.43-3.48 (m, 2H), 4.19-4.27 (m, 4H), 4.97 (t, 1H), 6.58 (d, 1H), 6.76 (t, 1H), 7.07 (d, 2H), 7.17 (d, 1H), 7.23-7.31 (m, 3H), 7.51 (t, 1H), 7.88 (d, 2H), 9.20 (s, 1H).

Example 52(75)

4-(3-carboxypropyl)-8-[(4-{3-[2-(trifluoromethyl)phenoxy]propoxy}benzoyl)amino]-3,4-dihydro-2H-1,4-benzoxazine-2-carboxylic acid TLC: Rf 0.51 (methylene chloride:methanol:water=8:2:0.2);
NMR(DMSO-$d_6$): δ 1.64-1.79 (m, 2H), 2.16-2.31 (m, 4H), 3.19-3.31 (m, 2H), 3.40-3.52 (m, 2H), 4.22 (t, 2H), 4.28 (t, 2H), 5.01 (t, 1H), 6.59 (d, 1H), 6.77 (t, 1H), 7.01-7.13 (m, 3H), 7.16 (d, 1H), 7.29 (d, 1H), 7.56-7.67 (m, 2H), 7.88 (d, 2H), 9.21 (s, 1H).

Example 52(76)

4-(3-carboxypropyl)-8-({4-[3-(2-methylphenoxy)propoxy]benzoyl}amino)-3,4-dihydro-2H-1,4-benzoxazine-2-carboxylic acid TLC: Rf 0.51 (methylene chloride:methanol:water=8:2:0.2);
NMR(DMSO-$d_6$): δ 1.64-1.81 (m, 2H), 2.14 (s, 3H), 2.16-2.31 (m, 4H), 3.19-3.29 (m, 2H), 3.39-3.55 (m, 2H), 4.13 (t, 2H), 4.25 (t, 2H), 5.01 (t, 1H), 6.59 (d, 1H), 6.73-6.86 (m, 2H), 6.94 (d, 1H), 7.08 (d, 2H), 7.10-7.15 (m, 2H), 7.17 (dd, 1H), 7.89 (d, 2H), 9.21 (s, 1H).

Example 52(77)

4-(3-carboxypropyl)-8-({4-[3-(4-fluorophenoxy)propoxy]benzoyl}amino)-3,4-dihydro-2H-1,4-benzoxazine-2-carboxylic acid TLC: Rf 0.23 (chloroform:methanol:acetic acid=90:10:1);
NMR(DMSO-$d_6$): δ 1.64-1.80 (m, 2H), 2.20 (t, 2H), 2.27 (t, 2H), 3.18-3.26 (m, 2H), 3.42-3.54 (m, 2H), 4.11 (t, 2H), 4.21 (t, 2H), 4.97 (s, 1H), 6.57-6.63 (m, 2H), 6.76 (t, 1H), 6.86-7.19 (m, 6H), 7.88 (d, 2H), 9.20 (s, 1H), 12.49 (bs, 2H).

Example 52(78)

4-(3-carboxypropyl)-8-({4-[3-(2-chloro-4-fluorophenoxy)propoxy]benzoyl}amino)-3,4-dihydro-2H-1,4-benzoxazine-2-carboxylic acid TLC: Rf 0.23 (chloroform:methanol:acetic acid=90:10:1);
NMR(DMSO-$d_6$): δ 1.67-1.83 (m, 2H), 2.10-2.39 (m, 4H), 3.19-3.29 (m, 2H), 3.41-3.54 (m, 2H), 4.13-4.42 (m, 4H), 4.96 (s, 1H), 6.58 (d, 1H), 6.76 (t, 1H), 7.00-7.30 (m, 5H), 7.42 (dd, 1H), 7.88 (d, 2H), 9.21 (s, 1H), 12.41 (bs, 2H).

Example 52(79)

4-(3-carboxypropyl)-8-({4-[3-(4-chlorophenoxy)propoxy]benzoyl}amino)-3,4-dihydro-2H-1,4-benzoxazine-2-carboxylic acid TLC: Rf 0.49 (methylene chloride:methanol:water=8:2:0.2);
NMR(DMSO-$d_6$): δ 1.66-1.81 (m, 2H), 2.12-2.36 (m, 4H), 3.19-3.29 (m, 2H), 3.39-3.54 (m, 2H), 4.13 (t, 2H), 4.21 (t, 2H), 5.01 (t, 1H), 6.60 (d, 1H), 6.77 (t, 1H), 6.99 (d, 2H), 7.07 (d, 2H), 7.19 (d, 1H), 7.31 (d, 2H), 7.88 (d, 2H), 9.20 (s, 1H).

Example 52(80)

4-(3-carboxypropyl)-8-({4-[3-(4-methylphenoxy)propoxy]benzoyl}amino)-3,4-dihydro-2H-1,4-benzoxazine-2-carboxylic acid TLC: Rf 0.51 (methylene chloride:methanol:water=8:2:0.2);
NMR(DMSO-$d_6$): δ 1.66-1.81 (m, 2H), 2.11-2.21 (m, 2H), 2.21 (s, 3H), 2.27 (t, 2H), 3.20-3.28 (m, 2H), 3.40-3.55 (m, 2H), 4.09 (t, 2H), 4.21 (t, 2H), 5.00 (t, 1H), 6.59 (d, 1H), 6.77 (t, 1H), 6.84 (d, 2H), 7.03-7.12 (m, 4H), 7.19 (d, 1H), 7.88 (d, 2H), 9.19 (s, 1H).

Example 52(81)

4-(3-carboxypropyl)-8-({4-[3-(3-methylphenoxy)propoxy]benzoyl}amino)-3,4-dihydro-2H-1,4-benzoxazine-2-carboxylic acid TLC: Rf 0.48 (methylene chloride:methanol:water=8:2:0.2);
NMR(DMSO-$d_6$): δ 1.67-1.80 (m, 2H), 2.12-2.25 (m, 2H), 2.23-2.34 (m, 5H), 3.19-3.29 (m, 2H), 3.39-3.56 (m, 2H), 4.12 (t, 2H), 4.21 (t, 2H), 5.00 (t, 1H), 6.59 (d, 1H), 6.70-6.82 (m, 4H), 7.07 (d, 2H), 7.11-7.24 (m, 2H), 7.89 (d, 2H), 9.19 (s, 1H).

Example 52(82)

4-(3-carboxypropyl)-8-({4-[4-(3-chlorophenoxy)butoxy]benzoyl}amino)-3,4-dihydro-2H-1,4-benzoxazine-2-carboxylic acid TLC: Rf 0.25 (methylene chloride:methanol=4:1);
NMR(DMSO-$d_6$): δ 0.76-1.29 (m, 4H), 1.67-1.78 (m, 2H), 1.82-1.95 (m, 4H), 2.20-2.34 (m, 2H), 3.98-4.18 (m, 4H), 4.63-4.77 (m, 1H), 6.54 (d, 1H), 6.63-7.37 (m, 8H), 7.88 (d, 2H), 9.15 (brs, 1H).

Example 52(83)

4-(3-carboxypropyl)-8-({4-[3-(2,6-dichlorophenoxy)propoxy]benzoyl}amino)-3,4-dihydro-2H-1,4-benzoxazine-2-carboxylic acid TLC: Rf 0.50 (methylene chloride:methanol:water=8:2:0.2);
NMR (DMSO-$d_6$): δ 1.66-1.81 (m, 2H), 2.18-2.32 (m, 4H), 3.20-3.28 (m, 2H), 3.40-3.54 (m, 2H), 4.16 (t, 2H), 4.30 (t, 2H), 4.97-5.02 (m, 1H), 6.59 (d, 1H), 6.76 (t, 1H), 7.08 (d, 2H), 7.12-7.22 (m, 2H), 7.44-7.51 (m, 2H) 7.85-7.94 (d, 2H), 9.20 (s, 1H).

Example 52(84)

4-(3-carboxypropyl)-8-({4-[3-(2,6-dimethylphenoxy)propoxy]benzoyl}amino)-3,4-dihydro-2H-1,4-benzoxazine-2-carboxylic acid TLC: Rf 0.50 (methylene chloride:methanol:water=8:2:0.2);
NMR (DMSO-$d_6$): δ 1.66-1.81 (m, 2H), 2.13-2.24 (m, 8H), 2.28 (t, 2H), 3.20-3.28 (m, 2H), 3.39-3.56 (m, 2H), 3.90 (t, 2H), 4.30 (t, 2H), 5.01 (t, 1H), 6.60 (d, 1H), 6.77 (t, 1H), 6.85-6.94 (m, 1H), 6.96-7.03 (m, 2H), 7.10 (d, 2H), 7.19 (d, 1H), 7.90 (d, 2H), 9.21 (s, 1H).

Example 52(85)

4-(3-carboxypropyl)-8-({4-[4-(2,6-difluorophenoxy)butoxy]benzoyl}amino)-3,4-dihydro-2H-1,4-benzoxazine-2-carboxylic acid TLC: Rf 0.27 (methylene chloride:methanol:acetic acid=90:10:0.5);
NMR (DMSO-$d_6$): δ 1.62-2.01 (m, 6H), 2.27 (t, 2H), 3.16-3.55 (m, 4H), 4.04-4.23 (m, 4H), 4.98 (t, 1H), 6.59 (d, 1H), 6.77 (t, 1H), 6.98-7.29 (m, 6H), 7.88 (d, 2H), 9.18 (s, 1H).

Example 52(86)

4-(3-carboxypropyl)-8-({4-[4-(2,6-dichlorophenoxy)butoxy]benzoyl}amino)-3,4-dihydro-2H-1,4-benzoxazine-2-carboxylic acid TLC: Rf 0.34 (methylene chloride:methanol:acetic acid=90:10:0.5);
NMR (DMSO-$d_6$): δ 1.61-2.08 (m, 6H), 2.27 (t, 2H), 3.16-3.57 (m, 4H), 3.97-4.26 (m, 4H) 4.98 (t, 1H) 6.59 (d, 1H), 6.77 (t, 1H), 7.06 (d, 2H), 7.12-7.26 (m, 2H), 7.49 (d, 2H), 7.89 (d, 2H), 9.19 (s, 1H).

Example 53

4-(4-methoxy-4-oxobutyl)-8-{[4-(4-phenylbutoxy)benzoyl]amino}-3,4-dihydro-2H-1,4-benzoxazine-2-carboxylic acid To a solution of the compound prepared in Example 30 (145 mg) in isopropanol (1 mL)-tetrahydrofuran (1 mL) was added 2M aqueous solution of sodium hydroxide (0.126 mL), and the mixture was stirred for 4 hours with ice cooling, and 11 hours at room temperature. To the mixture was added 2M hydrochloric acid (0.126 mL) and the reaction mixture was extracted with ethyl acetate. The organic layer was washed with water and saturated brine sequentially, dried and concentrated. The residue was purified by column chromatography on silica gel (methylene chloride:methanol=99:1 to 96:4) to give the title compound (101 mg).

TLC: Rf 0.41 (methylene chloride:methanol=85:15);
NMR(CDCl$_3$/CD$_3$OD): δ 1.71-1.91 (m, 6H), 2.35 (t, 2H), 2.65 (t, 2H), 3.14-3.31 (m, 2H), 3.40-3.55 (m, 2H), 3.63 (s, 3H), 3.97 (t, 2H), 4.70-4.75 (m, 1H), 6.53 (d, 1H), 6.79 (t, 1H), 6.91 (d, 2H), 7.10-7.26 (m, 5H), 7.34 (d, 1H), 7.85 (d, 2H).

Example 54 methyl 4-(8-[4-(4-phenylbutoxy)benzoyl]amino-2-[(phenylsulfonyl)amino]carbonyl-2,3-dihydro-4H-1,4-benzoxazin-4-yl)butanoate To a solution of the compound prepared in Example 53 (100 mg) in methylene chloride (2 mL) were added benzenesulfonamide (29 mg), 1-ethyl-3-(3-dimethylaminopropyl)-carbodimide (42 mg) and 4-dimethylaminopyridine (27 mg), and the resulting mixture was stirred for 15 hours at room temperature. To the mixture were added a saturated aqueous solution of ammonium chloride and ethyl acetate, and the resulting mixture was extracted with ethyl acetate. The organic layer was washed with water and saturated brine sequentially, dried and concentrated. The residue was purified by column chromatography on silica gel (methylene chloride ethyl acetate=90:10→methylene chloride:methanol=97:3→80:20) to give the desired compound (68 mg).

TLC: Rf 0.57 (methylene chloride:methanol=90:10);
NMR(CD$_3$OD): δ 1.63-1.93 (m, 6H), 2.22-2.78 (m, 2H), 2.69 (t, 2H), 3.02-3.18 (m, 2H), 3.30-3.34 (m, 1H), 3.49 (dd, 1H), 3.65 (s, 3H), 4.05-4.10 (m, 2H), 4.78 (t, 1H), 6.60 (dd, 1H), 6.85 (t, 1H), 6.90-6.96 (m, 1H), 7.01 (d, 2H), 7.12-7.28 (m, 5H), 7.41-7.47 (m, 2H), 7.53-7.59 (m, 1H), 7.78-7.80 (m, 2H), 7.95 (d, 2H).

Example 55

4-(8-{[4-(4-phenylbutoxy)benzoyl]amino}-2-{[(phenylsulfonyl)amino]carbonyl}-2,3-dihydro-4H-1,4-benzoxazin-4-yl)butanoic acid The compound of the present invention having the following physical data was prepared by substituting the compound prepared in Example 7 for the compound prepared in Example 54 in the process of Example 8.

TLC: Rf 0.48 (methylene chloride:methanol:acetic acid=90:10:1);
NMR(DMSO-d$_6$): δ 1.43-1.82 (m, 6H), 2.16 (t, 2H), 2.64 (t, 2H), 2.98-3.18 (m, 2H), 3.24-3.42 (m, 2H), 4.02-4.16 (m, 2H), 4.93-5.03 (m, 1H), 6.58-6.61 (m, 1H), 6.79-6.89 (m, 2H), 7.05 (d, 2H), 7.13-7.30 (m, 5H), 7.50-7.55 (m, 2H), 7.65 (t, 1H), 7.75 (d, 2H), 7.94 (d, 2H), 9.83 (brs, 1H), 12.06 (brs, 1H), 12.55 (brs, 1H).

Example 55(1)-Example 55(21)

The compounds of the present invention having the following physical data were prepared by using the compound prepared in Example 30 or its corresponding compound and using benzenesulfonamide or its corresponding sulfonamide according to the process of Example 53→Example 54→Example 8.

Example 55(1)

4-(2-({[(2-methylphenyl)sulfonyl]amino}carbonyl)-8-{[4-(4-phenylbutoxy)benzoyl]amino}-2,3-dihydro-4H-1,4-benzoxazin-4-yl)butanoic acid TLC: Rf 0.48 (methylene chloride:methanol:acetic acid=90:10:1);
NMR(DMSO-d$_6$): δ 1.36-1.61 (m, 2H), 1.66-1.83 (m, 4H), 2.12 (t, 2H), 2.28 (s, 3H), 2.65 (t, 2H), 2.96-3.15 (m, 2H), 3.16-3.49 (m, 2H), 4.02-4.15 (m, 2H), 4.84-5.13 (m, 1H), 6.55-6.67 (m, 1H), 6.76-6.92 (m, 2H), 7.05 (d, 2H), 7.11-7.60 (m, 8H), 7.80-8.10 (m, 3H), 9.94 (s, 1H), 12.04 (s, 1H), 12.62 (s, 1H).

Example 55(2)

4-(2-({[(4-methylphenyl)sulfonyl]amino}carbonyl)-8-{[4-(4-phenylbutoxy)benzoyl]amino}-2,3-dihydro-4H-1,4-benzoxazin-4-yl)butanoic acid TLC: Rf 0.47 (methylene chloride:methanol:acetic acid=90:10:1);
NMR(DMSO-d$_6$): δ 1.45-1.64 (m, 2H), 1.66-1.87 (m, 4H), 2.17 (t, 2H), 2.36 (s, 3H), 2.65 (t, 2H), 2.97-3.14 (m, 2H), 3.19-3.54 (m, 2H), 3.95-4.22 (m, 2H), 4.79-5.07 (m, 1H), 6.60 (d, 1H), 6.76-6.96 (m, 2H), 7.06 (d, 2H), 7.12-7.45 (m, 7H), 7.63 (d, 2H), 7.95 (d, 2H), 9.81 (s, 1H), 12.05 (s, 1H), 12.45 (s, 1H).

Example 55(3)

4-(2-({[(2-chlorophenyl)sulfonyl]amino}carbonyl)-8-{[4-(4-phenylbutoxy)benzoyl]amino}-2,3-dihydro-4H-1,4-benzoxazin-4-yl)butanoic acid TLC: Rf 0.58 (chloroform:methanol:acetic acid=90:10:1);
NMR(CDCl$_3$): δ 1.59-1.93 (m, 6H), 2.17 (t, 2H), 2.71 (t, 2H), 2.99-3.09 (m, 1H), 3.14-3.35 (m, 2H), 3.69 (dd, 1H), 4.04 (t, 2H), 4.82 (s, 1H), 6.62-6.70 (m, 2H), 6.89 (t, 1H), 6.95 (d, 2H), 7.14-7.34 (m, 4H), 7.34-7.52 (m, 3H), 7.74 (s, 1H), 7.93 (d, 2H), 8.25 (d, 1H).

Example 55(4)

4-(2-({[(3-chlorophenyl)sulfonyl]amino}carbonyl)-8-{[4-(4-phenylbutoxy)benzoyl]amino}-2,3-dihydro-4H-1,4-benzoxazin-4-yl)butanoic acid TLC: Rf 0.60 (chloroform:methanol:acetic acid=90:10:1);
NMR(CDCl$_3$): δ 1.62-1.94 (m, 6H), 2.28 (t, 2H), 2.71 (t, 2H), 3.04-3.24 (m, 2H), 3.29 (dd, 1H), 3.64 (dd, 1H), 4.05 (t, 2H), 4.71-4.85 (m, 1H), 6.61 (t, 2H), 6.89 (t, 1H), 6.97 (d, 2H), 7.12-7.42 (m, 5H), 7.43-7.58 (m, 1H), 7.71 (s, 1H), 7.81 (d, 1H), 7.85-7.99 (m, 2H).

Example 55(5)

4-(2-({[(4-chlorophenyl)sulfonyl]amino}carbonyl)-8-{[4-(4-phenylbutoxy)benzoyl]amino}-2,3-dihydro-4H-1,4-benzoxazin-4-yl)butanoic acid TLC: Rf 0.56 (chloroform:methanol:acetic acid=90:10:1);
NMR(DMSO-d$_6$): δ 1.62-1.64 (m, 2H), 1.73-1.75 (m, 4H), 2.21 (t, 2H), 2.65 (t, 2H), 3.12-3.14 (m, 2H), 3.30-3.40 (m, 2H), 4.05-4.08 (m, 2H), 4.72 (bs, 1H), 6.54 (d, 1H), 6.77 (t, 1H), 7.04 (d, 2H), 7.10-7.38 (m, 6H), 7.48-7.51 (m, 2H), 7.71 (d, 2H), 7.91 (d, 2H), 9.41 (bs, 1H), 12.06 (bs, 1H), 12.64 (bs, 1H).

Example 55(6)

4-(2-{[(methylsulfonyl)amino]carbonyl}-8-{[4-(4-phenylbutoxy)benzoyl]amino}-2,3-dihydro-4H-1,4-benzoxazin-4-yl)butanoic acid TLC: Rf 0.59 (chloroform:methanol:acetic acid=90:10:1);
NMR(CDCl$_3$): δ 1.72-2.02 (m, 6H), 2.40 (t, 2H), 2.70 (t, 2H), 3.13-3.22 (m, 1H), 3.21 (s, 3H), 3.32-3.27 (m, 2H), 3.73 (dd, 1H), 4.02 (t, 2H), 4.87 (s, 1H), 6.64 (t, 2H), 6.85 (t, 1H), 6.93 (d, 2H), 7.15-7.24 (m, 2H), 7.24-7.36 (m, 2H), 7.80 (s, 1H), 7.88 (d, 2H).

Example 55(7)

4-(2-{[(benzylsulfonyl)amino]carbonyl}-8-{[4-(4-phenylbutoxy)benzoyl]amino}-2,3-dihydro-4H-1,4-benzoxazin-4-yl)butanoic acid TLC: Rf 0.30 (chloroform:methanol:acetic acid=90:10:1);
NMR(DMSO-$d_6$): δ 1.73-1.78 (m, 6H), 2.31 (t, 2H), 2.64 (t, 2H), 3.30-3.38 (m, 1H), 3.45-3.55 (m, 1H), 4.03-4.05 (m, 2H), 4.71 (s, 2H), 5.06 (s, 1H), 6.72 (d, 1H), 6.83 (t, 1H), 6.93-7.05 (m, 3H), 7.14-7.30 (m, 10H), 7.80 (t, 2H), 9.68 (bs, 1H), 11.98 (bs, 1H), 12.09 (bs, 1H).

Example 55(8)

4-[8-{[4-(4-phenylbutoxy)benzoyl]amino}-2-({[(trifluoromethyl)sulfonyl]amino}carbonyl)-2,3-dihydro-4H-1,4-benzoxazin-4-yl]butanoic acid TLC: Rf 0.35 (chloroform:methanol:acetic acid=90:10:1);
NMR(CDCl$_3$): δ 1.82-1.83 (m, 6H), 2.24-2.26 (m, 2H), 2.69 (t, 2H), 3.03-3.08 (m, 1H), 3.31 (t, 2H), 3.60-3.64 (m, 1H), 3.98-4.00 (m, 2H), 4.78 (s, 1H), 6.49-6.53 (m, 1H), 6.78-6.80 (m, 1H), 6.91 (d, 2H), 7.16-7.20 (m, 3H), 7.26-7.31 (m, 3H), 7.80 (d, 2H).

Example 55(9)

4-(2-({[(4-methoxyphenyl)sulfonyl]amino}carbonyl)-8-{[4-(4-phenylbutoxy)benzoyl]amino}-2,3-dihydro-4H-1,4-benzoxazin-4-yl)butanoic acid TLC: Rf 0.52 (chloroform:methanol:acetic acid=90:10:1);
NMR(DMSO-$d_6$): δ 1.52-1.59 (m, 2H), 1.74-1.76 (m, 4H), 2.16-2.20 (m, 2H), 2.54-2.66 (m, 2H), 3.06-3.10 (m, 2H), 3.24-3.42 (m, 2H), 3.82 (s, 3H), 4.07-4.09 (s, 2H), 4.96 (s, 1H), 6.63 (d, 1H), 6.80-6.90 (m, 2H), 7.05 (dd, 4H), 7.15-7.31 (m, 5H), 7.71 (d, 2H), 7.95 (d, 2H), 9.81 (bs, 1H), 12.06 (bs, 1H), 12.37 (bs, 1H).

Example 55(10)

4-(2-({[(6-methyl-2-pyridinyl)sulfonyl]amino}carbonyl)-8-{[4-(4-phenylbutoxy)benzoyl]amino}-2,3-dihydro-4H-1,4-benzoxazin-4-yl)butanoic acid TLC: Rf 0.43 (chloroform:methanol:acetic acid=90:10:1);
NMR(DMSO-$d_6$): δ 1.57-1.66 (m, 2H), 1.74-1.75 (m, 4H), 2.20 (t, 2H), 2.37 (s, 3H), 2.62-2.66 (m, 2H), 3.14 (t, 2H), 3.39-3.33 (m, 2H), 4.06-4.08 (m, 2H), 4.95 (s, 1H), 6.62 (d, 1H), 6.81 (t, 1H), 7.02-7.03 (m, 3H), 7.14-7.30 (m, 5H), 7.85-7.94 (m, 4H), 8.48 (s, 1H), 9.68 (bs, 1H), 12.06 (bs, 1H), 12.58 (bs, 1H).

Example 55(11)

4-(8-{[4-(4-phenylbutoxy)benzoyl]amino}-2-{[(2-thienylsulfonyl)amino]carbonyl}-2,3-dihydro-4H-1,4-benzoxazin-4-yl)butanoic acid TLC: Rf 0.45 (chloroform:methanol:acetic acid=90:10:1);
NMR(DMSO-$d_6$): δ 1.58-1.66 (m, 2H), 1.74-1.76 (m, 4H), 2.21 (t, 2H), 2.65 (t, 2H), 3.10-3.14 (m, 2H), 3.41-3.47 (m, 2H), 4.07-4.08 (m, 2H), 5.00 (s, 1H), 6.61 (d, 1H), 6.81 (t, 1H), 6.92 (d, 1H), 7.05 (d, 2H), 7.14-7.31 (m, 6H), 7.66 (d, 1H), 7.94 (d, 2H), 7.99 (d, 1H), 9.79 (bs, 1H), 12.06 (bs, 1H), 12.64 (bs, 1H).

Example 55(12)

4-(2-({[(4-chloro-3-pyridinyl)sulfonyl]amino}carbonyl)-8-{[4-(4-phenylbutoxy)benzoyl]amino}-2,3-dihydro-4H-1,4-benzoxazin-4-yl)butanoic acid TLC: Rf 0.66 (chloroform:methanol:acetic acid=90:10:1);
NMR(DMSO-$d_6$): δ 1.52-1.60 (m, 2H), 1.73-1.76 (m, 4H), 2.19 (t, 2H), 2.65 (t, 2H), 3.04-3.13 (m, 2H), 3.41-3.45 (m, 2H), 4.07-4.09 (m, 2H), 5.01 (s, 1H), 6.60 (d, 1H), 6.80-6.92 (m, 2H), 7.06, 2H), 7.15-7.31 (m, 5H), 7.72 (d, 1H), 7.94 (d, 2H), 8.11 (dd, 1H), 8.71 (d, 1H), 9.81 (bs, 1H), 12.10 (bs, 1H), 12.70 (bs, 1H).

Example 55(13)

4-(2-({[(3-methylphenyl)sulfonyl]amino}carbonyl)-8-{[4-(4-phenylbutoxy)benzoyl]amino}-2,3-dihydro-4H-1,4-benzoxazin-4-yl)butanoic acid TLC: Rf 0.45 (chloroform:methanol:acetic acid=90:10:1);
NMR(DMSO-$d_6$): δ 1.50-1.57 (m, 2H), 1.75-1.77 (m, 4H), 2.16 (t, 2H), 2.33 (s, 3H), 2.65 (t, 2H), 3.03-3.09 (m, 2H), 3.39-3.45 (m, 2H), 4.07-4.09 (m, 1H), 5.00 (s, 1H), 6.50-6.63 (m, 1H), 6.80-6.85 (m, 2H), 7.06 (d, 2H), 7.16-7.31 (m, 5H), 7.39-7.50 (m, 2H), 7.53-7.57 (m, 2H), 7.96 (d, 2H), 9.88 (bs, 1H), 12.06 (bs, 1H), 12.50 (bs, 1H).

Example 55(14)

4-(2-{[(ethylsulfonyl)amino]carbonyl}-8-{[4-(4-phenylbutoxy)benzoyl]amino}-2,3-dihydro-4H-1,4-benzoxazin-4-yl)butanoic acid TLC: Rf 0.68 (chloroform:methanol:acetic acid=90:10:1);
NMR(DMSO-$d_6$): δ 1.06 (t, 3H), 1.73-1.75 (m, 6H), 2.28 (t, 2H), 2.65 (t, 2H), 3.24 (t, 2H), 3.37-3.31 (m, 2H), 3.54 (dd, 2H), 4.07 (t, 2H), 5.08 (s, 1H), 6.66 (d, 1H), 6.82 (t, 1H), 6.90 (t, 1H), 7.04 (d, 2H), 7.14-7.30 (m, 5H), 7.92 (d, 2H), 9.82 (bs, 1H), 12.01 (bs, 1H), 12.08 (bs, 1H).

Example 55(15)

4-{8-{[4-(4-phenylbutoxy)benzoyl]amino}-2-[({[(E)-2-phenylvinyl]sulfonyl}amino)carbonyl]-2,3-dihydro-4H-1,4-benzoxazin-4-yl}butanoic acid TLC: Rf 0.54 (chloroform:methanol:acetic acid=90:10:1);
NMR(DMSO-$d_6$): δ 1.64-1.74 (m, 6H), 2.20 (t, 2H), 2.65 (t, 2H), 3.19 (t, 2H), 3.31-3.56 (m, 3H), 3.48 (dd, 1H), 4.06-4.05 (m, 2H), 4.99 (s, 1H), 6.62 (d, 1H), 6.80 (t, 1H), 6.95 (d, 1H), 7.02 (d, 2H), 7.20-7.33 (m, 5H), 7.38-7.58 (m, 5H), 7.69-7.72 (m, 2H), 7.92 (d, 2H), 9.73 (bs, 1H), 12.06 (bs, 1H), 12.24 (bs, 1H).

Example 55(16)

4-(2-({[(1,2-dimethyl-1H-imidazol-4-yl)sulfonyl]amino}carbonyl)-8-{[4-(4-phenylbutoxy)benzoyl]amino}-2,3-dihydro-4H-1,4-benzoxazin-4-yl)butanoic acid TLC: Rf 0.46 (chloroform:methanol:acetic acid=90:10:1);
NMR(DMSO-$d_6$): δ 1.65-1.75 (m, 6H), 2.22-2.24 (m, 2H), 2.25 (s, 3H), 2.65 (t, 2H), 3.19 (t, 2H), 3.31-3.35 (m, 2H), 3.57 (s, 3H), 4.06-4.07 (m, 2H), 4.83 (s, 1H), 6.59 (d, 1H), 6.79 (t, 1H), 7.05 (t, 2H), 7.04-7.11 (m, 1H), 7.14-7.30 (m, 5H), 7.75-7.81 (m, 1H), 7.92 (d, 2H), 9.58 (bs, 1H), 12.11 (bs, 2H).

Example 55(17)

4-(2-({[(3,5-dimethyl-4-isoxazolyl)sulfonyl]amino}carbonyl)-8-{[4-(4-phenylbutoxy)benzoyl]amino}-2,3-dihydro-4H-1,4-benzoxazin-4-yl)butanoic acid TLC: Rf 0.56 (chloroform:methanol:acetic acid=90:10:1);
NMR(DMSO-$d_6$): δ 1.51-1.58 (m, 2H), 1.74-1.76 (m, 4H), 2.04 (s, 3H), 2.17 (t, 2H), 2.54 (s, 3H), 2.65 (t, 2H), 3.09 (t, 2H), 3.31-3.24 (m, 1H), 3.50 (dd, 1H), 4.08 (t, 1H), 5.11 (s, 1H), 6.64 (d, 1H), 6.75-6.78 (m, 1H), 6.83 (t, 1H), 7.05 (d, 2H), 7.15-7.31 (m, 5H), 7.95 (d, 2H), 10.04 (bs, 1H), 12.05 (bs, 1H), 12.88 (bs, 1H).

Example 55(18)

4-{8-{[4-(4-phenylbutoxy)benzoyl]amino}-2-[({[4-(trifluoromethyl)phenyl]sulfonyl}amino)carbonyl]-2,3-dihydro-4H-1,4-benzoxazin-4-yl}butanoic acid TLC: Rf 0.54 (chloroform:methanol:acetic acid=90:10:1);
NMR(DMSO-$d_6$): δ 1.50-1.56 (m, 2H), 1.74-1.76 (m, 4H), 2.15 (t, 2H), 2.65 (t, 2H), 3.02-3.04 (m, 2H), 3.30-3.44 (m, 2H), 4.07-4.08 (m, 2H), 5.02 (s, 1H), 6.58 (d, 1H), 6.82 (t, 1H), 6.85-6.90 (m, 1H), 7.06 (d, 2H), 7.15-7.30 (m, 5H), 7.91-7.97 (m, 6H), 9.85 (bs, 1H), 12.05 (bs, 1H), 12.87 (bs, 1H).

Example 55(19)

4-(2-({[(4-tert-butylphenyl)sulfonyl]amino}carbonyl)-8-{[4-(4-phenylbutoxy)benzoyl]amino}-2,3-dihydro-4H-1,4-benzoxazin-4-yl)butanoic acid TLC: Rf 0.55 (chloroform:methanol:acetic acid=90:10:1);
NMR(DMSO-$d_6$): δ 1.27 (s, 9H), 1.56-1.72 (m, 2H), 1.74-1.76 (m, 4H), 2.18 (t, 2H), 2.65 (t, 2H), 3.01-3.11 (m, 2H), 3.30-3.41 (m, 2H), 4.07-4.08 (s, 2H), 4.95 (s, 1H), 6.59 (d, 1H), 6.82 (t, 1H), 6.85-6.98 (m, 1H), 7.06 (d, 2H), 7.15-7.30 (m, 5H), 7.50-7.53 (m, 2H), 7.66 (d, 2H), 7.94 (d, 2H), 9.80 (bs, 1H), 12.05 (bs, 1H), 12.47 (bs, 1H).

Example 55(20)

4-(2-{[(tert-butylsulfonyl)amino]carbonyl}-8-{[4-(4-phenylbutoxy)benzoyl]amino}-2,3-dihydro-4H-1,4-benzoxazin-4-yl)butanoic acid TLC: Rf 0.57 (chloroform:methanol:acetic acid=90:10:1);
NMR(DMSO-$d_6$): δ 1.18 (s, 9H), 1.70-1.78 (m, 6H), 2.26-2.31 (m, 2H), 2.61-2.67 (m, 2H), 3.19-3.25 (m, 2H), 3.32-3.38 (m, 1H), 3.55-3.58 (m, 1H), 4.07-4.08 (m, 2H), 5.09 (s, 1H), 6.64-6.68 (m, 1H), 6.81-6.84 (m, 2H), 7.03 (d, 2H), 7.15-7.31 (m, 5H), 7.92 (d, 2H), 9.85 (bs, 1H), 11.59 (bs, 1H), 12.07 (bs, 1H).

Example 55(21)

4-(8-{(E)-2-[4-(4-phenylbutoxy)phenyl]vinyl}-2-{[(phenylsulfonyl)amino]carbonyl}-2,3-dihydro-4H-1,4-benzoxazin-4-yl)butanoic acid TLC: Rf 0.29 (methylene chloride:methanol:acetic acid=95:5:0.5);
NMR(DMSO-$d_6$): δ 1.56-1.78 (m, 6H), 2.23 (t, 2H), 2.59-2.63 (m, 2H), 3.15-3.18 (m, 2H), 3.30-3.42 (m, 2H), 3.92-4.02 (m, 2H), 4.81-4.90 (m, 1H), 6.58 (d, 1H), 6.73 (t, 1H), 6.88-6.93 (m, 3H), 7.04 (d, 1H), 7.10-7.30 (m, 6H), 7.40 (d, 2H), 7.56-7.61 (m, 2H), 7.66-7.71 (m, 1H), 7.90 (d, 2H), 12.08 (brs, 1H), 12.46 (brs, 1H).

Example 56

4-{4-[(methylsulfonyl)amino]-4-oxobutyl}-8-{[4-(4-phenylbutoxy)benzoyl]amino}-3,4-dihydro-2H-1,4-benzoxazine-2-carboxylic acid The compound of the present invention having the following physical data was prepared by substituting the compound prepared in Example 33 for the compound prepared in Example 53, and substituting methanesulfonamide for benzenesulfonamide in the process of Example 54 Example 8.

TLC: Rf 0.31 (methylene chloride:methanol:acetic acid=90:10:1);
NMR(CDCl$_3$): δ 1.74-2.08 (m, 6H), 2.20-2.40 (m, 2H), 2.69 (t, 2H), 2.93-3.05 (m, 1H), 3.20 (s, 3H), 3.34-3.55 (m, 2H), 3.66-3.74 (m, 1H), 4.02 (t, 2H), 4.92-4.98 (m, 1H), 6.55-6.61 (m, 1H), 6.80-6.99 (m, 2H), 6.94 (d, 2H), 7.16-7.31 (m, 5H), 7.85 (d, 2H), 7.95 (brs, 1H).

Example 57

4-(3-carboxypropyl)-7-{(E)-2-[4-(4-phenylbutoxy)phenyl]vinyl}-3,4-dihydro-2H-1,4-benzoxazine-2-carboxylic acid The compound of the present invention was prepared by substituting 3-hydroxy-4-nitrobenzaldehyde for 2-hydroxy-3-nitrobenzaldehyde, and substituting (bromomethyl)benzene for 1-(chloromethyl)-4-methoxybenzene in the process of Example 42→Example 43→Example 44→Example 45→Example 6→Example 28→Example 8.

TLC: Rf 0.33 (methylene chloride:methanol:acetic acid=90:10:0.5);
NMR(DMSO-$d_6$): δ 1.48-1.86 (m, 6H), 2.26 (t, 2H), 2.54-2.70 (m, 2H), 3.06-3.60 (m, 4H), 3.85-4.17 (m, 2H), 4.85 (t, 1H), 6.69 (d, 1H), 6.81-7.02 (m, 5H), 7.10-7.32 (m, 6H), 7.42 (d, 1H).

Example 57(1)-Example 57(39)

The compounds of the present invention were prepared by substituting a corresponding compound for triphenyl[4-(4-phenylbutoxy)benzyl]phosphonium chloride in the process of Example 43→Example 44→Example 45→Example 6→Example 28→Example 8.

Example 57(1)

4-(3-carboxypropyl)-8-((E)-2-{4-[(5-phenylpentyl)oxy]phenyl}vinyl)-3,4-dihydro-2H-1,4-benzoxazine-2-carboxylic acid TLC: Rf 0.48 (methylene chloride:methanol:acetic acid=9:1:0.05);
NMR(DMSO-$d_6$): δ 1.25-1.49 (m, 2H), 1.54-1.85 (m, 6H), 2.13-2.34 (m, 2H), 2.54-2.71 (m, 2H), 3.02-3.27 (m, 2H), 3.45 (d, 2H), 3.96 (t, 2H), 4.98 (t, 1H), 6.63 (dd, 1H), 6.75 (dd, 1H), 6.86-7.01 (m, 3H), 7.03-7.31 (m, 7H), 7.37-7.52 (m, 2H), 12.22 (s, 2H).

Example 57(2)

4-(3-carboxypropyl)-8-{(E)-2-[4-(4-phenoxybutoxy)phenyl]vinyl}-3,4-dihydro-2H-1,4-benzoxazine-2-carboxylic acid TLC: Rf 0.44 (chloroform:methanol:acetic acid=90:10:1);
NMR(DMSO-d$_6$): δ 1.72 (quintet, 2H), 1.84-1.88 (m, 4H), 2.26 (t, 2H), 3.22-3.30 (m, 2H), 3.42-3.44 (m, 2H), 4.02-4.04 (m, 4H), 4.83 (t, 1H), 6.61 (d, 1H), 6.73 (t, 1H), 6.88-6.94 (m, 6H), 7.10 (d, 1H), 7.23-7.30 (m, 3H), 7.43 (d, 2H), 12.60 (bs, 2H).

Example 57(3)

4-(3-carboxypropyl)-8-{(E)-2-[4-(3-phenylpropoxy)phenyl]vinyl}-3,4-dihydro-2H-1,4-benzoxazine-2-carboxylic acid TLC: Rf 0.47 (chloroform:methanol:acetic acid=90:10:1);
NMR(DMSO-d$_6$): δ 1.73 (quintet, 2H), 2.01 (quintet, 2H), 2.27 (t, 2H), 2.74 (t, 2H), 3.21-3.26 (m, 2H), 3.45 (d, 2H), 3.97 (t, 2H), 4.98 (t, 1H), 6.64 (d, 1H), 6.75 (t, 1H), 6.91-6.95 (m, 3H), 7.07-7.31 (m, 7H), 7.43 (d, 2H), 12.28 (bs, 2H).

Example 57(4)

4-(3-carboxypropyl)-8-{(E)-2-[4-(2,3-dihydro-1H-inden-2-ylmethoxy)phenyl]vinyl}-3,4-dihydro-2H-1,4-benzoxazine-2-carboxylic acid TLC: Rf 0.43 (chloroform:methanol:acetic acid=90:10:1);
NMR(DMSO-d$_6$): δ 1.72 (quintet, 1H), 2.27 (t, 2H), 2.71-2.94 (m, 3H), 3.04-3.12 (m, 2H), 3.21-3.25 (m, 2H), 3.45 (d, 2H), 3.99 (d, 2H), 4.98 (t, 1H), 6.65 (d, 1H), 6.75 (t, 1H), 6.93-6.96 (m, 3H), 7.04-7.14 (m, 3H), 7.19-7.24 (m, 3H), 7.43 (d, 2H), 12.34 (bs, 2H).

Example 57(5)

4-(3-carboxypropyl)-8-((E)-2-{4-[(7-chloro-2-quinolinyl)methoxy]phenyl}vinyl)-3,4-dihydro-2H-1,4-benzoxazine-2-carboxylic acid TLC: Rf 0.42 (chloroform:methanol:acetic acid=90:10:1);
NMR(DMSO-d$_6$): δ 1.72 (quintet, 2H), 2.26 (t, 2H), 3.20-3.25 (m, 2H), 3.43 (d, 2H), 4.83 (s, 1H), 5.38 (s, 2H), 6.61 (d, 1H), 6.73 (t, 1H), 6.91 (d, 1H), 7.05-7.12 (m, 3H), 7.28 (d, 1H), 7.46 (d, 2H), 7.65 (dd, 1H), 7.71 (d, 1H), 8.05 (d, 2H), 8.46 (d, 1H), 12.61 (bs, 2H).

Example 57(6)

4-(3-carboxypropyl)-8-{(E)-2-[4-({3-[(7-chloro-2-quinolynyl)methoxy]benzyl}oxy)phenyl]vinyl}-3,4-dihydro-2H-1,4-benzoxazine-2-carboxylic acid TLC: Rf 0.44 (chloroform:methanol:acetic acid=90:10:1);
NMR(DMSO-d$_6$): δ 1.70-1.77 (m, 2H), 2.27 (t, 2H), 3.21-3.30 (m, 2H), 3.46 (d, 2H), 5.00 (t, 1H), 5.08 (s, 2H), 5.38 (s, 2H), 6.64 (d, 1H), 6.76 (t, 1H), 6.93-6.95 (m, 3H), 6.99-7.15 (m, 4H), 7.24 (d, 1H), 7.31 (t, 1H), 7.39 (d, 2H), 7.65 (dd, 1H), 7.69 (d, 1H), 8.03-8.07 (m, 2H), 8.44 (d, 1H), 12.06 (bs, 1H), 13.09 (bs, 1H).

Example 57(7)

4-(3-carboxypropyl)-8-{(E)-2-[4-(2,3-dihydro-1H-inden-2-yloxy)phenyl]vinyl}-3,4-dihydro-2H-1,4-benzoxazine-2-carboxylic acid TLC: Rf 0.34 (methylene chloride:methanol:acetic acid=90:10:0.5);
NMR (DMSO-d$_6$): δ 1.62-1.81 (m, 2H) 2.27 (t, 2H), 2.96-3.07 (m, 2H), 3.13-3.58 (m, 6H), 4.89-5.05 (m, 1H), 5.15-5.34 (m, 1H), 6.64 (d, 1H), 6.75 (t, 1H), 6.89-6.98 (m, 3H), 7.03-7.21 (m, 3H), 7.21-7.33 (m, 3H), 7.45 (d, 2H).

Example 57(8)

4-(3-carboxypropyl)-8-((E)-2-{4-[3-(2,3-dihydro-1H-inden-2-yl)propoxy]phenyl}vinyl)-3,4-dihydro-2H-1,4-benzoxazine-2-carboxylic acid TLC: Rf 0.50 (chloroform:methanol:acetic acid=90:10:1);
NMR(DMSO-d$_6$): δ 1.55-1.64 (m, 2H), 1.70-1.82 (m, 4H), 2.27 (t, 2H), 2.38-2.59 (m, 3H), 3.02 (dd, 2H), 3.21-3.30 (m, 2H), 3.44-3.45 (m, 2H), 4.00 (t, 2H), 4.97-4.98 (m, 1H), 6.63 (d, 1H), 6.75 (t, 1H), 6.91-6.94 (m, 3H), 7.07-7.28 (m, 6H), 7.43 (d, 2H), 12.54 (bs, 2H).

Example 57(9)

8-((E)-2-{4-[4-(benzyloxy)butoxy]phenyl}vinyl)-4-(3-carboxypropyl)-3,4-dihydro-2H-1,4-benzoxazine-2-carboxylic acid TLC: Rf 0.48 (chloroform:methanol:ethyl acetate=90:10:1);
NMR(DMSO-d$_6$): δ 1.62-1.80 (m, 6H), 2.27 (t, 2H), 3.21-3.29 (m, 2H), 3.45-3.51 (m, 4H), 3.99 (t, 2H), 4.46 (s, 2H), 4.99 (t, 1H), 6.64 (d, 1H), 6.76 (t, 1H), 6.92 (dd, 2H), 7.10 (d, 1H), 7.25 (d, 1H), 7.26-7.46 (m, 8H), 12.45 (bs, 2H).

Example 57(10)

4-(3-carboxypropyl)-8-((E)-2-{4-[(5-phenoxypentyl)oxy]phenyl}vinyl)-3,4-dihydro-2H-1,4-benzoxazine-2-carboxylic acid TLC: Rf 0.43 (chloroform:methanol:acetic acid=90:10:1);
NMR(DMSO-d$_6$): δ 1.41-1.64 (m, 2H), 1.70-1.85 (m, 6H), 2.27 (t, 2H), 3.21-3.29 (m, 2H), 3.45 (d, 2H), 3.99 (q, 4H), 4.97 (t, 1H), 6.63 (dt, 1H), 6.75 (t, 1H), 6.88-6.95 (m, 6H), 7.10 (d, 1H), 7.22-7.29 (m, 3H), 7.43 (d, 2H), 12.48 (bs, 2H).

Example 57(11)

4-(3-carboxypropyl)-8-((E)-2-{4-[4-(3-methoxyphenoxy)butoxy]phenyl}vinyl)-3,4-dihydro-2H-1,4-benzoxazine-2-carboxylic acid TLC: Rf 0.47 (chloroform:methanol:acetic acid=90:10:1);
NMR(DMSO-d$_6$): δ 1.66-1.78 (m, 2H), 1.84-1.99 (m, 4H), 2.27 (t, 2H), 3.21-3.26 (m, 2H), 3.45 (d, 2H), 3.71 (s, 3H), 4.01-4.05 (m, 4H), 4.97 (d, 1H), 6.48-6.53 (m, 3H), 6.63 (d, 1H), 6.75 (t, 1H), 7.10 (d, 1H), 7.18 (t, 1H), 7.24 (d, 1H), 7.44 (d, 2H), 12.45 (bs, 2H).

Example 57(12)

4-(3-carboxypropyl)-8-((E)-2-{4-[4-(4-methoxyphenoxy)butoxy]phenyl}vinyl)-3,4-dihydro-2H-1,4-benzoxazine-2-carboxylic acid TLC: Rf 0.55 (methylene chloride:methanol:water=8:2:0.2);
NMR(DMSO-d$_6$): δ 1.66-1.78 (m, 2H), 1.79-1.89 (m, 4H), 2.27 (t, 2H), 3.16-3.28 (m, 2H), 3.41-3.49 (m, 2H), 3.68 (s, 3H), 3.90-3.99 (m, 2H), 3.99-4.08 (m, 2H), 4.98 (t, 1H), 6.63 (d, 1H), 6.75 (t, 1H), 6.81-6.86 (m, 4H), 6.89-6.97 (m, 3H), 7.10 (d, 1H), 7.25 (d, 1H), 7.44 (d, 2H).

Example 57(13)

4-(3-carboxypropyl)-8-((E)-2-{4-[4-(3-methylphenoxy)butoxy]phenyl}vinyl)-3,4-dihydro-2H-1,4-benzoxazine-2-carboxylic acid TLC: Rf 0.38 (chloroform:methanol:acetic acid=90:10:1);
NMR(DMSO-d$_6$): δ 1.65-1.77 (m 2H), 1.84-1.86 (m, 4H), 2.27 (s, 3H), 2.27 (t, 3H), 3.21-2.25 (m, 2H), 3.44 (d, 2H), 3.97-4.04 (m, 4H), 4.95 (t, 1H), 6.62 (d, 1H), 6.69-6.77 (m, 4H), 6.92-6.95 (m, 3H), 7.07-7.16 (m, 2H), 7.26 (d, 1H), 7.44 (d, 2H), 12.60 (bs, 2H).

Example 57(14)

4-(3-carboxypropyl)-8-((E)-2-{4-[4-(3-fluorophenoxy)butoxy]phenyl}vinyl)-3,4-dihydro-2H-1,4-benzoxazine-2-carboxylic acid TLC: Rf 0.39 (chloroform:methanol:acetic acid=90:10:1);
NMR(DMSO-d$_6$): δ 1.65-1.77 (m, 2H), 1.85-1.87 (m, 4H), 2.27 (t, 2H), 3.21-3.27 (m, 2H), 3.45 (d, 2H), 4.03-4.05 (m, 4H), 4.96 (t, 1H), 6.63 (d, 1H), 6.70-6.83 (m, 4H), 6.92-6.95 (m, 3H), 7.10 (d, 1H), 7.23-7.33 (m, 2H), 7.44 (d, 2H), 12.61 (bs, 2H).

Example 57(15)

4-(3-carboxypropyl)-8-((E)-2-{4-[4-(2-methylphenoxy)butoxy]phenyl}vinyl)-3,4-dihydro-2H-1,4-benzoxazine-2-carboxylic acid TLC: Rf 0.53 (methylene chloride:methanol:water=8:2:0.2);
NMR(DMSO-d$_6$): δ 1.62-1.81 (m, 2H), 1.83-1.94 (m, 4H), 2.13 (s, 3H), 2.27 (t, 2H), 3.17-3.30 (m, 2H), 3.45 (d, 2H), 3.96-4.11 (m, 4H), 4.99 (t, 1H), 6.63 (d, 1H), 6.75 (t, 1H), 6.81 (t, 1H), 6.87-6.98 (m, 4H), 7.05-7.17 (m, 3H), 7.25 (d, 1H), 7.43 (d, 2H).

Example 57(16)

4-(3-carboxypropyl)-8-((E)-2-{4-[4-(4-fluorophenoxy)butoxy]phenyl}vinyl)-3,4-dihydro-2H-1,4-benzoxazine-2-carboxylic acid TLC: Rf 0.47 (methylene chloride:methanol:water=8:2:0.2);
NMR(DMSO-d$_6$): δ 1.63-1.80 (m, 2H), 1.78-1.93 (m, 4H), 2.27 (t, 2H), 3.15-3.31 (m, 2H), 3.38-3.49 (m, 2H), 3.91-4.11 (m, 4H), 4.74-4.86 (m, 1H), 6.61 (d, 1H), 6.72 (t, 1H), 6.87-6.97 (m, 5H), 7.04-7.15 (m, 3H), 7.25 (d, 1H), 7.43 (d, 2H).

Example 57(17)

4-(3-carboxypropyl)-8-((E)-2-{4-[4-(4-methylphenoxy)butoxy]phenyl}vinyl)-3,4-dihydro-2H-1,4-benzoxazine-2-carboxylic acid TLC: Rf 0.47 (methylene chloride:methanol:water=8:2:0.2);
NMR(DMSO-d$_6$): δ 1.65-1.79 (m, 2H), 1.81-1.90 (m, 4H), 2.21 (s, 3H), 2.27 (t, 2H), 3.18-3.28 (m, 2H), 3.44 (d, 2H), 3.92-4.10 (m, 4H), 4.96 (t, 1H), 6.63 (d, 1H), 6.74 (t, 1H), 6.81 (d, 2H), 6.90-6.97 (m, 3H), 7.03-7.14 (m, 3H), 7.25 (d, 1H), 7.43 (d, 2H).

Example 57(18)

4-(3-carboxypropyl)-8-((E)-2-{4-[4-(2-methoxyphenoxy)butoxy]phenyl}vinyl)-3,4-dihydro-2H-1,4-benzoxazine-2-carboxylic acid TLC: Rf 0.46 (methylene chloride:methanol:water=8:2:0.2);
NMR(DMSO-d$_6$): δ 1.64-1.81 (m, 2H), 1.82-1.93 (m, 4H), 2.27 (t, 2H), 3.17-3.29 (m, 2H), 3.41-3.53 (m, 2H), 3.73 (s, 3H), 3.95-4.10 (m, 4H), 4.92-4.98 (m, 1H), 6.62 (d, 1H), 6.74 (t, 1H), 6.83-6.99 (m, 7H), 7.09 (d, 1H), 7.25 (d, 1H), 7.44 (d, 2H).

Example 57(19)

4-(3-carboxypropyl)-8-((E)-2-{4-[4-(2-fluorophenoxy)butoxy]phenyl}vinyl)-3,4-dihydro-2H-1,4-benzoxazine-2-carboxylic acid TLC: Rf 0.53 (methylene chloride:methanol:water=8:2:0.2);
NMR(DMSO-d$_6$): δ 1.64-1.79 (m, 2H), 1.81-1.95 (m, 4H), 2.27 (t, 2H), 3.17-3.29 (m, 2H), 3.45 (d, 2H), 4.00-4.16 (m, 4H), 4.98 (t, 1H), 6.63 (d, 1H), 6.75 (t, 1H), 6.87-6.99 (m, 4H), 7.06-7.21 (m, 4H), 7.24 (d, 1H), 7.43 (d, 2H).

Example 57(20)

4-(3-carboxypropyl)-8-[(E)-2-(4-{4-[2-(methylsulfanil)phenoxy]butoxy}phenyl)vinyl]-3,4-dihydro-2H-1,4-benzoxazine-2-carboxylic acid TLC: Rf 0.41 (chloroform:methanol:acetic acid=90:10:1);
NMR(DMSO-d$_6$): δ 1.66-1.76 (m, 2H), 1.85-1.93 (m, 4H), 2.27 (t, 2H), 2.35 (s, 3H), 3.21-3.26 (m, 2H), 3.36-3.38 (m, 2H), 4.04-4.09 (m, 4H), 4.99 (t, 1H), 6.63 (d, 1H), 6.75 (t, 1H), 6.92-6.97 (m, 5H), 7.07-7.14 (m, 3H), 7.25 (d, 1H), 7.43 (d, 2H), 12.11 (bs, 1H), 12.99 (bs, 1H).

Example 57(21)

4-(3-carboxypropyl)-8-((E)-2-(4-[3-{4-chlorophenyl)propoxy]phenyl}vinyl)-3,4-dihydro-2H-1,4-benzoxazine-2-carboxylic acid TLC: Rf 0.39 (chloroform:methanol:acetic acid=90:10:1);
NMR(DMSO-d$_5$): δ 1.67-1.75 (m, 2H), 2.00 (quintet, 2H), 2.27 (t, 2H), 2.73 (t, 2H), 3.21-3.26 (m, 2H), 3.44 (d, 2H), 3.96 (t, 2H), 4.99 (t, 1H), 6.63 (t, 1H), 6.75 (t, 1H), 6.90-6.95 (m, 3H), 7.10 (d, 1H), 7.22-7.34 (m, 5H), 7.43 (d, 2H), 12.14 (bs, 1H), 12.94 (bs, 1H).

Example 57(22)

4-(3-carboxypropyl)-8-((E)-2-{4-[3-(4-methoxyphenyl)propoxy]phenyl}vinyl)-3,4-dihydro-2H-1,4-benzoxazine-2-carboxylic acid TLC: Rf 0.37 (chloroform:methanol:acetic acid=90:10:1);
NMR(DMSO-d$_6$): δ 1.67-1.76 (m, 2H), 1.97 (quintet, 2H), 2.27 (t, 2H), 2.67 (t, 2H), 3.21-3.26 (m, 2H), 3.45 (d, 2H), 3.70 (s, 3H), 3.95 (t, 2H), 4.99 (t, 1H), 6.63 (d, 1H), 6.75 (t, 1H), 6.83 (t, 2H), 6.90-6.95 (m, 3H), 7.07-7.15 (m, 3H), 7.25 (d, 1H), 7.43 (d, 2H), 12.07 (bs, 1H), 12.94 (bs, 1H).

Example 57(23)

4-(3-carboxypropyl)-8-((E)-2-{4-[3-(3-methylphenoxy)propoxy]phenyl}vinyl)-3,4-dihydro-2H-1,4-benzoxazine-2-carboxylic acid TLC: Rf 0.36 (chloroform:methanol:acetic acid=90:10:1);
NMR(DMSO-d$_6$): δ 1.67-1.75 (m, 2H), 2.15 (quintet, 2H), 2.25 (s, 3H), 2.22-2.29 (m, 2H), 3.21-3.26 (m, 2H), 3.45 (d, 2H), 4.07-4.15 (m, 4H), 4.98 (t, 1H), 6.63 (d, 1H), 6.71-6.77 (m, 4H), 6.93-6.96 (m, 3H), 7.07-7.17 (m, 2H), 7.26 (d, 1H), 7.43-7.46 (m, 2H), 12.65 (bs, 2H).

Example 57(24)

4-(3-carboxypropyl)-8-((E)-2-{4-[3-(3-fluorophenoxy)propoxy]phenyl}vinyl)-3,4-dihydro-2H-1,4-benzoxazine-2-carboxylic acid TLC: Rf 0.40 (chloroform:methanol:acetic acid=90:10:1);
NMR(DMSO-d$_6$): δ 1.67-1.75 (m, 2H), 2.16 (quintet, 2H), 2.27 (t, 2H), 3.21-3.26 (m, 2H), 3.45 (d, 2H), 4.11-4.17 (m, 4H), 4.98 (s, 1H), 6.63 (d, 1H), 6.72-6.86 (m, 4H), 6.85-6.96 (m, 3H), 7.10 (d, 1H), 7.23-7.34 (m, 2H), 7.44 (d, 2H), 12.54 (bs, 2H).

Example 57(25)

4-(3-carboxypropyl)-8-((E)-2-{4-[3-(3-methoxyphenoxy)propoxy]phenyl}vinyl)-3,4-dihydro-2H-1,4-benzoxazine-2-carboxylic acid TLC: Rf 0.38 (chloroform:methanol:acetic acid=90:10:1);
NMR(DMSO-d$_6$): δ 1.67-1.75 (m, 2H), 2.15 (quintet, 2H), 2.26 (t, 2H), 3.21-3.25 (m, 2H), 3.44 (d, 2H), 3.71 (s, 3H), 4.12 (q, 4H), 4.97 (t, 1H), 6.49-6.54 (m, 3H), 6.63 (d, 1H), 6.75 (t, 1H), 6.92-6.96 (m, 3H), 7.07-7.29 (m, 3H), 7.44 (d, 2H), 12.49 (bs, 2H).

Example 57(26)

4-(3-carboxypropyl)-8-((E)-2-{4-[3-(4-methylphenoxy)propoxy]phenyl}vinyl)-3,4-dihydro-2H-1,4-benzoxazine-2-carboxylic acid TLC: Rf 0.67 (methylene chloride:methanol:water=8:2:0.2);
NMR(DMSO-d$_6$): δ 1.65-1.79 (m, 2H), 2.09-2.19 (m, 2H), 2.21 (s, 3H), 2.27 (t, 2H), 3.19-3.29 (m, 2H), 3.45 (d, 2H), 4.04-4.17 (m, 4H), 5.00 (t, 1H), 6.64 (d, 1H), 6.75 (t, 1H), 6.83 (d, 2H), 6.91-6.99 (m, 3H), 7.03-7.15 (m, 3H), 7.26 (d, 1H), 7.44 (d, 2H).

Example 57(27)

4-(3-carboxypropyl)-8-((E)-2-{4-[3-(2-methylphenoxy)propoxy]phenyl}vinyl)-3,4-dihydro-2H-1,4-benzoxazine-2-carboxylic acid TLC: Rf 0.65 (methylene chloride:methanol:water=8:2:0.2);
NMR(DMSO-d$_6$): δ 1.65-1.79 (m, 2H), 2.14 (s, 3H), 2.16-2.23 (m, 2H), 2.27 (t, 2H), 3.19-3.28 (m, 2H), 3.45 (d, 2H), 4.12 (t, 2H), 4.17 (t, 2H), 5.00 (t, 1H), 6.64 (d, 1H), 6.75 (t, 1H), 6.82 (t, 1H), 6.91-6.99 (m, 4H), 7.06-7.17 (m, 3H), 7.25 (d, 1H), 7.44 (d, 2H).

Example 57(28)

4-(3-carboxypropyl)-8-((E)-2-{4-[3-(4-fluorophenoxy)propoxy]phenyl}vinyl)-3,4-dihydro-2H-1,4-benzoxazine-2-carboxylic acid TLC: Rf 0.39 (methylene chloride:methanol:acetic acid=90:10:0.5);
NMR(DMSO-d$_6$): δ 1.64-1.80 (m, 2H), 2.08-2.22 (m, 2H), 2.27 (t, 2H), 3.17-3.28 (m, 2H), 3.45 (d, 2H), 4.06-4.17 (m, 4H), 4.93-5.02 (m, 1H), 6.63 (d, 1H), 6.75 (t, 1H), 6.90-7.01 (m, 5H), 7.04-7.16 (m, 3H), 7.26 (d, 1H), 7.44 (d, 2H).

Example 57(29)

4-(3-carboxypropyl)-8-((E)-2-{4-[3-(4-methoxyphenoxy)propoxy]phenyl}vinyl)-3,4-dihydro-2H-1,4-benzoxazine-2-carboxylic acid TLC: Rf 0.36 (methylene chloride:methanol:acetic acid=90:10:0.5);
NMR(DMSO-d$_6$): δ 1.61-1.81 (m, 2H), 2.04-2.20 (m, 2H), 2.27 (t, 2H), 3.15-3.30 (m, 2H), 3.45 (d, 2H), 3.68 (s, 3H), 4.06 (t, 2H), 4.09-4.17 (m, 2H), 4.91-5.02 (m, 1H), 6.63 (dd, 1H), 6.75 (t, 1H), 6.79-6.99 (m, 7H), 7.10 (d, 1H), 7.26 (d, 1H), 7.44 (d, 2H).

Example 57(30)

4-(3-carboxypropyl)-8-((E)-2-{4-[3-(3-chlorophenoxy)propoxy]phenyl}vinyl)-3,4-dihydro-2H-1,4-benzoxazine-2-carboxylic acid TLC: Rf 0.50 (chloroform:methanol:acetic acid=90:10:1);
NMR(DMSO-d$_6$): δ 1.65-1.76 (m, 2H), 2.16 (quintet, 2H), 2.26 (t, 2H), 3.19-3.25 (m, 2H), 3.43-3.44 (m, 2H), 4.14 (q, 4H), 4.92-4.94 (m, 1H), 6.62 (d, 1H), 6.74 (t, 1H), 6.92-7.12 (m, 7H), 7.23-7.32 (m, 2H), 7.44 (d, 2H), 12.59 (bs, 2H).

Example 57(31)

4-(3-carboxypropyl)-8-((E)-2-{4-[2-(2,3-dihydro-1H-inden-2-yl)ethoxy]phenyl}vinyl)-3,4-dihydro-2H-1,4-benzoxazine-2-carboxylic acid TLC: Rf 0.49 (chloroform:methanol:acetic acid=90:10:1);
NMR(DMSO-d$_6$): δ 1.66-1.77 (m, 2H), 1.89-1.95 (m, 2H), 2.27 (t, 2H), 2.48-2.67 (m, 3H), 2.99-3.07 (m, 2H), 3.21-3.26 (m, 2H), 3.45 (d, 2H), 4.07 (t, 2H), 4.98 (t, 1H), 6.63 (d, 1H), 6.75 (t, 1H), 6.94-6.97 (m, 3H), 7.08-7.29 (m, 6H), 7.45 (d, 2H), 12.58 (bs, 2H).

Example 57(32)

4-(3-carboxypropyl)-8-{(E)-2-[4-(3-phenoxypropoxy)phenyl]vinyl}-3,4-dihydro-2H-1,4-benzoxazine-2-carboxylic acid TLC: Rf 0.36 (methylene chloride:methanol:acetic acid=90:10:0.5);
NMR(DMSO-$d_6$): δ 1.63-1.82 (m, 2H), 2.08-2.32 (m, 4H), 3.09-3.52 (m, 4H), 4.07-4.18 (m, 4H), 4.77-4.98 (m, 1H), 6.62 (d, 1H), 6.73 (t, 1H), 6.86-7.00 (m, 6H), 7.09 (d, 1H), 7.21-7.32 (m, 3H), 7.44 (d, 2H).

Example 57(33)

4-(3-carboxypropyl)-8-((E)-2-{4-[3-(2-chlorophenoxy)propoxy]phenyl}vinyl)-3,4-dihydro-2H-1,4-benzoxazine-2-carboxylic acid TLC: Rf 0.36 (methylene chloride:methanol:acetic acid=90:10:0.5);
NMR(DMSO-$d_6$): δ 1.62-1.81 (m, 2H), 2.11-2.34 (m, 4H), 3.11-3.55 (m, 4H), 4.09-4.29 (m, 4H), 4.93 (t, 1H), 6.58-6.66 (m, 1H), 6.74 (t, 1H), 6.88-7.00 (m, 4H), 7.10 (d, 1H), 7.14-7.35 (m, 3H), 7.36-7.50 (m, 3H).

Example 57(34)

4-(3-carboxypropyl)-8-((E)-2-{4-[4-(2-chlorophenoxy)butoxy]phenyl}vinyl)-3,4-dihydro-2H-1,4-benzoxazine-2-carboxylic acid TLC: Rf 0.31 (chloroform:methanol:acetic acid=90:10:1);
NMR(DMSO-$d_6$): δ 1.63-1.80 (m, 2H), 1.83-1.96 (m, 4H), 2.27 (t, 2H), 3.19-3.26 (m, 2H), 3.45 (d, 2H), 4.02-4.17 (m, 4H), 4.95 (t, 1H), 6.63 (d, 1H), 6.75 (t, 1H), 6.89-6.99 (m, 4H), 7.03-7.34 (m, 4H), 7.36-7.48 (m, 3H), 12.49 (bs, 2H).

Example 57(35)

4-(3-carboxypropyl)-8-((E)-2-{4-[4-(3-chlorophenoxy)butoxy]phenyl}vinyl)-3,4-dihydro-2H-1,4-benzoxazine-2-carboxylic acid TLC: Rf 0.32 (chloroform:methanol:acetic acid=90:10:1);
NMR(DMSO-$d_6$): δ 1.62-1.79 (m, 2H), 1.73-1.86 (m, 4H), 2.27 (t, 2H), 3.19-3.26 (m, 2H), 3.44 (d, 2H), 3.95-4.12 (m, 4H), 4.93 (t, 1H), 6.62 (d, 1H), 6.74 (t, 1H), 6.85-7.04 (m, 6H), 7.09 (d, 1H), 7.20-7.34 (m, 2H), 7.44 (d, 2H), 12.43 (bs, 2H).

Example 57(36)

4-(3-carboxypropyl)-8-((E)-2-{4-[4-(2,6-dichlorophenoxy)butoxy]phenyl}vinyl)-3,4-dihydro-2H-1,4-benzoxazine-2-carboxylic acid TLC: Rf 0.37 (chloroform:methanol:acetic acid=90:10:1);
NMR (DMSO-$d_6$): δ 1.62-1.81 (m, 2H), 1.86-2.00 (m, 4H), 2.27 (t, 2H), 3.17-3.26 (m, 2H), 3.45 (d, 2H), 3.97-4.15 (m, 4H), 4.97 (t, 1H), 6.63 (d, 1H), 6.75 (t, 1H), 6.93-6.95 (m, 1H), 6.94 (d, 2H), 7.10 (d, 1H), 7.16 (dd, 1H), 7.26 (d, 1H), 7.44 (d, 2H), 7.49 (d, 2H), 12.65 (bs, 2H).

Example 57(37)

4-(3-carboxypropyl)-8-((E)-2-{4-[4-(2,6-dimethylphenoxy)butoxy]phenyl}vinyl)-3,4-dihydro-2H-1,4-benzoxazine-2-carboxylic acid TLC: Rf 0.32 (chloroform:methanol:acetic acid=90:10:1);
NMR(DMSO-$d_6$): δ 1.63-1.80 (m, 2H), 1.81-2.02 (m, 4H), 2.21 (s, 6H), 2.27 (t, 2H), 3.19-3.27 (m, 2H), 3.44 (d, 2H), 3.78 (t, 2H), 4.07 (t, 2H), 4.93 (t, 1H), 6.63 (d, 1H), 6.75 (t, 1H), 6.83-7.05 (m, 6H), 7.26 (d, 1H), 7.10 (d, 1H), 7.44 (d, 2H), 12.58 (bs, 2H).

Example 57(38)

4-(3-carboxypropyl)-8-((E)-2-{4-[4-(2-chloro-6-methylphenoxy)butoxy]phenyl}vinyl)-3,4-dihydro-2H-1,4-benzoxazine-2-carboxylic acid TLC: Rf 0.33 (chloroform:methanol:acetic acid=90:10:1);
NMR(DMSO-$d_6$): δ 1.66-1.80 (m, 2H), 1.85-2.02 (m, 4H), 2.27 (s, 3H), 2.25-2.29 (t, 2H), 3.18-3.26 (m, 2H), 3.44 (d, 2H), 3.93 (t, 2H), 4.07 (t, 2H), 4.90 (t, 1H), 6.63 (d, 1H), 6.74 (t, 1H), 6.88-7.34 (m, 8H), 7.44 (d, 2H), 12.50 (bs, 2H).

Example 57(39)

4-(3-carboxypropyl)-7-{(E)-2-[4-(4-phenylethoxy)phenyl]vinyl}-3,4-dihydro-2H-1,4-benzoxazine-2-carboxylic acid TLC: Rf 0.26 (methylene chloride:methanol:acetic acid=90:10:0.5);
NMR(DMSO-$d_6$): δ 1.59-1.82 (m, 2H), 2.27 (t, 2H), 3.03 (t, 2H), 3.17-3.28 (m, 2H), 3.44 (d, 2H), 4.20 (t, 2H), 4.91-5.03 (m, 1H), 6.57-6.67 (m, 1H), 6.75 (t, 1H), 6.88-6.98 (m, 3H), 7.09 (d, 1H), 7.15-7.37 (m, 7H), 7.43 (d, 2H).

Example 58

4-(3-carboxypropyl)-8-{2-[4-(4-phenoxybutoxy)phenyl]ethyl}-3,4-dihydro-2H-1,4-benzoxazine-2-carboxylic acid The compound of the present invention having the following physical data was prepared by substituting triphenyl[4-(4-phenoxybutoxy)benzyl]phosphonium chloride for triphenyl[4-(4-phenylbutoxy)benzyl]phosphonium chloride in the process of Example 43→Example 44→Example 45→Example 6→Example 28→Example 47→Example 48→Example 49.
TLC: Rf 0.47 (chloroform:methanol:acetic acid=90:10:1);
NMR(DMSO-$d_5$): δ 1.71 (quintet, 2H), 1.81-1.87 (m, 4H), 2.25 (td, 2H), 2.67-2.89 (m, 4H), 3.18-3.23 (m, 2H), 3.36-3.40 (m, 2H), 3.98-4.03 (m, 4H), 4.78 (t, 1H), 6.38 (dd, 1H), 6.54-6.64 (m, 2H), 6.81 (d, 2H), 6.88-6.93 (m, 3H), 7.11 (d, 2H), 7.24-7.29 (m, 2H), 12.55 (bs, 2H).

Example 58(1)-Example 58(17)

The compounds of the present invention having the following physical data were prepared by substituting corresponding compounds for triphenyl[4-(4-phenylbutoxy)benzyl]phosphonium chloride in the process of Example 43→Example 44→Example 45→Example 6→Example 28→Example 47→Example 48→Example 49.

Example 58(1)

4-(3-carboxypropyl)-8-{2-[4-(3-phenylpropoxy)phenyl]ethyl}-3,4-dihydro-2H-1,4-benzoxazine-2-carboxylic acid TLC: Rf 0.55 (chloroform:methanol:acetic acid=90:10:1);
NMR(DMSO-$d_6$): δ 1.63-1.78 (m, 2H), 1.94-2.03 (m, 2H), 2.26 (t, 2H), 2.67-2.85 (m, 6H), 3.21 (t, 2H), 3.42 (t, 2H), 3.91 (t, 2H), 4.92 (t, 1H), 6.40 (dd, 1H), 6.56-6.66 (m, 2H), 6.80 (d, 2H), 7.10 (d, 2H), 7.15-7.30 (m, 5H), 12.34 (bs, 2H).

Example 58(2)

4-(3-carboxypropyl)-8-{2-[4-(2,3-dihydro-1H-inden-2-ylmethoxy)phenyl]ethyl}-3,4-dihydro-2H-1,4-benzoxazine-2-carboxylic acid TLC: Rf 0.54 (chloroform:methanol:acetic acid=90:10:1);
NMR(DMSO-$d_6$): δ 1.71 (quintet, 2H), 2.26 (t, 2H), 2.66-2.90 (m, 7H), 3.03-3.10 (m, 2H), 3.21 (t, 2H), 3.42 (t, 2H), 3.92 (d, 2H), 4.91 (t, 1H), 6.40 (dd, 1H), 6.55-6.66 (m, 2H), 6.83 (d, 2H), 7.08-7.14 (m, 4H), 7.19-7.23 (m, 2H), 12.36 (bs, 2H).

Example 58(3)

4-(3-carboxypropyl)-8-(2-{4-[3-(2,3-dihydro-1H-inden-2-yl)propoxy]phenyl}ethyl)-3,4-dihydro-2H-1,4-benzoxazine-2-carboxylic acid TLC: Rf 0.56 (chloroform:methanol:acetic acid=90:10:1);
NMR(DMSO-$d_5$): δ 1.55-1.60 (m, 2H), 1.69-1.80 (m, 4H), 2.26 (t, 2H), 2.39-2.58 (m, 3H), 2.66-2.84 (m, 4H), 3.01 (dd, 2H), 3.19 (t 2H), 3.40-3.41 (m, 2H), 3.93 (t, 2H), 4.80-4.81 (m, 1H), 6.38 (d, 1H), 6.54-6.64 (m, 2H), 6.80 (d, 2H), 6.06-7.18 (m, 6H), 12.50 (bs, 2H).

Example 58(4)

4-(3-carboxypropyl)-8-(2-{4-[(5-phenoxypentyl)oxy]phenyl}ethyl)-3,4-dihydro-2H-1,4-benzoxazine-2-carboxylic acid TLC: Rf 0.59 (chloroform:methanol:acetic acid=90:10:1);
NMR(DMSO-$d_6$): δ 1.33-1.62 (m, 2H), 1.69-1.81 (m, 6H), 2.26 (d, 2H), 2.68-2.86 (m, 4H), 3.18-3.25 (m, 2H), 3.37-3.41 (m, 2H), 3.91-3.99 (m, 4H), 4.79 (bs, 1H), 6.38 (d, 1H), 6.54-6.66 (m, 2H), 6.80 (d, 2H), 6.88-6.92 (m, 3H), 7.10 (d, 2H), 7.23-7.29 (m, 2H), 12.17 (bs, 2H).

Example 58(5)

4-(3-carboxypropyl)-8-(2-{4-[4-(3-methoxyphenoxy)butoxy]phenyl}ethyl)-3,4-dihydro-2H-1,4-benzoxazine-2-carboxylic acid TLC: Rf 0.53 (chloroform:methanol:acetic acid=90:10:1);
NMR(DMSO-$d_6$): δ 1.58-1.77 (m, 2H), 1.82-1.84 (m, 4H), 2.26 (t, 2H), 2.66-2.86 (m, 4H), 3.18-3.23 (m, 2H), 3.40-3.42 (m, 2H), 3.71 (s, 3H), 3.97-4.00 (m, 4H), 4.90 (t, 1H), 6.40 (d, 1H), 6.47-6.51 (m, 3H), 6.56-6.66 (m, 2H), 6.81 (d, 2H), 7.10 (d, 2H), 7.15 (t, 1H), 12.54 (bs, 2H).

Example 58(6)

4-(3-carboxypropyl)-8-(2-{4-[4-(4-methoxyphenoxy)butoxy]phenyl}ethyl)-3,4-dihydro-2H-1,4-benzoxazine-2-carboxylic acid TLC: Rf 0.59 (methylene chloride:methanol:water=8:2:0.2);
NMR(DMSO-$d_6$): δ 1.66-1.76 (m, 2H), 1.78-1.88 (m, 4H), 2.26 (t, 2H), 2.63-2.87 (m, 4H), 3.15-3.25 (m, 2H), 3.37-3.46 (m, 2H), 3.68 (s, 3H), 3.89-4.02 (m, 4H), 4.84-4.89 (m, 1H), 6.37-6.41 (m, 1H), 6.53-6.66 (m, 2H), 6.77-6.87 (m, 6H), 7.10 (d, 2H).

Example 58(7)

4-(3-carboxypropyl)-8-(2-{4-[4-(3-methylphenoxy)butoxy]phenyl}ethyl)-3,4-dihydro-2H-1,4-benzoxazine-2-carboxylic acid TLC: Rf 0.41 (chloroform:methanol:acetic acid=90:10:1);
NMR(DMSO-$d_6$): δ 1.65-1.77 (m, 2H), 1.82-1.84 (m, 4H), 2.25 (s, 3H), 2.23-2.27 (m, 2H), 2.66-2.86 (m, 4H), 3.18-3.23 (m, 2H), 3.40-3.42 (m, 2H), 3.97-3.98 (s, 4H), 4.85-4.87 (m, 1H), 6.39 (d, 1H), 6.55-6.65 (m, 2H), 6.69-6.73 (m, 3H), 6.81 (d, 2H), 7.09-7.16 (m, 3H), 12.64 (bs, 2H).

Example 58(8)

4-(3-carboxypropyl)-8-(2-{4-[4-(3-fluorophenoxy)butoxy]phenyl}ethyl)-3,4-dihydro-2H-1,4-benzoxazine-2-carboxylic acid TLC: Rf 0.43 (chloroform:methanol:acetic acid=90:10:1);
NMR(DMSO-$d_6$): δ 1.65-1.75 (m, 2H), 1.83-1.85 (m, 4H), 2.26 (t, 2H), 2.66-2.85 (m, 4H), 3.18-3.23 (m, 2H), 3.40-3.42 (m, 2H), 3.97-4.03 (m, 4H), 4.85-4.87 (m, 1H), 6.39 (d, 1H), 6.55-6.65 (m, 2H), 6.71-6.82 (m, 4H), 7.11 (d, 2H), 7.25-7.33 (m, 2H), 12.59 (bs, 2H).

Example 58(9)

4-(3-carboxypropyl)-8-(2-{4-[4-(2-methylphenoxy)butoxy]phenyl}ethyl)-3,4-dihydro-2H-1,4-benzoxazine-2-carboxylic acid TLC: Rf 0.63 (methylene chloride:methanol:water=8:2:0.2);
NMR(DMSO-$d_6$): δ 1.65-1.77 (m, 2H), 1.83-1.92 (m, 4H), 2.13 (s, 3H), 2.26 (t, 2H), 2.60-2.87 (m, 4H), 3.16-3.26 (m, 2H), 3.39-3.45 (m, 2H), 3.94-4.05 (m, 4H), 4.90 (t, 1H), 6.39 (d, 1H), 6.54-6.66 (m, 2H), 6.76-6.85 (m, 3H), 6.90 (d, 1H), 7.05-7.16 (m, 4H).

Example 58(10)

4-(3-carboxypropyl)-8-(2-{4-[4-(4-methylphenoxy)butoxy]phenyl}ethyl)-3,4-dihydro-2H-1,4-benzoxazine-2-carboxylic acid TLC: Rf 0.60 (methylene chloride:methanol:water=8:2:0.2);
NMR(DMSO-$d_6$): δ 1.65-1.77 (m, 2H), 1.78-1.88 (m, 4H), 2.21 (s, 3H), 2.26 (t, 2H), 2.62-2.87 (m, 4H), 3.15-3.25 (m, 2H), 3.38-3.45 (m, 2H), 3.91-4.01 (m, 4H), 4.86-4.92 (m, 1H), 6.39 (d, 1H), 6.53-6.66 (m, 2H), 6.77-6.85 (m, 4H), 7.02-7.13 (m, 4H).

Example 58(11)

4-(3-carboxypropyl)-8-(2-{4-[4-(2-methoxyphenoxy)butoxy]phenyl}ethyl)-3,4-dihydro-2H-1,4-benzoxazine-2-carboxylic acid TLC: Rf 0.67 (methylene chloride:methanol:water=8:2:0.2);
NMR(DMSO-$d_6$): δ 1.63-1.78 (m, 2H), 1.79-1.89 (m, 4H), 2.26 (t, 2H), 2.62-2.89 (m, 4H), 3.15-3.25 (m, 2H), 3.39-3.46 (m, 2H), 3.73 (s, 3H), 3.94-4.04 (m, 4H), 4.89 (t, 1H), 6.36-6.42 (m, 1H), 6.53-6.66 (m, 2H), 6.81 (d, 2H), 6.83-6.90 (m, 2H), 6.91-6.99 (m, 2H), 7.10 (d, 2H).

Example 58(12)

4-(3-carboxypropyl)-8-(2-{4-[4-(2-fluorophenoxy)butoxy]phenyl}ethyl)-3,4-dihydro-2H-1,4-benzoxazine-2-carboxylic acid TLC: Rf 0.64 (methylene chloride:methanol:water=8:2:0.2);
NMR(DMSO-$d_6$): δ 1.64-1.78 (m, 2H), 1.81-1.93 (m, 4H), 2.26 (t, 2H), 2.64-2.88 (m, 4H), 3.15-3.25 (m, 2H), 3.39-3.45 (m, 2H), 3.98 (t, 2H), 4.09 (t, 2H), 4.91 (t, 1H), 6.40 (d, 1H), 6.54-6.66 (m, 2H), 6.81 (d, 2H), 6.87-6.96 (m, 1H), 7.06-7.24 (m, 5H).

Example 58(13)

4-(3-carboxypropyl)-8-(2-{4-[3-(4-methylphenoxy)propoxy]phenyl}ethyl)-3,4-dihydro-2H-1,4-benzoxazine-2-carboxylic acid TLC: Rf 0.64 (methylene chloride:methanol:water=8:2:0.2);
NMR(DMSO-$d_6$): δ 1.64-1.77 (m, 2H), 2.06-2.17 (m, 2H), 2.21 (s, 3H), 2.26 (t, 2H), 2.62-2.86 (m, 4H), 3.16-3.25 (m, 2H), 3.39-3.45 (m, 2H), 4.06 (t, 4H), 4.91 (t, 1H), 6.36-6.43 (m, 1H), 6.53-6.67 (m, 2H), 6.82 (d, 4H), 7.06 (d, 2H), 7.10 (d, 2H).

Example 58(14)

4-(3-carboxypropyl)-8-(2-{4-[3-(2-methylphenoxy)propoxy]phenyl}ethyl)-3,4-dihydro-2H-1,4-benzoxazine-2-carboxylic acid TLC: Rf 0.69 (methylene chloride:methanol:water=8:2:0.2);
NMR(DMSO-$d_6$): δ 1.64-1.78 (m, 2H), 2.11-2.21 (m, 2H), 2.14 (s, 3H), 2.26 (t, 2H), 2.64-2.87 (m, 4H), 3.16-3.25 (m, 2H), 3.39-3.45 (m, 2H), 4.11 (t, 4H), 4.92 (t, 1H), 6.37-6.42 (m, 1H), 6.54-6.67 (m, 2H), 6.78-6.87 (m, 3H), 6.93 (d, 1H), 7.07-7.17 (m, 4H).

Example 58(15)

4-(3-carboxypropyl)-8-(2-{4-[3-(3-methylphenoxy)propoxy]phenyl}ethyl)-3,4-dihydro-2H-1,4-benzoxazine-2-carboxylic acid TLC: Rf 0.38 (chloroform:methanol:acetic acid=90:10:1);
NMR(DMSO-$d_6$): δ 1.55-1.83 (m, 2H), 2.12 (quintet, 2H), 2.25 (s, 3H), 2.24-2.27 (m, 2H), 2.72-2.85 (m, 4H), 3.16-3.23 (m, 2H), 3.40-3.43 (m, 2H), 4.07 (d, 4H), 4.90 (s, 1H), 6.39 (q, 1H), 6.56-6.64 (m, 2H), 6.71-6.75 (m, 3H), 6.83 (d, 2H), 7.09-7.16 (m, 3H).

Example 58(16)

4-(3-carboxypropyl)-8-(2-{4-[3-(3-fluorophenoxy)propoxy]phenyl}ethyl)-3,4-dihydro-2H-1,4-benzoxazine-2-carboxylic acid TLC: Rf 0.41 (chloroform:methanol:acetic acid=90:10:1);
NMR(DMSO-$d_6$): δ 1.67-1.75 (m, 2H), 2.09-2.17 (m, 2H), 2.23-2.27 (m, 2H), 2.72-2.80 (m, 4H), 3.18-3.25 (m, 2H), 3.42-3.50 (m, 2H), 4.05-4.15 (m, 4H), 4.88 (s, 1H), 6.39 (d, 1H), 6.55-6.64 (m, 2H), 6.71-6.84 (m, 5H), 7.10 (d, 2H), 7.24-7.32 (m, 1H).

Example 58(17)

4-(3-carboxypropyl)-8-(2-{4-[3-(3-methoxyphenoxy)propoxy]phenyl}ethyl)-3,4-dihydro-2H-1,4-benzoxazine-2-carboxylic acid TLC: Rf 0.42 (chloroform:methanol:acetic acid=90:10:1);
NMR(DMSO-$d_6$): δ 1.67-1.75 (m, 2H), 2.10-2.16 (m, 2H), 2.24-2.27 (m, 2H), 2.72-2.82 (m, 4H), 3.20-3.26 (m, 2H), 3.49-3.51 (m, 2H), 3.71 (s, 3H), 4.08 (d, 4H), 4.92 (s, 1H), 6.39 (d, 1H), 6.48-6.62 (m, 4H), 6.82 (d, 1H), 7.09-7.18 (m, 4H).

Example 59 ethyl 4-[8-{[4-(4-phenylbutoxy)benzoyl]amino}-2-(1H-tetrazol-5-yl)-2,3-dihydro-4H-1,4-benzoxazin-4-yl]butanoate The compound of the present invention having the following physical data was prepared by substituting the compound prepared in Example 24 for the compound prepared in Example 10 in the process of Example 28→Example 47→Example 48→Example 10→Example 12.

TLC: Rf 0.39 (methylene chloride:methanol=9:1);
NMR(DMSO-$d_6$): δ 1.15 (t, 3H), 1.62-1.82 (m, 6H), 2.30 (t, 2H), 2.64 (t, 2H), 3.25-3.30 (m, 2H), 3.62-3.78 (m, 2H), 4.00-4.08 (m, 4H), 5.86 (t, 1H), 6.61 (d, 1H), 6.81 (t, 1H), 7.03 (d, 2H), 7.08-7.29 (m, 6H), 7.90 (d, 2H), 9.48 (s, 1H).

Example 59(1)

4-[8-{2-[4-(4-phenylbutoxy)phenyl]ethyl}-2-(1H-tetrazol-5-yl)-2,3-dihydro-4H-1,4-benzoxazin-4-yl]butanoic acid The compound having the following physical data was prepared by substituting the compound prepared in Example 45 for the compound prepared in Example 5 in the process of Example 6→Example 9→Example 28→Example 47→Example 10→Example 12→Example 48→Example 8.

TLC: Rf 0.40 (methylene chloride:methanol:acetic acid=90:10:1);
NMR(DMSO-$d_6$): δ 1.61-1.79 (m, 6H), 2.25 (t, 2H), 2.55-2.87 (m, 6H), 3.20-3.38 (m, 2H), 3.51-3.68 (m, 2H), 3.80-

3.95 (m, 2H), 5.61 (dd, 1H), 6.45 (d, 1H), 6.65-6.76 (m, 4H), 7.03 (d, 2H), 7.12-7.28 (m, 5H), 12.07 (brs, 1H).

Example 59(2)

ethyl 4-[8-{(E)-2-[4-(4-phenylbutoxy)phenyl]vinyl}-2-(1H-tetrazol-5-yl)-2,3-dihydro-4H-1,4-benzoxazin-4-yl]butanoate The compound having the following physical data was prepared by substituting the compound prepared in Example 45 for the compound prepared in Example 5 in the process of Example 6→Example 9→Example 28→Example 47→Example 10→Example 12.

TLC: Rf 0.32 (methylene chloride:methanol=9:1);

NMR(CDCl$_3$): δ 1.24 (t, 3H), 1.73-1.96 (m, 6H), 2.29-2.34 (m, 2H), 2.69 (t, 2H), 3.22-3.38 (m, 2H), 3.55 (dd, 1H), 3.75 (dd, 1H), 3.98 (t, 2H), 4.12 (q, 2H), 5.82 (dd, 1H), 6.67 (dd, 1H), 6.84-6.92 (m, 3H), 7.00-7.05 (m, 2H), 7.15-7.31 (m, 6H), 7.42 (d, 2H).

Example 59(3)

4-[8-{(E)-2-[4-(4-phenylbutoxy)phenyl]vinyl}-2-(1H-tetrazol-5-yl)-2,3-dihydro-4H-1,4-benzoxazin-4-yl]butanoic acid The compound of the present invention having the following physical data was prepared by substituting the compound prepared in Example 45 for the compound prepared in Example 5 in the process of Example 6→Example 9→Example 28→Example 47→Example 10→Example 12→Example 8.

TLC: Rf 0.46 (methylene chloride:methanol:acetic acid=90:10:1);

NMR(DMSO-d$_5$): δ 1.61-1.83 (m, 6H), 2.28 (t, 2H), 2.63 (t, 2H), 3.30-3.41 (m, 2H), 3.60 (dd, 1H), 3.74 (dd, 1H), 3.95-4.02 (m, 2H), 5.73 (dd, 1H), 6.70 (d, 1H), 6.82 (t, 1H), 6.91 (d, 2H), 6.99 (d, 1H), 7.08 (d, 1H), 7.14-7.30 (m, 5H), 7.36 (d, 1H), 7.48 (d, 2H), 12.12 (brs, 1H).

Example 60

4-(2-(aminocarbonyl)-8-{(E)-2-[4-(4-phenylbutoxy)phenyl]vinyl}-2,3-dihydro-4H-1,4-benzoxazin-4-yl)butanoic acid The compound of the present invention having the following physical data was prepared by substituting the compound prepared in Example 45 for the compound prepared in Example 5 in the process of Example 6→Example 9→Example 28.

TLC: Rf 0.54 (n-hexane:ethyl acetate=1:3);

NMR(CDCl$_3$): δ 1.72-1.99 (m, 6H), 2.38-2.43 (m, 2H), 2.69 (t, 2H), 3.10-3.20 (m, 1H), 3.37-3.50 (m, 2H) 3.53 (dd, 1H), 3.99 (t, 2H), 4.83 (dd, 1H), 6.38 (brs, 1H), 6.46 (brs, 1H), 6.62 (dd, 1H), 6.84-6.89 (m, 3H), 6.98-7.06 (m, 2H), 7.16-7.31 (m, 6H), 7.44 (d, 2H).

Example 61

4-(2-[(Z)-amino(hydroxylamino)methyl]-8-{[4-(4-phenylbutoxy)benzoyl]amino}-2,3-dihydro-4H-1,4-benzoxazin-4-yl)butanoic acid

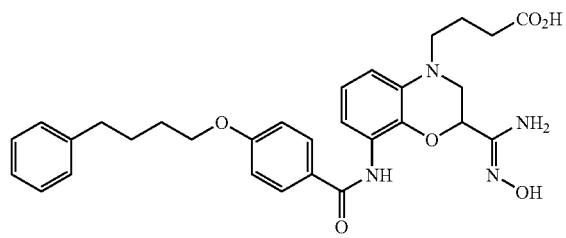

(1) To a solution of hydroxylamine hydrochloride (129 mg) in dimethylsulfoxide (1 mL) was added triethylamine (0.26 mL), and the mixture was stirred for 0.5 hour at room temperature. Insoluble matter was collected by filtration, and the solid was washed with tetrahydrofuran, followed by concentration. To the residue was added ethyl 4-(2-cyano-8-((4-(4-phenylbutoxy)benzoyl)amino)-2,3-dihydro-4H-1,4-benzoxazin-4-yl)butanoate (prepared by substituting the compound prepared in Example 10 for the compound prepared in Example 27 in the process of Example 28→Example 47)(200 mg), and the mixture was stirred for 3 hours at room temperature. To the reaction mixture were added ethyl acetate and water, and the resulting mixture was extracted with ethyl acetate. The organic layer was washed sequentially with water and saturated brine, dried over anhydrous sodium sulfate and concentrated. The residue was washed with t-butyl methyl ether/n-hexane (3:1) to give ethyl 4-(2-[amino(hydroxylamino)methyl]-8-{[4-(4-phenylbutoxy)benzoyl]amino}-2,3-dihydro-4H-1,4-benzoxazin-4-yl)butanoate (202 mg).

TLC: Rf 0.29 (n-hexane:ethyl acetate=1:2);

NMR(CDCl$_3$): δ 1.25 (t, 3H), 1.75-2.00 (m, 6H), 2.38 (t, 2H), 2.70 (t, 2H), 3.21-3.52 (m, 4H), 4.02 (t, 2H), 4.14 (q, 2H), 4.73-4.76 (m, 1H), 4.94 (brs, 2H), 6.48 (brs, 1H), 6.55 (dd, 1H), 6.87-6.95 (m, 3H), 7.16-7.32 (m, 5H), 7.71 (dd, 1H), 7.81 (d, 2H), 8.16 (s, 1H).

(2) The compound of the present invention having the following physical data was prepared by substituting the compound prepared in the above step (1) for the compound prepared in Example 7 in the process of Example 8.

TLC: Rf 0.63 (methylene chloride:methanol:acetic acid=90:10:1);

NMR(DMSO-d$_6$): δ 1.62-1.81 (m, 6H), 2.28 (t, 2H), 2.64 (t, 2H), 3.20-3.42 (m, 4H), 4.01-4.12 (m, 2H), 4.52-4.50 (m, 1H), 5.75 (brs, 2H), 6.59 (d, 1H), 6.76 (t, 1H), 7.02 (d, 2H), 7.09-7.30 (m, 6H), 7.87 (d, 2H), 9.26 (brs, 1H), 9.29 (brs, 1H), 12.10 (brs, 1H).

Example 62

4-(2-(5-oxo-4,5-dihydro-1,2,4-thiadiazol-3-yl)-8-{[4-(4-phenylbutoxy)benzoyl]amino}-2,3-dihydro-4H-1,4-benzoxazin-4-yl)butanoic acid

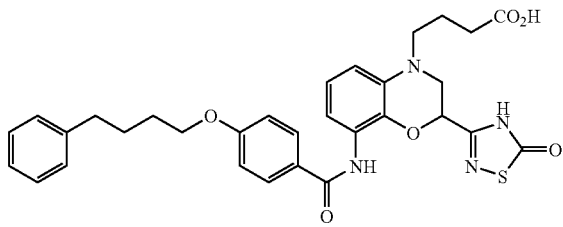

(1) To a solution of the compound prepared in the step (1) of Example 61 (70 mg) in methylene chloride (3 mL) was added thiocarbonyldiimidazole (29 mg) with ice cooling, and the mixture was stirred for 0.5 hour with ice cooling. To the reaction mixture was added water, and the reaction mixture was extracted with ethyl acetate. The organic layer was concentrated and to the resulting residue were added methylene chloride (2 mL) and trifluoroborane-diethyl ether complex (35 μL), and the resulting mixture was stirred for 0.5 hour at −78° C. To the reaction mixture was added ethyl acetate, and the resulting mixture was washed with water and brine sequentially, dried over anhydrous sodium sulfate and concentrated. The residue was purified by column chromatography on silica gel (n-hexane:ethyl acetate=(7:3) to (6:4) to give ethyl 4-(2-(5-oxo-4,5-dihydro-1,2,4-thiadiazol-3-yl)-8-([4-(4-phenylbutoxy)benzoyl]amino)-2,3-dihydro-4H-1,4-benzoxazin-4-yl)butanoate (16 mg).

TLC: Rf 0.42 (n-hexane:ethyl acetate=2:3);

NMR(CDCl$_3$): δ 1.27 (t, 3H), 1.76-1.98 (m, 6H), 2.33 (t, 2H), 2.70 (t, 2H), 3.32 (t, 2H), 3.56 (dd, 1H), 3.86 (dd, 1H), 4.03 (t, 2H), 4.14 (q, 2H), 5.26 (t, 1H), 6.63-6.66 (m, 2H), 6.87 (t, 1H), 6.94 (d, 2H), 7.16-7.32 (m, 5H), 7.68 (s, 1H), 7.89 (d, 2H), 12.59 (brs, 1H).

(2) To a solution of the compound prepared in the above (1) (i.e. ethyl 4-(2-(5-oxo-4,5-dihydro-1,2,4-thiadiazol-3-yl)-8-[4-(4-phenylbutoxy)benzoyl]amino)-2,3-dihydro-4H-1,4-benzoxazin-4-yl)butanoate) (90 mg) in a mixture of tetrahydrofuran (1 mL) and ethanol (1 mL), was added 2N aqueous solution of sodium hydroxide (0.29 ml) and the mixture was stirred for 3 hours at room temperature. To the reaction mixture were added 2M hydrochloric acid (0.29 mL) and water, and the resulting mixture was extracted with ethyl acetate. The organic layer was washed with water and brine sequentially, dried and concentrated. The residue was washed with tert-butyl methyl ether/n-hexane to give the title compound (4-(2-(5-oxo-4,5-dihydro-1,2,4-thiadiazol-3-yl)-8-([4-(4-phenylbutoxy)benzoyl]amino)-2,3-dihydro-4H-1,4-benzoxazin-4-yl)butanoic acid) (69 mg).

TLC: Rf 0.56 (methylene chloride:methanol:acetic acid=90:10:1).

NMR(DMSO-d$_6$): δ 1.62-1.71 (m, 6H), 2.25 (t, 2H), 2.64 (t, 2H), 3.32-3.35 (m, 2H), 3.53 (dd, 1H), 3.62 (dd, 1H), 4.06 (t, 2H), 5.30-5.39 (m, 1H), 6.62 (dd, 1H), 6.79 (t, 1H), 7.02-7.29 (m, 8H), 7.88 (d, 2H), 9.55 (s, 1H), 12.08 (brs, 1H), 13.16 (brs, 1H).

Example 62(1)

4-(2-(5-oxo-4,5-dihydro-1,2,4-thiadiazol-3-yl)-8-{(E)-2-[4-(4-phenylbutoxy)phenyl]vinyl}-2,3-dihydro-4H-1,4-benzoxazin-4-yl)butanoic acid The compound of the present invention having the following physical data was prepared by substituting ethyl 4-(2-[amino(hydroxylamino)methyl]-8-{(Z)-2-[4-(4-phenylbutoxy)phenyl]vinyl}-2,3-dihydro-4H-1,4-benzoxazin-4-yl)butanoate for the compound prepared in the step (1) of Example 61 in the process of Example 62.

TLC: Rf 0.33 (methylene chloride:methanol=95:5);

NMR(DMSO-d$_6$): δ 1.61-1.82 (m, 6H), 2.27 (t, 2H), 2.55-2.67 (m, 2H), 3.17-3.30 (m, 2H), 3.45-3.61 (m, 2H), 3.90-4.03 (m, 2H), 5.14-5.17 (m, 1H), 6.66 (d, 1H), 6.79 (t, 1H), 6.89-6.96 (m, 3H), 7.06 (d, 1H), 7.12-7.29 (m, 5H), 7.34 (d, 1H), 7.47 (d, 2H), 12.10 (brs, 1H), 13.27 (brs, 1H).

Example 63

4-(2-(5-oxo-4,5-dihydro-1,2,4-oxadiazol-3-yl)-8-{(E)-2-[4-(4-phenylbutoxy)phenyl]vinyl}-2,3-dihydro-4H-1,4-benzoxazin-4-yl)butanoic acid (1) Ethyl (4-(2-[amino(hydroxyimino)methyl]-8-[4-(4-phenylbutoxy)styryl]-2,3-dihydro-4H-1,4-benzoxazin-4-yl)butanoate, having the following physical data, was prepared by substituting the compound prepared in Example 45 for the compound prepared in Example 5 in the process of Example 6→Example 9→Example 10→Example 28→Example 47.

TLC: Rf 0.47 (n-hexane:ethyl acetate=1:4);

NMR(CDCl$_3$): δ 1.26 (t, 3H), 1.78-2.20 (m, 6H), 2.38 (t, 2H), 2.69 (t, 2H), 3.21-3.54 (m, 4H), 3.98 (t, 2H), 4.16 (q, 2H), 4.74 (dd, 1H), 4.90 (brs, 2H), 6.64 (dd, 1H), 6.38-6.89 (m, 3H), 6.96-6.98 (m, 1H), 7.03 (d, 1H), 7.19-7.31 (m, 6H), 7.43 (d, 2H).

(2) The compound prepared in the above step (1) (40 mg) was dissolved in methylene chloride (1 mL) and to the resulting solution was added 1,1'-carbonyldiimidazole (15 mg) and it was stirred for 0.5 hour at room temperature. To the mixture was added 1,8-diazabicyclo[5.4.0]undec-7-ene (0.032 mL), and the resulting mixture was stirred at room temperature for 0.5 hour. To the reaction mixture were added water and ethyl acetate, and the resulting mixture was extracted with ethyl acetate. The organic layer was washed sequentially with water, a saturated aqueous solution of ammonium chloride and saturated brine, dried and concentrated. The residue was washed with t-butylmethyl ether/n-hexane (1:2) to give ethyl 4-(2-(5-oxo-4,5-dihydro-1,2,4-oxadiazol-3-yl)-8-{(E)-2-[4-(4-phenylbutoxy)phenyl]vinyl}-2,3-dihydro-4H-1,4-benzoxazin-4-yl)butanoate (34 mg), having the following physical data.

TLC: Rf 0.49 (ethyl acetate);

NMR(CDCl$_3$): δ 1.24 (t, 3H), 1.72-1.99 (m, 6H), 2.36 (t, 2H), 2.68 (t, 2H), 3.32 (t, 2H), 3.51 (dd, 1H), 3.62 (dd, 1H), 3.97 (t, 2H), 4.12 (q, 2H), 5.30-5.33 (m, 1H), 6.68 (d, 1H), 6.84-7.03 (m, 5H), 7.15-7.30 (m, 6H), 7.42 (d, 2H).

(3) The compound of the present invention having the following physical data was prepared by substituting the compound prepared in the above step (2) for the compound prepared in Example 7 in the process of Example 8.

TLC: Rf 0.26 (methylene chloride:methanol=95:5);

NMR(DMSO-d$_6$): δ 1.62-1.80 (m, 6H), 2.27 (t, 2H), 2.63 (t, 2H), 3.22-3.30 (m, 2H), 3.49 (dd, 1H), 3.59 (dd, 1H), 5.34 (dd, 1H), 6.68 (d, 1H), 6.81 (t, 1H), 6.91 (d, 2H), 6.96 (d, 1H), 7.06 (d, 1H), 7.14-7.32 (m, 6H), 7.47 (d, 2H).

Example 64 ethyl 5-(benzyloxy)-1-(4-methoxy-4-oxobutyl)-1-1H-indole-2-carboxylate

To a solution of ethyl 5-(benzyloxy)-1H-indole-2-carboxylate (295 mg) in dimethylformamide (2.00 mL) was added sodium hydride (60%, 42.0 mg) at 0° C., and the mixture was stirred for 30 minutes at room temperature. To the mixture was dropwise added methyl 4-iodobutanoate (251 mg) at 0° C., and the mixture was stirred for 3 hours at room temperature. After addition of water thereto at 0° C., the reaction mixture was extracted with ethyl acetate. The organic layer was washed sequentially with water and saturated brine, dried and concentrated. The residue was purified by column chromatography on silica gel (ethyl acetate:n-hexane=1:4) to give the title compound (395 mg) having the following physical data.

TLC: Rf 0.43 (n-hexane:ethyl acetate=7:3);
NMR (CDCl$_3$): δ 1.40 (t, 3H), 2.10-2.16 (m, 2H), 2.31-2.36 (m, 2H), 3.66 (s, 3H), 4.35 (q, 2H), 4.58-4.63 (m, 2H), 5.10 (s, 2H), 7.09-7.13 (m, 2H), 7.21 (s, 1H), 7.32-7.49 (m, 6H).

Example 65

5-(benzyloxy)-1-(3-carboxypropyl)-1H-indol-2-carboxylic acid

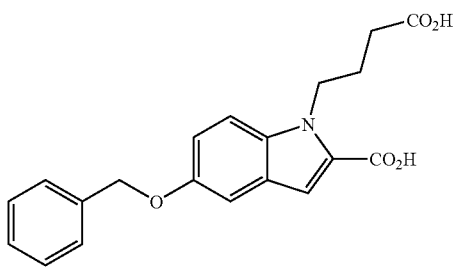

The compound of the present invention having the following physical data was prepared by substituting the compound prepared in Example 64 for the compound prepared in Example 7 in the process of Example 8.

TLC: Rf 0.50 (methanol:methylene chloride=1:4);
NMR(DMSO-d$_5$): δ 1.88-1.91 (m, 2H), 2.16 (t, 2H), 4.52-4.57 (m, 2H), 5.10 (s, 2H), 7.04-7.53 (m, 9H), 12.4 (brs, 2H).

Example 65(1)-Example 65(3)

The compounds of the present invention having the following physical data were prepared by substituting corresponding compounds for ethyl 5-(benzyloxy)-1H-indole-2-carboxylate in the process of Example 64→Example 8.

Example 65(1)

1-(3-carboxypropyl)-5-({3-[(7-chloro-2-quinolinyl)methoxy]benzyl}oxy)-1H-indole-2-carboxylic acid TLC: Rf 0.56 (methanol:methylene chloride=1:4);
NMR(DMSO-d$_6$): δ 1.87-1.91 (m, 2H), 2.16 (t, 2H), 4.51-4.55 (m, 2H), 5.07 (s, 2H), 5.38 (s, 2H), 6.97-7.33 (m, 7H), 7.48 (d, 1H), 7.63-7.71 (m, 2H), 8.02-8.07 (m, 2H), 8.45 (d, 1H), 12.4 (brs, 2H).

Example 65(2)

1-(3-carboxypropyl)-5-[(7-chloro-2-quinolinyl)methoxy]-1H-indole-2-carboxylic acid TLC: Rf 0.41 (methanol:methylene chloride=1:4);
NMR(DMSO-d$_6$): δ 1.87-1.94 (m, 2H), 2.16 (t, 2H), 4.53 (t, 2H), 5.39 (s, 2H), 7.10 (s, 1H), 7.14 (dd, 1H), 7.25 (d, 1H), 7.55 (d, 1H), 7.64 (dd, 1H), 7.74 (d, 1H), 8.05 (d, 1H), 8.08 (d, 1H), 8.45 (d, 1H), 12.45 (brs, 2H).

Example 65(3)

5-({4-[3-(benzyloxy)propyl]benzyl}oxy)-1-(3-carboxypropyl)-1H-indole-2-carboxylic acid TLC: Rf 0.45 (methanol:methylene chloride=1:9);
NMR(DMSO-d$_6$): δ 1.78-1.89 (m, 4H), 2.16 (t, 2H), 3.31-3.44 (m, 4H), 4.44 (s, 2H), 4.53 (t, 2H), 5.04 (s, 2H), 7.03 (dd, 1H), 7.11 (s, 1H), 7.18-7.37 (m, 10H), 7.51 (d, 1H), 12.60 (brs, 2H).

Example 66

4-(2-(ethoxycarbonyl)-8-{2-[4-(4-phenylbutoxy)phenyl]ethyl}-2,3-dihydro-4H-1,4-benzoxazin-4-yl)butanoic acid The compound of the present invention having the following physical data was prepared by substituting the compound prepared in Example 46 for the compound prepared in Example 47 in the process of Example 48.

TLC: Rf 0.53 (methylene chloride:methanol=9:1);
NMR(CDCl$_3$): δ 1.25 (t, 3H), 1.72-1.99 (m, 6H), 2.43 (t, 2H), 2.66-2.70 (m, 2H), 2.75-3.00 (m, 4H), 3.20-3.40 (m, 2H), 3.41-3.56 (m, 2H), 3.92-3.96 (m, 2H), 4.23 (q, 2H), 4.81 (t, 1H), 6.51-6.58 (m, 2H), 6.74 (d, 1H), 6.80 (d, 2H), 7.13 (d, 2H), 7.18-7.30 (m, 5H).

Example 67

4-(5-carboxypentyl)-8-({[4-(4-phenylbutoxy)phenyl]amino}carbonyl)-3,4-dihydro-2H-1,4-benzoxazine-2-carboxylic acid The compound of the present invention having the following physical data was prepared by substituting the compound prepared in Example 38 for the compound prepared in Example 4, and substituting 6-oxohexanoic acid for 4-oxobutanoic acid in the process of Example 5→Example 6→Example 28→Example 29→Example 25.

TLC: Rf 0.39 (methanol:methylene chloride=1:4);
NMR(DMSO-d$_5$): δ 1.28-1.34 (m, 2H), 1.48-1.56 (m, 4H), 1.68-1.74 (m, 4H), 2.21 (t, 2H), 2.51-2.66 (m, 2H), 3.24-3.32 (m, 4H), 3.49 (dd, 1H), 3.59 (dd, 1H), 3.93-3.96 (m, 2H), 5.12 (t, 1H), 6.82-6.88 (m, 2H), 6.89 (d, 2H), 7.04 (dd, 1H), 7.16-7.30 (m, 5H), 7.62 (d, 2H), 10.10 (s, 1H).

Example 67(1)

4-(3-carboxypropyl)-8-({methyl[4-(4-phenylbutoxy)phenyl]amino}carbonyl)-3,4-dihydro-2H-1,4-benzoxazine-2-carboxylic acid (1) To a solution of the compound prepared in Example (497 mg) in dimethylformamide (3.00 mL) was added sodium hydride (60%, 44.0 mg) at 0° C., and the mixture was stirred for 30 minutes at room temperature. To the mixture was added methyl iodide (213 mg) at 0° C., and the mixture was stirred for 2 hours at room temperature. To the reaction mixture was added water at 0° C. and it was extracted with ethyl acetate. The organic layer was washed sequentially with water and saturated brine, dried and concentrated. The residue was purified by column chromatography on silica gel (ethyl acetate:n-hexane=3:7) to give 2-(benzyloxy)-N-methyl-3-nitro-N-[4-(4-phenylbutoxy)phenyl]benzamide (454 mg).

TLC: Rf 0.15 (n-hexane:ethyl acetate=7:3);

NMR(CDCl$_3$): δ 1.71-1.75 (m, 4H), 2.60-2.67 (m, 2H), 3.40 (s, 3H), 3.81 (t, 2H), 5.21 (s, 2H), 6.58 (d, 2H), 6.85 (d, 2H), 7.06 (dd, 1H), 7.14-7.46 (m, 9H), 7.54 (dd, 2H), 7.69 (dd, 1H).

(2) The compound of the present invention having the following physical data was prepared by substituting the compound prepared in Example 4 for the compound prepared in the above step (1) in the process of Example 5→Example 6→Example 28→Example 8.

TLC: Rf 0.40 (methanol:methylene chloride:acetic acid=1:9:0.1);

NMR(CDCl$_3$): δ 1.75-1.91 (m, 6H), 2.39 (t, 2H), 2.66 (t, 2H), 3.23-3.30 (m, 2H), 3.48 (s, 3H), 3.67 (dd, 1H), 3.75 (dd, 1H), 3.89 (t, 2H), 4.86 (m, 1H), 6.09 (dd, 1H), 6.51 (dd, 1H), 6.57 (dd, 1H), 6.74 (d, 2H), 7.04 (d, 2H), 7.16-7.20 (m, 2H), 7.25-7.31 (m, 3H).

Example 68

4-(3-carboxypropanoyl)-8-{(E)-2-[4-(4-phenylbutoxy)phenyl]vinyl}-3,4-dihydro-2H-1,4-benzoxazine-2-carboxylic acid The compound of the present invention having the following physical data was prepared from the compound prepared in Example 45, using a procedure analogous to that described for Example 6→Example 7→Example 8.

TLC: Rf 0.46 (methanol:methylene chloride:acetic acid=1:9:0.1);

NMR(DMSO-d$_6$): δ 1.57-1.86 (m, 4H), 2.35-2.99 (m, 6H), 3.80-4.08 (m, 3H), 4.15-4.35 (m, 1H), 4.97-5.25 (m, 1H), 6.83-7.01 (m, 3H), 7.09-7.35 (m, 7H), 7.41-7.65 (m, 4H).

The effects of the compound of formula (I) of the present invention was illustrated by the following experiments, but the present invention is not limited to them.

Biological Example 1

Effect on LTD$_4$-Induced Increase of Intracellular Calcium

Expression cells of cysLT$_2$ receptor (HEK293) were seeded in a 96-well plate each containing 1×10$^5$ cells. The cells were cultured for 24 hours in a 5% CO$_2$ at 37° C. using DMEM (Dulbecco's Modified Eagle Medium). The cells were incubated in 7.5 µM Fura2-AM, 20 mM HEPES (2-[4-(2-hydroxyethyl)-1-piperazinyl]ethanesulfonic acid) and 2.5 mM probenecid for approximately 30 minutes at 37° C. The cells with uptake of Fura2-AM were once washed with assay buffer (Hank's buffer containing 20 mM HEPES) and intracellular calcium influx induced by LTD$_4$ was measured by FDSS2000 (Hamamatsu Photonics K.K.). The compound of the present invention was administered 180 seconds before LTD$_4$ stimulation, and the reaction induced by 100 nM LTD$_4$ was measured in time course for 90 seconds. The effect of the compound of the present invention was evaluated by maximum fluorescence intensity, and 50% inhibitory concentration (IC$_{50}$) was calculated on each compound.

As a result, the compound of formula (I) showed an IC$_{50}$ value of under 10 µM. For example, the IC$_{50}$ value of the compound of Example 12 was 101 nmol/L, and that of the compound of Example 25 was 30 nmol/L.

Biological Example 2

Effect on LTC$_4$-Induced Contraction in Guinea Pig Trachea

Four Hartley male guinea pigs (Charles River Laboratories Japan, Inc.) per group were used in the present experiment. The guinea pigs were sacrificed by blood loss from carotid artery, and their tracheas were removed immediately. The tracheas were cut in a zigzag way with a razor to prepare a specimen with 3 mm width. The specimen was kept at 37° C. and suspended in a 10 mL Magnus tube containing Tyrode solution (NaCl 137 mM, KCl 2.68 mM, MgCl$_2$ 1.05 mM, CaCl$_2$ 1.80 mM, NaHCO$_3$ 11.9 mM, NaH$_2$PO$_4$ 0.417 mM and glucose 5.55 mM) aerated with mixed gas (95% O$_2$+5% CO$_2$) at 37° C. The tracheal specimen was given 1 G of tension and washed with Tyrode solution 3 times every 15 minutes. When the response being reached a steady state, the specimen was incubated in 45 mM serine-borate complex and 3 mM cysteine before LTC$_4$ stimulation. The contraction of trachea induced by LTC$_4$ was measured as the change of isometric tension by an isometric transducer. The compound of the present invention was administered 15 minutes before LTC$_4$ stimulation, and the time course of the tension induced by LTC$_4$ was observed. The rate of trachea contraction induced by LTC$_4$ was measured from the maximum response at the final concentration 1 mM of acetylcholine to calculate it on each compound. The antagonistic effect of the compound of the present invention against LT was determined by Schild plot analysis giving the pA$_2$ values.

The results showed that the compound of formula (I) inhibited the contraction of guinea pig trachea significantly, and the pA$_2$ value was 6 or more. For example, the pA$_2$ value of the compound of Example 12 was 8.5±0.1 and that of the compound of Example 25 was 9.2±0.3.

Biological Example 3

Effect on OVA-Induced Bronchocontraction Involved in Endogenous LT in Guinea Pigs Guinea pigs were actively sensitized by intraperitoneal administration of 1 ml of saline containing 1 mg ovalbumin (OVA) containing 5×10$^9$ killed Bordetella pertussis cells. Two or three weeks after the sensitization, the guinea pigs were anesthetized with pentobarbital sodium (75 mg/kg, i.p.), and a polyethylene tube was inserted into the trachea which had been incised. For administration of the compound of the present invention and OVA, the jugular vein was cannulated. One side of the tracheal cannula was connected to a constant volume respirator and the animals were artificially ventilated with a constant volume of 5 mL at a frequency of 70 strokes/min. Bronchocontraction was induced by intravenous administration of OVA, and airway resistance was measured by Konzett & Rössler method. In order to avoid the influence of cyclooxygenase metabolites and histamine, indomethacin (5 mg/kg/mL) and pyrilamine (1 mg/kg/mL) were intravenously administered 3 and 1 minute(s) before OVA challenge. Bronchocontraction was measured until the time of 20 minutes after OVA challenge, and brochocontraction rate was calculated with time wherein the maximal insufflation pressure obtained by completely clamping off the trachea is set to 100%.

It was revealed from the results that the compound of formula (I) suppresses bronchocontraction significantly, and is useful for the treatment of respiratory diseases, particularly of bronchial asthma.

Formulation Example

The formulations to be used in order to carry out the present invention are shown below.

Formulation Example 1

The following components were admixed by conventional techniques, thereby to give 10,000 tablets each containing 10 mg of active ingredient.

4-(3-carboxypropanoyl)-8-((4-(4-phenylbutoxy)benzoyl)amino)-3,4-dihydro-2H-1,4-benzoxazine-2-carboxylic acid (100 g);
carboxymethyl cellulose calcium (disintegrating agent) (20 g);
magnesium stearate (lubricating agent) (10 g);
microcrystalline cellulose (870 g).

Formulation Example 2

The following components were admixed by conventional method, filtered over a dust-removable filter, and filled 5 ml each in ampoules, and heat-sterilized with an autoclave, giving 10,000 ampoules each containing 20 mg of active ingredient.

4-(3-carboxypropanoyl)-8-((4-(4-phenylbutoxy)benzoyl)amino)-3,4-dihydro-2H-1,4-benzoxazine-2-carboxylic acid (200 g);
mannitol (2 kg);
distilled water for injection (50 L).

INDUSTRIAL APPLICABILITY

Since the compound of formula (I), an N-oxide thereof, a salt thereof, a solvate thereof or a prodrug thereof antagonizes cysLT$_2$ receptor, it is useful as an inhibitor of airway contraction, an inhibitor of infiltration of inflammatory cells (e.g. eosinophils, neutrophils, lymphocytes, basophils, etc.), an inhibitor of mucus secretion or an inhibitor of increased airway hyperreactivity. And the compound of formula (I), an N-oxide thereof, a salt thereof, a solvate thereof or a prodrug thereof is also useful for the prevention and/or treatment of those diseases with which cysLT$_2$ receptor is involved, e.g. respiratory diseases (e.g. bronchial asthma, chronic obstructive pulmonary diseases, lung emphysema, chronic bronchitis, pneumonia (e.g. interstitial pneumonitis, etc.), severe acute respiratory syndrome (SARS), acute respiratory distress syndrome (ARDS), allergic rhinitis, sinusitis (e.g. acute sinusitis, chronic sinusitis, etc.), etc., and as an expectorant or an antitussive agent. And the compound of formula (I) of the present invention, an N-oxide thereof, a salt thereof, a solvate thereof or a prodrug thereof is also useful as an agent for the improvement of respiratory functions.

CysLT$_2$ receptor is also concerned with cardiovascular diseases, e.g. angina pectoris, cardiac infarction, acute coronary syndromes, heart failure, arrhythmia, cardiomyopathy (dilative cardiomyopathy hypertrophic cardiomyopathy, etc.), pericarditis, valvulitis, myocarditis, cardiac tamponade, low cardiac output syndrome, mitral stenosis, etc. The compound of formula (I), an N-oxide thereof, a salt thereof, a solvate thereof or a prodrug thereof is useful for the treatment and/or prevention of these diseases.

The invention claimed is:

1. A method for treating asthma, said method comprising: administering to a mammal an effective amount of a compound of formula (I-b),

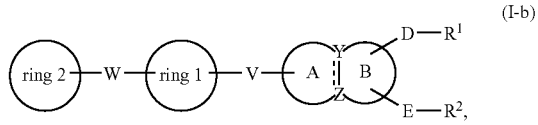

wherein:
$R^1$ and $R^2$ are each —COOH
-D-$R^1$ is C1-4 alkylene-$R^1$,
E is a bond or C1-4 alkylene,
ring A is a benzene ring which may optionally be substituted by group(s) selected from the group consisting of (1) hydroxy, (2) methyl, ethyl, n-propyl, isopropyl, n-butyl, isobutyl, sec-butyl or tert-butyl, each of which may optionally be substituted by 1-4 of halogen, (3) methoxy, ethoxy, n-propyloxy, isopropyloxy, n-butyloxy, isobutyloxy, sec-butyloxy, or tert-butyloxy, (4) amino, (5) nitro and (6) halogen,
ring B is a pyrrole ring which may optionally be substituted by group(s) selected from the group consisting of (1) hydroxy, (2) methyl, ethyl, n-propyl, isopropyl, n-butyl, isobutyl, sec-butyl or tert-butyl, each of which may optionally be substituted by 1-4 of halogen, (3) methoxy, ethoxy, n-propyloxy, isopropyloxy, n-butyloxy, isobutyloxy, sec-butyloxy, or tert-butyloxy, (4) amino, (5) nitro and (6) halogen,
Y and Z are each a carbon atom,
the ring of the formula

is 1H-indole ring,
W is —O—CH$_2$—, —O—(CH$_2$)$_2$—, —O—(CH$_2$)$_3$—, —O—(CH$_2$)$_4$—, —O—(CH$_2$)$_5$—, —CH$_2$—O—, —(CH$_2$)$_2$—O—, —(CH$_2$)$_3$—O—, —(CH$_2$)$_4$—O—, —(CH$_2$)$_5$—O—, —O—(CH$_2$)$_3$—O—, —O—(CH$_2$)$_4$—O—, —O—(CH$_2$)$_5$—O—C1-6 alkylene or —CH$_2$—O—(CH$_2$)$_3$—,
V is

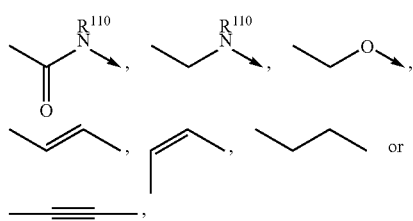

(wherein $R^{110}$ is hydrogen or C1-8 alkyl, and the arrow means that it attaches to the ring A),
ring 1 is a benzene ring which may optionally be substituted by group(s) selected from the group consisting of C1-10 straight or branched alkyl, alkenyl and alkynyl group, and
ring 2 is a benzene ring which may optionally be substituted by group(s) selected from the group consisting of hydroxy, methyl, ethyl, propyl, n-butyl, n-pentyl, n-hexyl, fluorine, chlorine, bromine, methoxy, ethoxy, propoxy, butoxy, trifluoromethyl and methylthio,
or a pharmaceutical acceptable salt thereof.

2. The method according to claim 1, wherein the compound of formula (I-b) is 5-({4-[3-(benzyloxy)propyl]benzyl}oxy)-1-(3-carboxypropyl)-1H-indole-2-carboxylic acid.

* * * * *